US012545893B2

(12) United States Patent
Cayouette et al.

(10) Patent No.: US 12,545,893 B2
(45) Date of Patent: Feb. 10, 2026

(54) RECOMBINANT NERVOUS SYSTEM CELLS AND METHODS TO GENERATE THEM

(71) Applicant: ADAERATA, LIMITED PARTNERSHIP, Québec (CA)

(72) Inventors: Michel Cayouette, Carignan (CA); Camille Boudreau-Pinsonneault, Montréal (CA); Awais Javed, Montréal (CA); Michel Fries, Montréal (CA); Pierre Mattar, Ottawa (CA)

(73) Assignee: ADAERATA, LIMITED PARTNERSHIP, Québec (CA)

( * ) Notice: Subject to any disclaimer, the term of this patent is extended or adjusted under 35 U.S.C. 154(b) by 818 days.

(21) Appl. No.: 17/309,044

(22) PCT Filed: Nov. 5, 2019

(86) PCT No.: PCT/CA2019/051568
§ 371 (c)(1),
(2) Date: Apr. 16, 2021

(87) PCT Pub. No.: WO2020/093147
PCT Pub. Date: May 14, 2020

(65) Prior Publication Data

US 2021/0253999 A1 Aug. 19, 2021

Related U.S. Application Data

(60) Provisional application No. 62/755,657, filed on Nov. 5, 2018.

(51) Int. Cl.

| | |
|---|---|
| ***C12N 5/079*** | (2010.01) |
| ***C07K 14/47*** | (2006.01) |
| ***C07K 14/705*** | (2006.01) |
| ***C12N 5/0793*** | (2010.01) |
| ***C12N 15/86*** | (2006.01) |

(52) U.S. Cl.
CPC ........ *C12N 5/0621* (2013.01); *C07K 14/4702* (2013.01); *C07K 14/705* (2013.01); *C12N 5/0619* (2013.01); *C12N 5/0622* (2013.01); *C12N 15/86* (2013.01); *C12N 2510/00* (2013.01); *C12N 2750/14143* (2013.01)

(58) Field of Classification Search
CPC .. C12N 5/0621; C12N 5/0619; C12N 5/0622; C12N 15/86; C12N 2510/00; C12N 2750/14143; C12N 2501/60; C12N 5/062; C12N 2740/16043; C07K 14/4702; C07K 14/705; A01K 2217/15; A01K 2227/105; A61K 38/00
See application file for complete search history.

(56) References Cited

U.S. PATENT DOCUMENTS

2007/0042433 A1* 2/2007 Bao .................... G01N 33/6875 435/325

FOREIGN PATENT DOCUMENTS

WO WO2020093147 A1 5/2020

OTHER PUBLICATIONS

Balaggan, K., Ali, R. Ocular gene delivery using lentiviral vectors. Gene Ther 19, 145-153 (2012). https://doi.org/10.1038/gt.2011.153 (Year: 2012).*

Volland, S., Esteve-Rudd, J., Hoo, J., Yee, C., & Williams, D. S. (2015). A comparison of some organizational characteristics of the mouse central retina and the human macula. PloS one, 10(4), e0125631. (Year: 2015).*

Karlstetter, M., Ebert, S., & Langmann, T. (2010). Microglia in the healthy and degenerating retina: insights from novel mouse models. Immunobiology, 215(9-10), 685-691. (Year: 2010).*

DuVal, Michèle G.1; Allison, W. Ted Ph.D.1,2, *. Impacts of the retinal environment and photoreceptor type on functional regeneration. Neural Regeneration Research 12(3):p. 376-379, Mar. 2017. | DOI: 10.4103/1673-5374.202930 (Year: 2017).*

Li, Z., Perez-Casellas, L. A., Savic, A., Song, C., & Dovat, S. (2011). Ikaros isoforms: the saga continues. World journal of biological chemistry, 2(6), 140. (Year: 2011).*

Broun, P., Shanklin, J., Whittle, E., & Somerville, C. (1998). Catalytic plasticity of fatty acid modification enzymes underlying chemical diversity of plant lipids. Science, 282(5392), 1315-1317. (Year: 1998).*

Serre, Karine, et al. "Helios is associated with CD4 T cells differentiating to T helper 2 and follicular helper T cells in vivo independently of Foxp3 expression." PloS one 6.6 (2011): e20731. (Year: 2011).*

Alsio, J.M., Tarchini, B., Cayouette, M., Livesey, F.J. (2013) Ikaros promotes early-born neuronal fates in the cerebral cortex. Proc Natl Acad Sci USA Feb. 13, 2019;110(8):E716-25.

(Continued)

*Primary Examiner* — Jennifer Dunston
*Assistant Examiner* — Christina Tran
(74) *Attorney, Agent, or Firm* — Lavery, de Billy, L.L.P.; Julie Gauvreau

(57) ABSTRACT

The instant disclosure provides a recombinant nervous system cell comprising nucleic acid encoding IKAROS Family Zinc Finger 4 (Ikzf4) and/or IKAROS Family Zinc Finger 1 (Ikzf1)); a vector comprising a glial specific promotor operably-linked to a nucleic acid molecule encoding IKAROS Family Zinc Finger 1 (Ikzf1) and/or a nucleic acid molecule encoding IKAROS Family Zinc Finger 4 (Ikzf4); and methods of producing a recombinant cone photoreceptor, comprising: (A) (a) introducing a nucleic acid molecule encoding IKAROS Family Zinc Finger 1 (Ikzf1) in a Müller glia cell; and (b) introducing a nucleic acid molecule encoding IKAROS Family Zinc Finger 4 (Ikzf4) in the Müller glia cell; or (B) introducing a nucleic acid molecule encoding Ikzf4 in a retinal neuroepithelial cell; whereby the retinal neuroepithelial cell or the Müller glia is reprogrammed into a recombinant cone photoreceptor.

19 Claims, 105 Drawing Sheets

Figure 1E:
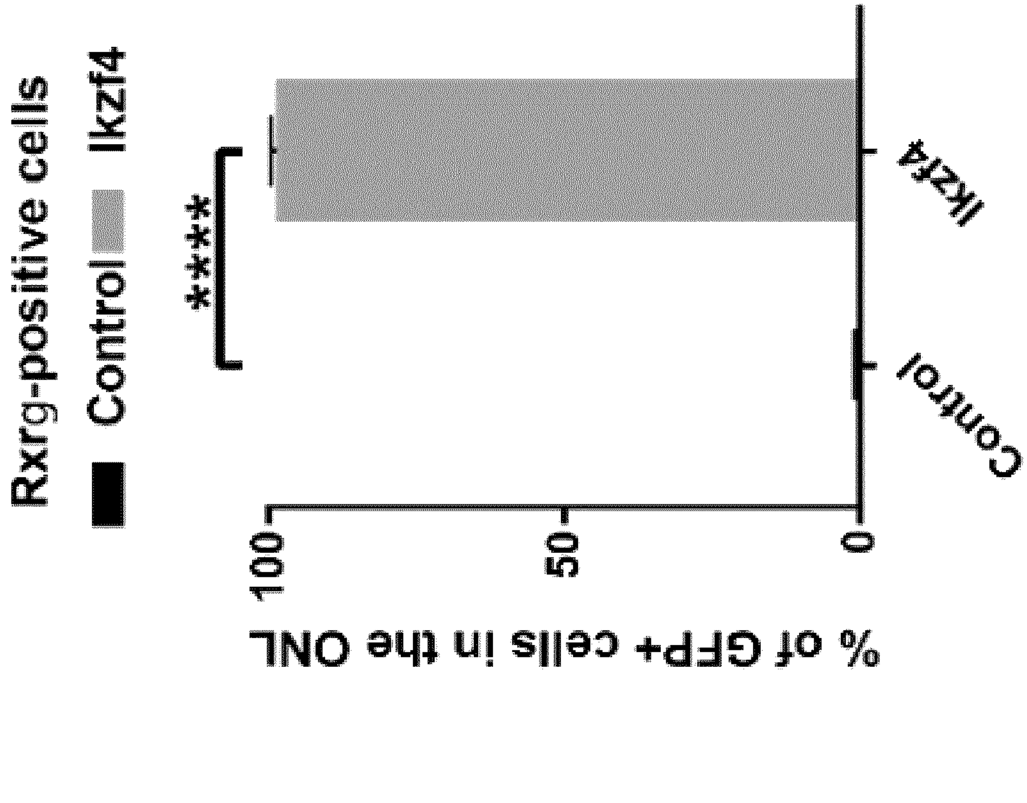

Specification includes a Sequence Listing.

(56) References Cited

OTHER PUBLICATIONS

Bernardos, R.L., Barthel, L.K., Meyers, J.R., and Raymond, P.A. (2007). Late-stage neuronal progenitors in the retina are radial Muller glia that function as retinal stem cells. The Journal of neuroscience : the official journal of the Society for Neuroscience 27, 7028-7040.
Blackshaw, S., Harpavat, S., Trimarchi, J., Cai, L., Huang, H., Kuo, W.P., Weber, G., Lee, K., Fraioli, R.E., Cho, S.H., et al. (2004). Genomic analysis of mouse retinal development. PLoS biology 2, E247.
Elliott, J., Jolicoeur, C., Ramamurthy, V., and Cayouette, M. (2008). Ikaros confers early temporal competence to mouse retinal progenitor cells. Neuron 60, 26-39.
Fausett, B.V., and Goldman, D. (2006). A role for alpha1 tubulin-expressing Muller glia in regeneration of the injured zebrafish retina. The Journal of neuroscience : the official journal of the Society for Neuroscience 26, 6303-6313.
Fimbel, S.M., Montgomery, J.E., Burket, C.T., and Hyde, D.R. (2007). Regeneration of inner retinal neurons after intravitreal injection of ouabain in zebrafish. The Journal of neuroscience : the official journal of the Society for Neuroscience 27, 1712-1724.
Gonzalez-Cordero, A., Kruczek, K., Naeem, A., Fernando, M., Kloc, M., Ribeiro, J., Goh, D., Duran, Y., Blackford, S.J. I., Abelleira-Hervas, L., et al. (2017). Recapitulation of Human Retinal Development from Human Pluripotent Stem Cells Generates Transplantable Populations of Cone Photoreceptors. Stem cell reports 9, 820-837.
Hamon, A., Roger, J.E., Yang, X .- J., and Perron, M. (2016). Muller Glial Cell-Dependent Regeneration of the Neural Retina—An Overview Across Vertebrate Model Systems. Developmental dynamics reviews.
Honma, Y., Kiyosawa, H., Mori, T., Oguri, A., Nikaido, T., Kanazawa, K., Tojo, M., Takeda, J., Tanno, Y., Yokoya, S., Kawabata, I., Ikeda, H., Wanaka, A. (1999) Eos: a novel member of the Ikaros gene family expressed predominantly in the developing nervous system FEBS Letters 447(1): 76-80.
Jadhav, A.P., Roesch, K., and Cepko, C.L. (2009). Development and neurogenic potential of Muller glial cells in the vertebrate retina. Progress in retinal and eye research 28, 249-262.
Javed, A., Cayouette, M. (2017) Temporal Progression of Retinal Progenitor Cell Identity: Implications in Cell Replacement Therapies. Front. Neural Circuits, vol. 11, Article 105, Dec. 19, 2017, 1-7.
Johnson M, et al. (2008) NCBI BLAST: a better web interface. Nucleic Acids Res. 36:W5-W9; Papadopoulos JS and Agarwala R (2007) Bioinformatics 23:1073-79.
Jorstad, N.L., Wilken, M.S., Grimes, W.N., Wohl, S.G., VandenBosch, L.S., Yoshimatsu, T., Wong, R.O., Rieke, F., and Reh, T.A. (2017). Stimulation of functional neuronal regeneration from Muller glia in adult mice. Nature 548, 103-107.
Mattar, P., Ericson, J., Blackshaw, S., and Cayouette, M. (2015). A conserved regulatory logic controls temporal identity in mouse neural progenitors. Neuron 85, 497-504.
Nakano, T., Ando S., Takata N., Kawada M., Muguruma K., Sekiguchi K., Saito K., Yonemura S., Eiraku M., Sasai Y., (2012) Self-Formation of Optic Cups and Storable Stratified Neural Retina from Human ESCs Cell Stem Cell 10, 771-785.
Ortin-Martinez, A., Tsai, E.L., Nickerson, P.E., Bergeret, M., Lu, Y., Smiley, S., Comanita, L., and Wallace, V.A. (2016). A Reinterpretation of Cell Transplantation: GFP Transfer from Donor to Host Photoreceptors. Stem cells 35, 932-939.
PCT/CA2019/051568 to Cayouette et al., International Search Report and Written Opinion dated Jan. 17, 2020.
Pearson, R.A., Gonzalez-Cordero, A., West, E.L., Ribeiro, J.R., Aghaizu, N., Goh, D., Sampson, R.D., Georgiadis, A., Waldron, P.V., Duran, Y., et al. (2016). Donor and host photoreceptors engage in material transfer following transplantation of post-mitotic photoreceptor precursors. Nature communications 7, 13029.
Pellissier, L.P., Hoek, R.M., Vos, R.M., Aartsen, W.M., Klimczak, R.R., Hoyng, S.A., Flannery, J.G., and Wijnholds, J. (2014). Specific tools for targeting and expression in Muller glial cells. Molecular therapy Methods & clinical development 1, 14009.
Petit, L., Khanna, H., and Punzo, C. (2016). Advances in Gene Therapy for Diseases of the Eye. Hum Gene Ther 27, 563-579.
Powell, C., Elsaeidi, F., and Goldman, D. (2012). Injury-dependent Muller glia and ganglion cell reprogramming during tissue regeneration requires Apobec2a and Apobec2b. The Journal of neuroscience : the official journal of the Society for Neuroscience 32, 1096-1109.
Roesch, K., Jadhav, A.P., Trimarchi, J.M., Stadler, M.B., Roska, B., Sun, B.B., and Cepko, C.L. (2008). The transcriptome of retinal Muller glial cells. The Journal of comparative neurology 509, 225-238.
Santos-Ferreira, T., Llonch, S., Borsch, O., Postel, K., Haas, J., and Ader, M. (2016). Retinal transplantation of photoreceptors results in donor-host cytoplasmic exchange. Nature communications 7, 13028.
Santos-Ferreira, T.F., Borsch, O., and Ader, M. (2017). Rebuilding the Missing Part-A Review on Photoreceptor Transplantation. Front Syst Neurosci 10, 1-14.
Senut, M.C., Gulati-Leekha, A., and Goldman, D. (2004). An element in the alpha1-tubulin promoter is necessary for retinal expression during optic nerve regeneration but not after eye injury in the adult zebrafish. The Journal of neuroscience : the official journal of the Society for Neuroscience 24, 7663-7673.
Singh, M.S., Balmer, J., Barnard, A.R., Aslam, S.A., Moralli, D., Green, C.M., Barnea-Cramer, A., Duncan, I., and MacLaren, R.E. (2016). Transplanted photoreceptor precursors transfer proteins to host photoreceptors by a mechanism of cytoplasmic fusion. Nature communications 7, 13537.
Tao Y., Chen T., Fang W., Peng G., Wang L., Qin L., Liu B., Huang Y.F. The temporal topography of the N-Methyl-N-nitrosourea induced photoreceptor degeneration in mouse retina (2015) Scientific Reports vol. 5, Article No. 18612.
Ueki, Y., Wilken, M.S., Cox, K.E., Chipman, L., Jorstad, N., Sternhagen, K., Simic, M., Ullom, K., Nakafuku, M., and Reh, T.A. (2015). Transgenic expression of the proneural transcription factor Ascl1 in Muller glia stimulates retinal regeneration in young mice. Proceedings of the National Academy of Sciences of the United States of America 112, 13717-13722.
Vierbuchen, T., Ostermeier, A., Pang, Z.P., Kokubu, Y., Sudhof, T.C., and Wernig, M. (2010). Direct conversion of fibroblasts to functional neurons by defined factors. Nature 463, 1035-1041.
Von Jonquieres G, Mersmann N, Klugmann CB, Harasta AE, Lutz B, Teahan O, et al. (2013) Glial Promoter Selectivity following AAV-Delivery to the Immature Brain. PLoS ONE 8(6): e65646.
Yao, K., Qiu, S., Wang, Y.V., Park, S.J.H., Mohns, E.J., Mehta, B., Liu, X., Chang, B., Zenisek, D., Crair, M.C., et al. (2018). Restoration of vision after de novo genesis of rod photoreceptors in mammalian retinas. Nature 560, 484-488.
Zhong X., Gutierrez C., Xue T., Hampton C., Vergara M. N., Cao L., Peters A., Soon Park T., Zambidis E.T., Meyer J. S., Gamm D.M., Yau K.-W., Canto-Soler M.V., Generation of three-dimensional retinal tissue with functional photoreceptors from human iPSCs, (2014) Nature Communications 5:4047. DOI: 10.1038.

* cited by examiner

FIGs. 1A-B
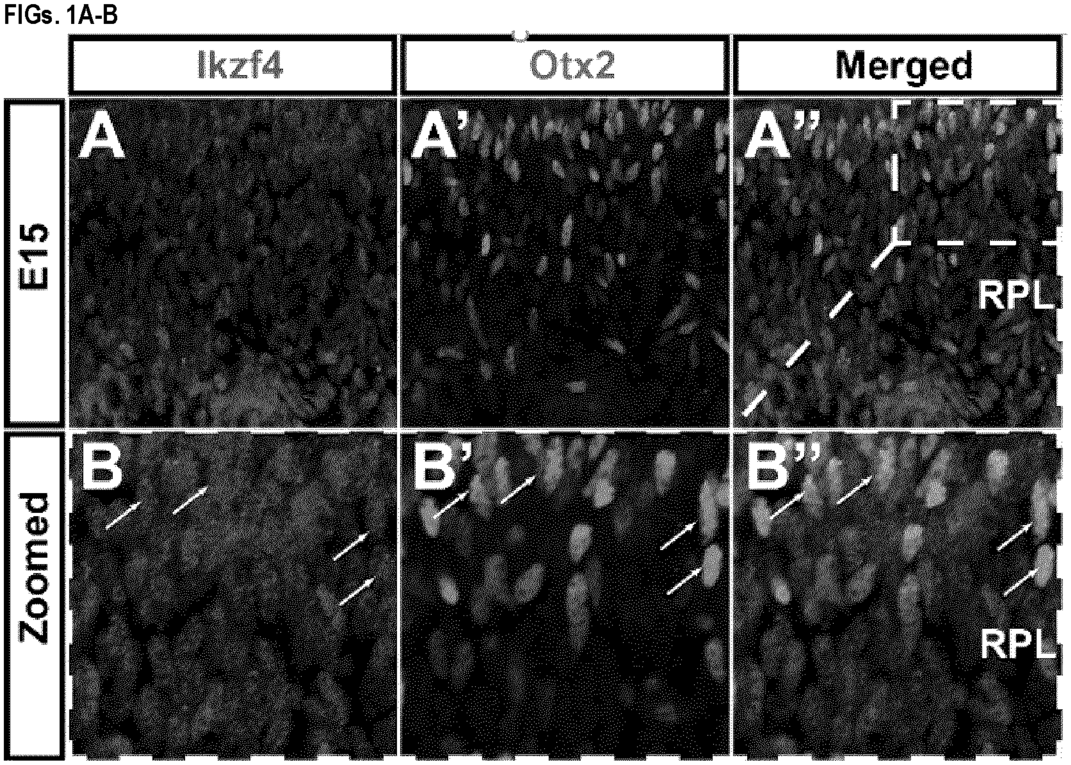
FIGs. 1C-D
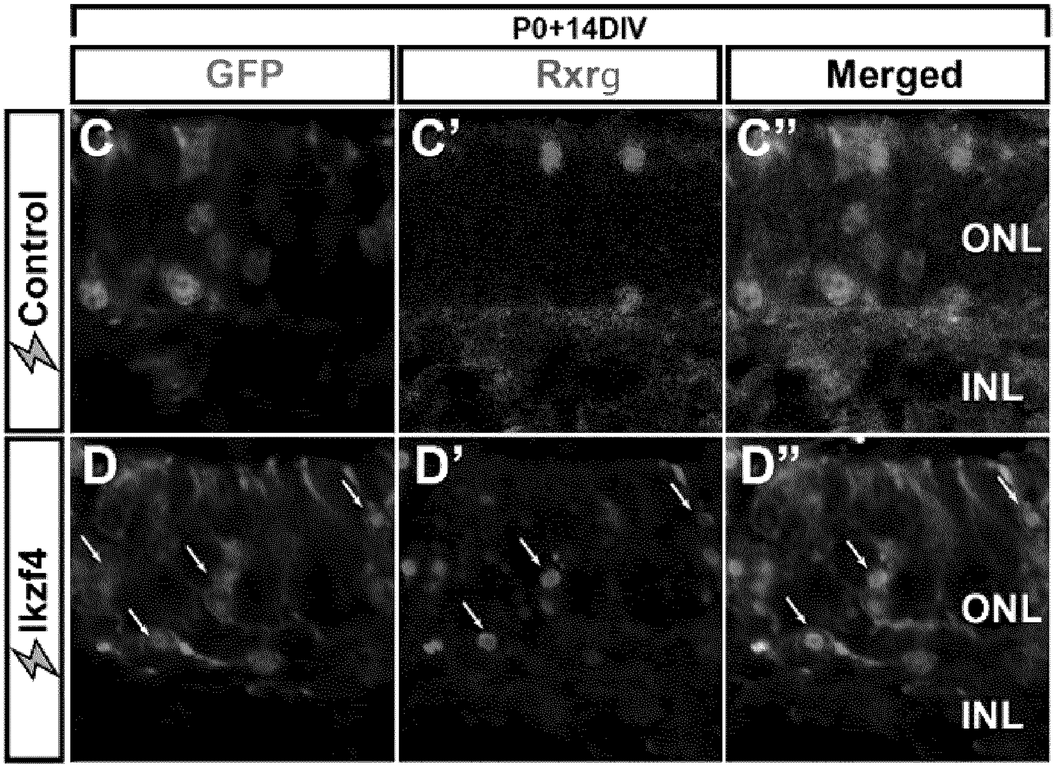

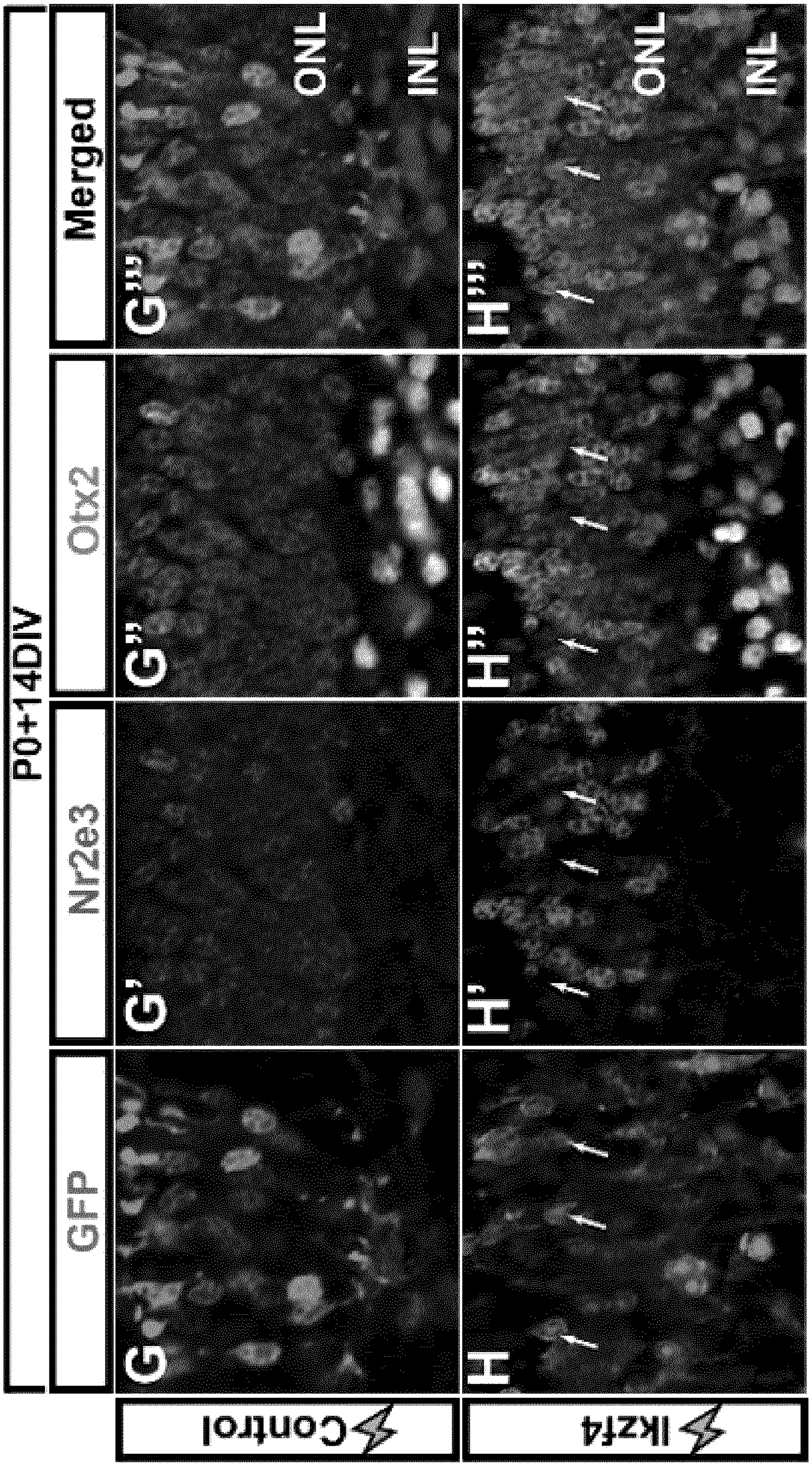
FIGs. 1G-H

FIG. 2B

Electroporated conditions:

| | | | |
|---|---|---|---|
| Control | Pou2f2 | Ascl1+Ikzf4 | Ikzf1+Ikzf4+Apobec2b |
| Ascl1 | Apobec2b | Ikzf1+Ikzf4 | Apobec2b+Ikzf1 |
| Ikzf1 | Pou2f1+Pou2f2 | Ikzf4+Pou2f1 | Apobec2b+Ikzf4 |
| Cas1v2 | Brn2+Ikzf1+Myt1l | Ikzf4+Pou2f2 | Apobec2b+Ascl1 |
| Ikzf4 | Brn2+Ascl1+Myt1l | Ikzf1+Ikzf4+Pou2f1 | Casz1v2+Ascl1 |
| Pou2f1 | Ascl1+Ikzf1 | Ikzf1+Ikzf4+Pou2f2 | |

FIGs. 3C-E
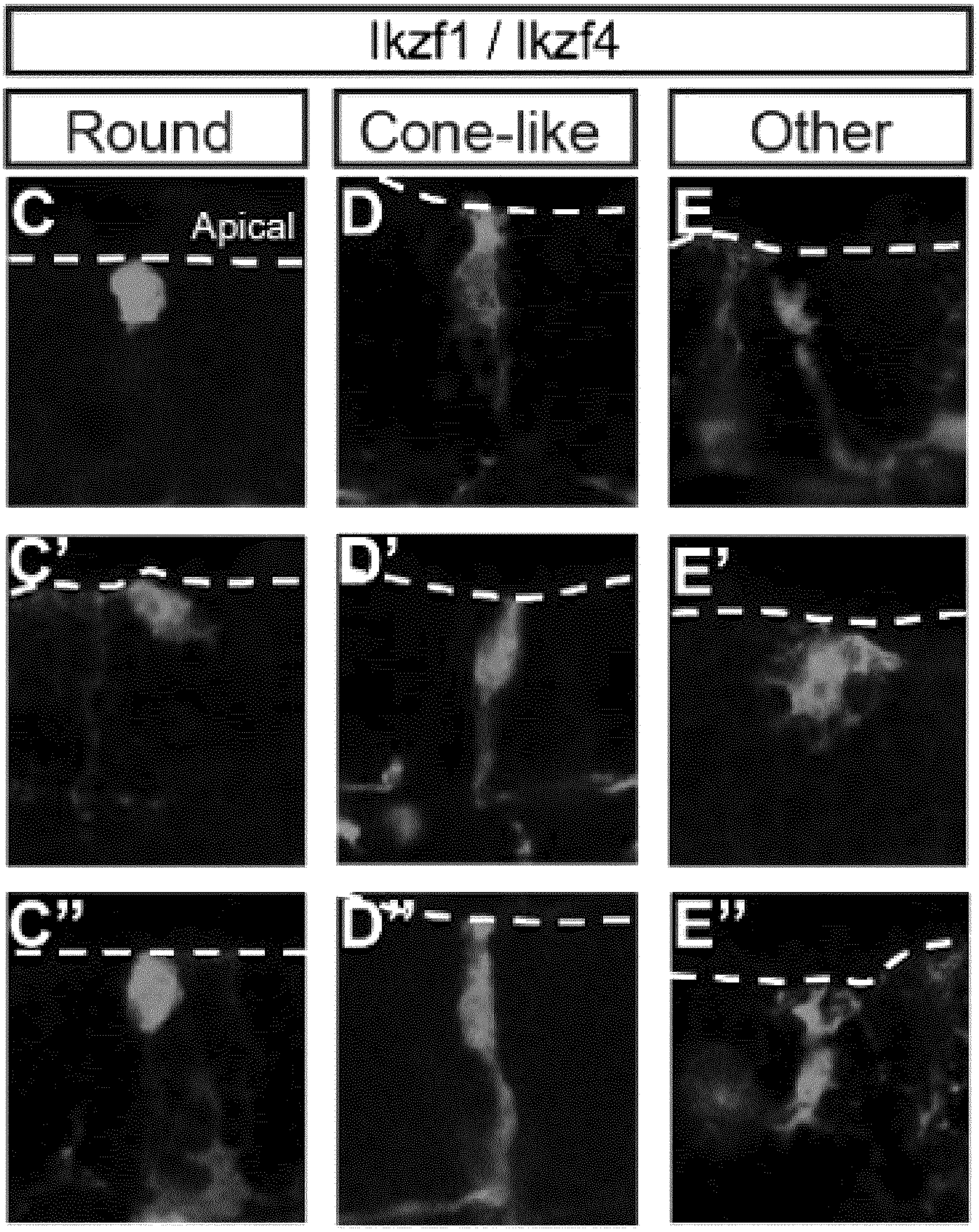

FIGs. 4A-C
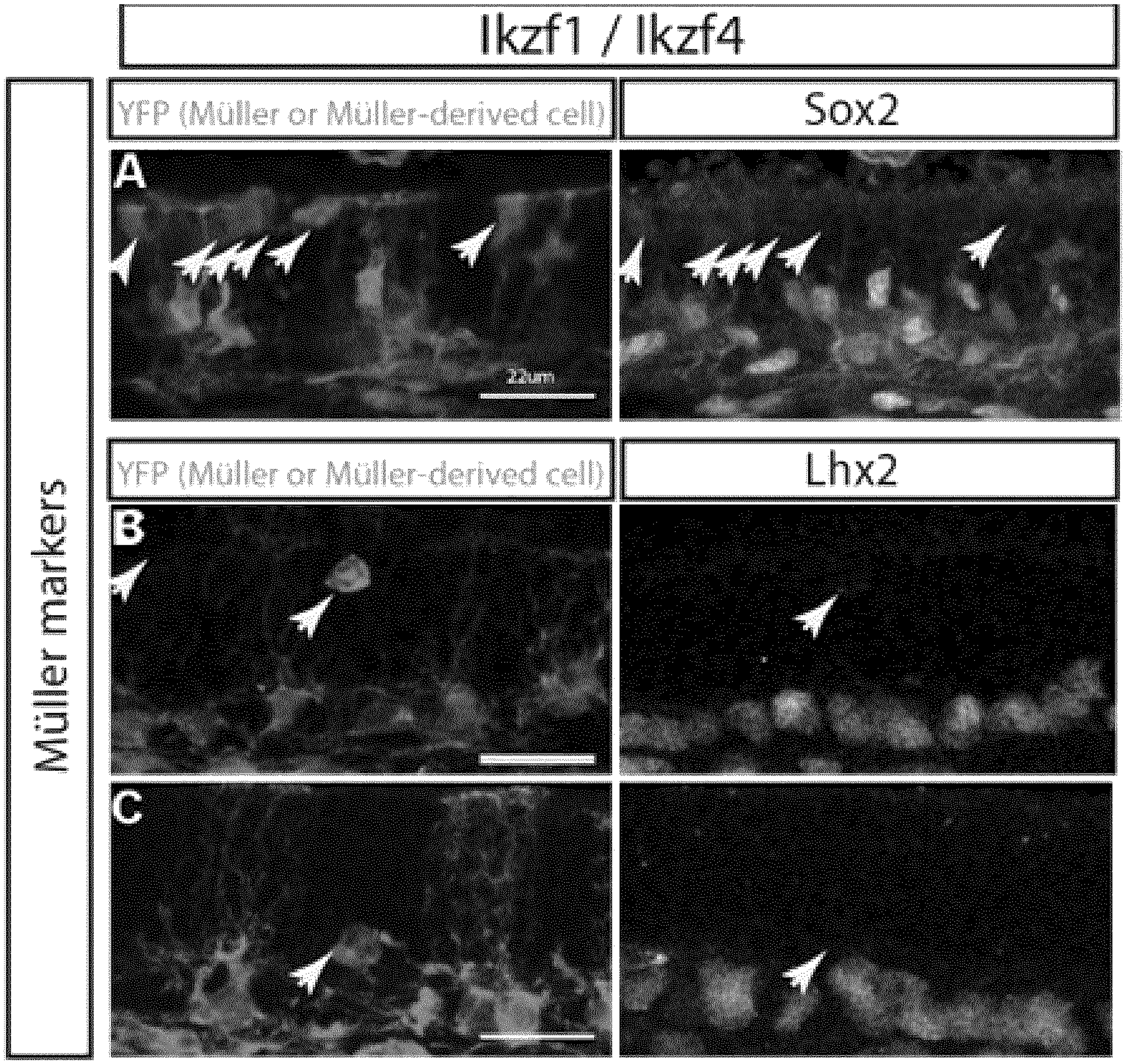

FIGs. 5A-D
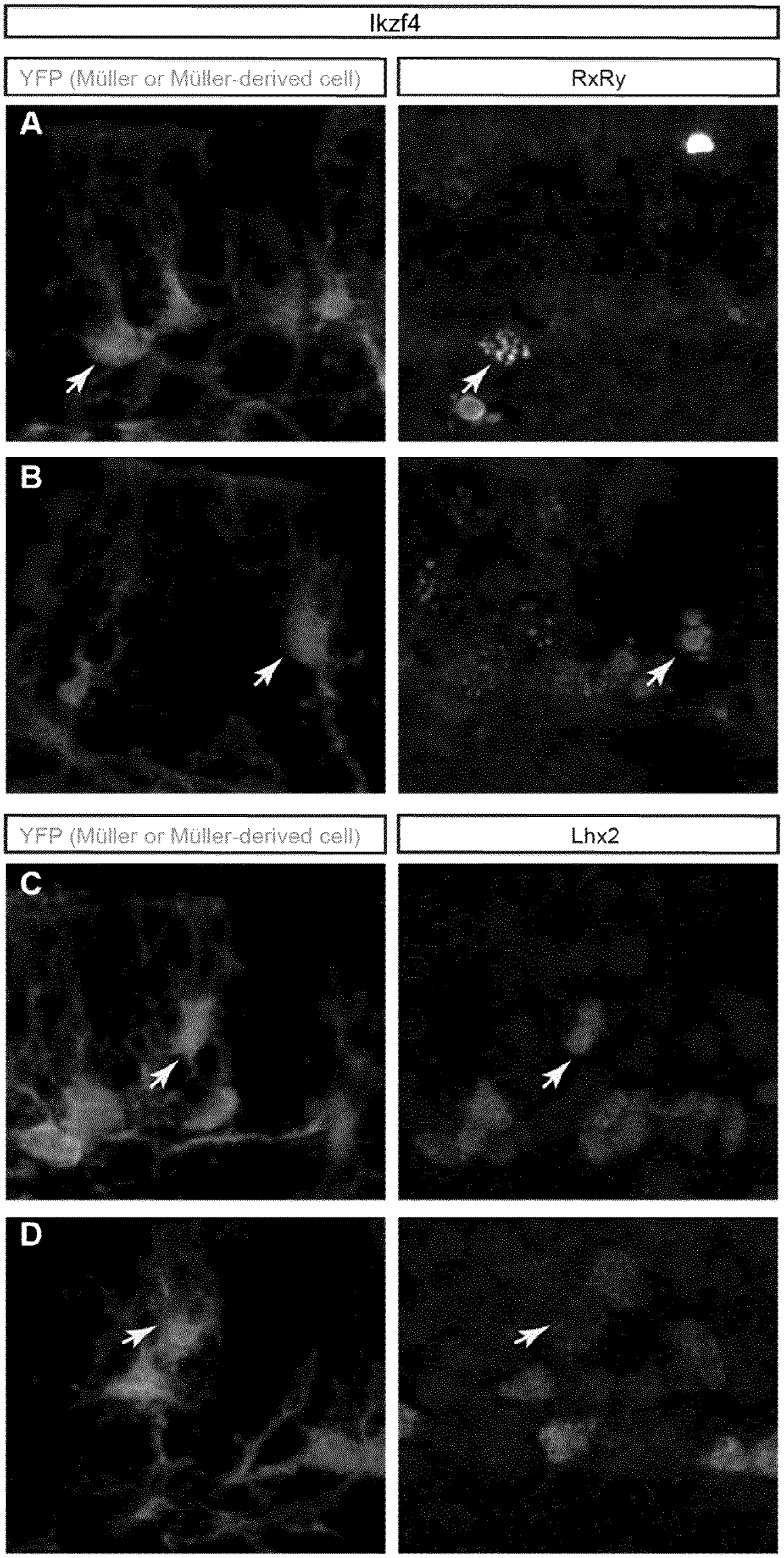

FIG. 7A-B
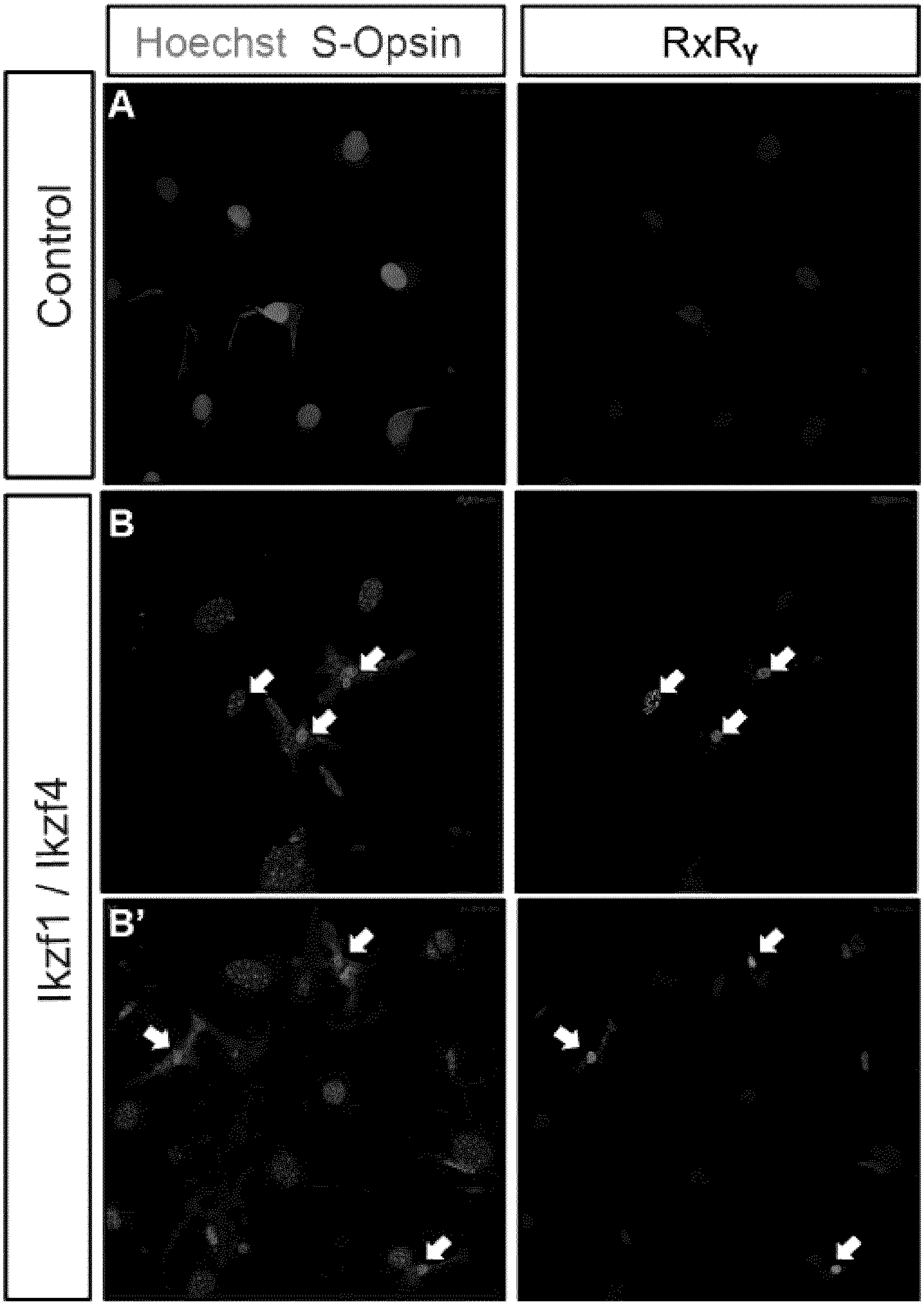

FIGs. 11B-C
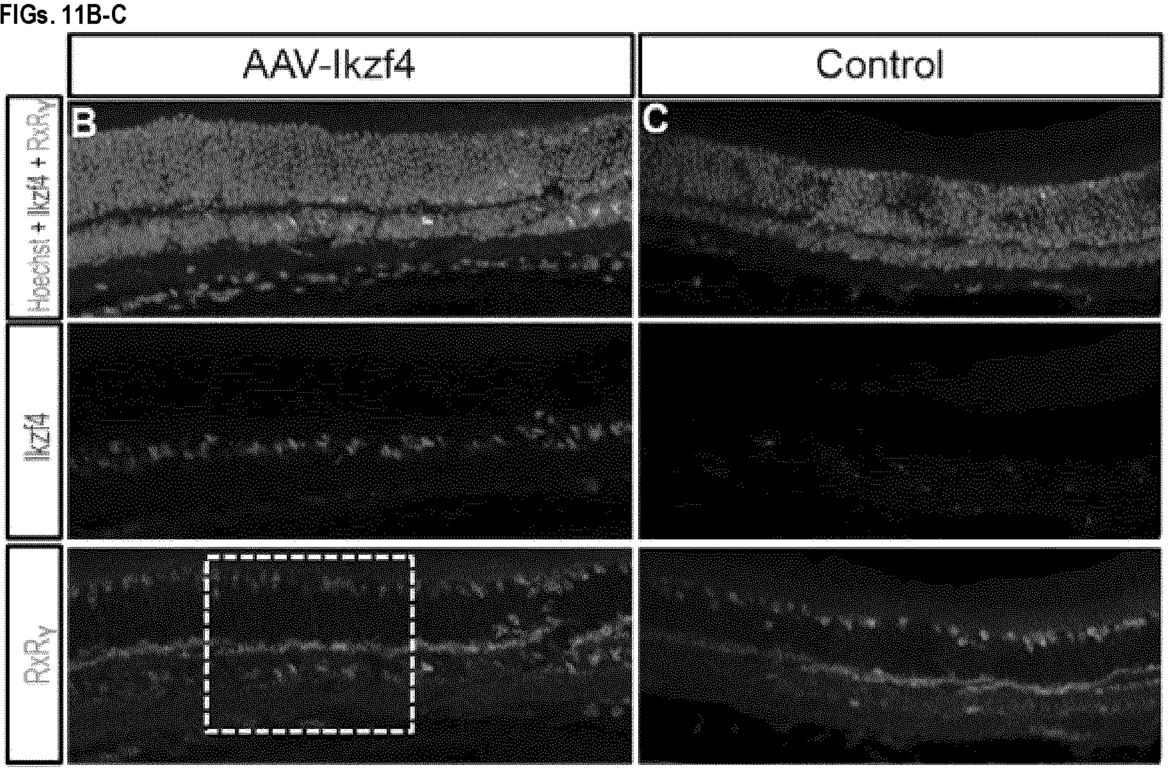
FIGs. 11B'-B'''
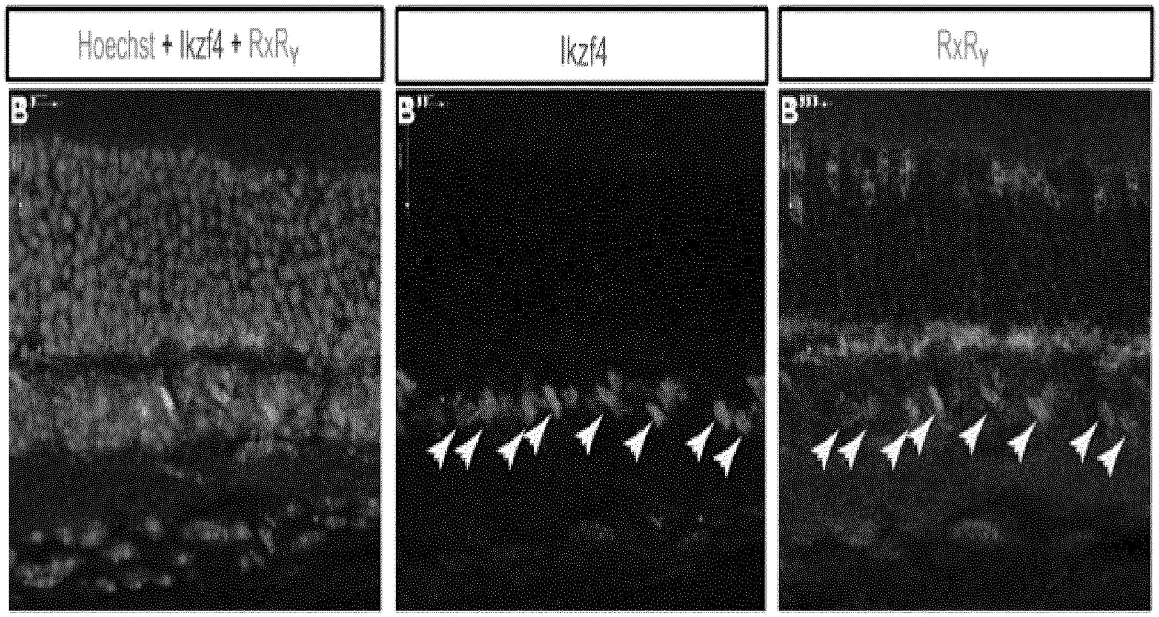

FIG. 12A

IKZF1

Mouse

Proteins

>NP_001020768.1 DNA-binding protein Ikaros 1 isoform a [Mus musculus] (used in examples herein)(SEQ ID NO:1)
MDVDEGQDMSQVSGKESPPVSDTPDEGDEPMPVPEDLSTTSGAQQNSKSDRGMASNVKVETQSDEENGRACEMNGEE
CAEDLRMLDASGEKMNGSHRDQGSSALSGVGGIRLPNGKLKCDICGIVCIGPNVLMVHKRSHTGERPFQCNQCGASF
TQKGNLLRHIKLHSGEKPFKCHLCNYACRRRDALTGHLRTHSVGKPHKCGYCGRSYKQRSSLEEHKERCHNYLESMG
LPGMYPVIKEETNHNEMAEDLCKIGAERSLVLDRLASNVAKRKSSMPQKFLGDKCLSDMPYDSANYEKEDMMTSHVM
DQAINNAINYLGAESLRPLVQTPPGSSEVVPVISSMYQLHKPPSDGPPRSNHSAQDAVDNLLLLSKAKSVSSEREAS
PSNSCQDSTDTESNAEEQRSGLIYLTNHINPHARNGLALKEEQRAYEVLRAASENSQDAFRVVSTSGEQLKVYKCEH
CRVLFLDHVMYTIHMGCHGFRDPFECNMCGYHSQDRYEFSSHITRGEHRYHLS >NP_001288794.1 DNA-binding protein Ikaros 1 isoform b [Mus musculus] (SEQ ID NO: 2)
MDVDEGQDMSQVSGKESPPVSDTPDEGDEPMPVPEDLSTTSGAQQNSKSDRGMGERPFQCNQCGASFTQKGNLLRHI
KLHSGEKPFKCHLCNYACRRRDALTGHLRTHSVGKPHKCGYCGRSYKQRSSLEEHKERCHNYLESMGLPGMYPVIKE
ETNHNEMAEDLCKIGAERSLVLDRLASNVAKRKSSMPQKFLGDKCLSDMPYDSANYEKEDMMTSHVMDQAINNAINY
LGAESLRPLVQTPPGSSEVVPVISSMYQLHKPPSDGPPRSNHSAQDAVDNLLLLSKAKSVSSEREASPSNSCQDSTD
TESNAEEQRSGLIYLTNHINPHARNGLALKEEQRAYEVLRAASENSQDAFRVVSTSGEQLKVYKCEHCRVLFLDHVM
YTIHMGCHGFRDPFECNMCGYHSQDRYEFSSHITRGEHRYHLS >NP_001288795.1 DNA-binding protein Ikaros 1 isoform c [Mus musculus] (SEQ ID NO:3)
MDVDEGQDMSQVSGKESPPVSDTPDEGDEPMPVPEDLSTTSGAQQNSKSDRGMGERPFQCNQCGASFTQKGNLLRHI
KLHSGEKPFKCHLCNYACRRRDALTGHLRTHSVIKEETNHNEMAEDLCKIGAERSLVLDRLASNVAKRKSSMPQKFL
GDKCLSDMPYDSANYEKEDMMTSHVMDQAINNAINYLGAESLRPLVQTPPGSSEVVPVISSMYQLHKPPSDGPPRSN
HSAQDAVDNLLLLSKAKSVSSEREASPSNSCQDSTDTESNAEEQRSGLIYLTNHINPHARNGLALKEEQRAYEVLRA
ASENSQDAFRVVSTSGEQLKVYKCEHCRVLFLDHVMYTIHMGCHGFRDPFECNMCGYHSQDRYEFSSHITRGEHRYH
LS >NP_001288797.1 DNA-binding protein Ikaros isoform d [Mus musculus] (SEQ ID NO:4)
MDVDEGQDMSQVSGKESPPVSDTPDEGDEPMPVPEDLSTTSGAQQNSKSDRGMASNVKVETQSDEENGRACEMNGEE
CAEDLRMLDASGEKMNGSHRDQGSSALSGVGGIRLPNGKLKCDICGIVCIGPNVLMVHKRSHTGERPFQCNQCGASF
TQKGNLLRHIKLHSGEKPFKCHLCNYACRRRDALTGHLRTHSVGKPHKCGYCGRSYKQRSSLEEHKERCHNYLESMG
LPGMYPVIKEETNHNEMAEDLCKIGAERSLVLDRLASNVAKRDKCLSDMPYDSANYEKEDMMTSHVMDQAINNAINY
LGAESLRPLVQTPPGSSEVVPVISSMYQLHKPPSDGPPRSNHSAQDAVDNLLLLSKAKSVSSEREASPSNSCQDSTD
TESNAEEQRSGLIYLTNHINPHARNGLALKEEQRAYEVLRAASENSQDAFRVVSTSGEQLKVYKCEHCRVLFLDHVM
YTIHMGCHGFRDPFECNMCGYHSQDRYEFSSHITRGEHRYHLS >Consensus of mouse Ikzf1 isoforms above (SEQ ID NO:5)
MDVDEGQDMSQVSGKESPPVSDTPDEGDEPMPVPEDLSTTSGAQQNSKSDRGMXXXXXXXXXXXXXXXXXXXXXXXXXXXXXXXXX
XXXXXXXXXXXXXXXXXXXXXXXXXXXXXXXXXXXXXXXXXXXXXXXXXXXXXXGERPFQCNQCGASFTQKGNLLRHIKLHSGEKP
FKCHLCNYACRRRDALTGHLRTHSXXXXXXXXXXXXXXXXXXXXXXXXXXXXXXXXXXXXXXXXXVIKEETNHNEMAEDLCKIGAE
RSLVLDRLASNVAKRXXXXXXXXXXDKCLSDMPYDSANYEKEDMMTSHVMDQAINNAINYLGAESLRPLVQTPPGSSEVVPVISSM
YQLHKPPSDGPPRSNHSAQDAVDNLLLLSKAKSVSSEREASPSNSCQDSTDTESNAEEQRSGLIYLTNHINPHARNGLALKEEQRA
YEVLRAASENSQDAFRVVSTSGEQLKVYKCEHCRVLFLDHVMYTIHMGCHGFRDPFECNMCGYHSQDRYEFSSHITRGEHRYHLS

FIG. 12B

Alignment of mouse Ikzf1 isoforms a to d

```
c      MDVDEGQDMSQVSGKESPPVSDTPDEGDEPMPVPEDLSTTSGAQQNSKSDRGM------- 53
b      MDVDEGQDMSQVSGKESPPVSDTPDEGDEPMPVPEDLSTTSGAQQNSKSDRGM------- 53
a      MDVDEGQDMSQVSGKESPPVSDTPDEGDEPMPVPEDLSTTSGAQQNSKSDRGMASNVKVE 60
d      MDVDEGQDMSQVSGKESPPVSDTPDEGDEPMPVPEDLSTTSGAQQNSKSDRGMASNVKVE 60
       *****************************************************

c      ------------------------------------------------------------ 53
b      ------------------------------------------------------------ 53
a      TQSDEENGRACEMNGEECAEDLRMLDASGEKMNGSHRDQGSSALSGVGGIRLPNGKLKCD 120
d      TQSDEENGRACEMNGEECAEDLRMLDASGEKMNGSHRDQGSSALSGVGGIRLPNGKLKCD 120


c      --------------------GERPFQCNQCGASFTQKGNLLRHIKLHSGEKPFKCHLCNY 93
b      --------------------GERPFQCNQCGASFTQKGNLLRHIKLHSGEKPFKCHLCNY 93
a      ICGIVCIGPNVLMVHKRSHTGERPFQCNQCGASFTQKGNLLRHIKLHSGEKPFKCHLCNY 180
d      ICGIVCIGPNVLMVHKRSHTGERPFQCNQCGASFTQKGNLLRHIKLHSGEKPFKCHLCNY 180
       ****************************************

c      ACRRRDALTGHLRTHS-----------------------------------------VIK 112
b      ACRRRDALTGHLRTHSVGKPHKCGYCGRSYKQRSSLEEHKERCHNYLESMGLPGMYPVIK 153
a      ACRRRDALTGHLRTHSVGKPHKCGYCGRSYKQRSSLEEHKERCHNYLESMGLPGMYPVIK 240
d      ACRRRDALTGHLRTHSVGKPHKCGYCGRSYKQRSSLEEHKERCHNYLESMGLPGMYPVIK 240
       ****************                                         ***

c      EETNHNEMAEDLCKIGAERSLVLDRLASNVAKRKSSMPQKFLGDKCLSDMPYDSANYEKE 172
b      EETNHNEMAEDLCKIGAERSLVLDRLASNVAKRKSSMPQKFLGDKCLSDMPYDSANYEKE 213
a      EETNHNEMAEDLCKIGAERSLVLDRLASNVAKRKSSMPQKFLGDKCLSDMPYDSANYEKE 300
d      EETNHNEMAEDLCKIGAERSLVLDRLASNVAKR----------DKCLSDMPYDSANYEKE 290
       *********************************          *****************

c      DMMTSHVMDQAINNAINYLGAESLRPLVQTPPGSSEVVPVISSMYQLHKPPSDGPPRSNH 232
b      DMMTSHVMDQAINNAINYLGAESLRPLVQTPPGSSEVVPVISSMYQLHKPPSDGPPRSNH 273
a      DMMTSHVMDQAINNAINYLGAESLRPLVQTPPGSSEVVPVISSMYQLHKPPSDGPPRSNH 360
d      DMMTSHVMDQAINNAINYLGAESLRPLVQTPPGSSEVVPVISSMYQLHKPPSDGPPRSNH 350
       ************************************************************

c      SAQDAVDNLLLLSKAKSVSSEREASPSNSCQDSTDTESNAEEQRSGLIYLTNHINPHARN 292
b      SAQDAVDNLLLLSKAKSVSSEREASPSNSCQDSTDTESNAEEQRSGLIYLTNHINPHARN 333
a      SAQDAVDNLLLLSKAKSVSSEREASPSNSCQDSTDTESNAEEQRSGLIYLTNHINPHARN 420
d      SAQDAVDNLLLLSKAKSVSSEREASPSNSCQDSTDTESNAEEQRSGLIYLTNHINPHARN 410
       ************************************************************

c      GLALKEEQRAYEVLRAASENSQDAFRVVSTSGEQLKVYKCEHCRVLFLDHVMYTIHMGCH 352
b      GLALKEEQRAYEVLRAASENSQDAFRVVSTSGEQLKVYKCEHCRVLFLDHVMYTIHMGCH 393
a      GLALKEEQRAYEVLRAASENSQDAFRVVSTSGEQLKVYKCEHCRVLFLDHVMYTIHMGCH 480
d      GLALKEEQRAYEVLRAASENSQDAFRVVSTSGEQLKVYKCEHCRVLFLDHVMYTIHMGCH 470
       ************************************************************

c      GFRDPFECNMCGYHSQDRYEFSSHITRGEHRYHLS 387
b      GFRDPFECNMCGYHSQDRYEFSSHITRGEHRYHLS 428
a      GFRDPFECNMCGYHSQDRYEFSSHITRGEHRYHLS 515
d      GFRDPFECNMCGYHSQDRYEFSSHITRGEHRYHLS 505
       ***********************************
```

FIG. 12C

Nucleic acids

>NM_001025597.2 Mus musculus IKAROS family zinc finger 1 (Ikzf1), transcript variant 1, mRNA (CDS shown bolded (corresponds to Ikzf1 mus musculus transcript variant X3 below, untranslated shown highlighted in grey; stop codon underlined) (SEQ ID NO: 6)

GTCAGGGTCCCGAAGCCGCGTGCCGTGCGCGCAGGCCGGGTGGGCTGTGGGACAAGCCGAGCGGGAGGCGAGTCGCA
AGCGCCAACCCAAAGTTTGCACGGTGCGGGGCGAGGGGCGCGCGCTCCGGGCTGCCGCAGGTGGCGGCGCGGTGAGC
CCGGGCCAGGTGCCCCGGCAGCGGGGCGGCGCTGTCGTGCGGGACAGCCGGGCTGCCAGGGGCTCGGAGCCGGGTCG
GAGCCCGCGGGGGGCGGGGAGTGTGGCGAGAAATGGGGAACAATGCGAGTGAGCAACTTGAGGAAGTCATTGTGAAA
GAAAGCTGGGAATTGCTCCGCAGCCAACTTAGCAGGGCACTCTAACAAGTGCCTGCGCGGCCGCGCCCGGGCCGGGG
ACAGGGGCAGCCCGGCGCAGTACAGCCCATCCCGGGACGCTCGGCCGCGGCTGCCGGAGACCCGGTAGGTCCCGCGG
GGTGCAGGAGCCCCCAGATCCCCGGCTGCTCTTCGCGCCCCAGGATCATTCTTGGCCCCCAAAGCGCGGCGCACAAA
TCCACATAACCTGAAGACAATGGATGTCGATGAGGGTCAAGACATGTCCCAAGTTTCAGGAAAGGAGAGCCCCCCAG
TCAGTGACACTCCAGATGAAGGGGATGAGCCCATGCCTGTCCCTGAGGACCTGTCCACTACCTCTGGAGCACAGCAG
AACTCCAAGAGTGATCGAGGCATGGCCAGTAATGTTAAAGTAGAGACTCAGAGTGATGAAGAGAATGGGCGTGCCTG
TGAAATGAATGGGGAAGAATGTGCAGAGGATTTACGAATGCTTGATGCCTCGGGAGAGAAAATGAATGGCTCCCACA
GGGACCAAGGCAGCTCGGCTTTGTCAGGAGTTGGAGGCATTCGACTTCCTAACGGAAAACTAAAGTGTGATATCTGT
GGGATCGTTTGCATCGGGCCCAATGTGCTCATGGTTCACAAAAGAAGTCATACTGGTGAACGGCCTTTCCAGTGCAA
CCAGTGTGGGGCCTCCTTTACCCAGAAAGGCAACCTCCTGCGGCACATCAAGCTGCACTCGGGTGAGAAGCCCTTCA
AATGCCATCTTTGCAACTATGCCTGCCGCCGGAGGGACGCCCTCACCGGCCACCTGAGGACGCACTCCGTTGGTAAG
CCTCACAAATGTGGATATTGTGGCCGGAGCTATAAACAGCGAAGCTCTTTAGAGGAGCATAAAGAGCGATGCCACAA
CTACTTGGAAAGCATGGGCCTTCCGGGCATGTACCCAGTCATTAAGGAAGAAACTAACCACAACGAGATGGCAGAAG
ACCTGTGCAAGATAGGAGCAGAGAGGTCCCTTGTCCTGGACAGGCTGGCAAGCAATGTCGCCAAACGTAAGAGCTCT
ATGCCTCAGAAATTTCTTGGAGACAAGTGCCTGTCAGACATGCCCTATGACAGTGCCAACTATGAGAAGGAGGATAT
GATGACATCCCACGTGATGGACCAGGCCATCAACAATGCCATCAACTACCTGGGGGCTGAGTCCCTGCGCCCATTGG
TGCAGACACCCCCCGGTAGCTCCGAGGTGGTGCCAGTCATCAGCTCCATGTACCAGCTGCACAAGCCCCCCTCAGAT
GGCCCCCCACGGTCCAACCATTCAGCACAGGACGCCGTGGATAACTTGCTGCTGCTGTCCAAGGCCAAGTCTGTGTC
ATCGGAGCGAGAGGCCTCCCCGAGCAACAGCTGCCAAGACTCCACAGATACAGAGAGCAACGCGGAGGAACAGCGCA
GCGGCCTTATCTACCTAACCAACCACATCAACCCGCATGCACGCAATGGGCTGGCTCTCAAGGAGGAGCAGCGCGCC
TACGAGGTGCTGAGGGCGGCCTCAGAGAACTCGCAGGATGCCTTCCGTGTGGTCAGCACGAGTGGCGAGCAGCTGAA
GGTGTACAAGTGCGAACACTGCCGCGTGCTCTTCCTGGATCACGTCATGTATACCATTCACATGGGCTGCCATGGCT
TTCGGGATCCCTTTGAGTGTAACATGTGTGGTTATCACAGCCAGGACAGGTACGAGTTCTCATCCCATATCACGCGG
GGGGAGCATCGTTACCACCTGAGCTAAACCCAGCCAGGCCCCACTGAAGCACAAAGATAGCTGGTTATGCCTCCTTC
CCGGCAGCTGGACCCACAGCGGACAATGTTGGGAGTGGATTTGCAGGCAGCATTTGTTCTTTTATGTTGGTTGTTTG
GCGTTTGATTTGCGTTGGAAGATAAGTTTTTAATGTTAGTGACAGGATTGCATTGCATCAGGAACATTCACAACATC
CATCCTTCTAGCCAGTTTTGTTCACTGGTAGCTGAGGTTTCCCGGATATGTGGCTTCCTAACACTCTCCCCACCCAC
CCCACCCCCCAAAACAGAGCCTGAATCTTCATGAAGTGAATAAAACAATTATCCAAGAAGGAGTAAGGTGGATCTTG
CCCTAAGCAGAGTTTATGCCACAAAGATTCTCCAAATCCCCCAAGACAGCACAGCCACTGGGGTTGAGCCATCTCAG
GGAGCTCTGCAGGTGAGCCAGAGGACCAGATATAAGGCAGCTGGGGAGGAGCAGGGACATCAGCCTGTGCAGAGACC
AAGGCCAAAGGTTGAACTTTGAAAGACTATTAAGTCATATATTGTATGGCAATATGGTGTCTGGACAAGTTGTGCAA
TGTGCTGAAGGGAAGGGATTGGAGAGCCTTGAAGACTCTTCTTCATTTGCCTGATCAACCCGACCTCCAGAGGGTTT
GTTGCCCAGTAAGACGAGCTCAGTGCTCTTGTGATCATTTTTCTCTTATCGTTTCCATGCCGTTGATGGCCCTGAAG
CTCATCACTGCATTTTAGAACCCAATCCTGAAATTGGGACCTTTTTTTTAAACTTCTGATACTGTAAAACTTCTTGG
AAGCCAAAGCTTTCTTCCAAGCCCCATCCTCAGTTATCCTGGTTCCTGTTCTTCCCCGAGCTGATAGTACCAGGACC
TGTTATTCCACAAAAGCACAGGCATCCGTCACTTCAATTCAATCCCTGTTCAGATTATAGATATGGACTTTGCTATC
TTGATAAATGTCTTCTCTATGTTATTTTGTCTGAAAAACCTATAAAACCATTATTAAGAATGACCATTTTTAGATGG
AAGAAATGAGCCCAGCATCTCAGTGGCTAAAACACAAAATATCCATGCTTTTAAACAAAATTGTTAAATATTCCGAA
GCTCTCTAGTATAAACACCAAGTAGCATGTGTTTTCACATAAAGAAGACAGGGGCCATGCAACCTTTATCAAGTGGA
GGTATTAGAATGTTGTAATGTTTGGAGACACAGTGTGACCAGTACAGGTTCCCAGAGAGGAATGCCCACCATATCAC
AGAAAGGTAGAGGTGGGATCTGGTATAGCCAGACCAAGACAGGGATGTCACGCTGAAGCCAAGTCAGTTAGCTGAAG
ATTCTCAACAGGAAGGCCTCTCTTAAGAGTCAGTAATAGGGTTGTTACCATCCACCACCTCAACAAAACAAAAAGCT
TATAATTGTAAATGTTTACAGCACTGTCTTCGCAGAAACTTTCTGAGGTGATTCCAAAGAACTAGAGGGGAGATGGT
CTATAACAGCTCTTGAAGTAAACGAGGTTCTTAGTCTCAGCTCTCCTGACATATAGGGCTTGATCATTACTGGTAGG
GATTGTTCTGTGAATTGCTTACTACTACCCCTGGTCTCTCCCCAGTAGATGCCAGGAACATTCTAGCTGATACCTAA
CTGTCTTCCCAGGTGTTCGAGGGAGCAAACCACTGATCTAAACTCTAAACGCTGAAGTACGCAGGTTTTCTAAAAAT
GACAAGCCCTTGAAACCTTTCCCAGTAGGCAGCCTCGAGCTGGACTTGTGTCTTTGGAATGCTGATGAATTCTATAG
ATCAGCATTGCAAATACACTTCAAATACGTCTGAGTTCAAGTGCAGGGACTGAGTTCACCAAGGTGTGAAATGTGCT
CAAAAAGTTCAAAA

FIG. 12D

GTGTGTGTTTCTTTGTTTCTAAAACATTGTGGCATCTTTTTCATTTGTTTCTAAAACTTTTTTTTTAGAAACAAATG
AAGCACTTGGAAAGTGAAAGTAAAATTACAAATATAAGGATTTACACTGAAGAGAGAAAAATTTTAGGAACTATAGC
TGTGAAAAGATTTTGTTCAAAAGGCAGGCTAGCCTTACCCAAATTCATATATGGCAGGTGTCAACCTCCCAAGCTTA
CAGTTAGCAGGCAGCTTTTGCTCACTCATCCTTAGCCATGAGAGCCATTAAGTGTGGTCCAAGAAAGATGGCTCCAA
ACCCTACCCCCGACCCACCAGTGGTATTCAGAGATTAAAGCAGAATTGTAAATAGTGGCTTCAGGAGCTCTTTTTTA
GAATGCTTTGCCCCTTCCTCTCACTGCCTTTTTTAGCCAATATAAATGTCAATTTGCACACCTTTTGTTGTGGTTTT
ATATTGTAACAGCATTTTTTTGAAACTATTGTATTTAAGATAAGGTTTCATATTATGTCCACAAGTAATTAAATTAT
GTTTGAAGGTGGCTATATGCTGTATCAGAAGTTGATGATGTTTTTCTTTAGCTGGTAAAGGAGGGTTTTGCATGACC
TCACTGTTTGTTCTGTGGTTTGTTCTGTTGTATGATGTGTGTCTTGAGTTTTGCTGTGTGATGAAGTGCGCTGAGAT
TCCAGTGCCCTCAAGTTGTGTTTTAAGTAGCTATCAGAGGCAAGAGGGTTCCTAAGAGCAGGTTGACCTGTTGGCGA
CAGATGGCAATCACCATTTCTCATTCCTTCTTCTCCCTGTTACCCCAGCTTCCTGTCCCAGGTCCCTTCTGTGATTC
TTACCTTAGTGTGCATGTGTGTCTGTCCTGGTGAGAGTCAGGAGCATCGATATGTTATCATTGCATTATCACCAAGG
GCACGCACAGCCTAGCACCTGTTGCTTCAGATACCGTCACACTCTGTTTCCAATTTAGATACAACCACATAATAAAA
TGTTAGAGTCTTCAATGGGAAGCAGAGGTGCTTGTTATAAAGATGGGGGCTTATGCTTGTGTCACATTTTGTGTTCT
TTTCTTCTTTTGTTTGGTTTTAACTTAATTGTGACCCTTGTAACATCATCTTGCCAAAAAAAAAAAAAAAAGTTGAAC
TGGATTTATGTAGACATGTCAAGACGTACTATCTATTTCTTTGTCAGTTATAGCAATAAGAGTGGATAAACTCTAAA
ATCCAGATCTCCCACAATGAACATCCGTGTTCTTTCTATGATTTTTCTTTCTTTATGGTGAGCCACAATTAAACTTG
AGATGTACAGCCACCCAAACCCAGGAAGCTCATGTGCATCTGGTGCTATGGCACTCACTGTGAATAAGTGTGACCAG
ATATTAATATGCAATATTGTTTCCAATCCTTTCTAATACATTTTTTC

> Ikzf1 Mus musculus IKAROS family zinc finger 1 (Ikzf1, transcript variant X3, mRNA (used in examples herein; stop codon underlined) (SEQ ID NO: 7)

ATGGATGTCGATGAGGGTCAAGACATGTCCCAAGTTTCAGGAAAGGAGAGCCCCCCAGTCAGTGACACTCCAGATGAAGGG
GATGAGCCCATGCCTGTCCCTGAGGACCTGTCCACTACCTCTGGAGCACAGCAGAACTCCAAGAGTGATCGAGGCATGGCCA
GTAATGTTAAAGTAGAGACTCAGAGTGATGAAGAGAATGGGCGTGCCTGTGAAATGAATGGGGAAGAATGTGCAGAGGATT
TACGAATGCTTGATGCCTCGGGAGAGAAAATGAATGGCTCCCACAGGGACCAAGGCAGCTCGGCTTTGTCAGGAGTTGGAG
GCATTCGACTTCCTAACGGAAAACTAAAGTGTGATATCTGTGGGATCGTTTGCATCGGGCCCAATGTGCTCATGGTTCACAAA
AGAAGTCATACTGGTGAACGGCCTTTCCAGTGCAACCAGTGTGGGGCCTCCTTTACCCAGAAAGGCAACCTCCTGCGGCACAT
CAAGCTGCACTCGGGTGAGAAGCCCTTCAAATGCCATCTTTGCAACTATGCCTGCCGCCGGAGGGACGCCCTCACCGGCCACC
TGAGGACGCACTCCGTTGGTAAGCCTCACAAATGTGGATATTGTGGCCGGAGCTATAAACAGCGAAGCTCTTTAGAGGAGCA
TAAAGAGCGATGCCACAACTACTTGGAAAGCATGGGCCTTCCGGGCATGTACCCAGTCATTAAGGAAGAAACTAACCACAAC
GAGATGGCAGAAGACCTGTGCAAGATAGGAGCAGAGAGGTCCCTTGTCCTGGACAGGCTGGCAAGCAATGTCGCCAAACGT
AAGAGCTCTATGCCTCAGAAATTTCTTGGAGACAAGTGCCTGTCAGACATGCCCTATGACAGTGCCAACTATGAGAAGGAGG
ATATGATGACATCCCACGTGATGGACCAGGCCATCAACAATGCCATCAACTACCTGGGGGCTGAGTCCCTGCGCCCATTGGTG
CAGACACCCCCCGGTAGCTCCGAGGTGGTGCCAGTCATCAGCTCCATGTACCAGCTGCACAAGCCCCCCTCAGATGGCCCCCC
ACGGTCCAACCATTCAGCACAGGACGCCGTGGATAACTTGCTGCTGCTGTCCAAGGCCAAGTCTGTGTCATCGGAGCGAGAG
GCCTCCCCGAGCAACAGCTGCCAAGACTCCACAGATACAGAGAGCAACGCGGAGGAACAGCGCAGCGGCCTTATCTACCTAA
CCAACCACATCAACCCGCATGCACGCAATGGGCTGGCTCTCAAGGAGGAGCAGCGCGCCTACGAGGTGCTGAGGGCGGCCT
CAGAGAACTCGCAGGATGCCTTCCGTGTGGTCAGCACGAGTGGCGAGCAGCTGAAGGTGTACAAGTGCGAACACTGCCGCG
TGCTCTTCCTGGATCACGTCATGTATACCATTCACATGGGCTGCCATGGCTTTCGGGATCCCTTTGAGTGTAACATGTGTGGTT
ATCACAGCCAGGACAGGTACGAGTTCTCATCCCATATCACGCGGGGGGAGCATCGTTACCACCTGAGCTAA

FIG. 12E

>NM_001301865.1 Mus musculus IKAROS family zinc finger 1 (Ikzf1), transcript variant 4, mRNA (SEQ ID NO: 8)
TGGAGACTGGTTCTACCTTTCTCTGAACCCCAGTGGTGTGTGAAGGCCGGACTGGGAGCTTGGGGGAAGAGGAAGAG
GAAGAGGAATCTGCGGCTCATCCAGGGATCAGGGTCCTTCCCAAGTGGCCACTCAGAGGGGACTCAGAGCAAGTCTA
GATTTGTGTGGCAGAGAGAGACAGCTCTCGTTTGGCCTTGGGGAGGCACAAGTCTGTTGATAACCTGAAGACAATGG
ATGTCGATGAGGGTCAAGACATGTCCCAAGTTTCAGGAAAGGAGAGCCCCCCAGTCAGTGACACTCCAGATGAAGGG
GATGAGCCCATGCCTGTCCCTGAGGACCTGTCCACTACCTCTGGAGCACAGCAGAACTCCAAGAGTGATCGAGGCAT
GGGTGAACGGCCTTTCCAGTGCAACCAGTGTGGGGCCTCCTTTACCCAGAAAGGCAACCTCCTGCGGCACATCAAGC
TGCACTCGGGTGAGAAGCCCTTCAAATGCCATCTTTGCAACTATGCCTGCCGCCGGAGGGACGCCCTCACCGGCCAC
CTGAGGACGCACTCCGTTGGTAAGCCTCACAAATGTGGATATTGTGGCCGGAGCTATAAACAGCGAAGCTCTTTAGA
GGAGCATAAAGAGCGATGCCACAACTACTTGGAAAGCATGGGCCTTCCGGGCATGTACCCAGTCATTAAGGAAGAAA
CTAACCACAACGAGATGGCAGAAGACCTGTGCAAGATAGGAGCAGAGAGGTCCCTTGTCCTGGACAGGCTGGCAAGC
AATGTCGCCAAACGTAAGAGCTCTATGCCTCAGAAATTTCTTGGAGACAAGTGCCTGTCAGACATGCCCTATGACAG
TGCCAACTATGAGAAGGAGGATATGATGACATCCCACGTGATGGACCAGGCCATCAACAATGCCATCAACTACCTGG
GGGCTGAGTCCCTGCGCCCATTGGTGCAGACACCCCCCGGTAGCTCCGAGGTGGTGCCAGTCATCAGCTCCATGTAC
CAGCTGCACAAGCCCCCCTCAGATGGCCCCCCACGGTCCAACCATTCAGCACAGGACGCCGTGGATAACTTGCTGCT
GCTGTCCAAGGCCAAGTCTGTGTCATCGGAGCGAGAGGCCTCCCCGAGCAACAGCTGCCAAGACTCCACAGATACAG
AGAGCAACGCGGAGGAACAGCGCAGCGGCCTTATCTACCTAACCAACCACATCAACCCGCATGCACGCAATGGGCTG
GCTCTCAAGGAGGAGCAGCGCGCCTACGAGGTGCTGAGGGCGGCCTCAGAGAACTCGCAGGATGCCTTCCGTGTGGT
CAGCACGAGTGGCGAGCAGCTGAAGGTGTACAAGTGCGAACACTGCCGCGTGCTCTTCCTGGATCACGTCATGTATA
CCATTCACATGGGCTGCCATGGCTTTCGGGATCCCTTTGAGTGTAACATGTGTGGTTATCACAGCCAGGACAGGTAC
GAGTTCTCATCCCATATCACGCGGGGGGAGCATCGTTACCACCTGAGCTAAACCCAGCCAGGCCCCACTGAAGCACA
AAGATAGCTGGTTATGCCTCCTTCCCGGCAGCTGGACCCACAGCGGACAATGTTGGGAGTGGATTTGCAGGCAGCAT
TTGTTCTTTTATGTTGGTTGTTTGGCGTTTGATTTGCGTTGGAAGATAAGTTTTTAATGTTAGTGACAGGATTGCAT
TGCATCAGGAACATTCACAACATCCATCCTTCTAGCCAGTTTTGTTCACTGGTAGCTGAGGTTTCCCGGATATGTGG
CTTCCTAACACTCTCCCCACCCACCCCACCCCCCAAAACAGAGCCTGAATCTTCATGAAGTGAATAAAACAATTATC
CAAGAAGGAGTAAGGTGGATCTTGCCCTAAGCAGAGTTTATGCCACAAAGATTCTCCAAATCCCCCAAGACAGCACA
GCCACTGGGGTTGAGCCATCTCAGGGAGCTCTGCAGGTGAGCCAGAGGACCAGATATAAGGCAGCTGGGGAGGAGCA
GGGACATCAGCCTGTGCAGAGACCAAGGCCAAAGGTTGAACTTTGAAAGACTATTAAGTCATATATTGTATGGCAAT
ATGGTGTCTGGACAAGTTGTGCAATGTGCTGAAGGGAAGGGATTGGAGAGCCTTGAAGACTCTTCTTCATTTGCCTG
ATCAACCCGACCTCCAGAGGGTTTGTTGCCCAGTAAGACGAGCTCAGTGCTCTTGTGATCATTTTTCTCTTATCGTT
TCCATGCCGTTGATGGCCCTGAAGCTCATCACTGCATTTTAGAACCCAATCCTGAAATTGGGACCTTTTTTTTAAAC
TTCTGATACTGTAAAACTTCTTGGAAGCCAAAGCTTTCTTCCAAGCCCCATCCTCAGTTATCCTGGTTCCTGTTCTT
CCCCGAGCTGATAGTACCAGGACCTGTTATTCCACAAAAGCACAGGCATCCGTCACTTCAATTCAATCCCTGTTCAG
ATTATAGATATGGACTTTGCTATCTTGATAAATGTCTTCTCTATGTTATTTTGTCTGAAAAACCTATAAAACCATTA
TTAAGAATGACCATTTTTAGATGGAAGAAATGAGCCCAGCATCTCAGTGGCTAAAACACAAAATATCCATGCTTTTA
AACAAAATTGTTAAATATTCCGAAGCTCTCTAGTATAAACACCAAGTAGCATGTGTTTTCACATAAAGAAGACAGGG
GCCATGCAACCTTTATCAAGTGGAGGTATTAGAATGTTGTAATGTTTGGAGACACAGTGTGACCAGTACAGGTTCCC
AGAGAGGAATGCCCACCATATCACAGAAAGGTAGAGGTGGGATCTGGTATAGCCAGACCAAGACAGGGATGTCACGC
TGAAGCCAAGTCAGTTAGCTGAAGATTCTCAACAGGAAGGCCTCTCTTAAGAGTCAGTAATAGGGTTGTTACCATCC
ACCACCTCAACAAAACAAAAAGCTTATAATTGTAAATGTTTACAGCACTGTCTTCGCAGAAACTTTCTGAGGTGATT
CCAAAGAACTAGAGGGGAGATGGTCTATAACAGCTCTTGAAGTAAACGAGGTTCTTAGTCTCAGCTCTCCTGACATA
TAGGGCTTGATCATTACTGGTAGGGATTGTTCTGTGAATTGCTTACTACTACCCCTGGTCTCTCCCCAGTAGATGCC
AGGAACATTCTAGCTGATACCTAACTGTCTTCCCAGGTGTTCGAGGGAGCAAACCACTGATCTAAACTCTAAACGCT
GAAGTACGCAGGTTTTCTAAAAATGACAAGCCCTTGAAACCTTTCCCAGTAGGCAGCCTCGAGCTGGACTTGTGTCT
TTGGAATGCTGATGAATTCTATAGATCAGCATTGCAAATACACTTCAAATACGTCTGAGTTCAAGTGCAGGGACTGA
GTTCACCAAGGTGTGAAATGTGCTCAAAAAGTTCAAAAGTGTGTGTTTCTTTGTTTCTAAAACATTGTGGCATCTTT
TTCATTTGTTTCTAAAACTTTTTTTTTAGAAACAAATGAAGCACTTGGAAAGTGAAAGTAAAATTACAAATATAAGG
ATTTACACTGAAGAGAGAAAAATTTTAGGAACTATAGCTGTGAAAAGATTTTGTTCAAAAGGCAGGCTAGCCTTACC
CAAATTCATATATGGCAGGTGTCAACCTCCCAAGCTTACAGTTAGCAGGCAGCTTTTGCTCACTCATCCTTAGCCAT
GAGAGCCATTAAGTGTGGTCCAAGAAAGATGGCTCCAAACCCTACCCCCGACCCACCAGTGGTATTCAGAGATTAAA
GCAGAATTGTAAATAGTGGCTTCAGGAGCTCTTTTTTAGAATGCTTTGCCCCTTCCTCTCACTGCCTTTTTTAGCCA
ATATAAATGTCAATTTGCACACCTTTTGTTGTGGTTTTATATTGTAACAGCATTTTTTTGAAACTATTGTATTTAAG
ATAAGGTTTCATATTATGTCCACAAGTAATTAAATTATGTTTGAAGGTGGCTATATGCTGTATCAGAAGTTGATGAT
GTTTTTCTTTAGCTGGTAAAGGAGGGTTTTGCATGACCTCACTGTTTGTTCTGTGGTTTGTTCTGTTGTATGATGTG
TGTCTTGAGTTTTGCTGTGTGATGAAGTGCGCTGAGATTCCAGTGCCCTCAAGTTGTGTTTTAAGTAGCTATCAGAG
GCAAGAGGGTTCCTAAGAGCAGGTTGACCTGTTGGCGACAGATGGCAATCACCATTTCTCATTCCTTCTTCTCCCTG
TTACCCCAGCTTCCTGTCCCAGGTCCCTTCTGTGATTCTTACCTTAGTGTGCATGTGTGTCTGTCCTGGTGAGAGTC
AGGAGCATCGATATGTTATCATTGCATTATCACC

FIG. 12F

AAGGGCACGCACAGCCTAGCACCTGTTGCTTCAGATACCGTCACACTCTGTTTCCAATTTAGATACAACCACATAAT
AAAATGTTAGAGTCTTCAATGGGAAGCAGAGGTGCTTGTTATAAAGATGGGGGCTTATGCTTGTGTCACATTTTGTG
TTCTTTTCTTCTTTTGTTTGGTTTTAACTTAATTGTGACCCTTGTAACATCATCTTGCCAAAAAAAAAAAAAAAGTT
GAACTGGATTTATGTAGACATGTCAAGACGTACTATCTATTTCTTTGTCAGTTATAGCAATAAGAGTGGATAAACTC
TAAAATCCAGATCTCCCACAATGAACATCCGTGTTCTTTCTATGATTTTTCTTTCTTTATGGTGAGCCACAATTAAA
CTTGAGATGTACAGCCACCCAAACCCAGGAAGCTCATGTGCATCTGGTGCTATGGCACTCACTGTGAATAAGTGTGA
CCAGATATTAATATGCAATATTGTTTCCAATCCTTTCTAATACATTTTTTC

>NM_001301866.1 Mus musculus IKAROS family zinc finger 1 (Ikzf1), transcript variant 5, mRNA (SEQ ID NO: 9)
TGGAGACTGGTTCTACCTTTCTCTGAACCCCAGTGGTGTGTGAAGGCCGGACTGGGAGCTTGGGGGAAGAGGAAGAG
GAAGAGGAATCTGCGGCTCATCCAGGGATCAGGGTCCTTCCCAAGTGGCCACTCAGAGGGGACTCAGAGCAAGTCTA
GATTTGTGTGGCAGAGAGAGACAGCTCTCGTTTGGCCTTGGGGAGGCACAAGTCTGTTGATAACCTGAAGACAATGG
ATGTCGATGAGGGTCAAGACATGTCCCAAGTTTCAGGAAAGGAGAGCCCCCCAGTCAGTGACACTCCAGATGAAGGG
GATGAGCCCATGCCTGTCCCTGAGGACCTGTCCACTACCTCTGGAGCACAGCAGAACTCCAAGAGTGATCGAGGCAT
GGGTGAACGGCCTTTCCAGTGCAACCAGTGTGGGGCCTCCTTTACCCAGAAAGGCAACCTCCTGCGGCACATCAAGC
TGCACTCGGGTGAGAAGCCCTTCAAATGCCATCTTTGCAACTATGCCTGCCGCCGGAGGGACGCCCTCACCGGCCAC
CTGAGGACGCACTCCGTCATTAAGGAAGAAACTAACCACAACGAGATGGCAGAAGACCTGTGCAAGATAGGAGCAGA
GAGGTCCCTTGTCCTGGACAGGCTGGCAAGCAATGTCGCCAAACGTAAGAGCTCTATGCCTCAGAAATTTCTTGGAG
ACAAGTGCCTGTCAGACATGCCCTATGACAGTGCCAACTATGAGAAGGAGGATATGATGACATCCCACGTGATGGAC
CAGGCCATCAACAATGCCATCAACTACCTGGGGGCTGAGTCCCTGCGCCCATTGGTGCAGACACCCCCCGGTAGCTC
CGAGGTGGTGCCAGTCATCAGCTCCATGTACCAGCTGCACAAGCCCCCCTCAGATGGCCCCCCACGGTCCAACCATT
CAGCACAGGACGCCGTGGATAACTTGCTGCTGCTGTCCAAGGCCAAGTCTGTGTCATCGGAGCGAGAGGCCTCCCCG
AGCAACAGCTGCCAAGACTCCACAGATACAGAGAGCAACGCGGAGGAACAGCGCAGCGGCCTTATCTACCTAACCAA
CCACATCAACCCGCATGCACGCAATGGGCTGGCTCTCAAGGAGGAGCAGCGCGCCTACGAGGTGCTGAGGGCGGCCT
CAGAGAACTCGCAGGATGCCTTCCGTGTGGTCAGCACGAGTGGCGAGCAGCTGAAGGTGTACAAGTGCGAACACTGC
CGCGTGCTCTTCCTGGATCACGTCATGTATACCATTCACATGGGCTGCCATGGCTTTCGGGATCCCTTTGAGTGTAA
CATGTGTGGTTATCACAGCCAGGACAGGTACGAGTTCTCATCCCATATCACGCGGGGGGAGCATCGTTACCACCTGA
GCTAAACCCAGCCAGGCCCCACTGAAGCACAAAGATAGCTGGTTATGCCTCCTTCCCGGCAGCTGGACCCACAGCGG
ACAATGTTGGGAGTGGATTTGCAGGCAGCATTTGTTCTTTTATGTTGGTTGTTTGGCGTTTGATTTGCGTTGGAAGA
TAAGTTTTTAATGTTAGTGACAGGATTGCATTGCATCAGGAACATTCACAACATCCATCCTTCTAGCCAGTTTTGTT
CACTGGTAGCTGAGGTTTCCCGGATATGTGGCTTCCTAACACTCTCCCCACCCACCCCACCCCCCAAAACAGAGCCT
GAATCTTCATGAAGTGAATAAAACAATTATCCAAGAAGGAGTAAGGTGGATCTTGCCCTAAGCAGAGTTTATGCCAC
AAAGATTCTCCAAATCCCCCAAGACAGCACAGCCACTGGGGTTGAGCCATCTCAGGGAGCTCTGCAGGTGAGCCAGA
GGACCAGATATAAGGCAGCTGGGGAGGAGCAGGGACATCAGCCTGTGCAGAGACCAAGGCCAAAGGTTGAACTTTGA
AAGACTATTAAGTCATATATTGTATGGCAATATGGTGTCTGGACAAGTTGTGCAATGTGCTGAAGGGAAGGGATTGG
AGAGCCTTGAAGACTCTTCTTCATTTGCCTGATCAACCCGACCTCCAGAGGGTTTGTTGCCCAGTAAGACGAGCTCA
GTGCTCTTGTGATCATTTTTCTCTTATCGTTTCCATGCCGTTGATGGCCCTGAAGCTCATCACTGCATTTTAGAACC
CAATCCTGAAATTGGGACCTTTTTTTTAAACTTCTGATACTGTAAAACTTCTTGGAAGCCAAAGCTTTCTTCCAAGC
CCCATCCTCAGTTATCCTGGTTCCTGTTCTTCCCCGAGCTGATAGTACCAGGACCTGTTATTCCACAAAAGCACAGG
CATCCGTCACTTCAATTCAATCCCTGTTCAGATTATAGATATGGACTTTGCTATCTTGATAAATGTCTTCTCTATGT
TATTTTGTCTGAAAAACCTATAAAACCATTATTAAGAATGACCATTTTTAGATGGAAGAAATGAGCCCAGCATCTCA
GTGGCTAAAACACAAAATATCCATGCTTTTAAACAAAATTGTTAAATATTCCGAAGCTCTCTAGTATAAACACCAAG
TAGCATGTGTTTTCACATAAAGAAGACAGGGGCCATGCAACCTTTATCAAGTGGAGGTATTAGAATGTTGTAATGTT
TGGAGACACAGTGTGACCAGTACAGGTTCCCAGAGAGGAATGCCCACCATATCACAGAAAGGTAGAGGTGGGATCTG
GTATAGCCAGACCAAGACAGGGATGTCACGCTGAAGCCAAGTCAGTTAGCTGAAGATTCTCAACAGGAAGGCCTCTC
TTAAGAGTCAGTAATAGGGTTGTTACCATCCACCACCTCAACAAAACAAAAAGCTTATAATTGTAAATGTTTACAGC
ACTGTCTTCGCAGAAACTTTCTGAGGTGATTCCAAAGAACTAGAGGGGAGATGGTCTATAACAGCTCTTGAAGTAAA
CGAGGTTCTTAGTCTCAGCTCTCCTGACATATAGGGCTTGATCATTACTGGTAGGGATTGTTCTGTGAATTGCTTAC
TACTACCCCTGGTCTCTCCCCAGTAGATGCCAGGAACATTCTAGCTGATACCTAACTGTCTTCCCAGGTGTTCGAGG
GAGCAAACCACTGATCTAAACTCTAAACGCTGAAGTACGCAGGTTTTCTAAAAATGACAAGCCCTTGAAACCTTTCC
CAGTAGGCAGCCTCGAGCTGGACTTGTGTCTTTGGAATGCTGATGAATTCTATAGATCAGCATTGCAAATACACTTC
AAATACGTCTGAGTTCAAGTGCAGGGACTGAGTTCACCAAGGTGTGAAATGTGCTCAAAAAGTTCAAAAGTGTGTGT
TTCTTTGTTTCTAAAACATTGTGGCATCTTTTTCATTTGTTTCTAAAACTTTTTTTTTAGAAACAAATGAAGCACTT
GGAAAGTGAAAGTAAAATTACAAATATAAGGATTTACACTGAAGAGAGAAAAATTTTAGGAACTATAGCTGTGAAAA
GATTTTGTTCAAAAGGCAGGCTAGCCTTACCCAAATTCATATATGGCAGGTGTCAACCTCCCAAGCTTACAGTTAGC
AGGCAGCTTTTGCTCACTCATCCTTAGCCATGAGAGCCATTAAGTGTGGTCCAAGAAAGATGGCTCCAAACCCTACC
CCCGACCCACCAGTGGTATTCAGAGATTAAAGCAGAATTGTAAATAGTGGCTTCAGGAGCTCTTTTTTAGA

FIG. 12G

ATGCTTTGCCCCTTCCTCTCACTGCCTTTTTTAGCCAATATAAATGTCAATTTGCACACCTTTTGTTGTGGTTTTAT
ATTGTAACAGCATTTTTTTGAAACTATTGTATTTAAGATAAGGTTTCATATTATGTCCACAAGTAATTAAATTATGT
TTGAAGGTGGCTATATGCTGTATCAGAAGTTGATGATGTTTTTCTTTAGCTGGTAAAGGAGGGTTTTGCATGACCTC
ACTGTTTGTTCTGTGGTTTGTTCTGTTGTATGATGTGTGTCTTGAGTTTTGCTGTGTGATGAAGTGCGCTGAGATTC
CAGTGCCCTCAAGTTGTGTTTTAAGTAGCTATCAGAGGCAAGAGGGTTCCTAAGAGCAGGTTGACCTGTTGGCGACA
GATGGCAATCACCATTTCTCATTCCTTCTTCTCCCTGTTACCCCAGCTTCCTGTCCCAGGTCCCTTCTGTGATTCTT
ACCTTAGTGTGCATGTGTGTCTGTCCTGGTGAGAGTCAGGAGCATCGATATGTTATCATTGCATTATCACCAAGGGC
ACGCACAGCCTAGCACCTGTTGCTTCAGATACCGTCACACTCTGTTTCCAATTTAGATACAACCACATAATAAAATG
TTAGAGTCTTCAATGGGAAGCAGAGGTGCTTGTTATAAAGATGGGGGCTTATGCTTGTGTCACATTTTGTGTTCTTT
TCTTCTTTTGTTTGGTTTTAACTTAATTGTGACCCTTGTAACATCATCTTGCCAAAAAAAAAAAAAAAAGTTGAACTG
GATTTATGTAGACATGTCAAGACGTACTATCTATTTCTTTGTCAGTTATAGCAATAAGAGTGGATAAACTCTAAAAT
CCAGATCTCCCACAATGAACATCCGTGTTCTTTCTATGATTTTTCTTTCTTTATGGTGAGCCACAATTAAACTTGAG
ATGTACAGCCACCCAAACCCAGGAAGCTCATGTGCATCTGGTGCTATGGCACTCACTGTGAATAAGTGTGACCAGAT
ATTAATATGCAATATTGTTTCCAATCCTTTCTAATACATTTTTTC

>NM_001301868.1 Mus musculus IKAROS family zinc finger 1 (Ikzf1), transcript variant 6, mRNA (SEQ ID NO: 10)
GTCAGGGTCCCGAAGCCGCGTGCCGTGCGCGCAGGCCGGGTGGGCTGTGGGACAAGCCGAGCGGGAGGCGAGTCGCA
AGCGCCAACCCAAAGTTTGCACGGTGCGGGGCGAGGGGCGCGCGCTCCGGGCTGCCGCAGGTGGCGGCGCGGTGAGC
CCGGGCCAGGTGCCCCGGCAGCGGGGCGGCGCTGTCGTGCGGGACAGCCGGGCTGCCAGGGGCTCGGAGCCGGGTCG
GAGCCCGCGGGGGGCGGGGAGTGTGGCGAGAAATGGGGAACAATGCGAGTGAGCAACTTGAGGAAGTCATTGTGAAA
GAAAGCTGGGAATTGCTCCGCAGCCAACTTAGCAGGGCACTCTAACAAGTGCCTGCGCGGCCGCGCCCGGGCCGGGG
ACAGGGGCAGCCCGGCGCAGTACAGCCCATCCCGGGACGCTCGGCCGCGGCTGCCGGAGACCCGGTAGGTCCCGCGG
GGTGCAGGAGCCCCCAGATCCCCGGCTGCTCTTCGCGCCCCAGGATCATTCTTGGCCCCCAAAGCGCGGCGCACAAA
TCCACATAACCTGAAGACAATGGATGTCGATGAGGGTCAAGACATGTCCCAAGTTTCAGGAAAGGAGAGCCCCCCAG
TCAGTGACACTCCAGATGAAGGGGATGAGCCCATGCCTGTCCCTGAGGACCTGTCCACTACCTCTGGAGCACAGCAG
AACTCCAAGAGTGATCGAGGCATGGCCAGTAATGTTAAAGTAGAGACTCAGAGTGATGAAGAGAATGGGCGTGCCTG
TGAAATGAATGGGGAAGAATGTGCAGAGGATTTACGAATGCTTGATGCCTCGGGAGAGAAAATGAATGGCTCCCACA
GGGACCAAGGCAGCTCGGCTTTGTCAGGAGTTGGAGGCATTCGACTTCCTAACGGAAAACTAAAGTGTGATATCTGT
GGGATCGTTTGCATCGGGCCCAATGTGCTCATGGTTCACAAAAGAAGTCATACTGGTGAACGGCCTTTCCAGTGCAA
CCAGTGTGGGGCCTCCTTTACCCAGAAAGGCAACCTCCTGCGGCACATCAAGCTGCACTCGGGTGAGAAGCCCTTCA
AATGCCATCTTTGCAACTATGCCTGCCGCCGGAGGGACGCCCTCACCGGCCACCTGAGGACGCACTCCGTTGGTAAG
CCTCACAAATGTGGATATTGTGGCCGGAGCTATAAACAGCGAAGCTCTTTAGAGGAGCATAAAGAGCGATGCCACAA
CTACTTGGAAAGCATGGGCCTTCCGGGCATGTACCCAGTCATTAAGGAAGAAACTAACCACAACGAGATGGCAGAAG
ACCTGTGCAAGATAGGAGCAGAGAGGTCCCTTGTCCTGGACAGGCTGGCAAGCAATGTCGCCAAACGAGACAAGTGC
CTGTCAGACATGCCCTATGACAGTGCCAACTATGAGAAGGAGGATATGATGACATCCCACGTGATGGACCAGGCCAT
CAACAATGCCATCAACTACCTGGGGGCTGAGTCCCTGCGCCCATTGGTGCAGACACCCCCCGGTAGCTCCGAGGTGG
TGCCAGTCATCAGCTCCATGTACCAGCTGCACAAGCCCCCCTCAGATGGCCCCCCACGGTCCAACCATTCAGCACAG
GACGCCGTGGATAACTTGCTGCTGCTGTCCAAGGCCAAGTCTGTGTCATCGGAGCGAGAGGCCTCCCCGAGCAACAG
CTGCCAAGACTCCACAGATACAGAGAGCAACGCGGAGGAACAGCGCAGCGGCCTTATCTACCTAACCAACCACATCA
ACCCGCATGCACGCAATGGGCTGGCTCTCAAGGAGGAGCAGCGCGCCTACGAGGTGCTGAGGGCGGCCTCAGAGAAC
TCGCAGGATGCCTTCCGTGTGGTCAGCACGAGTGGCGAGCAGCTGAAGGTGTACAAGTGCGAACACTGCCGCGTGCT
CTTCCTGGATCACGTCATGTATACCATTCACATGGGCTGCCATGGCTTTCGGGATCCCTTTGAGTGTAACATGTGTG
GTTATCACAGCCAGGACAGGTACGAGTTCTCATCCCATATCACGCGGGGGGAGCATCGTTACCACCTGAGCTAAACC
CAGCCAGGCCCCACTGAAGCACAAAGATAGCTGGTTATGCCTCCTTCCCGGCAGCTGGACCCACAGCGGACAATGTT
GGGAGTGGATTTGCAGGCAGCATTTGTTCTTTTATGTTGGTTGTTTGGCGTTTGATTTGCGTTGGAAGATAAGTTTT
TAATGTTAGTGACAGGATTGCATTGCATCAGGAACATTCACAACATCCATCCTTCTAGCCAGTTTTGTTCACTGGTA
GCTGAGGTTTCCCGGATATGTGGCTTCCTAACACTCTCCCCACCCACCCCACCCCCCAAAACAGAGCCTGAATCTTC
ATGAAGTGAATAAAACAATTATCCAAGAAGGAGTAAGGTGGATCTTGCCCTAAGCAGAGTTTATGCCACAAAGATTC
TCCAAATCCCCCAAGACAGCACAGCCACTGGGGTTGAGCCATCTCAGGGAGCTCTGCAGGTGAGCCAGAGGACCAGA
TATAAGGCAGCTGGGGAGGAGCAGGGACATCAGCCTGTGCAGAGACCAAGGCCAAAGGTTGAACTTTGAAAGACTAT
TAAGTCATATATTGTATGGCAATATGGTGTCTGGACAAGTTGTGCAATGTGCTGAAGGGAAGGGATTGGAGAGCCTT
GAAGACTCTTCTTCATTTGCCTGATCAACCCGACCTCCAGAGGGTTTGTTGCCCAGTAAGACGAGCTCAGTGCTCTT
GTGATCATTTTTCTCTTATCGTTTCCATGCCGTTGATGGCCCTGAAGCTCATCACTGCATTTTAGAACCCAATCCTG
AAATTGGGACCTTTTTTTTAAACTTCTGATACTGTAAAACTTCTTGGAAGCCAAAGCTTTCTTCCAAGCCCCATCCT
CAGTTATCCTGGTTCCTGTTCTTCCCCGAGCTGATAGTACCAGGACCTGTTATTCCACAAAAGCACAGGCATCCGTC
ACTTCAATTCAATCCCTGTTCAGATTATAGATATGGACTTTGCTATCTTGATAAATGTCTTCTCTATGTTATTTTGT
CTGAAAAACCTATAAAACCATTATTAAGAATGACCATTTTTAGATGGAAGAAATGAGCCCAGCATCTCAGTGGCTAA
AACACAAAATATCCATGCTTTTAAACAAAATTGTTAAATAT

FIG. 12H

TCCGAAGCTCTCTAGTATAAACACCAAGTAGCATGTGTTTTCACATAAAGAAGACAGGGGCCATGCAACCTTTATCA
AGTGGAGGTATTAGAATGTTGTAATGTTTGGAGACACAGTGTGACCAGTACAGGTTCCCAGAGAGGAATGCCCACCA
TATCACAGAAAGGTAGAGGTGGGATCTGGTATAGCCAGACCAAGACAGGGATGTCACGCTGAAGCCAAGTCAGTTAG
CTGAAGATTCTCAACAGGAAGGCCTCTCTTAAGAGTCAGTAATAGGGTTGTTACCATCCACCACCTCAACAAAACAA
AAAGCTTATAATTGTAAATGTTTACAGCACTGTCTTCGCAGAAACTTTCTGAGGTGATTCCAAAGAACTAGAGGGGA
GATGGTCTATAACAGCTCTTGAAGTAAACGAGGTTCTTAGTCTCAGCTCTCCTGACATATAGGGCTTGATCATTACT
GGTAGGGATTGTTCTGTGAATTGCTTACTACTACCCCTGGTCTCTCCCCAGTAGATGCCAGGAACATTCTAGCTGAT
ACCTAACTGTCTTCCCAGGTGTTCGAGGGAGCAAACCACTGATCTAAACTCTAAACGCTGAAGTACGCAGGTTTTCT
AAAAATGACAAGCCCTTGAAACCTTTCCCAGTAGGCAGCCTCGAGCTGGACTTGTGTCTTTGGAATGCTGATGAATT
CTATAGATCAGCATTGCAAATACACTTCAAATACGTCTGAGTTCAAGTGCAGGGACTGAGTTCACCAAGGTGTGAAA
TGTGCTCAAAAAGTTCAAAAGTGTGTGTTTCTTTGTTTCTAAAACATTGTGGCATCTTTTTCATTTGTTTCTAAAAC
TTTTTTTTTAGAAACAAATGAAGCACTTGGAAAGTGAAAGTAAAATTACAAATATAAGGATTTACACTGAAGAGAGA
AAAATTTTAGGAACTATAGCTGTGAAAAGATTTTGTTCAAAAGGCAGGCTAGCCTTACCCAAATTCATATATGGCAG
GTGTCAACCTCCCAAGCTTACAGTTAGCAGGCAGCTTTTGCTCACTCATCCTTAGCCATGAGAGCCATTAAGTGTGG
TCCAAGAAAGATGGCTCCAAACCCTACCCCCGACCCACCAGTGGTATTCAGAGATTAAAGCAGAATTGTAAATAGTG
GCTTCAGGAGCTCTTTTTTAGAATGCTTTGCCCCTTCCTCTCACTGCCTTTTTTAGCCAATATAAATGTCAATTTGC
ACACCTTTTGTTGTGGTTTTATATTGTAACAGCATTTTTTTGAAACTATTGTATTTAAGATAAGGTTTCATATTATG
TCCACAAGTAATTAAATTATGTTTGAAGGTGGCTATATGCTGTATCAGAAGTTGATGATGTTTTTCTTTAGCTGGTA
AAGGAGGGTTTTGCATGACCTCACTGTTTGTTCTGTGGTTTGTTCTGTTGTATGATGTGTGTCTTGAGTTTTGCTGT
GTGATGAAGTGCGCTGAGATTCCAGTGCCCTCAAGTTGTGTTTTAAGTAGCTATCAGAGGCAAGAGGGTTCCTAAGA
GCAGGTTGACCTGTTGGCGACAGATGGCAATCACCATTTCTCATTCCTTCTTCTCCCTGTTACCCCAGCTTCCTGTC
CCAGGTCCCTTCTGTGATTCTTACCTTAGTGTGCATGTGTGTCTGTCCTGGTGAGAGTCAGGAGCATCGATATGTTA
TCATTGCATTATCACCAAGGGCACGCACAGCCTAGCACCTGTTGCTTCAGATACCGTCACACTCTGTTTCCAATTTA
GATACAACCACATAATAAAATGTTAGAGTCTTCAATGGGAAGCAGAGGTGCTTGTTATAAAGATGGGGGCTTATGCT
TGTGTCACATTTTGTGTTCTTTTCTTCTTTTGTTTGGTTTTAACTTAATTGTGACCCTTGTAACATCATCTTGCCAA
AAAAAAAAAAAAAGTTGAACTGGATTTATGTAGACATGTCAAGACGTACTATCTATTTCTTTGTCAGTTATAGCAAT
AAGAGTGGATAAACTCTAAAATCCAGATCTCCCACAATGAACATCCGTGTTCTTTCTATGATTTTTCTTTCTTTATG
GTGAGCCACAATTAAACTTGAGATGTACAGCCACCCAAACCCAGGAAGCTCATGTGCATCTGGTGCTATGGCACTCA
CTGTGAATAAGTGTGACCAGATATTAATATGCAATATTGTTTCCAATCCTTTCTAATACATTTTTTC

FIG. 13A

Human

Proteins

>sp|Q13422|IKZF1_HUMAN DNA-binding protein Ikaros OS=Homo sapiens OX=9606 GN=IKZF1 PE=1 SV=1 (SEQ ID NO: 11)
MDADEGQDMSQVSGKESPPVSDTPDEGDEPMPIPEDLSTTSGGQQSSKSDRVVASNVKVETQSDEENGRACEMNGEE
CAEDLRMLDASGEKMNGSHRDQGSSALSGVGGIRLPNGKLKCDICGIICIGPNVLMVHKRSHTGERPFQCNQCGASF
TQKGNLLRHIKLHSGEKPFKCHLCNYACRRRDALTGHLRTHSVGKPHKCGYCGRSYKQRSSLEEHKERCHNYLESMG
LPGTLYPVIKEETNHSEMAEDLCKIGSERSLVLDRLASNVAKRKSSMPQKFLGDKGLSDTPYDSSASYEKENEMMKS
HVMDQAINNAINYLGAESLRPLVQTPPGGSEVVPVISPMYQLHKPLAEGTPRSNHSAQDSAVENLLLLSKAKLVPSE
REASPSNSCQDSTDTESNNEEQRSGLIYLTNHIAPHARNGLSLKEEHRAYDLLRAASENSQDALRVVSTSGEQMKVY
KCEHCRVLFLDHVMYTIHMGCHGFRDPFECNMCGYHSQDRYEFSSHITRGEHRFHMS >sp|Q13422-2|IKZF1_HUMAN Isoform Ik2 of DNA-binding protein Ikaros OS=Homo sapiens OX=9606 GN=IKZF1(SEQ ID NO: 12)
MDADEGQDMSQVSGKESPPVSDTPDEGDEPMPIPEDLSTTSGGQQSSKSDRVVGERPFQCNQCGASFTQKGNLLRHI
KLHSGEKPFKCHLCNYACRRRDALTGHLRTHSVGKPHKCGYCGRSYKQRSSLEEHKERCHNYLESMGLPGTLYPVIK
EETNHSEMAEDLCKIGSERSLVLDRLASNVAKRKSSMPQKFLGDKGLSDTPYDSSASYEKENEMMKSHVMDQAINNA
INYLGAESLRPLVQTPPGGSEVVPVISPMYQLHKPLAEGTPRSNHSAQDSAVENLLLLSKAKLVPSEREASPSNSCQ
DSTDTESNNEEQRSGLIYLTNHIAPHARNGLSLKEEHRAYDLLRAASENSQDALRVVSTSGEQMKVYKCEHCRVLFL
DHVMYTIHMGCHGFRDPFECNMCGYHSQDRYEFSSHITRGEHRFHMS >sp|Q13422-3|IKZF1_HUMAN Isoform Ik3 of DNA-binding protein Ikaros OS=Homo sapiens OX=9606 GN=IKZF1(SEQ ID NO: 13)
MDADEGQDMSQVSGKESPPVSDTPDEGDEPMPIPEDLSTTSGGQQSSKSDRVVASNVKVETQSDEENGRACEMNGEE
CAEDLRMLDASGEKMNGSHRDQGSSALSGVGGIRLPNGKLKCDICGIICIGPNVLMVHKRSHTGERPFQCNQCGASF
TQKGNLLRHIKLHSGEKPFKCHLCNYACRRRDALTGHLRTHSGDKGLSDTPYDSSASYEKENEMMKSHVMDQAINNA
INYLGAESLRPLVQTPPGGSEVVPVISPMYQLHKPLAEGTPRSNHSAQDSAVENLLLLSKAKLVPSEREASPSNSCQ
DSTDTESNNEEQRSGLIYLTNHIAPHARNGLSLKEEHRAYDLLRAASENSQDALRVVSTSGEQMKVYKCEHCRVLFL
DHVMYTIHMGCHGFRDPFECNMCGYHSQDRYEFSSITRGEHRFHMS >sp|Q13422-4|IKZF1_HUMAN Isoform Ik4 of DNA-binding protein Ikaros OS=Homo sapiens OX=9606 GN=IKZF1(SEQ ID NO: 14)
MDADEGQDMASNVKVETQSDEENGRACEMNGEECAEDLRMLDASGEKMNGSHRDQGSSALSGVGGIRLPNGKLKCDI
CGIICIGPNVLMVHKRSHTGERPFQCNQCGASFTQKGNLLRHIKLHSGEKPFKCHLCNYACRRRDALTGHLRTHSGD
KGLSDTPYDSSASYEKENEMMKSHVMDQAINNAINYLGAESLRPLVQTPPGGSEVVPVISPMYQLHKPLAEGTPRSN
HSAQDSAVENLLLLSKAKLVPSEREASPSNSCQDSTDTESNNEEQRSGLIYLTNHIAPHARNGLSLKEEHRAYDLLR
AASENSQDALRVVSTSGEQMKVYKCEHCRVLFLDHVMYTIHMGCHGFRDPFECNMCGYHSQDRYEFSSHITRGEHRF
HMS >sp|Q13422-5|IKZF1_HUMAN Isoform Ik5 of DNA-binding protein Ikaros OS=Homo sapiens OX=9606 GN=IKZF1(SEQ ID NO: 15)
MDADEGQDMSQVSGKESPPVSDTPDEGDEPMPIPEDLSTTSGGQQSSKSDRVVASNVKVETQSDEENGRACEMNGEE
CAEDLRMLDASGEKMNGSHRDQGSSALSGVGGIRLPNGKLKCDICGIICIGPNVLMVHKRSHTGDKGLSDTPYDSSA
SYEKENEMMKSHVMDQAINNAINYLGAESLRPLVQTPPGGSEVVPVISPMYQLHKPLAEGTPRSNHSAQDSAVENLL
LLSKAKLVPSEREASPSNSCQDSTDTESNNEEQRSGLIYLTNHIAPHARNGLSLKEEHRAYDLLRAASENSQDALRV
VSTSGEQMKVYKCEHCRVLFLDHVMYTIHMGCHGFRDPFECNMCGYHSQDRYEFSSHITRGEHRFHMS >sp|Q13422-6|IKZF1_HUMAN Isoform Ik6 of DNA-binding protein Ikaros OS=Homo sapiens OX=9606 GN=IKZF1(SEQ ID NO: 16)
MDADEGQDMSQVSGKESPPVSDTPDEGDEPMPIPEDLSTTSGGQQSSKSDRVVGDKGLSDTPYDSSASYEKENEMMK
SHVMDQAINNAINYLGAESLRPLVQTPPGGSEVVPVISPMYQLHKPLAEGTPRSNHSAQDSAVENLLLLSKAKLVPS
EREASPSNSCQDSTDTESNNEEQRSGLIYLTNHIAPHARNGLSLKEEHRAYDLLRAASENSQDALRVVSTSGEQMKV
YKCEHCRVLFLDHVMYTIHMGCHGFRDPFECNMCGYHSQDRYEFSSHITRGEHRFHMS

FIG. 13B

>sp|Q13422-7|IKZF1_HUMAN Isoform Ik7 of DNA-binding protein Ikaros OS=Homo sapiens OX=9606 GN=IKZF1(SEQ ID NO: 17)
MDADEGQDMSQVSGKESPPVSDTPDEGDEPMPIPEDLSTTSGGQQSSKSDRVVASNVKVETQSDEENGRACEMNGEE
CAEDLRMLDASGEKMNGSHRDQGSSALSGVGGIRLPNGKLKCDICGIICIGPNVLMVHKRSHTGERPFQCNQCGASF
TQKGNLLRHIKLHSGEKPFKCHLCNYACRRRDALTGHLRTHSVIKEETNHSEMAEDLCKIGSERSLVLDRLASNVAK
RKSSMPQKFLGDKGLSDTPYDSSASYEKENEMMKSHVMDQAINNAINYLGAESLRPLVQTPPGGSEVVPVISPMYQL
HKPLAEGTPRSNHSAQDSAVENLLLLSKAKLVPSEREASPSNSCQDSTDTESNNEEQRSGLIYLTNHIAPHARNGLS
LKEEHRAYDLLRAASENSQDALRVVSTSGEQMKVYKCEHCRVLFLDHVMYTIHMGCHGFRDPFECNMCGYHSQDRYE
FSSHITRGEHRFHMS >sp|Q13422-8|IKZF1_HUMAN Isoform Ikx of DNA-binding protein Ikaros OS=Homo sapiens OX=9606 GN=IKZF1(SEQ ID NO: 18)
MDADEGQDMSQVSGKESPPVSDTPDEGDEPMPIPEDLSTTSGGQQSSKSDRVVASNVKVETQSDEENGRACEMNGEE
CAEDLRMLDASGEKMNGSHRDQGSSALSGVGGIRLPNGKLKCDICGIICIGPNVLMVHKRSHTGERPFQCNQCGASF
TQKGNLLRHIKLHSGEKPFKCHLCNYACRRRDALTGHLRTHSVIKEETNHSEMAEDLCKIGSEISRAGQTSK >Consensus of human Ikzf1 isoforms above(SEQ ID NO:19)
XXXXXXXXXXXXXXXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXXXXXXXXXXXXXXXX
XXXXXXXXXXXXXXXXXXXXXXXXXXXXXXXXXXXXXXXXXGDKGLSDTPYDSSASYE
KENEMMKSHVMDQAINNAINYLGAESLRPLVQTPPGGSEVVPVISPMYQLHKPLAEGTPR
SNHSAQDSAVENLLLLSKAKLVPSEREASPSNSCQDSTDTESNNEEQRSGLIYLTNHIAP
HARNGLSLKEEHRAYDLLRAASENSQDALRVVSTSGEQMKVYKCEHCRVLFLDHVMYTIH
MGCHGFRDPFECNMCGYHSQDRYEFSSXITRGEHRFHMS

FIG. 13C

Alignment of human Ikzf1 isoforms

```
4       --------------------------------------------MDADEGQDMASNVKVE  16
3       MDADEGQDMSQVSGKESPPVSDTPDEGDEPMPIPEDLSTTSGGQQSSKSDRVVASNVKVE  60
5       MDADEGQDMSQVSGKESPPVSDTPDEGDEPMPIPEDLSTTSGGQQSSKSDRVVASNVKVE  60
2       MDADEGQDMSQVSGKESPPVSDTPDEGDEPMPIPEDLSTTSGGQQSSKSDRV--------  52
1       MDADEGQDMSQVSGKESPPVSDTPDEGDEPMPIPEDLSTTSGGQQSSKSDRVVASNVKVE  60
7       MDADEGQDMSQVSGKESPPVSDTPDEGDEPMPIPEDLSTTSGGQQSSKSDRVVASNVKVE  60
6       MDADEGQDMSQVSGKESPPVSDTPDEGDEPMPIPEDLSTTSGGQQSSKSDRV--------  52
                                                            .:...:

4       TQSDEENGRACEMNGEECAEDLRMLDASGEKMNGSHRDQGSSALSGVGGIRLPNGKLKCD  76
3       TQSDEENGRACEMNGEECAEDLRMLDASGEKMNGSHRDQGSSALSGVGGIRLPNGKLKCD  120
5       TQSDEENGRACEMNGEECAEDLRMLDASGEKMNGSHRDQGSSALSGVGGIRLPNGKLKCD  120
2       ------------------------------------------------------------  52
1       TQSDEENGRACEMNGEECAEDLRMLDASGEKMNGSHRDQGSSALSGVGGIRLPNGKLKCD  120
7       TQSDEENGRACEMNGEECAEDLRMLDASGEKMNGSHRDQGSSALSGVGGIRLPNGKLKCD  120
6       ------------------------------------------------------------  52


4       ICGIICIGPNVLMVHKRSHTGERPFQCNQCGASFTQKGNLLRHIKLHSGEKPFKCHLCNY  136
3       ICGIICIGPNVLMVHKRSHTGERPFQCNQCGASFTQKGNLLRHIKLHSGEKPFKCHLCNY  180
5       ICGIICIGPNVLMVHKRSHT----------------------------------------  140
2       -------------------VGERPFQCNQCGASFTQKGNLLRHIKLHSGEKPFKCHLCNY  93
1       ICGIICIGPNVLMVHKRSHTGERPFQCNQCGASFTQKGNLLRHIKLHSGEKPFKCHLCNY  180
7       ICGIICIGPNVLMVHKRSHTGERPFQCNQCGASFTQKGNLLRHIKLHSGEKPFKCHLCNY  180
6       ------------------------------------------------------------  52


4       ACRRRDALTGHLRTHS--------------------------------------------  152
3       ACRRRDALTGHLRTHS--------------------------------------------  196
5       ------------------------------------------------------------  140
2       ACRRRDALTGHLRTHSVGKPHKCGYCGRSYKQRSSLEEHKERCHNYLESMGLPGTLYPVI  153
1       ACRRRDALTGHLRTHSVGKPHKCGYCGRSYKQRSSLEEHKERCHNYLESMGLPGTLYPVI  240
7       ACRRRDALTGHLRTHS------------------------------------------VI  198
6       ------------------------------------------------------------  52


4       -------------------------------------------GDKGLSDTPYDSSASYE  169
3       -------------------------------------------GDKGLSDTPYDSSASYE  213
5       -------------------------------------------GDKGLSDTPYDSSASYE  157
2       KEETNHSEMAEDLCKIGSERSLVLDRLASNVAKRKSSMPQKFLGDKGLSDTPYDSSASYE  213
1       KEETNHSEMAEDLCKIGSERSLVLDRLASNVAKRKSSMPQKFLGDKGLSDTPYDSSASYE  300
7       KEETNHSEMAEDLCKIGSERSLVLDRLASNVAKRKSSMPQKFLGDKGLSDTPYDSSASYE  258
6       ------------------------------------------VGDKGLSDTPYDSSASYE  70
                                                   *****************

4       KENEMMKSHVMDQAINNAINYLGAESLRPLVQTPPGGSEVVPVISPMYQLHKPLAEGTPR  229
3       KENEMMKSHVMDQAINNAINYLGAESLRPLVQTPPGGSEVVPVISPMYQLHKPLAEGTPR  273
5       KENEMMKSHVMDQAINNAINYLGAESLRPLVQTPPGGSEVVPVISPMYQLHKPLAEGTPR  217
2       KENEMMKSHVMDQAINNAINYLGAESLRPLVQTPPGGSEVVPVISPMYQLHKPLAEGTPR  273
1       KENEMMKSHVMDQAINNAINYLGAESLRPLVQTPPGGSEVVPVISPMYQLHKPLAEGTPR  360
7       KENEMMKSHVMDQAINNAINYLGAESLRPLVQTPPGGSEVVPVISPMYQLHKPLAEGTPR  318
6       KENEMMKSHVMDQAINNAINYLGAESLRPLVQTPPGGSEVVPVISPMYQLHKPLAEGTPR  130
        ************************************************************
```

FIG. 13D

```
4      SNHSAQDSAVENLLLLSKAKLVPSEREASPSNSCQDSTDTESNNEEQRSGLIYLTNHIAP  289
3      SNHSAQDSAVENLLLLSKAKLVPSEREASPSNSCQDSTDTESNNEEQRSGLIYLTNHIAP  333
5      SNHSAQDSAVENLLLLSKAKLVPSEREASPSNSCQDSTDTESNNEEQRSGLIYLTNHIAP  277
2      SNHSAQDSAVENLLLLSKAKLVPSEREASPSNSCQDSTDTESNNEEQRSGLIYLTNHIAP  333
1      SNHSAQDSAVENLLLLSKAKLVPSEREASPSNSCQDSTDTESNNEEQRSGLIYLTNHIAP  420
7      SNHSAQDSAVENLLLLSKAKLVPSEREASPSNSCQDSTDTESNNEEQRSGLIYLTNHIAP  378
6      SNHSAQDSAVENLLLLSKAKLVPSEREASPSNSCQDSTDTESNNEEQRSGLIYLTNHIAP  190
       ************************************************************

4      HARNGLSLKEEHRAYDLLRAASENSQDALRVVSTSGEQMKVYKCEHCRVLFLDHVMYTIH  349
3      HARNGLSLKEEHRAYDLLRAASENSQDALRVVSTSGEQMKVYKCEHCRVLFLDHVMYTIH  393
5      HARNGLSLKEEHRAYDLLRAASENSQDALRVVSTSGEQMKVYKCEHCRVLFLDHVMYTIH  337
2      HARNGLSLKEEHRAYDLLRAASENSQDALRVVSTSGEQMKVYKCEHCRVLFLDHVMYTIH  393
1      HARNGLSLKEEHRAYDLLRAASENSQDALRVVSTSGEQMKVYKCEHCRVLFLDHVMYTIH  480
7      HARNGLSLKEEHRAYDLLRAASENSQDALRVVSTSGEQMKVYKCEHCRVLFLDHVMYTIH  438
6      HARNGLSLKEEHRAYDLLRAASENSQDALRVVSTSGEQMKVYKCEHCRVLFLDHVMYTIH  250
       ************************************************************

4      MGCHGFRDPFECNMCGYHSQDRYEFSSHITRGEHRFHMS       388
3      MGCHGFRDPFECNMCGYHSQDRYEFSS-ITRGEHRFHMS       431
5      MGCHGFRDPFECNMCGYHSQDRYEFSSHITRGEHRFHMS       376
2      MGCHGFRDPFECNMCGYHSQDRYEFSSHITRGEHRFHMS       432
1      MGCHGFRDPFECNMCGYHSQDRYEFSSHITRGEHRFHMS       519
7      MGCHGFRDPFECNMCGYHSQDRYEFSSHITRGEHRFHMS       477
6      MGCHGFRDPFECNMCGYHSQDRYEFSSHITRGEHRFHMS       289
       *************************** ***********
```

FIG. 13E

Alignment of Ikzf1 human isoform 1(1) and of mouse Ikzf1 isoform a (a)

```
a      MDVDEGQDMSQVSGKESPPVSDTPDEGDEPMPVPEDLSTTSGAQQNSKSDRGMASNVKVE  60
1      MDADEGQDMSQVSGKESPPVSDTPDEGDEPMPIPEDLSTTSGGQQSSKSDRVVASNVKVE  60
       **.*****************************:*********.**.***** :*******

a      TQSDEENGRACEMNGEECAEDLRMLDASGEKMNGSHRDQGSSALSGVGGIRLPNGKLKCD  120
1      TQSDEENGRACEMNGEECAEDLRMLDASGEKMNGSHRDQGSSALSGVGGIRLPNGKLKCD  120
       ************************************************************

a      ICGIVCIGPNVLMVHKRSHTGERPFQCNQCGASFTQKGNLLRHIKLHSGEKPFKCHLCNY  180
1      ICGIICIGPNVLMVHKRSHTGERPFQCNQCGASFTQKGNLLRHIKLHSGEKPFKCHLCNY  180
       ****:*******************************************************

a      ACRRRDALTGHLRTHSVGKPHKCGYCGRSYKQRSSLEEHKERCHNYLESMGLPG-MYPVI  239
1      ACRRRDALTGHLRTHSVGKPHKCGYCGRSYKQRSSLEEHKERCHNYLESMGLPGTLYPVI  240
       ****************************************************** :****
```

FIG. 13F

```
a      KEETNHNEMAEDLCKIGAERSLVLDRLASNVAKRKSSMPQKFLGDKCLSDMPYDSAN-YE  298
1      KEETNHSEMAEDLCKIGSERSLVLDRLASNVAKRKSSMPQKFLGDKGLSDTPYDSSASYE  300
       ******.**********:**************************** *** ****:  **

a      -KEDMMTSHVMDQAINNAINYLGAESLRPLVQTPPGSSEVVPVISSMYQLHKPPSDGPPR  357
1      KENEMMKSHVMDQAINNAINYLGAESLRPLVQTPPGGSEVVPVISPMYQLHKPLAEGTPR  360
       :::**.**************************.******** ******* ::* **

a      SNHSAQD-AVDNLLLLSKAKSVSSEREASPSNSCQDSTDTESNAEEQRSGLIYLTNHINP  416
1      SNHSAQDSAVENLLLLSKAKLVPSEREASPSNSCQDSTDTESNNEEQRSGLIYLTNHIAP  420
       ******* **:********* * ******************* ************* *

a      HARNGLALKEEQRAYEVLRAASENSQDAFRVVSTSGEQLKVYKCEHCRVLFLDHVMYTIH  476
1      HARNGLSLKEEHRAYDLLRAASENSQDALRVVSTSGEQMKVYKCEHCRVLFLDHVMYTIH  480
       ******:****:***::***********:*********:*********************

a      MGCHGFRDPFECNMCGYHSQDRYEFSSHITRGEHRYHLS       515
1      MGCHGFRDPFECNMCGYHSQDRYEFSSHITRGEHRFHMS       519
       ***********************************:*:*
```

>Consensus of human Ikzf1 isoform 1 and mouse Ikzf1 isoform a (SEQ ID NO:20)
MDXDEGQDMSQVSGKESPPVSDTPDEGDEPMPXPEDLSTTSGXQQXSKSDRXXASNVKVETQSDEENGRACEMNGEE
CAEDLRMLDASGEKMNGSHRDQGSSALSGVGGIRLPNGKLKCDICGIXCIGPNVLMVHKRSHTGERPFQCNQCGASF
TQKGNLLRHIKLHSGEKPFKCHLCNYACRRRDALTGHLRTHSVGKPHKCGYCGRSYKQRSSLEEHKERCHNYLESMG
LPGXXYPVIKEETNHXEMAEDLCKIGXERSLVLDRLASNVAKRKSSMPQKFLGDKXLSDXPYDSXXXYEXXXEMXKS
HVMDQAINNAINYLGAESLRPLVQTPPXGSEVVPVIXPMYQLHKXXXEXTPRSNHSAQDXAVXNLLLLSKAKXVXSE
REASPSNSCQDSTDTESNXEEQRSGLIYLTNHIXPHARNGLXLKEEXRAYXXLRAASENSQDAXRVVSTSGEQXKVY
KCEHCRVLFLDHVMYTIHMGCHGFRDPFECNMCGYHSQDRYEFSSHITRGEHRXHXS

FIG. 14A

Nucleic acids

>NM_006060.6 Homo sapiens IKAROS family zinc finger 1 (IKZF1), transcript variant 1, mRNA (CDS shown bolded, untranslated shown highlighted in grey; stop codon underlined) (SEQ ID NO:21)
ACTCTAACAAGTGACTGCGCGGCCCGCGCCCGGGGCGGTGACTGCGGCAAGCCCCCTGGGTCCCCGCGCGGCGCATC
CCAGCCTGGGCGGGACGCTCGGCCGCGGCGAGGCGGGCAAGCCTGGCAGGGCAGAGGGAGCCCCGGCTCCGAGGTTG
CTCTTCGCACCCGAGGATCAGTCTTGGCCCCAAAGCGCGACGCACAAATCCACATAACCTGAGGACCATGGATGCTG
**ATGAGGGTCAAGACATGTCCCAAGTTTCAGGGAAGGAAAGCCCCCCTGTAAGCGATACTCCAGATGAGGGCGATGAG
CCCATGCCGATCCCCGAGGACCTCTCCACCACCTCGGGAGGACAGCAAAGCTCCAAGAGTGACAGAGTCGTGGCCAG
TAATGTTAAAGTAGAGACTCAGAGTGATGAAGAGAATGGGCGTGCCTGTGAAATGAATGGGGAAGAATGTGCGGAGG
ATTTACGAATGCTTGATGCCTCGGGAGAGAAAATGAATGGCTCCCACAGGGACCAAGGCAGCTCGGCTTTGTCGGGA
GTTGGAGGCATTCGACTTCCTAACGGAAAACTAAAGTGTGATATCTGTGGGATCATTTGCATCGGGCCCAATGTGCT
CATGGTTCACAAAAGAAGCCACACTGGAGAACGGCCCTTCCAGTGCAATCAGTGCGGGGCCTCATTCACCCAGAAGG
GCAACCTGCTCCGGCACATCAAGCTGCATTCCGGGGAGAAGCCCTTCAAATGCCACCTCTGCAACTACGCCTGCCGC
CGGAGGGACGCCCTCACTGGCCACCTGAGGACGCACTCCGTTGGTAAACCTCACAAATGTGGATATTGTGGCCGAAG
CTATAAACAGCGAAGCTCTTTAGAGGAACATAAAGAGCGCTGCCACAACTACTTGGAAAGCATGGGCCTTCCGGGCA
CACTGTACCCAGTCATTAAAGAAGAAACTAATCACAGTGAAATGGCAGAAGACCTGTGCAAGATAGGATCAGAGAGA
TCTCTCGTGCTGGACAGACTAGCAAGTAACGTCGCCAAACGTAAGAGCTCTATGCCTCAGAAATTTCTTGGGGACAA
GGGCCTGTCCGACACGCCCTACGACAGCAGCGCCAGCTACGAGAAGGAGAACGAAATGATGAAGTCCCACGTGATGG
ACCAAGCCATCAACAACGCCATCAACTACCTGGGGGCCGAGTCCCTGCGCCCGCTGGTGCAGACGCCCCCGGGCGGT
TCCGAGGTGGTCCCGGTCATCAGCCCGATGTACCAGCTGCACAAGCCGCTCGCGGAGGGCACCCCGCGCTCCAACCA
CTCGGCCCAGGACAGCGCCGTGGAGAACCTGCTGCTGCTCTCCAAGGCCAAGTTGGTGCCCTCGGAGCGCGAGGCGT
CCCCGAGCAACAGCTGCCAAGACTCCACGGACACCGAGAGCAACAACGAGGAGCAGCGCAGCGGTCTCATCTACCTG
ACCAACCACATCGCCCCGCACGCGCGCAACGGGCTGTCGCTCAAGGAGGAGCACCGCGCCTACGACCTGCTGCGCGC
CGCCTCCGAGAACTCGCAGGACGCGCTCCGCGTGGTCAGCACCAGCGGGGAGCAGATGAAGGTGTACAAGTGCGAAC
ACTGCCGGGTGCTCTTCCTGGAT**

FIG 14B

CACGTCATGTACACCATCCACATGGGCTGCCACGGCTTCCGTGATCCTTTTGAGTGCAACATGTGCGGCTACCACAG
CCAGGACCGGTACGAGTTCTCGTCGCACATAACGCGAGGGGAGCACCGCTTCCACATGAGCTAAAGCCCTCCCGCGC
CCCCACCCCAGACCCCGAGCCACCCCAGGAAAAGCACAAGGACTGCCGCCTTCTCGCTCCCGCCAGCAGCATAGACT
GGACTGGACCAGACAATGTTGTGTTTGGATTTGTAACTGTTTTTTGTTTTTTGTTTGAGTTGGTTGATTGGGGTTTG
ATTTGCTTTTGAAAAGATTTTTATTTTTAGAGGCAGGGCTGCATTGGGAGCATCCAGAACTGCTACCTTCCTAGATG
TTTCCCCAGACCGCTGGCTGAGATTCCCTCACCTGTCGCTTCCTAGAATCCCCTTCTCCAAACGATTAGTCTAAATT
TTCAGAGAGAAATAGATAAAACACGCCACAGCCTGGGAAGGAGCGTGCTCTACCCTGTGCTAAGCACGGGGTTCGCG
CACCAGGTGTCTTTTTCCAGTCCCCAGAAGCAGAGAGCACAGCCCCTGCTGTGTGGGTCTGCAGGTGAGCAGACAGG
ACAGGTGTGCCGCCACCCAAGTGCCAAGACACAGCAGGGCCAACAACCTGTGCCCAGGCCAGCTTCGAGCTACATGC
ATCTAGGGCGGAGAGGCTGCACTTGTGAGAGAAAATACTATTTCAAGTCATATTCTGCGTAGGAAAATGAATTGGTT
GGGGAAAGTCGTGTCTGTCAGACTGCCCTGGGTGGAGGGAGACGCCGGGCTAGAGCCTTTGGGATCGTCCTGGATTC
ACTGGCTTTGCGGAGGCTGCTCAGATGGCCTGAGCCTCCCGAGGCTTGCTGCCCCGTAGGAGGAGACTGTCTTCCCG
TGGGCATATCTGGGGAGCCCTGTTCCCCGCTTTTTCACTCCCATACCTTTAATGGCCCCCAAAATCTGTCACTACAA
TTTAAACACCAGTCCCGAAATTTGGATCTTCTTTCTTTTTGAATCTCTCAAACGGCAACATTCCTCAGAAACCAAAG
CTTTATTTCAAATCTCTTCCTTCCCTGGCTGGTTCCATCTAGTACCAGAGGCCTCTTTTCCTGAAGAAATCCAATCC
TAGCCCTCATTTTAATTATGTACATCTGTTTGTAGCCACAAGCCTGAATTTCTCAGTGTTGGTAAGTTTCTTTACCT
ACCCTCACTATATATTATTCTCGTTTTAAAACCCATAAAGGAGTGATTTAGAACAGTCATTAATTTTCAACTCAATG
AAATATGTGAAGCCCAGCATCTCTGTTGCTAACACACAGAGCTCACCTGTTTGAAACCAAGCTTTCAAACATGTTGA
AGCTCTTTACTGTAAAGGCAAGCCAGCATGTGTGTCCACACATACATAGGATGGCTGGCTCTGCACCTGTAGGATAT
TGGAATGCACAGGGCAATTGAGGGACTGAGCCAGACCTTCGGAGAGTAATGCCACCAGATCCCCTAGGAAAGAGGAG
GCAAATGGCACTGCAGGTGAGAACCCCGCCCATCCGTGCTATGACATGGAGGCACTGAAGCCCGAGGAAGGTGTGTG
GAGATTCTAATCCCAACAAGCAAGGGTCTCCTTCAAGATTAATGCTATCAATCATTAAGGTCATTACTCTCAACCAC
CTAGGCAATGAAGAATATACCATTTCAAATATTTACAGTACTTGTCTTCACCAACACTGTCCCAAGGTGAAATGAAG
CAACAGAGAGGAAATTGTACATAAGTACCTCAGCATTTAATCCAAACAGGGGTTCTTAGTCTCAGCACTATGACATT
TTGGGCTGACTACTTATTTGTTAGGCGGGAGCTCTCCTGTGCATTGTAGGATAATTAGCAGTATCCCTGGTGGCTAC
CCAATAGACGCCAGTAGCACCCCGAATTGACAACCCAAACTCTCCAGACATCACCAACTGTCCCCTGCGAGGAGAAA
TCACTCCTGGGGGAGAACCACTGACCCAAATGAATTCTAAACCAATCAAATGTCTGGGAAGCCCTCCAAGAAAAAA
ATAGAAAAGCACTTGAAGAATATTCCCAATATTCCCGGTCAGCAGTATCAAGGCTGACTTGTGTTCATGTGGAGTCA
TTATAAATTCTATAAATCAATTATTCCCCTTCGGTCTTAAAAATATATTTCCTCATAAACATTTGAGTTTTGTTGAA
AAGATGGAGTTTACAAAGATACCATTCTTGAGTCATGGATTTCTCTGCTCACAGAAGGGTGTGGCATTTGGAAACGG
GAATAAACAAAATTGCTGCACCAATGCACTGAGTGAAGGAAGAGAGACAGAGGATCAAGGGCTTTAGACAGCACTCC
TTCAATATGCAATCACAGAGAAAGATGCGCCTTATCCAAGTTAATATCTCTAAGGTGAGAGCCTTCTTAGAGTCAGT
TTGTTGCAAATTTCACCTACTCTGTTCTTTTCCATCCATCCCCCTGAGTCAGTTGGTTGAAGGGAGTTATTTTTTCA
AGTGGAATTCAAACAAAGCTCAAACCAGAACTGTAAATAGTGATTGCAGGAATTCTTTTCTAAACTGCTTTGCCCTT
TCCTCTCACTGCCTTTTATAGCCAATATAAATGTCTCTTTGCACACCTTTTGTTGTGGTTTTATATTGTAACACCAT
TTTTCTTTGAAACTATTGTATTTAAAGTAAGGTTTCATATTATGTCAGCAAGTAATTAACTTATGTTTAAAAGGTGG
CCATATCATGTACCAAAAGTTGCTGAAGTTTCTCTTCTAGCTGGTAAAGTAGGAGTTTGCATGACTTCACACTTTTT
TTGCGTAGTTTCTTCTGTTGTATGATGGCGTGAGTGTGTGTCTTGGGTACCGCTGTGTACTACTGTGTGCCTAGATT
CCATGCACTCTCGTTGTGTTTGAAGTAAATATTGGAGACCGGAGGGTAACAGGTTGGCCTGTTGATTACAGCTAGTA
ATCGCTGTGTCTTGTTCCGCCCCCTCCCTGACACCCCAGCTTCCCAGGATGTGGAAAGCCTGGATCTCAGCTCCTTG
CCCCATATCCCTTCTGTAATTTGTACCTAAAGAGTGTGATTATCCTAATTCAAGAGTCACTAAAACTCATCACATTA
TCATTGCATATCAGCAAAGGGTAAAGTCCTAGCACCAATTGCTTCACATACCAGCATGTTCCATTTCCAATTTAGAA
TTAGCCACATAATAAAATCTTAGAATCTTCCTTGAGAAAGAGCTGCCTGAGATGTAGTTTTGTTATATGGTTCCCCA
CCGACCATTTTTGTGCTTTTTTCTTGTTTTGTTTTGTTTTGACTGCACTGTGAGTTTTGTAGTGTCCTCTTCTTGCC
AAAACAAACGCGAGATGAACTGGACTTATGTAGACAAATCGTGATGCCAGTGTATCCTTCCTTTCTTCAGTTCCAGC
AATAATGAATGGTCAACTTTTTTAAAATCTAGATCTCTCTCATTCATTTCAATGTATTTTTACTTTAAGATGAACCA
AAATTATTAGACTTATTTAAGATGTACAGGCATCAGAAAAAAGAAGCACATAATGCTTTTGGTGCGATGGCACTCAC
TGTGAACATGTGTAACCACATATTAATATGCAATATTGTTTCCAATACTTTCTAATACAGTTTTTTATAATGTTGTG
TGTGGTGATTGTTCAGGTCGAATCTGTTGTATCCAGTACAGCTTTAGGTCTTCAGCTGCCCTTCTGGCGAGTACATG
CACAGGATTGTAAATGAGAAATGCAGTCATATTTCCAGTCTGCCTCTATGATGATGTTAAATTATTGCTGTTTAGCT
GTGAACAAGGGATGTACCACTGGAGGAATAGAGTATCCTTTTGTACACATTTTGAAATGCTTCTTCTGTAGTGATAG
AACAAATAAATGCAACGAATACTCTGTCTGCCCTATCCCGTGAAGTCCACACTGGCGTAAGAGAAGGCCCAGCAGAG
CAGGAATCTGCCTAGACTTTCTCCCAATGAGATCCCAATATGAGAGGGAGAAGAGATGGGCCTCAGGACAGCTGCAA
TACCACTTGGGAACACATGTGGTGTCTTGATGTGGCCAGCGCAGCAGTTCAGCACAACGTACCTCCCATCTACAACA
GTGCTGGACGTGGGAATTCTAAGTCCCAGTCTTGAGGGTGGGTGGAGATGGAGGGCAACAAGAGATACATTTCCAGT
TCTCCACTGCAGCATGCTTCAGTCATTCTGTGAGTGGCCGGGCCCAGGGCCCTCACAATTTCACTACCTTGTCTTTT
ACATAGTCATAAGAATTATCCTCAACATAGCCTTTTGACGCTGTAAATCTTGAGTATTCATTTACCCTTTTCTGATC
TCCTGGAAACAGCTGCCTGCCTGCATTGCACTTCTCTTC

FIG. 14C

CCGAGGAGTGGGGTAAATTTAAAAGTCAAGTTATAGTTTGGATGTTAGTATAGAATTTTGAAATTGGGAATTAAAAA
TCAGGACTGGGGACTGGGAGACCAAAAATTTCTGATCCCATTTCTGATGGATGTGTCACACCTTTTCTGTCAAAATA
AAATGTCTTGGAGGTTATGACTCCTTGGTGAAA

>NM_001220765.2 Homo sapiens IKAROS family zinc finger 1 (IKZF1), transcript variant 2, mRNA (SEQ ID NO:22)
ATTGTGAAAGAAAGCTGGGAAGAGCTCCGCGGCCAAGTTAGCAGGACACTCTAACAAGTGACTGCGCGGCCCGCGCC
CGGGGCGGTGACTGCGGCAAGCCCCCTGGGTCCCCGCGCGGCGCATCCCAGCCTGGGCGGGACGCTCGGCCGCGGCG
AGGCGGGCAAGCCTGGCAGGGCAGAGGGAGCCCCGGCTCCGAGGTTGCTCTTCGCACCCGAGGATCAGTCTTGGCCC
CAAAGCGCGACGCACAAATCCACATAACCTGAGGACCATGGATGCTGATGAGGGTCAAGACATGTCCCAAGTTTCAG
GGAAGGAAAGCCCCCCTGTAAGCGATACTCCAGATGAGGGCGATGAGCCCATGCCGATCCCCGAGGACCTCTCCACC
ACCTCGGGAGGACAGCAAAGCTCCAAGAGTGACAGAGTCGTGGCCAGTAATGTTAAAGTAGAGACTCAGAGTGATGA
AGAGAATGGGCGTGCCTGTGAAATGAATGGGGAAGAATGTGCGGAGGATTTACGAATGCTTGATGCCTCGGGAGAGA
AAATGAATGGCTCCCACAGGGACCAAGGCAGCTCGGCTTTGTCGGGAGTTGGAGGCATTCGACTTCCTAACGGAAAA
CTAAAGTGTGATATCTGTGGGATCATTTGCATCGGGCCCAATGTGCTCATGGTTCACAAAAGAAGCCACACTGGAGA
ACGGCCCTTCCAGTGCAATCAGTGCGGGGCCTCATTCACCCAGAAGGGCAACCTGCTCCGGCACATCAAGCTGCATT
CCGGGGAGAAGCCCTTCAAATGCCACCTCTGCAACTACGCCTGCCGCCGGAGGGACGCCCTCACTGGCCACCTGAGG
ACGCACTCCGTCATTAAAGAAGAAACTAATCACAGTGAAATGGCAGAAGACCTGTGCAAGATAGGATCAGAGAGATC
TCTCGTGCTGGACAGACTAGCAAGTAACGTCGCCAAACGTAAGAGCTCTATGCCTCAGAAATTTCTTGGGGACAAGG
GCCTGTCCGACACGCCCTACGACAGCAGCGCCAGCTACGAGAAGGAGAACGAAATGATGAAGTCCCACGTGATGGAC
CAAGCCATCAACAACGCCATCAACTACCTGGGGGCCGAGTCCCTGCGCCCGCTGGTGCAGACGCCCCCGGGCGGTTC
CGAGGTGGTCCCGGTCATCAGCCCGATGTACCAGCTGCACAAGCCGCTCGCGGAGGGCACCCCGCGCTCCAACCACT
CGGCCCAGGACAGCGCCGTGGAGAACCTGCTGCTGCTCTCCAAGGCCAAGTTGGTGCCCTCGGAGCGCGAGGCGTCC
CCGAGCAACAGCTGCCAAGACTCCACGGACACCGAGAGCAACAACGAGGAGCAGCGCAGCGGTCTCATCTACCTGAC
CAACCACATCGCCCCGCACGCGCGCAACGGGCTGTCGCTCAAGGAGGAGCACCGCGCCTACGACCTGCTGCGCGCCG
CCTCCGAGAACTCGCAGGACGCGCTCCGCGTGGTCAGCACCAGCGGGGAGCAGATGAAGGTGTACAAGTGCGAACAC
TGCCGGGTGCTCTTCCTGGATCACGTCATGTACACCATCCACATGGGCTGCCACGGCTTCCGTGATCCTTTTGAGTG
CAACATGTGCGGCTACCACAGCCAGGACCGGTACGAGTTCTCGTCGCACATAACGCGAGGGGAGCACCGCTTCCACA
TGAGCTAAAGCCCTCCCGCGCCCCCACCCCAGACCCCGAGCCACCCCAGGAAAAGCACAAGGACTGCCGCCTTCTCG
CTCCCGCCAGCAGCATAGACTGGACTGGACCAGACAATGTTGTGTTTGGATTTGTAACTGTTTTTTGTTTTTTGTTT
GAGTTGGTTGATTGGGGTTTGATTTGCTTTTGAAAAGATTTTTATTTTTAGAGGCAGGGCTGCATTGGGAGCATCCA
GAACTGCTACCTTCCTAGATGTTTCCCCAGACCGCTGGCTGAGATTCCCTCACCTGTCGCTTCCTAGAATCCCCTTC
TCCAAACGATTAGTCTAAATTTTCAGAGAGAAATAGATAAAACACGCCACAGCCTGGGAAGGAGCGTGCTCTACCCT
GTGCTAAGCACGGGGTTCGCGCACCAGGTGTCTTTTTCCAGTCCCCAGAAGCAGAGAGCACAGCCCCTGCTGTGTGG
GTCTGCAGGTGAGCAGACAGGACAGGTGTGCCGCCACCCAAGTGCCAAGACACAGCAGGGCCAACAACCTGTGCCCA
GGCCAGCTTCGAGCTACATGCATCTAGGGCGGAGAGGCTGCACTTGTGAGAGAAAATACTATTTCAAGTCATATTCT
GCGTAGGAAAATGAATTGGTTGGGGAAAGTCGTGTCTGTCAGACTGCCCTGGGTGGAGGGAGACGCCGGGCTAGAGC
CTTTGGGATCGTCCTGGATTCACTGGCTTTGCGGAGGCTGCTCAGATGGCCTGAGCCTCCCGAGGCTTGCTGCCCCG
TAGGAGGAGACTGTCTTCCCGTGGGCATATCTGGGGAGCCCTGTTCCCCGCTTTTTCACTCCCATACCTTTAATGGC
CCCCAAAATCTGTCACTACAATTTAAACACCAGTCCCGAAATTTGGATCTTCTTTCTTTTTGAATCTCTCAAACGGC
AACATTCCTCAGAAACCAAAGCTTTATTTCAAATCTCTTCCTTCCCTGGCTGGTTCCATCTAGTACCAGAGGCCTCT
TTTCCTGAAGAAATCCAATCCTAGCCCTCATTTTAATTATGTACATCTGTTTGTAGCCACAAGCCTGAATTTCTCAG
TGTTGGTAAGTTTCTTTACCTACCCTCACTATATATTATTCTCGTTTTAAAACCCATAAAGGAGTGATTTAGAACAG
TCATTAATTTTCAACTCAATGAAATATGTGAAGCCCAGCATCTCTGTTGCTAACACACAGAGCTCACCTGTTTGAAA
CCAAGCTTTCAAACATGTTGAAGCTCTTTACTGTAAAGGCAAGCCAGCATGTGTGTCCACACATACATAGGATGGCT
GGCTCTGCACCTGTAGGATATTGGAATGCACAGGGCAATTGAGGGACTGAGCCAGACCTTCGGAGAGTAATGCCACC
AGATCCCCTAGGAAAGAGGAGGCAAATGGCACTGCAGGTGAGAACCCCGCCCATCCGTGCTATGACATGGAGGCACT
GAAGCCCGAGGAAGGTGTGTGGAGATTCTAATCCCAACAAGCAAGGGTCTCCTTCAAGATTAATGCTATCAATCATT
AAGGTCATTACTCTCAACCACCTAGGCAATGAAGAATATACCATTTCAAATATTTACAGTACTTGTCTTCACCAACA
CTGTCCCAAGGTGAAATGAAGCAACAGAGAGGAAATTGTACATAAGTACCTCAGCATTTAATCCAAACAGGGGTTCT
TAGTCTCAGCACTATGACATTTTGGGCTGACTACTTATTTGTTAGGCGGGAGCTCTCCTGTGCATTGTAGGATAATT
AGCAGTATCCCTGGTGGCTACCCAATAGACGCCAGTAGCACCCCGAATTGACAACCCAAACTCTCCAGACATCACCA
ACTGTCCCCTGCGAGGAGAAATCACTCCTGGGGGAGAACCACTGACCCAAATGAATTCTAAACCAATCAAATGTCTG
GGAAGCCCTCCAAGAAAAAAAATAGAAAAGCACTTGAAGAATATTCCCAATATTCCCGGTCAGCAGTATCAAGGCTG
ACTTGTGTTCATGTGGAGTCATTATAAATTCTATAAATCAATTATTCCCCTTCGGTCTTAAAAATATATTTCCTCAT
AAACATTTGAGTTTTGTTGAAAAGATGGAGTTTACAAAGATACCATTCTTGAGTCATGGATTTCTCTGCTCACAGAA
GGGTGTGGCATTTGGAAACGGGAATAAACAAAATTGCTGCACCAATGCACTGAGTGAAGGAAGAGAGACAGAGGATC
AAGGGCTTT

FIG. 14D

AGACAGCACTCCTTCAATATGCAATCACAGAGAAAGATGCGCCTTATCCAAGTTAATATCTCTAAGGTGAGAGCCTT
CTTAGAGTCAGTTTGTTGCAAATTTCACCTACTCTGTTCTTTTCCATCCATCCCCCTGAGTCAGTTGGTTGAAGGGA
GTTATTTTTTCAAGTGGAATTCAAACAAAGCTCAAACCAGAACTGTAAATAGTGATTGCAGGAATTCTTTTCTAAAC
TGCTTTGCCCTTTCCTCTCACTGCCTTTTATAGCCAATATAAATGTCTCTTTGCACACCTTTTGTTGTGGTTTTATA
TTGTAACACCATTTTTCTTTGAAACTATTGTATTTAAAGTAAGGTTTCATATTATGTCAGCAAGTAATTAACTTATG
TTTAAAAGGTGGCCATATCATGTACCAAAAGTTGCTGAAGTTTCTCTTCTAGCTGGTAAAGTAGGAGTTTGCATGAC
TTCACACTTTTTTTGCGTAGTTTCTTCTGTTGTATGATGGCGTGAGTGTGTGTCTTGGGTACCGCTGTGTACTACTG
TGTGCCTAGATTCCATGCACTCTCGTTGTGTTTGAAGTAAATATTGGAGACCGGAGGGTAACAGGTTGGCCTGTTGA
TTACAGCTAGTAATCGCTGTGTCTTGTTCCGCCCCCTCCCTGACACCCCAGCTTCCCAGGATGTGGAAAGCCTGGAT
CTCAGCTCCTTGCCCCATATCCCTTCTGTAATTTGTACCTAAAGAGTGTGATTATCCTAATTCAAGAGTCACTAAAA
CTCATCACATTATCATTGCATATCAGCAAAGGGTAAAGTCCTAGCACCAATTGCTTCACATACCAGCATGTTCCATT
TCCAATTTAGAATTAGCCACATAATAAAATCTTAGAATCTTCCTTGAGAAAGAGCTGCCTGAGATGTAGTTTTGTTA
TATGGTTCCCCACCGACCATTTTTGTGCTTTTTTCTTGTTTTGTTTTGTTTTGACTGCACTGTGAGTTTTGTAGTGT
CCTCTTCTTGCCAAAACAAACGCGAGATGAACTGGACTTATGTAGACAAATCGTGATGCCAGTGTATCCTTCCTTTC
TTCAGTTCCAGCAATAATGAATGGTCAACTTTTTTAAAATCTAGATCTCTCTCATTCATTTCAATGTATTTTTACTT
TAAGATGAACCAAAATTATTAGACTTATTTAAGATGTACAGGCATCAGAAAAAAGAAGCACATAATGCTTTTGGTGC
GATGGCACTCACTGTGAACATGTGTAACCACATATTAATATGCAATATTGTTTCCAATACTTTCTAATACAGTTTTT
TATAATGTTGTGTGTGGTGATTGTTCAGGTCGAATCTGTTGTATCCAGTACAGCTTTAGGTCTTCAGCTGCCCTTCT
GGCGAGTACATGCACAGGATTGTAAATGAGAAATGCAGTCATATTTCCAGTCTGCCTCTATGATGATGTTAAATTAT
TGCTGTTTAGCTGTGAACAAGGGATGTACCACTGGAGGAATAGAGTATCCTTTTGTACACATTTTGAAATGCTTCTT
CTGTAGTGATAGAACAAATAAATGCAACGAATACTCTGTCTGCCCTATCCCGTGAAGTCCACACTGGCGTAAGAGAA
GGCCCAGCAGAGCAGGAATCTGCCTAGACTTTCTCCCAATGAGATCCCAATATGAGAGGGAGAAGAGATGGGCCTCA
GGACAGCTGCAATACCACTTGGGAACACATGTGGTGTCTTGATGTGGCCAGCGCAGCAGTTCAGCACAACGTACCTC
CCATCTACAACAGTGCTGGACGTGGGAATTCTAAGTCCCAGTCTTGAGGGTGGGTGGAGATGGAGGGCAACAAGAGA
TACATTTCCAGTTCTCCACTGCAGCATGCTTCAGTCATTCTGTGAGTGGCCGGGCCCAGGGCCCTCACAATTTCACT
ACCTTGTCTTTTACATAGTCATAAGAATTATCCTCAACATAGCCTTTTGACGCTGTAAATCTTGAGTATTCATTTAC
CCTTTTCTGATCTCCTGGAAACAGCTGCCTGCCTGCATTGCACTTCTCTTCCCGAGGAGTGGGGTAAATTTAAAAGT
CAAGTTATAGTTTGGATGTTAGTATAGAATTTTGAAATTGGGAATTAAAAATCAGGACTGGGGACTGGGAGACCAAA
AATTTCTGATCCCATTTCTGATGGATGTGTCACACCTTTTCTGTCAAAATAAAATGTCTTGGAGGTTATGACTCCTT
GGTGAAAAAAAAAAAAAAAAAA

>NM_001291838.1 Homo sapiens IKAROS family zinc finger 1 (IKZF1), transcript variant Ik-2, mRNA (SEQ ID NO:23)
ATATTTGGCAAGTGGTTCCACCTTTCTCTGCACCCTGGTGGAGTGTGAAGGCAGCAGAGGAACCTTTTGGAGGAGGA
AGAGGACACAGAGGCCCTGTAGCCAGGCACCAAGATCCCTCCCAGGTGGCTGGGTCTGAGGGGAACTCCGAGCAGCC
CTAGGTCCTCAAAGTCTGGATTTGTGTGGAAAAGGCAGCTCTCACTTGGCCTTGGCGAGGCCTCGGTTGGTTGATAA
CCTGAGGACCATGGATGCTGATGAGGGTCAAGACATGTCCCAAGTTTCAGGGAAGGAAAGCCCCCCTGTAAGCGATA
CTCCAGATGAGGGCGATGAGCCCATGCCGATCCCCGAGGACCTCTCCACCACCTCGGGAGGACAGCAAAGCTCCAAG
AGTGACAGAGTCGTGGGAGAACGGCCCTTCCAGTGCAATCAGTGCGGGGCCTCATTCACCCAGAAGGGCAACCTGCT
CCGGCACATCAAGCTGCATTCCGGGGAGAAGCCCTTCAAATGCCACCTCTGCAACTACGCCTGCCGCCGGAGGGACG
CCCTCACTGGCCACCTGAGGACGCACTCCGTTGGTAAACCTCACAAATGTGGATATTGTGGCCGAAGCTATAAACAG
CGAAGCTCTTTAGAGGAACATAAAGAGCGCTGCCACAACTACTTGGAAAGCATGGGCCTTCCGGGCACACTGTACCC
AGTCATTAAAGAAGAAACTAATCACAGTGAAATGGCAGAAGACCTGTGCAAGATAGGATCAGAGAGATCTCTCGTGC
TGGACAGACTAGCAAGTAACGTCGCCAAACGTAAGAGCTCTATGCCTCAGAAATTTCTTGGGGACAAGGGCCTGTCC
GACACGCCCTACGACAGCAGCGCCAGCTACGAGAAGGAGAACGAAATGATGAAGTCCCACGTGATGGACCAAGCCAT
CAACAACGCCATCAACTACCTGGGGGCCGAGTCCCTGCGCCCGCTGGTGCAGACGCCCCCGGGCGGTTCCGAGGTGG
TCCCGGTCATCAGCCCGATGTACCAGCTGCACAAGCCGCTCGCGGAGGGCACCCCGCGCTCCAACCACTCGGCCCAG
GACAGCGCCGTGGAGAACCTGCTGCTGCTCTCCAAGGCCAAGTTGGTGCCCTCGGAGCGCGAGGCGTCCCCGAGCAA
CAGCTGCCAAGACTCCACGGACACCGAGAGCAACAACGAGGAGCAGCGCAGCGGTCTCATCTACCTGACCAACCACA
TCGCCCCGCACGCGCGCAACGGGCTGTCGCTCAAGGAGGAGCACCGCGCCTACGACCTGCTGCGCGCCGCCTCCGAG
AACTCGCAGGACGCGCTCCGCGTGGTCAGCACCAGCGGGGAGCAGATGAAGGTGTACAAGTGCGAACACTGCCGGGT
GCTCTTCCTGGATCACGTCATGTACACCATCCACATGGGCTGCCACGGCTTCCGTGATCCTTTTGAGTGCAACATGT
GCGGCTACCACAGCCAGGACCGGTACGAGTTCTCGTCGCACATAACGCGAGGGGAGCACCGCTTCCACATGAGCTAA
AGCCCTCCCGCGCCCCCACCCCAGACCCCGAGCCACCCCAGGAAAAGCACAAGGACTGCCGCCTTCTCGCTCCCGCC
AGCAGCATAGACTGGACTGGACCAGACAATGTTGTGTTTGGATTTGTAACTGTTTTTTGTTTTTTGTTTGAGTTGGT
TGATTGGGGTTTGATTTGCTTTTGAAAAGATTTTTATTTTTAGAGGCAGGGCTGCATTGGGAGCATCCAGAACTGCT
ACCTTCCTAGATGTTTCCCCAGACCGCTGGCTGAGATTCCCTCACCTGTCGCTTCCTAGAATCCCCTTCTCCAAACG
ATTAGTCTAAATTTTCAGAGAGAAATAGATAAAACACGCCACAGCCTGGGAAGGAGCGTGCTCTACCCTGTGCTAAG
CACGGGGTTCGCGCACCAGGTGTCTTTTTCCAGTCCCCAGAAG

FIG. 14E

CAGAGAGCACAGCCCCTGCTGTGTGGGTCTGCAGGTGAGCAGACAGGACAGGTGTGCCGCCACCCAAGTGCCAAGAC
ACAGCAGGGCCAACAACCTGTGCCCAGGCCAGCTTCGAGCTACATGCATCTAGGGCGGAGAGGCTGCACTTGTGAGA
GAAAATACTATTTCAAGTCATATTCTGCGTAGGAAAATGAATTGGTTGGGGAAAGTCGTGTCTGTCAGACTGCCCTG
GGTGGAGGGAGACGCCGGGCTAGAGCCTTTGGGATCGTCCTGGATTCACTGGCTTTGCGGAGGCTGCTCAGATGGCC
TGAGCCTCCCGAGGCTTGCTGCCCCGTAGGAGGAGACTGTCTTCCCGTGGGCATATCTGGGGAGCCCTGTTCCCCGC
TTTTTCACTCCCATACCTTTAATGGCCCCCAAAATCTGTCACTACAATTTAAACACCAGTCCCGAAATTTGGATCTT
CTTTCTTTTTGAATCTCTCAAACGGCAACATTCCTCAGAAACCAAAGCTTTATTTCAAATCTCTTCCTTCCCTGGCT
GGTTCCATCTAGTACCAGAGGCCTCTTTTCCTGAAGAAATCCAATCCTAGCCCTCATTTTAATTATGTACATCTGTT
TGTAGCCACAAGCCTGAATTTCTCAGTGTTGGTAAGTTTCTTTACCTACCCTCACTATATATTATTCTCGTTTTAAA
ACCCATAAAGGAGTGATTTAGAACAGTCATTAATTTTCAACTCAATGAAATATGTGAAGCCCAGCATCTCTGTTGCT
AACACACAGAGCTCACCTGTTTGAAACCAAGCTTTCAAACATGTTGAAGCTCTTTACTGTAAAGGCAAGCCAGCATG
TGTGTCCACACATACATAGGATGGCTGGCTCTGCACCTGTAGGATATTGGAATGCACAGGGCAATTGAGGGACTGAG
CCAGACCTTCGGAGAGTAATGCCACCAGATCCCCTAGGAAAGAGGAGGCAAATGGCACTGCAGGTGAGAACCCCGCC
CATCCGTGCTATGACATGGAGGCACTGAAGCCCGAGGAAGGTGTGTGGAGATTCTAATCCCAACAAGCAAGGGTCTC
CTTCAAGATTAATGCTATCAATCATTAAGGTCATTACTCTCAACCACCTAGGCAATGAAGAATATACCATTTCAAAT
ATTTACAGTACTTGTCTTCACCAACACTGTCCCAAGGTGAAATGAAGCAACAGAGAGGAAATTGTACATAAGTACCT
CAGCATTTAATCCAAACAGGGGTTCTTAGTCTCAGCACTATGACATTTTGGGCTGACTACTTATTTGTTAGGCGGGA
GCTCTCCTGTGCATTGTAGGATAATTAGCAGTATCCCTGGTGGCTACCCAATAGACGCCAGTAGCACCCCGAATTGA
CAACCCAAACTCTCCAGACATCACCAACTGTCCCCTGCGAGGAGAAATCACTCCTGGGGGAGAACCACTGACCCAAA
TGAATTCTAAACCAATCAAATGTCTGGGAAGCCCTCCAAGAAAAAAAATAGAAAAGCACTTGAAGAATATTCCCAAT
ATTCCCGGTCAGCAGTATCAAGGCTGACTTGTGTTCATGTGGAGTCATTATAAATTCTATAAATCAATTATTCCCCT
TCGGTCTTAAAAATATATTTCCTCATAAACATTTGAGTTTTGTTGAAAAGATGGAGTTTACAAAGATACCATTCTTG
AGTCATGGATTTCTCTGCTCACAGAAGGGTGTGGCATTTGGAAACGGGAATAAACAAAATTGCTGCACCAATGCACT
GAGTGAAGGAAGAGAGACAGAGGATCAAGGGCTTTAGACAGCACTCCTTCAATATGCAATCACAGAGAAAGATGCGC
CTTATCCAAGTTAATATCTCTAAGGTGAGAGCCTTCTTAGAGTCAGTTTGTTGCAAATTTCACCTACTCTGTTCTTT
TCCATCCATCCCCCTGAGTCAGTTGGTTGAAGGGAGTTATTTTTTCAAGTGGAATTCAAACAAAGCTCAAACCAGAA
CTGTAAATAGTGATTGCAGGAATTCTTTTCTAAACTGCTTTGCCCTTTCCTCTCACTGCCTTTTATAGCCAATATAA
ATGTCTCTTTGCACACCTTTTGTTGTGGTTTTATATTGTAACACCATTTTTCTTTGAAACTATTGTATTTAAAGTAA
GGTTTCATATTATGTCAGCAAGTAATTAACTTATGTTTAAAAGGTGGCCATATCATGTACCAAAAGTTGCTGAAGTT
TCTCTTCTAGCTGGTAAAGTAGGAGTTTGCATGACTTCACACTTTTTTTGCGTAGTTTCTTCTGTTGTATGATGGCG
TGAGTGTGTGTCTTGGGTACCGCTGTGTACTACTGTGTGCCTAGATTCCATGCACTCTCGTTGTGTTTGAAGTAAAT
ATTGGAGACCGGAGGGTAACAGGTTGGCCTGTTGATTACAGCTAGTAATCGCTGTGTCTTGTTCCGCCCCCTCCCTG
ACACCCCAGCTTCCCAGGATGTGGAAAGCCTGGATCTCAGCTCCTTGCCCCATATCCCTTCTGTAATTTGTACCTAA
AGAGTGTGATTATCCTAATTCAAGAGTCACTAAAACTCATCACATTATCATTGCATATCAGCAAAGGGTAAAGTCCT
AGCACCAATTGCTTCACATACCAGCATGTTCCATTTCCAATTTAGAATTAGCCACATAATAAAATCTTAGAATCTTC
CTTGAGAAAGAGCTGCCTGAGATGTAGTTTTGTTATATGGTTCCCCACCGACCATTTTTGTGCTTTTTTCTTGTTTT
GTTTTGTTTTGACTGCACTGTGAGTTTTGTAGTGTCCTCTTCTTGCCAAAACAAACGCGAGATGAACTGGACTTATG
TAGACAAATCGTGATGCCAGTGTATCCTTCCTTTCTTCAGTTCCAGCAATAATGAATGGTCAACTTTTTTAAAATCT
AGATCTCTCTCATTCATTTCAATGTATTTTTACTTTAAGATGAACCAAAATTATTAGACTTATTTAAGATGTACAGG
CATCAGAAAAAAGAAGCACATAATGCTTTTGGTGCGATGGCACTCACTGTGAACATGTGTAACCACATATTAATATG
CAATATTGTTTCCAATACTTTCTAATACAGTTTTTTATAATGTTGTGTGTGGTGATTGTTCAGGTCGAATCTGTTGT
ATCCAGTACAGCTTTAGGTCTTCAGCTGCCCTTCTGGCGAGTACATGCACAGGATTGTAAATGAGAAATGCAGTCAT
ATTTCCAGTCTGCCTCTATGATGATGTTAAATTATTGCTGTTTAGCTGTGAACAAGGGATGTACCACTGGAGGAATA
GAGTATCCTTTTGTACACATTTTGAAATGCTTCTTCTGTAGTGATAGAACAAATAAATGCAACGAATACTCTGTCTG
CCCTATCCCGTGAAGTCCACACTGGCGTAAGAGAAGGCCCAGCAGAGCAGGAATCTGCCTAGACTTTCTCCCAATGA
GATCCCAATATGAGAGGGAGAAGAGATGGGCCTCAGGACAGCTGCAATACCACTTGGGAACACATGTGGTGTCTTGA
TGTGGCCAGCGCAGCAGTTCAGCACAACGTACCTCCCATCTACAACAGTGCTGGACGTGGGAATTCTAAGTCCCAGT
CTTGAGGGTGGGTGGAGATGGAGGGCAACAAGAGATACATTTCCAGTTCTCCACTGCAGCATGCTTCAGTCATTCTG
TGAGTGGCCGGGCCCAGGGCCCTCACAATTTCACTACCTTGTCTTTTACATAGTCATAAGAATTATCCTCAACATAG
CCTTTTGACGCTGTAAATCTTGAGTATTCATTTACCCTTTTCTGATCTCCTGGAAACAGCTGCCTGCCTGCATTGCA
CTTCTCTTCCCGAGGAGTGGGGTAAATTTAAAAGTCAAGTTATAGTTTGGATGTTAGTATAGAATTTTGAAATTGGG
AATTAAAAATCAGGACTGGGGACTGGGAGACCAAAAATTTCTGATCCCATTTCTGATGGATGTGTCACACCTTTTCT
GTCAAAATAAAATGTCTTGGAGGTTATGACTCCTTGGTGAAAAAAAAAAAAAAAAAA

>NM_001220767.2 Homo sapiens IKAROS family zinc finger 1 (IKZF1), transcript variant 4, mRNA (SEQ ID NO:24)
ATAACCTGAGGACCATGGATGCTGATGAGGGTCAAGACATGTCCCAAGTTTCAGGGAAGGAAAGCCCCCCTGTAAGC
GATACTCCAGATGAGGGCGATGAGCCCATGCCGATCCCCGAGGACCTCTCCACCACCTCGGGAGGACAGCAAAGCTC
CAAGAGTGAC

FIG. 14F

AGAGTCGTGGGAGAACGGCCCTTCCAGTGCAATCAGTGCGGGGCCTCATTCACCCAGAAGGGCAACCTGCTCCGGCA
CATCAAGCTGCATTCCGGGGAGAAGCCCTTCAAATGCCACCTCTGCAACTACGCCTGCCGCCGGAGGGACGCCCTCA
CTGGCCACCTGAGGACGCACTCCGTTGGTAAACCTCACAAATGTGGATATTGTGGCCGAAGCTATAAACAGCGAAGC
TCTTTAGAGGAACATAAAGAGCGCTGCCACAACTACTTGGAAAGCATGGGCCTTCCGGGCACACTGTACCCAGTCAT
TAAAGAAGAAACTAATCACAGTGAAATGGCAGAAGACCTGTGCAAGATAGGATCAGAGAGATCTCTCGTGCTGGACA
GACTAGCAAGTAACGTCGCCAAACGGGACAAGGGCCTGTCCGACACGCCCTACGACAGCAGCGCCAGCTACGAGAAG
GAGAACGAAATGATGAAGTCCCACGTGATGGACCAAGCCATCAACAACGCCATCAACTACCTGGGGGCCGAGTCCCT
GCGCCCGCTGGTGCAGACGCCCCCGGGCGGTTCCGAGGTGGTCCCGGTCATCAGCCCGATGTACCAGCTGCACAAGC
CGCTCGCGGAGGGCACCCCGCGCTCCAACCACTCGGCCCAGGACAGCGCCGTGGAGAACCTGCTGCTGCTCTCCAAG
GCCAAGTTGGTGCCCTCGGAGCGCGAGGCGTCCCCGAGCAACAGCTGCCAAGACTCCACGGACACCGAGAGCAACAA
CGAGGAGCAGCGCAGCGGTCTCATCTACCTGACCAACCACATCGCCCCGCACGCGCGCAACGGGCTGTCGCTCAAGG
AGGAGCACCGCGCCTACGACCTGCTGCGCGCCGCCTCCGAGAACTCGCAGGACGCGCTCCGCGTGGTCAGCACCAGC
GGGGAGCAGATGAAGGTGTACAAGTGCGAACACTGCCGGGTGCTCTTCCTGGATCACGTCATGTACACCATCCACAT
GGGCTGCCACGGCTTCCGTGATCCTTTTGAGTGCAACATGTGCGGCTACCACAGCCAGGACCGGTACGAGTTCTCGT
CGCACATAACGCGAGGGGAGCACCGCTTCCACATGAGCTAAAGCCCTCCCGCGCCCCCACCCCAGACCCCGAGCCAC
CCCAGGAAAAGCACAAGGACTGCCGCCTTCTCGCTCCCGCCAGCAGCATAGACTGGACTGGACCAGACAATGTTGTG
TTTGGATTTGTAACTGTTTTTTGTTTTTTGTTTGAGTTGGTTGATTGGGGTTTGATTTGCTTTTGAAAAGATTTTTA
TTTTTAGAGGCAGGGCTGCATTGGGAGCATCCAGAACTGCTACCTTCCTAGATGTTTCCCCAGACCGCTGGCTGAGA
TTCCCTCACCTGTCGCTTCCTAGAATCCCCTTCTCCAAACGATTAGTCTAAATTTTCAGAGAGAAATAGATAAAACA
CGCCACAGCCTGGGAAGGAGCGTGCTCTACCCTGTGCTAAGCACGGGGTTCGCGCACCAGGTGTCTTTTTCCAGTCC
CCAGAAGCAGAGAGCACAGCCCCTGCTGTGTGGGTCTGCAGGTGAGCAGACAGGACAGGTGTGCCGCCACCCAAGTG
CCAAGACACAGCAGGGCCAACAACCTGTGCCCAGGCCAGCTTCGAGCTACATGCATCTAGGGCGGAGAGGCTGCACT
TGTGAGAGAAAATACTATTTCAAGTCATATTCTGCGTAGGAAAATGAATTGGTTGGGGAAAGTCGTGTCTGTCAGAC
TGCCCTGGGTGGAGGGAGACGCCGGGCTAGAGCCTTTGGGATCGTCCTGGATTCACTGGCTTTGCGGAGGCTGCTCA
GATGGCCTGAGCCTCCCGAGGCTTGCTGCCCCGTAGGAGGAGACTGTCTTCCCGTGGGCATATCTGGGGAGCCCTGT
TCCCCGCTTTTTCACTCCCATACCTTTAATGGCCCCCAAAATCTGTCACTACAATTTAAACACCAGTCCCGAAATTT
GGATCTTCTTTCTTTTTGAATCTCTCAAACGGCAACATTCCTCAGAAACCAAAGCTTTATTTCAAATCTCTTCCTTC
CCTGGCTGGTTCCATCTAGTACCAGAGGCCTCTTTTCCTGAAGAAATCCAATCCTAGCCCTCATTTTAATTATGTAC
ATCTGTTTGTAGCCACAAGCCTGAATTTCTCAGTGTTGGTAAGTTTCTTTACCTACCCTCACTATATATTATTCTCG
TTTTAAAACCCATAAAGGAGTGATTTAGAACAGTCATTAATTTTCAACTCAATGAAATATGTGAAGCCCAGCATCTC
TGTTGCTAACACACAGAGCTCACCTGTTTGAAACCAAGCTTTCAAACATGTTGAAGCTCTTTACTGTAAAGGCAAGC
CAGCATGTGTGTCCACACATACATAGGATGGCTGGCTCTGCACCTGTAGGATATTGGAATGCACAGGGCAATTGAGG
GACTGAGCCAGACCTTCGGAGAGTAATGCCACCAGATCCCCTAGGAAAGAGGAGGCAAATGGCACTGCAGGTGAGAA
CCCCGCCCATCCGTGCTATGACATGGAGGCACTGAAGCCCGAGGAAGGTGTGTGGAGATTCTAATCCCAACAAGCAA
GGGTCTCCTTCAAGATTAATGCTATCAATCATTAAGGTCATTACTCTCAACCACCTAGGCAATGAAGAATATACCAT
TTCAAATATTTACAGTACTTGTCTTCACCAACACTGTCCCAAGGTGAAATGAAGCAACAGAGAGGAAATTGTACATA
AGTACCTCAGCATTTAATCCAAACAGGGGTTCTTAGTCTCAGCACTATGACATTTTGGGCTGACTACTTATTTGTTA
GGCGGGAGCTCTCCTGTGCATTGTAGGATAATTAGCAGTATCCCTGGTGGCTACCCAATAGACGCCAGTAGCACCCC
GAATTGACAACCCAAACTCTCCAGACATCACCAACTGTCCCCTGCGAGGAGAAATCACTCCTGGGGGAGAACCACTG
ACCCAAATGAATTCTAAACCAATCAAATGTCTGGGAAGCCCTCCAAGAAAAAAAATAGAAAAGCACTTGAAGAATAT
TCCCAATATTCCCGGTCAGCAGTATCAAGGCTGACTTGTGTTCATGTGGAGTCATTATAAATTCTATAAATCAATTA
TTCCCCTTCGGTCTTAAAAATATATTTCCTCATAAACATTTGAGTTTTGTTGAAAAGATGGAGTTTACAAAGATACC
ATTCTTGAGTCATGGATTTCTCTGCTCACAGAAGGGTGTGGCATTTGGAAACGGGAATAAACAAAATTGCTGCACCA
ATGCACTGAGTGAAGGAAGAGAGACAGAGGATCAAGGGCTTTAGACAGCACTCCTTCAATATGCAATCACAGAGAAA
GATGCGCCTTATCCAAGTTAATATCTCTAAGGTGAGAGCCTTCTTAGAGTCAGTTTGTTGCAAATTTCACCTACTCT
GTTCTTTTCCATCCATCCCCCTGAGTCAGTTGGTTGAAGGGAGTTATTTTTTCAAGTGGAATTCAAACAAAGCTCAA
ACCAGAACTGTAAATAGTGATTGCAGGAATTCTTTTCTAAACTGCTTTGCCCTTTCCTCTCACTGCCTTTTATAGCC
AATATAAATGTCTCTTTGCACACCTTTTGTTGTGGTTTTATATTGTAACACCATTTTTCTTTGAAACTATTGTATTT
AAAGTAAGGTTTCATATTATGTCAGCAAGTAATTAACTTATGTTTAAAAGGTGGCCATATCATGTACCAAAAGTTGC
TGAAGTTTCTCTTCTAGCTGGTAAAGTAGGAGTTTGCATGACTTCACACTTTTTTTGCGTAGTTTCTTCTGTTGTAT
GATGGCGTGAGTGTGTGTCTTGGGTACCGCTGTGTACTACTGTGTGCCTAGATTCCATGCACTCTCGTTGTGTTTGA
AGTAAATATTGGAGACCGGAGGGTAACAGGTTGGCCTGTTGATTACAGCTAGTAATCGCTGTGTCTTGTTCCGCCCC
CTCCCTGACACCCCAGCTTCCCAGGATGTGGAAAGCCTGGATCTCAGCTCCTTGCCCCATATCCCTTCTGTAATTTG
TACCTAAAGAGTGTGATTATCCTAATTCAAGAGTCACTAAAACTCATCACATTATCATTGCATATCAGCAAAGGGTA
AAGTCCTAGCACCAATTGCTTCACATACCAGCATGTTCCATTTCCAATTTAGAATTAGCCACATAATAAAATCTTAG
AATCTTCCTTGAGAAAGAGCTGCCTGAGATGTAGTTTTGTTATATGGTTCCCCACCGACCATTTTTGTGCTTTTTTC
TTGTTTTGTTTTGTTTTGACTGCACTGTGAGTTTTGTAGTGTCCTCTTCTTGCCAAAACAAACGCGAGATGAACTGG
ACTTATGTAGACAAATCGTGATGCCAGTGTATCCTTCCTTTCTTCAGTTCCAGCAATAATGAATGGTCAACTTTTTT
AAAATCTAGATCTCTCTCATTCATTTCAATGTATTTTTACTTTA

FIG. 14G

AGATGAACCAAAATTATTAGACTTATTTAAGATGTACAGGCATCAGAAAAAAGAAGCACATAATGCTTTTGGTGCGA
TGGCACTCACTGTGAACATGTGTAACCACATATTAATATGCAATATTGTTTCCAATACTTTCTAATACAGTTTTTTA
TAATGTTGTGTGTGGTGATTGTTCAGGTCGAATCTGTTGTATCCAGTACAGCTTTAGGTCTTCAGCTGCCCTTCTGG
CGAGTACATGCACAGGATTGTAAATGAGAAATGCAGTCATATTTCCAGTCTGCCTCTATGATGATGTTAAATTATTG
CTGTTTAGCTGTGAACAAGGGATGTACCACTGGAGGAATAGAGTATCCTTTTGTACACATTTTGAAATGCTTCTTCT
GTAGTGATAGAACAAATAAATGCAACGAATACTCTGTCTGCCCTATCCCGTGAAGTCCACACTGGCGTAAGAGAAGG
CCCAGCAGAGCAGGAATCTGCCTAGACTTTCTCCCAATGAGATCCCAATATGAGAGGGAGAAGAGATGGGCCTCAGG
ACAGCTGCAATACCACTTGGGAACACATGTGGTGTCTTGATGTGGCCAGCGCAGCAGTTCAGCACAACGTACCTCCC
ATCTACAACAGTGCTGGACGTGGGAATTCTAAGTCCCAGTCTTGAGGGTGGGTGGAGATGGAGGGCAACAAGAGATA
CATTTCCAGTTCTCCACTGCAGCATGCTTCAGTCATTCTGTGAGTGGCCGGGCCCAGGGCCCTCACAATTTCACTAC
CTTGTCTTTTACATAGTCATAAGAATTATCCTCAACATAGCCTTTTGACGCTGTAAATCTTGAGTATTCATTTACCC
TTTTCTGATCTCCTGGAAACAGCTGCCTGCCTGCATTGCACTTCTCTTCCCGAGGAGTGGGGTAAATTTAAAAGTCA
AGTTATAGTTTGGATGTTAGTATAGAATTTTGAAATTGGGAATTAAAAATCAGGACTGGGGACTGGGAGACCAAAAA
TTTCTGATCCCATTTCTGATGGATGTGTCACACCTTTTCTGTCAAAATAAAATGTCTTGGAGGTTATGACTCCTTGG
TGAAAAAAAAAAAAAAAAAA

>NM_001220768.2 Homo sapiens IKAROS family zinc finger 1 (IKZF1), transcript variant 5, mRNA (SEQ ID NO:25)
ATAACCTGAGGACCATGGATGCTGATGAGGGTCAAGACATGTCCCAAGTTTCAGGGAAGGAAAGCCCCCCTGTAAGC
GATACTCCAGATGAGGGCGATGAGCCCATGCCGATCCCCGAGGACCTCTCCACCACCTCGGGAGGACAGCAAAGCTC
CAAGAGTGACAGAGTCGTGGCCAGTAATGTTAAAGTAGAGACTCAGAGTGATGAAGAGAATGGGCGTGCCTGTGAAA
TGAATGGGGAAGAATGTGCGGAGGATTTACGAATGCTTGATGCCTCGGGAGAGAAAATGAATGGCTCCCACAGGGAC
CAAGGCAGCTCGGCTTTGTCGGGAGTTGGAGGCATTCGACTTCCTAACGGAAAACTAAAGTGTGATATCTGTGGGAT
CATTTGCATCGGGCCCAATGTGCTCATGGTTCACAAAAGAAGCCACACTGGAGAACGGCCCTTCCAGTGCAATCAGT
GCGGGGCCTCATTCACCCAGAAGGGCAACCTGCTCCGGCACATCAAGCTGCATTCCGGGGAGAAGCCCTTCAAATGC
CACCTCTGCAACTACGCCTGCCGCCGGAGGGACGCCCTCACTGGCCACCTGAGGACGCACTCCGGGGACAAGGGCCT
GTCCGACACGCCCTACGACAGCAGCGCCAGCTACGAGAAGGAGAACGAAATGATGAAGTCCCACGTGATGGACCAAG
CCATCAACAACGCCATCAACTACCTGGGGGCCGAGTCCCTGCGCCCGCTGGTGCAGACGCCCCCGGGCGGTTCCGAG
GTGGTCCCGGTCATCAGCCCGATGTACCAGCTGCACAAGCCGCTCGCGGAGGGCACCCCGCGCTCCAACCACTCGGC
CCAGGACAGCGCCGTGGAGAACCTGCTGCTGCTCTCCAAGGCCAAGTTGGTGCCCTCGGAGCGCGAGGCGTCCCCGA
GCAACAGCTGCCAAGACTCCACGGACACCGAGAGCAACAACGAGGAGCAGCGCAGCGGTCTCATCTACCTGACCAAC
CACATCGCCCCGCACGCGCGCAACGGGCTGTCGCTCAAGGAGGAGCACCGCGCCTACGACCTGCTGCGCGCCGCCTC
CGAGAACTCGCAGGACGCGCTCCGCGTGGTCAGCACCAGCGGGGAGCAGATGAAGGTGTACAAGTGCGAACACTGCC
GGGTGCTCTTCCTGGATCACGTCATGTACACCATCCACATGGGCTGCCACGGCTTCCGTGATCCTTTTGAGTGCAAC
ATGTGCGGCTACCACAGCCAGGACCGGTACGAGTTCTCGTCGCACATAACGCGAGGGGAGCACCGCTTCCACATGAG
CTAAAGCCCTCCCGCGCCCCCACCCCAGACCCCGAGCCACCCCAGGAAAAGCACAAGGACTGCCGCCTTCTCGCTCC
CGCCAGCAGCATAGACTGGACTGGACCAGACAATGTTGTGTTTGGATTTGTAACTGTTTTTTGTTTTTTGTTTGAGT
TGGTTGATTGGGGTTTGATTTGCTTTTGAAAAGATTTTTATTTTTAGAGGCAGGGCTGCATTGGGAGCATCCAGAAC
TGCTACCTTCCTAGATGTTTCCCCAGACCGCTGGCTGAGATTCCCTCACCTGTCGCTTCCTAGAATCCCCTTCTCCA
AACGATTAGTCTAAATTTTCAGAGAGAAATAGATAAAACACGCCACAGCCTGGGAAGGAGCGTGCTCTACCCTGTGC
TAAGCACGGGGTTCGCGCACCAGGTGTCTTTTTCCAGTCCCCAGAAGCAGAGAGCACAGCCCCTGCTGTGTGGGTCT
GCAGGTGAGCAGACAGGACAGGTGTGCCGCCACCCAAGTGCCAAGACACAGCAGGGCCAACAACCTGTGCCCAGGCC
AGCTTCGAGCTACATGCATCTAGGGCGGAGAGGCTGCACTTGTGAGAGAAAATACTATTTCAAGTCATATTCTGCGT
AGGAAAATGAATTGGTTGGGGAAAGTCGTGTCTGTCAGACTGCCCTGGGTGGAGGGAGACGCCGGGCTAGAGCCTTT
GGGATCGTCCTGGATTCACTGGCTTTGCGGAGGCTGCTCAGATGGCCTGAGCCTCCCGAGGCTTGCTGCCCCGTAGG
AGGAGACTGTCTTCCCGTGGGCATATCTGGGGAGCCCTGTTCCCCGCTTTTTCACTCCCATACCTTTAATGGCCCCC
AAAATCTGTCACTACAATTTAAACACCAGTCCCGAAATTTGGATCTTCTTTCTTTTTGAATCTCTCAAACGGCAACA
TTCCTCAGAAACCAAAGCTTTATTTCAAATCTCTTCCTTCCCTGGCTGGTTCCATCTAGTACCAGAGGCCTCTTTTC
CTGAAGAAATCCAATCCTAGCCCTCATTTTAATTATGTACATCTGTTTGTAGCCACAAGCCTGAATTTCTCAGTGTT
GGTAAGTTTCTTTACCTACCCTCACTATATATTATTCTCGTTTTAAAACCCATAAAGGAGTGATTTAGAACAGTCAT
TAATTTTCAACTCAATGAAATATGTGAAGCCCAGCATCTCTGTTGCTAACACACAGAGCTCACCTGTTTGAAACCAA
GCTTTCAAACATGTTGAAGCTCTTTACTGTAAAGGCAAGCCAGCATGTGTGTCCACACATACATAGGATGGCTGGCT
CTGCACCTGTAGGATATTGGAATGCACAGGGCAATTGAGGGACTGAGCCAGACCTTCGGAGAGTAATGCCACCAGAT
CCCCTAGGAAAGAGGAGGCAAATGGCACTGCAGGTGAGAACCCCGCCCATCCGTGCTATGACATGGAGGCACTGAAG
CCCGAGGAAGGTGTGTGGAGATTCTAATCCCAACAAGCAAGGGTCTCCTTCAAGATTAATGCTATCAATCATTAAGG
TCATTACTCTCAACCACCTAGGCAATGAAGAATATACCATTTCAAATATTTACAGTACTTGTCTTCACCAACACTGT
CCCAAGGTGAAATGAAGCAACAGAGAGGAAATTGTACATAAGTACCTCAGCATTTAATCCAAACAGGGGTTCTTAGT
CTCAGCACTATGACATTTTGGGCTGACTACT

FIG. 14H

TATTTGTTAGGCGGGAGCTCTCCTGTGCATTGTAGGATAATTAGCAGTATCCCTGGTGGCTACCCAATAGACGCCAG
TAGCACCCCGAATTGACAACCCAAACTCTCCAGACATCACCAACTGTCCCCTGCGAGGAGAAATCACTCCTGGGGGA
GAACCACTGACCCAAATGAATTCTAAACCAATCAAATGTCTGGGAAGCCCTCCAAGAAAAAAAATAGAAAAGCACTT
GAAGAATATTCCCAATATTCCCGGTCAGCAGTATCAAGGCTGACTTGTGTTCATGTGGAGTCATTATAAATTCTATA
AATCAATTATTCCCCTTCGGTCTTAAAAATATATTTCCTCATAAACATTTGAGTTTTGTTGAAAAGATGGAGTTTAC
AAAGATACCATTCTTGAGTCATGGATTTCTCTGCTCACAGAAGGGTGTGGCATTTGGAAACGGGAATAAACAAAATT
GCTGCACCAATGCACTGAGTGAAGGAAGAGAGACAGAGGATCAAGGGCTTTAGACAGCACTCCTTCAATATGCAATC
ACAGAGAAAGATGCGCCTTATCCAAGTTAATATCTCTAAGGTGAGAGCCTTCTTAGAGTCAGTTTGTTGCAAATTTC
ACCTACTCTGTTCTTTTCCATCCATCCCCCTGAGTCAGTTGGTTGAAGGGAGTTATTTTTTCAAGTGGAATTCAAAC
AAAGCTCAAACCAGAACTGTAAATAGTGATTGCAGGAATTCTTTTCTAAACTGCTTTGCCCTTTCCTCTCACTGCCT
TTTATAGCCAATATAAATGTCTCTTTGCACACCTTTTGTTGTGGTTTTATATTGTAACACCATTTTTCTTTGAAACT
ATTGTATTTAAAGTAAGGTTTCATATTATGTCAGCAAGTAATTAACTTATGTTTAAAAGGTGGCCATATCATGTACC
AAAAGTTGCTGAAGTTTCTCTTCTAGCTGGTAAAGTAGGAGTTTGCATGACTTCACACTTTTTTTGCGTAGTTTCTT
CTGTTGTATGATGGCGTGAGTGTGTGTCTTGGGTACCGCTGTGTACTACTGTGTGCCTAGATTCCATGCACTCTCGT
TGTGTTTGAAGTAAATATTGGAGACCGGAGGGTAACAGGTTGGCCTGTTGATTACAGCTAGTAATCGCTGTGTCTTG
TTCCGCCCCCTCCCTGACACCCCAGCTTCCCAGGATGTGGAAAGCCTGGATCTCAGCTCCTTGCCCCATATCCCTTC
TGTAATTTGTACCTAAAGAGTGTGATTATCCTAATTCAAGAGTCACTAAAACTCATCACATTATCATTGCATATCAG
CAAAGGGTAAAGTCCTAGCACCAATTGCTTCACATACCAGCATGTTCCATTTCCAATTTAGAATTAGCCACATAATA
AAATCTTAGAATCTTCCTTGAGAAAGAGCTGCCTGAGATGTAGTTTTGTTATATGGTTCCCCACCGACCATTTTTGT
GCTTTTTTCTTGTTTTGTTTTGTTTTGACTGCACTGTGAGTTTTGTAGTGTCCTCTTCTTGCCAAAACAAACGCGAG
ATGAACTGGACTTATGTAGACAAATCGTGATGCCAGTGTATCCTTCCTTTCTTCAGTTCCAGCAATAATGAATGGTC
AACTTTTTTAAAATCTAGATCTCTCTCATTCATTTCAATGTATTTTTACTTTAAGATGAACCAAAATTATTAGACTT
ATTTAAGATGTACAGGCATCAGAAAAAAGAAGCACATAATGCTTTTGGTGCGATGGCACTCACTGTGAACATGTGTA
ACCACATATTAATATGCAATATTGTTTCCAATACTTTCTAATACAGTTTTTTATAATGTTGTGTGTGGTGATTGTTC
AGGTCGAATCTGTTGTATCCAGTACAGCTTTAGGTCTTCAGCTGCCCTTCTGGCGAGTACATGCACAGGATTGTAAA
TGAGAAATGCAGTCATATTTCCAGTCTGCCTCTATGATGATGTTAAATTATTGCTGTTTAGCTGTGAACAAGGGATG
TACCACTGGAGGAATAGAGTATCCTTTTGTACACATTTTGAAATGCTTCTTCTGTAGTGATAGAACAAATAAATGCA
ACGAATACTCTGTCTGCCCTATCCCGTGAAGTCCACACTGGCGTAAGAGAAGGCCCAGCAGAGCAGGAATCTGCCTA
GACTTTCTCCCAATGAGATCCCAATATGAGAGGGAGAAGAGATGGGCCTCAGGACAGCTGCAATACCACTTGGGAAC
ACATGTGGTGTCTTGATGTGGCCAGCGCAGCAGTTCAGCACAACGTACCTCCCATCTACAACAGTGCTGGACGTGGG
AATTCTAAGTCCCAGTCTTGAGGGTGGGTGGAGATGGAGGGCAACAAGAGATACATTTCCAGTTCTCCACTGCAGCA
TGCTTCAGTCATTCTGTGAGTGGCCGGGCCCAGGGCCCTCACAATTTCACTACCTTGTCTTTTACATAGTCATAAGA
ATTATCCTCAACATAGCCTTTTGACGCTGTAAATCTTGAGTATTCATTTACCCTTTTCTGATCTCCTGGAAACAGCT
GCCTGCCTGCATTGCACTTCTCTTCCCGAGGAGTGGGGTAAATTTAAAAGTCAAGTTATAGTTTGGATGTTAGTATA
GAATTTTGAAATTGGGAATTAAAAATCAGGACTGGGGACTGGGAGACCAAAAATTTCTGATCCCATTTCTGATGGAT
GTGTCACACCTTTTCTGTCAAAATAAAATGTCTTGGAGGTTATGACTCCTTGGTGAAAAAAAAAAAAAAAAAA

>NM_001291839.1 Homo sapiens IKAROS family zinc finger 1 (IKZF1), transcript variant Ik-4, mRNA (SEQ ID NO:26)
GAGCGGGCTGCAGCCGGCGGCGGCGCCAGCAGATAACCTGAGGACCATGGATGCTGATGAGGGTCAAGACATGTCCC
AAGTTTCAGGGAAGGAAAGCCCCCCTGTAAGCGATACTCCAGATGAGGGCGATGAGCCCATGCCGATCCCCGAGGAC
CTCTCCACCACCTCGGGAGGACAGCAAAGCTCCAAGAGTGACAGAGTCGTGGGAGAACGGCCCTTCCAGTGCAATCA
GTGCGGGGCCTCATTCACCCAGAAGGGCAACCTGCTCCGGCACATCAAGCTGCATTCCGGGGAGAAGCCCTTCAAAT
GCCACCTCTGCAACTACGCCTGCCGCCGGAGGGACGCCCTCACTGGCCACCTGAGGACGCACTCCGTCATTAAAGAA
GAAACTAATCACAGTGAAATGGCAGAAGACCTGTGCAAGATAGGATCAGAGAGATCTCTCGTGCTGGACAGACTAGC
AAGTAACGTCGCCAAACGTAAGAGCTCTATGCCTCAGAAATTTCTTGGGGACAAGGGCCTGTCCGACACGCCCTACG
ACAGCAGCGCCAGCTACGAGAAGGAGAACGAAATGATGAAGTCCCACGTGATGGACCAAGCCATCAACAACGCCATC
AACTACCTGGGGGCCGAGTCCCTGCGCCCGCTGGTGCAGACGCCCCCGGGCGGTTCCGAGGTGGTCCCGGTCATCAG
CCCGATGTACCAGCTGCACAAGCCGCTCGCGGAGGGCACCCCGCGCTCCAACCACTCGGCCCAGGACAGCGCCGTGG
AGAACCTGCTGCTGCTCTCCAAGGCCAAGTTGGTGCCCTCGGAGCGCGAGGCGTCCCCGAGCAACAGCTGCCAAGAC
TCCACGGACACCGAGAGCAACAACGAGGAGCAGCGCAGCGGTCTCATCTACCTGACCAACCACATCGCCCCGCACGC
GCGCAACGGGCTGTCGCTCAAGGAGGAGCACCGCGCCTACGACCTGCTGCGCGCCGCCTCCGAGAACTCGCAGGACG
CGCTCCGCGTGGTCAGCACCAGCGGGGAGCAGATGAAGGTGTACAAGTGCGAACACTGCCGGGTGCTCTTCCTGGAT
CACGTCATGTACACCATCCACATGGGCTGCCACGGCTTCCGTGATCCTTTTGAGTGCAACATGTGCGGCTACCACAG
CCAGGACCGGTACGAGTTCTCGTCGCACATAACGCGAGGGGAGCACCGCTTCCACATGAGCTAAAGCCCTCCCGCGC
CCCCACCCCAGACCCCGAGCCACCCCAGGAAAAGCACAAGGACTGCCGCCTTCTCGCTCCCGCCAGCAGCATAGACT
GGACTGGACCAGACAATGTTGTGTTTGGATTTGTAACTGTTTTTTGTTTTTTGTTTGAGTTGGTTGATTGGGGTTTG
ATTTGCTT

FIG. 14I

TTGAAAAGATTTTTATTTTTAGAGGCAGGGCTGCATTGGGAGCATCCAGAACTGCTACCTTCCTAGATGTTTCCCCA
GACCGCTGGCTGAGATTCCCTCACCTGTCGCTTCCTAGAATCCCCTTCTCCAAACGATTAGTCTAAATTTTCAGAGA
GAAATAGATAAAACACGCCACAGCCTGGGAAGGAGCGTGCTCTACCCTGTGCTAAGCACGGGGTTCGCGCACCAGGT
GTCTTTTTCCAGTCCCCAGAAGCAGAGAGCACAGCCCCTGCTGTGTGGGTCTGCAGGTGAGCAGACAGGACAGGTGT
GCCGCCACCCAAGTGCCAAGACACAGCAGGGCCAACAACCTGTGCCCAGGCCAGCTTCGAGCTACATGCATCTAGGG
CGGAGAGGCTGCACTTGTGAGAGAAAATACTATTTCAAGTCATATTCTGCGTAGGAAAATGAATTGGTTGGGGAAAG
TCGTGTCTGTCAGACTGCCCTGGGTGGAGGGAGACGCCGGGCTAGAGCCTTTGGGATCGTCCTGGATTCACTGGCTT
TGCGGAGGCTGCTCAGATGGCCTGAGCCTCCCGAGGCTTGCTGCCCCGTAGGAGGAGACTGTCTTCCCGTGGGCATA
TCTGGGGAGCCCTGTTCCCCGCTTTTTCACTCCCATACCTTTAATGGCCCCCAAAATCTGTCACTACAATTTAAACA
CCAGTCCCGAAATTTGGATCTTCTTTCTTTTTGAATCTCTCAAACGGCAACATTCCTCAGAAACCAAAGCTTTATTT
CAAATCTCTTCCTTCCCTGGCTGGTTCCATCTAGTACCAGAGGCCTCTTTTCCTGAAGAAATCCAATCCTAGCCCTC
ATTTTAATTATGTACATCTGTTTGTAGCCACAAGCCTGAATTTCTCAGTGTTGGTAAGTTTCTTTACCTACCCTCAC
TATATATTATTCTCGTTTTAAAACCCATAAAGGAGTGATTTAGAACAGTCATTAATTTTCAACTCAATGAAATATGT
GAAGCCCAGCATCTCTGTTGCTAACACACAGAGCTCACCTGTTTGAAACCAAGCTTTCAAACATGTTGAAGCTCTTT
ACTGTAAAGGCAAGCCAGCATGTGTGTCCACACATACATAGGATGGCTGGCTCTGCACCTGTAGGATATTGGAATGC
ACAGGGCAATTGAGGGACTGAGCCAGACCTTCGGAGAGTAATGCCACCAGATCCCCTAGGAAAGAGGAGGCAAATGG
CACTGCAGGTGAGAACCCCGCCCATCCGTGCTATGACATGGAGGCACTGAAGCCCGAGGAAGGTGTGTGGAGATTCT
AATCCCAACAAGCAAGGGTCTCCTTCAAGATTAATGCTATCAATCATTAAGGTCATTACTCTCAACCACCTAGGCAA
TGAAGAATATACCATTTCAAATATTTACAGTACTTGTCTTCACCAACACTGTCCCAAGGTGAAATGAAGCAACAGAG
AGGAAATTGTACATAAGTACCTCAGCATTTAATCCAAACAGGGGTTCTTAGTCTCAGCACTATGACATTTTGGGCTG
ACTACTTATTTGTTAGGCGGGAGCTCTCCTGTGCATTGTAGGATAATTAGCAGTATCCCTGGTGGCTACCCAATAGA
CGCCAGTAGCACCCCGAATTGACAACCCAAACTCTCCAGACATCACCAACTGTCCCCTGCGAGGAGAAATCACTCCT
GGGGGAGAACCACTGACCCAAATGAATTCTAAACCAATCAAATGTCTGGGAAGCCCTCCAAGAAAAAAAATAGAAAA
GCACTTGAAGAATATTCCCAATATTCCCGGTCAGCAGTATCAAGGCTGACTTGTGTTCATGTGGAGTCATTATAAAT
TCTATAAATCAATTATTCCCCTTCGGTCTTAAAAATATATTTCCTCATAAACATTTGAGTTTTGTTGAAAAGATGGA
GTTTACAAAGATACCATTCTTGAGTCATGGATTTCTCTGCTCACAGAAGGGTGTGGCATTTGGAAACGGGAATAAAC
AAAATTGCTGCACCAATGCACTGAGTGAAGGAAGAGAGACAGAGGATCAAGGGCTTTAGACAGCACTCCTTCAATAT
GCAATCACAGAGAAAGATGCGCCTTATCCAAGTTAATATCTCTAAGGTGAGAGCCTTCTTAGAGTCAGTTTGTTGCA
AATTTCACCTACTCTGTTCTTTTCCATCCATCCCCCTGAGTCAGTTGGTTGAAGGGAGTTATTTTTTCAAGTGGAAT
TCAAACAAAGCTCAAACCAGAACTGTAAATAGTGATTGCAGGAATTCTTTTCTAAACTGCTTTGCCCTTTCCTCTCA
CTGCCTTTTATAGCCAATATAAATGTCTCTTTGCACACCTTTTGTTGTGGTTTTATATTGTAACACCATTTTTCTTT
GAAACTATTGTATTTAAAGTAAGGTTTCATATTATGTCAGCAAGTAATTAACTTATGTTTAAAAGGTGGCCATATCA
TGTACCAAAAGTTGCTGAAGTTTCTCTTCTAGCTGGTAAAGTAGGAGTTTGCATGACTTCACACTTTTTTTGCGTAG
TTTCTTCTGTTGTATGATGGCGTGAGTGTGTGTCTTGGGTACCGCTGTGTACTACTGTGTGCCTAGATTCCATGCAC
TCTCGTTGTGTTTGAAGTAAATATTGGAGACCGGAGGGTAACAGGTTGGCCTGTTGATTACAGCTAGTAATCGCTGT
GTCTTGTTCCGCCCCCTCCCTGACACCCCAGCTTCCCAGGATGTGGAAAGCCTGGATCTCAGCTCCTTGCCCCATAT
CCCTTCTGTAATTTGTACCTAAAGAGTGTGATTATCCTAATTCAAGAGTCACTAAAACTCATCACATTATCATTGCA
TATCAGCAAAGGGTAAAGTCCTAGCACCAATTGCTTCACATACCAGCATGTTCCATTTCCAATTTAGAATTAGCCAC
ATAATAAAATCTTAGAATCTTCCTTGAGAAAGAGCTGCCTGAGATGTAGTTTTGTTATATGGTTCCCCACCGACCAT
TTTTGTGCTTTTTTCTTGTTTTGTTTTGTTTTGACTGCACTGTGAGTTTTGTAGTGTCCTCTTCTTGCCAAAACAAA
CGCGAGATGAACTGGACTTATGTAGACAAATCGTGATGCCAGTGTATCCTTCCTTTCTTCAGTTCCAGCAATAATGA
ATGGTCAACTTTTTTAAAATCTAGATCTCTCTCATTCATTTCAATGTATTTTTACTTTAAGATGAACCAAAATTATT
AGACTTATTTAAGATGTACAGGCATCAGAAAAAAGAAGCACATAATGCTTTTGGTGCGATGGCACTCACTGTGAACA
TGTGTAACCACATATTAATATGCAATATTGTTTCCAATACTTTCTAATACAGTTTTTTATAATGTTGTGTGTGGTGA
TTGTTCAGGTCGAATCTGTTGTATCCAGTACAGCTTTAGGTCTTCAGCTGCCCTTCTGGCGAGTACATGCACAGGAT
TGTAAATGAGAAATGCAGTCATATTTCCAGTCTGCCTCTATGATGATGTTAAATTATTGCTGTTTAGCTGTGAACAA
GGGATGTACCACTGGAGGAATAGAGTATCCTTTTGTACACATTTTGAAATGCTTCTTCTGTAGTGATAGAACAAATA
AATGCAACGAATACTCTGTCTGCCCTATCCCGTGAAGTCCACACTGGCGTAAGAGAAGGCCCAGCAGAGCAGGAATC
TGCCTAGACTTTCTCCCAATGAGATCCCAATATGAGAGGGAGAAGAGATGGGCCTCAGGACAGCTGCAATACCACTT
GGGAACACATGTGGTGTCTTGATGTGGCCAGCGCAGCAGTTCAGCACAACGTACCTCCCATCTACAACAGTGCTGGA
CGTGGGAATTCTAAGTCCCAGTCTTGAGGGTGGGTGGAGATGGAGGGCAACAAGAGATACATTTCCAGTTCTCCACT
GCAGCATGCTTCAGTCATTCTGTGAGTGGCCGGGCCCAGGGCCCTCACAATTTCACTACCTTGTCTTTTACATAGTC
ATAAGAATTATCCTCAACATAGCCTTTTGACGCTGTAAATCTTGAGTATTCATTTACCCTTTTCTGATCTCCTGGAA
ACAGCTGCCTGCCTGCATTGCACTTCTCTTCCCGAGGAGTGGGGTAAATTTAAAAGTCAAGTTATAGTTTGGATGTT
AGTATAGAATTTTGAAATTGGGAATTAAAAATCAGGACTGGGGACTGGGAGACCAAAAATTTCTGATCCCATTTCTG
ATGGATGTGTCACACCTTTTCTGTCAAAATAAAATGTCTTGGAGGTTATGACTCCTTGGTGAAAAAAAAAAAAAAAA
AA

FIG. 14J

>NM_001220770.2 Homo sapiens IKAROS family zinc finger 1 (IKZF1), transcript variant 7, mRNA (SEQ ID NO:27)
ATAACCTGAGGACCATGGATGCTGATGAGGGTCAAGACATGTCCCAAGTTTCAGGGAAGGAAAGCCCCCCTGTAAGC
GATACTCCAGATGAGGGCGATGAGCCCATGCCGATCCCCGAGGACCTCTCCACCACCTCGGGAGGACAGCAAAGCTC
CAAGAGTGACAGAGTCGTGGGAGAACGGCCCTTCCAGTGCAATCAGTGCGGGGCCTCATTCACCCAGAAGGGCAACC
TGCTCCGGCACATCAAGCTGCATTCCGGGGAGAAGCCCTTCAAATGCCACCTCTGCAACTACGCCTGCCGCCGGAGG
GACGCCCTCACTGGCCACCTGAGGACGCACTCCGTCATTAAAGAAGAAACTAATCACAGTGAAATGGCAGAAGACCT
GTGCAAGATAGGATCAGAGAGATCTCTCGTGCTGGACAGACTAGCAAGTAACGTCGCCAAACGGGACAAGGGCCTGT
CCGACACGCCCTACGACAGCAGCGCCAGCTACGAGAAGGAGAACGAAATGATGAAGTCCCACGTGATGGACCAAGCC
ATCAACAACGCCATCAACTACCTGGGGGCCGAGTCCCTGCGCCCGCTGGTGCAGACGCCCCCGGGCGGTTCCGAGGT
GGTCCCGGTCATCAGCCCGATGTACCAGCTGCACAAGCCGCTCGCGGAGGGCACCCCGCGCTCCAACCACTCGGCCC
AGGACAGCGCCGTGGAGAACCTGCTGCTGCTCTCCAAGGCCAAGTTGGTGCCCTCGGAGCGCGAGGCGTCCCCGAGC
AACAGCTGCCAAGACTCCACGGACACCGAGAGCAACAACGAGGAGCAGCGCAGCGGTCTCATCTACCTGACCAACCA
CATCGCCCCGCACGCGCGCAACGGGCTGTCGCTCAAGGAGGAGCACCGCGCCTACGACCTGCTGCGCGCCGCCTCCG
AGAACTCGCAGGACGCGCTCCGCGTGGTCAGCACCAGCGGGGAGCAGATGAAGGTGTACAAGTGCGAACACTGCCGG
GTGCTCTTCCTGGATCACGTCATGTACACCATCCACATGGGCTGCCACGGCTTCCGTGATCCTTTTGAGTGCAACAT
GTGCGGCTACCACAGCCAGGACCGGTACGAGTTCTCGTCGCACATAACGCGAGGGGAGCACCGCTTCCACATGAGCT
AAAGCCCTCCCGCGCCCCCACCCCAGACCCCGAGCCACCCCAGGAAAAGCACAAGGACTGCCGCCTTCTCGCTCCCG
CCAGCAGCATAGACTGGACTGGACCAGACAATGTTGTGTTTGGATTTGTAACTGTTTTTTGTTTTTTGTTTGAGTTG
GTTGATTGGGGTTTGATTTGCTTTTGAAAAGATTTTTATTTTTAGAGGCAGGGCTGCATTGGGAGCATCCAGAACTG
CTACCTTCCTAGATGTTTCCCCAGACCGCTGGCTGAGATTCCCTCACCTGTCGCTTCCTAGAATCCCCTTCTCCAAA
CGATTAGTCTAAATTTTCAGAGAGAAATAGATAAAACACGCCACAGCCTGGGAAGGAGCGTGCTCTACCCTGTGCTA
AGCACGGGGTTCGCGCACCAGGTGTCTTTTTCCAGTCCCCAGAAGCAGAGAGCACAGCCCCTGCTGTGTGGGTCTGC
AGGTGAGCAGACAGGACAGGTGTGCCGCCACCCAAGTGCCAAGACACAGCAGGGCCAACAACCTGTGCCCAGGCCAG
CTTCGAGCTACATGCATCTAGGGCGGAGAGGCTGCACTTGTGAGAGAAAATACTATTTCAAGTCATATTCTGCGTAG
GAAAATGAATTGGTTGGGGAAAGTCGTGTCTGTCAGACTGCCCTGGGTGGAGGGAGACGCCGGGCTAGAGCCTTTGG
GATCGTCCTGGATTCACTGGCTTTGCGGAGGCTGCTCAGATGGCCTGAGCCTCCCGAGGCTTGCTGCCCCGTAGGAG
GAGACTGTCTTCCCGTGGGCATATCTGGGGAGCCCTGTTCCCCGCTTTTTCACTCCCATACCTTTAATGGCCCCCAA
AATCTGTCACTACAATTTAAACACCAGTCCCGAAATTTGGATCTTCTTTCTTTTTGAATCTCTCAAACGGCAACATT
CCTCAGAAACCAAAGCTTTATTTCAAATCTCTTCCTTCCCTGGCTGGTTCCATCTAGTACCAGAGGCCTCTTTTCCT
GAAGAAATCCAATCCTAGCCCTCATTTTAATTATGTACATCTGTTTGTAGCCACAAGCCTGAATTTCTCAGTGTTGG
TAAGTTTCTTTACCTACCCTCACTATATATTATTCTCGTTTTAAAACCCATAAAGGAGTGATTTAGAACAGTCATTA
ATTTTCAACTCAATGAAATATGTGAAGCCCAGCATCTCTGTTGCTAACACACAGAGCTCACCTGTTTGAAACCAAGC
TTTCAAACATGTTGAAGCTCTTTACTGTAAAGGCAAGCCAGCATGTGTGTCCACACATACATAGGATGGCTGGCTCT
GCACCTGTAGGATATTGGAATGCACAGGGCAATTGAGGGACTGAGCCAGACCTTCGGAGAGTAATGCCACCAGATCC
CCTAGGAAAGAGGAGGCAAATGGCACTGCAGGTGAGAACCCCGCCCATCCGTGCTATGACATGGAGGCACTGAAGCC
CGAGGAAGGTGTGTGGAGATTCTAATCCCAACAAGCAAGGGTCTCCTTCAAGATTAATGCTATCAATCATTAAGGTC
ATTACTCTCAACCACCTAGGCAATGAAGAATATACCATTTCAAATATTTACAGTACTTGTCTTCACCAACACTGTCC
CAAGGTGAAATGAAGCAACAGAGAGGAAATTGTACATAAGTACCTCAGCATTTAATCCAAACAGGGGTTCTTAGTCT
CAGCACTATGACATTTTGGGCTGACTACTTATTTGTTAGGCGGGAGCTCTCCTGTGCATTGTAGGATAATTAGCAGT
ATCCCTGGTGGCTACCCAATAGACGCCAGTAGCACCCCGAATTGACAACCCAAACTCTCCAGACATCACCAACTGTC
CCCTGCGAGGAGAAATCACTCCTGGGGGAGAACCACTGACCCAAATGAATTCTAAACCAATCAAATGTCTGGGAAGC
CCTCCAAGAAAAAAAATAGAAAAGCACTTGAAGAATATTCCCAATATTCCCGGTCAGCAGTATCAAGGCTGACTTGT
GTTCATGTGGAGTCATTATAAATTCTATAAATCAATTATTCCCCTTCGGTCTTAAAAATATATTTCCTCATAAACAT
TTGAGTTTTGTTGAAAAGATGGAGTTTACAAAGATACCATTCTTGAGTCATGGATTTCTCTGCTCACAGAAGGGTGT
GGCATTTGGAAACGGGAATAAACAAAATTGCTGCACCAATGCACTGAGTGAAGGAAGAGAGACAGAGGATCAAGGGC
TTTAGACAGCACTCCTTCAATATGCAATCACAGAGAAAGATGCGCCTTATCCAAGTTAATATCTCTAAGGTGAGAGC
CTTCTTAGAGTCAGTTTGTTGCAAATTTCACCTACTCTGTTCTTTTCCATCCATCCCCCTGAGTCAGTTGGTTGAAG
GGAGTTATTTTTTCAAGTGGAATTCAAACAAAGCTCAAACCAGAACTGTAAATAGTGATTGCAGGAATTCTTTTCTA
AACTGCTTTGCCCTTTCCTCTCACTGCCTTTTATAGCCAATATAAATGTCTCTTTGCACACCTTTTGTTGTGGTTTT
ATATTGTAACACCATTTTTCTTTGAAACTATTGTATTTAAAGTAAGGTTTCATATTATGTCAGCAAGTAATTAACTT
ATGTTTAAAAGGTGGCCATATCATGTACCAAAAGTTGCTGAAGTTTCTCTTCTAGCTGGTAAAGTAGGAGTTTGCAT
GACTTCACACTTTTTTTGCGTAGTTTCTTCTGTTGTATGATGGCGTGAGTGTGTGTCTTGGGTACCGCTGTGTACTA
CTGTGTGCCTAGATTCCATGCACTCTCGTTGTGTTTGAAGTAAATATTGGAGACCGGAGGGTAACAGGTTGGCCTGT
TGATTACAGCTAGTAATCGCTGTGTCTTGTTCCGCCCCCTCCCTGACACCCCAGCTTCCCAGGATGTGGAAAGCCTG
GATCTCAGCTCCTTGCCCCATATCCCTTCTGTAATTTGTACCTAAAGAGTGTGATTATCCTAATTCAAGAGTCACTA
AAACTCATCACATTATCATTGCATATCAGCAAAGGGTAAAGTCCTAGCACCAATTGCTTCACATACCAGCATGTTCC
ATTTCCAATTTAGAATTAGCCACATAATAAAATCTTAGAATCTTCCTTGAGAAAGAGCTGCCTGAGATGTAGTTTTG
TTATATGGTTCCCCACCGACCATTTTTGTGCTTT

FIG. 14K

TTTCTTGTTTTGTTTTGTTTTGACTGCACTGTGAGTTTTGTAGTGTCCTCTTCTTGCCAAAACAAACGCGAGATGAA
CTGGACTTATGTAGACAAATCGTGATGCCAGTGTATCCTTCCTTTCTTCAGTTCCAGCAATAATGAATGGTCAACTT
TTTTAAAATCTAGATCTCTCTCATTCATTTCAATGTATTTTTACTTTAAGATGAACCAAAATTATTAGACTTATTTA
AGATGTACAGGCATCAGAAAAAAGAAGCACATAATGCTTTTGGTGCGATGGCACTCACTGTGAACATGTGTAACCAC
ATATTAATATGCAATATTGTTTCCAATACTTTCTAATACAGTTTTTTATAATGTTGTGTGTGGTGATTGTTCAGGTC
GAATCTGTTGTATCCAGTACAGCTTTAGGTCTTCAGCTGCCCTTCTGGCGAGTACATGCACAGGATTGTAAATGAGA
AATGCAGTCATATTTCCAGTCTGCCTCTATGATGATGTTAAATTATTGCTGTTTAGCTGTGAACAAGGGATGTACCA
CTGGAGGAATAGAGTATCCTTTTGTACACATTTTGAAATGCTTCTTCTGTAGTGATAGAACAAATAAATGCAACGAA
TACTCTGTCTGCCCTATCCCGTGAAGTCCACACTGGCGTAAGAGAAGGCCCAGCAGAGCAGGAATCTGCCTAGACTT
TCTCCCAATGAGATCCCAATATGAGAGGGAGAAGAGATGGGCCTCAGGACAGCTGCAATACCACTTGGGAACACATG
TGGTGTCTTGATGTGGCCAGCGCAGCAGTTCAGCACAACGTACCTCCCATCTACAACAGTGCTGGACGTGGGAATTC
TAAGTCCCAGTCTTGAGGGTGGGTGGAGATGGAGGGCAACAAGAGATACATTTCCAGTTCTCCACTGCAGCATGCTT
CAGTCATTCTGTGAGTGGCCGGGCCCAGGGCCCTCACAATTTCACTACCTTGTCTTTTACATAGTCATAAGAATTAT
CCTCAACATAGCCTTTTGACGCTGTAAATCTTGAGTATTCATTTACCCTTTTCTGATCTCCTGGAAACAGCTGCCTG
CCTGCATTGCACTTCTCTTCCCGAGGAGTGGGGTAAATTTAAAAGTCAAGTTATAGTTTGGATGTTAGTATAGAATT
TTGAAATTGGGAATTAAAAATCAGGACTGGGGACTGGGAGACCAAAAATTTCTGATCCCATTTCTGATGGATGTGTC
ACACCTTTTCTGTCAAAATAAAATGTCTTGGAGGTTATGACTCCTTGGTGAAAAAAAAAAAAAAAAAA

>NM_001220771.2 Homo sapiens IKAROS family zinc finger 1 (IKZF1), transcript variant 8, mRNA (SEQ ID NO:28)
ATAACCTGAGGACCATGGATGCTGATGAGGGTCAAGACATGTCCCAAGTTTCAGGGAAGGAAAGCCCCCCTGTAAGC
GATACTCCAGATGAGGGCGATGAGCCCATGCCGATCCCCGAGGACCTCTCCACCACCTCGGGAGGACAGCAAAGCTC
CAAGAGTGACAGAGTCGTGGCCAGTAATGTTAAAGTAGAGACTCAGAGTGATGAAGAGAATGGGCGTGCCTGTGAAA
TGAATGGGGAAGAATGTGCGGAGGATTTACGAATGCTTGATGCCTCGGGAGAGAAAATGAATGGCTCCCACAGGGAC
CAAGGCAGCTCGGCTTTGTCGGGAGTTGGAGGCATTCGACTTCCTAACGGAAAACTAAAGTGTGATATCTGTGGGAT
CATTTGCATCGGGCCCAATGTGCTCATGGTTCACAAAAGAAGCCACACTGGGGACAAGGGCCTGTCCGACACGCCCT
ACGACAGCAGCGCCAGCTACGAGAAGGAGAACGAAATGATGAAGTCCCACGTGATGGACCAAGCCATCAACAACGCC
ATCAACTACCTGGGGGCCGAGTCCCTGCGCCCGCTGGTGCAGACGCCCCCGGGCGGTTCCGAGGTGGTCCCGGTCAT
CAGCCCGATGTACCAGCTGCACAAGCCGCTCGCGGAGGGCACCCCGCGCTCCAACCACTCGGCCCAGGACAGCGCCG
TGGAGAACCTGCTGCTGCTCTCCAAGGCCAAGTTGGTGCCCTCGGAGCGCGAGGCGTCCCCGAGCAACAGCTGCCAA
GACTCCACGGACACCGAGAGCAACAACGAGGAGCAGCGCAGCGGTCTCATCTACCTGACCAACCACATCGCCCCGCA
CGCGCGCAACGGGCTGTCGCTCAAGGAGGAGCACCGCGCCTACGACCTGCTGCGCGCCGCCTCCGAGAACTCGCAGG
ACGCGCTCCGCGTGGTCAGCACCAGCGGGGAGCAGATGAAGGTGTACAAGTGCGAACACTGCCGGGTGCTCTTCCTG
GATCACGTCATGTACACCATCCACATGGGCTGCCACGGCTTCCGTGATCCTTTTGAGTGCAACATGTGCGGCTACCA
CAGCCAGGACCGGTACGAGTTCTCGTCGCACATAACGCGAGGGGAGCACCGCTTCCACATGAGCTAAAGCCCTCCCG
CGCCCCCACCCCAGACCCCGAGCCACCCCAGGAAAAGCACAAGGACTGCCGCCTTCTCGCTCCCGCCAGCAGCATAG
ACTGGACTGGACCAGACAATGTTGTGTTTGGATTTGTAACTGTTTTTTGTTTTTTGTTTGAGTTGGTTGATTGGGGT
TTGATTTGCTTTTGAAAAGATTTTTATTTTTAGAGGCAGGGCTGCATTGGGAGCATCCAGAACTGCTACCTTCCTAG
ATGTTTCCCCAGACCGCTGGCTGAGATTCCCTCACCTGTCGCTTCCTAGAATCCCCTTCTCCAAACGATTAGTCTAA
ATTTTCAGAGAGAAATAGATAAAACACGCCACAGCCTGGGAAGGAGCGTGCTCTACCCTGTGCTAAGCACGGGGTTC
GCGCACCAGGTGTCTTTTTCCAGTCCCCAGAAGCAGAGAGCACAGCCCCTGCTGTGTGGGTCTGCAGGTGAGCAGAC
AGGACAGGTGTGCCGCCACCCAAGTGCCAAGACACAGCAGGGCCAACAACCTGTGCCCAGGCCAGCTTCGAGCTACA
TGCATCTAGGGCGGAGAGGCTGCACTTGTGAGAGAAAATACTATTTCAAGTCATATTCTGCGTAGGAAAATGAATTG
GTTGGGGAAAGTCGTGTCTGTCAGACTGCCCTGGGTGGAGGGAGACGCCGGGCTAGAGCCTTTGGGATCGTCCTGGA
TTCACTGGCTTTGCGGAGGCTGCTCAGATGGCCTGAGCCTCCCGAGGCTTGCTGCCCCGTAGGAGGAGACTGTCTTC
CCGTGGGCATATCTGGGGAGCCCTGTTCCCCGCTTTTTCACTCCCATACCTTTAATGGCCCCCAAAATCTGTCACTA
CAATTTAAACACCAGTCCCGAAATTTGGATCTTCTTTCTTTTTGAATCTCTCAAACGGCAACATTCCTCAGAAACCA
AAGCTTTATTTCAAATCTCTTCCTTCCCTGGCTGGTTCCATCTAGTACCAGAGGCCTCTTTTCCTGAAGAAATCCAA
TCCTAGCCCTCATTTTAATTATGTACATCTGTTTGTAGCCACAAGCCTGAATTTCTCAGTGTTGGTAAGTTTCTTTA
CCTACCCTCACTATATATTATTCTCGTTTTAAAACCCATAAAGGAGTGATTTAGAACAGTCATTAATTTTCAACTCA
ATGAAATATGTGAAGCCCAGCATCTCTGTTGCTAACACACAGAGCTCACCTGTTTGAAACCAAGCTTTCAAACATGT
TGAAGCTCTTTACTGTAAAGGCAAGCCAGCATGTGTGTCCACACATACATAGGATGGCTGGCTCTGCACCTGTAGGA
TATTGGAATGCACAGGGCAATTGAGGGACTGAGCCAGACCTTCGGAGAGTAATGCCACCAGATCCCCTAGGAAAGAG
GAGGCAAATGGCACTGCAGGTGAGAACCCCGCCCATCCGTGCTATGACATGGAGGCACTGAAGCCCGAGGAAGGTGT
GTGGAGATTCTAATCCCAACAAGCAAGGGTCTCCTTCAAGATTAATGCTATCAATCATTAAGGTCATTACTCTCAAC
CACCTAGGCAATGAAGAATATACCATTTCAAATATTTACAGTACTTGTCTTCACCAACACTGTCCCAAGGTGAAATG
AAGCAACAGAGAGGAAATTGTACATAAGTACCTCAGCATTTAATCCAAACAGGGGTTCTTAGTCTCAGCACTATGAC
ATTTTGGGCTGACTACTTATT

FIG. 14L

TGTTAGGCGGGAGCTCTCCTGTGCATTGTAGGATAATTAGCAGTATCCCTGGTGGCTACCCAATAGACGCCAGTAGC
ACCCCGAATTGACAACCCAAACTCTCCAGACATCACCAACTGTCCCCTGCGAGGAGAAATCACTCCTGGGGGAGAAC
CACTGACCCAAATGAATTCTAAACCAATCAAATGTCTGGGAAGCCCTCCAAGAAAAAAAATAGAAAAGCACTTGAAG
AATATTCCCAATATTCCCGGTCAGCAGTATCAAGGCTGACTTGTGTTCATGTGGAGTCATTATAAATTCTATAAATC
AATTATTCCCCTTCGGTCTTAAAAATATATTTCCTCATAAACATTTGAGTTTTGTTGAAAAGATGGAGTTTACAAAG
ATACCATTCTTGAGTCATGGATTTCTCTGCTCACAGAAGGGTGTGGCATTTGGAAACGGGAATAAACAAAATTGCTG
CACCAATGCACTGAGTGAAGGAAGAGAGACAGAGGATCAAGGGCTTTAGACAGCACTCCTTCAATATGCAATCACAG
AGAAAGATGCGCCTTATCCAAGTTAATATCTCTAAGGTGAGAGCCTTCTTAGAGTCAGTTTGTTGCAAATTTCACCT
ACTCTGTTCTTTTCCATCCATCCCCCTGAGTCAGTTGGTTGAAGGGAGTTATTTTTTCAAGTGGAATTCAAACAAAG
CTCAAACCAGAACTGTAAATAGTGATTGCAGGAATTCTTTTCTAAACTGCTTTGCCCTTTCCTCTCACTGCCTTTTA
TAGCCAATATAAATGTCTCTTTGCACACCTTTTGTTGTGGTTTTATATTGTAACACCATTTTTCTTTGAAACTATTG
TATTTAAAGTAAGGTTTCATATTATGTCAGCAAGTAATTAACTTATGTTTAAAAGGTGGCCATATCATGTACCAAAA
GTTGCTGAAGTTTCTCTTCTAGCTGGTAAAGTAGGAGTTTGCATGACTTCACACTTTTTTTGCGTAGTTTCTTCTGT
TGTATGATGGCGTGAGTGTGTGTCTTGGGTACCGCTGTGTACTACTGTGTGCCTAGATTCCATGCACTCTCGTTGTG
TTTGAAGTAAATATTGGAGACCGGAGGGTAACAGGTTGGCCTGTTGATTACAGCTAGTAATCGCTGTGTCTTGTTCC
GCCCCCTCCCTGACACCCCAGCTTCCCAGGATGTGGAAAGCCTGGATCTCAGCTCCTTGCCCCATATCCCTTCTGTA
ATTTGTACCTAAAGAGTGTGATTATCCTAATTCAAGAGTCACTAAAACTCATCACATTATCATTGCATATCAGCAAA
GGGTAAAGTCCTAGCACCAATTGCTTCACATACCAGCATGTTCCATTTCCAATTTAGAATTAGCCACATAATAAAAT
CTTAGAATCTTCCTTGAGAAAGAGCTGCCTGAGATGTAGTTTTGTTATATGGTTCCCCACCGACCATTTTTGTGCTT
TTTTCTTGTTTTGTTTTGTTTTGACTGCACTGTGAGTTTTGTAGTGTCCTCTTCTTGCCAAAACAAACGCGAGATGA
ACTGGACTTATGTAGACAAATCGTGATGCCAGTGTATCCTTCCTTTCTTCAGTTCCAGCAATAATGAATGGTCAACT
TTTTTAAAATCTAGATCTCTCTCATTCATTTCAATGTATTTTTACTTTAAGATGAACCAAAATTATTAGACTTATTT
AAGATGTACAGGCATCAGAAAAAAGAAGCACATAATGCTTTTGGTGCGATGGCACTCACTGTGAACATGTGTAACCA
CATATTAATATGCAATATTGTTTCCAATACTTTCTAATACAGTTTTTTATAATGTTGTGTGTGGTGATTGTTCAGGT
CGAATCTGTTGTATCCAGTACAGCTTTAGGTCTTCAGCTGCCCTTCTGGCGAGTACATGCACAGGATTGTAAATGAG
AAATGCAGTCATATTTCCAGTCTGCCTCTATGATGATGTTAAATTATTGCTGTTTAGCTGTGAACAAGGGATGTACC
ACTGGAGGAATAGAGTATCCTTTTGTACACATTTTGAAATGCTTCTTCTGTAGTGATAGAACAAATAAATGCAACGA
ATACTCTGTCTGCCCTATCCCGTGAAGTCCACACTGGCGTAAGAGAAGGCCCAGCAGAGCAGGAATCTGCCTAGACT
TTCTCCCAATGAGATCCCAATATGAGAGGGAGAAGAGATGGGCCTCAGGACAGCTGCAATACCACTTGGGAACACAT
GTGGTGTCTTGATGTGGCCAGCGCAGCAGTTCAGCACAACGTACCTCCCATCTACAACAGTGCTGGACGTGGGAATT
CTAAGTCCCAGTCTTGAGGGTGGGTGGAGATGGAGGGCAACAAGAGATACATTTCCAGTTCTCCACTGCAGCATGCT
TCAGTCATTCTGTGAGTGGCCGGGCCCAGGGCCCTCACAATTTCACTACCTTGTCTTTTACATAGTCATAAGAATTA
TCCTCAACATAGCCTTTTGACGCTGTAAATCTTGAGTATTCATTTACCCTTTTCTGATCTCCTGGAAACAGCTGCCT
GCCTGCATTGCACTTCTCTTCCCGAGGAGTGGGGTAAATTTAAAAGTCAAGTTATAGTTTGGATGTTAGTATAGAAT
TTTGAAATTGGGAATTAAAAATCAGGACTGGGGACTGGGAGACCAAAAATTTCTGATCCCATTTCTGATGGATGTGT
CACACCTTTTCTGTCAAAATAAAATGTCTTGGAGGTTATGACTCCTTGGTGAAAAAAAAAAAAAAAAAA

FIG. 15A

IKZF4

Mouse
Proteins

>sp|Q8C208|IKZF4_MOUSE Zinc finger protein Eos OS=Mus musculus OX=10090 GN=Ikzf4 PE=1 SV=2 (used in examples herein) (SEQ ID NO:29)
MHTPPALPRRFQGGGRVRTPGSHRQGKDNLERELSGGCAPDFLPQAQDSNHFIMESLFCESSGDSSLEKEFLGAPVG
PSVSTPNSQHSSPSRSLSANSIKVEMYSDEESSRLLGPDERLLDKDDSVIVEDSLSEPLGYCDGSGPEPHSPGGIRL
PNGKLKCDVCGMVCIGPNVLMVHKRSHTGERPFHCNQCGASFTQKGNLLRHIKLHSGEKPFKCPFCNYACRRRDALT
GHLRTHSVSSPTVGKPYKCNYCGRSYKQQSTLEEHKERCHNYLQSLSTDAQALTGQPGDEIRDLEMVPDSMLHPSTE
RPTFIDRLANSLTKRKRSTPQKFVGEKQMRFSLSDLPYDVNASGGYEKDVELVAHHGLEPGFGGSLAFVGTEHLRPL
RLPPTNCISELTPVISSVYTQMQPIPSRLELPGSREAGEGPEDLGDGGPLLYRARGSLTDPGASPSNGCQDSTDTES
NHEDRIGGVVSLPQGPPPQPPPTIVVGRHSPAYAKEDPKPQEGLLRGTPGPSKEVLRVVGESGEPVKAFKCEHCRIL
FLDHVMFTIHMGCHGFRDPFECNICGYHSQDRYEFSSHIVRGEHKVG >sp|Q8C208-2|IKZF4_MOUSE Isoform 2 of Zinc finger protein Eos OS=Mus musculus OX=10090 GN=Ikzf4 (SEQ ID NO:30)
MESLFCESSGDSSLEKEFLGAPVGPSVSTPNSQHSSPSRSLSANSIKVEMYSDEESSRLLGPDERLLDKDDSVIVED
SLSEPLGYCDGSGPEPHSPGGIRLPNGKLKCDVCGMVCIGPNVLMVHKRSHTGERPFHCNQCGASFTQKGNLLRHIK
LHSGEKPFKCPFCNYACRRRDALTGHLRTHSVSSPTVGKPYKCNYCGRSYKQQSTLEEHKERCHNYLQSLSTDAQAL
TGQPGDEIRDLEMVPDSMLHPSTERPTFIDRLANSLTKRKRSTPQKFVGEKQMRFSLSDLPYDVNASGGYEKDVELV
AHHGLEPGFGGSLAFVGTEHLRPLRLPPTNCISELTPVISSVYTQMQPIPSRLELPGSREAGEGPEDLGDGGPLLYR
ARGSLTDPGASPSNGCQDSTDTESNHEDRIGGVVSLPQGPPPQPPPTIVVGRHSPAYAKEDPKPQEGLLRGTPGPSK
EVLRVVGESGEPVKAFKCEHCRILFLDHVMFTIHMGCHGFRDPFECNICGYHSQDRYEFSSHIVRGEHKVG >sp|Q8C208-3|IKZF4_MOUSE Isoform 3 of Zinc finger protein Eos OS=Mus musculus OX=10090 GN=Ikzf4(SEQ ID NO:31)
MFIPVGSGDSSLEKEFLGAPVGPSVSTPNSQHSSPSRSLSANSIKVEMYSDEESSRLLGPDERLLDKDDSVIVEDSL
SEPLGYCDGSGPEPHSPGGIRLPNGKLKCDVCGMVCIGPNVLMVHKRSHTGERPFHCNQCGASFTQKGNLLRHIKLH
SGEKPFKCPFCNYACRRRDALTGHLRTHSVSSPTVGKPYKCNYCGRSYKQQSTLEEHKERCHNYLQSLSTDAQALTG
QPGDEIRDLEMVPDSMLHPSTERPTFIDRLANSLTKRKRSTPQKFVGEKQMRFSLSDLPYDVNASGGYEKDVELVAH
HGLEPGFGGSLAFVGTEHLRPLRLPPTNCISELTPVISSVYTQMQPIPSRLELPGSREAGEGPEDLGDGGPLLYRAR
GSLTDPGASPSNGCQDSTDTESNHEDRIGGVVSLPQGPPPQPPPTIVVGRHSPAYAKEDPKPQEGLLRGTPGPSKEV
LRVVGESGEPVKAFKCEHCRILFLDHVMFTIHMGCHGFRDPFECNICGYHSQDRYEFSSHIVRGEHKVG >sp|Q8C208-4|IKZF4_MOUSE Isoform 4 of Zinc finger protein Eos OS=Mus musculus OX=10090 GN=Ikzf4 (SEQ ID NO:32)
MHTPPALPRRFQGGGRVRTPGSHRQGKDNLERELSGGCAPDFLPQAQDSNHFIMESLFCESSGDSSLEKEFLGAPVG
PSVSTPNSQHSSPSRSLSANSIKVEMYSDEESSRLLGPDERLLDKDDSVIVEDSLSEPLGYCDGSGPEPHSPGGIRL
PNGKLKCDVCGMVCIGPNVLMVHKRSHTGERPFHCNQCGASFTQKGNLLRHIKLHSGEKPFKCPFCNYACRRRDALT
GHLRTHSVSSPTVGKPYKCNYCGRSYKQQSTLEEHKERCHNYLQSLSTDAQALTGQPGDEIRDLEMVPDSMLHPSTE
RPTFIDRLANSLTKRKRSTPQKFVGEKQMRFSLSDLPYDVNASGGYEKDVELVAHHGLEPGFGGSLAFVGTEHLRPL
RLPPTNCISELTPVISSVYTQMQPIPSRLELPGSREAGEGPEDLGDGGPLLYRARGSLTDPGASPSNGCQDSTDTES
NHEDRIGGVVSLPQGPPPQPPPTIVVGRHSPAYAKEDPKPQEGLLRGTPGPSKEVLRVVGESGEPVKAFKCEHCRIL
FLDHVMFTIHMGCHGFRDPFECNICGYHSQDRTRRLVPRLLGPVMINGREKGDVSFLSANFQYNQKNCPRMNYTYVP
VNHSTLVPARMGRTQLGVTSTALSILSSRHRAGEAVFSGGCRHSGYSDNRGFVRPCRRRHSSIAGGSLSL >Consensus of mouse Ikzf4 isoforms above (SEQ ID NO:33)
XXXXXXXXXXXXXXXXXXXXXXXXXXXXXXXXXXXXXXXXXXXXXXXXXXXXXXXXXXXSGDSSLEKEFLGAPVGPSV
STPNSQHSSPSRSLSANSIKVEMYSDEESSRLLGPDERLLDKDDSVIVEDSLSEPLGYCDGSGPEPHSPGGIRLPNGKLK
CDVCGMVCIGPNVLMVHKRSHTGERPFHCNQCGASFTQKGNLLRHIKLHSGEKPFKCPFCNYACRRRDALTGHLRTHSVS
SPTVGKPYKCNYCGRSYKQQSTLEEHKERCHNYLQSLSTDAQALTGQPGDEIRDLEMVPDSMLHPSTERPTFIDRLANSL
TKRKRSTPQKFVGEKQMRFSLSDLPYDVNASGGYEKDVELVAHHGLEPGFGGSLAFVGTEHLRPLRLPPTNCISELTPVI
SSVYTQMQPIPSRLELPGSREAGEGPEDLGDGGPLLYRARGSLTDPGASPSNGCQDSTDTESNHEDRIGGVVSLPQGPPP
QPPPTIVVGRHSPAYAKEDPKPQEGLLRGTPGPSKEVLRVVGESGEPVKAFKCEHCRILFLDHVMFTIHMGCHGFRDPFE
CNICGYHSQDRXXXXXXXXXGXXXXXXXXXXXXXXXXXXXXXXXXXXXXXXXXXXXXXXXXXXXXXXXXXXXXXXXXXXX
XXXXXXXXXXXXXXXXXXXXXXXXXXXXXXXXXXXXXXXXXX

FIG. 15B

```
mIkzf4-4     MHTPPALPRRFQGGGRVRTPGSHRQGKDNLERELSGGCAPDFLPQAQDSNHFIMESLFCE  60
mIkzf4-1     MHTPPALPRRFQGGGRVRTPGSHRQGKDNLERELSGGCAPDFLPQAQDSNHFIMESLFCE  60
mIkzf4-2     -----------------------------------------------------MESLFCE  7
mIkzf4-3     -------------------------------------------------------MFIPV  5
                                                                     ::

mIkzf4-4     SSGDSSLEKEFLGAPVGPSVSTPNSQHSSPSRSLSANSIKVEMYSDEESSRLLGPDERLL  120
mIkzf4-1     SSGDSSLEKEFLGAPVGPSVSTPNSQHSSPSRSLSANSIKVEMYSDEESSRLLGPDERLL  120
mIkzf4-2     SSGDSSLEKEFLGAPVGPSVSTPNSQHSSPSRSLSANSIKVEMYSDEESSRLLGPDERLL  67
mIkzf4-3     GSGDSSLEKEFLGAPVGPSVSTPNSQHSSPSRSLSANSIKVEMYSDEESSRLLGPDERLL  65
             .***********************************************************

mIkzf4-4     DKDDSVIVEDSLSEPLGYCDGSGPEPHSPGGIRLPNGKLKCDVCGMVCIGPNVLMVHKRS  180
mIkzf4-1     DKDDSVIVEDSLSEPLGYCDGSGPEPHSPGGIRLPNGKLKCDVCGMVCIGPNVLMVHKRS  180
mIkzf4-2     DKDDSVIVEDSLSEPLGYCDGSGPEPHSPGGIRLPNGKLKCDVCGMVCIGPNVLMVHKRS  127
mIkzf4-3     DKDDSVIVEDSLSEPLGYCDGSGPEPHSPGGIRLPNGKLKCDVCGMVCIGPNVLMVHKRS  125
             ************************************************************

mIkzf4-4     HTGERPFHCNQCGASFTQKGNLLRHIKLHSGEKPFKCPFCNYACRRRDALTGHLRTHSVS  240
mIkzf4-1     HTGERPFHCNQCGASFTQKGNLLRHIKLHSGEKPFKCPFCNYACRRRDALTGHLRTHSVS  240
mIkzf4-2     HTGERPFHCNQCGASFTQKGNLLRHIKLHSGEKPFKCPFCNYACRRRDALTGHLRTHSVS  187
mIkzf4-3     HTGERPFHCNQCGASFTQKGNLLRHIKLHSGEKPFKCPFCNYACRRRDALTGHLRTHSVS  185
             ************************************************************

mIkzf4-4     SPTVGKPYKCNYCGRSYKQQSTLEEHKERCHNYLQSLSTDAQALTGQPGDEIRDLEMVPD  300
mIkzf4-1     SPTVGKPYKCNYCGRSYKQQSTLEEHKERCHNYLQSLSTDAQALTGQPGDEIRDLEMVPD  300
mIkzf4-2     SPTVGKPYKCNYCGRSYKQQSTLEEHKERCHNYLQSLSTDAQALTGQPGDEIRDLEMVPD  247
mIkzf4-3     SPTVGKPYKCNYCGRSYKQQSTLEEHKERCHNYLQSLSTDAQALTGQPGDEIRDLEMVPD  245
             ************************************************************

mIkzf4-4     SMLHPSTERPTFIDRLANSLTKRKRSTPQKFVGEKQMRFSLSDLPYDVNASGGYEKDVEL  360
mIkzf4-1     SMLHPSTERPTFIDRLANSLTKRKRSTPQKFVGEKQMRFSLSDLPYDVNASGGYEKDVEL  360
mIkzf4-2     SMLHPSTERPTFIDRLANSLTKRKRSTPQKFVGEKQMRFSLSDLPYDVNASGGYEKDVEL  307
mIkzf4-3     SMLHPSTERPTFIDRLANSLTKRKRSTPQKFVGEKQMRFSLSDLPYDVNASGGYEKDVEL  305
             ************************************************************

mIkzf4-4     VAHHGLEPGFGGSLAFVGTEHLRPLRLPPTNCISELTPVISSVYTQMQPIPSRLELPGSR  420
mIkzf4-1     VAHHGLEPGFGGSLAFVGTEHLRPLRLPPTNCISELTPVISSVYTQMQPIPSRLELPGSR  420
mIkzf4-2     VAHHGLEPGFGGSLAFVGTEHLRPLRLPPTNCISELTPVISSVYTQMQPIPSRLELPGSR  367
mIkzf4-3     VAHHGLEPGFGGSLAFVGTEHLRPLRLPPTNCISELTPVISSVYTQMQPIPSRLELPGSR  365
             ************************************************************

mIkzf4-4     EAGEGPEDLGDGGPLLYRARGSLTDPGASPSNGCQDSTDTESNHEDRIGGVVSLPQGPPP  480
mIkzf4-1     EAGEGPEDLGDGGPLLYRARGSLTDPGASPSNGCQDSTDTESNHEDRIGGVVSLPQGPPP  480
mIkzf4-2     EAGEGPEDLGDGGPLLYRARGSLTDPGASPSNGCQDSTDTESNHEDRIGGVVSLPQGPPP  427
mIkzf4-3     EAGEGPEDLGDGGPLLYRARGSLTDPGASPSNGCQDSTDTESNHEDRIGGVVSLPQGPPP  425
             ************************************************************

mIkzf4-4     QPPPTIVVGRHSPAYAKEDPKPQEGLLRGTPGPSKEVLRVVGESGEPVKAFKCEHCRILF  540
mIkzf4-1     QPPPTIVVGRHSPAYAKEDPKPQEGLLRGTPGPSKEVLRVVGESGEPVKAFKCEHCRILF  540
mIkzf4-2     QPPPTIVVGRHSPAYAKEDPKPQEGLLRGTPGPSKEVLRVVGESGEPVKAFKCEHCRILF  487
mIkzf4-3     QPPPTIVVGRHSPAYAKEDPKPQEGLLRGTPGPSKEVLRVVGESGEPVKAFKCEHCRILF  485
             ************************************************************
```

FIG. 15C

```
mIkzf4-4     LDHVMFTIHMGCHGFRDPFECNICGYHSQDRTRRLVPRLLGPVMINGREKGDVSFLSANF  600
mIkzf4-1     LDHVMFTIHMGCHGFRDPFECNICGYHSQDRYEFSSHIVRGEHKVG--------------  586
mIkzf4-2     LDHVMFTIHMGCHGFRDPFECNICGYHSQDRYEFSSHIVRGEHKVG--------------  533
mIkzf4-3     LDHVMFTIHMGCHGFRDPFECNICGYHSQDRYEFSSHIVRGEHKVG--------------  531
             ******************************* .     : *   :.

mIkzf4-4     QYNQKNCPRMNYTYVPVNHSTLVPARMGRTQLGVTSTALSILSSRHRAGEAVFSGGCRHS  660
mIkzf4-1     ------------------------------------------------------------  586
mIkzf4-2     ------------------------------------------------------------  533
mIkzf4-3     ------------------------------------------------------------  531

mIkzf4-4     GYSDNRGFVRPCRRRHSSIAGGSLSL      686
mIkzf4-1     --------------------------      586
mIkzf4-2     --------------------------      533
mIkzf4-3     --------------------------      531
```

FIG. 16A

Nucleic acid

>NM_011772.3 Mus musculus IKAROS family zinc finger 4 (Ikzf4), transcript variant 1, mRNA (CDS shown bolded; untranslated shown highlighted in grey; stop codon underlined) (SEQ ID NO:34)

ACACACGAGGCTCTCAGCACATACACCCTGGGCTGAGCGGTTCTGCCGGCTGCAGCCGTGGGCCCCTGCTCACCGTG
CGGCTGCCACTGCCTGCGAAATGACGGCGGTTCCCCTCACTTCCAGGAATCCACGCTTCCTGGAAGGTGAGTGGCTG
GGCTCACCCCTGCCTGCCACCGAGACGCAGACATGCACACACCACCCGCACTCCCTCGCCGTTTCCAAGGCGGCGGC
CGCGTTCGCACCCCAGGGTCTCACCGGCAAGGGAAGGATAATCTGGAGAGGGAGCTCTCAGGAGGGTGTGCTCCGGA
TTTCTTGCCTCAGGCCCAGGACTCCAACCATTTTATAATGGAATCTTTATTTTGTGAAAGTAGCGGGGACTCATCTC
TGGAGAAGGAGTTCCTTGGGGCCCCAGTGGGGCCCTCGGTGAGCACCCCAAACAGCCAACACTCTTCACCCAGCCGC
TCGCTCAGTGCCAACTCCATCAAGGTGGAGATGTACAGCGATGAGGAGTCGAGCAGACTGCTGGGGCCGGATGAACG
GCTCCTGGATAAGGATGACAGTGTGATTGTGGAAGACTCATTGTCAGAGCCCTTAGGCTACTGCGATGGAAGTGGGC
CAGAGCCTCACTCCCCTGGCGGCATCCGGCTACCCAACGGCAAGCTCAAGTGCGACGTCTGCGGCATGGTCTGCATT
GGGCCCAATGTGCTCATGGTACACAAGCGCAGCCACACTGGGGAGAGGCCCTTCCACTGTAATCAGTGTGGTGCCTC
CTTCACACAGAAGGGCAATCTGCTTCGCCACATCAAGCTGCACTCGGGGGAGAAGCCCTTCAAGTGCCCCTTCTGCA
ACTATGCCTGCCGCCGGCGTGACGCACTCACTGGCCACCTCCGCACACACTCAGTCTCCTCCCCCACCGTGGGCAAA
CCCTACAAGTGCAACTACTGTGGCCGGAGCTACAAACAGCAAAGTACCCTGGAGGAGCACAAGGAGAGGTGCCACAA
CTACCTACAGAGTCTCAGCACTGATGCCCAAGCTCTGACTGGCCAGCCAGGTGATGAAATCCGTGACCTGGAGATGG
TGCCTGACTCAATGCTGCACCCATCGACTGAACGGCCAACTTTCATTGATCGTTTGGCCAACAGCCTCACCAAACGC
AAGCGTTCCACCCCACAGAAGTTTGTAGGTGAAAAGCAGATGCGCTTCAGCCTCTCAGACCTTCCCTATGATGTGAA
TGCCAGCGGTGGCTATGAAAAGGACGTAGAGTTGGTGGCACACCATGGCCTGGAGCCTGGCTTTGGAGGGTCTCTAG
CCTTTGTGGGTACAGAGCATCTGCGTCCCCTCCGCCTCCCACCCACCAACTGCATCTCAGAACTCACACCTGTCATC
AGCTCTGTGTACACCCAAATGCAGCCCATCCCCAGCCGACTGGAGCTTCCAGGGTCCCGAGAAGCAGGTGAGGGACC
GGAGGACCTGGGAGATGGAGGTCCCCTCCTTTATCGGGCCCGAGGCTCTCTGACTGACCCTGGGGCATCCCCCAGCA
ATGGCTGCCAGGACTCCACAGATACAGAGAGCAACCACGAAGACCGGATTGGTGGGGTGGTATCCCTTCCTCAGGGT
CCCCCACCCCAACCTCCTCCCACCATAGTGGTGGGCCGGCACAGTCCCGCCTATGCCAAAGAGGACCCCAAACCACA
GGAGGGGTTACTGCGGGGCACCCCAGGCCCCTCCAAGGAAGTGCTTCGGGTGGTGGGTGAGAGTGGTGAGCCAGTGA
AGGCCTTTAAGTGTGAACACTGCCGCATCCTCTTTCTGGACCACGTCATGTTCACCATCCACATGGGCTGCCACGGC
TTCAGAGACCCTTTTGAGTGTAACATCTGTGGTTATCACAGCCAGGATCGGTATGAGTTCTCTTCCCACATCGTCCG
GGGGGAACATAAGGTGGGCTAGAGACCTCTTTCCCCACAGCCTGCTCTCAGCCCGGCCCCCACCCTACTGCCCTACC
TACAGGGGTCTAGCCCAATTCCTGTTACACCCTAAGGAGTTTTGCGTTGTAGCCCCACCCACTGGCCGCCTCACTTC
ACACTTGACTCCAACCGTCTTTGCCTGTTCCCTTCTACCCTGACCGATTTGAGCATTTCGACAAGACAAGTCTCTTG
CTTATATTTCTCCTTCTAACCTCTCTCCCCGGCACATTTGCTTTTTAAATTGACTTTAACTTGGCCTTTTCTTAGTT
TACTGCAATCTCTGGCCACTCCTTCATTCTTCTGCCCATGGCTCCCTTCTGCTCTAAGCCTAGATTTTTTTTTATTT
TATTATTATTATTATTATTATTACTTGTGTGTGTGTGTGGATCCCACATCCTCCAACAGCTCCAGGGGTTGGAAGCT
CCTCTCTGTGCTAAGAGACGTTGGGCTTCTTGCTTTAATCCTCACCCTTATTTATCTGACCCTTCACTTTTGA

FIG. 16B

TGCTGATACCTCCCAACGGCCCCACCTTAGCTCTGTGGCATTATTATCTCCTCTCTGGGACCTTTCAGCCCGGCACT
CCATACCTCTCGTGCCCACTCACTTTAGGCAGCTTGCACTATTCTTAAATGAATGAAGAATTTCCTCATTTGCAGGT
AGGAGGGGCTGTAGAAACTCTCCCCAGGCACTGTGGACTGAGGGTCCTCTTGACCTCACCTGGGAATCCGAGCTCCC
TAAAGACTACATTCAGGACCTCCCTCTAGGATGTGATACCACCCTTCCCTCTCCCTGGCTCACCCCTCAACACCACT
CTGGTCTCAACTCGCCACTCTTGTCAGTTGGTGGCTTTTCTCTCCTTGGAATGCCCCCATTTTATATTCTCAGGGGC
TAAGGCTAGACCTGCTACCCTTTCTCTGACACACAGAGAGAGCTGCAGGTACCTAGCTGAGAACCAGGGCATGGGAA
GGGGGATGGGTAGAACTCTCTCCTCCACCTTTCAAACACTTACACTCCAGTGACCTTCCTAGGCTCTCAGGGACTCC
TTCTGTCCCCATATTATGAGAAACCAGCGGGTTGCTGCTCGATGACCAGGGGTCTCTCAACCCTGTCAGTCACGCTG
CCTTTTTCCTCCCTTCCAGCAGGACTCGCCGTCTCGTCCCCAGGCTCCTGGGCCCTGTTATGATCAATGGCAGGGAG
AAAGGGGATGTCTCTTTTCTCTCTGCCAATTTTCAGTATAACCAAAAAAACTGTCCCAGGATGAACTACACGTATGT
GCCCGTCAACCATTCCACCCTTGTCCCAGCAAGAATGGGACGGACACAGCTGGGAGTCACCTCCACTGCCCTTTCCA
TACTTAGCTCCAGACACAGGGCAGGAGAGGCAGTCTTCTCTGGTGGTTGCAGACACTCTGGCTATTCGGATAATCGA
GGATTCGTGAGACCATGCAGGAGGAGGCATAGCTCCATTGCAGGTGGAAGTCTCTCTCTCTAAAGAGTTCCCTGCCA
GGGCCACAACCATCCCACTCTCTGCTTCTTTGAGATTCAAACCAAAGGATGTTTTTTCTATATTTAAAGAAAAGGAA
AAAAAAAGAAAAGAAAAAAAAAAAAAAACCAAACACAACACCTCATAAGTTATAGTCTTGGTCTTCACCCTCCCTTTC
TCTTCCCTTCCGTCCATCTTCCTTCCCACGTGCCCTTTCTTTATCTCTTCTGCCTCTCCCTACTTTCCTCACTCCCT
GTTAGGGACGTTGAGAGGCACGAGAAAGGGTGGGCTAGATCAGATCCTGGGACTGGGGCTCTTAAGCATTCCGAAGA
GAGTCGACTTTCTCCTATCGGGAGAAGGGTAGTGGGGTGAAAACCACTCTTTTCTCTTCTTCCTTCGGCCCTGGCAC
TGCTTCCCAAAAGGACCAGATTGGCAGAGAGCAGCTCTGTGGGGCTGTTCTTCCCTGACAATGTAGCAATAAGCAGG
TGCTGCCAAAGGCAAGAGAATGAGGTCTGAGCTCTGAAAGGAGTGGTCCCGAGACAAGGGAAGGGTCGCCACAACAG
AGCCTTGGCACTAATTCCTTCTTGGGCTGGCACACAGCTGAGGTTACTGTCTGGGCTTCTCCTCAACCATTCTGGTT
GTGAGCTCCCATTAGACCCGCTCCCACCTCTTCTGTGTCTGCCCTGTATTCGAGGACACCTCAGAAGGACTTAGTCC
CTCTGAGGCGCTAGAGCCTTAGAGTGCCCCACCCCTCCCTTTGTTTAGTCAGTCTTAGCACCTGTGACCTCCCAGGA
ACACAAAGGACTATGCTCCTCCGAGGCTATGCTAACGCCCATGAGAGCAGAGGTGGAAGGGACAAGACCAGGTGCTA
GGGAGGAGGGGGCATGGCGTCTCTCTCCAGCCCACCACTGCACTTTAACCAGGGTCTTAGGTACAAAATGCTACTTT
TCAGGGCCTTCCAGCTCTGGAACCTCAAACATCCTCATGCTCTCTCCCAGATCCTTTTGCATAAAAAAAAACAAAAC
AAAAAAACCAACAACAAAAAAAGTAAAGAAAAAGAAGAAAACAACAACAAAAAACAAAATGCCAAAATCCACACAGA
GAAAAGAGGTGTTCTCTCTCTCTCTTTTTTTTTATTACTCTTAAAAAAACAACACCACAAAAAAGTGGAGGGAAGGGA
GAGAATTTCTAAATAGACACTTTTCCAGACCTTTGTGTGTGTGTGTGTGTGTGTGTGTGTGTGTGTGTGTATGTGTG
TGTGTGTGTGTGTGTGTGTGTGTGTGTGTGTGTGTGTCAGTGTCCAAGCTGCAAGTGGAATTTTATAATACTTCTGGCA
GCTTCTTTCCTTGTGTATATAATATATATATATTTTTAATCAGAAATTATGAAGATCAAAAATAGAATAAACACAGA
AGCAAGTGCAATACCACCTCTCCTTCTCCCCAGAGTTCCTCTGTAGCCTGTTCGGTGTCCCCTTTGGCCCTTGACCC
TTGACCTTGTCTCTCTTCCTCTGGTTCCTGACCTATTCTCCCCTTCCCTCTTTTTAAAGAGTTTTTCTCTTTTCTCA
AAGGGGGTTAAACCAGCTTTTGAGACTTACTGCAAAGCATTTTGTATATGTAACATACTGTAAGTAAATATTTGTGT
AATGGAGAAATACTACTGTAAGTTTTGTACTGTACTGGCTGAAGGTCTGTTATAAATAAACACGAGTAATTTAA

FIG. 16C

>Ikzf4 Mus musculus IKAROS family zinc finger 4 (Ikzf4), transcript variant 1, mRNA (used in examples herein; untranslated shown highlighted in grey; stop codon underlined) (SEQ ID NO:35)

ATGCACACACCACCCGCACTCCCTCGCCGTTTCCAAGGCGGCGGCCGCGTTCGCACCCCAGGGTCTCACCGGCAA
GGGAAGGATAATCTGGAGAGGGAGCTCTCAGGAGGGTGTGCTCCGGATTTCTTGCCTCAGGCCCAGGACTCCAA
CCATTTTATAATGGAATCTTTATTTTGTGAAAGTAGCGGGGACTCATCTCTGGAGAAGGAGTTCCTTGGGGCCCCA
GTGGGGCCCTCGGTGAGCACCCCAAACAGCCAACACTCTTCACCCAGCCGCTCGCTCAGTGCCAACTCCATCAAG
GTGGAGATGTACAGCGATGAGGAGTCGAGCAGACTGCTGGGGCCGGATGAACGGCTCCTGGATAAGGATGACA
GTGTGATTGTGGAAGACTCATTGTCAGAGCCCTTAGGCTACTGCGATGGAAGTGGGCCAGAGCCTCACTCCCCTG
GCGGCATCCGGCTACCCAACGGCAAGCTCAAGTGCGACGTCTGCGGCATGGTCTGCATTGGGCCCAATGTGCTCA
TGGTACACAAGCGCAGCCACACTGGGGAGAGGCCCTTCCACTGTAATCAGTGTGGTGCCTCCTTCACACAGAAGG
GCAATCTGCTTCGCCACATCAAGCTGCACTCGGGGGAGAAGCCCTTCAAGTGCCCCTTCTGCAACTATGCCTGCCG
CCGGCGTGACGCACTCACTGGCCACCTCCGCACACACTCAGTCTCCTCCCCCACCGTGGGCAAACCCTACAAGTGC
AACTACTGTGGCCGGAGCTACAAACAGCAAAGTACCCTGGAGGAGCACAAGGAGAGGTGCCACAACTACCTACA
GAGTCTCAGCACTGATGCCCAAGCTCTGACTGGCCAGCCAGGTGATGAAATCC

FIG. 16D

GTGACCTGGAGATGGTGCCTGACTCAATGCTGCACCCATCGACTGAACGGCCAACTTTCATTGATCGTTTGGCCAA
CAGCCTCACCAAACGCAAGCGTTCCACCCCACAGAAGTTTGTAGGTGAAAAGCAGATGCGCTTCAGCCTCTCAGA
CCTTCCCTATGATGTGAATGCCAGCGGTGGCTATGAAAAGGACGTAGAGTTGGTGGCACACCATGGCCTGGAGC
CTGGCTTTGGAGGGTCTCTAGCCTTTGTGGGTACAGAGCATCTGCGTCCCCTCCGCCTCCCACCCACCAACTGCAT
CTCAGAACTCACACCTGTCATCAGCTCTGTGTACACCCAAATGCAGCCCATCCCCAGCCGACTGGAGCTTCCAGGG
TCCCGAGAAGCAGGTGAGGGACCGGAGGACCTGGGAGATGGAGGTCCCCTCCTTTATCGGGCCCGAGGCTCTCT
GACTGACCCTGGGGCATCCCCCAGCAATGGCTGCCAGGACTCCACAGATACAGAGAGCAACCACGAAGACCGGA
TTGGTGGGGTGGTATCCCTTCCTCAGGGTCCCCCACCCCAACCTCCTCCCACCATAGTGGTGGGCCGGCACAGTCC
CGCCTATGCCAAAGAGGACCCCAAACCACAGGAGGGGTTACTGCGGGGCACCCCAGGCCCCTCCAAGGAAGTGC
TTCGGGTGGTGGGTGAGAGTGGTGAGCCAGTGAAGGCCTTTAAGTGTGAACACTGCCGCATCCTCTTTCTGGACC
ACGTCATGTTCACCATCCACATGGGCTGCCACGGCTTCAGAGACCCTTTTGAGTGTAACATCTGTGGTTATCACAG
CCAGGATCGGTATGAGTTCTCTTCCCACATCGTCCGGGGGGAACATAAGGTGGGCTAG

>NM_001358536.1 Mus musculus IKAROS family zinc finger 4 (Ikzf4), transcript variant 2, mRNA(SEQ ID NO:36)
ACACACGAGGCTCTCAGCACATACACCCTGGGCTGAGCGGTTCTGCCGGCTGCAGCCGTGGGCCCCTGCTCACCGTG
CGGCTGCCACTGCCTGCGAAATGACGGCGGTTCCCCTCACTTCCAGGAATCCACGCTTCCTGGAAGGTGAGTGGCTG
GGCTCACCCCTGCCTGCCACCGAGACGCAGACATGCACACACCACCCGCACTCCCTCGCCGTTTCCAAGGCGGCGGC
CGCGTTCGCACCCCAGGGTCTCACCGGCAAGGGAAGGATAATCTGGAGAGGGAGCTCTCAGGAGGGTGTGCTCCGGA
TTTCTTGCCTCAGGCCCAGGACTCCAACCATTTTATAATGGAATCTTTATTTTGTGAAAGCCTTTGCGCATATACCC
ATGCATGTTCATGTTAGCAGATAATATAGACGGCTGTGATGTTTATCCCAGTAGGTAGCGGGGACTCATCTCTGGAG
AAGGAGTTCCTTGGGGCCCCAGTGGGGCCCTCGGTGAGCACCCCAAACAGCCAACACTCTTCACCCAGCCGCTCGCT
CAGTGCCAACTCCATCAAGGTGGAGATGTACAGCGATGAGGAGTCGAGCAGACTGCTGGGGCCGGATGAACGGCTCC
TGGATAAGGATGACAGTGTGATTGTGGAAGACTCATTGTCAGAGCCCTTAGGCTACTGCGATGGAAGTGGGCCAGAG
CCTCACTCCCCTGGCGGCATCCGGCTACCCAACGGCAAGCTCAAGTGCGACGTCTGCGGCATGGTCTGCATTGGGCC
CAATGTGCTCATGGTACACAAGCGCAGCCACACTGGGGAGAGGCCCTTCCACTGTAATCAGTGTGGTGCCTCCTTCA
CACAGAAGGGCAATCTGCTTCGCCACATCAAGCTGCACTCGGGGGAGAAGCCCTTCAAGTGCCCCTTCTGCAACTAT
GCCTGCCGCCGGCGTGACGCACTCACTGGCCACCTCCGCACACACTCAGTCTCCTCCCCCACCGTGGGCAAACCCTA
CAAGTGCAACTACTGTGGCCGGAGCTACAAACAGCAAAGTACCCTGGAGGAGCACAAGGAGAGGTGCCACAACTACC
TACAGAGTCTCAGCACTGATGCCCAAGCTCTGACTGGCCAGCCAGGTGATGAAATCCGTGACCTGGAGATGGTGCCT
GACTCAATGCTGCACCCATCGACTGAACGGCCAACTTTCATTGATCGTTTGGCCAACAGCCTCACCAAACGCAAGCG
TTCCACCCCACAGAAGTTTGTAGGTGAAAAGCAGATGCGCTTCAGCCTCTCAGACCTTCCCTATGATGTGAATGCCA
GCGGTGGCTATGAAAAGGACGTAGAGTTGGTGGCACACCATGGCCTGGAGCCTGGCTTTGGAGGGTCTCTAGCCTTT
GTGGGTACAGAGCATCTGCGTCCCCTCCGCCTCCCACCCACCAACTGCATCTCAGAACTCACACCTGTCATCAGCTC
TGTGTACACCCAA

FIG. 16E

ATGCAGCCCATCCCCAGCCGACTGGAGCTTCCAGGGTCCCGAGAAGCAGGTGAGGGACCGGAGGACCTGGGAGATGG
AGGTCCCCTCCTTTATCGGGCCCGAGGCTCTCTGACTGACCCTGGGGCATCCCCCAGCAATGGCTGCCAGGACTCCA
CAGATACAGAGAGCAACCACGAAGACCGGATTGGTGGGGTGGTATCCCTTCCTCAGGGTCCCCCACCCCAACCTCCT
CCCACCATAGTGGTGGGCCGGCACAGTCCCGCCTATGCCAAAGAGGACCCCAAACCACAGGAGGGGTTACTGCGGGG
CACCCCAGGCCCCTCCAAGGAAGTGCTTCGGGTGGTGGGTGAGAGTGGTGAGCCAGTGAAGGCCTTTAAGTGTGAAC
ACTGCCGCATCCTCTTTCTGGACCACGTCATGTTCACCATCCACATGGGCTGCCACGGCTTCAGAGACCCTTTTGAG
TGTAACATCTGTGGTTATCACAGCCAGGATCGGTATGAGTTCTCTTCCCACATCGTCCGGGGGGAACATAAGGTGGG
CTAGAGACCTCTTTCCCCACAGCCTGCTCTCAGCCCGGCCCCCACCCTACTGCCCTACCTACAGGGGTCTAGCCCAA
TTCCTGTTACACCCTAAGGAGTTTTGCGTTGTAGCCCCACCCACTGGCCGCCTCACTTCACACTTGACTCCAACCGT
CTTTGCCTGTTCCCTTCTACCCTGACCGATTTGAGCATTTCGACAAGACAAGTCTCTTGCTTATATTTCTCCTTCTA
ACCTCTCTCCCCGGCACATTTGCTTTTTAAATTGACTTTAACTTGGCCTTTTCTTAGTTTACTGCAATCTCTGGCCA
CTCCTTCATTCTTCTGCCCATGGCTCCCTTCTGCTCTAAGCCTAGATTTTTTTTTATTTTATTATTATTATTATTAT
TATTACTTGTGTGTGTGTGTGGATCCCACATCCTCCAACAGCTCCAGGGGTTGGAAGCTCCTCTCTGTGCTAAGAGA
CGTTGGGCTTCTTGCTTTAATCCTCACCCTTATTTATCTGACCCTTCACTTTTGATGCTGATACCTCCCAACGGCCC
CACCTTAGCTCTGTGGCATTATTATCTCCTCTCTGGGACCTTTCAGCCCGGCACTCCATACCTCTCGTGCCCACTCA
CTTTAGGCAGCTTGCACTATTCTTAAATGAATGAAGAATTTCCTCATTTGCAGGTAGGAGGGGCTGTAGAAACTCTC
CCCAGGCACTGTGGACTGAGGGTCCTCTTGACCTCACCTGGGAATCCGAGCTCCCTAAAGACTACATTCAGGACCTC
CCTCTAGGATGTGATACCACCCTTCCCTCTCCCTGGCTCACCCCTCAACACCACTCTGGTCTCAACTCGCCACTCTT
GTCAGTTGGTGGCTTTTCTCTCCTTGGAATGCCCCCATTTTATATTCTCAGGGGCTAAGGCTAGACCTGCTACCCTT
TCTCTGACACACAGAGAGAGCTGCAGGTACCTAGCTGAGAACCAGGGCATGGGAAGGGGGATGGGTAGAACTCTCTC
CTCCACCTTTCAAACACTTACACTCCAGTGACCTTCCTAGGCTCTCAGGGACTCCTTCTGTCCCCATATTATGAGAA
ACCAGCGGGTTGCTGCTCGATGACCAGGGGTCTCTCAACCCTGTCAGTCACGCTGCCTTTTTCCTCCCTTCCAGCAG
GACTCGCCGTCTCGTCCCCAGGCTCCTGGGCCCTGTTATGATCAATGGCAGGGAGAAAGGGGATGTCTCTTTTCTCT
CTGCCAATTTTCAGTATAACCAAAAAAACTGTCCCAGGATGAACTACACGTATGTGCCCGTCAACCATTCCACCCTT
GTCCCAGCAAGAATGGGACGGACACAGCTGGGAGTCACCTCCACTGCCCTTTCCATACTTAGCTCCAGACACAGGGC
AGGAGAGGCAGTCTTCTCTGGTGGTTGCAGACACTCTGGCTATTCGGATAATCGAGGATTCGTGAGACCATGCAGGA
GGAGGCATAGCTCCATTGCAGGTGGAAGTCTCTCTCTCTAAAGAGTTCCCTGCCAGGGCCACAACCATCCCACTCTC
TGCTTCTTTGAGATTCAAACCAAAGGATGTTTTTTCTATATTTAAAGAAAAGGAAAAAAAAAGAAAAGAAAAAAAAA
AAAAACCAAACACAACACCTCATAAGTTATAGTCTTGGTCTTCACCCTCCCTTTCTCTTCCCTTCCGTCCATCTTCC
TTCCCACGTGCCCTTTCTTTATCTCTTCTGCCTCTCCCTACTTTCCTCACTCCCTGTTAGGGACGTTGAGAGGCACG
AGAAAGGGTGGGCTAGATCAGATCCTGGGACTGGGGCTCTTAAGCATTCCGAAGAGAGTCGACTTTCTCCTATCGGG
AGAAGGGTAGTGGGGTGAAAACCACTCTTTTCTCTTCTTCCTTCGGCCCTGGCACTGCTTCCCAAAAGGACCAGATT
GGCAGAGAGCAGCTCTGTGGGGCTGTTCTTCCCTGACAATGTAGCAATAAGCAGGTGCTGCCAAAGGCAAGAGAATG
AGGTCTGAGCTCTGAAAGGAGTGGTCCCGAGACAAGGGAAGGGTCGCCACAACAGAGCCTTGGCACTAATTCCTTCT
TGGGCTGGCACACAGCTGAGGTTACTGTCTGGGCTTCTCCTCAACCATTCTGGTTGTGAGCTCCCATTAGACCCGCT
CCCACCTCTTCTGTGTCTGCCCTGTATTCGAGGACACCTCAGAAGGACTTAGTCCCTCTGAGGCGCTAGAGCCTTAG
AGTGCCCCACCCCTCCCTTTGTTTAGTCAGTCTTAGCACCTGTGACCTCCCAGGAACACAAAGGACTATGCTCCTCC
GAGGCTATGCTAACGCCCATGAGAGCAGAGGTGGAAGGGACAAGACCAGGTGCTAGGGAGGAGGGGGCATGGCGTCT
CTCTCCAGCCCACCACTGCACTTTAACCAGGGTCTTAGGTACAAAATGCTACTTTTCAGGGCCTTCCAGCTCTGGAA
CCTCAAACATCCTCATGCTCTCTCCCAGATCCTTTTGCATAAAAAAAAACAAAACAAAAAAACCAACAACAAAAAAA
GTAAAGAAAAAGAAGAAAACAACAACAAAAAACAAAATGCCAAAATCCACACAGAGAAAAGAGGTGTTCTCTCTCTC
TCTTTTTTTTATTACTCTTAAAAAAACAACACCACAAAAAAGTGGAGGGAAGGGAGAGAATTTCTAAATAGACACTT
TTCCAGACCTTTGTGTGTGTGTGTGTGTGTGTGTGTGTGTGTGTGTGTATGTGTGTGTGTGTGTGTGTGTGTGTG
TGTGTGTGTGTGTCAGTGTCCAAGCTGCAAGTGGAATTTTATAATACTTCTGGCAGCTTCTTTCCTTGTGTATATAA
TATATATATATTTTTAATCAGAAATTATGAAGATCAAAAATAGAATAAACACAGAAGCAAGTGCAATACCACCTCTC
CTTCTCCCCAGAGTTCCTCTGTAGCCTGTTCGGTGTCCCCTTTGGCCCTTGACCCTTGACCTTGTCTCTCTTCCTCT
GGTTCCTGACCTATTCTCCCCTTCCCTCTTTTTAAAGAGTTTTTCTCTTTTCTCAAAGGGGGTTAAACCAGCTTTTG
AGACTTACTGCAAAGCATTTTGTATATGTAACATACTGTAAGTAAATATTTGTGTAATGGAGAAATACTACTGTAAG
TTTTGTACTGTACTGGCTGAAGGTCTGTTATAAATAAACACGAGTAATTTAA

FIG. 17A
Human
Proteins

>NP_071910.3 zinc finger protein 4 Eos isoform a [Homo sapiens] (isoform a) (SEQ ID NO:37)
MHTPPALPRRFQGGGRVRTPGSHRQGKDNLERDPSGGCVPDFLPQAQDSNHFIMESLFCESSGDSSLEKEFLGAPVG
PSVSTPNSQHSSPSRSLSANSIKVEMYSDEESSRLLGPDERLLEKDDSVIVEDSLSEPLGYCDGSGPEPHSPGGIRL
PNGKLKCDVCGMVCIGPNVLMVHKRSHTGERPFHCNQCGASFTQKGNLLRHIKLHSGEKPFKCPFCNYACRRRDALT
GHLRTHSVSSPTVGKPYKCNYCGRSYKQQSTLEEHKERCHNYLQSLSTEAQALAGQPGDEIRDLEMVPDSMLHSSSE
RPTFIDRLANSLTKRKRSTPQKFVGEKQMRFSLSDLPYDVNSGGYEKDVELVAHHSLEPGFGSSLAFVGAEHLRPLR
LPPTNCISELTPVISSVYTQMQPLPGRLELPGSREAGEGPEDLADGGPLLYRPRGPLTDPGASPSNGCQDSTDTESN
HEDRVAGVVSLPQGPPPQPPPTIVVGRHSPAYAKEDPKPQEGLLRGTPGPSKEVLRVVGESGEPVKAFKCEHCRILF
LDHVMFTIHMGCHGFRDPFEC
NICGYHSQDRYEFSSHIVRGEHKVG >NP_001338018.1 zinc finger protein 4 Eos isoform a [Homo sapiens](isoform a1) (SEQ ID NO:38)
MHTPPALPRRFQGGGRVRTPGSHRQGKDNLERDPSGGCVPDFLPQAQDSNHFIMESLFCESSGDSSLEKEFLGAPVG
PSVSTPNSQHSSPSRSLSANSIKVEMYSDEESSRLLGPDERLLEKDDSVIVEDSLSEPLGYCDGSGPEPHSPGGIRL
PNGKLKCDVCGMVCIGPNVLMVHKRSHTGERPFHCNQCGASFTQKGNLLRHIKLHSGEKPFKCPFCNYACRRRDALT
GHLRTHSVSSPTVGKPYKCNYCGRSYKQQSTLEEHKERCHNYLQSLSTEAQALAGQPGDEIRDLEMVPDSMLHSSSE
RPTFIDRLANSLTKRKRSTPQKFVGEKQMRFSLSDLPYDVNSGGYEKDVELVAHHSLEPGFGSSLAFVGAEHLRPLR
LPPTNCISELTPVISSVYTQMQPLPGRLELPGSREAGEGPEDLADGGPLLYRPRGPLTDPGASPSNGCQDSTDTESN
HEDRVAGVVSLPQGPPPQPPPTIVVGRHSPAYAKEDPKPQEGLLRGTPGPSKEVLRVVGESGEPVKAFKCEHCRILF
LDHVMFTIHMGCHGFRDPFECNICGYHSQDRYEFSSHIVRGEHKVG >NP_001338019.1 zinc finger protein Eos 4 isoform b [Homo sapiens] (SEQ ID NO:39)
MTAVPLTSRNPRFLEGSGDSSLEKEFLGAPVGPSVSTPNSQHSSPSRSLSANSIKVEMYSDEESSRLLGPDERLLEK
DDSVIVEDSLSEPLGYCDGSGPEPHSPGGIRLPNGKLKCDVCGMVCIGPNVLMVHKRSHTGERPFHCNQCGASFTQK
GNLLRHIKLHSGEKPFKCPFCNYACRRRDALTGHLRTHSVSSPTVGKPYKCNYCGRSYKQQSTLEEHKERCHNYLQS
LSTEAQALAGQPGDEIRDLEMVPDSMLHSSSERPTFIDRLANSLTKRKRSTPQKFVGEKQMRFSLSDLPYDVNSGGY
EKDVELVAHHSLEPGFGSSLAFVGAEHLRPLRLPPTNCISELTPVISSVYTQMQPLPGRLELPGSREAGEGPEDLAD
GGPLLYRPRGPLTDPGASPSNGCQDSTDTESNHEDRVAGVVSLPQGPPPQPPPTIVVGRHSPAYAKEDPKPQEGLLR
GTPGPSKEVLRVVGESGEPVKAFKCEHCRILFLDHVMFTIHMGCHGFRDPFECNICGYHSQDRYEFSSHIVRGEHKV
G >NP_001338020.1 zinc finger protein Eos 4 isoform c [Homo sapiens] (SEQ ID NO:40)
MDIEDCNGRSYVSGSGDSSLEKEFLGAPVGPSVSTPNSQHSSPSRSLSANSIKVEMYSDEESSRLLGPDERLLEKDD
SVIVEDSLSEPLGYCDGSGPEPHSPGGIRLPNGKLKCDVCGMVCIGPNVLMVHKRSHTGERPFHCNQCGASFTQKGN
LLRHIKLHSGEKPFKCPFCNYACRRRDALTGHLRTHSVSSPTVGKPYKCNYCGRSYKQQSTLEEHKERCHNYLQSLS
TEAQALAGQPGDEIRDLEMVPDSMLHSSSERPTFIDRLANSLTKRKRSTPQKFVGEKQMRFSLSDLPYDVNSGGYEK
DVELVAHHSLEPGFGSSLAFVGAEHLRPLRLPPTNCISELTPVISSVYTQMQPLPGRLELPGSREAGEGPEDLADGG
PLLYRPRGPLTDPGASPSNGCQDSTDTESNHEDRVAGVVSLPQGPPPQPPPTIVVGRHSPAYAKEDPKPQEGLLRGT
PGPSKEVLRVVGESGEPVKAFKCEHCRILFLDHVMFTIHMGCHGFRDPFECNICGYHSQDRYEFSSHIVRGEHKVG >NP_001338021.1 zinc finger protein Eos 4 isoform d [Homo sapiens] (SEQ ID NO:41)
MYSDEESSRLLGPDERLLEKDDSVIVEDSLSEPLGYCDGSGPEPHSPGGIRLPNGKLKCDVCGMVCIGPNVLMVHKR
SHTGERPFHCNQCGASFTQKGNLLRHIKLHSGEKPFKCPFCNYACRRRDALTGHLRTHSVSSPTVGKPYKCNYCGRS
YKQQSTLEEHKERCHNYLQSLSTEAQALAGQPGDEIRDLEMVPDSMLHSSSERPTFIDRLANSLTKRKRSTPQKFVG
EKQMRFSLSDLPYDVNSGGYEKDVELVAHHSLEPGFGSSLAFVGAEHLRPLRLPPTNCISELTPVISSVYTQMQPLP
GRLELPGSREAGEGPEDLADGGPLLYRPRGPLTDPGASPSNGCQDSTDTESNHEDRVAGVVSLPQGPPPQPPPTIVV
GRHSPAYAKEDPKPQEGLLRGTPGPSKEVLRVVGESGEPVKAFKCEHCRILFLDHVMFTIHMGCHGFRDPFECNICG
YHSQDRYEFSSHIVRGEHKVG

```
>Consensus of human Ikzf4 isoforms above (SEQ ID NO:42)
XXXXXXXXXXXXXXXXXXXXXXXXXXXXXXXXXXXXXXXXXXXXXXXXXXXXXXXXXXXXXXXXXXXXXXXXXXXXXXXXXXXXXXXX
XXXXXXXXXXXXXMYSDEESSRLLGPDERLLEKDDSVIVEDSLSEPLGYCDGSGPEPHSPGGIRLPNGKLKCDVCGMVCIGPNVLMVHK
RSHTGERPFHCNQCGASFTQKGNLLRHIKLHSGEKPFKCPFCNYACRRRDALTGHLRTHSVSSPTVGKPYKCNYCGRSYKQQSTLEEHK
ERCHNYLQSLSTEAQALAGQPGDEIRDLEMVPDSMLHSSSERPTFIDRLANSLTKRKRSTPQKFVGEKQMRFSLSDLPYDVNSGGYEKD
VELVAHHSLEPGFGSSLAFVGAEHLRPLRLPPTNCISELTPVISSVYTQMQPLPGRLELPGSREAGEGPEDLADGGPLLYRPRGPLTDP
GASPSNGCQDSTDTESNHEDRVAGVVSLPQGPPPQPPPTIVVGRHSPAYAKEDPKPQEGLLRGTPGPSKEVLRVVGESGEPVKAFKCEH
CRILFLDHVMFTIHMGCHGFRDPFECNICGYHSQDRYEFSSHIVRGEHKVG
```

FIG. 17B

Alignment of human Ikzf4 isoforms

```
c       -----------------------------------------------MDIEDCNGRSYVS      13
b       ---------------------------------------------MTAVPLTSRNPRFLE      15
a       MHTPPALPRRFQGGGRVRTPGSHRQGKDNLERDPSGGCVPDFLPQAQDSNHFIMESLFCE      60
a1      MHTPPALPRRFQGGGRVRTPGSHRQGKDNLERDPSGGCVPDFLPQAQDSNHFIMESLFCE      60
d       ------------------------------------------------------------      0

c       GSGDSSLEKEFLGAPVGPSVSTPNSQHSSPSRSLSANSIKVEMYSDEESSRLLGPDERLL      73
b       GSGDSSLEKEFLGAPVGPSVSTPNSQHSSPSRSLSANSIKVEMYSDEESSRLLGPDERLL      75
a       SSGDSSLEKEFLGAPVGPSVSTPNSQHSSPSRSLSANSIKVEMYSDEESSRLLGPDERLL      120
a1      SSGDSSLEKEFLGAPVGPSVSTPNSQHSSPSRSLSANSIKVEMYSDEESSRLLGPDERLL      120
d       ------------------------------------------MYSDEESSRLLGPDERLL      18
                                                  ******************
c       EKDDSVIVEDSLSEPLGYCDGSGPEPHSPGGIRLPNGKLKCDVCGMVCIGPNVLMVHKRS      133
b       EKDDSVIVEDSLSEPLGYCDGSGPEPHSPGGIRLPNGKLKCDVCGMVCIGPNVLMVHKRS      135
a       EKDDSVIVEDSLSEPLGYCDGSGPEPHSPGGIRLPNGKLKCDVCGMVCIGPNVLMVHKRS      180
a1      EKDDSVIVEDSLSEPLGYCDGSGPEPHSPGGIRLPNGKLKCDVCGMVCIGPNVLMVHKRS      180
d       EKDDSVIVEDSLSEPLGYCDGSGPEPHSPGGIRLPNGKLKCDVCGMVCIGPNVLMVHKRS      78
        ************************************************************
c       HTGERPFHCNQCGASFTQKGNLLRHIKLHSGEKPFKCPFCNYACRRRDALTGHLRTHSVS      193
b       HTGERPFHCNQCGASFTQKGNLLRHIKLHSGEKPFKCPFCNYACRRRDALTGHLRTHSVS      195
a       HTGERPFHCNQCGASFTQKGNLLRHIKLHSGEKPFKCPFCNYACRRRDALTGHLRTHSVS      240
a1      HTGERPFHCNQCGASFTQKGNLLRHIKLHSGEKPFKCPFCNYACRRRDALTGHLRTHSVS      240
d       HTGERPFHCNQCGASFTQKGNLLRHIKLHSGEKPFKCPFCNYACRRRDALTGHLRTHSVS      138
        ************************************************************
c       SPTVGKPYKCNYCGRSYKQQSTLEEHKERCHNYLQSLSTEAQALAGQPGDEIRDLEMVPD      253
b       SPTVGKPYKCNYCGRSYKQQSTLEEHKERCHNYLQSLSTEAQALAGQPGDEIRDLEMVPD      255
a       SPTVGKPYKCNYCGRSYKQQSTLEEHKERCHNYLQSLSTEAQALAGQPGDEIRDLEMVPD      300
a1      SPTVGKPYKCNYCGRSYKQQSTLEEHKERCHNYLQSLSTEAQALAGQPGDEIRDLEMVPD      300
d       SPTVGKPYKCNYCGRSYKQQSTLEEHKERCHNYLQSLSTEAQALAGQPGDEIRDLEMVPD      198
        ************************************************************
c       SMLHSSSERPTFIDRLANSLTKRKRSTPQKFVGEKQMRFSLSDLPYDVNSGGYEKDVELV      313
b       SMLHSSSERPTFIDRLANSLTKRKRSTPQKFVGEKQMRFSLSDLPYDVNSGGYEKDVELV      315
a       SMLHSSSERPTFIDRLANSLTKRKRSTPQKFVGEKQMRFSLSDLPYDVNSGGYEKDVELV      360
a1      SMLHSSSERPTFIDRLANSLTKRKRSTPQKFVGEKQMRFSLSDLPYDVNSGGYEKDVELV      360
d       SMLHSSSERPTFIDRLANSLTKRKRSTPQKFVGEKQMRFSLSDLPYDVNSGGYEKDVELV      258
        ************************************************************
c       AHHSLEPGFGSSLAFVGAEHLRPLRLPPTNCISELTPVISSVYTQMQPLPGRLELPGSRE      373
b       AHHSLEPGFGSSLAFVGAEHLRPLRLPPTNCISELTPVISSVYTQMQPLPGRLELPGSRE      375
a       AHHSLEPGFGSSLAFVGAEHLRPLRLPPTNCISELTPVISSVYTQMQPLPGRLELPGSRE      420
a1      AHHSLEPGFGSSLAFVGAEHLRPLRLPPTNCISELTPVISSVYTQMQPLPGRLELPGSRE      420
d       AHHSLEPGFGSSLAFVGAEHLRPLRLPPTNCISELTPVISSVYTQMQPLPGRLELPGSRE      318
        ************************************************************
c       AGEGPEDLADGGPLLYRPRGPLTDPGASPSNGCQDSTDTESNHEDRVAGVVSLPQGPPPQ      433
b       AGEGPEDLADGGPLLYRPRGPLTDPGASPSNGCQDSTDTESNHEDRVAGVVSLPQGPPPQ      435
a       AGEGPEDLADGGPLLYRPRGPLTDPGASPSNGCQDSTDTESNHEDRVAGVVSLPQGPPPQ      480
a1      AGEGPEDLADGGPLLYRPRGPLTDPGASPSNGCQDSTDTESNHEDRVAGVVSLPQGPPPQ      480
d       AGEGPEDLADGGPLLYRPRGPLTDPGASPSNGCQDSTDTESNHEDRVAGVVSLPQGPPPQ      378
        ************************************************************
```

FIG. 17C

```
c       PPPTIVVGRHSPAYAKEDPKPQEGLLRGTPGPSKEVLRVVGESGEPVKAFKCEHCRILFL         493
b       PPPTIVVGRHSPAYAKEDPKPQEGLLRGTPGPSKEVLRVVGESGEPVKAFKCEHCRILFL         495
a       PPPTIVVGRHSPAYAKEDPKPQEGLLRGTPGPSKEVLRVVGESGEPVKAFKCEHCRILFL         540
a1      PPPTIVVGRHSPAYAKEDPKPQEGLLRGTPGPSKEVLRVVGESGEPVKAFKCEHCRILFL         540
d       PPPTIVVGRHSPAYAKEDPKPQEGLLRGTPGPSKEVLRVVGESGEPVKAFKCEHCRILFL         438
        ************************************************************

c       DHVMFTIHMGCHGFRDPFECNICGYHSQDRYEFSSHIVRGEHKVG      538
b       DHVMFTIHMGCHGFRDPFECNICGYHSQDRYEFSSHIVRGEHKVG      540
a       DHVMFTIHMGCHGFRDPFECNICGYHSQDRYEFSSHIVRGEHKVG      585
a1      DHVMFTIHMGCHGFRDPFECNICGYHSQDRYEFSSHIVRGEHKVG      585
d       DHVMFTIHMGCHGFRDPFECNICGYHSQDRYEFSSHIVRGEHKVG      483
        *********************************************
```

FIG. 17D

Alignment of human Ikzf4 isoform a and mouse Ikzf4 isoform 1

```
1       MHTPPALPRRFQGGGRVRTPGSHRQGKDNLERELSGGCAPDFLPQAQDSNHFIMESLFCE  60
a       MHTPPALPRRFQGGGRVRTPGSHRQGKDNLERDPSGGCVPDFLPQAQDSNHFIMESLFCE  60
        ********************************: ****.*********************

1       SSGDSSLEKEFLGAPVGPSVSTPNSQHSSPSRSLSANSIKVEMYSDEESSRLLGPDERLL  120
a       SSGDSSLEKEFLGAPVGPSVSTPNSQHSSPSRSLSANSIKVEMYSDEESSRLLGPDERLL  120
        ************************************************************

1       DKDDSVIVEDSLSEPLGYCDGSGPEPHSPGGIRLPNGKLKCDVCGMVCIGPNVLMVHKRS  180
a       EKDDSVIVEDSLSEPLGYCDGSGPEPHSPGGIRLPNGKLKCDVCGMVCIGPNVLMVHKRS  180
        :***********************************************************

1       HTGERPFHCNQCGASFTQKGNLLRHIKLHSGEKPFKCPFCNYACRRRDALTGHLRTHSVS  240
a       HTGERPFHCNQCGASFTQKGNLLRHIKLHSGEKPFKCPFCNYACRRRDALTGHLRTHSVS  240
        ************************************************************

1       SPTVGKPYKCNYCGRSYKQQSTLEEHKERCHNYLQSLSTDAQALTGQPGDEIRDLEMVPD  300
a       SPTVGKPYKCNYCGRSYKQQSTLEEHKERCHNYLQSLSTEAQALAGQPGDEIRDLEMVPD  300
        ***************************************:****:***************

1       SMLHPSTERPTFIDRLANSLTKRKRSTPQKFVGEKQMRFSLSDLPYDVNASGGYEKDVEL  360
a       SMLHSSSERPTFIDRLANSLTKRKRSTPQKFVGEKQMRFSLSDLPYDVN-SGGYEKDVEL  359
        **** *:****************************************** **********

1       VAHHGLEPGFGGSLAFVGTEHLRPLRLPPTNCISELTPVISSVYTQMQPIPSRLELPGSR  420
a       VAHHSLEPGFGSSLAFVGAEHLRPLRLPPTNCISELTPVISSVYTQMQPLPGRLELPGSR  419
        ****.******.******:******************************:*.********

1       EAGEGPEDLGDGGPLLYRARGSLTDPGASPSNGCQDSTDTESNHEDRIGGVVSLPQGPPP  480
a       EAGEGPEDLADGGPLLYRPRGPLTDPGASPSNGCQDSTDTESNHEDRVAGVVSLPQGPPP  479
        *********.******** ** *************************:.***********

1       QPPPTIVVGRHSPAYAKEDPKPQEGLLRGTPGPSKEVLRVVGESGEPVKAFKCEHCRILF  540
a       QPPPTIVVGRHSPAYAKEDPKPQEGLLRGTPGPSKEVLRVVGESGEPVKAFKCEHCRILF  539
        ************************************************************

1       LDHVMFTIHMGCHGFRDPFECNICGYHSQDRYEFSSHIVRGEHKVG 586
a       LDHVMFTIHMGCHGFRDPFECNICGYHSQDRYEFSSHIVRGEHKVG 585
        **********************************************
```

>Consensus of human Ikzf4 isoform a and mouse Ikzf4 isoform 1 (SEQ ID NO:43)

```
MHTPPALPRRFQGGGRVRTPGSHRQGKDNLERXXSGGCXPDFLPQAQDSNHFIMESLFCESSGDSSLEKEFLGAPVGPSV
STPNSQHSSPSRSLSANSIKVEMYSDEESSRLLGPDERLLXKDDSVIVEDSLSEPLGYCDGSGPEPHSPGGIRLPNGKLK
CDVCGMVCIGPNVLMVHKRSHTGERPFHCNQCGASFTQKGNLLRHIKLHSGEKPFKCPFCNYACRRRDALTGHLRTHSVS
SPTVGKPYKCNYCGRSYKQQSTLEEHKERCHNYLQSLSTXAQALXGQPGDEIRDLEMVPDSMLHXSXERPTFIDRLANSL
TKRKRSTPQKFVGEKQMRFSLSDLPYDVNXSGGYEKDVELVAHHXLEPGFGXSLAFVGXEHLRPLRLPPTNCISELTPVI
SSVYTQMQPXPXRLELPGSREAGEGPEDLXDGGPLLYRXRGXLTDPGASPSNGCQDSTDTESNHEDRXXGVVSLPQGPPP
QPPPTIVVGRHSPAYAKEDPKPQEGLLRGTPGPSKEVLRVVGESGEPVKAFKCEHCRILFLDHVMFTIHMGCHGFRDPFE
CNICGYHSQDRYEFSSHIVRGEHKVG
```

FIG. 18A

Nucleic acids

>NM_022465.3 Homo sapiens IKAROS family zinc finger 4 (IKZF4), transcript variant 1, mRNA (CDS shown bolded; untranslated shown highlighted in grey; stop codon underlined) (SEQ ID NO:44)

GAAGCTGTCCGTGTCCTGGGCCCCATGACCTCTGGGGCCTTGGCTTCCCCAGCTGGCAGAGGATTGGGCCTTCCCTA
GGGCCCCCCCTTTCTCCCTCCCACCCGCAGGCCCATCCATCTCTCTCTCTCTCTCTTGCACACACTCTTGCCTCTCT
CAGGCATTTGTTGTGCAGTTCCTCTTTGTCTGCTGGGCACGAGGGGCAACAGCATCTGCCTTTCCCTCCCTGTGCAC
ACACCCACCACCCACCCCCTTCACTGTCTTGGAAAAGGGATGCTGTAGCCTAGCATCTCCCCCACTATATACACATA
TACATTCTCTCCAGCCCCCTCCCCAAGCACATCCAAGCGTGCTCTCCCCTCTCCTTCTCTCCCTCTCTCTCTCTC
TCTCTCACACACACACACACACACACACTCAACACACATACACCCTGGGCTGAGCTGCTCTTGCTGGCTGCAGCCGT
GGGCCTCTGCTCACCGTGCCGCTGCTGCTGCCTGCGAAATGACGGCGGTTCCCCTCACTTCCAGGAATCCACGCTTC
CTGGAAGGTGAGTGGCTGGGCTCACCCCTGCCTGCCACTGAGACGCAGACATGCATACACCACCCGCACTCCCTCGC
CGTTTCCAAGGCGGCGGCCGCGTTCGCACCCCAGGGTCTCACCGGCAAGGGAAGGATAATCTGGAGAGGGATCCCTC
AGGAGGGTGTGTTCCGGATTTCTTGCCTCAGGCCCAAGACTCCAACCATTTTATAATGGAATCTTTATTTTGTGAAA
GTAGCGGGGACTCATCTCTGGAGAAGGAGTTCCTCGGGGCCCCAGTGGGGCCCTCGGTGAGCACCCCCAACAGCCAG
CACTCTTCTCCTAGCCGCTCACTCAGTGCCAACTCCATCAAGGTGGAGATGTACAGCGATGAGGAGTCAAGCAGACT
GCTGGGGCCAGATGAGCGGCTCCTGGAAAAGGACGACAGCGTGATTGTGGAAGATTCATTGTCTGAGCCCCTGGGCT
ACTGTGATGGGAGTGGGCCAGAGCCTCACTCCCCTGGGGGCATCCGGCTGCCCAATGGCAAGCTCAAGTGTGACGTC
TGCGGCATGGTCTGTATTGGACCCAACGTGCTCATGGTGCACAAGCGCAGTCACACTGGTGAAAGGCCCTTCCATTG
CAACCAGTGTGGTGCCTCCTTCACCCAGAAGGGGAACCTGCTGCGCCACATCAAGCTGCACTCTGGGGAGAAGCCCT
TTAAATGTCCCTTCTGCAACTATGCCTGCCGCCGGCGTGATGCACTCACTGGTCACCTCCGCACACACTCAGTCTCC
TCTCCCACAGTGGGCAAGCCCTACAAGTGTAACTACTGTGGCCGGAGCTACAAACAGCAGAGTACCCTGGAGGAGCA
CAAGGAGCGGTGCCATAACTACCTACAGAGTCTCAGCACTGAAGCCCAAGCTTTGGCTGGCCAACCAGGTGACGAAA
TACGTGACCTGGAGATGGTGCCAGACTCCATGCTGCACTCATCCTCTGAGCGGCCAACTTTCATCGATCGTCTGGCC
AATAGCCTCACCAAACGCAAGCGTTCCACACCCCAGAAGTTTGTAGGCGAAAAGCAGATGCGCTTCAGCCTCTCAGA
CCTCCCCTATGATGTGAACTCGGGTGGCTATGAAAAGGATGTGGAGTTGGTGGCACACCACAGCCTAGAGCCTGGCT
TTGGAAGTTCCCTGGCCTTTGTGGGTGCAGAGCATCTGCGTCCCCTCCGCCTTCCACCCACCAATTGCATCTCAGAA
CTCACGCCTGTCATCAGCTCTGTCTACACCCAGATGCAGCCCCTCCCTGGTCGACTGGAGCTTCCAGGATCCCGAGA
AGCAGGTGAGGGACCTGAGGACCTGGCTGATGGAGGTCCCCTCCTCTACCGGCCCCGAGGCCCCCTGACTGACCCTG
GGGCATCCCCCAGCAATGGCTGCCAGGACTCCACAGACACAGAAAGCAACCACGAAGATCGGGTTGCGGGGGTGGTA
TCCCTCCCTCAGGGTCCCCCACCCCAGCCACCTCCCACCATTGTGGTGGGCCGGCACAGTCCTGCCTACGCCAAAGA
GGACCCCAAGCCACAGGAGGGGTTATTGCGGGGCACCCCAGGCCCCTCCAAGGAAGTGCTTCGGGTGGTGGGCGAGA
GTGGTGAGCCTGTGAAGGCCTTCAAGTGTGAGCACTGCCGTATCCTCTTCCTGGACCACGTCATGTTCACTATCCAC
ATGGGCTGCCATGGCTTCAGAGACCCTTTTGAGTGCAACATCTGTGGTTATCACAGCCAGGACCGGTACGAATTCTC
TTCCCACATTGTCCGGGGGGAGCATAAGGTGGGCTAGCAACCTCTCCCTCTCTCCTCAGTCCACCACTCCACTGCCC
TGACTACAGGCATTGATCCCTGTCCCCACCATTTCCCAAGGAGTTTTGCTTTGTAGCCCTCACTACTGGCCACCTGA
CCTCACACCTGACCCTGACCCCTCCTCACCTATTCTCTTCCTCTATCCTGACCGATGTAAGCATTGTGATGAAACAG
ATCTTTTGCTTATGTTTTTCCTTTTTATCTTCTCTCATCCCAGCATACTGAGTTATTTATTAATTAGTTGATTTATT
TTTGCCTTTTTAAATTTTAACTTATATCAGTCACTTGCCACTCCCCCACCCTCCTGTCCACAACTCCTTTCCACTTT
AGGCCAATTTTTCTCTCTTAGATCTTCCAGCAGCCCCAGGGGTAGGAAGCTCCTCTTAGTACTAAGAGACTTCAAGC
TTCTTGCTTTAAGTCC

FIG. 18B

TCACCCTTTACATTATCTAATTCTTCAGTTTTGATGCTGATACCTGCCCCCGGCCCTACCTTAGCTCTGTGGCATTA
TATCTCCTCTCTGGGACTCTTCAACCTGGTACTCCATACCTCTTGTGCCCTCTCACTTTAGGCAGCTTGCACTATTC
TTGAATGAATGAAGAATTATTTCCTCATTTGGAAGTAGGAGGGACTGAAGAAATTCTCCCCAGGCACTGTGGGACTG
AGAGTCCTATTCCCCTAGTAATAGGTCATATTCCCCTAGTAATATGAGTTCTCAAAGCCTACATTCAGGATCTCCCT
CTAGGATGTGATAGATCTGGTCCCTCTCCTTGAACTACCCCTCCACACGCTCTAGTCCCTTCAACCTACCGGTCTAT
TAAGTGGTGGCTTTTCTCTCCTTGGAGTGCCCCAATTTTATATTCTCAGGGGCCAAGGCTAGGTCTGCAACCCTCTG
TCTCTGACAGATTGGGAGCCACAGGTGCCTAATTGGGAACCAGGGCATGGGAAAGGAGTGGGTCAAAATTCTTCTCT
TTCTCCTCCACCTCTCAAACTTCTTCACTATAGTGACCTTCCTAGGCTCTCAGGGGCTCCTTCAGTCCCCATCCTAT
GAGAAACTAGTGGGTTGCTGCCTGATGACAAGGGGTTGTTTCAGCCCCTCAGTCATGCTGCCTTCTGCTGCTCCCTC
CCAGCAGGATTCACCCTCTCATTCCCGGGCTCCTGGGCCCTGTTCTTAGGATCAGTGGCAGGGAGAAACGGGTATCT
CTTTTCTCTCTTCTAATTTTCAGTATAACCAAAAATTATCCCAGCATGAGCACGGGCACGTGCCCTTCACCCCATTC
CACCCTTGTTCCAGCAAGACTGGGATGGGTACAACTGAACTGGGGTCTTCCTTTACTACCCCCTTCTACACTCAGCT
CCCAGACACAGGGTAGGAGGGGGGACTGCTGGCTACTGCAGAGACCCTTGGCTATTTGAGTAACCTAGGATTAGTGA
GAAGGGGCAGAAGGAGATACAACTCCACTGCAAGTGGAGGTTTCTTTCTACAAGAGTTTTCTGCCCAAGGCCACAGC
CATCCCACTCTCTGCTTCCTTGAGATTCAAACCAAAGGCTGTTTTTCTATGTTTAAAGAAAAAAAAAAGTAAAAACC
AAACACAACACCTCACAAGTTGTAACTCTTGGTCCTTCTCTCTCTCCTTTTCTCTTCCCTTCCTTCCCCTTCCATCT
TTCTTTCCACATGTCCTTTCCTTATTGGCTCTTTTACCTCCTACTTTTCTCACTCCCTATCAGGGATATTTTGGGGG
GGGATGGTAAAGGGTGGGCTAAGGAACAGACCCTGGGATTAGGGCCTTAAGGGCTCTGAGAGGAGTCTACCTTGCCT
TCTTATGGGAAGGGAGACCCTAAAAAACTTTCTCCTCTTTGTCCTCCTTTTTCTCCCCCACTCTGAGGTTTCCCCAA
GAGAACCAGATTGGCAGGGAGAAGCATTGTGGGGCAATTGTTCCTCCTTGACAATGTAGCAATAAATAGATGCTGCC
AAGGGCAGAAAATGGGGAGGTTAGCTCAGAGCAGAGTAGTCTCTAGAGAAAGGAAGAATCCTCAACGGCACCCTGGG
GTGCTAGCTCCTTTTTAGAATGTCAGCAGAGCTGAGATTAATATCTGGGCTTTTCCTGAACTATTCTGGTTATTGAG
CCCTTCCTGTTAGACCTACCGCCTCCCACCTCTTCTGTGTCTGCTGTGTATTTGGTGACACTTCATAAGGACTAGTC
CCTTCTGGGGTATCAGAGCCTTAGGGTGCCCCCATCCCCTTCCCCAGTCAACTGTGGCACCTGTAACCTCCCGGAAC
ATGAAGGACTATGCTCTGAGGCTATACTCTGTGCCCATGAGAGCAGAGACTGGAAGGGCAAGACCAGGTGCTAAGGA
GGGGAGAGGGGGCATCCTGTCTCTCTCCAGACCATCACTGCACTTTAACCAGGGTCTTAGGTACAAAATCCTACTTT
TCAGAGCCTTCCAGCTCTGGAACCTCAAACATCCTCATGCTCTCTCCCAGCTCCTTTTGCATAAAAAAAAAAGTAAA
GAAAAAGAAAAAAAAATACACACACACTGAAACCCACATGGAGAAAAGAGGTGTTTCCTTTTATATTGCTATTCAAA
ATCAATACCACCAACAAAATATTTCTAAGTAGACACTTTTCCAGACCTTTGTTTTTTTGTGTCAGTGTCCAAGCTGC
AGATAGGATTTTGTAATACTTCTGGCAGCTTCTTTCCTTGTGTACATAATATATATATATACATATATATATATATT
TTTAATCAGAAGTTATGAAGAACAAAAAGAAAAAATAAACACAGAAGCAAGTGCAATACCACCTCTCTTCTCCCTCT
CTCCTAGGGTTTCCTTTGTAGCCTATGTTTGGTGTCTCTTTTGACCTTTACCCCTTCACCTCCTCCTCTCTTCTTCT
GATTCCCCTCCCCCCCTTTTTTAAAGAGTTTTTCTCCTTTCTCAAGGGGAGTTAAACTAGCTTTTGAGACTTATTGC
AAAGCATTTTGTATATGTAATATATTGTAAGTAAATATTTGTGTAACGGAGATATACTACTGTAAGTTTTGTACTGT
ACTGGCTGAAAGTCTGTTATAAATAAACATGAGTAATTTAACACCAAAAAAAAAAAAAAAAAAAAAAAAAAAAAAAA
AAAAAAAAAAAAAAAAAAAAAAA

>NM_001351089.1 Homo sapiens IKAROS family zinc finger 4 (IKZF4), transcript variant 2, mRNA (SEQ ID NO:45)
GGACCAATGAAGGAATTATTGGCATGCACTAAAGGAGATAGCAAGATGGGTCAGACACACATATGAGAGTCATTGGC
AACACCCGGGTAATGTAAGGAATCCACGCTTCCTGGAAGGTGAGTGGCTGGGCTCACCCCTGCCTGCCACTGAGACG
CAGACATGCATACACCACCCGCACTCCCTCGCCGTTTCCAAGGCGGCGGCCGCGTTCGCACCCCAGGGTCTCACCGG
CAAGGGAAGGATAATCTGGAGAGGGATCCCTCAGGAGGGTGTGTTCCGGATTTCTTGCCTCAGGCCCAAGACTCCAA
CCATTTTATAATGGAATCTTTATTTTGTGAAAGTAGCGGGGACTCATCTCTGGAGAAGGAGTTCCTCGGGGCCCCAG
TGGGGCCCTCGGTGAGCACCCCCAACAGCCAGCACTCTTCTCCTAGCCGCTCACTCAGTGCCAACTCCATCAAGGTG
GAGATGTACAGCGATGAGGAGTCAAGCAGACTGCTGGGGCCAGATGAGCGGCTCCTGGAAAAGGACGACAGCGTGAT
TGTGGAAGATTCATTGTCTGAGCCCCTGGGCTACTGTGATGGGAGTGGGCCAGAGCCTCACTCCCCTGGGGGCATCC
GGCTGCCCAATGGCAAGCTCAAGTGTGACGTCTGCGGCATGGTCTGTATTGGACCCAACGTGCTCATGGTGCACAAG
CGCAGTCACACTGGTGAAAGGCCCTTCCATTGCAACCAGTGTGGTGCCTCCTTCACCCAGAAGGGGAACCTGCTGCG
CCACATCAAGCTGCACTCTGGGGAGAAGCCCTTTAAATGTCCCTTCTGCAACTATGCCTGCCGCCGGCGTGATGCAC
TCACTGGTCACCTCCGCACACACTCAGTCTCCTCTCCCACAGTGGGCAAGCCCTACAAGTGTAACTACTGTGGCCGG
AGCTACAAACAGCAGAGTACCCTGGAGGAGCACAAGGAGCGGTGCCATAACTACCTACAGAGTCTCAGCACTGAAGC
CCAAGCTTTGGCTGGCCAACCAGGTGACGAAATACGTGACCTGGAGATGGTGCCAGACTCCATGCTGCACTCATCCT
CTGAGCGGCCAACTTTCATCGATCGTCTGGCCAATAGCCTCACCAAACGCAAGCGTTCCACACCCCAGAAGTTTGTA
GGCGAAAAGCAGATGCGCTTCAGCCTCTCAGACCTCCCCTATGATGTGAACTCGGGTGGCTATGAAAAGGATGTGGA
GTTGGTGGCACACCACAGCCTAGAGCCTGGCTTTGGAAGTTCCCTGGCCTTTGTGGGTGCAGAGCATCTGCGTCCCC
TCC

FIG. 18C

GCCTTCCACCCACCAATTGCATCTCAGAACTCACGCCTGTCATCAGCTCTGTCTACACCCAGATGCAGCCCCTCCCT
GGTCGACTGGAGCTTCCAGGATCCCGAGAAGCAGGTGAGGGACCTGAGGACCTGGCTGATGGAGGTCCCCTCCTCTA
CCGGCCCCGAGGCCCCCTGACTGACCCTGGGGCATCCCCCAGCAATGGCTGCCAGGACTCCACAGACACAGAAAGCA
ACCACGAAGATCGGGTTGCGGGGGTGGTATCCCTCCCTCAGGGTCCCCCACCCCAGCCACCTCCCACCATTGTGGTG
GGCCGGCACAGTCCTGCCTACGCCAAAGAGGACCCCAAGCCACAGGAGGGGTTATTGCGGGGCACCCCAGGCCCCTC
CAAGGAAGTGCTTCGGGTGGTGGGCGAGAGTGGTGAGCCTGTGAAGGCCTTCAAGTGTGAGCACTGCCGTATCCTCT
TCCTGGACCACGTCATGTTCACTATCCACATGGGCTGCCATGGCTTCAGAGACCCTTTTGAGTGCAACATCTGTGGT
TATCACAGCCAGGACCGGTACGAATTCTCTTCCCACATTGTCCGGGGGGAGCATAAGGTGGGCTAGCAACCTCTCCC
TCTCTCCTCAGTCCACCACTCCACTGCCCTGACTACAGGCATTGATCCCTGTCCCCACCATTTCCCAAGGAGTTTTG
CTTTGTAGCCCTCACTACTGGCCACCTGACCTCACACCTGACCCTGACCCCTCCTCACCTATTCTCTTCCTCTATCC
TGACCGATGTAAGCATTGTGATGAAACAGATCTTTTGCTTATGTTTTTCCTTTTTATCTTCTCTCATCCCAGCATAC
TGAGTTATTTATTAATTAGTTGATTTATTTTTGCCTTTTTAAATTTTAACTTATATCAGTCACTTGCCACTCCCCCA
CCCTCCTGTCCACAACTCCTTTCCACTTTAGGCCAATTTTTCTCTCTTAGATCTTCCAGCAGCCCCAGGGGTAGGAA
GCTCCTCTTAGTACTAAGAGACTTCAAGCTTCTTGCTTTAAGTCCTCACCCTTTACATTATCTAATTCTTCAGTTTT
GATGCTGATACCTGCCCCCGGCCCTACCTTAGCTCTGTGGCATTATATCTCCTCTCTGGGACTCTTCAACCTGGTAC
TCCATACCTCTTGTGCCCTCTCACTTTAGGCAGCTTGCACTATTCTTGAATGAATGAAGAATTATTTCCTCATTTGG
AAGTAGGAGGGACTGAAGAAATTCTCCCCAGGCACTGTGGGACTGAGAGTCCTATTCCCCTAGTAATAGGTCATATT
CCCCTAGTAATATGAGTTCTCAAAGCCTACATTCAGGATCTCCCTCTAGGATGTGATAGATCTGGTCCCTCTCCTTG
AACTACCCCTCCACACGCTCTAGTCCCTTCAACCTACCGGTCTATTAAGTGGTGGCTTTTCTCTCCTTGGAGTGCCC
CAATTTTATATTCTCAGGGGCCAAGGCTAGGTCTGCAACCCTCTGTCTCTGACAGATTGGGAGCCACAGGTGCCTAA
TTGGGAACCAGGGCATGGGAAAGGAGTGGGTCAAAATTCTTCTCTTTCTCCTCCACCTCTCAAACTTCTTCACTATA
GTGACCTTCCTAGGCTCTCAGGGGCTCCTTCAGTCCCCATCCTATGAGAAACTAGTGGGTTGCTGCCTGATGACAAG
GGGTTGTTTCAGCCCCTCAGTCATGCTGCCTTCTGCTGCTCCCTCCCAGCAGGATTCACCCTCTCATTCCCGGGCTC
CTGGGCCCTGTTCTTAGGATCAGTGGCAGGGAGAAACGGGTATCTCTTTTCTCTCTTCTAATTTTCAGTATAACCAA
AAATTATCCCAGCATGAGCACGGGCACGTGCCCTTCACCCCATTCCACCCTTGTTCCAGCAAGACTGGGATGGGTAC
AACTGAACTGGGGTCTTCCTTTACTACCCCCTTCTACACTCAGCTCCCAGACACAGGGTAGGAGGGGGGACTGCTGG
CTACTGCAGAGACCCTTGGCTATTTGAGTAACCTAGGATTAGTGAGAAGGGGCAGAAGGAGATACAACTCCACTGCA
AGTGGAGGTTTCTTTCTACAAGAGTTTTCTGCCCAAGGCCACAGCCATCCCACTCTCTGCTTCCTTGAGATTCAAAC
CAAAGGCTGTTTTTCTATGTTTAAAGAAAAAAAAAAAGTAAAAACCAAACACAACACCTCACAAGTTGTAACTCTTGG
TCCTTCTCTCTCTCCTTTTCTCTTCCCTTCCTTCCCCTTCCATCTTTCTTTCCACATGTCCTTTCCTTATTGGCTCT
TTTACCTCCTACTTTTCTCACTCCCTATCAGGGATATTTTGGGGGGGGATGGTAAAGGGTGGGCTAAGGAACAGACC
CTGGGATTAGGGCCTTAAGGGCTCTGAGAGGAGTCTACCTTGCCTTCTTATGGGAAGGGAGACCCTAAAAAACTTTC
TCCTCTTTGTCCTCCTTTTTCTCCCCCACTCTGAGGTTTCCCCAAGAGAACCAGATTGGCAGGGAGAAGCATTGTGG
GGCAATTGTTCCTCCTTGACAATGTAGCAATAAATAGATGCTGCCAAGGGCAGAAAATGGGGAGGTTAGCTCAGAGC
AGAGTAGTCTCTAGAGAAAGGAAGAATCCTCAACGGCACCCTGGGGTGCTAGCTCCTTTTTAGAATGTCAGCAGAGC
TGAGATTAATATCTGGGCTTTTCCTGAACTATTCTGGTTATTGAGCCCTTCCTGTTAGACCTACCGCCTCCCACCTC
TTCTGTGTCTGCTGTGTATTTGGTGACACTTCATAAGGACTAGTCCCTTCTGGGGTATCAGAGCCTTAGGGTGCCCC
CATCCCCTTCCCCAGTCAACTGTGGCACCTGTAACCTCCCGGAACATGAAGGACTATGCTCTGAGGCTATACTCTGT
GCCCATGAGAGCAGAGACTGGAAGGGCAAGACCAGGTGCTAAGGAGGGGAGAGGGGGCATCCTGTCTCTCTCCAGAC
CATCACTGCACTTTAACCAGGGTCTTAGGTACAAAATCCTACTTTTCAGAGCCTTCCAGCTCTGGAACCTCAAACAT
CCTCATGCTCTCTCCCAGCTCCTTTTGCATAAAAAAAAAAGTAAAGAAAAAGAAAAAAAAATACACACACACTGAAA
CCCACATGGAGAAAAGAGGTGTTTCCTTTTATATTGCTATTCAAAATCAATACCACCAACAAAATATTTCTAAGTAG
ACACTTTTCCAGACCTTTGTTTTTTTGTGTCAGTGTCCAAGCTGCAGATAGGATTTTGTAATACTTCTGGCAGCTTC
TTTCCTTGTGTACATAATATATATATATACATATATATATATATTTTTAATCAGAAGTTATGAAGAACAAAAAGAAA
AAATAAACACAGAAGCAAGTGCAATACCACCTCTCTTCTCCCTCTCTCCTAGGGTTTCCTTTGTAGCCTATGTTTGG
TGTCTCTTTTGACCTTTACCCCTTCACCTCCTCCTCTCTTCTTCTGATTCCCCTCCCCCCCTTTTTTAAAGAGTTTT
TCTCCTTTCTCAAGGGGGAGTTAAACTAGCTTTTGAGACTTATTGCAAAGCATTTTGTATATGTAATATATTGTAAGT
AAATATTTGTGTAACGGAGATATACTACTGTAAGTTTTGTACTGTACTGGCTGAAAGTCTGTTATAAATAAACATGA
GTAATTTAACACCAAAAAAAAAAAAAAAAAAAAAAAAAAAAAAAAAAAAAAAAAAAAAAAAAAAAA

>NM_001351090.1 Homo sapiens IKAROS family zinc finger 4 (IKZF4), transcript variant 3, mRNA(SEQ ID NO:46)
GAAGCTGTCCGTGTCCTGGGCCCCATGACCTCTGGGGCCTTGGCTTCCCCAGCTGGCAGAGGATTGGGCCTTCCCTA
GGGCCCCCCCTTTCTCCCTCCCACCCGCAGGCCCATCCATCTCTCTCTCTCTCTCTTGCACACACTCTTGCCTCTCT
CAGGCATTTGTTGTGCAGTTCCTCTTTGTCTGCTGGGCACGAGGGGCAACAGCATCTGCCTTTCCCTCCCTGTGCAC
ACACCCACCACCCACCCCCTTCACTGTCTTGGAAAAGGGATGCTGTAGCCTAGCATCTCCCCCACTATATACACATA
TACATTCTCTCCAGCCCCCTCCCCAAGCACATCCAAGCGTGCTCTCCCCTCTCCTTCTCTCCCTCTCTCTCTCTCTC
TCTCTCACACACACACACACACACACACTCAACACACATACACCCTGGGCTGAGCTGCTCTTGCTGGCTGCAGCCGT
GGGCCTCTGCTCACCGTGCCGCTGCTGCTG

FIG. 18D

CCTGCGAAATGACGGCGGTTCCCCTCACTTCCAGGAATCCACGCTTCCTGGAAGGTAGCGGGGACTCATCTCTGGAG
AAGGAGTTCCTCGGGGCCCCAGTGGGGCCCTCGGTGAGCACCCCCAACAGCCAGCACTCTTCTCCTAGCCGCTCACT
CAGTGCCAACTCCATCAAGGTGGAGATGTACAGCGATGAGGAGTCAAGCAGACTGCTGGGGCCAGATGAGCGGCTCC
TGGAAAAGGACGACAGCGTGATTGTGGAAGATTCATTGTCTGAGCCCCTGGGCTACTGTGATGGGAGTGGGCCAGAG
CCTCACTCCCCTGGGGGCATCCGGCTGCCCAATGGCAAGCTCAAGTGTGACGTCTGCGGCATGGTCTGTATTGGACC
CAACGTGCTCATGGTGCACAAGCGCAGTCACACTGGTGAAAGGCCCTTCCATTGCAACCAGTGTGGTGCCTCCTTCA
CCCAGAAGGGGAACCTGCTGCGCCACATCAAGCTGCACTCTGGGGAGAAGCCCTTTAAATGTCCCTTCTGCAACTAT
GCCTGCCGCCGGCGTGATGCACTCACTGGTCACCTCCGCACACACTCAGTCTCCTCTCCCACAGTGGGCAAGCCCTA
CAAGTGTAACTACTGTGGCCGGAGCTACAAACAGCAGAGTACCCTGGAGGAGCACAAGGAGCGGTGCCATAACTACC
TACAGAGTCTCAGCACTGAAGCCCAAGCTTTGGCTGGCCAACCAGGTGACGAAATACGTGACCTGGAGATGGTGCCA
GACTCCATGCTGCACTCATCCTCTGAGCGGCCAACTTTCATCGATCGTCTGGCCAATAGCCTCACCAAACGCAAGCG
TTCCACACCCCAGAAGTTTGTAGGCGAAAAGCAGATGCGCTTCAGCCTCTCAGACCTCCCCTATGATGTGAACTCGG
GTGGCTATGAAAAGGATGTGGAGTTGGTGGCACACCACAGCCTAGAGCCTGGCTTTGGAAGTTCCCTGGCCTTTGTG
GGTGCAGAGCATCTGCGTCCCCTCCGCCTTCCACCCACCAATTGCATCTCAGAACTCACGCCTGTCATCAGCTCTGT
CTACACCCAGATGCAGCCCCTCCCTGGTCGACTGGAGCTTCCAGGATCCCGAGAAGCAGGTGAGGGACCTGAGGACC
TGGCTGATGGAGGTCCCCTCCTCTACCGGCCCCGAGGCCCCCTGACTGACCCTGGGGCATCCCCCAGCAATGGCTGC
CAGGACTCCACAGACACAGAAAGCAACCACGAAGATCGGGTTGCGGGGGTGGTATCCCTCCCTCAGGGTCCCCCACC
CCAGCCACCTCCCACCATTGTGGTGGGCCGGCACAGTCCTGCCTACGCCAAAGAGGACCCCAAGCCACAGGAGGGGT
TATTGCGGGGCACCCCAGGCCCCTCCAAGGAAGTGCTTCGGGTGGTGGGCGAGAGTGGTGAGCCTGTGAAGGCCTTC
AAGTGTGAGCACTGCCGTATCCTCTTCCTGGACCACGTCATGTTCACTATCCACATGGGCTGCCATGGCTTCAGAGA
CCCTTTTGAGTGCAACATCTGTGGTTATCACAGCCAGGACCGGTACGAATTCTCTTCCCACATTGTCCGGGGGGAGC
ATAAGGTGGGCTAGCAACCTCTCCCTCTCTCCTCAGTCCACCACTCCACTGCCCTGACTACAGGCATTGATCCCTGT
CCCCACCATTTCCCAAGGAGTTTTGCTTTGTAGCCCTCACTACTGGCCACCTGACCTCACACCTGACCCTGACCCCT
CCTCACCTATTCTCTTCCTCTATCCTGACCGATGTAAGCATTGTGATGAAACAGATCTTTTGCTTATGTTTTTCCTT
TTTATCTTCTCTCATCCCAGCATACTGAGTTATTTATTAATTAGTTGATTTATTTTTGCCTTTTTAAATTTTAACTT
ATATCAGTCACTTGCCACTCCCCCACCCTCCTGTCCACAACTCCTTTCCACTTTAGGCCAATTTTTCTCTCTTAGAT
CTTCCAGCAGCCCCAGGGGTAGGAAGCTCCTCTTAGTACTAAGAGACTTCAAGCTTCTTGCTTTAAGTCCTCACCCT
TTACATTATCTAATTCTTCAGTTTTGATGCTGATACCTGCCCCCGGCCCTACCTTAGCTCTGTGGCATTATATCTCC
TCTCTGGGACTCTTCAACCTGGTACTCCATACCTCTTGTGCCCTCTCACTTTAGGCAGCTTGCACTATTCTTGAATG
AATGAAGAATTATTTCCTCATTTGGAAGTAGGAGGGACTGAAGAAATTCTCCCCAGGCACTGTGGGACTGAGAGTCC
TATTCCCCTAGTAATAGGTCATATTCCCCTAGTAATATGAGTTCTCAAAGCCTACATTCAGGATCTCCCTCTAGGAT
GTGATAGATCTGGTCCCTCTCCTTGAACTACCCCTCCACACGCTCTAGTCCCTTCAACCTACCGGTCTATTAAGTGG
TGGCTTTTCTCTCCTTGGAGTGCCCCAATTTTATATTCTCAGGGGCCAAGGCTAGGTCTGCAACCCTCTGTCTCTGA
CAGATTGGGAGCCACAGGTGCCTAATTGGGAACCAGGGCATGGGAAAGGAGTGGGTCAAAATTCTTCTCTTTCTCCT
CCACCTCTCAAACTTCTTCACTATAGTGACCTTCCTAGGCTCTCAGGGGCTCCTTCAGTCCCCATCCTATGAGAAAC
TAGTGGGTTGCTGCCTGATGACAAGGGGTTGTTTCAGCCCCTCAGTCATGCTGCCTTCTGCTGCTCCCTCCCAGCAG
GATTCACCCTCTCATTCCCGGGCTCCTGGGCCCTGTTCTTAGGATCAGTGGCAGGGAGAAACGGGTATCTCTTTTCT
CTCTTCTAATTTTCAGTATAACCAAAAATTATCCCAGCATGAGCACGGGCACGTGCCCTTCACCCCATTCCACCCTT
GTTCCAGCAAGACTGGGATGGGTACAACTGAACTGGGGTCTTCCTTTACTACCCCCTTCTACACTCAGCTCCCAGAC
ACAGGGTAGGAGGGGGGACTGCTGGCTACTGCAGAGACCCTTGGCTATTTGAGTAACCTAGGATTAGTGAGAAGGGG
CAGAAGGAGATACAACTCCACTGCAAGTGGAGGTTTCTTTCTACAAGAGTTTTCTGCCCAAGGCCACAGCCATCCCA
CTCTCTGCTTCCTTGAGATTCAAACCAAAGGCTGTTTTTCTATGTTTAAAGAAAAAAAAAAGTAAAAACCAAACACA
ACACCTCACAAGTTGTAACTCTTGGTCCTTCTCTCTCTCCTTTTCTCTTCCCTTCCTTCCCCTTCCATCTTTCTTTC
CACATGTCCTTTCCTTATTGGCTCTTTTACCTCCTACTTTTCTCACTCCCTATCAGGGATATTTTGGGGGGGGATGG
TAAAGGGTGGGCTAAGGAACAGACCCTGGGATTAGGGCCTTAAGGGCTCTGAGAGGAGTCTACCTTGCCTTCTTATG
GGAAGGGAGACCCTAAAAAACTTTCTCCTCTTTGTCCTCCTTTTTCTCCCCCACTCTGAGGTTTCCCCAAGAGAACC
AGATTGGCAGGGAGAAGCATTGTGGGGCAATTGTTCCTCCTTGACAATGTAGCAATAAATAGATGCTGCCAAGGGCA
GAAAATGGGGAGGTTAGCTCAGAGCAGAGTAGTCTCTAGAGAAAGGAAGAATCCTCAACGGCACCCTGGGGTGCTAG
CTCCTTTTTAGAATGTCAGCAGAGCTGAGATTAATATCTGGGCTTTTCCTGAACTATTCTGGTTATTGAGCCCTTCC
TGTTAGACCTACCGCCTCCCACCTCTTCTGTGTCTGCTGTGTATTTGGTGACACTTCATAAGGACTAGTCCCTTCTG
GGGTATCAGAGCCTTAGGGTGCCCCCATCCCCTTCCCCAGTCAACTGTGGCACCTGTAACCTCCCGGAACATGAAGG
ACTATGCTCTGAGGCTATACTCTGTGCCCATGAGAGCAGAGACTGGAAGGGCAAGACCAGGTGCTAAGGAGGGGAGA
GGGGGCATCCTGTCTCTCTCCAGACCATCACTGCACTTTAACCAGGGTCTTAGGTACAAAATCCTACTTTTCAGAGC
CTTCCAGCTCTGGAACCTCAAACATCCTCATGCTCTCTCCCAGCTCCTTTTGCATAAAAAAAAAAGTAAAGAAAAAG
AAAAAAAAATACACACACACTGAAACCCACATGGAGAAAAGAGGTGTTTCCTTTTATATTGCTATTCAAAATCAATA
CCACCAACAAAATATTTCTAAGTAGACACTTTTCCAGACCTTTGTTTTTTTGTGTCAGTGTCCAAGCTGCAGATAGG
ATTTTGTAATACTTCTGGCAGCTTCTTTCCTTGTGTACATAATATATATATATACATATATATATATATTTTTAATC
AGAAGTTATGAAGAACAAAAAGAAAAAATAAACACAGAAGCAAGTGCAATACCACCTCTCTTCTCCCTCTCTCCTAG
GGTTTCCTTTGTAGCCTATGTTTGGTGTCTCTTTTGACCTTTAC

FIG. 18E

CCCTTCACCTCCTCCTCTCTTCTTCTGATTCCCCTCCCCCCCTTTTTAAAGAGTTTTTCTCCTTTCTCAAGGGGAG
TTAAACTAGCTTTTGAGACTTATTGCAAAGCATTTTGTATATGTAATATATTGTAAGTAAATATTTGTGTAACGGAG
ATATACTACTGTAAGTTTTGTACTGTACTGGCTGAAAGTCTGTTATAAATAAACATGAGTAATTTAACACC

>NM_001351091.1 Homo sapiens IKAROS family zinc finger 4 (IKZF4), transcript variant 4, mRNA (SEQ ID NO:47)
GCGCGCGCGCGGAGACACCTCAGTCTACATGGGGAGGACAGAGAAGCGCAAAGAACAAGAGAAAAGATGCATCCATC
TGAGATCTAAAAGGAGACAATGAGAATCTCTTTAAAATGGACATAGAAGACTGCAATGGCCGCTCCTATGTGTCTGG
TAGCGGGGACTCATCTCTGGAGAAGGAGTTCCTCGGGGCCCCAGTGGGGCCCTCGGTGAGCACCCCCAACAGCCAGC
ACTCTTCTCCTAGCCGCTCACTCAGTGCCAACTCCATCAAGGTGGAGATGTACAGCGATGAGGAGTCAAGCAGACTG
CTGGGGCCAGATGAGCGGCTCCTGGAAAAGGACGACAGCGTGATTGTGGAAGATTCATTGTCTGAGCCCCTGGGCTA
CTGTGATGGGAGTGGGCCAGAGCCTCACTCCCCTGGGGGCATCCGGCTGCCCAATGGCAAGCTCAAGTGTGACGTCT
GCGGCATGGTCTGTATTGGACCCAACGTGCTCATGGTGCACAAGCGCAGTCACACTGGTGAAAGGCCCTTCCATTGC
AACCAGTGTGGTGCCTCCTTCACCCAGAAGGGGAACCTGCTGCGCCACATCAAGCTGCACTCTGGGGAGAAGCCCTT
TAAATGTCCCTTCTGCAACTATGCCTGCCGCCGGCGTGATGCACTCACTGGTCACCTCCGCACACACTCAGTCTCCT
CTCCCACAGTGGGCAAGCCCTACAAGTGTAACTACTGTGGCCGGAGCTACAAACAGCAGAGTACCCTGGAGGAGCAC
AAGGAGCGGTGCCATAACTACCTACAGAGTCTCAGCACTGAAGCCCAAGCTTTGGCTGGCCAACCAGGTGACGAAAT
ACGTGACCTGGAGATGGTGCCAGACTCCATGCTGCACTCATCCTCTGAGCGGCCAACTTTCATCGATCGTCTGGCCA
ATAGCCTCACCAAACGCAAGCGTTCCACACCCCAGAAGTTTGTAGGCGAAAAGCAGATGCGCTTCAGCCTCTCAGAC
CTCCCCTATGATGTGAACTCGGGTGGCTATGAAAAGGATGTGGAGTTGGTGGCACACCACAGCCTAGAGCCTGGCTT
TGGAAGTTCCCTGGCCTTTGTGGGTGCAGAGCATCTGCGTCCCCTCCGCCTTCCACCCCACCAATTGCATCTCAGAAC
TCACGCCTGTCATCAGCTCTGTCTACACCCAGATGCAGCCCCTCCCTGGTCGACTGGAGCTTCCAGGATCCCGAGAA
GCAGGTGAGGGACCTGAGGACCTGGCTGATGGAGGTCCCCTCCTCTACCGGCCCCGAGGCCCCCTGACTGACCCTGG
GGCATCCCCCAGCAATGGCTGCCAGGACTCCACAGACACAGAAAGCAACCACGAAGATCGGGTTGCGGGGGTGGTAT
CCCTCCCTCAGGGTCCCCCACCCCAGCCACCTCCCACCATTGTGGTGGGCCGGCACAGTCCTGCCTACGCCAAAGAG
GACCCCAAGCCACAGGAGGGGTTATTGCGGGGCACCCCAGGCCCCTCCAAGGAAGTGCTTCGGGTGGTGGGCGAGAG
TGGTGAGCCTGTGAAGGCCTTCAAGTGTGAGCACTGCCGTATCCTCTTCCTGGACCACGTCATGTTCACTATCCACA
TGGGCTGCCATGGCTTCAGAGACCCTTTTGAGTGCAACATCTGTGGTTATCACAGCCAGGACCGGTACGAATTCTCT
TCCCACATTGTCCGGGGGGAGCATAAGGTGGGCTAGCAACCTCTCCCTCTCTCCTCAGTCCACCACTCCACTGCCCT
GACTACAGGCATTGATCCCTGTCCCCACCATTTCCCAAGGAGTTTTGCTTTGTAGCCCTCACTACTGGCCACCTGAC
CTCACACCTGACCCTGACCCCTCCTCACCTATTCTCTTCCTCTATCCTGACCGATGTAAGCATTGTGATGAAACAGA
TCTTTTGCTTATGTTTTTCCTTTTTATCTTCTCTCATCCCAGCATACTGAGTTATTTATTAATTAGTTGATTTATTT
TTGCCTTTTTAAATTTTAACTTATATCAGTCACTTGCCACTCCCCCACCCTCCTGTCCACAACTCCTTTCCACTTTA
GGCCAATTTTTCTCTCTTAGATCTTCCAGCAGCCCCAGGGGTAGGAAGCTCCTCTTAGTACTAAGAGACTTCAAGCT
TCTTGCTTTAAGTCCTCACCCTTTACATTATCTAATTCTTCAGTTTTGATGCTGATACCTGCCCCCGGCCCTACCTT
AGCTCTGTGGCATTATATCTCCTCTCTGGGACTCTTCAACCTGGTACTCCATACCTCTTGTGCCCTCTCACTTTAGG
CAGCTTGCACTATTCTTGAATGAATGAAGAATTATTTCCTCATTTGGAAGTAGGAGGGACTGAAGAAATTCTCCCCA
GGCACTGTGGGACTGAGAGTCCTATTCCCCTAGTAATAGGTCATATTCCCCTAGTAATATGAGTTCTCAAAGCCTAC
ATTCAGGATCTCCCTCTAGGATGTGATAGATCTGGTCCCTCTCCTTGAACTACCCCTCCACACGCTCTAGTCCCTTC
AACCTACCGGTCTATTAAGTGGTGGCTTTTCTCTCCTTGGAGTGCCCCAATTTTATATTCTCAGGGGCCAAGGCTAG
GTCTGCAACCCTCTGTCTCTGACAGATTGGGAGCCACAGGTGCCTAATTGGGAACCAGGGCATGGGAAAGGAGTGGG
TCAAAATTCTTCTCTTTCTCCTCCACCTCTCAAACTTCTTCACTATAGTGACCTTCCTAGGCTCTCAGGGGCTCCTT
CAGTCCCCATCCTATGAGAAACTAGTGGGTTGCTGCCTGATGACAAGGGGTTGTTTCAGCCCCTCAGTCATGCTGCC
TTCTGCTGCTCCCTCCCAGCAGGATTCACCCTCTCATTCCCGGGCTCCTGGGCCCTGTTCTTAGGATCAGTGGCAGG
GAGAAACGGGTATCTCTTTTCTCTCTTCTAATTTTCAGTATAACCAAAAATTATCCCAGCATGAGCACGGGCACGTG
CCCTTCACCCCATTCCACCCTTGTTCCAGCAAGACTGGGATGGGTACAACTGAACTGGGGTCTTCCTTTACTACCCC
CTTCTACACTCAGCTCCCAGACACAGGGTAGGAGGGGGGACTGCTGGCTACTGCAGAGACCCTTGGCTATTTGAGTA
ACCTAGGATTAGTGAGAAGGGGCAGAAGGAGATACAACTCCACTGCAAGTGGAGGTTTCTTTCTACAAGAGTTTTCT
GCCCAAGGCCACAGCCATCCCACTCTCTGCTTCCTTGAGATTCAAACCAAAGGCTGTTTTTCTATGTTTAAAGAAAA
AAAAAAGTAAAAACCAAACACAACACCTCACAAGTTGTAACTCTTGGTCCTTCTCTCTCTCCTTTTCTCTTCCCTTC
CTTCCCCTTCCATCTTTCTTTCCACATGTCCTTTCCTTATTGGCTCTTTTACCTCCTACTTTTCTCACTCCCTATCA
GGGATATTTTGGGGGGGGATGGTAAAGGGTGGGCTAAGGAACAGACCCTGGGATTAGGGCCTTAAGGGCTCTGAGAG
GAGTCTACCTTGCCTTCTTATGGGAAGGGAGACCCTAAAAAACTTTCTCCTCTTTGTCCTCCTTTTTCTCCCCCACT
CTGAGGTTTCCCCAAGAGAACCAGATTGGCAGGGAGAAGCATTGTGGGGCAATTGTTCCTCCTTGACAATGTAGCAA
TAAATAGATGCTGCCAAGGGCAGAAAATGGGGAGGTTAGCTCAGAGCAGAGTAGTCTCTAGAGAAAGGAAGAATCCT
CAACGGCACCCTGGGGTGCTAGCTCCTTTTTAGAATGTCAGCAGAGCTGAGATTAATATCTGGGCTTTTCCTGAACT
ATTCTGGTTATTGAGCCCTTCCTGTTAGACCTACCGCCTCCCACCTCTTCTGTGTCTGCTGTGTATTTGGTGACACT
TCATAAGGA

FIG. 18F

CTAGTCCCTTCTGGGGTATCAGAGCCTTAGGGTGCCCCCATCCCCTTCCCCAGTCAACTGTGGCACCTGTAACCTCC
CGGAACATGAAGGACTATGCTCTGAGGCTATACTCTGTGCCCATGAGAGCAGAGACTGGAAGGGCAAGACCAGGTGC
TAAGGAGGGGAGAGGGGGCATCCTGTCTCTCTCCAGACCATCACTGCACTTTAACCAGGGTCTTAGGTACAAAATCC
TACTTTTCAGAGCCTTCCAGCTCTGGAACCTCAAACATCCTCATGCTCTCTCCCAGCTCCTTTTGCATAAAAAAAAA
AGTAAAGAAAAAGAAAAAAAAATACACACACACTGAAACCCACATGGAGAAAAGAGGTGTTTCCTTTTATATTGCTA
TTCAAAATCAATACCACCAACAAAATATTTCTAAGTAGACACTTTTCCAGACCTTTGTTTTTTTGTGTCAGTGTCCA
AGCTGCAGATAGGATTTTGTAATACTTCTGGCAGCTTCTTTCCTTGTGTACATAATATATATATATACATATATATA
TATATTTTTAATCAGAAGTTATGAAGAACAAAAAGAAAAAATAAACACAGAAGCAAGTGCAATACCACCTCTCTTCT
CCCTCTCTCCTAGGGTTTCCTTTGTAGCCTATGTTTGGTGTCTCTTTTGACCTTTACCCCTTCACCTCCTCCTCTCT
TCTTCTGATTCCCCTCCCCCCCTTTTTTAAAGAGTTTTTCTCCTTTCTCAAGGGGAGTTAAACTAGCTTTTGAGACT
TATTGCAAAGCATTTTGTATATGTAATATATTGTAAGTAAATATTTGTGTAACGGAGATATACTACTGTAAGTTTTG
TACTGTACTGGCTGAAAGTCTGTTATAAATAAACATGAGTAATTTAACACC

>NM_001351092.1 Homo sapiens IKAROS family zinc finger 4 (IKZF4), transcript variant 5, mRNA(SEQ ID NO:48)
GAAGCTGTCCGTGTCCTGGGCCCCATGACCTCTGGGGCCTTGGCTTCCCCAGCTGGCAGAGGATTGGGCCTTCCCTA
GGGCCCCCCCTTTCTCCCTCCCACCCGCAGGCCCATCCATCTCTCTCTCTCTCTCTTGCACACACTCTTGCCTCTCT
CAGGCATTTGTTGTGCAGTTCCTCTTTGTCTGCTGGGCACGAGGGGCAACAGCATCTGCCTTTCCCTCCCTGTGCAC
ACACCCACCACCCACCCCCTTCACTGTCTTGGAAAAGGGATGCTGTAGCCTAGCATCTCCCCCACTATATACACATA
TACATTCTCTCCAGCCCCCTCCCCAAGCACATCCAAGCGTGCTCTCCCCTCTCCTTCTCTCCCTCTCTCTCTCTC
TCTCTCACACACACACACACACACACACTCAACACACATACACCCTGGGCTGAGCTGCTCTTGCTGGCTGCAGCCGT
GGGCCTCTGCTCACCGTGCCGCTGCTGCTGCCTGCGAAATGACGGCGGTTCCCCTCACTTCCAGGAATCCACGCTTC
CTGGAAGGTGAGTGGCTGGGCTCACCCCTGCCTGCCACTGAGACGCAGACATGCATACACCACCCGCACTCCCTCGC
CGTTTCCAAGGCGGCGGCCGCGTTCGCACCCCAGGGTCTCACCGGCAAGGGAAGGATAATGTAGCGGGGACTCATCT
CTGGAGAAGGAGTTCCTCGGGGCCCCAGTGGGGCCCTCGGTGAGCACCCCCAACAGCCAGCACTCTTCTCCTAGCCG
CTCACTCAGTGCCAACTCCATCAAGGTGGAGATGTACAGCGATGAGGAGTCAAGCAGACTGCTGGGGCCAGATGAGC
GGCTCCTGGAAAAGGACGACAGCGTGATTGTGGAAGATTCATTGTCTGAGCCCCTGGGCTACTGTGATGGGAGTGGG
CCAGAGCCTCACTCCCCTGGGGGCATCCGGCTGCCCAATGGCAAGCTCAAGTGTGACGTCTGCGGCATGGTCTGTAT
TGGACCCAACGTGCTCATGGTGCACAAGCGCAGTCACACTGGTGAAAGGCCCTTCCATTGCAACCAGTGTGGTGCCT
CCTTCACCCAGAAGGGGAACCTGCTGCGCCACATCAAGCTGCACTCTGGGGAGAAGCCCTTTAAATGTCCCTTCTGC
AACTATGCCTGCCGCCGGCGTGATGCACTCACTGGTCACCTCCGCACACACTCAGTCTCCTCTCCCACAGTGGGCAA
GCCCTACAAGTGTAACTACTGTGGCCGGAGCTACAAACAGCAGAGTACCCTGGAGGAGCACAAGGAGCGGTGCCATA
ACTACCTACAGAGTCTCAGCACTGAAGCCCAAGCTTTGGCTGGCCAACCAGGTGACGAAATACGTGACCTGGAGATG
GTGCCAGACTCCATGCTGCACTCATCCTCTGAGCGGCCAACTTTCATCGATCGTCTGGCCAATAGCCTCACCAAACG
CAAGCGTTCCACACCCCAGAAGTTTGTAGGCGAAAAGCAGATGCGCTTCAGCCTCTCAGACCTCCCCTATGATGTGA
ACTCGGGTGGCTATGAAAAGGATGTGGAGTTGGTGGCACACCACAGCCTAGAGCCTGGCTTTGGAAGTTCCCTGGCC
TTTGTGGGTGCAGAGCATCTGCGTCCCCTCCGCCTTCCACCCACCAATTGCATCTCAGAACTCACGCCTGTCATCAG
CTCTGTCTACACCCAGATGCAGCCCCTCCCTGGTCGACTGGAGCTTCCAGGATCCCGAGAAGCAGGTGAGGGACCTG
AGGACCTGGCTGATGGAGGTCCCCTCCTCTACCGGCCCCGAGGCCCCCTGACTGACCCTGGGGCATCCCCCAGCAAT
GGCTGCCAGGACTCCACAGACACAGAAAGCAACCACGAAGATCGGGTTGCGGGGGTGGTATCCCTCCCTCAGGGTCC
CCCACCCCAGCCACCTCCCACCATTGTGGTGGGCCGGCACAGTCCTGCCTACGCCAAAGAGGACCCCAAGCCACAGG
AGGGGTTATTGCGGGGCACCCCAGGCCCCTCCAAGGAAGTGCTTCGGGTGGTGGGCGAGAGTGGTGAGCCTGTGAAG
GCCTTCAAGTGTGAGCACTGCCGTATCCTCTTCCTGGACCACGTCATGTTCACTATCCACATGGGCTGCCATGGCTT
CAGAGACCCTTTTGAGTGCAACATCTGTGGTTATCACAGCCAGGACCGGTACGAATTCTCTTCCCACATTGTCCGGG
GGGAGCATAAGGTGGGCTAGCAACCTCTCCCTCTCTCCTCAGTCCACCACTCCACTGCCCTGACTACAGGCATTGAT
CCCTGTCCCCACCATTTCCCAAGGAGTTTTGCTTTGTAGCCCTCACTACTGGCCACCTGACCTCACACCTGACCCTG
ACCCCTCCTCACCTATTCTCTTCCTCTATCCTGACCGATGTAAGCATTGTGATGAAACAGATCTTTTGCTTATGTTT
TTCCTTTTTATCTTCTCTCATCCCAGCATACTGAGTTATTTATTAATTAGTTGATTTATTTTTGCCTTTTTAAATTT
TAACTTATATCAGTCACTTGCCACTCCCCCACCCTCCTGTCCACAACTCCTTTCCACTTTAGGCCAATTTTTCTCTC
TTAGATCTTCCAGCAGCCCCAGGGGTAGGAAGCTCCTCTTAGTACTAAGAGACTTCAAGCTTCTTGCTTTAAGTCCT
CACCCTTTACATTATCTAATTCTTCAGTTTTGATGCTGATACCTGCCCCCGGCCCTACCTTAGCTCTGTGGCATTAT
ATCTCCTCTCTGGGACTCTTCAACCTGGTACTCCATACCTCTTGTGCCCTCTCACTTTAGGCAGCTTGCACTATTCT
TGAATGAATGAAGAATTATTTCCTCATTTGGAAGTAGGAGGGACTGAAGAAATTCTCCCCAGGCACTGTGGGACTGA
GAGTCCTATTCCCCTAGTAATAGGTCATATTCCCCTAGTAATATGAGTTCTCAAAGCCTACATTCAGGATCTCCCTC
TAGGATGTGATAGATCTGGTCCCTCTCCTTGAACTACCCCTCCACACGCTCTAGTCCCTTCAACCTACCGGTCTATT
AAGTGGTGGCTTTTCTCTCCTTGGAGTGCCCCAATTTTATATTCTCAGGGGCCAAGGCTAGGTCTGCAACCCTCTGT
CTCTGACAGATTGGGAGCCACAGGTGCCTAATTGGGAACCAGGGCATGGGAAAGGAGTGGGTCAAAATTCTTCTCTT
TCTCCTCCACCTCTCAAACTTCTTCACTATAGTGACCTTCCTAGGC

FIG. 18G

TCTCAGGGGCTCCTTCAGTCCCCATCCTATGAGAAACTAGTGGGTTGCTGCCTGATGACAAGGGGTTGTTTCAGCCC
CTCAGTCATGCTGCCTTCTGCTGCTCCCTCCCAGCAGGATTCACCCTCTCATTCCCGGGCTCCTGGGCCCTGTTCTT
AGGATCAGTGGCAGGGAGAAACGGGTATCTCTTTTCTCTCTTCTAATTTTCAGTATAACCAAAAATTATCCCAGCAT
GAGCACGGGCACGTGCCCTTCACCCCATTCCACCCTTGTTCCAGCAAGACTGGGATGGGTACAACTGAACTGGGGTC
TTCCTTTACTACCCCCTTCTACACTCAGCTCCCAGACACAGGGTAGGAGGGGGGACTGCTGGCTACTGCAGAGACCC
TTGGCTATTTGAGTAACCTAGGATTAGTGAGAAGGGGCAGAAGGAGATACAACTCCACTGCAAGTGGAGGTTTCTTT
CTACAAGAGTTTTCTGCCCAAGGCCACAGCCATCCCACTCTCTGCTTCCTTGAGATTCAAACCAAAGGCTGTTTTTC
TATGTTTAAAGAAAAAAAAAAAGTAAAAACCAAACACAACACCTCACAAGTTGTAACTCTTGGTCCTTCTCTCTCTCC
TTTTCTCTTCCCTTCCTTCCCCTTCCATCTTTCTTTCCACATGTCCTTTCCTTATTGGCTCTTTTACCTCCTACTTT
TCTCACTCCCTATCAGGGATATTTTGGGGGGGGATGGTAAAGGGTGGGCTAAGGAACAGACCCTGGGATTAGGGCCT
TAAGGGCTCTGAGAGGAGTCTACCTTGCCTTCTTATGGGAAGGGAGACCCTAAAAAACTTTCTCCTCTTTGTCCTCC
TTTTTCTCCCCCACTCTGAGGTTTCCCCAAGAGAACCAGATTGGCAGGGAGAAGCATTGTGGGGCAATTGTTCCTCC
TTGACAATGTAGCAATAAATAGATGCTGCCAAGGGCAGAAAATGGGGAGGTTAGCTCAGAGCAGAGTAGTCTCTAGA
GAAAGGAAGAATCCTCAACGGCACCCTGGGGTGCTAGCTCCTTTTTAGAATGTCAGCAGAGCTGAGATTAATATCTG
GGCTTTTCCTGAACTATTCTGGTTATTGAGCCCTTCCTGTTAGACCTACCGCCTCCCACCTCTTCTGTGTCTGCTGT
GTATTTGGTGACACTTCATAAGGACTAGTCCCTTCTGGGGTATCAGAGCCTTAGGGTGCCCCCATCCCCTTCCCCAG
TCAACTGTGGCACCTGTAACCTCCCGGAACATGAAGGACTATGCTCTGAGGCTATACTCTGTGCCCATGAGAGCAGA
GACTGGAAGGGCAAGACCAGGTGCTAAGGAGGGGAGAGGGGGCATCCTGTCTCTCTCCAGACCATCACTGCACTTTA
ACCAGGGTCTTAGGTACAAAATCCTACTTTTCAGAGCCTTCCAGCTCTGGAACCTCAAACATCCTCATGCTCTCTCC
CAGCTCCTTTTGCATAAAAAAAAAAAGTAAAGAAAAAGAAAAAAAAATACACACACACTGAAACCCACATGGAGAAAA
GAGGTGTTTCCTTTTATATTGCTATTCAAAATCAATACCACCAACAAAATATTTCTAAGTAGACACTTTTCCAGACC
TTTGTTTTTTTGTGTCAGTGTCCAAGCTGCAGATAGGATTTTGTAATACTTCTGGCAGCTTCTTTCCTTGTGTACAT
AATATATATATATACATATATATATATATTTTTAATCAGAAGTTATGAAGAACAAAAAGAAAAAATAAACACAGAAG
CAAGTGCAATACCACCTCTCTTCTCCCTCTCTCCTAGGGTTTCCTTTGTAGCCTATGTTTGGTGTCTCTTTTGACCT
TTACCCCTTCACCTCCTCCTCTCTTCTTCTGATTCCCCTCCCCCCCTTTTTTAAAGAGTTTTTCTCCTTTCTCAAGG
GGAGTTAAACTAGCTTTTGAGACTTATTGCAAAGCATTTTGTATATGTAATATATTGTAAGTAAATATTTGTGTAAC
GGAGATATACTACTGTAAGTTTTGTACTGTACTGGCTGAAAGTCTGTTATAAATAAACATGAGTAATTTAACACC

FIG. 19A

>Ascl1 (SEQ ID NO:49)
Atgggcggggagggccttcgtgcgtcgccgcgccgccgtccccttctccctctccagcctcggggctgtccgcggggggacggctgccttcggggggg
acggggcagggcggggttcggcttctggcgtgtgaccggcggctctagagcctctgctaaccatgttcatgccttcttctttttcctacagctcctgggc
aacgtgctggttattgtgctgtctcatcattttggcaaagaattgctcgagctcaagcttcgaattcgcgtccccaactcgttctcccccgcgacagtttg
gcccggcatggagagctctggcaagatggagagtggagccggccagcagccgcagcccccgcagcccttcctgcctcccgcagcctgcttctttgcg
accgcggcggcggcggcagcggcggcggccgcggcagctcagagcgcgcagcagcaacagccgcaggcgccgccgcagcaggcgccgcagctg
agcccggtggccgacagccagccctcagggggcggtcacaagtcagcggccaagcaggtcaagcgccagcgctcgtcctctccggaactgatgcgc
tgcaaacgccggctcaacttcagcggcttcggctacagcctgccacagcagcagccggccgccgtggcgcgccgcaacgagcgcgagcgcaaccg
ggtcaagttggtcaacctgggttttgccaccctccgggagcatgtccccaacggcgcggccaacaagaagatgagcaaggtggagacgctgcgctc
ggcggtcgagtacatccgcgcgctgcagcagctgctggacgagcacgacgcggtgagcgctgcctttcaggcgggcgtcctgtcgcccaccatctcc
cccaactactccaacgacttgaactctatggcgggttctccggtctcgtcctactcctccgacgagggatcctacgaccctcttagcccagaggaacaa
gagctgctggactttaccaactggttctga >Apobec2 (SEQ ID NO:50)
Atggcccagaaggaagaggctgctgtggccactgaggctgcctcccagaatggggaggatctggagaacctggacgaccctgagaagctgaaaga
gctgattgagctgccgccctttgagattgtcacaggagaacggctgcctgccaacttctttaaattccagttccggaatgtggagtacagttccgggag
gaacaagaccttcctctgctatgtggttgaagcacagggcaagggggggccaagtgcaggcatctcggggatacctagaggatgagcatgcggctgc
ccatgcagaggaagctttcttcaacaccatcctgccagccttcgacccagccctgcggtacaatgtcacctggtatgtgtcctccagcccctgtgcagc
gtgtgctgaccgcattatcaaaacccttagcaagaccaagaacctgcgtctgctcattctggtgggtcgactcttcatgtgggaggagccggagatcc
aggctgctctgaagaagctgaaggaggctggctgtaaactgcgcatcatgaagccccaggacttcgaatatgtctggcagaattttgtggagcaaga
agagggtgaatccaaggcctttcagccctgggaggacattcaggagaacttcctatactacgaggagaagttggcagacatcctgaaggggtga >Myt1l (SEQ ID NO:51)
atggacgtggactctgaggagaagcgccatcgcacacggtccaaaggggttcgagttcctgtggagccagccatacaagagctgttcagctgtccca
ctccaggctgcgacggcagtggtcacgtcagtggcaaatatgcacgacacagaagtgtatatggttgtcccttggctaaaaaaagaaaaacgcaag
ataaacagccccaagaacctgctcccaagcgaaaaccatttgcagtaaaagcagatagttcctcagtagacgaatgttatgagagtgatggtactga
agacatggatgataaggaggaagatgatgatgaggagttctctgaagacaatgatgagcaaggggatgatgacgacgaagatgaggtggatcgg
gaagacgaggaggagatcgaggaggaagatgatgaagaagatgatgatgatgaagatggtgacgatgtagaagaggaagaagaggatgatgat
gaagaggaggaagaagaggaagaggaagaagaaaatgaagaccatcaaatgagttgtactcgaataatgcaggacacagacaaggatgataac
aacaatgatgagtatgataactatgatgaactggtagctaagtcgctattaaatcttggcaaaattgctgaggatgcagcataccgagccaggactg
aatcagagatgaacagcaatacctccaatagtctggaggacgatagtgacaaaaacgaaaacctcggtcggaaaagcgaactgagtctagactta
gacagtgatgttgttagagaaacagtggactcccttaagctgttagcacaaggacatggtgttgtgctatcagagaatatcagtgacagaagttatgc
tgaggggatgtcacagcaggacagtagaaatatgaactatgtcatgctagggaagcccatgaacaatggactcatggagaagatggtggaggaga
gtgatgaggaagtgtgtctaagtagtctagagtgcctgaggaaccagtgctttgacctggccaggaaactcagcgagaccaacccacaggacagga
gtcagccacccaacatgagtgtgcgccaacatgtccggcaagaggacgacttccctgggaggacgccagacaggagctactcggatatgatgaacc
ttatgcggctggaggagcagctcagtcccaggtctagaacgttctccagctgtgccaaggaggatgggtgtcatgagagggatgatgacaccacctc
agtgaactcagacaggtctgaggaagtgtttgacatgaccaagggcaacctgactctgctagagaaagccattgccttggagacagagagagccaa
ggccatgcgggagaagatggccatggatgctgggagaagggataacctgagatcctatgaggaccagtctccaagacagctggctggggaagaca
gaaaatccaaatccagtgacagccatgtcaaaaagccatactatggtaaagatccctcaagaacagaaaagagagagagcaagtgtccaacccccc
gggtgtgatggaaccggccacgtaactgggctttacccgcatcaccgcagtctgtctggatgcccgcacaaagatagggtccctccagaaattcttgc
catgcatgaaaatgttctcaagtgtcccactccaggctgcacagggcgagggcatgtgaatagcaacaggaactcgcacagaagcctctctggatgc
cccattgctgctgcagaaaaactggcaaaggcccaagagaaacaccagagctgtgatgtgtccaaatccaaccaggcctcagaccgagtcctcagg
ccaatgtgctttgtcaaacagcttgagattcctcagtatggctacagaaacaatgttcccacaaccacaccacgctccaacctggccaaggagcttga
gaaatactccaagacttcgtttgagtacaacagttacgacaaccatacttatggcaaaagagccatagctcccaaggtgcaaaccagggacatatcc
cccaaaggatatgacgatgccaagcggtactgcaagaatgccagccccagcagcagcaccaccagcagctatgcacctagcagcagcagcaacct
cagctgtggtggtggcagcagcgccagtagcacgtgtagcaagagcagctttgactacacacatgacatggaggccgcacacatggcagccacagc
cattctcaacctgtccacacgttgtcgtgaaatgccacagaacctgtccaccaagccacaggacctgtgtactgcccggaacccagacatggaggtg
gatgagaatggcaccctggacctgagcatgaacaagcagaggcctcgagacagctgctgcccagtcctgacacccctggaacccatgtctccgcag
cagcaggccgtgatgagcagccgatgcttccagctgagcgagggggattgctgggact

FIG. 19B tgcctgtagactacaccaaaatgaagcctcggagggtagatgaggatgagcccaaagagattaccccagaagacttggacccattccaggaggctc
tggaagaaagacggtatccaggggaggtgaccatcccaagccccaaacccaagtaccctcagtgcaaggaaagcaaaaaggacttaataactctg
tctggctgccccctggcggacaaaagcattcgaagtatgctggccaccagttcccaagagctcaagtgccccacccctggctgtgacggttctggaca
catcactggcaattacgcttctcatcgaagcctttctgggtgcccgagagcaaagaagagtggcatccggatagcacagagcaaagaggacaagga
agaccaggagccaatcaggtgtccggtacctggctgtgacggtcagggacacatcactgggaagtatgcatcccaccgcagcgcctccgggtgtccc
ttggcagccaagaggcagaaagatgggtaccttaatggctcccagttctcctggaagtcggtcaagacggagggcatgtcctgccctacccccgggt
gtgatgggtcaggacacgtcagtggcagcttcctcacacaccgcagcttgtcaggatgtccaagagccacatcagcaatgaagaaagcaaagctgt
ctggagaacagatgttgactatcaagcagcgagccagcaacggtatagaaaatgatgaagaaatcaagcagttagatgaagagatcaaggagctt
aatgagtccaattcccagatggaggctgacatgatcaaactcagaactcagatcaccacaatggagagcaacctgaagacgattgaggaggagaa
caaagtcattgaacagcagaatgagtcgctcttgcacgagttggccaacctgagccagtccctgatccacagcctcgccaacatccagctgcctcaca
tggatccaatcaatgaacaaaattttgatgcttacgtgactactttgacggaaatgtatacaaatcaagatcgttatcagagtccagaaaataaagcc
ctactggaaaatataaagcaggctgtgagaggaattcaggtctga >Pou2f1 (SEQ ID NO:52)
ATGCTGGACTGCAGTGACTGTGTTCTAGACTCAAGAATGAATAATCCATCAGAAACCAATAAATCATCTATGGAG
AGTGAAGATGCCAGCACAGGCACACAAACCAATGGTCTGGACTTTCAGAAACAGCCCGTGCCCGTTGGAGGAGC
GATCTCCACAGCCCAGGCCCAGGCCTTCCTCGGACATCTTCACCAGGTCCAGCTAGCTGGGACAAGTTTACAGGC
TGCTGCTCAGTCTTTAAATGTACAGTCTAAATCCAGTGAAGAGTCGGGAGATTCGCAGCAGTCGAGCCAGCCTTC
TTCCCAGCCGCCTTCAGTGCAGTCAGCCATTCCCCAGACCCAGCTAATGCTGGCTGGGGGACAGATAACTGGGCT
CACGTTGACCCCAGCCCAGCAACAGTTACTGCTACAGCAGGCGCAGGCCCAGGCCCAGCTCCTGGCCGCTGCAGT
GCAGCAACACTCCGCCAGCCAACAGCACAGTGCTGCTGGGGCCACCATCTCAGCCTCCGCCGCCACACCCATGAC
GCAGATCCCCCTGTCTCAGCCCATACAGATTGCACAGGATCTTCAACAATTGCAACAGCTTCAGCAGCAAAATCTC
AACTTGCAACAGTTTGTGTTGGTGCACCCAACCACCAACCTGCAACCAGCACAGTTTATCATCTCACAGACCCCCC
AGGGCCAGCAGGGTCTCCTGCAAGCGCAAAATCTTTTAACGCAACTACCTCAGCAAAGCCAAGCCAACCTCCTAC
AGCCACAGCCAAGCATCACCCTCACGTCCCAGCCTACCACCCCAACTCGCACAATAGCAGCAGCCTCAGTTCAGAC
ACTTCCACAGAGCCAGTCAACACCAAAGCGAATTGACACTCCCAGCTTGGAGGAGCCCAGTGACCTTGAGGAGCT
TGAGCAGTTTGCCAAGACTTTCAAACAAAGACGAATCAAACTTGGATTCACTCAGGGTGATGTTGGGCTCGCTAT
GGGGAAATTATATGGAAATGACTTCAGCCAAACCACCATCTCTCGCTTTGAAGCCTTGAACCTCAGCTTTAAGAAC
ATGTGCAAGTTAAAGCCCCTTTTAGAGAAGTGGCTAAATGATGCAGAGAACCTCTCATCTGATTCTACAGCATCTA
GCCCAAGTGCTTTGAATTCTCCAGGATTGGGGGCTGAGGGCTTGAATCGTAGGAGGAAAAAACGCACCAGCATA
GAGACCAACATCCGTGTGGCCTTAGAGAAGAGTTTCATGGAGAATCAAAAGCCTACCTCGGAAGACATCACCTTG
ATTGCTGAACAGCTCAATATGGAAAAGGAGGTGATTCGTGTTTGGTTTTGTAACCGCCGCCAGAAGGAGAAAAG
AATCAACCCGCCCAGCAGTGGTGGGACCAGCAGCTCACCTATCAAAGCAATTTTCCCCAGCCCAGCCTCATTGGT
GGCAACCACTCCAAGCCTTGTGACAAGCAGTACGGCAACTACCCTCACAGTCAACCCTGTCCTCCCTTTAACCAGT
GCTGCTGTGACTAATCTCTCTCTTACAGATCAAGATCTTAGAAGAGGATGCAGCTGGGAAGTGCTTAGGAGTCTA
CCAGACAGAGTCACCACCACAGCAGGCACTACAGACTCGACGTCCAACAACAACACGGCCACGGTGATTTCCACA
GCACCCCCTGCTTCCTCAGCAGTCACATCCCCTTCCTTGAGTCCCTCTCCCTCTGCCTCGGCCTCCACCTCAGAGGC
CTCCAGTGCCAGTGAGACCAACACGACACAGACCACCTCCACGCCTCTTCCCTCCCCTCTCGGAGCCAGCCAGGTG
ATGGTGACCACGCCCGGCTTACAGACAGCAGCCGCCGCTCTCCAAGGAGCGGCACAGTTGCCAGCAAACGCCAG
TCTTGCTGCTATGGCTGCTGCTGCGGGACTCAGCCCAGGCCTCATGGCACCCTCACAGTTTGCTGCTGGAGGTGC
CTTACTCAGTCTCAGTCCGGGGACTCTGGGCAGTGCTCTCAGCCCAGCCCTAATGAGCAACAGTACACTGGCAAC
GATTCAAGCTCTTGCTTCTAGTGGCTCTCTTCCAATAACGTCTCTGGATGCAACTGGGAACCTGGTATTTGCCAAT
GCAGGAGGAGCCCCGAACATCGTGACTGCACCTCTGTTCCTGAACCCTCAGAACCTCTCTCTGCTCACCAGCAACC
CAGTAAGCTTGGTTTCTGCCGCTGCAGCCTCCACAGGGAACTCTGCACCTACAGCCAGCCTTCATGCCTCCTCCAC
CTCAACTGAGTCCATCCAGAGCTCTCTGTTCACAGTCGCCTCTGCCAGTGGGCCTGCTTCCACCACCACAGCTGCCT
CCAAGGCACAGTAA

FIG. 19C

>Pou2f2(SEQ ID NO:53)
ATGGTTCATTCCAGCATGGGGGCTCCAGAAATAAGAATGTCTAAGCCCCTGGAGGCCGAGAAGCAAAGTCTGGA
CTCCCCGTCAGAGCACACAGACACCGAAAGAAATGGACCCGACATTAACCATCAGAACCCCCAGAATAAAGCGTC
CCCATTCTCTGTGTCCCCAACTGGCCCCAGCACCAAGATCAAGGCTGAAGACCCCAGTGGCGATTCAGCCCCAGC
AGCACCCCCGCCCCCCCAGCCGGCTCAGCCTCATCTGCCCCAGGCCCAACTCATGCTGACGGGCAGCCAGCTAGC
TGGGGACATACAGCAACTCCTCCAGCTCCAGCAGCTGGTGCTTGTCCCCGGCCACCACCTCCAGCCACCTGCTCAG
TTCCTGCTGCCACAGGCACAGCAGAGTCAGCCAGGCCTGCTACCAACGCCAAATCTATTCCAGCTACCTCAACAAA
CCCAGGGAGCTCTCCTGACCTCCCAGCCCCGGGCTGGGCTTCCTACACAGCCCCCGAAATGCTTGGAGCCGCCCT
CCCACCCGGAGGAGCCCAGCGATCTGGAGGAGCTGGAACAGTTTGCTCGCACCTTCAAGCAACGCCGCATCAAG
CTGGGCTTCACACAGGGTGATGTGGGCCTGGCCATGGGCAAGCTCTATGGCAACGACTTCAGCCAAACGACCATT
TCCCGCTTCGAGGCCCTCAACCTGAGCTTCAAGAACATGTGTAAACTCAAGCCCCTCCTGGAGAAGTGGCTCAAC
GACGCAGAGACTATGTCTGTGGATTCAAGCCTACCCAGCCCAAACCAGCTGAGCAGCCCCAGCCTGGGTTTCGAC
GGGCTGCCGGGGCGGAGACGCAAGAAGAGGACCAGCATCGAGACGAATGTCCGCTTCGCCTTAGAGAAGAGTT
TCCTAGCGAACCAGAAGCCTACCTCAGAGGAGATCCTGCTGATCGCAGAGCAGCTGCACATGGAGAAGGAAGTG
ATCCGCGTCTGGTTCTGCAACCGGCGCCAGAAGGAGAAACGCATCAACCCTTGCAGTGCGGCCCCCATGCTGCCC
AGCCCGGGAAAGCCGACCAGCTACAGCCCTCACCTGGTCACACCCCAAGGGGGCGCAGGGACCTTACCATTGTC
CCAAGCTTCTAGCAGTCTGAGCACAACAGTTACTACCTTATCCTCAGCTGTGGGGACGCTCCATCCCAGCCGGACA
GCAGGAGGGGGTGGGGGTGGGGGCGGAGCTGCGCCCCCCCTCAATTCCATCCCCTCTGTCACTCCCCCACCCCCG
GCCACCACCAACAGCACAAACCCGAGCCCTCAAGGCAGCCACTCGGCTATTGGCTTGTCGGGCCTGAACCCCAGC
GCGGGCCCTGGCCTCTGGTGGAACCCTGCCCCTTACCAGCCTTGA

>Casz1v2 (SEQ ID NO:54)
atggatcttggaacagctgaaagcacccggtgcaccgacccacctgcaggcaagcctccaatggcagccaagcgcaaaggcggcctgaagctcaa
cgccatctgtgccaagctcagccgacaggtggtcgtggagaagggagcagaggccggctcccaagccgaaggtagcccactacatccccgggaca
aagagcgcagtggccctgagtctggggtgagccgggctccccgaagtgaagaagacaagaggcgggcagtgatcgagaaatgggtcaatggaga
gtactgtgaggatcccgcacccaccccagtgttggggcgtattgcccgtgatcaggagctgcccccagagggtgtctacatggtccagccacagggct
gcagtgacgaagaagaccatgcagaagagccctcaaaagataacagtgtcctggaggagaaggagtcagatggtacggcttctaaagatgacagc
ggccccagcaccaggcaggcttcaggagaaacctcctctgagggactacgctgcttccaccatgaccgagttcctcggcatgtttggctacgatga
ccagaacaccagggatgagctggccaagaagatcagctttgagaagccgcatgcaggctccacccccgaggtggctgcctcttccatgttgccctcct
ctgaggataccctcagcaagcgggcgcgcttctccaaatacgaggaatacatccgtaagctcaaggccggcgagcaacttccctggccagcccacg
ggagcaaagccgaggaccgggcaggcaaggaggtggtgggtcccttacccagcctacggctgcccagcaacacggcccacctggaaaccaaggcc
accatcctgccactgccatcacacagcagtgtccagatgcagaatctggtagctcgtgcttccaagtatgacttcttcatccacaaactgaagacagg
cgagaacctgaggccccagaatggaagcacttacaagaagccatccaagtatgacctggagaatgtcaagtacttgcacctcttcaaacccgggga
aggcagccctgacatgggcggggccatcgccttcaagacaggcaaggtggggcgcccctctaagtacgacgttcggggcatccagaagccaggccc
taccaagattccgcccgcccccagcctggttcctacacccctcaccaatgtgcccagtgctcccagcacccccggaccaggaccggagccacctgcct
ccttgtccttcaacactcccgagtacctgaagtcaacctttccaaaacagactccatcaccacaggaactgtctccactgtcaagaacggattgccca
cagataaaccagctgtcaccgaagatgtaaacatttaccagaaatatattgccaggttctcaggaagtcagcactgcggtcacatccactgcgcctac
cagtaccgtgagcactatcactgcctggacccggagtgcaactaccagcggttcacaagcaagcaggatgtgatccgacattacaacatgcacaag
aagcgcgacaactccctgcagcacggcttcatgcgcttcagcccgctggacgactgcagtgtctactaccacggctgccacctcaatgggaagagca
cccactaccactgcatgcaggtgggatgtaacaaggtatacacaagtacgtcggatgtgatgactcacgagaacttccacaagaagaacacccagc
tcatcaacgatggcttccagcgcttccgagccacggaggactgcggcacagctgactgtcagttctatggacagaagaccacacacttccactgcag
gcgccctggctgcacattcaccttcaagaacaagtgtgacatcgagaagcacaagagctaccacatcaaggatgatgcctacgccaaggacggctt
caagaagttctacaagtacgaggagtgcaaatacgagggctgcatgtacagcaaggccaccaaccatttccactgcatccgcgccggctgcggcttc
accttcacctccaccagccagatgacctcacacaagcgcaagcacgagcggcggcacatccggtcctcgggggccctggggctgccggcctccctgc
tgggcgccaaggacacggagcacgaggaatccagcaacgatgacctcgtggacttctctgccctgagcagcaagaactccagcctgagcgcctccc
ccaccagccagcaatcgtccgcatccctggccgctgcggctgccgccaccactgctgaggccatccccagtgccaccaagcctcccaatagcaagat
ggcaggcctgctgccccagggcctgtctggttccatccccttagcactggccctctctaactcaggcctgcccaccaccacaccctatttccctctgcttc
ctaaccgtgggagcgcctcattgcctgtgggatctccagggctcctgggctccatgtcctctggggccacaacctcagcaacccctgacatgccggcc
ctgatggcttccagagctggagactcggcccccacggctgccacctctctctcggtgccccctgcctcca

FIG. 19D tcattgagagaatctctgcaagcaaaggcctcatctcacccatgatggctagactggctgcggccgccctcaagccctctgccacctttgacccagga
agtgggcagcagcccacccccaccaagttcccccaggcccaggtgaagcaggagcctgacagtgctggcaccccaggtccccacgaggcctcccaa
gaccgcagtctagacctgaccgtgaaggatcccagtaatgaatcaaatggccacgcagtctcggcaaattcatctcttttatcctcgcttatgaataag
atgtctcagggcaaccccagcctcgaaagcttcctgagcatcaagacagaagcggaggggagccccgccggggagccctcgcctttcttgggcaag
gccgtgaaggcactagttcaagagaagctgtcagagccttggaaggtgtatctccgcaggtttggtaccaaggacttctgtgatgcccagtgtgactt
cctccacaaggcgcatttccattgtgtagtggaggagtgcggtgcgcttttcagcaccttggacggagccatcaaacatgcaaacttccacttccggac
agagggaggaacagcaaaaggaaccccagaggcttccttcccgacctctgctgctgagaccaaacctcccttggcaccctcgtccctgccagcacct
cctggcaccatggtcgctggatcttctctggaggggcctgctcccagcccggtctctgtgccctccacccccaccctgctcgcctggaagcagctggctt
ccaccataccccagatgcctcagattccctcctcagtgcctcacctgcccacctcgcccctggcgacgacgtctctagagagcgccaagcctcaggtc
aaacccgggttcctccagttccaggacaagtga >Brn2 (SEQ ID NO:55)
ATGGCGACCGCAGCGTCTAACCACTACAGCCTGCTCACCTCCAGCGCCTCCATCGTACATGCCGAGCCGCCTGGC
GGCATGCAGCAGGGCGCAGGGGGCTACCGCGAGGCGCAGAGCCTGGTGCAGGGCGACTACGGCGCGCTGCAG
AGCAACGGGCACCCGCTCAGCCACGCTCACCAGTGGATCACCGCGCTGTCCCACGGCGGCGGCGGCGGGGGCG
GCGGCGGCGGTGGAGGAGGCGGGGGAGGCGGCGGGGGAGGCGGCGACGGCTCCCCGTGGTCCACCAGCCCCC
TAGGCCAGCCGGACATCAAGCCCTCGGTGGTGGTACAGCAGGGTGGCCGAGGCGACGAGCTGCACGGGCCAGG
AGCGCTGCAGCAACAGCATCAACAGCAACAGCAACAGCAGCAGCAGCAGCAGCAGCAGCAGCAGCAGCAACAG
CAGCAGCAACAACAGCGACCGCCACATCTGGTGCACCACGCTGCCAACCACCATCCCGGGCCCGGGGCATGGCG
GAGTGCGGCGGCTGCAGCTCACCTCCCTCCCTCCATGGGAGCTTCCAACGGCGGTTTGCTCTATTCGCAGCCGAG
CTTCACGGTGAACGGCATGCTGGGCGCAGGAGGGCAGCCGGCTGGGCTGCACCACCACGGCCTGAGGGACGCC
CACGATGAGCCACACCATGCAGACCACCACCCGCATCCGCACTCTCACCCACACCAGCAACCGCCCCCGCCACCTC
CCCCACAAGGCCCACCGGGCCACCCAGGCGCGCACCACGACCCGCACTCGGACGAGGACACGCCGACCTCAGAC
GACCTGGAGCAGTTCGCCAAGCAATTCAAGCAGAGGCGGATCAAACTCGGATTTACTCAAGCAGACGTGGGGCT
GGCGCTTGGCACCCTGTACGGCAACGTGTTCTCGCAGACCACCATCTGCAGGTTTGAGGCCCTGCAGCTGAGCTT
CAAGAACATGTGCAAGCTGAAGCCTTTGTTGAACAAGTGGTTGGAAGAGGCAGACTCATCCTCGGGCAGCCCCA
CCAGCATAGACAAGATCGCAGCGCAAGGGCGCAAACGGAAAAAGCGGACCTCCATCGAGGTGAGCGTCAAGGG
GGCTCTGGAGAGCCATTTCCTCAAATGCCCTAAGCCCTCGGCCCAGGAGATCACCTCCCTCGCGGACAGCTTACA
GCTGGAGAAGGAGGTGGTGAGAGTTTGGTTTTGTAACAGGAGACAGAAAGAGAAAAGGATGACCCCTCCCGGA
GGGACTCTGCCGGGCGCCGAGGATGTGTATGGGGGTAGTAGGGACACGCCACCACACCACGGGGTGCAGACGC
CCGTCCAGTGA

FIG. 20A

Vectors

>pCALL2-loxp-mCherry-stop-loxp-multiple cloning sites (control) (SEQ ID NO:56) acGTCGACATTGATTATTGACTAGTTATTAATAGTAATCAATTACGGGGTCATTAGTTCATAGCCCATATA
TGGAGTTCCGCGTTACATAACTTACGGTAAATGGCCCGCCTGGCTGACCGCCCAACGACCCCCGCCCATTGACGTC
AATAATGACGTATGTTCCCATAGTAACGCCAATAGGGACTTTCCATTGACGTCAATGGGTGGACTATTTACGGTAA
ACTGCCCACTTGGCAGTACATCAAGTGTATCATATGCCAAGTACGCCCCCTATTGACGTCAATGACGGTAAATGGC
CCGCCTGGCATTATGCCCAGTACATGACCTTATGGGACTTTCCTACTTGGCAGTACATCTACGTATTAGTCATCGCT
ATTACCATGGGTCGAGGTGAGCCCCACGTTCTGCTTCACTCTCCCCATCTCCCCCCCCTCCCCACCCCCAATTTTGTA
TTTATTTATTTTTTAATTATTTTGTGCAGCGATGGGGGCGGGGGGGGGGGGGGCGCGCGCCAGGCGGGGCGGG
GCGGGGCGAGGGGCGGGGCGGGGCGAGGCGGAGAGGTGCGGCGGCAGCCAATCAGAGCGGCGCGCTCCGAA
AGTTTCCTTTTATGGCGAGGCGGCGGCGGCGGCGGCCCTATAAAAAGCGAAGCGCGCGGCGGGCGGGAGTCGC
TGCGTTGCCTTCGCCCCGTGCCCCGCTCCGCGCCGCCTCGCGCCGCCCGCCCCGGCTCTGACTGACCGCGTTACTC
CCACAGGTGAGCGGGCGGGACGGCCCTTCTCCTCCGGGCTGTAATTAGCGCTTGGTTTAATGACGGCTCGTTTCT
TTTCTGTGGCTGCGTGAAAGCCTTAAAGGGCTCCGGGAGGGCCCTTTGTGCGGGGGGGAGCGGCTCGGGGGGT
GCGTGCGTGTGTGTGTGCGTGGGGAGCGCCGCGTGCGGCCCGCGCTGCCCGGCGGCTGTGAGCGCTGCGGGCG
CGGCGCGGGGCTTTGTGCGCTCCGCGTGTGCGCGAGGGGAGCGCGGCCGGGGGCGGTGCCCCGCGGTGCGGG
GGGGCTGCGAGGGGAACAAAGGCTGCGTGCGGGGTGTGTGCGTGGGGGGGTGAGCAGGGGGTGTGGGCGCG
GCGGTCGGGCTGTAACCCCCCCCTGCACCCCCCTCCCCGAGTTGCTGAGCACGGCCCGGCTTCGGGTGCGGGGCT
CCGTGCGGGGCGTGGCGCGGGGCTCGCCGTGCCGGGCGGGGGGTGGCGGCAGGTGGGGGTGCCGGGCGGGG
CGGGGCCGCCTCGGGCCGGGGAGGGCTCGGGGGAGGGGCGCGGCGGCCCCGGAGCGCCGGCGGCTGTCGAG
GCGCGGCGAGCCGCAGCCATTGCCTTTTATGGTAATCGTGCGAGAGGGCGCAGGGACTTCCTTTGTCCCAAATCT
GGCGGAGCCGAAATCTGGGAGGCGCCGCCGCACCCCCTCTAGCGGGCGCGGGCGAAGCGGTGCGGCGCCGGCA
GGAAGGAAATGGGCGGGGAGGGCCTTCGTGCGTCGCCGCGCCGCCGTCCCCTTCTCCATCTCCAGCCTCGGGGC
TGCCGCAGGGGGACGGCTGCCTTCGGGGGGGACGGGGCAGGGCGGGGTTCGGCTTCTGGCGTGTGACCGGCG
GCTCTAGAGCCTCTGCTAACCATGTTCATGCCTTCTTCTTTTTCCTACAGCTCCTGGGCAACGTGCTGGTTATTGTG
CTGTCTCATCATTTTGGCAAAGAATTCCTCGATCGAGGGACCTAATAACTTCGTATAGCATACATTATACGAAGTT
ATATTAAGGGTTCCGCAAGCTTCCTAGACTAGTCGACGGTATCGATaccATGGTGAGCAAGGGCGAGGAGGATAA
CATGGCCATCATCAAGGAGTTCATGCGCTTCAAGGTGCACATGGAGGGCTCCGTGAACGGCCACGAGTTCGAGA
TCGAGGGCGAGGGCGAGGGCCGCCCCTACGAGGGCACCCAGACCGCCAAGCTGAAGGTGACCAAGGGTGGCCC
CCTGCCCTTCGCCTGGGACATCCTGTCCCCTCAGTTCATGTACGGCTCCAAGGCCTACGTGAAGCACCCCGCCGAC
ATCCCCGACTACTTGAAGCTGTCCTTCCCCGAGGGCTTCAAGTGGGAGCGCGTGATGAACTTCGAGGACGGCGGC
GTGGTGACCGTGACCCAGGACTCCTCCCTGCAGGACGGCGAGTTCATCTACAAGGTGAAGCTGCGCGGCACCAA
CTTCCCCTCCGACGGCCCCGTAATGCAGAAGAAGACGATGGGCTGGGAGGCCTCCTCCGAGCGGATGTACCCCG
AGGACGGCGCCCTGAAGGGCGAGATCAAGCAGAGGCTGAAGCTGAAGGACGGCGGCCACTACGACGCTGAGG
TCAAGACCACCTACAAGGCCAAGAAGCCCGTGCAGCTGCCCGGCGCCTACAACGTCAACATCAAGTTGGACATCA
CCTCCCACAACGAGGACTACACCATCGTGGAACAGTACGAACGCGCCGAGGGCCGCCACTCCACCGGCGGCATG
GACGAGCTGTACAAGTAAGCATGCCCGACGGCGAGGATCTCGTCGTGACCCATGGCGATGCCTGCTTGCCGAAT
ATCATGGTGGAAAATGGCCGCTTTTCTGGATTCATCGACTGTGGCCGGCTGGGTGTGGCGGACCGCTATCAGGAC
ATAGCGTTGGCTACCCGTGATATTGCTGAAGAGCTTGGCGGCGAATGGGCTGACCGCTTCCTCGTGCTTTACGGT
ATCGCCGCTCCCGATTCGCAGCGCATCGCCTTCTATCGCCTTCTTGACGAGTTCTTCTGAGGGGATCAATTCTCTAG
GCTTGGGATCTTTGTGAAGGAACCTTACTTCTGTGGTGTGACATAATTGGACAAACTACCTACAGAGATTTAAAGC
TCTAAGGTAAATATAAAATTTTTAAGTGTATAATGTGTTAAACTACTGATTCTAATTGTTTGTGTATTTTAGATTCAC
AGTCCCAAGGCTCATTTCAGGCCCCTCAGTCCTCACAGTCTGTTCATGATCATAATCAGCCATACCACATTTGTAGA
GGTTTTACTTGCTTTAAAAAACCTCCCACACCTCCCCCTGAACCTGAAACATAAAATGAATGCAATTGTTGTTGTTA
ACTTGTTTATTGCAGCTTATAATGGTTACAAATAAAGCAATAGCATCACAAATTTCACAAATAAAGCATTTTTTTCA
CTGCATTCTAGTTGTGTTTGTCCAAACTCATCAATGTATCTTATCATGTCTGGATCATAATCAGCCATACCACATTTG
TAGAGGTTTTACTTGCTTTAAAAAACCTTCCCCACACCTCCCCCTGAACTGAAACATAAAATGAATGCAATTGTTGT
TGTTAACTTGTTTATTGCAGCTTATAATGGTTACAAATAAAGCAATAGCATCACAAATTTCACAAATAAAGCATTTT
TTTCACTGCATTCTAGTTGTGGTTTGTCCAAACTCATCAATGTATCTTATCATGTCTGGATCATAATCAGCCATACCA
CAT

FIG. 20B

TTGTAGAGGTTTTACTTGCTTTAAAAAACCTCCCACACCTCCCCCTGAACCTGAAACATAAAATGAATGCAATTGTT
GTTGTTAACTTGTTTATTGCAGCTTATAATGGTTACAAATAAAGCAATAGCATCACAAATTTCACAAATAAAGCATT
TTTTTCACTGCATTCTAGTTGTGGTTTGTCCAAACTCATCAATGTATCTTATCATGTCTGGATCCACTAGTTCTAGCT
AGTCTAGGTCGATGCAGGATAACTTCGTATAGCATACATTATACGAAGTTATAGATCTTGGGTACCCGCTCGAGCT
CAAGCTTCGAATTCTGCAGTCGACGGTACCGCGGGCCCGGCCGCGATCTTTTTCCCTCTGCCAAAAATTATGGGG
ACATCATGAAGCCCCTTGAGCATCTGACTTCTGGCTAATAAAGGAAATTTATTTTCATTGCAATAGTGTGTTGGAA
TTTTTTGTGTCTCTCACTCGGAAGGACATATGGGAGGGCAAATCATTTAAAACATCAGAATGAGTATTTGGTTTAG
AGTTTGGCAACATATGCCATATGCTGGCTGCCATGAACAAAGGTGGCTATAAAGAGGTCATCAGTATATGAAACA
GCCCCCTGCTGTCCATTCCTTATTCCATAGAAAAGCCTTGACTTGAGGTTAGATTTTTTTTATATTTTGTTTTGTGTT
ATTTTTTTCTTTAACATCCCTAAAATTTTCCTTACATGTTTTACTAGCCAGATTTTTCCTCCTCTCCTGACTACTCCCA
GTCATAGCTGTCCCTCTTCTCTTATGAAGATCCCTCGACCTGCAGCCCAAGCTTGGCGTAATCATGGTCATAGCTGT
TTCCTGTGTGAAATTGTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGTCGGGAAACCTGTCGTG
CCAGCGGATCCGCATCTCAATTAGTCAGCAACCATAGTCCCGCCCCTAACTCCGCCCATCCCGCCCCTAACTCCGCC
CAGTTCCGCCCATTCTCCGCCCCATGGCTGACTAATTTTTTTTATTTATGCAGAGGCCGAGGCCGCCTCGGCCTCTG
AGCTATTCCAGAAGTAGTGAGGAGGCTTTTTTGGAGGCCTAGGCTTTTGCAAAAAGCTAACTTGTTTATTGCAGCT
TATAATGGTTACAAATAAAGCAATAGCATCACAAATTTCACAAATAAAGCATTTTTTTCACTGCATTCTAGTTGTGG
TTTGTCCAAACTCATCAATGTATCTTATCATGTCTGGATCCGCTGCATTAATGAATCGGCCAACGCGCGGGGAGAG
GCGGTTTGCGTATTGGGCGCTCTTCCGCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTCCATAGGCTCCGCCCCCCTG
ACGAGCATCACAAAAATCGACGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATACCTGTCCGCCTTTCTCCCTTC
GGGAAGCGTGGCGCTTTCTCAATGCTCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAGGTATGTAGGCGGTGCTAC
AGAGTTCTTGAAGTGGTGGCCTAACTACGGCTACACTAGAAGGACAGTATTTGGTATCTGCGCTCTGCTGAAGCC
AGTTACCTTCGGAAAAAGAGTTGGTAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTGATCTTTTCTACGGGGTCTGACGCT
CAGTGGAACGAAAACTCACGTTAAGGGATTTTGGTCATGAGATTATCAAAAAGGATCTTCACCTAGATCCTTTTAA
ATTAAAAATGAAGTTTTAAATCAATCTAAAGTATATATGAGTAAACTTGGTCTGACAGTTACCAATGCTTAATCAG
TGAGGCACCTATCTCAGCGATCTGTCTATTTCGTTCATCCATAGTTGCCTGACTCCCCGTCGTGTAGATAACTACGA
TACGGGAGGGCTTACCATCTGGCCCCAGTGCTGCAATGATACCGCGAGACCCACGCTCACCGGCTCCAGATTTAT
CAGCAATAAACCAGCCAGCCGGAAGGGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAACGATCAAGGCGAGTTACATGA
TCCCCCATGTTGTGCAAAAAAGCGGTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATCCGTAAGATGCTTTTCTGTGACTGGT
GAGTACTCAACCAAGTCATTCTGAGAATAGTGTATGCGGCGACCGAGTTGCTCTTGCCCGGCGTCAATACGGGAT
AATACCGCGCCACATAGCAGAACTTTAAAAGTGCTCATCATTGGAAAACGTTCTTCGGGGCGAAAACTCTCAAGG
ATCTTACCGCTGTTGAGATCCAGTTCGATGTAACCCACTCGTGCACCCAACTGATCTTCAGCATCTTTTACTTTCACC
AGCGTTTCTGGGTGAGCAAAAACAGGAAGGCAAAATGCCGCAAAAAAGGGAATAAGGGCGACACGGAAATGTT
GAATACTCATACTCTTCCTTTTTCAATATTATTGAAGCATTTATCAGGGTTATTGTCTCATGAGCGGATACATATTTG
AATGTATTTAGAAAAATAAACAAATAGGGGTTCCGCGCACATTTCCCCGAAAAGTGCCACCTG

FIG. 20C

>pCALL2-loxp-mCherry-stop-loxp-Gateway cassette (SEQ ID NO:57)
acGTCGACATTGATTATTGACTAGTTATTAATAGTAATCAATTACGGGGTCATTAGTTCATAGCCCATATATGGAGT
TCCGCGTTACATAACTTACGGTAAATGGCCCGCCTGGCTGACCGCCCAACGACCCCCGCCCATTGACGTCAATAAT
GACGTATGTTCCCATAGTAACGCCAATAGGGACTTTCCATTGACGTCAATGGGTGGACTATTTACGGTAAACTGCC
CACTTGGCAGTACATCAAGTGTATCATATGCCAAGTACGCCCCCTATTGACGTCAATGACGGTAAATGGCCCGCCT
GGCATTATGCCCAGTACATGACCTTATGGGACTTTCCTACTTGGCAGTACATCTACGTATTAGTCATCGCTATTACC
ATGGTCGAGGTGAGCCCCACGTTCTGCTTCACTCTCCCCATCTCCCCCCCCTCCCCACCCCCAATTTTGTATTTATT
TATTTTTTAATTATTTTGTGCAGCGATGGGGGCGGGGGGGGGGGGGGGCGCGCGCCAGGCGGGGCGGGGCGGG
GCGAGGGGCGGGGCGGGGCGAGGCGGAGAGGTGCGGCGGCAGCCAATCAGAGCGGCGCGCTCCGAAAGTTTC
CTTTTATGGCGAGGCGGCGGCGGCGGCGGCCCTATAAAAAGCGAAGCGCGCGGCGGGCGGGAGTCGCTGCGTT
GCCTTCGCCCCGTGCCCCGCTCCGCGCCGCCTCGCGCCGCCCGCCCCGGCTCTGACTGACCGCGTTACTCCCACAG
GTGAGCGGGCGGGACGGCCCTTCTCCTCCGGGCTGTAATTAGCGCTTGGTTTAATGACGGCTCGTTTCTTTTCTGT
GGCTGCGTGAAAGCCTTAAAGGGCTCCGGGAGGGCCCTTTGTGCGGGGGGGAGCGGCTCGGGGGGTGCGTGC
GTGTGTGTGTGCGTGGGGAGCGCCGCGTGCGGCCCGCGCTGCCCGGCGGCTGTGAGCGCTGCGGGCGCGGCGC
GGGGCTTTGTGCGCTCCGCGTGTGCGCGAGGGGAGCGCGGCCGGGGGCGGTGCCCCGCGGTGCGGGGGGGCT
GCGAGGGGAACAAAGGCTGCGTGCGGGGTGTGTGCGTGGGGGGGTGAGCAGGGGGTGTGGGCGCGGCGGTC
GGGCTGTAACCCCCCCCTGCACCCCCCTCCCCGAGTTGCTGAGCACGGCCCGGCTTCGGGTGCGGGGCTCCGTGC
GGGGCGTGGCGCGGGGCTCGCCGTGCCGGGCGGGGGGTGGCGGCAGGTGGGGGTGCCGGGCGGGGCGGGGC
CGCCTCGGGCCGGGGAGGGCTCGGGGGAGGGGCGCGGCGGCCCCGGAGCGCCGGCGGCTGTCGAGGCGCGGC
GAGCCGCAGCCATTGCCTTTTATGGTAATCGTGCGAGAGGGCGCAGGGACTTCCTTTGTCCCAAATCTGGCGGAG
CCGAAATCTGGGAGGCGCCGCCGCACCCCCTCTAGCGGGCGCGGGCGAAGCGGTGCGGCGCCGGCAGGAAGGA
AATGGGCGGGGAGGGCCTTCGTGCGTCGCCGCGCCGCCGTCCCCTTCTCCATCTCCAGCCTCGGGGCTGCCGCAG
GGGGACGGCTGCCTTCGGGGGGGACGGGGCAGGGCGGGGTTCGGCTTCTGGCGTGTGACCGGCGGCTCTAGA
GCCTCTGCTAACCATGTTCATGCCTTCTTCTTTTTCCTACAGCTCCTGGGCAACGTGCTGGTTATTGTGCTGTCTCAT
CATTTTGGCAAAGAATTCCTCGATCGAGGGACCTAATAACTTCGTATAGCATACATTATACGAAGTTATATTAAGG
GTTCCGCAAGCTTCCTAGACTAGTCGACGGTATCGATaccATGGTGAGCAAGGGCGAGGAGGATAACATGGCCAT
CATCAAGGAGTTCATGCGCTTCAAGGTGCACATGGAGGGCTCCGTGAACGGCCACGAGTTCGAGATCGAGGGCG
AGGGCGAGGGCCGCCCCTACGAGGGCACCCAGACCGCCAAGCTGAAGGTGACCAAGGGTGGCCCCCTGCCCTTC
GCCTGGGACATCCTGTCCCCTCAGTTCATGTACGGCTCCAAGGCCTACGTGAAGCACCCCGCCGACATCCCCGACT
ACTTGAAGCTGTCCTTCCCCGAGGGCTTCAAGTGGGAGCGCGTGATGAACTTCGAGGACGGCGGCGTGGTGACC
GTGACCCAGGACTCCTCCCTGCAGGACGGCGAGTTCATCTACAAGGTGAAGCTGCGCGGCACCAACTTCCCCTCC
GACGGCCCCGTAATGCAGAAGAAGACGATGGGCTGGGAGGCCTCCTCCGAGCGGATGTACCCCGAGGACGGCG
CCCTGAAGGGCGAGATCAAGCAGAGGCTGAAGCTGAAGGACGGCGGCCACTACGACGCTGAGGTCAAGACCAC
CTACAAGGCCAAGAAGCCCGTGCAGCTGCCCGGCGCCTACAACGTCAACATCAAGTTGGACATCACCTCCCACAA
CGAGGACTACACCATCGTGGAACAGTACGAACGCGCCGAGGGCCGCCACTCCACCGGCGGCATGGACGAGCTGT
ACAAGTAAGCATGCCCGACGGCGAGGATCTCGTCGTGACCCATGGCGATGCCTGCTTGCCGAATATCATGGTGG
AAAATGGCCGCTTTTCTGGATTCATCGACTGTGGCCGGCTGGGTGTGGCGGACCGCTATCAGGACATAGCGTTGG
CTACCCGTGATATTGCTGAAGAGCTTGGCGGCGAATGGGCTGACCGCTTCCTCGTGCTTTACGGTATCGCCGCTCC
CGATTCGCAGCGCATCGCCTTCTATCGCCTTCTTGACGAGTTCTTCTGAGGGGATCAATTCTCTAGGCTTGGGATC
TTTGTGAAGGAACCTTACTTCTGTGGTGTGACATAATTGGACAAACTACCTACAGAGATTTAAAGCTCTAAGGTAA
ATATAAAATTTTTAAGTGTATAATGTGTTAAACTACTGATTCTAATTGTTTGTGTATTTTAGATTCACAGTCCCAAG
GCTCATTTCAGGCCCCTCAGTCCTCACAGTCTGTTCATGATCATAATCAGCCATACCACATTTGTAGAGGTTTTACT
TGCTTTAAAAAACCTCCCACACCTCCCCCTGAACCTGAAACATAAAATGAATGCAATTGTTGTTGTTAACTTGTTTA
TTGCAGCTTATAATGGTTACAAATAAAGCAATAGCATCACAAATTTCACAAATAAAGCATTTTTTTCACTGCATTCT
AGTTGTGTTTGTCCAAACTCATCAATGTATCTTATCATGTCTGGATCATAATCAGCCATACCACATTTGTAGAGGTT
TTACTTGCTTTAAAAAACCTTCCCCACACCTCCCCCTGAACTGAAACATAAAATGAATGCAATTGTTGTTGTTAACT
TGTTTATTGCAGCTTATAATGGTTACAAATAAAGCAATAGCATCACAAATTTCACAAATAAAGCATTTTTTTCACTG
CATTCTAGTTGTGGTTTGTCCAAACTCATCAATGTATCTTATCATGTCTGGATCATAATCAGCCATACCACATTTGTA
GAGGTTTTACTTGCTTTAAAAAACCTCCCACACCTCCCCCTGAACCTGAAACATAAAATGAATGCAATTGTTGTTGT

FIG. 20D

TAACTTGTTTATTGCAGCTTATAATGGTTACAAATAAAGCAATAGCATCACAAATTTCACAAATAAAGCATTTTTTT
CACTGCATTCTAGTTGTGGTTTGTCCAAACTCATCAATGTATCTTATCATGTCTGGATCCACTAGTTCTAGCTAGTCT
AGGTCGATGCAGGATAACTTCGTATAGCATACATTATACGAAGTTATAGATCTTGGGTACCCGCTCGAATCACAA
GTTTGTACAAAAAAGCTGAACGAGAAACGTAAAATGATATAAATATCAATATATTAAATTAGATTTTGCATAAAAA
ACAGACTACATAATACTGTAAAACACAACATATCCAGTCACTATGGCGGCCGCATTAGGCACCCCAGGCTTTACAC
TTTATGCTTCCGGCTCGTATAATGTGTGGATTTTGAGTTAGGATCCGTCGAGATTTTCAGGAGCTAAGGAAGCTAA
AATGGAGAAAAAAATCACTGGATATACCACCGTTGATATATCCCAATGGCATCGTAAAGAACATTTTGAGGCATTT
CAGTCAGTTGCTCAATGTACCTATAACCAGACCGTTCAGCTGGATATTACGGCCTTTTTAAAGACCGTAAAGAAAA
ATAAGCACAAGTTTTATCCGGCCTTTATTCACATTCTTGCCCGCCTGATGAATGCTCATCCGGAATTCCGTATGGCA
ATGAAAGACGGTGAGCTGGTGATATGGGATAGTGTTCACCCTTGTTACACCGTTTTCCATGAGCAAACTGAAACG
TTTTCATCGCTCTGGAGTGAATACCACGACGATTTCCGGCAGTTTCTACACATATATTCGCAAGATGTGGCGTGTT
ACGGTGAAAACCTGGCCTATTTCCCTAAAGGGTTTATTGAGAATATGTTTTTCGTCTCAGCCAATCCCTGGGTGAG
TTTCACCAGTTTTGATTTAAACGTGGCCAATATGGACAACTTCTTCGCCCCCGTTTTCACCATGGGCAAATATTATA
CGCAAGGCGACAAGGTGCTGATGCCGCTGGCGATTCAGGTTCATCATGCCGTTTGTGATGGCTTCCATGTCGGCA
GAATGCTTAATGAATTACAACAGTACTGCGATGAGTGGCAGGGCGGGGCGTAAACGCGTGGATCCGGCTTACTA
AAAGCCAGATAACAGTATGCGTATTTGCGCGCTGATTTTTGCGGTATAAGAATATATACTGATATGTATACCCGAA
GTATGTCAAAAAGAGGTATGCTATGAAGCAGCGTATTACAGTGACAGTTGACAGCGACAGCTATCAGTTGCTCAA
GGCATATATGATGTCAATATCTCCGGTCTGGTAAGCACAACCATGCAGAATGAAGCCCGTCGTCTGCGTGCCGAA
CGCTGGAAAGCGGAAAATCAGGAAGGGATGGCTGAGGTCGCCCGGTTTATTGAAATGAACGGCTCTTTTGCTGA
CGAGAACAGGGGCTGGTGAAATGCAGTTTAAGGTTTACACCTATAAAAGAGAGAGCCGTTATCGTCTGTTTGTGG
ATGTACAGAGTGATATTATTGACACGCCCGGGCGACGGATGGTGATCCCCCTGGCCAGTGCACGTCTGCTGTCAG
ATAAAGTCTCCCGTGAACTTTACCCGGTGGTGCATATCGGGGATGAAAGCTGGCGCATGATGACCACCGATATGG
CCAGTGTGCCGGTCTCCGTTATCGGGGAAGAAGTGGCTGATCTCAGCCACCGCGAAAATGACATCAAAAACGCC
ATTAACCTGATGTTCTGGGGAATATAAATGTCAGGCTCCCTTATACACAGCCAGTCTGCAGGTCGACCATAGTGAC
TGGATATGTTGTGTTTTACAGTATTATGTAGTCTGTTTTTTATGCAAAATCTAATTTAATATATTGATATTTATATCA
TTTTACGTTTCTCGTTCAGCTTTCTTGTACAAAGTGGTGATTCGAGCTCAAGCTTCGAATTCTGCAGTCGACGGTAC
CGCGGGCCCGGCCGCGATCTTTTTCCCTCTGCCAAAAATTATGGGGACATCATGAAGCCCCTTGAGCATCTGACTT
CTGGCTAATAAAGGAAATTTATTTTCATTGCAATAGTGTGTTGGAATTTTTTGTGTCTCTCACTCGGAAGGACATAT
GGGAGGGCAAATCATTTAAAACATCAGAATGAGTATTTGGTTTAGAGTTTGGCAACATATGCCATATGCTGGCTG
CCATGAACAAAGGTGGCTATAAAGAGGTCATCAGTATATGAAACAGCCCCCTGCTGTCCATTCCTTATTCCATAGA
AAAGCCTTGACTTGAGGTTAGATTTTTTTTATATTTTGTTTTGTGTTATTTTTTTCTTTAACATCCCTAAAATTTTCCTT
ACATGTTTTACTAGCCAGATTTTTCCTCCTCTCCTGACTACTCCCAGTCATAGCTGTCCCTCTTCTCTTATGAAGATC
CCTCGACCTGCAGCCCAAGCTTGGCGTAATCATGGTCATAGCTGTTTCCTGTGTGAAATTGTTATCCGCTCACAATT
CCACACAACATACGAGCCGGAAGCATAAAGTGTAAAGCCTGGGGTGCCTAATGAGTGAGCTAACTCACATTAATT
GCGTTGCGCTCACTGCCCGCTTTCCAGTCGGGAAACCTGTCGTGCCAGCGGATCCGCATCTCAATTAGTCAGCAAC
CATAGTCCCGCCCCTAACTCCGCCCATCCCGCCCCTAACTCCGCCCAGTTCCGCCCATTCTCCGCCCCATGGCTGAC
TAATTTTTTTTATTTATGCAGAGGCCGAGGCCGCCTCGGCCTCTGAGCTATTCCAGAAGTAGTGAGGAGGCTTTTT
TGGAGGCCTAGGCTTTTGCAAAAAGCTAACTTGTTTATTGCAGCTTATAATGGTTACAAATAAAGCAATAGCATCA
CAAATTTCACAAATAAAGCATTTTTTTCACTGCATTCTAGTTGTGGTTTGTCCAAACTCATCAATGTATCTTATCATG
TCTGGATCCGCTGCATTAATGAATCGGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGAGCATCACAAAAATCGACGCTCAAGT
CAGAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCAATGCTCACG
CTGTAGGTATCTCAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCCACTGGCAGCAGCC
ACTGGTAACAGGATTAGCAGAGCGAGGTATGTAGGCGGTGCTACAGAGTTCTTGAAGTGGTGGCCTAACTACGG
CTACACTAGAAGGACAGTATTTGGTATCTGCGCTCTGCTGAAGCCAGTTACCTTCGGAAAAAGAGTTGGTAGC

FIG. 20E

TCTTGATCCGGCAAACAAACCACCGCTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACCTATCTCAGCGATCTGTCTA
TTTCGTTCATCCATAGTTGCCTGACTCCCCGTCGTGTAGATAACTACGATACGGGAGGGCTTACCATCTGGCCCCA
GTGCTGCAATGATACCGCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGCCGGGAAGCTAGAGTAA
GTAGTTCGCCAGTTAATAGTTTGCGCAACGTTGTTGCCATTGCTACAGGCATCGTGGTGTCACGCTCGTCGTTTGG
TATGGCTTCATTCAGCTCCGGTTCCCAACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTTATCACTCATGGTTATGGCAGCACTGC
ATAATTCTCTTACTGTCATGCCATCCGTAAGATGCTTTTCTGTGACTGGTGAGTACTCAACCAAGTCATTCTGAGAA
TAGTGTATGCGGCGACCGAGTTGCTCTTGCCCGGCGTCAATACGGGATAATACCGCGCCACATAGCAGAACTTTA
AAAGTGCTCATCATTGGAAAACGTTCTTCGGGGCGAAAACTCTCAAGGATCTTACCGCTGTTGAGATCCAGTTCG
ATGTAACCCACTCGTGCACCCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACTCATACTCTTCCTTTTTCAAT
ATTATTGAAGCATTTATCAGGGTTATTGTCTCATGAGCGGATACATATTTGAATGTATTTAGAAAAATAAACAAAT
AGGGGTTCCGCGCACATTTCCCCGAAAAGTGCCACCTG

>pCALL2-loxp-mCherry-stop-loxp-Ikzf1 (SEQ ID NO:58)
acGTCGACATTGATTATTGACTAGTTATTAATAGTAATCAATTACGGGGTCATTAGTTCATAGCCCATATATGGAGT
TCCGCGTTACATAACTTACGGTAAATGGCCCGCCTGGCTGACCGCCCAACGACCCCCGCCCATTGACGTCAATAAT
GACGTATGTTCCCATAGTAACGCCAATAGGGACTTTCCATTGACGTCAATGGGTGGACTATTTACGGTAAACTGCC
CACTTGGCAGTACATCAAGTGTATCATATGCCAAGTACGCCCCCTATTGACGTCAATGACGGTAAATGGCCCGCCT
GGCATTATGCCCAGTACATGACCTTATGGGACTTTCCTACTTGGCAGTACATCTACGTATTAGTCATCGCTATTACC
ATGGGTCGAGGTGAGCCCCACGTTCTGCTTCACTCTCCCCATCTCCCCCCCCTCCCCACCCCCAATTTTGTATTTATT
TATTTTTTAATTATTTTGTGCAGCGATGGGGGCGGGGGGGGGGGGGGCGCGCGCCAGGCGGGGCGGGGCGGG
GCGAGGGGCGGGGCGGGGCGAGGCGGAGAGGTGCGGCGGCAGCCAATCAGAGCGGCGCGCTCCGAAAGTTTC
CTTTTATGGCGAGGCGGCGGCGGCGGCGGCCCTATAAAAAGCGAAGCGCGCGGCGGGCGGGAGTCGCTGCGTT
GCCTTCGCCCCGTGCCCCGCTCCGCGCCGCCTCGCGCCGCCCGCCCCGGCTCTGACTGACCGCGTTACTCCCACAG
GTGAGCGGGCGGGACGGCCCTTCTCCTCCGGGCTGTAATTAGCGCTTGGTTTAATGACGGCTCGTTTCTTTTCTGT
GGCTGCGTGAAAGCCTTAAAGGGCTCCGGGAGGGCCCTTTGTGCGGGGGGGAGCGGCTCGGGGGGTGCGTGC
GTGTGTGTGTGCGTGGGGAGCGCCGCGTGCGGCCCGCGCTGCCCGGCGGCTGTGAGCGCTGCGGGCGCGGCGC
GGGGCTTTGTGCGCTCCGCGTGTGCGCGAGGGGAGCGCGGCCGGGGGCGGTGCCCCGCGGTGCGGGGGGGCT
GCGAGGGGAACAAAGGCTGCGTGCGGGGTGTGTGCGTGGGGGGGTGAGCAGGGGGTGTGGGCGCGGCGGTC
GGGCTGTAACCCCCCCCTGCACCCCCCTCCCCGAGTTGCTGAGCACGGCCCGGCTTCGGGTGCGGGGCTCCGTGC
GGGGCGTGGCGCGGGGCTCGCCGTGCCGGGCGGGGGGTGGCGGCAGGTGGGGGTGCCGGGCGGGGCGGGGC
CGCCTCGGGCCGGGGAGGGCTCGGGGGAGGGGCGCGGCGGCCCCGGAGCGCCGGCGGCTGTCGAGGCGCGGC
GAGCCGCAGCCATTGCCTTTTATGGTAATCGTGCGAGAGGGCGCAGGGACTTCCTTTGTCCCAAATCTGGCGGAG
CCGAAATCTGGGAGGCGCCGCCGCACCCCCTCTAGCGGGCGCGGGCGAAGCGGTGCGGCGCCGGCAGGAAGGA
AATGGGCGGGGAGGGCCTTCGTGCGTCGCCGCGCCGCCGTCCCCTTCTCCATCTCCAGCCTCGGGGCTGCCGCAG
GGGGACGGCTGCCTTCGGGGGGGACGGGGCAGGGCGGGGTTCGGCTTCTGGCGTGTGACCGGCGGCTCTAGA
GCCTCTGCTAACCATGTTCATGCCTTCTTCTTTTTCCTACAGCTCCTGGGCAACGTGCTGGTTATTGTGCTGTCTCAT
CATTTTGGCAAAGAATTCCTCGATCGAGGGACCTAATAACTTCGTATAGCATACATTATACGAAGTTATATTAAGG
GTTCCGCAAGCTTCCTAGACTAGTCGACGGTATCGATaccATGGTGAGCAAGGGCGAGGAGGATAACATGGCCAT
CATCAAGGAGTTCATGCGCTTCAAGGTGCACATGGAGGGCTCCGTGAACGGCCACGAGTTCGAGATCGAGGGCG
AGGGCGAGGGCCGCCCCTACGAGGGCACCCAGACCGCCAAGCTGAAGGTGACCAAGGGTGGCCCCCTGCCCTTC
GCCTGGGACATCCTGTCCCCTCAGTTCATGTACGGCTCCAAGGCCTACGTGAAGCACCCCGCCGACATCCCCGACT
ACTTGAAGCTGTCCTTCCCCGAGGGCTTCAAGTGGGAGCGCGTGATGAACTTCGAGGAC

FIG. 20F

GGCGGCGTGGTGACCGTGACCCAGGACTCCTCCCTGCAGGACGGCGAGTTCATCTACAAGGTGAAGCTGCGCGG
CACCAACTTCCCCTCCGACGGCCCCGTAATGCAGAAGAAGACGATGGGCTGGGAGGCCTCCTCCGAGCGGATGT
ACCCCGAGGACGGCGCCCTGAAGGGCGAGATCAAGCAGAGGCTGAAGCTGAAGGACGGCGGCCACTACGACGC
TGAGGTCAAGACCACCTACAAGGCCAAGAAGCCCGTGCAGCTGCCCGGCGCCTACAACGTCAACATCAAGTTGG
ACATCACCTCCCACAACGAGGACTACACCATCGTGGAACAGTACGAACGCGCCGAGGGCCGCCACTCCACCGGC
GGCATGGACGAGCTGTACAAGTAAGCATGCCCGACGGCGAGGATCTCGTCGTGACCCATGGCGATGCCTGCTTG
CCGAATATCATGGTGGAAAATGGCCGCTTTTCTGGATTCATCGACTGTGGCCGGCTGGGTGTGGCGGACCGCTAT
CAGGACATAGCGTTGGCTACCCGTGATATTGCTGAAGAGCTTGGCGGCGAATGGGCTGACCGCTTCCTCGTGCTT
TACGGTATCGCCGCTCCCGATTCGCAGCGCATCGCCTTCTATCGCCTTCTTGACGAGTTCTTCTGAGGGGATCAAT
TCTCTAGGCTTGGGATCTTTGTGAAGGAACCTTACTTCTGTGGTGTGACATAATTGGACAAACTACCTACAGAGAT
TTAAAGCTCTAAGGTAAATATAAAATTTTTAAGTGTATAATGTGTTAAACTACTGATTCTAATTGTTTGTGTATTTTA
GATTCACAGTCCCAAGGCTCATTTCAGGCCCCTCAGTCCTCACAGTCTGTTCATGATCATAATCAGCCATACCACAT
TTGTAGAGGTTTTACTTGCTTTAAAAAACCTCCCACACCTCCCCCTGAACCTGAAACATAAAATGAATGCAATTGTT
GTTGTTAACTTGTTTATTGCAGCTTATAATGGTTACAAATAAAGCAATAGCATCACAAATTTCACAAATAAAGCATT
TTTTTCACTGCATTCTAGTTGTGTTTGTCCAAACTCATCAATGTATCTTATCATGTCTGGATCATAATCAGCCATACC
ACATTTGTAGAGGTTTTACTTGCTTTAAAAAACCTTCCCCACACCTCCCCCTGAACTGAAACATAAAATGAATGCAA
TTGTTGTTGTTAACTTGTTTATTGCAGCTTATAATGGTTACAAATAAAGCAATAGCATCACAAATTTCACAAATAAA
GCATTTTTTTCACTGCATTCTAGTTGTGGTTTGTCCAAACTCATCAATGTATCTTATCATGTCTGGATCATAATCAGC
CATACCACATTTGTAGAGGTTTTACTTGCTTTAAAAAACCTCCCACACCTCCCCCTGAACCTGAAACATAAAATGAA
TGCAATTGTTGTTGTTAACTTGTTTATTGCAGCTTATAATGGTTACAAATAAAGCAATAGCATCACAAATTTCACAA
ATAAAGCATTTTTTTCACTGCATTCTAGTTGTGGTTTGTCCAAACTCATCAATGTATCTTATCATGTCTGGATCCACT
AGTTCTAGCTAGTCTAGGTCGATGCAGGATAACTTCGTATAGCATACATTATACGAAGTTATAGATCTTGGGTACC
CGCTCGAGCTCAAGCTTCGAATTCTGCAGTCGACGGTACCGCGGGCCCCAAATAATGATTTTATTTTGACTGATAG
TGACCTGTTCGTTGCAACAAATTGATAAGCAATGCTTTTTTATAATGCCAACTTTGTACAAAAAAGCAGGCTTTAA
AGGAACCAATTCAGTCGACTGGATCCGGTACCGaattccagcaggagataacctgaagacaatggatgtcgatgagggtcaagaca
tgtcccaagtttcaggaaaggagagcccccagtcagtgacactccagatgaaggggatgagcccatgcctgtccctgaggacctgtccactacctct
ggagcacagcagaactccaagagtgatcgaggcatggccagtaatgttaaagtagagactcagagtgatgaagagaatgggcgtgcctgtgaaat
gaatggggaagaatgtgcagaggatttacgaatgcttgatgcctcgggagagaaaatgaatggctcccacagggaccaaggcagctcggctttgtc
aggagttggaggcattcgacttcctaacggaaaactaaagtgtgatatctgtgggatcgtttgcatcgggcccaatgtgctcatggttcacaaaagaa
gtcatactggtgaacggcctttccagtgcaaccagtgtggggcctcctttacccagaaaggcaacctcctgcggcacatcaagctgcactcgggtgag
aagcccttcaaatgccatctttgcaactatgcctgccgccggagggacgccctcaccggccacctgaggacgcactccgttggtaagcctcacaaatg
tggatattgtggccggagctataaacagcgaagctctttagaggagcataaagagcgatgccacaactacttggaaagcatgggccttccgggcatg
tacccagtcattaaggaagaaactaaccacaacgagatggcagaagacctgtgcaagataggagcagagaggtcccttgtcctggacaggctggc
aagcaatgtcgccaaacgtaagagctctatgcctcagaaatttcttggagacaagtgcctgtcagacatgccctatgacagtgccaactatgagaag
gaggatatgatgacatcccacgtgatggaccaggccatcaacaatgccatcaactacctgggggctgagtccctgcgcccattggtgcagacacccc
ccggtagctccgaggtggtgccagtcatcagctccatgtaccagctgcacaagcccccctcagatggcccccacggtccaaccattcagcacagga
cgccgtggataacttgctgctgctgtccaaggccaagtctgtgtcatcggagcgagaggcctccccgagcaacagctgccaagactccacagataca
gagagcaacgcggaggaacagcgcagcggccttatctacctaaccaaccacatcaacccgcatgcacgcaatgggctggctctcaaggaggagca
gcgcgcctacgaggtgctgagggcggcctcagagaactcgcaggatgccttccgtgtggtcagcacgagtggcgagcagctgaaggtgtacaagtg
cgaacactgccgcgtgctcttcctggatcacgtcatgtataccattcacatgggctgccatggctttcgggatccctttgagtgtaacatgtgtggttatc
acagccaggacaggtacgagttctcatcccatatcacgcggggggagcatcgttaccacctgagctaagAATTCGCGGCCGCGATCTTTTT
CCCTCTGCCAAAAATTATGGGGACATCATGAAGCCCCTTGAGCATCTGACTTCTGGCTAATAAAGGAAATTTATTT
TCATTGCAATAGTGTGTTGGAATTTTTTGTGTCTCTCACTCGGAAGGACATATGGGAGGGCAAATCATTTAAAACA
TCAGAATGAGTATTTGGTTTAGAGTTTGGCAACATATGCCATATGCTGGCTGCCATGAACAAAGGTGGCTATAAA
GAGGTCATCAGTATATGAAACAGCCCCCTGCTGTCCATTCCTTATTCCATAGAAAAGCCTTGACTTGAGGTTAGAT
TTTTTTTATATTTTGTTTTGTGTTATTTTTTTCTTTAACATCCCTAAAATTTTCCTTACATGTTTTACTAGCCAGATTTT
TCCTCCTCTCCTGACTACTCCCAGTCATAGCTGTCCCTCTTCTCTTATGAAGATCCCTCGACCTGCAGCCCAAGCTTG
GCGTAATCATGGTCATAGCTGTTTCCTGTGTGAAATTGTTATCCGCTCACAATTCCACACAACATACGAGCCGGAA
GCATAAAGTGTAAAGCCTGGGGTGCCTAATGAGTGAGCTAACTCACATTAATTGCGTTGCGCTCACTGCCCGCTTT
CCAGTC

FIG. 20G

GGGAAACCTGTCGTGCCAGCGGATCCGCATCTCAATTAGTCAGCAACCATAGTCCCGCCCCTAACTCCGCCCATCC
CGCCCCTAACTCCGCCCAGTTCCGCCCATTCTCCGCCCCATGGCTGACTAATTTTTTTTATTTATGCAGAGGCCGAG
GCCGCCTCGGCCTCTGAGCTATTCCAGAAGTAGTGAGGAGGCTTTTTTGGAGGCCTAGGCTTTTGCAAAAAGCTA
ACTTGTTTATTGCAGCTTATAATGGTTACAAATAAAGCAATAGCATCACAAATTTCACAAATAAAGCATTTTTTTCA
CTGCATTCTAGTTGTGGTTTGTCCAAACTCATCAATGTATCTTATCATGTCTGGATCCGCTGCATTAATGAATCGGC
CAACGCGCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAACGC
AGGAAAGAACATGTGAGCAAAAGGCCAGCAAAAGGCCAGGAACCGTAAAAAGGCCGCGTTGCTGGCGTTTTTCC
ATAGGCTCCGCCCCCCTGACGAGCATCACAAAAATCGACGCTCAAGTCAGAGGTGGCGAAACCCGACAGGACTA
TAAAGATACCAGGCGTTTCCCCCTGGAAGCTCCCTCGTGCGCTCTCCTGTTCCGACCCTGCCGCTTACCGGATACCT
GTCCGCCTTTCTCCCTTCGGGAAGCGTGGCGCTTTCTCAATGCTCACGCTGTAGGTATCTCAGTTCGGTGTAGGTC
GTTCGCTCCAAGCTGGGCTGTGTGCACGAACCCCCCGTTCAGCCCGACCGCTGCGCCTTATCCGGTAACTATCGTC
TTGAGTCCAACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGGACAGTATTTGGTATC
TGCGCTCTGCTGAAGCCAGTTACCTTCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAAGGATCTCAAGAAGATCCTTTGATCTTTT
CTACGGGGTCTGACGCTCAGTGGAACGAAAACTCACGTTAAGGGATTTTGGTCATGAGATTATCAAAAAGGATCT
TCACCTAGATCCTTTTAAATTAAAAATGAAGTTTTAAATCAATCTAAAGTATATATGAGTAAACTTGGTCTGACAGT
TACCAATGCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCACGCTC
ACCGGCTCCAGATTTATCAGCAATAAACCAGCCAGCCGGAAGGGCCGAGCGCAGAAGTGGTCCTGCAACTTTATC
CGCCTCCATCCAGTCTATTAATTGTTGCCGGGAAGCTAGAGTAAGTAGTTCGCCAGTTAATAGTTTGCGCAACGTT
GTTGCCATTGCTACAGGCATCGTGGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAATTCTCTTACTGTCATGCCATCCGTAAG
ATGCTTTTCTGTGACTGGTGAGTACTCAACCAAGTCATTCTGAGAATAGTGTATGCGGCGACCGAGTTGCTCTTGC
CCGGCGTCAATACGGGATAATACCGCGCCACATAGCAGAACTTTAAAAGTGCTCATCATTGGAAAACGTTCTTCG
GGGCGAAAACTCTCAAGGATCTTACCGCTGTTGAGATCCAGTTCGATGTAACCCACTCGTGCACCCAACTGATCTT
CAGCATCTTTTACTTTCACCAGCGTTTCTGGGTGAGCAAAAACAGGAAGGCAAAATGCCGCAAAAAAGGGAATAA
GGGCGACACGGAAATGTTGAATACTCATACTCTTCCTTTTTCAATATTATTGAAGCATTTATCAGGGTTATTGTCTC
ATGAGCGGATACATATTTGAATGTATTTAGAAAAATAAACAAATAGGGGTTCCGCGCACATTTCCCCGAAAAGTG
CCACCTG

>pCALL2-loxp-mCherry-stop-loxp-Ikzf4 (SEQ ID NO:59)
acGTCGACATTGATTATTGACTAGTTATTAATAGTAATCAATTACGGGGTCATTAGTTCATAGCCCATATATGGAGT
TCCGCGTTACATAACTTACGGTAAATGGCCCGCCTGGCTGACCGCCCAACGACCCCCGCCCATTGACGTCAATAAT
GACGTATGTTCCCATAGTAACGCCAATAGGGACTTTCCATTGACGTCAATGGGTGGACTATTTACGGTAAACTGCC
CACTTGGCAGTACATCAAGTGTATCATATGCCAAGTACGCCCCCTATTGACGTCAATGACGGTAAATGGCCCGCCT
GGCATTATGCCCAGTACATGACCTTATGGGACTTTCCTACTTGGCAGTACATCTACGTATTAGTCATCGCTATTACC
ATGGGTCGAGGTGAGCCCCACGTTCTGCTTCACTCTCCCCATCTCCCCCCCCTCCCCACCCCCAATTTTGTATTTATT
TATTTTTTAATTATTTTGTGCAGCGATGGGGGCGGGGGGGGGGGGGGGCGCGCGCCAGGCGGGGCGGGGCGGG
GCGAGGGGCGGGGCGGGGCGAGGCGGAGAGGTGCGGCGGCAGCCAATCAGAGCGGCGCGCTCCGAAAGTTTC
CTTTTATGGCGAGGCGGCGGCGGCGGCGGCCCTATAAAAAGCGAAGCGCGCGGCGGGCGGGAGTCGCTGCGTT
GCCTTCGCCCCGTGCCCCGCTCCGCGCCGCCTCGCGCCGCCCGCCCCGGCTCTGACTGACCGCGTTACTCCCACAG
GTGAGCGGGCGGGACGGCCCTTCTCCTCCGGGCTGTAATTAGCGCTTGGTTTAATGACGGCTCGTTTCTTTTCTGT
GGCTGCGTGAAAGCCTTAAAGGGCTCCGGGAGGGCCCTTTGTGCGGGGGGGAGCGGCTCGGGGGGTGCGTGC
GTGTGTGTGTGCGTGGGGAGCGCCGCGTGCGGCCCGCGCTGCCCGGCGGCTGTGAGCGCTGCGGGCGCGGCGC
GGGGCTTTGTGCGCTCCGCGTGTGCGCGAGGGGAGCGCGGCCGGGGGCGGTGCCCCGCGGTGCGGGGGGGCT
GCGAGGGGAACAAAGGCTGCGTGCGGGGTGTGTGCGTGGGGGGGTGAGCAGGGGGTGTGGGCGCGGC

FIG. 20H

GGTCGGGCTGTAACCCCCCCCTGCACCCCCCTCCCCGAGTTGCTGAGCACGGCCCGGCTTCGGGTGCGGGGCTCC
GTGCGGGGCGTGGCGCGGGGCTCGCCGTGCCGGGCGGGGGGTGGCGGCAGGTGGGGGTGCCGGGCGGGGCG
GGGCCGCCTCGGGCCGGGGAGGGCTCGGGGGAGGGGCGCGGCGGCCCCGGAGCGCCGGCGGCTGTCGAGGC
GCGGCGAGCCGCAGCCATTGCCTTTTATGGTAATCGTGCGAGAGGGCGCAGGGACTTCCTTTGTCCCAAATCTGG
CGGAGCCGAAATCTGGGAGGCGCCGCCGCACCCCCTCTAGCGGGCGCGGGCGAAGCGGTGCGGCGCCGGCAGG
AAGGAAATGGGCGGGGAGGGCCTTCGTGCGTCGCCGCGCCGCCGTCCCCTTCTCCATCTCCAGCCTCGGGGCTG
CCGCAGGGGGACGGCTGCCTTCGGGGGGGACGGGGCAGGGCGGGGTTCGGCTTCTGGCGTGTGACCGGCGGC
TCTAGAGCCTCTGCTAACCATGTTCATGCCTTCTTCTTTTTCCTACAGCTCCTGGGCAACGTGCTGGTTATTGTGCT
GTCTCATCATTTTGGCAAAGAATTCCTCGATCGAGGGACCTAATAACTTCGTATAGCATACATTATACGAAGTTAT
ATTAAGGGTTCCGCAAGCTTCCTAGACTAGTCGACGGTATCGATaccATGGTGAGCAAGGGCGAGGAGGATAACA
TGGCCATCATCAAGGAGTTCATGCGCTTCAAGGTGCACATGGAGGGCTCCGTGAACGGCCACGAGTTCGAGATC
GAGGGCGAGGGCGAGGGCCGCCCCTACGAGGGCACCCAGACCGCCAAGCTGAAGGTGACCAAGGGTGGCCCCC
TGCCCTTCGCCTGGGACATCCTGTCCCCTCAGTTCATGTACGGCTCCAAGGCCTACGTGAAGCACCCCGCCGACAT
CCCCGACTACTTGAAGCTGTCCTTCCCCGAGGGCTTCAAGTGGGAGCGCGTGATGAACTTCGAGGACGGCGGCG
TGGTGACCGTGACCCAGGACTCCTCCCTGCAGGACGGCGAGTTCATCTACAAGGTGAAGCTGCGCGGCACCAACT
TCCCCTCCGACGGCCCCGTAATGCAGAAGAAGACGATGGGCTGGGAGGCCTCCTCCGAGCGGATGTACCCCGAG
GACGGCGCCCTGAAGGGCGAGATCAAGCAGAGGCTGAAGCTGAAGGACGGCGGCCACTACGACGCTGAGGTCA
AGACCACCTACAAGGCCAAGAAGCCCGTGCAGCTGCCCGGCGCCTACAACGTCAACATCAAGTTGGACATCACCT
CCCACAACGAGGACTACACCATCGTGGAACAGTACGAACGCGCCGAGGGCCGCCACTCCACCGGCGGCATGGAC
GAGCTGTACAAGTAAGCATGCCCGACGGCGAGGATCTCGTCGTGACCCATGGCGATGCCTGCTTGCCGAATATCA
TGGTGGAAAATGGCCGCTTTTCTGGATTCATCGACTGTGGCCGGCTGGGTGTGGCGGACCGCTATCAGGACATA
GCGTTGGCTACCCGTGATATTGCTGAAGAGCTTGGCGGCGAATGGGCTGACCGCTTCCTCGTGCTTTACGGTATC
GCCGCTCCCGATTCGCAGCGCATCGCCTTCTATCGCCTTCTTGACGAGTTCTTCTGAGGGGATCAATTCTCTAGGCT
TGGGATCTTTGTGAAGGAACCTTACTTCTGTGGTGTGACATAATTGGACAAACTACCTACAGAGATTTAAAGCTCT
AAGGTAAATATAAAATTTTTAAGTGTATAATGTGTTAAACTACTGATTCTAATTGTTTGTGTATTTTAGATTCACAG
TCCCAAGGCTCATTTCAGGCCCCTCAGTCCTCACAGTCTGTTCATGATCATAATCAGCCATACCACATTTGTAGAGG
TTTTACTTGCTTTAAAAAACCTCCCACACCTCCCCCTGAACCTGAAACATAAAATGAATGCAATTGTTGTTGTTAAC
TTGTTTATTGCAGCTTATAATGGTTACAAATAAAGCAATAGCATCACAAATTTCACAAATAAAGCATTTTTTTCACT
GCATTCTAGTTGTGTTTGTCCAAACTCATCAATGTATCTTATCATGTCTGGATCATAATCAGCCATACCACATTTGTA
GAGGTTTTACTTGCTTTAAAAAACCTTCCCCACACCTCCCCCTGAACTGAAACATAAAATGAATGCAATTGTTGTTG
TTAACTTGTTTATTGCAGCTTATAATGGTTACAAATAAAGCAATAGCATCACAAATTTCACAAATAAAGCATTTTTT
TCACTGCATTCTAGTTGTGGTTTGTCCAAACTCATCAATGTATCTTATCATGTCTGGATCATAATCAGCCATACCAC
ATTTGTAGAGGTTTTACTTGCTTTAAAAAACCTCCCACACCTCCCCCTGAACCTGAAACATAAAATGAATGCAATTG
TTGTTGTTAACTTGTTTATTGCAGCTTATAATGGTTACAAATAAAGCAATAGCATCACAAATTTCACAAATAAAGCA
TTTTTTTCACTGCATTCTAGTTGTGGTTTGTCCAAACTCATCAATGTATCTTATCATGTCTGGATCCACTAGTTCTAG
CTAGTCTAGGTCGATGCAGGATAACTTCGTATAGCATACATTATACGAAGTTATAGATCTTGGGTACCCGCTCGAG
CTCAAGCTTCGAATTCTGCAGTCGACGGTACCGCGGGCCCATCACAAGTTTGTACAAAAAAGCAGGCTTTAAAGG
AACCAATTCAGTCGACTGGATCCACAARTAACGGCCGCCAGTGTGCTGGAATTCGCCCTTCCAAGTCCCTGAGTG
GTTGTTTTCTTCCCACTGACCAAATCTGGAGAGGGAGCTCTCAGGAGGGTGTGCTCCGGATTTCTTGCCTCAGGCC
CAGGACTCCAACCATTTTATAATGGAATCTTTATTTTGTGAAAGTAGCGGGGACTCATCTCTGGAGAAGGAGTTCC
TTGGGGCCCCAGTGGGGCCCTCGGTGAGCACCCCAAACAGCCAACACTCTTCACCCAGCCGCTCGCTCAGTGCCA
ACTCCATCAAGGTGGAGATGTACAGCGATGAGGAGTCGAGCAGACTGCTGGGGCCGGATGAACGGCTCCTGGA
TAAGGATGACAGTGTGATTGTGGAAGACTCATTGTCAGAGCCCTTAGGCTACTGCGATGGAAGTGGGCCAGAGC
CTCACTCCCCTGGCGGCATCCGGCTACCCAACGGCAAGCTCAAGTGCGACGTCTGCGGCATGGTCTGCATTGGGC
CCAATGTGCTCATGGTACACAAGCGCAGCCACACTGGGGAGAGGCCCTTCCACTGTAATCAGTGTGGTGCCTCCT
TCACACAGAAGGGCAATCTGCTTCGCCACATCAAGCTGCACTCGGGGGAGAAGCCCTTCAAGTGCCCCTTCTGCA
ACTATGCCTGCCGCCGGCGTGACGCACTCACTGGCCACCTCCGCACACACTCAGTCTCCTCCCCCACCGTGGGCAA
ACCCTACAAGTGCAACTACTGTGGCCGGAGCTACAAACAGCAAAGTACCCTGGAGGAGCACAAGGAGAGGTGCC
ACAACTACCTACAGAGTCTCAGCACTGATGCCCAAGCTCTGACTGGCCAGCCAGGTGATGAAATCCGTGACCTGG
AGATGG

FIG. 20I

TGCCTGACTCAATGCTGCACCCATCGACTGAACGGCCAACTTTCATTGATCGTTTGGCCAACAGCCTCACCAAACG
CAAGCGTTCCACCCCACAGAAGTTTGTAGGTGAAAAGCAGATGCGCTTCAGCCTCTCAGACCTTCCCTATGATGTG
AATGCCAGCGGTGGCTATGAAAAGGACGTAGAGTTGGTGGCACACCATGGCCTGGAGCCTGGCTTTGGAGGGTC
TCTAGCCTTTGTGGGTACAGAGCATCTGCGTCCCCTCCGCCTCCCACCCACCAACTGCATCTCAGAACTCACACCTG
TCATCAGCTCTGTGTACACCCAAATGCAGCCCATCCCCAGCCGACTGGAGCTTCCAGGGTCCCGAGAAGCAGGTG
AGGGACCGGAGGACCTGGGAGATGGAGGTCCCCTCCTTTATCGGGCCCGAGGCTCTCTGACTGACCCTGGGGCA
TCCCCCAGCAATGGCTGCCAGGACTCCACAGATACAGAGAGCAACCACGAAGACCGGATTGGTGGGGTGGTATC
CCTTCCTCAGGGTCCCCCACCCCAACCTCCTCCCACCATAGTGGTGGGCCGGCACAGTCCCGCCTATGCCAAAGAG
GACCCCAAACCACAGGAGGGGTTACTGCGGGGCACCCCAGGCCCCTCCAAGGAAGTGCTTCGGGTGGTGGGTG
AGAGTGGTGAGCCAGTGAAGGCCTTTAAGTGTGAACACTGCCGCATCCTCTTTCTGGACCACGTCATGTTCACCAT
CCACATGGGCTGCCACGGCTTCAGAGACCCTTTTGAGTGTAACATCTGTGGTTATCACAGCCAGGATCGGTATGA
GTTCTCTTCCCACATCGTCCGGGGGGAACATAAGGTGGGCTAGGAATTCGCGGCCGCGATCTTTTTCCCTCTGCCA
AAAATTATGGGGACATCATGAAGCCCCTTGAGCATCTGACTTCTGGCTAATAAAGGAAATTTATTTTCATTGCAAT
AGTGTGTTGGAATTTTTTGTGTCTCTCACTCGGAAGGACATATGGGAGGGCAAATCATTTAAAACATCAGAATGA
GTATTTGGTTTAGAGTTTGGCAACATATGCCATATGCTGGCTGCCATGAACAAAGGTGGCTATAAAGAGGTCATC
AGTATATGAAACAGCCCCCTGCTGTCCATTCCTTATTCCATAGAAAAGCCTTGACTTGAGGTTAGATTTTTTTTATA
TTTTGTTTTGTGTTATTTTTTTCTTTAACATCCCTAAAATTTTCCTTACATGTTTTACTAGCCAGATTTTTCCTCCTCTC
CTGACTACTCCCAGTCATAGCTGTCCCTCTTCTCTTATGAAGATCCCTCGACCTGCAGCCCAAGCTTGGCGTAATCA
TGGTCATAGCTGTTTCCTGTGTGAAATTGTTATCCGCTCACAATTCCACACAACATACGAGCCGGAAGCATAAAGT
GTAAAGCCTGGGGTGCCTAATGAGTGAGCTAACTCACATTAATTGCGTTGCGCTCACTGCCCGCTTTCCAGTCGG
GAAACCTGTCGTGCCAGCGGATCCGCATCTCAATTAGTCAGCAACCATAGTCCCGCCCCTAACTCCGCCCATCCCG
CCCCTAACTCCGCCCAGTTCCGCCCATTCTCCGCCCCATGGCTGACTAATTTTTTTTATTTATGCAGAGGCCGAGGC
CGCCTCGGCCTCTGAGCTATTCCAGAAGTAGTGAGGAGGCTTTTTTGGAGGCCTAGGCTTTTGCAAAAAGCTAAC
TTGTTTATTGCAGCTTATAATGGTTACAAATAAAGCAATAGCATCACAAATTTCACAAATAAAGCATTTTTTTCACT
GCATTCTAGTTGTGGTTTGTCCAAACTCATCAATGTATCTTATCATGTCTGGATCCGCTGCATTAATGAATCGGCCA
ACGCGCGGGGAGAGGCGGTTTGCGTATTGGGCGCTCTTCCGCTTCCTCGCTCACTGACTCGCTGCGCTCGGTCGT
TCGGCTGCGGCGAGCGGTATCAGCTCACTCAAAGGCGGTAATACGGTTATCCACAGAATCAGGGGATAACGCAG
GAAAGAACATGTGAGCAAAAGGCCAGCAAAAGGCCAGGAACCGTAAAAAGGCCGCGTTGCTGGCGTTTTTCCAT
AGGCTCCGCCCCCCTGACGAGCATCACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCAATGCTCACGCTGTAGGTATCTCAGTTCGGTGTAGGTCG
TTCGCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGGTCATGAGATTATCAAAAAGGATCTT
CACCTAGATCCTTTTAAATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAGTTGCCTGACTCCCCGTC
GTGTAGATAACTACGATACGGGAGGGCTTACCATCTGGCCCCAGTGCTGCAATGATACCGCGAGACCCACGCTCA
CCGGCTCCAGATTTATCAGCAATAAACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCTTCATTCAGCTCCGGTTCCCAACGATC
AAGGCGAGTTACATGATCCCCCATGTTGTGCAAAAAAGCGGTTAGCTCCTTCGGTCCTCCGATCGTTGTCAGAAGT
AAGTTGGCCGCAGTGTTATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCATTGGAAAACGTTCTTCGGG
GCGAAAACTCTCAAGGATCTTACCGCTGTTGAGATCCAGTTCGATGTAACCCACTCGTGCACCCAACTGATCTTCA
G

FIG. 20J

CATCTTTTACTTTCACCAGCGTTTCTGGGTGAGCAAAAACAGGAAGGCAAAATGCCGCAAAAAAGGGAATAAGG
GCGACACGGAAATGTTGAATACTCATACTCTTCCTTTTTCAATATTATTGAAGCATTTATCAGGGTTATTGTCTCAT
GAGCGGATACATATTTGAATGTATTTAGAAAAATAAACAAATAGGGGTTCCGCGCACATTTCCCCGAAAAGTGCC
ACCTG

>pssAAV-CAG-GFP (SEQ ID NO:60)
gtcctgcaggcagctgcgcgctcgctcgctcactgaggccgcccgggcaaagcccgggcgtcgggcgacctttggtcgcccggcctcagtgagcgag
cgagcgcgcagagagggagtggccaactccatcactaggggttcctgcggccgcacgcgtcgtggtacctctggtcgttacataacttacggtaaatg
gcccgcctggctgaccgcccaacgacccccgcccattgacgtcaataatgacgtatgttcccatagtaacgccaatagggactttccattgacgtcaa
tgggtggagtatttacggtaaactgcccacttggcagtacatcaagtgtatcatatgccaagtacgccccctattgacgtcaatgacggtaaatggccc
gcctggcattatgcccagtacatgaccttatgggactttcctacttggcagtacattactcgaggccacgttctgcttcactctccccatctcccccccc
tccccacccccaattttgtatttatttattttttaattattttgtgcagcgatgggggcggggggggggggggggcgcgcgccaggcggggcggggcgg
ggcgaggggcggggcggggcgaggcggagaggtgcggcggcagccaatcagagcggcgcgctccgaaagtttccttttatggcgaggcggcggcg
gcggcggccctataaaaagcgaagcgcgcggcgggcgggagcgggatcagccaccgcggtggcggcctagagtcgacgaggaactgaaaaacca
gaaagttaactggtaagtttagtctttttgtcttttatttcaggtcccggatccggtggtggtgcaaatcaaagaactgctcctcagtggatgttgccttt
acttctaggcctgtacggaagtgttacttctgctctaaaagctgcggaattgtacccgcggccgatccaccggtcgccaccatggtgagcaagggcga
ggagctgttcaccggggtggtgcccatcctggtcgagctggacggcgacgtaaacggccacaagttcagcgtgtccggcgagggcgagggcgatgc
cacctacggcaagctgaccctgaagttcatctgcaccaccggcaagctgcccgtgccctggcccaccctcgtgaccaccctgacctacggcgtgcagt
gcttcagccgctaccccgaccacatgaagcagcacgacttcttcaagtccgccatgcccgaaggctacgtccaggagcgcaccatcttcttcaaggac
gacggcaactacaagacccgcgccgaggtgaagttcgagggcgacaccctggtgaaccgcatcgagctgaagggcatcgacttcaaggaggacgg
caacatcctggggcacaagctggagtacaactacaacagccacaacgtctatatcatggccgacaagcagaagaacggcatcaaggtgaacttca
agatccgccacaacatcgaggacggcagcgtgcagctcgccgaccactaccagcagaacacccccatcggcgacggccccgtgctgctgcccgaca
accactacctgagcacccagtccgccctgagcaaagaccccaacgagaagcgcgatcacatggtcctgctggagttcgtgaccgccgccgggatca
ctctcggcatggacgagctgtacaagtaaagcgaagcttgcctcgagcagcgctgctcgagagatctacgggtggcatccctgtgacccctccccagt
gcctctcctggccctggaagttgccactccagtgcccaccagccttgtcctaataaaattaagttgcatcattttgtctgactaggtgtccttctataata
ttatggggtggaggggggtggtatggagcaaggggcaagttgggaagacaacctgtagggcctgcggggtctattgggaaccaagctggagtgca
gtggcacaatcttggctcactgcaatctccgcctcctgggttcaagcgattctcctgcctcagcctcccgagttgttgggattccaggcatgcatgacca
ggctcagctaatttttgtttttttggtagagacggggtttcaccatattggccaggctggtctccaactcctaatctcaggtgatctacccaccttggcctc
ccaaattgctgggattacaggcgtgaaccactgctcccttccctgtccttctgattttgtaggtaaccacgtgcggaccgagcggccgcaggaacccct
agtgatggagttggccactccctctctgcgcgctcgctcgctcactgaggccgggcgaccaaaggtcgcccgacgcccgggctttgcccgggcggcct
cagtgagcgagcgagcgcgcagctgcctgcaggggcgcctgatgcggtattttctccttacgcatctgtgcggtatttcacaccgcatacgtcaaagc
aaccatagtacgcgccctgtagcggcgcattaagcgcggcgggtgtggtggttacgcgcagcgtgaccgctacacttgccagcgccctagcgcccgc
tcctttcgctttcttcccttcctttctcgccacgttcgccggctttccccgtcaagctctaaatcgggggctccctttagggttccgatttagtgctttacggc
acctcgaccccaaaaaacttgatttgggtgatggttcacgtagtgggccatcgccctgatagacggtttttcgccctttgacgttggagtccacgttcttt
aatagtggactcttgttccaaactggaacaacactcaaccctatctcgggctattcttttgatttataagggattttgccgatttcggcctattggttaaa
aaatgagctgatttaacaaaaatttaacgcgaattttaacaaaatattaacgtttacaattttatggtgcactctcagtacaatctgctctgatgccgca
tagttaagccagccccgacacccgccaacacccgctgacgcgccctgacgggcttgtctgctcccggcatccgcttacagacaagctgtgaccgtctc
cgggagctgcatgtgtcagaggttttcaccgtcatcaccgaaacgcgcgagacgaaagggcctcgtgatacgcctatttttataggttaatgtcatgat
aataatggtttcttagacgtcaggtggcacttttcggggaaatgtgcgcggaacccctatttgtttatttttctaaatacattcaaatatgtatccgctca
tgagacaataaccctgataaatgcttcaataatattgaaaaaggaagagtatgagtattcaacatttccgtgtcgcccttattcccttttttgcggcattt
tgccttcctgtttttgctcacccagaaacgctggtgaaagtaaaagatgctgaagatcagttgggtgcacgagtgggttacatcgaactggatctcaac
agcggtaagatccttgagagttttcgccccgaagaacgttttccaatgatgagcacttttaaagttctgctatgtggcgcggtattatcccgtattgacg
ccgggcaagagcaactcggtcgccgcatacactattctcagaatgacttggttgagtactcaccagtcacagaaaagcatcttacggatggcatgac
agtaagagaattatgcagtgctgccataaccatgagtgataacactgcggccaacttacttctgacaacgatcggaggaccgaaggagctaaccgct
tttttgcacaacatgggggatcatgtaactcgccttgatcgttgggaaccggagctgaatgaagccataccaaacgacgagcgtgacaccacgatgc
ctgtagcaatggcaacaacgttgcgcaaactattaactggcgaactacttactctagcttcccggcaacaattaatagactggatggaggcggataa
agttgcaggaccacttctgcgctcggcccttccggctggctggtttattgctgataaatctggagccggtgagcgtgggtctcgcggtatcattgcagca
ctggggccagatggtaagccctcccgtatcgtagttatctacacgacggggagtcaggcaactatggatgaacgaaatagacagatcgctgagata
ggtgcctcactgattaagcattggtaactgtcagaccaagtttactcatatatactttagattgatttaaaacttcatttttaatttaaaaggatctaggt
gaagatcctttttgataatctcatgaccaaaatcccttaacgtgagttttcgttccactgagcgtcaga

FIG. 20K ccccgtagaaaagatcaaaggatcttcttgagatcctttttttctgcgcgtaatctgctgcttgcaaacaaaaaaaccaccgctaccagcggtggtttg
tttgccggatcaagagctaccaactctttttccgaaggtaactggcttcagcagagcgcagataccaaatactgtccttctagtgtagccgtagttagg
ccaccacttcaagaactctgtagcaccgcctacatacctcgctctgctaatcctgttaccagtggctgctgccagtggcgataagtcgtgtcttaccggg
ttggactcaagacgatagttaccggataaggcgcagcggtcgggctgaacggggggttcgtgcacacagcccagcttggagcgaacgacctacacc
gaactgagatacctacagcgtgagctatgagaaagcgccacgcttcccgaagggagaaaggcggacaggtatccggtaagcggcagggtcggaac
aggagagcgcacgagggagcttccagggggaaacgcctggtatctttatagtcctgtcgggtttcgccacctctgacttgagcgtcgatttttgtgatg
ctcgtcaggggggcggagcctatggaaaaacgccagcaacgcggcctttttacggttcctggccttttgctggccttttgctcacat >pssAAV-CAG-Ikzf1(SEQ ID NO:61)
gtcctgcaggcagctgcgcgctcgctcgctcactgaggccgcccgggcaaagcccgggcgtcgggcgacctttggtcgcccggcctcagtgagcgag
cgagcgcgcagagagggagtggccaactccatcactaggggttcctgcggccgcacgcgtcgtggtacctctggtcgttacataacttacggtaaatg
gcccgcctggctgaccgcccaacgacccccgcccattgacgtcaataatgacgtatgttcccatagtaacgccaatagggactttccattgacgtcaa
tgggtggagtatttacggtaaactgcccacttggcagtacatcaagtgtatcatatgccaagtacgccccctattgacgtcaatgacggtaaatggccc
gcctggcattatgcccagtacatgaccttatgggactttcctacttggcagtacattactcgaggccacgttctgcttcactctccccatctcccccccc
tccccacccccaattttgtatttatttattttttaattattttgtgcagcgatgggggcgggggggggggggggcgcgcgccaggcggggcggggcgg
ggcgaggggcggggcggggcgaggcggagaggtgcggcggcagccaatcagagcggcgcgctccgaaagtttccttttatggcgaggcggcggcg
gcggcggccctataaaaagcgaagcgcgcggcgggcgggagcgggatcagccaccgcggtggcggcctagagtcgacgaggaactgaaaaacca
gaaagttaactggtaagtttagtctttttgtcttttatttcaggtcccggatccggtggtggtgcaaatcaaagaactgctcctcagtggatgttgccttt
acttctaggcctgtacggaagtgttacttctgctctaaaagctgcggaattgtacccgcggccgatccaccggtACCGaattccagcaggagataac
ctgaagacaatggatgtcgatgagggtcaagacatgtcccaagtttcaggaaaggagagcccccagtcagtgacactccagatgaaggggatga
gcccatgcctgtccctgaggacctgtccactacctctggagcacagcagaactccaagagtgatcgaggcatggccagtaatgttaaagtagagact
cagagtgatgaagagaatgggcgtgcctgtgaaatgaatggggaagaatgtgcagaggatttacgaatgcttgatgcctcgggagagaaaatgaat
ggctcccacagggaccaaggcagctcggctttgtcaggagttggaggcattcgacttcctaacggaaaactaaagtgtgatatctgtgggatcgtttg
catcgggcccaatgtgctcatggttcacaaaagaagtcatactggtgaacggcctttccagtgcaaccagtgtggggcctcctttacccagaaaggca
acctcctgcggcacatcaagctgcactcgggtgagaagcccttcaaatgccatctttgcaactatgcctgccgccggagggacgccctcaccggccac
ctgaggacgcactccgttggtaagcctcacaaatgtggatattgtggccggagctataaacagcgaagctctttagaggagcataaagagcgatgcc
acaactacttggaaagcatgggccttccgggcatgtacccagtcattaaggaagaaactaaccacaacgagatggcagaagacctgtgcaagatag
gagcagagaggtcccttgtcctggacaggctggcaagcaatgtcgccaaacgtaagagctctatgcctcagaaatttcttggagacaagtgcctgtc
agacatgccctatgacagtgccaactatgagaaggaggatatgatgacatcccacgtgatggaccaggccatcaacaatgccatcaactacctggg
ggctgagtccctgcgcccattggtgcagacacccccggtagctccgaggtggtgccagtcatcagctccatgtaccagctgcacaagccccccctcag
atggcccccccacggtccaaccattcagcacaggacgccgtggataacttgctgctgctgtccaaggccaagtctgtgtcatcggagcgagaggcctcc
ccgagcaacagctgccaagactccacagatacagagagcaacgcggaggaacagcgcagcggccttatctacctaaccaaccacatcaacccgca
tgcacgcaatgggctggctctcaaggaggagcagcgcgcctacgaggtgctgagggcggcctcagagaactcgcaggatgccttccgtgtggtcag
cacgagtggcgagcagctgaaggtgtacaagtgcgaacactgccgcgtgctcttcctggatcacgtcatgtataccattcacatgggctgccatggct
ttcgggatccctttgagtgtaacatgtgtggttatcacagccaggacaggtacgagttctcatcccatatcacgcgggggggagcatcgttaccacctga
gctaaaagcttgcctcgagcagcgctgctcgagagatctacgggtggcatccctgtgacccctccccagtgcctctcctggccctggaagttgccactc
cagtgcccaccagccttgtcctaataaaattaagttgcatcattttgtctgactaggtgtccttctataatattatggggtggaggggggtggtatggag
caaggggcaagttgggaagacaacctgtagggcctgcggggtctattgggaaccaagctggagtgcagtggcacaatcttggctcactgcaatctcc
gcctcctgggttcaagcgattctcctgcctcagcctcccgagttgttgggattccaggcatgcatgaccaggctcagctaatttttgtttttttggtagag
acggggtttcaccatattggccaggctggtctccaactcctaatctcaggtgatctacccaccttggcctcccaaattgctgggattacaggcgtgaac
cactgctcccttccctgtccttctgattttgtaggtaaccacgtgcggaccgagcggccgcaggaacccctagtgatggagttggccactccctctctgc
gcgctcgctcgctcactgaggccgggcgaccaaaggtcgcccgacgcccgggctttgcccgggcggcctcagtgagcgagcgagcgcgcagctgcc
tgcaggggcgcctgatgcggtattttctccttacgcatctgtgcggtatttcacaccgcatacgtcaaagcaaccatagtacgcgccctgtagcggcgc
attaagcgcggcgggtgtggtggttacgcgcagcgtgaccgctacacttgccagcgccctagcgcccgctcctttcgctttcttcccttcctttctcgcca
cgttcgccggctttccccgtcaagctctaaatcgggggctccctttagggttccgatttagtgctttacggcacctcgaccccaaaaaacttgatttggg
tgatggttcacgtagtgggccatcgccctgatagacggtttttcgccctttgacgttggagtccacgttctttaatagtggactcttgttccaaactggaa
caacactcaaccctatctcgggctattcttttgatttataagggattttgccgatttcggcctattggttaaaaaatgagctgatttaacaaaaatttaac
gcgaattttaacaaaatattaacgtttacaattttatgg

FIG. 20L tgcactctcagtacaatctgctctgatgccgcatagttaagccagccccgacacccgccaacacccgctgacgcgccctgacgggcttgtctgctcccg
gcatccgcttacagacaagctgtgaccgtctccgggagctgcatgtgtcagaggttttcaccgtcatcaccgaaacgcgcgagacgaaagggcctcg
tgatacgcctatttttataggttaatgtcatgataataatggtttcttagacgtcaggtggcacttttcggggaaatgtgcgcggaacccctatttgtttat
ttttctaaatacattcaaatatgtatccgctcatgagacaataaccctgataaatgcttcaataatattgaaaaaggaagagtatgagtattcaacatt
tccgtgtcgcccttattcccttttttgcggcattttgccttcctgtttttgctcacccagaaacgctggtgaaagtaaaagatgctgaagatcagttgggtg
cacgagtgggttacatcgaactggatctcaacagcggtaagatccttgagagttttcgccccgaagaacgttttccaatgatgagcacttttaaagttc
tgctatgtggcgcggtattatcccgtattgacgccgggcaagagcaactcggtcgccgcatacactattctcagaatgacttggttgagtactcaccag
tcacagaaaagcatcttacggatggcatgacagtaagagaattatgcagtgctgccataaccatgagtgataacactgcggccaacttacttctgac
aacgatcggaggaccgaaggagctaaccgcttttttgcacaacatgggggatcatgtaactcgccttgatcgttgggaaccggagctgaatgaagcc
ataccaaacgacgagcgtgacaccacgatgcctgtagcaatggcaacaacgttgcgcaaactattaactggcgaactacttactctagcttcccggc
aacaattaatagactggatggaggcggataaagttgcaggaccacttctgcgctcggcccttccggctggctggtttattgctgataaatctggagcc
ggtgagcgtgggtctcgcggtatcattgcagcactggggccagatggtaagccctcccgtatcgtagttatctacacgacggggagtcaggcaactat
ggatgaacgaaatagacagatcgctgagataggtgcctcactgattaagcattggtaactgtcagaccaagtttactcatatatactttagattgattt
aaaacttcatttttaatttaaaaggatctaggtgaagatcctttttgataatctcatgaccaaaatcccttaacgtgagttttcgttccactgagcgtcag
accccgtagaaaagatcaaaggatcttcttgagatcctttttttctgcgcgtaatctgctgcttgcaaacaaaaaaaccaccgctaccagcggtggttt
gtttgccggatcaagagctaccaactctttttccgaaggtaactggcttcagcagagcgcagataccaaatactgtccttctagtgtagccgtagttag
gccaccacttcaagaactctgtagcaccgcctacatacctcgctctgctaatcctgttaccagtggctgctgccagtggcgataagtcgtgtcttaccgg
gttggactcaagacgatagttaccggataaggcgcagcggtcgggctgaacggggggttcgtgcacacagcccagcttggagcgaacgacctacac
cgaactgagatacctacagcgtgagctatgagaaagcgccacgcttcccgaagggagaaaggcggacaggtatccggtaagcggcagggtcggaa
caggagagcgcacgagggagcttccagggggaaacgcctggtatctttatagtcctgtcgggtttcgccacctctgacttgagcgtcgatttttgtgat
gctcgtcaggggggcggagcctatggaaaaacgccagcaacgcggcctttttacggttcctggccttttgctggccttttgctcacat >pssAAV-CAG-Ikzf4 (SEQ ID NO:62)
gtcctgcaggcagctgcgcgctcgctcgctcactgaggccgcccgggcaaagcccgggcgtcgggcgacctttggtcgcccggcctcagtgagcgag
cgagcgcgcagagagggagtggccaactccatcactaggggttcctgcggccgcacgcgtcgtggtacctctggtcgttacataacttacggtaaatg
gcccgcctggctgaccgcccaacgacccccgcccattgacgtcaataatgacgtatgttcccatagtaacgccaatagggactttccattgacgtcaa
tgggtggagtatttacggtaaactgcccacttggcagtacatcaagtgtatcatatgccaagtacgccccctattgacgtcaatgacggtaaatggccc
gcctggcattatgcccagtacatgaccttatgggactttcctacttggcagtacattactcgaggccacgttctgcttcactctccccatctcccccccc
tccccacccccaattttgtatttatttattttttaattattttgtgcagcgatgggggcgggggggggggggggcgcgcgccaggcggggcggggcgg
ggcgaggggcggggcggggcgaggcggagaggtgcggcggcagccaatcagagcggcgcgctccgaaagtttccttttatggcgaggcggcggcg
gcggcggccctataaaaagcgaagcgcgcggcgggcgggagcgggatcagccaccgcggtggcggcctagagtcgacgaggaactgaaaaacca
gaaagttaactggtaagtttagtctttttgtcttttatttcaggtcccggatccggtggtggtgcaaatcaaagaactgctcctcagtggatgttgccttt
acttctaggcctgtacggaagtgttacttctgctctaaaagctgcggaattgtacccgcggccgatccaccggtAATCTGGAGAGGGAGCTCT
CAGGAGGGTGTGCTCCGGATTTCTTGCCTCAGGCCCAGGACTCCAACCATTTTATAATGGAATCTTTATTTTGTGA
AAGTAGCGGGGACTCATCTCTGGAGAAGGAGTTCCTTGGGGCCCCAGTGGGGCCCTCGGTGAGCACCCCAAACA
GCCAACACTCTTCACCCAGCCGCTCGCTCAGTGCCAACTCCATCAAGGTGGAGATGTACAGCGATGAGGAGTCGA
GCAGACTGCTGGGGCCGGATGAACGGCTCCTGGATAAGGATGACAGTGTGATTGTGGAAGACTCATTGTCAGAG
CCCTTAGGCTACTGCGATGGAAGTGGGCCAGAGCCTCACTCCCCTGGCGGCATCCGGCTACCCAACGGCAAGCTC
AAGTGCGACGTCTGCGGCATGGTCTGCATTGGGCCCAATGTGCTCATGGTACACAAGCGCAGCCACACTGGGGA
GAGGCCCTTCCACTGTAATCAGTGTGGTGCCTCCTTCACACAGAAGGGCAATCTGCTTCGCCACATCAAGCTGCAC
TCGGGGGAGAAGCCCTTCAAGTGCCCCTTCTGCAACTATGCCTGCCGCCGGCGTGACGCACTCACTGGCCACCTC
CGCACACACTCAGTCTCCTCCCCCACCGTGGGCAAACCCTACAAGTGCAACTACTGTGGCCGGAGCTACAAACAG
CAAAGTACCCTGGAGGAGCACAAGGAGAGGTGCCACAACTACCTACAGAGTCTCAGCACTGATGCCCAAGCTCT
GACTGGCCAGCCAGGTGATGAAATCCGTGACCTGGAGATGGTGCCTGACTCAATGCTGCACCCATCGACTGAAC
GGCCAACTTTCATTGATCGTTTGGCCAACAGCCTCACCAAACGCAAGCGTTCCACCCCACAGAAGTTTGTAGGTGA
AAAGCAGATGCGCTTCAGCCTCTCAGACCTTCCCTATGATGTGAATGCCAGCGGTGGCTATGAAAAGGACGTAGA
GTTGGTGGCACACCATGGCCTGGAGCCTGGCTTTGGAGGGTCTCTAGCCTTTGTGGGTACAGAGCATCTGCGTCC
CCTCCGCCTCCCACCCACCAACTGCATCTCAGAACTCACACCTGTCATCAGCTCTGTGTACACCCAAATGCAGCCCA
TCCCCAGCCGACTGGAGCTTCCAGGGTCCCGAGAAGCAGG

FIG. 20M

TGAGGGACCGGAGGACCTGGGAGATGGAGGTCCCCTCCTTTATCGGGCCCGAGGCTCTCTGACTGACCCTGGGG
CATCCCCCAGCAATGGCTGCCAGGACTCCACAGATACAGAGAGCAACCACGAAGACCGGATTGGTGGGGTGGTA
TCCCTTCCTCAGGGTCCCCCACCCCAACCTCCTCCCACCATAGTGGTGGGCCGGCACAGTCCCGCCTATGCCAAAG
AGGACCCCAAACCACAGGAGGGGTTACTGCGGGGCACCCCAGGCCCCTCCAAGGAAGTGCTTCGGGTGGTGGG
TGAGAGTGGTGAGCCAGTGAAGGCCTTTAAGTGTGAACACTGCCGCATCCTCTTTCTGGACCACGTCATGTTCACC
ATCCACATGGGCTGCCACGGCTTCAGAGACCCTTTTGAGTGTAACATCTGTGGTTATCACAGCCAGGATCGGTAT
GAGTTCTCTTCCCACATCGTCCGGGGGGAACATAAGGTGGGCTAGaagcttgcctcgagcagcgctgctcgagagatctacgg
gtggcatccctgtgacccctccccagtgcctctcctggccctggaagttgccactccagtgcccaccagccttgtcctaataaaattaagttgcatcatt
ttgtctgactaggtgtccttctataatattatggggtggaggggggtggtatggagcaaggggcaagttgggaagacaacctgtagggcctgcggggt
ctattgggaaccaagctggagtgcagtggcacaatcttggctcactgcaatctccgcctcctgggttcaagcgattctcctgcctcagcctcccgagttg
ttgggattccaggcatgcatgaccaggctcagctaattttttgttttttggtagagacggggtttcaccatattggccaggctggtctccaactcctaatc
tcaggtgatctacccaccttggcctcccaaattgctgggattacaggcgtgaaccactgctcccttccctgtccttctgattttgtaggtaaccacgtgcg
gaccgagcggccgcaggaacccctagtgatggagttggccactccctctctgcgcgctcgctcgctcactgaggccgggcgaccaaaggtcgcccga
cgcccgggctttgcccgggcggcctcagtgagcgagcgagcgcgcagctgcctgcaggggcgcctgatgcggtattttctccttacgcatctgtgcgg
tatttcacaccgcatacgtcaaagcaaccatagtacgcgccctgtagcggcgcattaagcgcggcgggtgtggtggttacgcgcagcgtgaccgcta
cacttgccagcgccctagcgcccgctcctttcgctttcttcccttcctttctcgccacgttcgccggctttccccgtcaagctctaaatcgggggctcccttt
agggttccgatttagtgctttacggcacctcgaccccaaaaaacttgatttgggtgatggttcacgtagtgggccatcgccctgatagacggtttttcgc
cctttgacgttggagtccacgttctttaatagtggactcttgttccaaactggaacaacactcaaccctatctcgggctattcttttgatttataagggatt
ttgccgatttcggcctattggttaaaaaatgagctgatttaacaaaaatttaacgcgaattttaacaaaatattaacgtttacaattttatggtgcactct
cagtacaatctgctctgatgccgcatagttaagccagccccgacacccgccaacacccgctgacgcgccctgacgggcttgtctgctcccggcatccg
cttacagacaagctgtgaccgtctccgggagctgcatgtgtcagaggttttcaccgtcatcaccgaaacgcgcgagacgaaagggcctcgtgatacg
cctatttttataggttaatgtcatgataataatggtttcttagacgtcaggtggcacttttcggggaaatgtgcgcggaacccctatttgtttatttttcta
aatacattcaaatatgtatccgctcatgagacaataaccctgataaatgcttcaataatattgaaaaaggaagagtatgagtattcaacatttccgtgt
cgcccttattcccttttttgcggcattttgccttcctgtttttgctcacccagaaacgctggtgaaagtaaaagatgctgaagatcagttgggtgcacgag
tgggttacatcgaactggatctcaacagcggtaagatccttgagagttttcgccccgaagaacgttttccaatgatgagcacttttaaagttctgctatg
tggcgcggtattatcccgtattgacgccgggcaagagcaactcggtcgccgcatacactattctcagaatgacttggttgagtactcaccagtcacag
aaaagcatcttacggatggcatgacagtaagagaattatgcagtgctgccataaccatgagtgataacactgcggccaacttacttctgacaacgat
cggaggaccgaaggagctaaccgcttttttgcacaacatgggggatcatgtaactcgccttgatcgttgggaaccggagctgaatgaagccatacca
aacgacgagcgtgacaccacgatgcctgtagcaatggcaacaacgttgcgcaaactattaactggcgaactacttactctagcttcccggcaacaat
taatagactggatggaggcggataaagttgcaggaccacttctgcgctcggcccttccggctggctggtttattgctgataaatctggagccggtgag
cgtgggtctcgcggtatcattgcagcactggggccagatggtaagccctcccgtatcgtagttatctacacgacggggagtcaggcaactatggatga
acgaaatagacagatcgctgagataggtgcctcactgattaagcattggtaactgtcagaccaagtttactcatatatactttagattgatttaaaact
tcatttttaatttaaaaggatctaggtgaagatcctttttgataatctcatgaccaaaatcccttaacgtgagttttcgttccactgagcgtcagaccccg
tagaaaagatcaaaggatcttcttgagatcctttttttctgcgcgtaatctgctgcttgcaaacaaaaaaaccaccgctaccagcggtggtttgtttgcc
ggatcaagagctaccaactctttttccgaaggtaactggcttcagcagagcgcagataccaaatactgtccttctagtgtagccgtagttaggccacc
acttcaagaactctgtagcaccgcctacatacctcgctctgctaatcctgttaccagtggctgctgccagtggcgataagtcgtgtcttaccgggttgga
ctcaagacgatagttaccggataaggcgcagcggtcgggctgaacggggggttcgtgcacacagcccagcttggagcgaacgacctacaccgaact
gagatacctacagcgtgagctatgagaaagcgccacgcttcccgaagggagaaaggcggacaggtatccggtaagcggcagggtcggaacagga
gagcgcacgagggagcttccagggggaaacgcctggtatctttatagtcctgtcgggtttcgccacctctgacttgagcgtcgatttttgtgatgctcgt
caggggggcggagcctatggaaaaacgccagcaacgcggcctttttacggttcctggccttttgctggccttttgctcacat

FIG. 21A

>FUW-M2rtTA (Addgene Plasmid #20342) (lentiviral vector) (SEQ ID NO:63)
TCGACGGATCGGGAGATCTCCCGATCCCCTATGGTGCACTCTCAGTACAATCTGCTCTGATGCCGCATAGTTAAGC
CAGTATCTGCTCCCTGCTTGTGTGTTGGAGGTCGCTGAGTAGTGCGCGAGCAAAATTTAAGCTACAACAAGGCAA
GGCTTGACCGACAATTGCATGAAGAATCTGCTTAGGGTTAGGCGTTTTGCGCTGCTTCGCGATGTACGGGCCAGA
TATACGCGTTGACATTGATTATTGACTAGTTATTAATAGTAATCAATTACGGGGTCATTAGTTCATAGCCCATATAT
GGAGTTCCGCGTTACATAACTTACGGTAAATGGCCCGCCTGGCTGACCGCCCAACGACCCCCGCCCATTGACGTC
AATAATGACGTATGTTCCCATAGTAACGCCAATAGGGACTTTCCATTGACGTCAATGGGTGGAGTATTTACGGTA
AACTGCCCACTTGGCAGTACATCAAGTGTATCATATGCCAAGTACGCCCCCTATTGACGTCAATGACGGTAAATGG
CCCGCCTGGCATTATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGGGGATTTCCAAG
TCTCCACCCCATTGACGTCAATGGGAGTTTGTTTTGGCACCAAAATCAACGGGACTTTCCAAAATGTCGTAACAAC
TCCGCCCCATTGACGCAAATGGGCGGTAGGCGTGTACGGTGGGAGGTCTATATAAGCAGCGCGTTTTGCCTGTAC
TGGGTCTCTCTGGTTAGACCAGATCTGAGCCTGGGAGCTCTCTGGCTAACTAGGGAACCCACTGCTTAAGCCTCA
ATAAAGCTTGCCTTGAGTGCTTCAAGTAGTGTGTGCCCGTCTGTTGTGTGACTCTGGTAACTAGAGATCCCTCAGA
CCCTTTTAGTCAGTGTGGAAAATCTCTAGCAGTGGCGCCCGAACAGGGACTTGAAAGCGAAAGGGAAACCAGAG
GAGCTCTCTCGACGCAGGACTCGGCTTGCTGAAGCGCGCACGGCAAGAGGCGAGGGGCGGCGACTGGTGAGTA
CGCCAAAAATTTTGACTAGCGGAGGCTAGAAGGAGAGAGATGGGTGCGAGAGCGTCAGTATTAAGCGGGGGAG
AATTAGATCGCGATGGGAAAAAATTCGGTTAAGGCCAGGGGGAAAGAAAAAATATAAATTAAAACATATAGTAT
GGGCAAGCAGGGAGCTAGAACGATTCGCAGTTAATCCTGGCCTGTTAGAAACATCAGAAGGCTGTAGACAAATA
CTGGGACAGCTACAACCATCCCTTCAGACAGGATCAGAAGAACTTAGATCATTATATAATACAGTAGCAACCCTCT
ATTGTGTGCATCAAAGGATAGAGATAAAAGACACCAAGGAAGCTTTAGACAAGATAGAGGAAGAGCAAAACAA
AAGTAAGACCACCGCACAGCAAGCGGCCGCTGATCTTCAGACCTGGAGGAGGAGATATGAGGGACAATTGGAG
AAGTGAATTATATAAATATAAAGTAGTAAAAATTGAACCATTAGGAGTAGCACCCACCAAGGCAAAGAGAAGAG
TGGTGCAGAGAGAAAAAAGAGCAGTGGGAATAGGAGCTTTGTTCCTTGGGTTCTTGGGAGCAGCAGGAAGCAC
TATGGGCGCAGCGTCAATGACGCTGACGGTACAGGCCAGACAATTATTGTCTGGTATAGTGCAGCAGCAGAACA
ATTTGCTGAGGGCTATTGAGGCGCAACAGCATCTGTTGCAACTCACAGTCTGGGGCATCAAGCAGCTCCAGGCAA
GAATCCTGGCTGTGGAAAGATACCTAAAGGATCAACAGCTCCTGGGGATTTGGGGTTGCTCTGGAAAACTCATTT
GCACCACTGCTGTGCCTTGGAATGCTAGTTGGAGTAATAAATCTCTGGAACAGATTTGGAATCACACGACCTGGA
TGGAGTGGGACAGAGAAATTAACAATTACACAAGCTTAATACACTCCTTAATTGAAGAATCGCAAAACCAGCAAG
AAAAGAATGAACAAGAATTATTGGAATTAGATAAATGGGCAAGTTTGTGGAATTGGTTTAACATAACAAATTGGC
TGTGGTATATAAAATTATTCATAATGATAGTAGGAGGCTTGGTAGGTTTAAGAATAGTTTTTGCTGTACTTTCTATA
GTGAATAGAGTTAGGCAGGGATATTCACCATTATCGTTTCAGACCCACCTCCCAACCCCGAGGGGACCCGACAGG
CCCGAAGGAATAGAAGAAGAAGGTGGAGAGAGAGACAGAGACAGATCCATTCGATTAGTGAACGGATCGGCAC
TGCGTGCGCCAATTCTGCAGACAAATGGCAGTATTCATCCACAATTTTAAAAGAAAAGGGGGGATTGGGGGGTA
CAGTGCAGGGGAAAGAATAGTAGACATAATAGCAACAGACATACAAACTAAAGAATTACAAAAACAAATTACAA
AAATTCAAAATTTTCGGGTTTATTACAGGGACAGCAGAGATCCAGTTTGGTTAATTAACCCGTGTCGGCTCCAGAT
CTGGCCTCCGCGCCGGGTTTTGGCGCCTCCCGCGGGCGCCCCCCTCCTCACGGCGAGCGCTGCCACGTCAGACGA
AGGGCGCAGCGAGCGTCCTGATCCTTCCGCCCGGACGCTCAGGACAGCGGCCCGCTGCTCATAAGACTCGGCCTT
AGAACCCCAGTATCAGCAGAAGGACATTTTAGGACGGGACTTGGGTGACTCTAGGGCACTGGTTTTCTTTCCAGA
GAGCGGAACAGGCGAGGAAAAGTAGTCCCTTCTCGGCGATTCTGCGGAGGGATCTCCGTGGGGCGGTGAACGC
CGATGATTATATAAGGACGCGCCGGGTGTGGCACAGCTAGTTCCGTCGCAGCCGGGATTTGGGTCGCGGTTCTT
GTTTGTGGATCGCTGTGATCGTCACTTGGTGAGTAGCGGGCTGCTGGGCTGGCCGGGGCTTTCGTGGCCGCCGG
GCCGCTCGGTGGGACGGAAGCGTGTGGAGAGACCGCCAAGGGCTGTAGTCTGGGTCCGCGAGCAAGGTTGCCC
TGAACTGGGGGTT

FIG. 21B

GGGGGGAGCGCAGCAAAATGGCGGCTGTTCCCGAGTCTTGAATGGAAGACGCTTGTGAGGCGGGCTGTGAGGTCGT
TGAAACAAGGTGGGGGGCATGGTGGGCGGCAAGAACCCAAGGTCTTGAGGCCTTCGCTAATGCGGGAAAGCTCTTA
TTCGGGTGAGATGGGCTGGGGCACCATCTGGGGACCCTGACGTGAAGTTTGTCACTGACTGGAGAACTCGGTTTGTC
GTCTGTTGCGGGGGCGGCAGTTATGGCGGTGCCGTTGGGCAGTGCACCCGTACCTTTGGGAGCGCGCGCCCTCGTCG
TGTCGTGACGTCACCCGTTCTGTTGGCTTATAATGCAGGGTGGGGCCACCTGCCGGTAGGTGTGCGGTAGGCTTTTCT
CCGTCGCAGGACGCAGGGTTCGGGCCTAGGGTAGGCTCTCCTGAATCGACAGGCGCCGGACCTCTGGTGAGGGGAG
GGATAAGTGAGGCGTCAGTTTCTTTGGTCGGTTTTATGTACCTATCTTCTTAAGTAGCTGAAGCTCCGGTTTTGAACTA
TGCGCTCGGGGTTGGCGAGTGTGTTTTGTGAAGTTTTTTAGGCACCTTTTGAAATGTAATCATTTGGGTCAATATGTAA
TTTTCAGTGTTAGACTAGTAAATTGTCCGCTAAATTCTGGCCGTTTTTGGCTTTTTTGTTAGACGAAGCTTGGGCCCGG
GAATTAATTCACCATGTCTAGACTGGACAAGAGCAAAGTCATAAACGGCGCTCTGGAATTACTCAATGGAGTCGGTAT
CGAAGGCCTGACGACAAGGAAACTCGCTCAAAAGCTGGGAGTTGAGCAGCCTACCCTGTACTGGCACGTGAAGAACA
AGCGGGCCCTGCTCGATGCCCTGCCAATCGAGATGCTGGACAGGCATCATACCCACTTCTGCCCCCTGGAAGGCGAGT
CATGGCAAGACTTTCTGCGGAACAACGCCAAGTCATTCCGCTGTGCTCTCCTCTCACATCGCGACGGGGCTAAAGTGC
ATCTCGGCACCCGCCCAACAGAGAAACAGTACGAAACCCTGGAAAATCAGCTCGCGTTCCTGTGTCAGCAAGGCTTCT
CCCTGGAGAACGCACTGTACGCTCTGTCCGCCGTGGGCCACTTTACACTGGGCTGCGTATTGGAGGAACAGGAGCAT
CAAGTAGCAAAAGAGGAAAGAGAGACACCTACCACCGATTCTATGCCCCCACTTCTGAGACAAGCAATTGAGCTGTTC
GACCGGCAGGGAGCCGAACCTGCCTTCCTTTTCGGCCTGGAACTAATCATATGTGGCCTGGAGAAACAGCTAAAGTG
CGAAAGCGGCGGGCCGGCCGACGCCCTTGACGATTTTGACTTAGACATGCTCCCAGCCGATGCCCTTGACGACTTTGA
CCTTGATATGCTGCCTGCTGACGCTCTTGACGATTTTGACCTTGACATGCTCCCCGGGTAACTAAGTAAGGATCAATTC
GATATCAAGCTTATCGATAATCAACCTCTGGATTACAAAATTTGTGAAAGATTGACTGGTATTCTTAACTATGTTGCTCC
TTTTACGCTATGTGGATACGCTGCTTTAATGCCTTTGTATCATGCTATTGCTTCCCGTATGGCTTTCATTTTCTCCTCCTT
GTATAAATCCTGGTTGCTGTCTCTTTATGAGGAGTTGTGGCCCGTTGTCAGGCAACGTGGCGTGGTGTGCACTGTGTT
TGCTGACGCAACCCCCACTGGTTGGGGCATTGCCACCACCTGTCAGCTCCTTTCCGGGACTTTCGCTTTCCCCCTCCCTA
TTGCCACGGCGGAACTCATCGCCGCCTGCCTTGCCCGCTGCTGGACAGGGGCTCGGCTGTTGGGCACTGACAATTCCG
TGGTGTTGTCGGGGAAATCATCGTCCTTTCCTTGGCTGCTCGCCTGTGTTGCCACCTGGATTCTGCGCGGGACGTCCTT
CTGCTACGTCCCTTCGGCCCTCAATCCAGCGGACCTTCCTTCCCGCGGCCTGCTGCCGGCTCTGCGGCCTCTTCCGCGT
CTTCGCCTTCGCCCTCAGACGAGTCGGATCTCCCTTTGGGCCGCCTCCCCGCATCGATACCGTCGACCTCGAGACCTAG
AAAAACATGGAGCAATCACAAGTAGCAATACAGCAGCTACCAATGCTGATTGTGCCTGGCTAGAAGCACAAGAGGAG
GAGGAGGTGGGTTTTCCAGTCACACCTCAGGTACCTTTAAGACCAATGACTTACAAGGCAGCTGTAGATCTTAGCCAC
TTTTTAAAAGAAAAGGGGGGACTGGAAGGGCTAATTCACTCCCAACGAAGACAAGATATCCTTGATCTGTGGATCTAC
CACACACAAGGCTACTTCCCTGATTGGCAGAACTACACACCAGGGCCAGGGATCAGATATCCACTGACCTTTGGATGG
TGCTACAAGCTAGTACCAGTTGAGCAAGAGAAGGTAGAAGAAGCCAATGAAGGAGAGAACACCCGCTTGTTACACCC
TGTGAGCCTGCATGGGATGGATGACCCGGAGAGAGAAGTATTAGAGTGGAGGTTTGACAGCCGCCTAGCATTTCATC
ACATGGCCCGAGAGCTGCATCCGGACTGTACTGGGTCTCTCTGGTTAGACCAGATCTGAGCCTGGGAGCTCTCTGGCT
AACTAGGGAACCCACTGCTTAAGCCTCAATAAAGCTTGCCTTGAGTGCTTCAAGTAGTGTGTGCCCGTCTGTTGTGTG
ACTCTGGTAACTAGAGATCCCTCAGACCCTTTTAGTCAGTGTGGAAAATCTCTAGCAGGGCCCGTTTAAACCCGCTGAT
CAGCCTCGACTGTGCCTTCTAGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCATTCTATTCTGGGGGGTG
GGGTGGGGCAGGACAGCAAGGGGGAGGATTGGGAAGACAATAGCAGGCATGTGAGCAAAAGGCCAGCAAAAGGC
CAGGAACCGTAAAAAGGCCGCGTTGCTGGCGTTTTTCCATAGGCTCCGCCCCCCTGACGAGCATCACAAAAATCGACG
CTCAAGTCAGAGGTGGCGAAACCCGACAGGACTATAAAGATACCAGGCGTTTCCCCCTGGAAGCTCCCTCGTGCGCTC
TCCTGTTCCGACCCTGCCGCTT

FIG. 21C

ACCGGATACCTGTCCGCCTTTCTCCCTTCGGGAAGCGTGGCGCTTTCTCATAGCTCACGCTGTAGGTATCTCAGTTC
GGTGTAGGTCGTTCGCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACACTAGAAGAACAG
TATTTGGTATCTGCGCTCTGCTGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAAAAAGGATCTCAAGAAGATCC
TTTGATCTTTTCTACGGGGTCTGACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCTAAAGTATATATGAGTAAACTTG
GTCTGACAGTTACCAATGCTTAATCAGTGAGGCACCTATCTCAGCGATCTGTCTATTTCGTTCATCCATAGTTGCCT
GACTCCCCGTCGTGTAGATAACTACGATACGGGAGGGCTTACCATCTGGCCCCAGTGCTGCAATGATACCGCGAG
ACCCACGCTCACCGGCTCCAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGTAGTTCGCCAGTTAATAGTT
TGCGCAACGTTGTTGCCATTGCTACAGGCATCGTGGTGTCACGCTCGTCGTTTGGTATGGCTTCATTCAGCTCCGG
TTCCCAACGATCAAGGCGAGTTACATGATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGCACTGCATAATTCTCTTACTGTCATGC
CATCCGTAAGATGCTTTTCTGTGACTGGTGAGTACTCAACCAAGTCATTCTGAGAATAGTGTATGCGGCGACCGA
GTTGCTCTTGCCCGGCGTCAATACGGGATAATACCGCGCCACATAGCAGAACTTTAAAAGTGCTCATCATTGGAA
AACGTTCTTCGGGGCGAAAACTCTCAAGGATCTTACCGCTGTTGAGATCCAGTTCGATGTAACCCACTCGTGCACC
CAACTGATCTTCAGCATCTTTTACTTTCACCAGCGTTTCTGGGTGAGCAAAAACAGGAAGGCAAAATGCCGCAAA
AAAGGGAATAAGGGCGACACGGAAATGTTGAATACTCATACTCTTCCTTTTTCAATATTATTGAAGCATTTATCAG
GGTTATTGTCTCATGAGCGGATACATATTTGAATGTATTTAGAAAAATAAACAAATAGGGGTTCCGCGCACATTTC
CCCGAAAAGTGCCACCTGACG

FIG. 21D

>pMule-Lenti-Dest-Ikzf1-iRFP (lentiviral vector) (SEQ ID NO:64)
CGCGTATGCATCTCGAGGGCCCGGTACCTTTAAGACCAATGACTTACAAGGCAGCTGTAGATCTTAGCCACTTTTT
AAAAGAAAAGGGGGGACTGGAAGGGCTAGCTCACTCCCAACGAAGACAAGATCTGCTTTTTGCTTGTACTGGGT
CTCTCTGGTTAGACCAGATCTGAGCCTGGGAGCTCTCTGGCTAACTAGGGAACCCACTGCTTAAGCCTCAATAAA
GCTTGCCTTGAGTGCTTCAAGTAGTGTGTGCCCGTCTGTTGTGTGACTCTGGTAACTAGAGATCCCTCAGACCCTT
TTAGTCAGTGTGGAAAATCTCTAGCAGTAGTAGTTCATGTCATCTTATTATTCAGTATTTATAACTTGCAAAGAAAT
GAATATCAGAGAGTGAGAGGAACTTGTTTATTGCAGCTTATAATGGTTACAAATAAAGCAATAGCATCACAAATT
TCACAAATAAAGCATTTTTTTCACTGCATTCTAGTTGTGGTTTGTCCAAACTCATCAATGTATCTTATCATGTCTGGC
TCTAGCTATCCCGCCCCTAACTCCGCCCAGTTCCGCCCATTCTCCGCCCCATGGCTGACTAATTTTTTTTATTTATGC
AGAGGCCGAGGCCGCCTCGGCCTCTGAGCTATTCCAGAAGTAGTGAGGAGGCTTTTTTGGAGGCCTAGGCTTTTG
CGTCGAGACGTACCCAATTCGCCCTATAGTGAGTCGTATTACGCGCGCTCACTGGCCGTCGTTTTACAACGTCGTG
ACTGGGAAAACCCTGGCGTTACCCAACTTAATCGCCTTGCAGCACATCCCCCTTTCGCCAGCTGGCGTAATAGCGA
AGAGGCCCGCACCGATCGCCCTTCCCAACAGTTGCGCAGCCTGAATGGCGAATGGCGCGACGCGCCCTGTAGCG
GCGCATTAAGCGCGGCGGGTGTGGTGGTTACGCGCAGCGTGACCGCTACACTTGCCAGCGCCCTAGCGCCCGCT
CCTTTCGCTTTCTTCCCTTCCTTTCTCGCCACGTTCGCCGGCTTTCCCCGTCAAGCTCTAAATCGGGGGCTCCCTTTA
GGGTTCCGATTTAGTGCTTTACGGCACCTCGACCCCAAAAAACTTGATTAGGGTGATGGTTCACGTAGTGGGCCA
TCGCCCTGATAGACGGTTTTTCGCCCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCCGATTTCGGCCTATTGGTTAAAAA
ATGAGCTGATTTAACAAAAATTTAACGCGAATTTTAACAAAATATTAACGTTTACAATTTCCCAGGTGGCACTTTTC
GGGGAAATGTGCGCGGAACCCCTATTTGTTTATTTTTCTAAATACATTCAAATATGTATCCGCTCATGAGACAATA
ACCCTGATAAATGCTTCAATAATATTGAAAAAGGAAGAGTATGAGTATTCAACATTTCCGTGTCGCCCTTATTCCCT
TTTTTGCGGCATTTTGCCTTCCTGTTTTTGCTCACCCAGAAACGCTGGTGAAAGTAAAAGATGCTGAAGATCAGTT
GGGTGCACGAGTGGGTTACATCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGTATTGACGCCGGGCAAGAGCA
ACTCGGTCGCCGCATACACTATTCTCAGAATGACTTGGTTGAGTACTCACCAGTCACAGAAAAGCATCTTACGGAT
GGCATGACAGTAAGAGAATTATGCAGTGCTGCCATAACCATGAGTGATAACACTGCGGCCAACTTACTTCTGACA
ACGATCGGAGGACCGAAGGAGCTAACCGCTTTTTTGCACAACATGGGGGATCATGTAACTCGCCTTGATCGTTGG
GAACCGGAGCTGAATGAAGCCATACCAAACGACGAGCGTGACACCACGATGCCTGTAGCAATGGCAACAACGTT
GCGCAAACTATTAACTGGCGAACTACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTGATAAATCTGGAGCCGGTGAGCG
TGGGTCTCGCGGTATCATTGCAGCACTGGGGCCAGATGGTAAGCCCTCCCGTATCGTAGTTATCTACACGACGGG
GAGTCAGGCAACTATGGATGAACGAAATAGACAGATCGCTGAGATAGGTGCCTCACTGATTAAGCATTGGTAAC
TGTCAGACCAAGTTTACTCATATATACTTTAGATTGATTTAAAACTTCATTTTTAATTTAAAAGGATCTAGGTGAAG
ATCCTTTTTGATAATCTCATGACCAAAATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCTTGCAAACAAAAAAACCACCGCTACCA
GCGGTGGTTTGTTTGCCGGATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTAGCACCGCCTACATACCTCG
CTCTGCTAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACGACC
TACACCGAACTGAGATACCTACAGCGTGAGCTATGAGAAAGCGCCACGCTTCCCGAAGGGAGAAAGGCGGACAG
GTATCCGGTAAGCGGCAGGGTCGGAACAGGAGAGCGCACGAGGGAGCTTCCAGGGGGAAACGCCTGGTATCTT
TATAGTCCTGTCGGGTTTCGCCACCTCTGACTTGAGCGTCGATTTTTGTGATGCTCGTCAGGGGGGCGGAGCCTAT
GGAAAAACGCCAGCAACGCGGCCTTTTTACGGTTCCTGGCCTTTTGCTGGCCTTTTGCTCACATGTTCTTTCCTGCG
TTATCCCCTGATTCTGTGGATAACCGTATTACCGCCTTTGAGTGAGCTGATACCGCTCGCCGCAGCCGAACGACCG
AGCGCAGCGAGTCAGTGAGCGAGGAAGCGGAAGAGCGCCCAATACGCAAACCGCCTCTCCCCGCGCGTTGGCC
GATTCATTAATGCAGCTGGCACGACAGGTTTCCCGACTGGAAAGCGGGCAGTGAGCGCAACGCAATTAATGTGA
GTTAGCTCACTCATTAGGCACCCCAGGCTTTACACTTTATGCTTCCGGCTCGTATGTTGTGTGGAATTGTGAGCGG
ATAACAATTTCACACAGGAAACAGCTATGACCATGATTACGCCAAGCGCGCAATTAACCCTCACTAAAGGGAACA
AAAGCTGGAGCTGCAAGCTTAATGTAGTCTTATGCAATACTCTTGTAGTCTTGCAACATGGTAACGATGAGTTAGC
AAC

FIG. 21E

ATGCCTTACAAGGAGAGAAAAAGCACCGTGCATGCCGATTGGTGGAAGTAAGGTGGTACGATCGTGCCTTATTA
GGAAGGCAACAGACGGGTCTGACATGGATTGGACGAACCACTGAATTGCCGCATTGCAGAGATATTGTATTTAA
GTGCCTAGCTCGATACAATAAACGGGTCTCTCTGGTTAGACCAGATCTGAGCCTGGGAGCTCTCTGGCTAACTAG
GGAACCCACTGCTTAAGCCTCAATAAAGCTTGCCTTGAGTGCTTCAAGTAGTGTGTGCCCGTCTGTTGTGTGACTC
TGGTAACTAGAGATCCCTCAGACCCTTTTAGTCAGTGTGGAAAATCTCTAGCAGTGGCGCCCGAACAGGGACCTG
AAAGCGAAAGGGAAACCAGAGCTCTCTCGACGCAGGACTCGGCTTGCTGAAGCGCGCACGGCAAGAGGCGAGG
GGCGGCGACTGGTGAGTACGCCAAAAATTTTGACTAGCGGAGGCTAGAAGGAGAGAGATGGGTGCGAGAGCGT
CAGTATTAAGCGGGGGAGAATTAGATCGCGATGGGAAAAAATTCGGTTAAGGCCAGGGGGAAAGAAAAAATAT
AAATTAAAACATATAGTATGGGCAAGCAGGGAGCTAGAACGATTCGCAGTTAATCCTGGCCTGTTAGAAACATCA
GAAGGCTGTAGACAAATACTGGGACAGCTACAACCATCCCTTCAGACAGGATCAGAAGAACTTAGATCATTATAT
AATACAGTAGCAACCCTCTATTGTGTGCATCAAAGGATAGAGATAAAAGACACCAAGGAAGCTTTAGACAAGATA
GAGGAAGAGCAAAACAAAAGTAAGACCACCGCACAGCAAGCGGCCGCTGATCTTCAGACCTGGAGGAGGAGAT
ATGAGGGACAATTGGAGAAGTGAATTATATAAATATAAAGTAGTAAAAATTGAACCATTAGGAGTAGCACCCACC
AAGGCAAAGAGAAGAGTGGTGCAGAGAGAAAAAAGAGCAGTGGGAATAGGAGCTTTGTTCCTTGGGTTCTTGG
GAGCAGCAGGAAGCACTATGGGCGCAGCCTCAATGACGCTGACGGTACAGGCCAGACAATTATTGTCTGGTATA
GTGCAGCAGCAGAACAATTTGCTGAGGGCTATTGAGGCGCAACAGCATCTGTTGCAACTCACAGTCTGGGGCATC
AAGCAGCTCCAGGCAAGAATCCTGGCTGTGGAAAGATACCTAAAGGATCAACAGCTCCTGGGGATTTGGGGTTG
CTCTGGAAAACTCATTTGCACCACTGCTGTGCCTTGGAATGCTAGTTGGAGTAATAAATCTCTGGAACAGATTGGA
ATCACACGACCTGGATGGAGTGGGACAGAGAAATTAACAATTACACAAGCTTAATACACTCCTTAATTGAAGAAT
CGCAAAACCAGCAAGAAAAGAATGAACAAGAATTATTGGAATTAGATAAATGGGCAAGTTTGTGGAATTGGTTT
AACATAACAAATTGGCTGTGGTATATAAAATTATTCATAATGATAGTAGGAGGCTTGGTAGGTTTAAGAATAGTTT
TTGCTGTACTTTCTATAGTGAATAGAGTTAGGCAGGGATATTCACCATTATCGTTTCAGACCCACCTCCCAACCCCG
AGGGGACCCGACAGGCCCGAAGGAATAGAAGAAGAAGGTGGAGAGAGAGACAGAGACAGATCCATTCGATTA
GTGAACGGATCTCGACGGTTAACTTTTAAAAGAAAAGGGGGGATTGGGGGGTACAGTGCAGGGGAAAGAATAG
TAGACATAATAGCAACAGACATACAAACTAAAGAATTACAAAAACAAATTACAAAAATTCAAAATTTTATTCCAGT
GTGGTGGAATTGAGTATTCCAGTGTGGTGGAATTCTGCAGATATCAACAAGTTTGTACAAAAAAGCAGGCTTATC
CCTATCAGTGATAGAGAAAAGTGAAAGTCGAGTTTACCACTCCCTATCAGTGATAGAGAAAAGTGAAAGTCGAGT
TTACCACTCCCTATCAGTGATAGAGAAAAGTGAAAGTCGAGTTTACCACTCCCTATCAGTGATAGAGAAAAGTGA
AAGTCGAGTTTACCACTCCCTATCAGTGATAGAGAAAAGTGAAAGTCGAGTTTACCACTCCCTATCAGTGATAGA
GAAAAGTGAAAGTCGAGTTTACCACTCCCTATCAGTGATAGAGAAAAGTGAAAGTCGAGCTCGGTACCCGGGTC
GAGGTAGGCGTGTACGGTGGGAGGCCTATATAAGCAGAGCTCGTTTAGTGAACCGTCAGATCGCCTGGAGACGC
CATCCACGCTGTTTTGACCTCCATAGAAGACACCGGGACCGATCCAGCCTCCGCGGCCCCGAATTCATGGATGTC
GATGAGGGTCAAGACATGTCCCAAGTTTCAGGAAAGGAGAGCCCCCCAGTCAGTGACACTCCAGATGAAGGGGA
TGAGCCCATGCCTGTCCCTGAGGACCTGTCCACTACCTCTGGAGCACAGCAGAACTCCAAGAGTGATCGAGGCAT
GGCCAGTAATGTTAAAGTAGAGACTCAGAGTGATGAAGAGAATGGGCGTGCCTGTGAAATGAATGGGGAAGAA
TGTGCAGAGGATTTACGAATGCTTGATGCCTCGGGAGAGAAAATGAATGGCTCCCACAGGGACCAAGGCAGCTC
GGCTTTGTCAGGAGTTGGAGGCATTCGACTTCCTAACGGAAAACTAAAGTGTGATATCTGTGGGATCGTTTGCAT
CGGGCCCAATGTGCTCATGGTTCACAAAAGAAGTCATACTGGTGAACGGCCTTTCCAGTGCAACCAGTGTGGGGC
CTCCTTTACCCAGAAAGGCAACCTCCTGCGGCACATCAAGCTGCACTCGGGTGAGAAGCCCTTCAAATGCCATCTT
TGCAACTATGCCTGCCGCCGGAGGGACGCCCTCACCGGCCACCTGAGGACGCACTCCGTTGGTAAGCCTCACAAA
TGTGGATATTGTGGCCGGAGCTATAAACAGCGAAGCTCTTTAGAGGAGCATAAAGAGCGATGCCACAACTACTT
GGAAAGCATGGGCCTTCCGGGCATGTACCCAGTCATTAAGGAAGAAACTAACCACAACGAGATGGCAGAAGACC
TGTGCAAGATAGGAGCAGAGAGGTCCCTTGTCCTGGACAGGCTGGCAAGCAATGTCGCCAAACGTAAGAGCTCT
ATGCCTCAGAAATTTCTTGGAGACAAGTGCCTGTCAGACATGCCCTATGACAGTGCCAACTATGAGAAGGAGGAT
ATGATGACATCCCACGTGATGGACCAGGCCATCAACAATGCCATCAACTACCTGGGGGCTGAGTCCCTGCGCCCA
TTGGTGCAGACACCCCCCGGTAGCTCCGAGGTGGTGCCAGTCATCAGCTCCATGTACCAGCTGCACAAGCCCCCC
TCAGATGGCCCCCCACGGTCCAACCATTCAGCACAGGACGCCGTGGATAACTTGCTGCTGCTGTCCAAGGCCAAG
TCTGTGTCATCGGAGCGAGAGGCCTCCCCGAGCAACAGCTGCCAAGACTCCACAGATACAGAGAGCAACGCGGA
GGAACAGCGCAGCGGCCTTATCTACCTAACCAACCACATCAACCCGCATGCACGCAATGGGCTGGCTCTCAAGGA
GGAGC

FIG. 21F

AGCGCGCCTACGAGGTGCTGAGGGCGGCCTCAGAGAACTCGCAGGATGCCTTCCGTGTGGTCAGCACGAGTGGC
GAGCAGCTGAAGGTGTACAAGTGCGAACACTGCCGCGTGCTCTTCCTGGATCACGTCATGTATACCATTCACATG
GGCTGCCATGGCTTTCGGGATCCCTTTGAGTGTAACATGTGTGGTTATCACAGCCAGGACAGGTACGAGTTCTCA
TCCCATATCACGCGGGGGGAGCATCGTTACCACCTGAGCTAAAACCCAGCTTTCTTGTACAAAGTGGTTGATATCC
AGCACAGTGGCGGCCGCTCGACAATCAACCTCTGGATTACAAAATTTGTGAAAGATTGACTGGTATTCTTAACTAT
GTTGCTCCTTTTACGCTATGTGGATACGCTGCTTTAATGCCTTTGTATCATGCTATTGCTTCCCGTATGGCTTTCATT
TTCTCCTCCTTGTATAAATCCTGGTTGCTGTCTCTTTATGAGGAGTTGTGGCCCGTTGTCAGGCAACGTGGCGTGG
TGTGCACTGTGTTTGCTGACGCAACCCCCACTGGTTGGGGCATTGCCACCACCTGTCAGCTCCTTTCCGGGACTTT
CGCTTTCCCCCTCCCTATTGCCACGGCGGAACTCATCGCCGCCTGCCTTGCCCGCTGCTGGACAGGGGCTCGGCTG
TTGGGCACTGACAATTCCGTGGTGTTGTCGGGGAAGCTGACGTCCTTTCCATGGCTGCTCGCCTGTGTTGCCACCT
GGATTCTGCGCGGGACGTCCTTCTGCTACGTCCCTTCGGCCCTCAATCCAGCGGACCTTCCTTCCCGCGGCCTGCT
GCCGGCTCTGCGGCCTCTTCCGCGTCTTCGCCTTCGCCCTCAGACGAGTCGGATCTCCCTTTGGGCCGCCTCCCCG
CCTGGAATTCTACCGGGTAGGGGAGGCGCTTTTCCCAAGGCAGTCTGGAGCATGCGCTTTAGCAGCCCCGCTGG
GCACTTGGCGCTACACAAGTGGCCTCTGGCCTCGCACACATTCCACATCCACCGGTAGGCGCCAACCGGCTCCGTT
CTTTGGTGGCCCCTTCGCGCCACCTTCTACTCCTCCCCTAGTCAGGAAGTTCCCCCCCGCCCCGCAGCTCGCGTCGT
GCAGGACGTGACAAATGGAAGTAGCACGTCTCACTAGTCTCGTGCAGATGGACAGCACCGCTGAGCAATGGAAG
CGGGTAGGCCTTTGGGGCAGCGGCCAATAGCAGCTTTGCTCCTTCGCTTTCTGGGCTCAGAGGCTGGGAAGGGG
TGGGTCCGGGGGCGGGCTCAGGGGCGGGCTCAGGGGCGGGGCGGGCGCCCGAAGGTCCTCCGGAGGCCCGGC
ATTCTGCACGCTTCAAAAGCGCACGTCTGCCGCGCTGTTCTCCTCTTCCTCATCTCCGGGCCTTTCGACCTGCAGCC
CAAGCTTACCACACTCCTGCATCTGCCGCCACCATGGCGGAAGGATCCGTCGCCAGGCAGCCTGACCTCTTGACCT
GCGACGATGAGCCGATCCATATCCCCGGTGCCATCCAACCGCATGGACTGCTGCTCGCCCTCGCCGCCGACATGA
CGATCGTTGCCGGCAGCGACAACCTTCCCGAACTCACCGGACTGGCGATCGGCGCCCTGATCGGCCGCTCTGCGG
CCGATGTCTTCGACTCGGAGACGCACAACCGTCTGACGATCGCCTTGGCCGAGCCCGGGGCGGCCGTCGGAGCA
CCGATCACTGTCGGCTTCACGATGCGAAAGGACGCAGGCTTCATCGGCTCCTGGCATCGCCATGATCAGCTCATCT
TCCTCGAGCTCGAGCCTCCCCAGCGGGACGTCGCCGAGCCGCAGGCGTTCTTCCGCCGCACCAACAGCGCCATCC
GCCGCCTGCAGGCCGCCGAAACCTTGGAAAGCGCCTGCGCCGCCGCGGCGCAAGAGGTGCGGAAGATTACCGG
CTTCGATCGGGTGATGATCTATCGCTTCGCCTCCGACTTCAGCGGCGAAGTGATCGCAGAGGATCGGTGCGCCGA
GGTCGAGTCAAAACTAGGCCTGCACTATCCTGCCTCAACCGTGCCGGCGCAGGCCCGTCGGCTCTATACCATCAA
CCCGGTACGGATCATTCCCGATATCAATTATCGGCCGGTGCCGGTCACCCCAGACCTCAATCCGGTCACCGGGCG
GCCGATTGATCTTAGCTTCGCCATCCTGCGCAGCGTCTCGCCCGTCCATCTGGAATTCATGCGCAACATAGGCATG
CACGGCACGATGTCGATCTCGATTTTGCGCGGCGAGCGACTGTGGGGATTGATCGTTTGCCATCACCGAACGCCG
TACTACGTCGATCTCGATGGCCGCCAAGCCTGCGAGCTAGTCGCCCAGGTTCTGGCCTGGCAGATCGGCGTGATG
GAAGAGTGAGTCGACGCGA

FIG. 21G

>TET-o-FUW-EGFP (lentiviral vector) (SEQ ID NO:65)
CGCGTTGACATTGATTATTGACTAGTTATTAATAGTAATCAATTACGGGGTCATTAGTTCATAGCCCATATATGGA
GTTCCGCGTTACATAACTTACGGTAAATGGCCCGCCTGGCTGACCGCCCAACGACCCCCGCCCATTGACGTCAATA
ATGACGTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTACGCCCCCTATTGACGTCAATGACGGTAAATGGCCC
GCCTGGCATTATGCCCAGTACATGACCTTATGGGACTTTCCTACTTGGCAGTACATCTACGTATTAGTCATCGCTAT
TACCATGGTGATGCGGTTTTGGCAGTACATCAATGGGCGTGGATAGCGGTTTGACTCACGGGGATTTCCAAGTCT
CCACCCCATTGACGTCAATGGGAGTTTGTTTTGGCACCAAAATCAACGGGACTTTCCAAAATGTCGTAACAACTCC
GCCCCATTGACGCAAATGGGCGGTAGGCGTGTACGGTGGGAGGTCTATATAAGCAGCGCGTTTTGCCTGTACTG
GGTCTCTCTGGTTAGACCAGATCTGAGCCTGGGAGCTCTCTGGCTAACTAGGGAACCCACTGCTTAAGCCTCAATA
AAGCTTGCCTTGAGTGCTTCAAGTAGTGTGTGCCCGTCTGTTGTGTGACTCTGGTAACTAGAGATCCCTCAGACCC
TTTTAGTCAGTGTGGAAAATCTCTAGCAGTGGCGCCCGAACAGGGACTTGAA

FIG. 21H

AGCGAAAGGGAAACCAGAGGAGCTCTCTCGACGCAGGACTCGGCTTGCTGAAGCGCGCACGGCAAGAGGCGAG
GGGCGGCGACTGGTGAGTACGCCAAAAATTTTGACTAGCGGAGGCTAGAAGGAGAGAGATGGGTGCGAGAGC
GTCAGTATTAAGCGGGGGAGAATTAGATCGCGATGGGAAAAAATTCGGTTAAGGCCAGGGGGAAAGAAAAAAT
ATAAATTAAAACATATAGTATGGGCAAGCAGGGAGCTAGAACGATTCGCAGTTAATCCTGGCCTGTTAGAAACAT
CAGAAGGCTGTAGACAAATACTGGGACAGCTACAACCATCCCTTCAGACAGGATCAGAAGAACTTAGATCATTAT
ATAATACAGTAGCAACCCTCTATTGTGTGCATCAAAGGATAGAGATAAAAGACACCAAGGAAGCTTTAGACAAGA
TAGAGGAAGAGCAAAACAAAAGTAAGACCACCGCACAGCAAGCGGCCGCTGATCTTCAGACCTGGAGGAGGAG
ATATGAGGGACAATTGGAGAAGTGAATTATATAAATATAAAGTAGTAAAAATTGAACCATTAGGAGTAGCACCCA
CCAAGGCAAAGAGAAGAGTGGTGCAGAGAGAAAAAAGAGCAGTGGGAATAGGAGCTTTGTTCCTTGGGTTCTT
GGGAGCAGCAGGAAGCACTATGGGCGCAGCGTCAATGACGCTGACGGTACAGGCCAGACAATTATTGTCTGGTA
TAGTGCAGCAGCAGAACAATTTGCTGAGGGCTATTGAGGCGCAACAGCATCTGTTGCAACTCACAGTCTGGGGC
ATCAAGCAGCTCCAGGCAAGAATCCTGGCTGTGGAAAGATACCTAAAGGATCAACAGCTCCTGGGGATTTGGGG
TTGCTCTGGAAAACTCATTTGCACCACTGCTGTGCCTTGGAATGCTAGTTGGAGTAATAAATCTCTGGAACAGATT
TGGAATCACACGACCTGGATGGAGTGGGACAGAGAAATTAACAATTACACAAGCTTAATACACTCCTTAATTGAA
GAATCGCAAAACCAGCAAGAAAAGAATGAACAAGAATTATTGGAATTAGATAAATGGGCAAGTTTGTGGAATTG
GTTTAACATAACAAATTGGCTGTGGTATATAAAATTATTCATAATGATAGTAGGAGGCTTGGTAGGTTTAAGAATA
GTTTTTGCTGTACTTTCTATAGTGAATAGAGTTAGGCAGGGATATTCACCATTATCGTTTCAGACCCACCTCCCAAC
CCCGAGGGGACCCGACAGGCCCGAAGGAATAGAAGAAGAAGGTGGAGAGAGAGACAGAGACAGATCCATTCG
ATTAGTGAACGGATCGGCACTGCGTGCGCCAATTCTGCAGACAAATGGCAGTATTCATCCACAATTTTAAAAGAA
AAGGGGGGATTGGGGGGTACAGTGCAGGGGAAAGAATAGTAGACATAATAGCAACAGACATACAAACTAAAGA
ATTACAAAAACAAATTACAAAAATTCAAAATTTTCGGGTTTATTACAGGGACAGCAGAGATCCAGTTTGGTTAGAT
CTCGAGTTTACCACTCCCTATCAGTGATAGAGAAAAGTGAAAGTCGAGTTTACCACTCCCTATCAGTGATAGAGAA
AAGTGAAAGTCGAGTTTACCACTCCCTATCAGTGATAGAGAAAAGTGAAAGTCGAGTTTACCACTCCCTATCAGT
GATAGAGAAAAGTGAAAGTCGAGTTTACCACTCCCTATCAGTGATAGAGAAAAGTGAAAGTCGAGTTTACCACTC
CCTATCAGTGATAGAGAAAAGTGAAAGTCGAGTTTACCACTCCCTATCAGTGATAGAGAAAAGTGAAAGTCGAGC
TCGGTACCCGGGTCGAGGTAGGCGTGTACGGTGGGAGGCCTATATAAGCAGAGCTCGTTTAGTGAACCGTCAGA
TCGCCTGGAGACGCCATCCACGCTGTTTTGACCTCCATAGAAGACACCGGGACCGATCCAGCCTCCGCGGCCCCG
AATTCCGCCACCATGGTGAGCAAGGGCGAGGAGCTGTTCACCGGGGTGGTGCCCATCCTGGTCGAGCTGGACGG
CGACGTAAACGGCCACAAGTTCAGCGTGTCCGGCGAGGGCGAGGGCGATGCCACCTACGGCAAGCTGACCCTGA
AGTTCATCTGCACCACCGGCAAGCTGCCCGTGCCCTGGCCCACCCTCGTGACCACCCTGACCTACGGCGTGCAGT
GCTTCAGCCGCTACCCCGACCACATGAAGCAGCACGACTTCTTCAAGTCCGCCATGCCCGAAGGCTACGTCCAGG
AGCGCACCATCTTCTTCAAGGACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTGGGGCACAAGCTGGAGTACA
ACTACAACAGCCACAACGTCTATATCATGGCCGACAAGCAGAAGAACGGCATCAAGGTGAACTTCAAGATCCGCC
ACAACATCGAGGACGGCAGCGTGCAGCTCGCCGACCACTACCAGCAGAACACCCCCATCGGCGACGGCCCCGTG
CTGCTGCCCGACAACCACTACCTGAGCACCCAGTCCGCCCTGAGCAAAGACCCCAACGAGAAGCGCGATCACATG
GTCCTGCTGGAGTTCGTGACCGCCGCCGGGATCACTCTCGGCATGGACGAGCTGTACAAGTAAACGCGTGAATTC
GATATCAAGCTTATCGATAATCAACCTCTGGATTACAAAATTTGTGAAAGATTGACTGGTATTCTTAACTATGTTGC
TCCTTTTACGCTATGTGGATACGCTGCTTTAATGCCTTTGTATCATGCTATTGCTTCCCGTATGGCTTTCATTTTCTCC
TCCTTGTATAAATCCTGGTTGCTGTCTCTTTATGAGGAGTTGTGGCCCGTTGTCAGGCAACGTGGCGTGGTGTGCA
CTGTGTTTGCTGACGCAACCCCCACTGGTTGGGGCATTGCCACCACCTGTCAGCTCCTTTCCGGGACTTTCGCTTTC
CCCCTCCCTATTGCCACGGCGGAACTCATCGCCGCCTGCCTTGCCCGCTGCTGGACAGGGGCTCGGCTGTTGGGC
ACTGACAATTCCGTGGTGTTGTCGGGGAAATCATCGTCCTTTCCTTGGCTGCTCGCCTGTGTTGCCACCTGGATTCT
GCGCGGGACGTCCTTCTGCTACGTCCCTTCGGCCCTCAATCCAGCGGACCTTCCTTCCCGCGGCCTGCTGCCGGCT
CTGCGGCCTCTTCCGCGTCTTCGCCTTCGCCCTCAGACGAGTCGGATCTCCCTTTGGGCCGCCTCCCCGCATCGATA
CCGTCGACCTCGAGACCTAGAAAAACATGGAGCAATCACAAGTAGCAATACAGCAGCTACCAATGCTGATTGTGC
CTGGCTAGAAGCACAAGAGGAGGAGGAGGTGGGTTTTCCAGTCACACCTCAGGTACCTTTAAGACCAATGACTT
ACAAGGCAGCTGTAGATCTTAGCCACTTTTTAAAAGAAAAGGGGGGACTGGAAGGGCTAATTCACTCCCAACGA
AGACAAGATATCCTTGATCTGTGGATCTACCACACACAAGGCTACTTCCCTGATTGGCAGAACTACACACCAGGG
CCAG

FIG. 21I

GGATCAGATATCCACTGACCTTTGGATGGTGCTACAAGCTAGTACCAGTTGAGCAAGAGAAGGTAGAAGAAGCC
AATGAAGGAGAGAACACCCGCTTGTTACACCCTGTGAGCCTGCATGGGATGGATGACCCGGAGAGAGAAGTATT
AGAGTGGAGGTTTGACAGCCGCCTAGCATTTCATCACATGGCCCGAGAGCTGCATCCGGACTGTACTGGGTCTCT
CTGGTTAGACCAGATCTGAGCCTGGGAGCTCTCTGGCTAACTAGGGAACCCACTGCTTAAGCCTCAATAAAGCTT
GCCTTGAGTGCTTCAAGTAGTGTGTGCCCGTCTGTTGTGTGACTCTGGTAACTAGAGATCCCTCAGACCCTTTTAG
TCAGTGTGGAAAATCTCTAGCAGGGCCCGTTTAAACCCGCTGATCAGCCTCGACTGTGCCTTCTAGTTGCCAGCCA
TCTGTTGTTTGCCCCTCCCCCGTGCCTTCCTTGACCCTGGAAGGTGCCACTCCCACTGTCCTTTCCTAATAAAATGA
GGAAATTGCATCGCATTGTCTGAGTAGGTGTCATTCTATTCTGGGGGGTGGGGTGGGGCAGGACAGCAAGGGG
GAGGATTGGGAAGACAATAGCAGGCATGCTGGGGATGCGGTGGGCTCTATGGCTTCTGAGGCGGAAAGAACCA
GCTGGGGCTCTAGGGGGTATCCCCACGCGCCCTGTAGCGGCGCATTAAGCGCGGCGGGTGTGGTGGTTACGCGC
AGCGTGACCGCTACACTTGCCAGCGCCCTAGCGCCCGCTCCTTTCGCTTTCTTCCCTTCCTTTCTCGCCACGTTCGCC
GGCTTTCCCCGTCAAGCTCTAAATCGGGGGCTCCCTTTAGGGTTCCGATTTAGTGCTTTACGGCACCTCGACCCCA
AAAAACTTGATTAGGGTGATGGTTCACGTAGTGGGCCATCGCCCTGATAGACGGTTTTTCGCCCTTTGACGTTGG
AGTCCACGTTCTTTAATAGTGGACTCTTGTTCCAAACTGGAACAACACTCAACCCTATCTCGGTCTATTCTTTTGATT
TATAAGGGATTTTGCCGATTTCGGCCTATTGGTTAAAAAATGAGCTGATTTAACAAAAATTTAACGCGAATTAATT
CTGTGGAATGTGTGTCAGTTAGGGTGTGGAAAGTCCCCAGGCTCCCCAGCAGGCAGAAGTATGCAAAGCATGCA
TCTCAATTAGTCAGCAACCAGGTGTGGAAAGTCCCCAGGCTCCCCAGCAGGCAGAAGTATGCAAAGCATGCATCT
CAATTAGTCAGCAACCATAGTCCCGCCCCTAACTCCGCCCATCCCGCCCCTAACTCCGCCCAGTTCCGCCCATTCTC
CGCCCCATGGCTGACTAATTTTTTTTATTTATGCAGAGGCCGAGGCCGCCTCTGCCTCTGAGCTATTCCAGAAGTA
GTGAGGAGGCTTTTTTGGAGGCCTAGGCTTTTGCAAAAAGCTCCCGGGAGCTTGTATATCCATTTTCGGATCTGAT
CAGCACGTGTTGACAATTAATCATCGGCATAGTATATCGGCATAGTATAATACGACAAGGTGAGGAACTAAACCA
TGGCCAAGTTGACCAGTGCCGTTCCGGTGCTCACCGCGCGCGACGTCGCCGGAGCGGTCGAGTTCTGGACCGAC
CGGCTCGGGTTCTCCCGGGACTTCGTGGAGGACGACTTCGCCGGTGTGGTCCGGGACGACGTGACCCTGTTCATC
AGCGCGGTCCAGGACCAGGTGGTGCCGGACAACACCCTGGCCTGGGTGTGGGTGCGCGGCCTGGACGAGCTGT
ACGCCGAGTGGTCGGAGGTCGTGTCCACGAACTTCCGGGACGCCTCCGGGCCGGCCATGACCGAGATCGGCGAG
CAGCCGTGGGGGCGGGAGTTCGCCCTGCGCGACCCGGCCGGCAACTGCGTGCACTTCGTGGCCGAGGAGCAGG
ACTGACACGTGCTACGAGATTTCGATTCCACCGCCGCCTTCTATGAAAGGTTGGGCTTCGGAATCGTTTTCCGGGA
CGCCGGCTGGATGATCCTCCAGCGCGGGGATCTCATGCTGGAGTTCTTCGCCCACCCCAACTTGTTTATTGCAGCT
TATAATGGTTACAAATAAAGCAATAGCATCACAAATTTCACAAATAAAGCATTTTTTTCACTGCATTCTAGTTGTGG
TTTGTCCAAACTCATCAATGTATCTTATCATGTCTGTATACCGTCGACCTCTAGCTAGAGCTTGGCGTAATCATGGT
CATAGCTGTTTCCTGTGTGAAATTGTTATCCGCTCACAATTCCACACAACATACGAGCCGGAAGCATAAAGTGTAA
AGCCTGGGGTGCCTAATGAGTGAGCTAACTCACATTAATTGCGTTGCGCTCACTGCCCGCTTTCCAGTCGGGAAA
CCTGTCGTGCCAGCTGcattaatgaatcggccaacgcgcggggagaggcggtttgcgtattgggcgctCTTCCGCTTCCTCGCTCACT
GACTCGCTGCGCTCGGTCGTTCGGCTGCGGCGAGCGGTATCAGCTCACTCAAAGGCGGTAATACGGTTATCCACA
GAATCAGGGGATAACGCAGGAAAGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAAAAATCGACGCTCAAGTCAGAGGTGG
CGAAACCCGACAGGACTATAAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCATAGCTCACGCTGTAGGTA
TCTCAGTTCGGTGTAGGTCGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGGCAGCAGCCACTGGTAAC
AGGATTAGCAGAGCGAGGTATGTAGGCGGTGCTACAGAGTTCTTGAAGTGGTGGCCTAACTACGGCTACACTAG
AAGAACAGTATTTGGTATCTGCGCTCTGCTGAAGCCAGTTACCTTCGGAAAAAGAGTTGGTAGCTCTTGATCCGG
CAAACAAACCACCGCTGGTAGCGGTGGTTTTTTTGTTTGCAAGCAGCAGATTACGCGCAGAAAAAAAGGATCTCA
AGAAGATCCTTTGATCTTTTCTACGGGGTCTGACGCTCAGTGGAACGAAAACTCACGTTAAGGGATTTTGGTCATG
AGATTATCAAAAAGGATCTTCACCTAGATCCTTTTAAATTAAAAATGAAGTTTTAAATCAATCTAAAGTATATATGA
GTAAACTTGGTCTGACAGTTACCAATGCTTAATCAGTGAGGCACCTATCTCAGCGATCTGTCTATTTCGTTCATCCA
TAGTTGCCTGACTCCCCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAAGGGCCGAGCGCAGA
AGTGGTCCTGCAACTTTATCCGCCTCCATCCAGTCTATTAATTGTTGCCGGGAAGCTAGAGTAAGTAGTTCGCCAG
TTAATAG

FIG. 21J

TTTGCGCAACGTTGTTGCCATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATAATTCTCTTACTGTCAT
GCCATCCGTAAGATGCTTTTCTGTGACTGGTGAGTACTCAACCAAGTCATTCTGAGAATAGTGTATGCGGCGACC
GAGTTGCTCTTGCCCGGCGTCAATACGGGATAATACCGCGCCACATAGCAGAACTTTAAAAGTGCTCATCATTGG
AAAACGTTCTTCGGGGCGAAAACTCTCAAGGATCTTACCGCTGTTGAGATCCAGTTCGATGTAACCCACTCGTGCA
CCCAACTGATCTTCAGCATCTTTTACTTTCACCAGCGTTTCTGGGTGAGCAAAAACAGGAAGGCAAAATGCCGCAA
AAAAGGGAATAAGGGCGACACGGAAATGTTGAATACTCATACTCTTCCTTTTTCAATATTATTGAAGCATTTATCA
GGGTTATTGTCTCATGAGCGGATACATATTTGAATGTATTTAGAAAAATAAACAAATAGGGGTTCCGCGCACATTT
CCCCGAAAAGTGCCACCTGACGTCGACGGATCGGGAGATCTCCCGATCCCCTATGGTGCACTCTCAGTACAATCT
GCTCTGATGCCGCATAGTTAAGCCAGTATCTGCTCCCTGCTTGTGTGTTGGAGGTCGCTGAGTAGTGCGCGAGCA
AAATTTAAGCTACAACAAGGCAAGGCTTGACCGACAATTGCATGAAGAATCTGCTTAGGGTTAGGCGTTTTGCGC
TGCTTCGCGATGTACGGGCCAGATATA

FIG. 21k

>TET-O-FUS-Ikzf4 (Lentiviral vector) (SEQ ID NO:66)
CGCGTTGACATTGATTATTGACTAGTTATTAATAGTAATCAATTACGGGGTCATTAGTTCATAGCCCATATATGGA
GTTCCGCGTTACATAACTTACGGTAAATGGCCCGCCTGGCTGACCGCCCAACGACCCCCGCCCATTGACGTCAATA
ATGACGTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTACGCCCCCTATTGACGTCAATGACGGTAAATGGCCC
GCCTGGCATTATGCCCAGTACATGACCTTATGGGACTTTCCTACTTGGCAGTACATCTACGTATTAGTCATCGCTAT
TACCATGGTGATGCGGTTTTGGCAGTACATCAATGGGCGTGGATAGCGGTTTGACTCACGGGGATTTCCAAGTCT
CCACCCCATTGACGTCAATGGGAGTTTGTTTTGGCACCAAAATCAACGGGACTTTCCAAAATGTCGTAACAACTCC
GCCCCATTGACGCAAATGGGCGGTAGGCGTGTACGGTGGGAGGTCTATATAAGCAGCGCGTTTTGCCTGTACTG
GGTCTCTCTGGTTAGACCAGATCTGAGCCTGGGAGCTCTCTGGCTAACTAGGGAACCCACTGCTTAAGCCTCAATA
AAGCTTGCCTTGAGTGCTTCAAGTAGTGTGTGCCCGTCTGTTGTGTGACTCTGGTAACTAGAGATCCCTCAGACCC
TTTTAGTCAGTGTGGAAAATCTCTAGCAGTGGCGCCCGAACAGGGACTTGAAAGCGAAAGGGAAACCAGAGGAG
CTCTCTCGACGCAGGACTCGGCTTGCTGAAGCGCGCACGGCAAGAGGCGAGGGGCGGCGACTGGTGAGTACGC
CAAAAATTTTGACTAGCGGAGGCTAGAAGGAGAGAGATGGGTGCGAGAGCGTCAGTATTAAGCGGGGGAGAAT
TAGATCGCGATGGGAAAAAATTCGGTTAAGGCCAGGGGGAAAGAAAAAATATAAATTAAAACATATAGTATGGG
CAAGCAGGGAGCTAGAACGATTCGCAGTTAATCCTGGCCTGTTAGAAACATCAGAAGGCTGTAGACAAATACTG
GGACAGCTACAACCATCCCTTCAGACAGGATCAGAAGAACTTAGATCATTATATAATACAGTAGCAACCCTCTATT
GTGTGCATCAAAGGATAGAGATAAAAGACACCAAGGAAGCTTTAGACAAGATAGAGGAAGAGCAAAACAAAAG
TAAGACCACCGCACAGCAAGCGGCCGCTGATCTTCAGACCTGGAGGAGGAGATATGAGGGACAATTGGAGAAG
TGAATTATATAAATATAAAGTAGTAAAAATTGAACCATTAGGAGTAGCACCCACCAAGGCAAAGAGAAGAGTGG
TGCAGAGAGAAAAAAGAGCAGTGGGAATAGGAGCTTTGTTCCTTGGGTTCTTGGGAGCAGCAGGAAGCACTATG
GGCGCAGCGTCAATGACGCTGACGGTACAGGCCAGACAATTATTGTCTGGTATAGTGCAGCAGCAGAACAATTT
GCTGAGGGCTATTGAGGCGCAACAGCATCTGTTGCAACTCACAGTCTGGGGCATCAAGCAGCTCCAGGCAAGAA
TCCTGGCTGTGGAAAGATACCTAAAGGATCAACAGCTCCTGGGGATTTGGGGTTGCTCTGGAAAACTCATTTGCA
CCACTGCTGTGCCTTGGAATGCTAGTTGGAGTAATAAATCTCTGGAACAGATTTGGAATCACACGACCTGGATGG
AGTGGGACAGAGAAATTAACAATTACACAAGCTTAATACACTCCTTAATTGAAGAATCGCAAAACCAGCAAGAAA
AGAATGAACAAGAATTATTGGAATTAGATAAATGGGCAAGTTTGTGGAATTGGTTTAACATAACAAATTGGCTGT
GGTATATAAAATTATTCATAATGATAGTAGGAGGCTTGGTAGGTTTAAGAATAGTTTTTGCTGTACTTTCTATAGT
GAATAGAGTTAGGCAGGGATATTCACCATTATCGTTTCAGACCCACCTCCCAACCCCGAGGGGACCCGACAGGCC
CGAAGGAATAGAAGAAGAAGGTGGAGAGAGAGACAGAGACAGATCCATTCGATTAGTGAACGGATCGGCACTG
CGTGCGCCAATTCTGCAGACAAATGGCAGTATTCATCCACAATTTTAAAAGAAAAGGGGGGATTGGGGGGTACA
GTGCAGGGGAAAGAATAGTAGACATAATAGCAACAGACATACAAACTAAAGAATTACAAAAACAAATTACAAAA
ATTCAAAATTTTCGGGTTTATTACAGGGACAGCAGAGATCCAGTTTGGTTAGATCTCGAGTTTACCACTCCCTATC
AG

FIG. 21L

TGATAGAGAAAAGTGAAAGTCGAGTTTACCACTCCCTATCAGTGATAGAGAAAAGTGAAAGTCGAGTTTACCACT
CCCTATCAGTGATAGAGAAAAGTGAAAGTCGAGTTTACCACTCCCTATCAGTGATAGAGAAAAGTGAAAGTCGAG
TTTACCACTCCCTATCAGTGATAGAGAAAAGTGAAAGTCGAGTTTACCACTCCCTATCAGTGATAGAGAAAAGTG
AAAGTCGAGTTTACCACTCCCTATCAGTGATAGAGAAAAGTGAAAGTCGAGCTCGGTACCCGGGTCGAGGTAGG
CGTGTACGGTGGGAGGCCTATATAAGCAGAGCTCGTTTAGTGAACCGTCAGATCGCCTGGAGACGCCATCCACG
CTGTTTTGACCTCCATAGAAGACACCGGGACCGATCCAGCCTCCGCGGCCCCGAATTAATTCGCCCTTCCAAGTCC
CTGAGTGGTTGTTTTCTTCCCACTGACCAAAGCTGGAGAGGGAGCTCTCAGGAGGGTGTGCTCCGGATTTCTTGC
CTCAGGCCCAGGACTCCAACCATTTTATAATGGAATCTTTATTTTGTGAAAGTAGCGGGGACTCATCTCTGGAGAA
GGAGTTCCTTGGGGCCCCAGTGGGGCCCTCGGTGAGCACCCCAAACAGCCAACACTCTTCACCCAGCCGCTCGCT
CAGTGCCAACTCCATCAAGGTGGAGATGTACAGCGATGAGGAGTCGAGCAGACTGCTGGGGCCGGATGAACGG
CTCCTGGATAAGGATGACAGTGTGATTGTGGAAGACTCATTGTCAGAGCCCTTAGGCTACTGCGATGGAAGTGG
GCCAGAGCCTCACTCCCCTGGCGGCATCCGGCTACCCAACGGCAAGCTCAAGTGCGACGTCTGCGGCATGGTCTG
CATTGGGCCCAATGTGCTCATGGTACACAAGCGCAGCCACACTGGGGAGAGGCCCTTCCACTGTAATCAGTGTGG
TGCCTCCTTCACACAGAAGGGCAATCTGCTTCGCCACATCAAGCTGCACTCGGGGGAGAAGCCCTTCAAGTGCCC
CTTCTGCAACTATGCCTGCCGCCGGCGTGACGCACTCACTGGCCACCTCCGCACACACTCAGTCTCCTCCCCCACC
GTGGGCAAACCCTACAAGTGCAACTACTGTGGCCGGAGCTACAAACAGCAAAGTACCCTGGAGGAGCACAAGGA
GAGGTGCCACAACTACCTACAGAGTCTCAGCACTGATGCCCAAGCTCTGACTGGCCAGCCAGGTGATGAAATCCG
TGACCTGGAGATGGTGCCTGACTCAATGCTGCACCCATCGACTGAACGGCCAACTTTCATTGATCGTTTGGCCAAC
AGCCTCACCAAACGCAAGCGTTCCACCCCACAGAAGTTTGTAGGTGAAAAGCAGATGCGCTTCAGCCTCTCAGAC
CTTCCCTATGATGTGAATGCCAGCGGTGGCTATGAAAAGGACGTAGAGTTGGTGGCACACCATGGCCTGGAGCC
TGGCTTTGGAGGGTCTCTAGCCTTTGTGGGTACAGAGCATCTGCGTCCCCTCCGCCTCCCACCCACCAACTGCATC
TCAGAACTCACACCTGTCATCAGCTCTGTGTACACCCAAATGCAGCCCATCCCCAGCCGACTGGAGCTTCCAGGGT
CCCGAGAAGCAGGTGAGGGACCGGAGGACCTGGGAGATGGAGGTCCCCTCCTTTATCGGGCCCGAGGCTCTCTG
ACTGACCCTGGGGCATCCCCCAGCAATGGCTGCCAGGACTCCACAGATACAGAGAGCAACCACGAAGACCGGAT
TGGTGGGGTGGTATCCCTTCCTCAGGGTCCCCCACCCCAACCTCCTCCCACCATAGTGGTGGGCCGGCACAGTCCC
GCCTATGCCAAAGAGGACCCCAAACCACAGGAGGGGTTACTGCGGGGCACCCCAGGCCCCTCCAAGGAAGTGCT
TCGGGTGGTGGGTGAGAGTGGTGAGCCAGTGAAGGCCTTTAAGTGTGAACACTGCCGCATCCTCTTCTGGACCA
CGTCATGTTCACCATCCACATGGGCTGCCACGGCTTCAGAGACCCTTTTGAGTGTAACATCTGTGGTTATCACAGC
CAGGATCGGTATGAGTTCTCTTCCCACATCGTCCGGGGGGAACATAAGGTGGGCTAGGAATTCGATATCAAGCTT
ATCGATAATCAACCTCTGGATTACAAAATTTGTGAAAGATTGACTGGTATTCTTAACTATGTTGCTCCTTTTACGCT
ATGTGGATACGCTGCTTTAATGCCTTTGTATCATGCTATTGCTTCCCGTATGGCTTTCATTTTCTCCTCCTTGTATAA
ATCCTGGTTGCTGTCTCTTTATGAGGAGTTGTGGCCCGTTGTCAGGCAACGTGGCGTGGTGTGCACTGTGTTTGCT
GACGCAACCCCCACTGGTTGGGGCATTGCCACCACCTGTCAGCTCCTTTCCGGGACTTTCGCTTTCCCCCTCCCTAT
TGCCACGGCGGAACTCATCGCCGCCTGCCTTGCCCGCTGCTGGACAGGGGCTCGGCTGTTGGGCACTGACAATTC
CGTGGTGTTGTCGGGGAAATCATCGTCCTTTCCTTGGCTGCTCGCCTGTGTTGCCACCTGGATTCTGCGCGGGACG
TCCTTCTGCTACGTCCCTTCGGCCCTCAATCCAGCGGACCTTCCTTCCCGCGGCCTGCTGCCGGCTCTGCGGCCTCT
TCCGCGTCTTCGCCTTCGCCCTCAGACGAGTCGGATCTCCCTTTGGGCCGCCTCCCCGCATCGATACCGTCGACCTC
GAGACCTAGAAAAACATGGAGCAATCACAAGTAGCAATACAGCAGCTACCAATGCTGATTGTGCCTGGCTAGAA
GCACAAGAGGAGGAGGAGGTGGGTTTTCCAGTCACACCTCAGGTACCTTTAAGACCAATGACTTACAAGGCAGC
TGTAGATCTTAGCCACTTTTTAAAAGAAAAGGGGGGACTGGAAGGGCTAATTCACTCCCAACGAAGACAAGATAT
CCTTGATCTGTGGATCTACCACACACAAGGCTACTTCCCTGATTGGCAGAACTACACACCAGGGCCAGGGATCAG
ATATCCACTGACCTTTGGATGGTGCTACAAGCTAGTACCAGTTGAGCAAGAGAAGGTAGAAGAAGCCAATGAAG
GAGAGAACACCCGCTTGTTACACCCTGTGAGCCTGCATGGGATGGATGACCCGGAGAGAGAAGTATTAGAGTGG
AGGTTTGACAGCCGCCTAGCATTTCATCACATGGCCCGAGAGCTGCATCCGGACTGTACTGGGTCTCTCTGGTTAG
ACCAGATCTGAGCCTGGGAGCTCTCTGGCTAACTAGGGAACCCACTGCTTAAGCCTCAATAAAGCTTGCCTTGAG
TGCTTCAAGTAGTGTGTGCCCGTCTGTTGTGTGACTCTGGTAACTAGAGATCCCTCAGACCCTTTTAGTCAGTGTG
GAAAATCTCTAGCAGGGCCCGTTTAAACCCGCTGATCAGCCTCGACTGTGCCTTCTAGTTGCCAGCCATCTGTTGT
TTGCCCCTCCCCCGTGCCTTCCTTGACCCTGGAAGGTGCCACTCCCACTGTCCTTTCCTAATAAAATGAGGAAATTG
CATCGCATTGTCTGAGTAGGTGTCATTCTATTCTGGGGGGTGGGGTGGGGCAGGACAGCAAGGGGGAGGATTG
GGAAGAC

FIG. 21M

AATAGCAGGCATGCTGGGGATGCGGTGGGCTCTATGGCTTCTGAGGCGGAAAGAACCAGCTGGGGCTCTAGGG
GGTATCCCCACGCGCCCTGTAGCGGCGCATTAAGCGCGGCGGGTGTGGTGGTTACGCGCAGCGTGACCGCTACA
CTTGCCAGCGCCCTAGCGCCCGCTCCTTTCGCTTTCTTCCCTTCCTTTCTCGCCACGTTCGCCGGCTTTCCCCGTCAA
GCTCTAAATCGGGGGCTCCCTTTAGGGTTCCGATTTAGTGCTTTACGGCACCTCGACCCCAAAAAACTTGATTAGG
GTGATGGTTCACGTAGTGGGCCATCGCCCTGATAGACGGTTTTTCGCCCTTTGACGTTGGAGTCCACGTTCTTTAA
TAGTGGACTCTTGTTCCAAACTGGAACAACACTCAACCCTATCTCGGTCTATTCTTTTGATTTATAAGGGATTTTGC
CGATTTCGGCCTATTGGTTAAAAAATGAGCTGATTTAACAAAAATTTAACGCGAATTAATTCTGTGGAATGTGTGT
CAGTTAGGGTGTGGAAAGTCCCCAGGCTCCCCAGCAGGCAGAAGTATGCAAAGCATGCATCTCAATTAGTCAGC
AACCAGGTGTGGAAAGTCCCCAGGCTCCCCAGCAGGCAGAAGTATGCAAAGCATGCATCTCAATTAGTCAGCAAC
CATAGTCCCGCCCCTAACTCCGCCCATCCCGCCCCTAACTCCGCCCAGTTCCGCCCATTCTCCGCCCCATGGCTGAC
TAATTTTTTTTATTTATGCAGAGGCCGAGGCCGCCTCTGCCTCTGAGCTATTCCAGAAGTAGTGAGGAGGCTTTTT
TGGAGGCCTAGGCTTTTGCAAAAAGCTCCCGGGAGCTTGTATATCCATTTTCGGATCTGATCAGCACGTGTTGACA
ATTAATCATCGGCATAGTATATCGGCATAGTATAATACGACAAGGTGAGGAACTAAACCATGGCCAAGTTGACCA
GTGCCGTTCCGGTGCTCACCGCGCGCGACGTCGCCGGAGCGGTCGAGTTCTGGACCGACCGGCTCGGGTTCTCCC
GGGACTTCGTGGAGGACGACTTCGCCGGTGTGGTCCGGGACGACGTGACCCTGTTCATCAGCGCGGTCCAGGAC
CAGGTGGTGCCGGACAACACCCTGGCCTGGGTGTGGGTGCGCGGCCTGGACGAGCTGTACGCCGAGTGGTCGG
AGGTCGTGTCCACGAACTTCCGGGACGCCTCCGGGCCGGCCATGACCGAGATCGGCGAGCAGCCGTGGGGGCG
GGAGTTCGCCCTGCGCGACCCGGCCGGCAACTGCGTGCACTTCGTGGCCGAGGAGCAGGACTGACACGTGCTAC
GAGATTTCGATTCCACCGCCGCCTTCTATGAAAGGTTGGGCTTCGGAATCGTTTTCCGGGACGCCGGCTGGATGA
TCCTCCAGCGCGGGGATCTCATGCTGGAGTTCTTCGCCCACCCCAACTTGTTTATTGCAGCTTATAATGGTTACAAA
TAAAGCAATAGCATCACAAATTTCACAAATAAAGCATTTTTTTCACTGCATTCTAGTTGTGGTTTGTCCAAACTCAT
CAATGTATCTTATCATGTCTGTATACCGTCGACCTCTAGCTAGAGCTTGGCGTAATCATGGTCATAGCTGTTTCCTG
TGTGAAATTGTTATCCGCTCACAATTCCACACAACATACGAGCCGGAAGCATAAAGTGTAAAGCCTGGGGTGCCT
AATGAGTGAGCTAACTCACATTAATTGCGTTGCGCTCACTGCCCGCTTTCCAGTCGGGAAACCTGTCGTGCCAGCT
GcattaatgaatcggccaacgcgcggggagaggcggtttgcgtattgggcgctCTTCCGCTTCCTCGCTCACTGACTCGCTGCGCTCG
GTCGTTCGGCTGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTGCTGGCGTTT
TTCCATAGGCTCCGCCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCACTGGTAACAGGATTAGCAGAGCG
AGGTATGTAGGCGGTGCTACAGAGTTCTTGAAGTGGTGGCCTAACTACGGCTACACTAGAAGAACAGTATTTGGT
ATCTGCGCTCTGCTGAAGCCAGTTACCTTCGGAAAAAGAGTTGGTAGCTCTTGATCCGGCAAACAAACCACCGCT
GGTAGCGGTGGTTTTTTTGTTTGCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTTGGTCATGAGATTATCAAAAAGG
ATCTTCACCTAGATCCTTTTAAATTAAAAATGAAGTTTTAAATCAATCTAAAGTATATATGAGTAAACTTGGTCTGA
CAGTTACCAATGCTTAATCAGTGAGGCACCTATCTCAGCGATCTGTCTATTTCGTTCATCCATAGTTGCCTGACTCC
CCGTCGTGTAGATAACTACGATACGGGAGGGCTTACCATCTGGCCCCAGTGCTGCAATGATACCGCGAGACCCAC
GCTCACCGGCTCCAGATTTATCAGCAATAAACCAGCCAGCCGGAAGGGCCGAGCGCAGAAGTGGTCCTGCAACT
TTATCCGCCTCCATCCAGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCATTCAGCTCCGGTTCCCA
ACGATCAAGGCGAGTTACATGATCCCCCATGTTGTGCAAAAAAGCGGTTAGCTCCTTCGGTCCTCCGATCGTTGTC
AGAAGTAAGTTGGCCGCAGTGTTATCACTCATGGTTATGGCAGCACTGCATAATTCTCTTACTGTCATGCCATCCG
TAAGATGCTTTTCTGTGACTGGTGAGTACTCAACCAAGTCATTCTGAGAATAGTGTATGCGGCGACCGAGTTGCTC
TTGCCCGGCGTCAATACGGGATAATACCGCGCCACATAGCAGAACTTTAAAAGTGCTCATCATTGGAAAACGTTC
TTCGGGGCGAAAACTCTCAAGGATCTTACCGCTGTTGAGATCCAGTTCGATGTAACCCACTCGTGCACCCAACTGA
TCTTCAGCATCTTTTACTTTCACCAGCGTTTCTGGGTGAGCAAAAACAGGAAGGCAAAATGCCGCAAAAAAGGGA
ATAAGGGCGACACGGAAATGTTGAATACTCATACTCTTCCTTTTTCAATATTATTGAAGCATTTATCAGGGTTATTG
TCTCA

FIG. 21N

TGAGCGGATACATATTTGAATGTATTTAGAAAAATAAACAAATAGGGGTTCCGCGCACATTTCCCCGAAAAGTGC
CACCTGACGTCGACGGATCGGGAGATCTCCCGATCCCCTATGGTGCACTCTCAGTACAATCTGCTCTGATGCCGCA
TAGTTAAGCCAGTATCTGCTCCCTGCTTGTGTGTTGGAGGTCGCTGAGTAGTGCGCGAGCAAAATTTAAGCTACA
ACAAGGCAAGGCTTGACCGACAATTGCATGAAGAATCTGCTTAGGGTTAGGCGTTTTGCGCTGCTTCGCGATGTA
CGGGCCAGATATA

FIG. 22A

>pCIG-GFP (control for FIGs. 1) (SEQ ID NO:67)
CAAAAGGCCAGGAACCGTAAAAAGGCCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTGAGTCCAACCCGGTAAGACACGACTTA
TCGCCACTGGCAGCAGCCACTGGTAACAGGATTAGCAGAGCGAGGTATGTAGGCGGTGCTACAGAGTTCTTGAA
GTGGTGGCCTAACTACGGCTACACTAGAAGACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGCTCAGTGGAACGAA
AACTCACGTTAAGGGATTTTGGTCATGAGATTATCAAAAAGGATCTTCACCTAGATCCTTTTAAATTAAAAATGAA
GTTTTAAATCAATCTAAAGTATATATGAGTAAACTTGGTCTGACAGTTACCAATGCTTAATCAGTGAGGCACCTAT
CTCAGCGATCTGTCTATTTCGTTCATCCATAGTTGCCTGACTCCCCGTCGTGTAGATAACTACGATACGGGAGGGC
TTACCATCTGGCCCCAGTGCTGCAATGATACCGCGAGACCCACGCTCACCGGCTCCAGATTTATCAGCAATAAACC
AGCCAGCCGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATCGTGGTGT
CACGCTCGTCGTTTGGTATGGCTTCATTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTAAGTTGGCCGCAGTGTTATCACTCATG
GTTATGGCAGCACTGCATAATTCTCTTACTGTCATGCCATCCGTAAGATGCTTTTCTGTGACTGGTGAGTACTCAAC
CAAGTCATTCTGAGAATAGTGTATGCGGCGACCGAGTTGCTCTTGCCCGGCGTCAATACGGGATAATACCGCGCC
ACATAGCAGAACTTTAAAAGTGCTCATCATTGGAAAACGTTCTTCGGGGCGAAAACTCTCAAGGATCTTACCGCT
GTTGAGATCCAGTTCGATGTAACCCACTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGGGTCGACATTGATTATTGACTA
GTTATTAATAGTAATCAATTACGGGGTCATTAGTTCATAGCCCATATATGGAGTTCCGCGTTACATAACTTACGGT
AAATGGCCCGCCTGGCTGACCGCCCAACGACCCCCGCCCATTGACGTCAATAATGACGTATGTTCCCATAGTAAC
GCCAATAGGGACTTTCCATTGACGTCAATGGGTGGAGTATTTACGGTAAACTGCCCACTTGGCAGTACATCAAGT
GTATCATATGCCAAGTACGCCCCCTATTGACGTCAATGACGGTAAATGGCCCGCCTGGCATTATGCCCAGTACATG
ACCTTATGGGACTTTCCTACTTGGCAGTACATCTACGTATTAGTCATCGCTATTACCATGGTCGAGGTGAGCCCCA
CGTTCTGCTTCACTCTCCCCATCTCCCCCCCCTCCCCACCCCCAATTTTGTATTTATTTATTTTTTAATTATTTTGTGCA
GCGATGGGGGCGGGGGGGGGGGGGGGGCGCGCGCCAGGCGGGGCGGGGCGGGGCGAGGGGCGGGGCGGG
GCGAGGCGGAGAGGTGCGGCGGCAGCCAATCAGAGCGGCGCGCTCCGAAAGTTTCCTTTTATGGCGAGGCGGC
GGCGGCGGCGGCCCTATAAAAAGCGAAGCGCGCGGCGGGCGGGAGTCGCTGCGTTGCCTTCGCCCCGTGCCCC
GCTCCGCGCCGCCTCGCGCCGCCCGCCCCGGCTCTGACTGACCGCGTTACTCCCACAGGTGAGCGGGCGGGACG
GCCCTTCTCCTCCGGGCTGTAATTAGCGCTTGGTTTAATGACGGCTCGTTTCTTTTCTGTGGCTGCGTGAAAGCCTT
AAAGGGCTCCGGGAGGGCCCTTTGTGCGGGGGGGAGCGGCTCGGGGGGTGCGTGCGTGTGTGTGTGCGTGGG
GAGCGCCGCGTGCGGCCCGCGCTGCCCGGCGGCTGTGAGCGCTGCGGGCGCGGCGCGGGGCTTTGTGCGCTCC
GCGTGTGCGCGAGGGGAGCGCGGCCGGGGGCGGTGCCCCGCGGTGCGGGGGGGCTGCGAGGGGAACAAAGG
CTGCGTGCGGGGTGTGTGCGTGGGGGGGTGAGCAGGGGGTGTGGGCGCGGCGGTCGGGCTGTAACCCCCCCCT
GCACCCCCCTCCCCGAGTTGCTGAGCACGGCCCGGCTTCGGGTGCGGGGCTCCGTACGGGGCGTGGCGCGGGGC
TCGCCGTGCCGGGCGGGGGGTGGCGGCAGGTGGGGGTGCCGGGC

FIG. 22B

GGGGCGGGGCCGCCTCGGGCCGGGGAGGGCTCGGGGGAGGGGCGCGGCGGCCCCCGGAGCGCCGGCGGCTG
TCGAGGCGCGGCGAGCCGCAGCCATTGCCTTTTATGGTAATCGTGCGAGAGGGCGCAGGGACTTCCTTTGTCCCA
AATCTGTGCGGAGCCGAAATCTGGGAGGCGCCGCCGCACCCCCTCTAGCGGGCGCGGGGCGAAGCGGTGCGGC
GCCGGCAGGAAGGAAATGGGCGGGGAGGGCCTTCGTGCGTCGCCGCGCCGCCGTCCCCTTCTCCCTCTCCAGCC
TCGGGGCTGTCCGCGGGGGGACGGCTGCCTTCGGGGGGGACGGGGCAGGGCGGGGTTCGGCTTCTGGCGTGT
GACCGGCGGCTCTAGAGCCTCTGCTAACCATGTTCATGCCTTCTTCTTTTTCCTACAGCTCCTGGGCAACGTGCTGG
TTATTGTGCTGTCTCATCATTTTGGCAAAGAATTGCTCGAGCTCAAGCTTCGAATTCTGCAGTCGACGGTACCGCG
GGCCCGGGATCCGCCCCTCTCCCTCCCCCCCCCCTAACGTTACTGGCCGAAGCCGCTTGGAATAAGGCCGGTGTG
CGTTTGTCTATATGTTATTTTCCACCATATTGCCGTCTTTTGGCAATGTGAGGGCCCGGAAACCTGGCCCTGTCTTC
TTGACGAGCATTCCTAGGGGTCTTTCCCCTCTCGCCAAAGGAATGCAAGGTCTGTTGAATGTCGTGAAGGAAGCA
GTTCCTCTGGAAGCTTCTTGAAGACAAACAACGTCTGTAGCGACCCTTTGCAGGCAGCGGAACCCCCCACCTGGC
GACAGGTGCCTCTGCGGCCAAAAGCCACGTGTATAAGATACACCTGCAAAGGCGGCACAACCCCAGTGCCACGTT
GTGAGTTGGATAGTTGTGGAAAGAGTCAAATGGCTCTCCTCAAGCGTATTCAACAAGGGGCTGAAGGATGCCCA
GAAGGTACCCCATTGTATGGGATCTGATCTGGGGCCTCGGTACACATGCTTTACATGTGTTTAGTCGAGGTTAAA
AAAACGTCTAGGCCCCCCGAACCACGGGGACGTGGTTTTCCTTTGAAAAACACGATGATAATATGGCCACAACCA
TGGTGAGCAAGGGCGAGGAGCTGTTCACCGGGGTGGTGCCCATCCTGGTCGAGCTGGACGGCGACGTAAACGG
CCACAAGTTCAGCGTGTCCGGCGAGGGCGAGGGCGATGCCACCTACGGCAAGCTGACCCTGAAGTTCATCTGCA
CCACCGGCAAGCTGCCCGTGCCCTGGCCCACCCTCGTGACCACCCTGACCTACGGCGTGCAGTGCTTCAGCCGCT
ACCCCGACCACATGAAGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACCCTGGTGAACCGCATC
GAGCTGAAGGGCATCGACTTCAAGGAGGACGGCAACATCCTGGGGCACAAGCTGGAGTACAACTACAACAGCCA
CAACGTCTATATCATGGCCGACAAGCAGAAGAACGGCATCAAGGTGAACTTCAAGATCCGCCACAACATCGAGG
ACGGCAGCGTGCAGCTCGCCGACCACTACCAGCAGAACACCCCCATCGGCGACGGCCCCGTGCTGCTGCCCGAC
AACCACTACCTGAGCACCCAGTCCGCCCTGAGCAAAGACCCCAACGAGAAGCGCGATCACATGGTCCTGCTGGAG
TTCGTGACCGCCGCCGGGATCACTCTCGGCATGGACGAGCTGTACAAGTAAAGCGGCCGCAATTCACTCCTCAGG
TGCAGGCTGCCTATCAGAAGGTGGTGGCTGGTGTGGCCAATGCCCTGGCTCACAAATACCACTGAGATCTTTTTC
CCTCTGCCAAAAATTATGGGGACATCATGAAGCCCCTTGAGCATCTGACTTCTGGCTAATAAAGGAAATTTATTTT
CATTGCAATAGTGTGTTGGAATTTTTTGTGTCTATCACTCGGAAGGACATATGGGAGGGCAAATCATTTAAAACAT
CAGAATGAGTATTTGGTTTAGAGTTTGGCAACATATGCCCATATGCTGGCTGCCATGAACAAAGGTTGGCTATAA
AGAGGTCATCAGTATATGAAACAGCCCCCTGCTGTCCATTCCTTATTCCATAGAAAAGCCTTGACTTGAGGTTAGA
TTTTTTTTATATTTTGTTTTGTGTTATTTTTTTCTTTAACATCCCTAAAATTTTCCTTACATGTTTTACTAGCCAGATTT
TTCCTCCTCTCCTGACTACTCCCAGTCATAGCTGTCCCTCTTCTCTTATGGAGATCCCTCGACCTGCACCGTCGACCA
GCTGGTCGACGGTGCACCGTCGACCAGCTTGGCGTAATCATGGTCATAGCTGTTTCCTGTGTGAAATTGTTATCCG
CTCACAATTCCACACAACATACGAGCCGGAAGCATAAAGTGTAAAGCCTGGGGTGCCTAATGAGTGAGCTAACTC
ACATTAATTGCGTTGCGCTCACTGCCCGCTTTCCAGTCGGGAAACCTGTCGTGCCAGCGGATCCGCATCTCAATTA
GTCAGCAACCATAGTCCCGCCCCTAACTCCGCCCATCCCGCCCCTAACTCCGCCCAGTTCCGCCCATTCTCCGCCCC
ATGGCTGACTAATTTTTTTTATTTATGCAGAGGCCGAGGCCGCCTCGGCCTCTGAGCTATTCCAGAAGTAGTGAGG
AGGCTTTTTTGGAGGCCTAGGCTTTTGCAAAAAGCTAACTTGTTTATTGCAGCTTATAATGGTTACAAATAAAGCA
ATAGCATCACAAATTTCACAAATAAAGCATTTTTTTCACTGCATTCTAGTTGTGGTTTGTCCAAACTCATCAATGTAT
CTTATCATGTCTGGATCCGCTGCATTAATGAATCGGCCAACGCGCGGGGAGAGGCGGTTTGCGTATTGGGCGCTC
TTCCGCTTCCTCGCTCACTGACTCGCTGCGCTCGGTCGTTCGGCTGCGGCGAGCGGTATCAGCTCACTCAAAGGCG
GTAATACGGTTATCCACAGAATCAGGGGATAACGCAGGAAAGAACATGTGAGCAAAAGGCCAG

FIG. 22C

>pCIG-Ikzf4-GFP (used in FIGs. 1) (SEQ ID NO:68)
CAAAAGGCCAGGAACCGTAAAAAGGCCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTGAGTCCAACCCGGTAAGACACGACTTA
TCGCCACTGGCAGCAGCCACTGGTAACAGGATTAGCAGAGCGAGGTATGTAGGCGGTGCTACAGAGTTCTTGAA
GTGGTGGCCTAACTACGGCTACACTAGAAGACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGCTCAGTGGAACGAA
AACTCACGTTAAGGGATTTTGGTCATGAGATTATCAAAAAGGATCTTCACCTAGATCCTTTTAAATTAAAAATGAA
GTTTTAAATCAATCTAAAGTATATATGAGTAAACTTGGTCTGACAGTTACCAATGCTTAATCAGTGAGGCACCTAT
CTCAGCGATCTGTCTATTTCGTTCATCCATAGTTGCCTGACTCCCCGTCGTGTAGATAACTACGATACGGGAGGGC
TTACCATCTGGCCCCAGTGCTGCAATGATACCGCGAGACCCACGCTCACCGGCTCCAGATTTATCAGCAATAAACC
AGCCAGCCGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATCGTGGTGT
CACGCTCGTCGTTTGGTATGGCTTCATTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTAAGTTGGCCGCAGTGTTATCACTCATG
GTTATGGCAGCACTGCATAATTCTCTTACTGTCATGCCATCCGTAAGATGCTTTTCTGTGACTGGTGAGTACTCAAC
CAAGTCATTCTGAGAATAGTGTATGCGGCGACCGAGTTGCTCTTGCCCGGCGTCAATACGGGATAATACCGCGCC
ACATAGCAGAACTTTAAAAGTGCTCATCATTGGAAAACGTTCTTCGGGGCGAAAACTCTCAAGGATCTTACCGCT
GTTGAGATCCAGTTCGATGTAACCCACTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGGGTCGACATTGATTATTGACTA
GTTATTAATAGTAATCAATTACGGGGTCATTAGTTCATAGCCCATATATGGAGTTCCGCGTTACATAACTTACGGT
AAATGGCCCGCCTGGCTGACCGCCCAACGACCCCCGCCCATTGACGTCAATAATGACGTATGTTCCCATAGTAAC
GCCAATAGGGACTTTCCATTGACGTCAATGGGTGGAGTATTTACGGTAAACTGCCCACTTGGCAGTACATCAAGT
GTATCATATGCCAAGTACGCCCCCTATTGACGTCAATGACGGTAAATGGCCCGCCTGGCATTATGCCCAGTACATG
ACCTTATGGGACTTTCCTACTTGGCAGTACATCTACGTATTAGTCATCGCTATTACCATGGTCGAGGTGAGCCCCA
CGTTCTGCTTCACTCTCCCCATCTCCCCCCCCTCCCCACCCCCAATTTTGTATTTATTTATTTTTTAATTATTTTGTGCA
GCGATGGGGGCGGGGGGGGGGGGGGGGCGCGCGCCAGGCGGGGCGGGGCGGGGCGAGGGGCGGGGCGGG
GCGAGGCGGAGAGGTGCGGCGGCAGCCAATCAGAGCGGCGCGCTCCGAAAGTTTCCTTTTATGGCGAGGCGGC
GGCGGCGGCGGCCCTATAAAAAGCGAAGCGCGCGGCGGGCGGGAGTCGCTGCGTTGCCTTCGCCCCGTGCCCC
GCTCCGCGCCGCCTCGCGCCGCCCGCCCCGGCTCTGACTGACCGCGTTACTCCCACAGGTGAGCGGGCGGGACG
GCCCTTCTCCTCCGGGCTGTAATTAGCGCTTGGTTTAATGACGGCTCGTTTCTTTTCTGTGGCTGCGTGAAAGCCTT
AAAGGGCTCCGGGAGGGCCCTTTGTGCGGGGGGGAGCGGCTCGGGGGGTGCGTGCGTGTGTGTGTGCGTGGG
GAGCGCCGCGTGCGGCCCGCGCTGCCCGGCGGCTGTGAGCGCTGCGGGCGCGGCGCGGGGCTTTGTGCGCTCC
GCGTGTGCGCGAGGGGAGCGCGGCCGGGGGCGGTGCCCCGCGGTGCGGGGGGGCTGCGAGGGGAACAAAGG
CTGCGTGCGGGGTGTGTGCGTGGGGGGGTGAGCAGGGGGTGTGGGCGCGGCGGTCGGGCTGTAACCCCCCCCT
GCACCCCCCTCCCCGAGTTGCTGAGCACGGCCCGGCTTCGGGTGCGGGGCTCCGTACGGGGCGTGGCGCGGGGC
TCGCCGTGCCGGGCGGGGGGTGGCGGCAGGTGGGGGTGCCGGGCGGGGCGGGGCCGCCTCGGGCCGGGGAG
GGCTCGGGGGAGGGGCGCGGCGGCCCCCGGAGCGCCGGCGGCTGTCGAGGCGCGGCGAGCCGCAGCCATTGC
CTTTTATGGTAATCGTGCGAGAGGGCGCAGGGACTTCCTTTGTCCCAAATCTGTGCGGAGCCGAAATCTGGGAGG
CGCCGCCGCACCCCCTCTAGCGGGCGCGGGGCGAAGCGGTGCGGCGCCGGCAGGAAGGAAATGGGCGGGGAG
GGCCTTCGTGCGTCGCCGCGCCGCCGTCCCCTTCTCCCTCTCCAGCCTCGGGGCTGTCCGCGGGGGGACGGCTGC
CTTCGGGGGGGACGGGGCAGGGCGGGGTTCGGCTTCTGGCGTGTGACCGGCGGCTCTAGAGCCTCTGCTAACC
ATGTTCATGCCTTCTTCTTTTTCCTACAGCTCCTGGGCAACGTGCTGGTTATTGTGCTGTCTCATCATTTTGGCAAAG
AATTGCTCGAGCTCAAGCTTCGAATTATCAACAAGTTTGTACAAAAAAGCAGGCTTTAAAGGAACCAATTCAGTCG
ACTGG

FIG. 22D

ATCCGGTACCGAATTCATGCACACACCACCCGCACTCCCTCGCCGTTTCCAAGGCGGCGGCCGCGTTCGCACCCCA
GGGTCTCACCGGCAAGGGAAGGATAATCTGGAGAGGGAGCTCTCAGGAGGGTGTGCTCCGGATTTCTTGCCTCA
GGCCCAGGACTCCAACCATTTTATAATGGAATCTTTATTTTGTGAAAGTAGCGGGGACTCATCTCTGGAGAAGGA
GTTCCTTGGGGCCCCAGTGGGGCCCTCGGTGAGCACCCCAAACAGCCAACACTCTTCACCCAGCCGCTCGCTCAG
TGCCAACTCCATCAAGGTGGAGATGTACAGCGATGAGGAGTCGAGCAGACTGCTGGGGCCGGATGAACGGCTCC
TGGATAAGGATGACAGTGTGATTGTGGAAGACTCATTGTCAGAGCCCTTAGGCTACTGCGATGGAAGTGGGCCA
GAGCCTCACTCCCCTGGCGGCATCCGGCTACCCAACGGCAAGCTCAAGTGCGACGTCTGCGGCATGGTCTGCATT
GGGCCCAATGTGCTCATGGTACACAAGCGCAGCCACACTGGGGAGAGGCCCTTCCACTGTAATCAGTGTGGTGC
CTCCTTCACACAGAAGGGCAATCTGCTTCGCCACATCAAGCTGCACTCGGGGGAGAAGCCCTTCAAGTGCCCCTTC
TGCAACTATGCCTGCCGCCGGCGTGACGCACTCACTGGCCACCTCCGCACACACTCAGTCTCCTCCCCCACCGTGG
GCAAACCCTACAAGTGCAACTACTGTGGCCGGAGCTACAAACAGCAAAGTACCCTGGAGGAGCACAAGGAGAG
GTGCCACAACTACCTACAGAGTCTCAGCACTGATGCCCAAGCTCTGACTGGCCAGCCAGGTGATGAAATCCGTGA
CCTGGAGATGGTGCCTGACTCAATGCTGCACCCATCGACTGAACGGCCAACTTTCATTGATCGTTTGGCCAACAGC
CTCACCAAACGCAAGCGTTCCACCCCACAGAAGTTTGTAGGTGAAAAGCAGATGCGCTTCAGCCTCTCAGACCTTC
CCTATGATGTGAATGCCAGCGGTGGCTATGAAAAGGACGTAGAGTTGGTGGCACACCATGGCCTGGAGCCTGGC
TTTGGAGGGTCTCTAGCCTTTGTGGGTACAGAGCATCTGCGTCCCCTCCGCCTCCCACCCACCAACTGCATCTCAG
AACTCACACCTGTCATCAGCTCTGTGTACACCCAAATGCAGCCCATCCCCAGCCGACTGGAGCTTCCAGGGTCCCG
AGAAGCAGGTGAGGGACCGGAGGACCTGGGAGATGGAGGTCCCCTCCTTTATCGGGCCCGAGGCTCTCTGACTG
ACCCTGGGGCATCCCCCAGCAATGGCTGCCAGGACTCCACAGATACAGAGAGCAACCACGAAGACCGGATTGGT
GGGGTGGTATCCCTTCCTCAGGGTCCCCCACCCCAACCTCCTCCCACCATAGTGGTGGGCCGGCACAGTCCCGCCT
ATGCCAAAGAGGACCCCAAACCACAGGAGGGGTTACTGCGGGGCACCCCAGGCCCCTCCAAGGAAGTGCTTCGG
GTGGTGGGTGAGAGTGGTGAGCCAGTGAAGGCCTTTAAGTGTGAACACTGCCGCATCCTCTTTCTGGACCACGTC
ATGTTCACCATCCACATGGGCTGCCACGGCTTCAGAGACCCTTTTGAGTGTAACATCTGTGGTTATCACAGCCAGG
ATCGGTATGAGTTCTCTTCCCACATCGTCCGGGGGGAACATAAGGTGGGCTAGGAATTCGCGGCCGCACTCGAG
ATATCTAGACCCAGCTTTCTTGTACAAAGTGGTTGATAATTCTGCAGTCGACGGTACCGCGGGCCCGGGATCCGC
CCCTCTCCCTCCCCCCCCCCTAACGTTACTGGCCGAAGCCGCTTGGAATAAGGCCGGTGTGCGTTTGTCTATATGTT
ATTTTCCACCATATTGCCGTCTTTTGGCAATGTGAGGGCCCGGAAACCTGGCCCTGTCTTCTTGACGAGCATTCCTA
GGGGTCTTTCCCCTCTCGCCAAAGGAATGCAAGGTCTGTTGAATGTCGTGAAGGAAGCAGTTCCTCTGGAAGCTT
CTTGAAGACAAACAACGTCTGTAGCGACCCTTTGCAGGCAGCGGAACCCCCCACCTGGCGACAGGTGCCTCTGCG
GCCAAAAGCCACGTGTATAAGATACACCTGCAAAGGCGGCACAACCCCAGTGCCACGTTGTGAGTTGGATAGTT
GTGGAAAGAGTCAAATGGCTCTCCTCAAGCGTATTCAACAAGGGGCTGAAGGATGCCCAGAAGGTACCCCATTG
TATGGGATCTGATCTGGGGCCTCGGTACACATGCTTTACATGTGTTTAGTCGAGGTTAAAAAAACGTCTAGGCCCC
CCGAACCACGGGGACGTGGTTTTCCTTTGAAAAACACGATGATAATATGGCCACAACCATGGTGAGCAAGGGCG
AGGAGCTGTTCACCGGGGTGGTGCCCATCCTGGTCGAGCTGGACGGCGACGTAAACGGCCACAAGTTCAGCGTG
TCCGGCGAGGGCGAGGGCGATGCCACCTACGGCAAGCTGACCCTGAAGTTCATCTGCACCACCGGCAAGCTGCC
CGTGCCCTGGCCCACCCTCGTGACCACCCTGACCTACGGCGTGCAGTGCTTCAGCCGCTACCCCGACCACATGAA
GCAGCACGACTTCTTCAAGTCCGCCATGCCCGAAGGCTACGTCCAGGAGCGCACCATCTTCTTCAAGGACGACGG
CAACTACAAGACCCGCGCCGAGGTGAAGTTCGAGGGCGACACCCTGGTGAACCGCATCGAGCTGAAGGGCATCG
ACTTCAAGGAGGACGGCAACATCCTGGGGCACAAGCTGGAGTACAACTACAACAGCCACAACGTCTATATCATG
GCCGACAAGCAGAAGAACGGCATCAAGGTGAACTTCAAGATCCGCCACAACATCGAGGACGGCAGCGTGCAGCT
CGCCGACCACTACCAGCAGAACACCCCCATCGGCGACGGCCCCGTGCTGCTGCCCGACAACCACTACCTGAGCAC
CCAGTCCGCCCTGAGCAAAGACCCCAACGAGAAGCGCGATCACATGGTCCTGCTGGAGTTCGTGACCGCCGCCG
GGATCACTCTCGGCATGGACGAGCTGTACAAGTAAAGCGGCCGCAATTCACTCCTCAGGTGCAGGCTGCCTATCA
GAAGGTGGTGGCTGGTGTGGCCAATGCCCTGGCTCACAAATACCACTGAGATCTTTTTCCCTCTGCCAAAAATTAT
GGGGACATCATGAAGCCCCTTGAGCATCTGACTTCTGGCTAATAAAGGAAATTTATTTTCATTGCAATAGTGTGTT
GGAATTTTTTGTGTCTATCACTCGGAAGGACATATGGGAGGGCAAATCATTTAAAACATCAGAATGAGTATTTGG
TTTAGAGTTTGGCAACATATGCCCATATGCTGGCTGCCATGAACAAAGGTTGGCTATAAAGAGGTCATCAGTATA
TGAAACAGCCCCCTGCTGTCCATTCCTTATTCCATAGAAAAGCCTTGACTTGAGGTTAGATTTTTTTTATATTTTGTT
TTGTGTTATTTTTTTCTTTAACATCCCTAAAATTTTCCTTACATGTTTTACTAGCCAGATTTTTCCTCCTCTCCTGACTA
CTCCC

FIG. 22E

AGTCATAGCTGTCCCTCTTCTCTTATGGAGATCCCTCGACCTGCACCGTCGACCAGCTGGTCGACGGTGCACCGTC
GACCAGCTTGGCGTAATCATGGTCATAGCTGTTTCCTGTGTGAAATTGTTATCCGCTCACAATTCCACACAACATAC
GAGCCGGAAGCATAAAGTGTAAAGCCTGGGGTGCCTAATGAGTGAGCTAACTCACATTAATTGCGTTGCGCTCAC
TGCCCGCTTTCCAGTCGGGAAACCTGTCGTGCCAGCGGATCCGCATCTCAATTAGTCAGCAACCATAGTCCCGCCC
CTAACTCCGCCCATCCCGCCCCTAACTCCGCCCAGTTCCGCCCATTCTCCGCCCCATGGCTGACTAATTTTTTTTATT
TATGCAGAGGCCGAGGCCGCCTCGGCCTCTGAGCTATTCCAGAAGTAGTGAGGAGGCTTTTTTGGAGGCCTAGG
CTTTTGCAAAAAGCTAACTTGTTTATTGCAGCTTATAATGGTTACAAATAAAGCAATAGCATCACAAATTTCACAAA
TAAAGCATTTTTTTCACTGCATTCTAGTTGTGGTTTGTCCAAACTCATCAATGTATCTTATCATGTCTGGATCCGCTG
CATTAATGAATCGGCCAACGCGCGGGGAGAGGCGGTTTGCGTATTGGGCGCTCTTCCGCTTCCTCGCTCACTGAC
TCGCTGCGCTCGGTCGTTCGGCTGCGGCGAGCGGTATCAGCTCACTCAAAGGCGGTAATACGGTTATCCACAGAA
TCAGGGGATAACGCAGGAAAGAACATGTGAGCAAAAGGCCAG

SEQUENCE LISTING

```
<160> NUMBER OF SEQ ID NOS: 72

<210> SEQ ID NO 1
<211> LENGTH: 515
<212> TYPE: PRT
<213> ORGANISM: mus musculus

<400> SEQUENCE: 1

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Val Cys Ile Gly
```

-continued

```
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Met Tyr Pro Val Ile Lys
225                 230                 235                 240

Glu Glu Thr Asn His Asn Glu Met Ala Glu Asp Leu Cys Lys Ile Gly
                245                 250                 255

Ala Glu Arg Ser Leu Val Leu Asp Arg Leu Ala Ser Asn Val Ala Lys
            260                 265                 270

Arg Lys Ser Ser Met Pro Gln Lys Phe Leu Gly Asp Lys Cys Leu Ser
        275                 280                 285

Asp Met Pro Tyr Asp Ser Ala Asn Tyr Glu Lys Glu Asp Met Met Thr
    290                 295                 300

Ser His Val Met Asp Gln Ala Ile Asn Asn Ala Ile Asn Tyr Leu Gly
305                 310                 315                 320

Ala Glu Ser Leu Arg Pro Leu Val Gln Thr Pro Pro Gly Ser Ser Glu
                325                 330                 335

Val Val Pro Val Ile Ser Ser Met Tyr Gln Leu His Lys Pro Pro Ser
            340                 345                 350

Asp Gly Pro Pro Arg Ser Asn His Ser Ala Gln Asp Ala Val Asp Asn
        355                 360                 365

Leu Leu Leu Leu Ser Lys Ala Lys Ser Val Ser Ser Glu Arg Glu Ala
    370                 375                 380

Ser Pro Ser Asn Ser Cys Gln Asp Ser Thr Asp Thr Glu Ser Asn Ala
385                 390                 395                 400

Glu Glu Gln Arg Ser Gly Leu Ile Tyr Leu Thr Asn His Ile Asn Pro
                405                 410                 415

His Ala Arg Asn Gly Leu Ala Leu Lys Glu Glu Gln Arg Ala Tyr Glu
            420                 425                 430

Val Leu Arg Ala Ala Ser Glu Asn Ser Gln Asp Ala Phe Arg Val Val
        435                 440                 445

Ser Thr Ser Gly Glu Gln Leu Lys Val Tyr Lys Cys Glu His Cys Arg
    450                 455                 460

Val Leu Phe Leu Asp His Val Met Tyr Thr Ile His Met Gly Cys His
465                 470                 475                 480

Gly Phe Arg Asp Pro Phe Glu Cys Asn Met Cys Gly Tyr His Ser Gln
                485                 490                 495

Asp Arg Tyr Glu Phe Ser Ser His Ile Thr Arg Gly Glu His Arg Tyr
            500                 505                 510

His Leu Ser
        515

<210> SEQ ID NO 2
```

```
<211> LENGTH: 428
<212> TYPE: PRT
<213> ORGANISM: mus musculus

<400> SEQUENCE: 2

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Gly Glu Arg Pro Phe Gln Cys Asn Gln Cys Gly
    50                  55                  60

Ala Ser Phe Thr Gln Lys Gly Asn Leu Leu Arg His Ile Lys Leu His
65                  70                  75                  80

Ser Gly Glu Lys Pro Phe Lys Cys His Leu Cys Asn Tyr Ala Cys Arg
                85                  90                  95

Arg Arg Asp Ala Leu Thr Gly His Leu Arg Thr His Ser Val Gly Lys
            100                 105                 110

Pro His Lys Cys Gly Tyr Cys Gly Arg Ser Tyr Lys Gln Arg Ser Ser
        115                 120                 125

Leu Glu Glu His Lys Glu Arg Cys His Asn Tyr Leu Glu Ser Met Gly
    130                 135                 140

Leu Pro Gly Met Tyr Pro Val Ile Lys Glu Glu Thr Asn His Asn Glu
145                 150                 155                 160

Met Ala Glu Asp Leu Cys Lys Ile Gly Ala Glu Arg Ser Leu Val Leu
                165                 170                 175

Asp Arg Leu Ala Ser Asn Val Ala Lys Arg Lys Ser Ser Met Pro Gln
            180                 185                 190

Lys Phe Leu Gly Asp Lys Cys Leu Ser Asp Met Pro Tyr Asp Ser Ala
        195                 200                 205

Asn Tyr Glu Lys Glu Asp Met Met Thr Ser His Val Met Asp Gln Ala
    210                 215                 220

Ile Asn Asn Ala Ile Asn Tyr Leu Gly Ala Glu Ser Leu Arg Pro Leu
225                 230                 235                 240

Val Gln Thr Pro Pro Gly Ser Ser Glu Val Val Pro Val Ile Ser Ser
                245                 250                 255

Met Tyr Gln Leu His Lys Pro Pro Ser Asp Gly Pro Pro Arg Ser Asn
            260                 265                 270

His Ser Ala Gln Asp Ala Val Asp Asn Leu Leu Leu Leu Ser Lys Ala
        275                 280                 285

Lys Ser Val Ser Ser Glu Arg Glu Ala Ser Pro Ser Asn Ser Cys Gln
    290                 295                 300

Asp Ser Thr Asp Thr Glu Ser Asn Ala Glu Glu Gln Arg Ser Gly Leu
305                 310                 315                 320

Ile Tyr Leu Thr Asn His Ile Asn Pro His Ala Arg Asn Gly Leu Ala
                325                 330                 335

Leu Lys Glu Glu Gln Arg Ala Tyr Glu Val Leu Arg Ala Ala Ser Glu
            340                 345                 350

Asn Ser Gln Asp Ala Phe Arg Val Val Ser Thr Ser Gly Glu Gln Leu
        355                 360                 365

Lys Val Tyr Lys Cys Glu His Cys Arg Val Leu Phe Leu Asp His Val
    370                 375                 380

Met Tyr Thr Ile His Met Gly Cys His Gly Phe Arg Asp Pro Phe Glu
```

```
385                 390                 395                 400

Cys Asn Met Cys Gly Tyr His Ser Gln Asp Arg Tyr Glu Phe Ser Ser
                405                 410                 415

His Ile Thr Arg Gly Glu His Arg Tyr His Leu Ser
            420                 425


<210> SEQ ID NO 3
<211> LENGTH: 387
<212> TYPE: PRT
<213> ORGANISM: mus musculus

<400> SEQUENCE: 3

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Gly Glu Arg Pro Phe Gln Cys Asn Gln Cys Gly
    50                  55                  60

Ala Ser Phe Thr Gln Lys Gly Asn Leu Leu Arg His Ile Lys Leu His
65                  70                  75                  80

Ser Gly Glu Lys Pro Phe Lys Cys His Leu Cys Asn Tyr Ala Cys Arg
                85                  90                  95

Arg Arg Asp Ala Leu Thr Gly His Leu Arg Thr His Ser Val Ile Lys
            100                 105                 110

Glu Glu Thr Asn His Asn Glu Met Ala Glu Asp Leu Cys Lys Ile Gly
        115                 120                 125

Ala Glu Arg Ser Leu Val Leu Asp Arg Leu Ala Ser Asn Val Ala Lys
    130                 135                 140

Arg Lys Ser Ser Met Pro Gln Lys Phe Leu Gly Asp Lys Cys Leu Ser
145                 150                 155                 160

Asp Met Pro Tyr Asp Ser Ala Asn Tyr Glu Lys Glu Asp Met Met Thr
                165                 170                 175

Ser His Val Met Asp Gln Ala Ile Asn Asn Ala Ile Asn Tyr Leu Gly
            180                 185                 190

Ala Glu Ser Leu Arg Pro Leu Val Gln Thr Pro Pro Gly Ser Ser Glu
        195                 200                 205

Val Val Pro Val Ile Ser Ser Met Tyr Gln Leu His Lys Pro Pro Ser
    210                 215                 220

Asp Gly Pro Pro Arg Ser Asn His Ser Ala Gln Asp Ala Val Asp Asn
225                 230                 235                 240

Leu Leu Leu Leu Ser Lys Ala Lys Ser Val Ser Ser Glu Arg Glu Ala
                245                 250                 255

Ser Pro Ser Asn Ser Cys Gln Asp Ser Thr Asp Thr Glu Ser Asn Ala
            260                 265                 270

Glu Glu Gln Arg Ser Gly Leu Ile Tyr Leu Thr Asn His Ile Asn Pro
        275                 280                 285

His Ala Arg Asn Gly Leu Ala Leu Lys Glu Glu Gln Arg Ala Tyr Glu
    290                 295                 300

Val Leu Arg Ala Ala Ser Glu Asn Ser Gln Asp Ala Phe Arg Val Val
305                 310                 315                 320

Ser Thr Ser Gly Glu Gln Leu Lys Val Tyr Lys Cys Glu His Cys Arg
                325                 330                 335
```

```
Val Leu Phe Leu Asp His Val Met Tyr Thr Ile His Met Gly Cys His
            340                 345                 350

Gly Phe Arg Asp Pro Phe Glu Cys Asn Met Cys Gly Tyr His Ser Gln
        355                 360                 365

Asp Arg Tyr Glu Phe Ser Ser His Ile Thr Arg Gly Glu His Arg Tyr
    370                 375                 380

His Leu Ser
385


<210> SEQ ID NO 4
<211> LENGTH: 505
<212> TYPE: PRT
<213> ORGANISM: mus musculus

<400> SEQUENCE: 4

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Val Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Met Tyr Pro Val Ile Lys
225                 230                 235                 240

Glu Glu Thr Asn His Asn Glu Met Ala Glu Asp Leu Cys Lys Ile Gly
                245                 250                 255

Ala Glu Arg Ser Leu Val Leu Asp Arg Leu Ala Ser Asn Val Ala Lys
            260                 265                 270

Arg Asp Lys Cys Leu Ser Asp Met Pro Tyr Asp Ser Ala Asn Tyr Glu
        275                 280                 285

Lys Glu Asp Met Met Thr Ser His Val Met Asp Gln Ala Ile Asn Asn
    290                 295                 300

Ala Ile Asn Tyr Leu Gly Ala Glu Ser Leu Arg Pro Leu Val Gln Thr
305                 310                 315                 320
```

```
Pro Pro Gly Ser Ser Glu Val Val Pro Val Ile Ser Ser Met Tyr Gln
                325                 330                 335

Leu His Lys Pro Pro Ser Asp Gly Pro Pro Arg Ser Asn His Ser Ala
            340                 345                 350

Gln Asp Ala Val Asp Asn Leu Leu Leu Leu Ser Lys Ala Lys Ser Val
        355                 360                 365

Ser Ser Glu Arg Glu Ala Ser Pro Ser Asn Ser Cys Gln Asp Ser Thr
    370                 375                 380

Asp Thr Glu Ser Asn Ala Glu Glu Gln Arg Ser Gly Leu Ile Tyr Leu
385                 390                 395                 400

Thr Asn His Ile Asn Pro His Ala Arg Asn Gly Leu Ala Leu Lys Glu
                405                 410                 415

Glu Gln Arg Ala Tyr Glu Val Leu Arg Ala Ala Ser Glu Asn Ser Gln
            420                 425                 430

Asp Ala Phe Arg Val Val Ser Thr Ser Gly Glu Gln Leu Lys Val Tyr
        435                 440                 445

Lys Cys Glu His Cys Arg Val Leu Phe Leu Asp His Val Met Tyr Thr
    450                 455                 460

Ile His Met Gly Cys His Gly Phe Arg Asp Pro Phe Glu Cys Asn Met
465                 470                 475                 480

Cys Gly Tyr His Ser Gln Asp Arg Tyr Glu Phe Ser Ser His Ile Thr
                485                 490                 495

Arg Gly Glu His Arg Tyr His Leu Ser
            500                 505


<210> SEQ ID NO 5
<211> LENGTH: 515
<212> TYPE: PRT
<213> ORGANISM: ARTIFICIAL SEQUENCE
<220> FEATURE:
<223> OTHER INFORMATION: synthetic construct
<220> FEATURE:
<221> NAME/KEY: misc_feature
<222> LOCATION: (54)..(140)
<223> OTHER INFORMATION: Xaa can be any naturally occurring amino acid
<220> FEATURE:
<221> NAME/KEY: misc_feature
<222> LOCATION: (197)..(237)
<223> OTHER INFORMATION: Xaa can be any naturally occurring amino acid
<220> FEATURE:
<221> NAME/KEY: misc_feature
<222> LOCATION: (274)..(283)
<223> OTHER INFORMATION: Xaa can be any naturally occurring amino acid

<400> SEQUENCE: 5

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110
```

-continued

```
Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Val Ile Lys
225                 230                 235                 240

Glu Glu Thr Asn His Asn Glu Met Ala Glu Asp Leu Cys Lys Ile Gly
                245                 250                 255

Ala Glu Arg Ser Leu Val Leu Asp Arg Leu Ala Ser Asn Val Ala Lys
            260                 265                 270

Arg Xaa Xaa Xaa Xaa Xaa Xaa Xaa Xaa Xaa Xaa Asp Lys Cys Leu Ser
        275                 280                 285

Asp Met Pro Tyr Asp Ser Ala Asn Tyr Glu Lys Glu Asp Met Met Thr
    290                 295                 300

Ser His Val Met Asp Gln Ala Ile Asn Asn Ala Ile Asn Tyr Leu Gly
305                 310                 315                 320

Ala Glu Ser Leu Arg Pro Leu Val Gln Thr Pro Pro Gly Ser Ser Glu
                325                 330                 335

Val Val Pro Val Ile Ser Ser Met Tyr Gln Leu His Lys Pro Pro Ser
            340                 345                 350

Asp Gly Pro Pro Arg Ser Asn His Ser Ala Gln Asp Ala Val Asp Asn
        355                 360                 365

Leu Leu Leu Leu Ser Lys Ala Lys Ser Val Ser Ser Glu Arg Glu Ala
    370                 375                 380

Ser Pro Ser Asn Ser Cys Gln Asp Ser Thr Asp Thr Glu Ser Asn Ala
385                 390                 395                 400

Glu Glu Gln Arg Ser Gly Leu Ile Tyr Leu Thr Asn His Ile Asn Pro
                405                 410                 415

His Ala Arg Asn Gly Leu Ala Leu Lys Glu Glu Gln Arg Ala Tyr Glu
            420                 425                 430

Val Leu Arg Ala Ala Ser Glu Asn Ser Gln Asp Ala Phe Arg Val Val
        435                 440                 445

Ser Thr Ser Gly Glu Gln Leu Lys Val Tyr Lys Cys Glu His Cys Arg
    450                 455                 460

Val Leu Phe Leu Asp His Val Met Tyr Thr Ile His Met Gly Cys His
465                 470                 475                 480

Gly Phe Arg Asp Pro Phe Glu Cys Asn Met Cys Gly Tyr His Ser Gln
                485                 490                 495

Asp Arg Tyr Glu Phe Ser Ser His Ile Thr Arg Gly Glu His Arg Tyr
            500                 505                 510

His Leu Ser
        515
```

<210> SEQ ID NO 6
<211> LENGTH: 5451
<212> TYPE: DNA
<213> ORGANISM: mus musculus

<400> SEQUENCE: 6
gtcagggtcc cgaagccgcg tgccgtgcgc gcaggccggg tgggctgtgg gacaagccga 60
gcgggaggcg agtcgcaagc gccaacccaa agtttgcacg gtgcggggcg aggggcgcgc 120
gctccgggct gccgcaggtg gcggcgcggt gagcccgggc caggtgcccc ggcagcgggg 180
cggcgctgtc gtgcgggaca gccgggctgc caggggctcg gagccgggtc ggagcccgcg 240
gggggcgggg agtgtggcga gaaatgggga acaatgcgag tgagcaactt gaggaagtca 300
ttgtgaaaga aagctgggaa ttgctccgca gccaacttag cagggcactc taacaagtgc 360
ctgcgcggcc gcgcccgggc cggggacagg ggcagcccgg cgcagtacag cccatcccgg 420
gacgctcggc cgcggctgcc ggagacccgg taggtcccgc ggggtgcagg agcccccaga 480
tccccggctg ctcttcgcgc cccaggatca ttcttggccc ccaaagcgcg gcgcacaaat 540
ccacataacc tgaagacaat ggatgtcgat gagggtcaag acatgtccca agtttcagga 600
aaggagagcc ccccagtcag tgacactcca gatgaagggg atgagcccat gcctgtccct 660
gaggacctgt ccactacctc tggagcacag cagaactcca agagtgatcg aggcatggcc 720
agtaatgtta aagtagagac tcagagtgat gaagagaatg ggcgtgcctg tgaaatgaat 780
ggggaagaat gtgcagagga tttacgaatg cttgatgcct cgggagagaa aatgaatggc 840
tcccacaggg accaaggcag ctcggctttg tcaggagttg gaggcattcg acttcctaac 900
ggaaaactaa agtgtgatat ctgtgggatc gtttgcatcg ggcccaatgt gctcatggtt 960
cacaaaagaa gtcatactgg tgaacggcct ttccagtgca accagtgtgg ggcctccttt 1020
acccagaaag gcaacctcct gcggcacatc aagctgcact cgggtgagaa gcccttcaaa 1080
tgccatcttt gcaactatgc ctgccgccgg agggacgccc tcaccggcca cctgaggacg 1140
cactccgttg gtaagcctca caaatgtgga tattgtggcc ggagctataa acagcgaagc 1200
tctttagagg agcataaaga gcgatgccac aactacttgg aaagcatggg ccttccgggc 1260
atgtacccag tcattaagga agaaactaac cacaacgaga tggcagaaga cctgtgcaag 1320
ataggagcag agaggtccct tgtcctggac aggctggcaa gcaatgtcgc caaacgtaag 1380
agctctatgc ctcagaaatt tcttggagac aagtgcctgt cagacatgcc ctatgacagt 1440
gccaactatg agaaggagga tatgatgaca tcccacgtga tggaccaggc catcaacaat 1500
gccatcaact acctgggggc tgagtccctg cgcccattgg tgcagacacc ccccggtagc 1560
tccgaggtgg tgccagtcat cagctccatg taccagctgc acaagccccc ctcagatggc 1620
cccccacggt ccaaccattc agcacaggac gccgtggata acttgctgct gctgtccaag 1680
gccaagtctg tgtcatcgga gcgagaggcc tccccgagca acagctgcca agactccaca 1740
gatacagaga gcaacgcgga ggaacagcgc agcggcctta tctacctaac caaccacatc 1800
aacccgcatg cacgcaatgg gctggctctc aaggaggagc agcgcgccta cgaggtgctg 1860
agggcggcct cagagaactc gcaggatgcc ttccgtgtgg tcagcacgag tggcgagcag 1920
ctgaaggtgt acaagtgcga acactgccgc gtgctcttcc tggatcacgt catgtatacc 1980
attcacatgg gctgccatgg ctttcgggat ccctttgagt gtaacatgtg tggttatcac 2040
agccaggaca ggtacgagtt ctcatcccat atcacgcggg gggagcatcg ttaccacctg 2100
agctaaaccc agccaggccc cactgaagca caaagatagc tggttatgcc tccttcccgg 2160
cagctggacc cacagcggac aatgttggga gtggatttgc aggcagcatt tgttctttta 2220
tgttggttgt ttggcgtttg atttgcgttg gaagataagt ttttaatgtt agtgacagga 2280
ttgcattgca tcaggaacat tcacaacatc catccttcta gccagttttg ttcactggta 2340
gctgaggttt cccggatatg tggcttccta acactctccc cacccacccc accccccaaa 2400
acagagcctg aatcttcatg aagtgaataa aacaattatc caagaaggag taaggtggat 2460
cttgccctaa gcagagttta tgccacaaag attctccaaa tcccccaaga cagcacagcc 2520
actggggttg agccatctca gggagctctg caggtgagcc agaggaccag atataaggca 2580
gctggggagg agcagggaca tcagcctgtg cagagaccaa ggccaaaggt tgaactttga 2640
aagactatta agtcatatat tgtatggcaa tatggtgtct ggacaagttg tgcaatgtgc 2700
tgaagggaag ggattggaga gccttgaaga ctcttcttca tttgcctgat caacccgacc 2760
tccagagggt ttgttgccca gtaagacgag ctcagtgctc ttgtgatcat ttttctctta 2820
tcgtttccat gccgttgatg gccctgaagc tcatcactgc attttagaac ccaatcctga 2880
aattgggacc ttttttttaa acttctgata ctgtaaaact tcttggaagc caaagctttc 2940
ttccaagccc catcctcagt tatcctggtt cctgttcttc cccgagctga tagtaccagg 3000
acctgttatt ccacaaaagc acaggcatcc gtcacttcaa ttcaatccct gttcagatta 3060
tagatatgga ctttgctatc ttgataaatg tcttctctat gttattttgt ctgaaaaacc 3120
tataaaacca ttattaagaa tgaccatttt tagatggaag aaatgagccc agcatctcag 3180
tggctaaaac acaaaatatc catgctttta aacaaaattg ttaaatattc cgaagctctc 3240
tagtataaac accaagtagc atgtgttttc acataaagaa gacaggggcc atgcaacctt 3300
tatcaagtgg aggtattaga atgttgtaat gtttggagac acagtgtgac cagtacaggt 3360
tcccagagag gaatgcccac catatcacag aaaggtagag gtgggatctg gtatagccag 3420
accaagacag ggatgtcacg ctgaagccaa gtcagttagc tgaagattct caacaggaag 3480
gcctctctta agagtcagta atagggttgt taccatccac cacctcaaca aaacaaaaag 3540
cttataattg taaatgttta cagcactgtc ttcgcagaaa ctttctgagg tgattccaaa 3600
gaactagagg ggagatggtc tataacagct cttgaagtaa acgaggttct tagtctcagc 3660
tctcctgaca tatagggctt gatcattact ggtagggatt gttctgtgaa ttgcttacta 3720
ctacccctgg tctctcccca gtagatgcca ggaacattct agctgatacc taactgtctt 3780
cccaggtgtt cgagggagca aaccactgat ctaaactcta aacgctgaag tacgcaggtt 3840
ttctaaaaat gacaagccct tgaaaccttt cccagtaggc agcctcgagc tggacttgtg 3900
tctttggaat gctgatgaat tctatagatc agcattgcaa atacacttca aatacgtctg 3960
agttcaagtg cagggactga gttcaccaag gtgtgaaatg tgctcaaaaa gttcaaaagt 4020
gtgtgtttct ttgtttctaa aacattgtgg catctttttc atttgtttct aaaacttttt 4080
ttttagaaac aaatgaagca cttggaaagt gaaagtaaaa ttacaaatat aaggatttac 4140
actgaagaga gaaaaatttt aggaactata gctgtgaaaa gattttgttc aaaaggcagg 4200
ctagccttac ccaaattcat atatggcagg tgtcaacctc ccaagcttac agttagcagg 4260
cagcttttgc tcactcatcc ttagccatga gagccattaa gtgtggtcca agaaagatgg 4320
ctccaaaccc tacccccgac ccaccagtgg tattcagaga ttaaagcaga attgtaaata 4380
gtggcttcag gagctctttt ttagaatgct ttgccccttc ctctcactgc ctttttttagc 4440 caatataaat gtcaatttgc acaccttttg ttgtggtttt atattgtaac agcatttttt 4500

```
tgaaactatt gtatttaaga taaggtttca tattatgtcc acaagtaatt aaattatgtt   4560

tgaaggtggc tatatgctgt atcagaagtt gatgatgttt ttctttagct ggtaaaggag   4620

ggttttgcat gacctcactg tttgttctgt ggtttgttct gttgtatgat gtgtgtcttg   4680

agttttgctg tgtgatgaag tgcgctgaga ttccagtgcc ctcaagttgt gttttaagta   4740

gctatcagag gcaagagggt tcctaagagc aggttgacct gttggcgaca gatggcaatc   4800

accatttctc attccttctt ctccctgtta ccccagcttc ctgtcccagg tcccttctgt   4860

gattcttacc ttagtgtgca tgtgtgtctg tcctggtgag agtcaggagc atcgatatgt   4920

tatcattgca ttatcaccaa gggcacgcac agcctagcac ctgttgcttc agataccgtc   4980

acactctgtt tccaatttag atacaaccac ataataaaat gttagagtct tcaatgggaa   5040

gcagaggtgc ttgttataaa gatgggggct tatgcttgtg tcacattttg tgttcttttc   5100

ttcttttgtt tggttttaac ttaattgtga cccttgtaac atcatcttgc caaaaaaaaa   5160

aaaaaagttg aactggattt atgtagacat gtcaagacgt actatctatt tctttgtcag   5220

ttatagcaat aagagtggat aaactctaaa atccagatct cccacaatga acatccgtgt   5280

tctttctatg atttttcttt ctttatggtg agccacaatt aaacttgaga tgtacagcca   5340

cccaaaccca ggaagctcat gtgcatctgg tgctatggca ctcactgtga ataagtgtga   5400

ccagatatta atatgcaata ttgtttccaa tcctttctaa tacatttttt c            5451
```

<210> SEQ ID NO 7
<211> LENGTH: 1548
<212> TYPE: DNA
<213> ORGANISM: mus musculus

<400> SEQUENCE: 7

```
atggatgtcg atgagggtca agacatgtcc caagtttcag gaaaggagag ccccccagtc     60

agtgacactc cagatgaagg ggatgagccc atgcctgtcc ctgaggacct gtccactacc    120

tctggagcac agcagaactc caagagtgat cgaggcatgg ccagtaatgt taaagtagag    180

actcagagtg atgaagagaa tgggcgtgcc tgtgaaatga atggggaaga atgtgcagag    240

gatttacgaa tgcttgatgc ctcgggagag aaaatgaatg gctcccacag ggaccaaggc    300

agctcggctt tgtcaggagt tggaggcatt cgacttccta acggaaaact aaagtgtgat    360

atctgtggga tcgtttgcat cgggcccaat gtgctcatgg ttcacaaaag aagtcatact    420

ggtgaacggc ctttccagtg caaccagtgt ggggcctcct ttacccagaa aggcaacctc    480

ctgcggcaca tcaagctgca ctcgggtgag aagcccttca aatgccatct ttgcaactat    540

gcctgccgcc ggagggacgc cctcaccggc cacctgagga cgcactccgt tggtaagcct    600

cacaaatgtg gatattgtgg ccggagctat aaacagcgaa gctctttaga ggagcataaa    660

gagcgatgcc acaactactt ggaaagcatg ggccttccgg gcatgtaccc agtcattaag    720

gaagaaacta accacaacga gatggcagaa gacctgtgca agataggagc agagaggtcc    780

cttgtcctgg acaggctggc aagcaatgtc gccaaacgta agagctctat gcctcagaaa    840

tttcttggag acaagtgcct gtcagacatg ccctatgaca gtgccaacta tgagaaggag    900

gatatgatga catcccacgt gatggaccag gccatcaaca atgccatcaa ctacctgggg    960

gctgagtccc tgcgcccatt ggtgcagaca ccccccggta gctccgaggt ggtgccagtc   1020

atcagctcca tgtaccagct gcacaagccc ccctcagatg gcccccccacg gtccaaccat   1080

tcagcacagg acgccgtgga taacttgctg ctgctgtcca aggccaagtc tgtgtcatcg   1140

gagcgagagg cctccccgag caacagctgc caagactcca cagatacaga gagcaacgcg   1200
```

gaggaacagc gcagcggcct tatctaccta accaaccaca tcaacccgca tgcacgcaat 1260
gggctggctc tcaaggagga gcagcgcgcc tacgaggtgc tgagggcggc ctcagagaac 1320
tcgcaggatg ccttccgtgt ggtcagcacg agtggcgagc agctgaaggt gtacaagtgc 1380
gaacactgcc gcgtgctctt cctggatcac gtcatgtata ccattcacat gggctgccat 1440
ggctttcggg atccctttga gtgtaacatg tgtggttatc acagccagga caggtacgag 1500
ttctcatccc atatcacgcg gggggagcat cgttaccacc tgagctaa 1548

<210> SEQ ID NO 8
<211> LENGTH: 4859
<212> TYPE: DNA
<213> ORGANISM: mus musculus

<400> SEQUENCE: 8
tggagactgg ttctaccttt ctctgaaccc cagtggtgtg tgaaggccgg actgggagct 60
tgggggaaga ggaagaggaa gaggaatctg cggctcatcc agggatcagg gtccttccca 120
agtggccact cagaggggac tcagagcaag tctagatttg tgtggcagag agagacagct 180
ctcgtttggc cttggggagg cacaagtctg ttgataacct gaagacaatg gatgtcgatg 240
agggtcaaga catgtcccaa gtttcaggaa aggagagccc cccagtcagt gacactccag 300
atgaagggga tgagcccatg cctgtccctg aggacctgtc cactacctct ggagcacagc 360
agaactccaa gagtgatcga ggcatgggtg aacggccttt ccagtgcaac cagtgtgggg 420
cctcctttac ccagaaaggc aacctcctgc ggcacatcaa gctgcactcg ggtgagaagc 480
ccttcaaatg ccatctttgc aactatgcct gccgccggag ggacgccctc accggccacc 540
tgaggacgca ctccgttggt aagcctcaca aatgtggata ttgtggccgg agctataaac 600
agcgaagctc tttagaggag cataaagagc gatgccacaa ctacttggaa agcatgggcc 660
ttccgggcat gtacccagtc attaaggaag aaactaacca caacgagatg gcagaagacc 720
tgtgcaagat aggagcagag aggtcccttg tcctggacag gctggcaagc aatgtcgcca 780
aacgtaagag ctctatgcct cagaaatttc ttggagacaa gtgcctgtca gacatgccct 840
atgacagtgc caactatgag aaggaggata tgatgacatc ccacgtgatg gaccaggcca 900
tcaacaatgc catcaactac ctgggggctg agtccctgcg cccattggtg cagacacccc 960
ccggtagctc cgaggtggtg ccagtcatca gctccatgta ccagctgcac aagcccccct 1020
cagatggccc cccacggtcc aaccattcag cacaggacgc cgtggataac ttgctgctgc 1080
tgtccaaggc caagtctgtg tcatcggagc gagaggcctc cccgagcaac agctgccaag 1140
actccacaga tacagagagc aacgcggagg aacagcgcag cggccttatc tacctaacca 1200
accacatcaa cccgcatgca cgcaatgggc tggctctcaa ggaggagcag cgcgcctacg 1260
aggtgctgag ggcggcctca gagaactcgc aggatgcctt ccgtgtggtc agcacgagtg 1320
gcgagcagct gaaggtgtac aagtgcgaac actgccgcgt gctcttcctg gatcacgtca 1380
tgtataccat tcacatgggc tgccatggct ttcgggatcc ctttgagtgt aacatgtgtg 1440
gttatcacag ccaggacagg tacgagttct catcccatat cacgcggggg gagcatcgtt 1500
accacctgag ctaaacccag ccaggcccca ctgaagcaca aagatagctg gttatgcctc 1560
cttcccggca gctggaccca cagcggacaa tgttgggagt ggatttgcag gcagcatttg 1620
ttcttttatg ttggttgttt ggcgtttgat ttgcgttgga agataagttt ttaatgttag 1680
tgacaggatt gcattgcatc aggaacattc acaacatcca tccttctagc cagttttgtt 1740
cactggtagc tgaggtttcc cggatatgtg gcttcctaac actctcccca cccaccccac 1800
cccccaaaac agagcctgaa tcttcatgaa gtgaataaaa caattatcca agaaggagta 1860
aggtggatct tgccctaagc agagtttatg ccacaaagat tctccaaatc ccccaagaca 1920
gcacagccac tggggttgag ccatctcagg gagctctgca ggtgagccag aggaccagat 1980
ataaggcagc tggggaggag cagggacatc agcctgtgca gagaccaagg ccaaaggttg 2040
aactttgaaa gactattaag tcatatattg tatggcaata tggtgtctgg acaagttgtg 2100
caatgtgctg aagggaaggg attggagagc cttgaagact cttcttcatt tgcctgatca 2160
acccgacctc cagagggttt gttgcccagt aagacgagct cagtgctctt gtgatcattt 2220
ttctcttatc gtttccatgc cgttgatggc cctgaagctc atcactgcat tttagaaccc 2280
aatcctgaaa ttgggacctt ttttttaaac ttctgatact gtaaaacttc ttggaagcca 2340
aagctttctt ccaagcccca tcctcagtta tcctggttcc tgttcttccc cgagctgata 2400
gtaccaggac ctgttattcc acaaaagcac aggcatccgt cacttcaatt caatccctgt 2460
tcagattata gatatggact ttgctatctt gataaatgtc ttctctatgt tattttgtct 2520
gaaaaaccta taaaaccatt attaagaatg accattttta gatggaagaa atgagcccag 2580
catctcagtg gctaaaacac aaaatatcca tgcttttaaa caaaattgtt aaatattccg 2640
aagctctcta gtataaacac caagtagcat gtgttttcac ataaagaaga caggggccat 2700
gcaaccttta tcaagtggag gtattagaat gttgtaatgt ttggagacac agtgtgacca 2760
gtacaggttc ccagagagga atgcccacca tatcacagaa aggtagaggt gggatctggt 2820
atagccagac caagacaggg atgtcacgct gaagccaagt cagttagctg aagattctca 2880
acaggaaggc ctctcttaag agtcagtaat agggttgtta ccatccacca cctcaacaaa 2940
acaaaaagct tataattgta aatgtttaca gcactgtctt cgcagaaact ttctgaggtg 3000
attccaaaga actagagggg agatggtcta taacagctct tgaagtaaac gaggttctta 3060
gtctcagctc tcctgacata tagggcttga tcattactgg tagggattgt tctgtgaatt 3120
gcttactact accccctggtc tctccccagt agatgccagg aacattctag ctgataccta 3180
actgtcttcc caggtgttcg agggagcaaa ccactgatct aaactctaaa cgctgaagta 3240
cgcaggtttt ctaaaaatga caagcccttg aaacctttcc cagtaggcag cctcgagctg 3300
gacttgtgtc tttggaatgc tgatgaattc tatagatcag cattgcaaat acacttcaaa 3360
tacgtctgag ttcaagtgca gggactgagt tcaccaaggt gtgaaatgtg ctcaaaaagt 3420
tcaaaagtgt gtgtttcttt gtttctaaaa cattgtggca tctttttcat ttgtttctaa 3480
aacttttttt ttagaaacaa atgaagcact tggaaagtga aagtaaaatt acaaatataa 3540
ggatttacac tgaagagaga aaaattttag gaactatagc tgtgaaaaga ttttgttcaa 3600
aaggcaggct agccttaccc aaattcatat atggcaggtg tcaacctccc aagcttacag 3660
ttagcaggca gcttttgctc actcatcctt agccatgaga gccattaagt gtggtccaag 3720
aaagatggct ccaaacccta cccccgaccc accagtggta ttcagagatt aaagcagaat 3780
tgtaaatagt ggcttcagga gctctttttt agaatgcttt gccccttcct ctcactgcct 3840
tttttagcca atataaatgt caatttgcac accttttgtt gtggttttat attgtaacag 3900
cattttttttg aaactattgt atttaagata aggtttcata ttatgtccac aagtaattaa 3960
attatgtttg aaggtggcta tatgctgtat cagaagttga tgatgttttt ctttagctgg 4020
taaaggaggg ttttgcatga cctcactgtt tgttctgtgg tttgttctgt tgtatgatgt 4080
gtgtcttgag ttttgctgtg tgatgaagtg cgctgagatt ccagtgccct caagttgtgt 4140
tttaagtagc tatcagaggc aagagggttc ctaagagcag gttgacctgt tggcgacaga 4200
tggcaatcac catttctcat tccttcttct ccctgttacc ccagcttcct gtcccaggtc 4260
ccttctgtga ttcttacctt agtgtgcatg tgtgtctgtc ctggtgagag tcaggagcat 4320
cgatatgtta tcattgcatt atcaccaagg gcacgcacag cctagcacct gttgcttcag 4380
ataccgtcac actctgtttc caatttagat acaaccacat aataaaatgt tagagtcttc 4440
aatgggaagc agaggtgctt gttataaaga tgggggctta tgcttgtgtc acattttgtg 4500
ttcttttctt cttttgtttg gttttaactt aattgtgacc cttgtaacat catcttgcca 4560
aaaaaaaaaa aaaagttgaa ctggatttat gtagacatgt caagacgtac tatctatttc 4620
tttgtcagtt atagcaataa gagtggataa actctaaaat ccagatctcc cacaatgaac 4680
atccgtgttc tttctatgat ttttctttct ttatggtgag ccacaattaa acttgagatg 4740
tacagccacc caaacccagg aagctcatgt gcatctggtg ctatggcact cactgtgaat 4800
aagtgtgacc agatattaat atgcaatatt gtttccaatc ctttctaata catttttttc 4859

<210> SEQ ID NO 9
<211> LENGTH: 4736
<212> TYPE: DNA
<213> ORGANISM: mus musculus

<400> SEQUENCE: 9
tggagactgg ttctaccttt ctctgaaccc cagtggtgtg tgaaggccgg actgggagct 60
tgggggaaga ggaagaggaa gaggaatctg cggctcatcc agggatcagg gtccttccca 120
agtggccact cagaggggac tcagagcaag tctagatttg tgtggcagag agagacagct 180
ctcgtttggc cttggggagg cacaagtctg ttgataacct gaagacaatg gatgtcgatg 240
agggtcaaga catgtcccaa gtttcaggaa aggagagccc cccagtcagt gacactccag 300
atgaagggga tgagcccatg cctgtccctg aggacctgtc cactacctct ggagcacagc 360
agaactccaa gagtgatcga ggcatgggtg aacggccttt ccagtgcaac cagtgtgggg 420
cctcctttac ccagaaaggc aacctcctgc ggcacatcaa gctgcactcg ggtgagaagc 480
ccttcaaatg ccatctttgc aactatgcct gccgccggag ggacgccctc accggccacc 540
tgaggacgca ctccgtcatt aaggaagaaa ctaaccacaa cgagatggca gaagacctgt 600
gcaagatagg agcagagagg tcccttgtcc tggacaggct ggcaagcaat gtcgccaaac 660
gtaagagctc tatgcctcag aaatttcttg gagacaagtg cctgtcagac atgccctatg 720
acagtgccaa ctatgagaag gaggatatga tgacatccca cgtgatggac caggccatca 780
acaatgccat caactacctg gggctgagt ccctgcgccc attggtgcag acaccccccg 840
gtagctccga ggtggtgcca gtcatcagct ccatgtacca gctgcacaag cccccctcag 900
atggcccccc acggtccaac cattcagcac aggacgccgt ggataacttg ctgctgctgt 960
ccaaggccaa gtctgtgtca tcggagcgag aggcctcccc gagcaacagc tgccaagact 1020
ccacagatac agagagcaac gcggaggaac agcgcagcgg ccttatctac ctaaccaacc 1080
acatcaaccc gcatgcacgc aatgggctgg ctctcaagga ggagcagcgc gcctacgagg 1140
tgctgagggc ggcctcagag aactcgcagg atgccttccg tgtggtcagc acgagtggcg 1200
agcagctgaa ggtgtacaag tgcgaacact gccgcgtgct cttcctggat cacgtcatgt 1260
ataccattca catgggctgc catggctttc gggatccctt tgagtgtaac atgtgtggtt 1320
atcacagcca ggacaggtac gagttctcat cccatatcac gcggggggag catcgttacc 1380
acctgagcta aacccagcca ggccccactg aagcacaaag atagctggtt atgcctcctt 1440
cccggcagct ggacccacag cggacaatgt tgggagtgga tttgcaggca gcatttgttc 1500
ttttatgttg gttgtttggc gtttgatttg cgttggaaga taagttttta atgttagtga 1560
caggattgca ttgcatcagg aacattcaca acatccatcc ttctagccag ttttgttcac 1620
tggtagctga ggtttcccgg atatgtggct tcctaacact ctccccaccc accccacccc 1680
ccaaaacaga gcctgaatct tcatgaagtg aataaaacaa ttatccaaga aggagtaagg 1740
tggatcttgc cctaagcaga gtttatgcca caaagattct ccaaatcccc caagacagca 1800
cagccactgg ggttgagcca tctcagggag ctctgcaggt gagccagagg accagatata 1860
aggcagctgg ggaggagcag ggacatcagc ctgtgcagag accaaggcca aaggttgaac 1920
tttgaaagac tattaagtca tatattgtat ggcaatatgg tgtctggaca agttgtgcaa 1980
tgtgctgaag ggaagggatt ggagagcctt gaagactctt cttcatttgc ctgatcaacc 2040
cgacctccag agggtttgtt gcccagtaag acgagctcag tgctcttgtg atcatttttc 2100
tcttatcgtt tccatgccgt tgatggccct gaagctcatc actgcatttt agaacccaat 2160
cctgaaattg ggaccttttt tttaaacttc tgatactgta aaacttcttg gaagccaaag 2220
ctttcttcca agccccatcc tcagttatcc tggttcctgt tcttccccga gctgatagta 2280
ccaggacctg ttattccaca aaagcacagg catccgtcac ttcaattcaa tccctgttca 2340
gattatagat atggactttg ctatcttgat aaatgtcttc tctatgttat tttgtctgaa 2400
aaacctataa aaccattatt aagaatgacc atttttagat ggaagaaatg agcccagcat 2460
ctcagtggct aaaacacaaa atatccatgc ttttaaacaa aattgttaaa tattccgaag 2520
ctctctagta taaacaccaa gtagcatgtg ttttcacata aagaagacag gggccatgca 2580
acctttatca agtggaggta ttagaatgtt gtaatgtttg gagacacagt gtgaccagta 2640
caggttccca gagaggaatg cccaccatat cacagaaagg tagaggtggg atctggtata 2700
gccagaccaa gacagggatg tcacgctgaa gccaagtcag ttagctgaag attctcaaca 2760
ggaaggcctc tcttaagagt cagtaatagg gttgttacca tccaccacct caacaaaaca 2820
aaaagcttat aattgtaaat gtttacagca ctgtcttcgc agaaactttc tgaggtgatt 2880
ccaaagaact agaggggaga tggtctataa cagctcttga agtaaacgag gttcttagtc 2940
tcagctctcc tgacatatag ggcttgatca ttactggtag ggattgttct gtgaattgct 3000
tactactacc cctggtctct ccccagtaga tgccaggaac attctagctg atacctaact 3060
gtcttcccag gtgttcgagg gagcaaacca ctgatctaaa ctctaaacgc tgaagtacgc 3120
aggttttcta aaaatgacaa gcccttgaaa cctttcccag taggcagcct cgagctggac 3180
ttgtgtcttt ggaatgctga tgaattctat agatcagcat tgcaaataca cttcaaatac 3240
gtctgagttc aagtgcaggg actgagttca ccaaggtgtg aaatgtgctc aaaaagttca 3300
aaagtgtgtg tttctttgtt tctaaaacat tgtggcatct ttttcatttg tttctaaaac 3360
ttttttttta gaaacaaatg aagcacttgg aaagtgaaag taaaattaca aatataagga 3420
tttacactga agagagaaaa attttaggaa ctatagctgt gaaaagattt tgttcaaaag 3480
gcaggctagc cttacccaaa ttcatatatg gcaggtgtca acctcccaag cttacagtta 3540
gcaggcagct tttgctcact catccttagc catgagagcc attaagtgtg gtccaagaaa 3600
gatggctcca aaccctaccc ccgacccacc agtggtattc agagattaaa gcagaattgt 3660
aaatagtggc ttcaggagct cttttttaga atgctttgcc ccttcctctc actgcctttt 3720
ttagccaata taaatgtcaa tttgcacacc ttttgttgtg gttttatatt gtaacagcat 3780 tttttttgaaa ctattgtatt taagataagg tttcatatta tgtccacaag taattaaatt 3840
atgtttgaag gtggctatat gctgtatcag aagttgatga tgttttttctt tagctggtaa 3900 aggagggttt tgcatgacct cactgtttgt tctgtggttt gttctgttgt atgatgtgtg 3960
tcttgagttt tgctgtgtga tgaagtgcgc tgagattcca gtgccctcaa gttgtgtttt 4020
aagtagctat cagaggcaag agggttccta agagcaggtt gacctgttgg cgacagatgg 4080
caatcaccat ttctcattcc ttcttctccc tgttacccca gcttcctgtc ccaggtccct 4140
tctgtgattc ttaccttagt gtgcatgtgt gtctgtcctg gtgagagtca ggagcatcga 4200
tatgttatca ttgcattatc accaagggca cgcacagcct agcacctgtt gcttcagata 4260
ccgtcacact ctgtttccaa tttagataca accacataat aaaatgttag agtcttcaat 4320
gggaagcaga ggtgcttgtt ataaagatgg gggcttatgc ttgtgtcaca ttttgtgttc 4380
ttttcttctt ttgtttggtt ttaacttaat tgtgaccctt gtaacatcat cttgccaaaa 4440
aaaaaaaaaa agttgaactg gatttatgta gacatgtcaa gacgtactat ctatttcttt 4500
gtcagttata gcaataagag tggataaact ctaaaatcca gatctcccac aatgaacatc 4560
cgtgttcttt ctatgatttt tctttcttta tggtgagcca caattaaact tgagatgtac 4620
agccacccaa acccaggaag ctcatgtgca tctggtgcta tggcactcac tgtgaataag 4680
tgtgaccaga tattaatatg caatattgtt tccaatcctt tctaatacat tttttc 4736

<210> SEQ ID NO 10
<211> LENGTH: 5421
<212> TYPE: DNA
<213> ORGANISM: mus musculus

<400> SEQUENCE: 10
gtcagggtcc cgaagccgcg tgccgtgcgc gcaggccggg tgggctgtgg gacaagccga 60
gcgggaggcg agtcgcaagc gccaacccaa agtttgcacg gtgcggggcg aggggcgcgc 120
gctccgggct gccgcaggtg gcggcgcggt gagcccgggc caggtgcccc ggcagcgggg 180
cggcgctgtc gtgcgggaca gccgggctgc caggggctcg gagccgggtc ggagcccgcg 240
gggggcgggg agtgtggcga gaaatgggga acaatgcgag tgagcaactt gaggaagtca 300
ttgtgaaaga aagctgggaa ttgctccgca gccaacttag cagggcactc taacaagtgc 360
ctgcgcggcc gcgcccgggc cggggacagg ggcagcccgg cgcagtacag cccatcccgg 420
gacgctcggc cgcggctgcc ggagacccgg taggtcccgc ggggtgcagg agcccccaga 480
tccccggctg ctcttcgcgc cccaggatca ttcttggccc ccaaagcgcg gcgcacaaat 540
ccacataacc tgaagacaat ggatgtcgat gagggtcaag acatgtccca agtttcagga 600
aaggagagcc ccccagtcag tgacactcca gatgaagggg atgagcccat gcctgtccct 660
gaggacctgt ccactacctc tggagcacag cagaactcca agagtgatcg aggcatggcc 720
agtaatgtta aagtagagac tcagagtgat gaagagaatg ggcgtgcctg tgaaatgaat 780
ggggaagaat gtgcagagga tttacgaatg cttgatgcct cgggagagaa aatgaatggc 840
tcccacaggg accaaggcag ctcggctttg tcaggagttg gaggcattcg acttcctaac 900
ggaaaactaa agtgtgatat ctgtgggatc gtttgcatcg ggcccaatgt gctcatggtt 960
cacaaaagaa gtcatactgg tgaacggcct ttccagtgca accagtgtgg ggcctccttt 1020
acccagaaag gcaacctcct gcggcacatc aagctgcact cgggtgagaa gcccttcaaa 1080
tgccatcttt gcaactatgc ctgccgccgg agggacgccc tcaccggcca cctgaggacg 1140
cactccgttg gtaagcctca caaatgtgga tattgtggcc ggagctataa acagcgaagc 1200
tctttagagg agcataaaga gcgatgccac aactacttgg aaagcatggg ccttccgggc 1260
atgtacccag tcattaagga agaaactaac cacaacgaga tggcagaaga cctgtgcaag 1320
ataggagcag agaggtccct tgtcctggac aggctggcaa gcaatgtcgc caaacgagac 1380
aagtgcctgt cagacatgcc ctatgacagt gccaactatg agaaggagga tatgatgaca 1440
tcccacgtga tggaccaggc catcaacaat gccatcaact acctgggggc tgagtccctg 1500
cgcccattgg tgcagacacc ccccggtagc tccgaggtgg tgccagtcat cagctccatg 1560
taccagctgc acaagccccc ctcagatggc ccccccacggt ccaaccattc agcacaggac 1620
gccgtggata acttgctgct gctgtccaag gccaagtctg tgtcatcgga gcgagaggcc 1680
tccccgagca acagctgcca agactccaca gatacagaga gcaacgcgga ggaacagcgc 1740
agcggcctta tctacctaac caaccacatc aacccgcatg cacgcaatgg gctggctctc 1800
aaggaggagc agcgcgccta cgaggtgctg agggcggcct cagagaactc gcaggatgcc 1860
ttccgtgtgg tcagcacgag tggcgagcag ctgaaggtgt acaagtgcga acactgccgc 1920
gtgctcttcc tggatcacgt catgtatacc attcacatgg gctgccatgg ctttcgggat 1980
ccctttgagt gtaacatgtg tggttatcac agccaggaca ggtacgagtt ctcatcccat 2040
atcacgcggg gggagcatcg ttaccacctg agctaaaccc agccaggccc cactgaagca 2100
caaagatagc tggttatgcc tccttcccgg cagctggacc cacagcggac aatgttggga 2160
gtggatttgc aggcagcatt tgttctttta tgttggttgt ttggcgtttg atttgcgttg 2220
gaagataagt ttttaatgtt agtgacagga ttgcattgca tcaggaacat tcacaacatc 2280
catccttcta gccagttttg ttcactggta gctgaggttt cccggatatg tggcttccta 2340
acactctccc cacccacccc accccccaaa acagagcctg aatcttcatg aagtgaataa 2400
aacaattatc caagaaggag taaggtggat cttgccctaa gcagagttta tgccacaaag 2460
attctccaaa tcccccaaga cagcacagcc actggggttg agccatctca gggagctctg 2520
caggtgagcc agaggaccag atataaggca gctggggagg agcagggaca tcagcctgtg 2580
cagagaccaa ggccaaaggt tgaactttga aagactatta agtcatatat tgtatggcaa 2640
tatggtgtct ggacaagttg tgcaatgtgc tgaagggaag ggattggaga gccttgaaga 2700
ctcttcttca tttgcctgat caacccgacc tccagagggt ttgttgccca gtaagacgag 2760
ctcagtgctc ttgtgatcat ttttctctta tcgtttccat gccgttgatg gccctgaagc 2820
tcatcactgc attttagaac ccaatcctga aattgggacc tttttttaa acttctgata 2880
ctgtaaaact tcttggaagc caaagctttc ttccaagccc catcctcagt tatcctggtt 2940
cctgttcttc cccgagctga tagtaccagg acctgttatt ccacaaaagc acaggcatcc 3000
gtcacttcaa ttcaatccct gttcagatta tagatatgga ctttgctatc ttgataaatg 3060
tcttctctat gttattttgt ctgaaaaacc tataaaacca ttattaagaa tgaccatttt 3120
tagatggaag aaatgagccc agcatctcag tggctaaaac acaaaatatc catgctttta 3180
aacaaaattg ttaaatattc cgaagctctc tagtataaac accaagtagc atgtgttttc 3240
acataaagaa gacaggggcc atgcaacctt tatcaagtgg aggtattaga atgttgtaat 3300
gtttggagac acagtgtgac cagtacaggt tcccagagag gaatgcccac catatcacag 3360
aaaggtagag gtgggatctg gtatagccag accaagacag ggatgtcacg ctgaagccaa 3420
gtcagttagc tgaagattct caacaggaag gcctctctta agagtcagta atagggttgt 3480
taccatccac cacctcaaca aaacaaaaag cttataattg taaatgttta cagcactgtc 3540
ttcgcagaaa ctttctgagg tgattccaaa gaactagagg ggagatggtc tataacagct 3600
cttgaagtaa acgaggttct tagtctcagc tctcctgaca tatagggctt gatcattact 3660
ggtagggatt gttctgtgaa ttgcttacta ctacccctgg tctctcccca gtagatgcca 3720
ggaacattct agctgatacc taactgtctt cccaggtgtt cgagggagca aaccactgat 3780
ctaaactcta aacgctgaag tacgcaggtt ttctaaaaat gacaagccct tgaaaccttt 3840
cccagtaggc agcctcgagc tggacttgtg tctttggaat gctgatgaat tctatagatc 3900
agcattgcaa atacacttca aatacgtctg agttcaagtg cagggactga gttcaccaag 3960
gtgtgaaatg tgctcaaaaa gttcaaaagt gtgtgtttct ttgtttctaa aacattgtgg 4020
catctttttc atttgtttct aaaacttttt ttttagaaac aaatgaagca cttggaaagt 4080
gaaagtaaaa ttacaaatat aaggatttac actgaagaga gaaaaatttt aggaactata 4140
gctgtgaaaa gattttgttc aaaaggcagg ctagccttac ccaaattcat atatggcagg 4200
tgtcaacctc ccaagcttac agttagcagg cagcttttgc tcactcatcc ttagccatga 4260
gagccattaa gtgtggtcca agaaagatgg ctccaaaccc tacccccgac ccaccagtgg 4320
tattcagaga ttaaagcaga attgtaaata gtggcttcag gagctctttt ttagaatgct 4380
ttgccccttc ctctcactgc cttttttagc caatataaat gtcaatttgc acaccttttg 4440
ttgtggtttt atattgtaac agcatttttt tgaaactatt gtatttaaga taaggtttca 4500
tattatgtcc acaagtaatt aaattatgtt tgaaggtggc tatatgctgt atcagaagtt 4560
gatgatgttt ttctttagct ggtaaaggag ggttttgcat gacctcactg tttgttctgt 4620
ggtttgttct gttgtatgat gtgtgtcttg agttttgctg tgtgatgaag tgcgctgaga 4680
ttccagtgcc ctcaagttgt gttttaagta gctatcagag gcaagagggt tcctaagagc 4740
aggttgacct gttggcgaca gatggcaatc accatttctc attccttctt ctccctgtta 4800
ccccagcttc ctgtcccagg tcccttctgt gattcttacc ttagtgtgca tgtgtgtctg 4860
tcctggtgag agtcaggagc atcgatatgt tatcattgca ttatcaccaa gggcacgcac 4920
agcctagcac ctgttgcttc agataccgtc acactctgtt tccaatttag atacaaccac 4980
ataataaaat gttagagtct tcaatgggaa gcagaggtgc ttgttataaa gatgggggct 5040
tatgcttgtg tcacattttg tgttcttttc ttcttttgtt tggttttaac ttaattgtga 5100
cccttgtaac atcatcttgc caaaaaaaaa aaaaaagttg aactggattt atgtagacat 5160
gtcaagacgt actatctatt tctttgtcag ttatagcaat aagagtggat aaactctaaa 5220
atccagatct cccacaatga acatccgtgt tctttctatg atttttcttt ctttatggtg 5280
agccacaatt aaacttgaga tgtacagcca cccaaaccca ggaagctcat gtgcatctgg 5340
tgctatggca ctcactgtga ataagtgtga ccagatatta atatgcaata ttgtttccaa 5400
tcctttctaa tacatttttt c 5421

<210> SEQ ID NO 11
<211> LENGTH: 519
<212> TYPE: PRT
<213> ORGANISM: homo sapiens

<400> SEQUENCE: 11

Met Asp Ala Asp Glu Gly Gln Asp Met Ser Gln Val Ser Gly Lys Glu
1 5 10 15

Ser Pro Pro Val Ser Asp Thr Pro Asp Glu Gly Asp Glu Pro Met Pro
20 25 30

-continued

```
Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Thr Leu Tyr Pro Val Ile
225                 230                 235                 240

Lys Glu Glu Thr Asn His Ser Glu Met Ala Glu Asp Leu Cys Lys Ile
                245                 250                 255

Gly Ser Glu Arg Ser Leu Val Leu Asp Arg Leu Ala Ser Asn Val Ala
            260                 265                 270

Lys Arg Lys Ser Ser Met Pro Gln Lys Phe Leu Gly Asp Lys Gly Leu
        275                 280                 285

Ser Asp Thr Pro Tyr Asp Ser Ser Ala Ser Tyr Glu Lys Glu Asn Glu
    290                 295                 300

Met Met Lys Ser His Val Met Asp Gln Ala Ile Asn Asn Ala Ile Asn
305                 310                 315                 320

Tyr Leu Gly Ala Glu Ser Leu Arg Pro Leu Val Gln Thr Pro Pro Gly
                325                 330                 335

Gly Ser Glu Val Val Pro Val Ile Ser Pro Met Tyr Gln Leu His Lys
            340                 345                 350

Pro Leu Ala Glu Gly Thr Pro Arg Ser Asn His Ser Ala Gln Asp Ser
        355                 360                 365

Ala Val Glu Asn Leu Leu Leu Leu Ser Lys Ala Lys Leu Val Pro Ser
    370                 375                 380

Glu Arg Glu Ala Ser Pro Ser Asn Ser Cys Gln Asp Ser Thr Asp Thr
385                 390                 395                 400

Glu Ser Asn Asn Glu Glu Gln Arg Ser Gly Leu Ile Tyr Leu Thr Asn
                405                 410                 415

His Ile Ala Pro His Ala Arg Asn Gly Leu Ser Leu Lys Glu Glu His
            420                 425                 430

Arg Ala Tyr Asp Leu Leu Arg Ala Ala Ser Glu Asn Ser Gln Asp Ala
        435                 440                 445

Leu Arg Val Val Ser Thr Ser Gly Glu Gln Met Lys Val Tyr Lys Cys
```

```
    450                 455                 460

Glu His Cys Arg Val Leu Phe Leu Asp His Val Met Tyr Thr Ile His
465                 470                 475                 480

Met Gly Cys His Gly Phe Arg Asp Pro Phe Glu Cys Asn Met Cys Gly
                485                 490                 495

Tyr His Ser Gln Asp Arg Tyr Glu Phe Ser Ser His Ile Thr Arg Gly
            500                 505                 510

Glu His Arg Phe His Met Ser
        515


<210> SEQ ID NO 12
<211> LENGTH: 432
<212> TYPE: PRT
<213> ORGANISM: homo sapiens

<400> SEQUENCE: 12

Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Ile Pro Glu Asp Leu Ser Thr Thr Ser Gly Gly Gln Gln Ser Ser Lys
        35                  40                  45

Ser Asp Arg Val Val Gly Glu Arg Pro Phe Gln Cys Asn Gln Cys Gly
    50                  55                  60

Ala Ser Phe Thr Gln Lys Gly Asn Leu Leu Arg His Ile Lys Leu His
65                  70                  75                  80

Ser Gly Glu Lys Pro Phe Lys Cys His Leu Cys Asn Tyr Ala Cys Arg
                85                  90                  95

Arg Arg Asp Ala Leu Thr Gly His Leu Arg Thr His Ser Val Gly Lys
            100                 105                 110

Pro His Lys Cys Gly Tyr Cys Gly Arg Ser Tyr Lys Gln Arg Ser Ser
        115                 120                 125

Leu Glu Glu His Lys Glu Arg Cys His Asn Tyr Leu Glu Ser Met Gly
    130                 135                 140

Leu Pro Gly Thr Leu Tyr Pro Val Ile Lys Glu Glu Thr Asn His Ser
145                 150                 155                 160

Glu Met Ala Glu Asp Leu Cys Lys Ile Gly Ser Glu Arg Ser Leu Val
                165                 170                 175

Leu Asp Arg Leu Ala Ser Asn Val Ala Lys Arg Lys Ser Ser Met Pro
            180                 185                 190

Gln Lys Phe Leu Gly Asp Lys Gly Leu Ser Asp Thr Pro Tyr Asp Ser
        195                 200                 205

Ser Ala Ser Tyr Glu Lys Glu Asn Glu Met Met Lys Ser His Val Met
    210                 215                 220

Asp Gln Ala Ile Asn Asn Ala Ile Asn Tyr Leu Gly Ala Glu Ser Leu
225                 230                 235                 240

Arg Pro Leu Val Gln Thr Pro Pro Gly Gly Ser Glu Val Val Pro Val
                245                 250                 255

Ile Ser Pro Met Tyr Gln Leu His Lys Pro Leu Ala Glu Gly Thr Pro
            260                 265                 270

Arg Ser Asn His Ser Ala Gln Asp Ser Ala Val Glu Asn Leu Leu Leu
        275                 280                 285

Leu Ser Lys Ala Lys Leu Val Pro Ser Glu Arg Glu Ala Ser Pro Ser
    290                 295                 300
```

```
Asn Ser Cys Gln Asp Ser Thr Asp Thr Glu Ser Asn Asn Glu Glu Gln
305                 310                 315                 320

Arg Ser Gly Leu Ile Tyr Leu Thr Asn His Ile Ala Pro His Ala Arg
                325                 330                 335

Asn Gly Leu Ser Leu Lys Glu Glu His Arg Ala Tyr Asp Leu Leu Arg
            340                 345                 350

Ala Ala Ser Glu Asn Ser Gln Asp Ala Leu Arg Val Val Ser Thr Ser
        355                 360                 365

Gly Glu Gln Met Lys Val Tyr Lys Cys Glu His Cys Arg Val Leu Phe
    370                 375                 380

Leu Asp His Val Met Tyr Thr Ile His Met Gly Cys His Gly Phe Arg
385                 390                 395                 400

Asp Pro Phe Glu Cys Asn Met Cys Gly Tyr His Ser Gln Asp Arg Tyr
                405                 410                 415

Glu Phe Ser Ser His Ile Thr Arg Gly Glu His Arg Phe His Met Ser
            420                 425                 430


<210> SEQ ID NO 13
<211> LENGTH: 431
<212> TYPE: PRT
<213> ORGANISM: homo sapiens

<400> SEQUENCE: 13

Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Gly Asp Lys Gly Leu Ser Asp Thr Pro Tyr Asp Ser
        195                 200                 205

Ser Ala Ser Tyr Glu Lys Glu Asn Glu Met Met Lys Ser His Val Met
    210                 215                 220

Asp Gln Ala Ile Asn Asn Ala Ile Asn Tyr Leu Gly Ala Glu Ser Leu
225                 230                 235                 240

Arg Pro Leu Val Gln Thr Pro Pro Gly Gly Ser Glu Val Val Pro Val
                245                 250                 255
```

```
Ile Ser Pro Met Tyr Gln Leu His Lys Pro Leu Ala Glu Gly Thr Pro
            260                 265                 270

Arg Ser Asn His Ser Ala Gln Asp Ser Ala Val Glu Asn Leu Leu Leu
        275                 280                 285

Leu Ser Lys Ala Lys Leu Val Pro Ser Glu Arg Glu Ala Ser Pro Ser
    290                 295                 300

Asn Ser Cys Gln Asp Ser Thr Asp Thr Glu Ser Asn Asn Glu Glu Gln
305                 310                 315                 320

Arg Ser Gly Leu Ile Tyr Leu Thr Asn His Ile Ala Pro His Ala Arg
                325                 330                 335

Asn Gly Leu Ser Leu Lys Glu Glu His Arg Ala Tyr Asp Leu Leu Arg
            340                 345                 350

Ala Ala Ser Glu Asn Ser Gln Asp Ala Leu Arg Val Val Ser Thr Ser
        355                 360                 365

Gly Glu Gln Met Lys Val Tyr Lys Cys Glu His Cys Arg Val Leu Phe
    370                 375                 380

Leu Asp His Val Met Tyr Thr Ile His Met Gly Cys His Gly Phe Arg
385                 390                 395                 400

Asp Pro Phe Glu Cys Asn Met Cys Gly Tyr His Ser Gln Asp Arg Tyr
                405                 410                 415

Glu Phe Ser Ser Ile Thr Arg Gly Glu His Arg Phe His Met Ser
            420                 425                 430


<210> SEQ ID NO 14
<211> LENGTH: 388
<212> TYPE: PRT
<213> ORGANISM: homo sapiens

<400> SEQUENCE: 14

Met Asp Ala Asp Glu Gly Gln Asp Met Ala Ser Asn Val Lys Val Glu
1               5                   10                  15

Thr Gln Ser Asp Glu Glu Asn Gly Arg Ala Cys Glu Met Asn Gly Glu
            20                  25                  30

Glu Cys Ala Glu Asp Leu Arg Met Leu Asp Ala Ser Gly Glu Lys Met
        35                  40                  45

Asn Gly Ser His Arg Asp Gln Gly Ser Ser Ala Leu Ser Gly Val Gly
    50                  55                  60

Gly Ile Arg Leu Pro Asn Gly Lys Leu Lys Cys Asp Ile Cys Gly Ile
65                  70                  75                  80

Ile Cys Ile Gly Pro Asn Val Leu Met Val His Lys Arg Ser His Thr
                85                  90                  95

Gly Glu Arg Pro Phe Gln Cys Asn Gln Cys Gly Ala Ser Phe Thr Gln
            100                 105                 110

Lys Gly Asn Leu Leu Arg His Ile Lys Leu His Ser Gly Glu Lys Pro
        115                 120                 125

Phe Lys Cys His Leu Cys Asn Tyr Ala Cys Arg Arg Arg Asp Ala Leu
    130                 135                 140

Thr Gly His Leu Arg Thr His Ser Gly Asp Lys Gly Leu Ser Asp Thr
145                 150                 155                 160

Pro Tyr Asp Ser Ser Ala Ser Tyr Glu Lys Glu Asn Glu Met Met Lys
                165                 170                 175

Ser His Val Met Asp Gln Ala Ile Asn Asn Ala Ile Asn Tyr Leu Gly
            180                 185                 190

Ala Glu Ser Leu Arg Pro Leu Val Gln Thr Pro Pro Gly Gly Ser Glu
```

```
        195                 200                 205

Val Val Pro Val Ile Ser Pro Met Tyr Gln Leu His Lys Pro Leu Ala
    210                 215                 220

Glu Gly Thr Pro Arg Ser Asn His Ser Ala Gln Asp Ser Ala Val Glu
225                 230                 235                 240

Asn Leu Leu Leu Leu Ser Lys Ala Lys Leu Val Pro Ser Glu Arg Glu
                245                 250                 255

Ala Ser Pro Ser Asn Ser Cys Gln Asp Ser Thr Asp Thr Glu Ser Asn
            260                 265                 270

Asn Glu Glu Gln Arg Ser Gly Leu Ile Tyr Leu Thr Asn His Ile Ala
        275                 280                 285

Pro His Ala Arg Asn Gly Leu Ser Leu Lys Glu Glu His Arg Ala Tyr
    290                 295                 300

Asp Leu Leu Arg Ala Ala Ser Glu Asn Ser Gln Asp Ala Leu Arg Val
305                 310                 315                 320

Val Ser Thr Ser Gly Glu Gln Met Lys Val Tyr Lys Cys Glu His Cys
                325                 330                 335

Arg Val Leu Phe Leu Asp His Val Met Tyr Thr Ile His Met Gly Cys
            340                 345                 350

His Gly Phe Arg Asp Pro Phe Glu Cys Asn Met Cys Gly Tyr His Ser
        355                 360                 365

Gln Asp Arg Tyr Glu Phe Ser Ser His Ile Thr Arg Gly Glu His Arg
    370                 375                 380

Phe His Met Ser
385


<210> SEQ ID NO 15
<211> LENGTH: 376
<212> TYPE: PRT
<213> ORGANISM: homo sapiens

<400> SEQUENCE: 15

Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Asp Lys Gly
    130                 135                 140

Leu Ser Asp Thr Pro Tyr Asp Ser Ser Ala Ser Tyr Glu Lys Glu Asn
145                 150                 155                 160

Glu Met Met Lys Ser His Val Met Asp Gln Ala Ile Asn Asn Ala Ile
                165                 170                 175
```

```
Asn Tyr Leu Gly Ala Glu Ser Leu Arg Pro Leu Val Gln Thr Pro Pro
            180                 185                 190

Gly Gly Ser Glu Val Val Pro Val Ile Ser Pro Met Tyr Gln Leu His
        195                 200                 205

Lys Pro Leu Ala Glu Gly Thr Pro Arg Ser Asn His Ser Ala Gln Asp
    210                 215                 220

Ser Ala Val Glu Asn Leu Leu Leu Leu Ser Lys Ala Lys Leu Val Pro
225                 230                 235                 240

Ser Glu Arg Glu Ala Ser Pro Ser Asn Ser Cys Gln Asp Ser Thr Asp
                245                 250                 255

Thr Glu Ser Asn Asn Glu Glu Gln Arg Ser Gly Leu Ile Tyr Leu Thr
            260                 265                 270

Asn His Ile Ala Pro His Ala Arg Asn Gly Leu Ser Leu Lys Glu Glu
        275                 280                 285

His Arg Ala Tyr Asp Leu Leu Arg Ala Ala Ser Glu Asn Ser Gln Asp
    290                 295                 300

Ala Leu Arg Val Val Ser Thr Ser Gly Glu Gln Met Lys Val Tyr Lys
305                 310                 315                 320

Cys Glu His Cys Arg Val Leu Phe Leu Asp His Val Met Tyr Thr Ile
                325                 330                 335

His Met Gly Cys His Gly Phe Arg Asp Pro Phe Glu Cys Asn Met Cys
            340                 345                 350

Gly Tyr His Ser Gln Asp Arg Tyr Glu Phe Ser Ser His Ile Thr Arg
        355                 360                 365

Gly Glu His Arg Phe His Met Ser
    370                 375
```

<210> SEQ ID NO 16
<211> LENGTH: 289
<212> TYPE: PRT
<213> ORGANISM: homo sapiens

<400> SEQUENCE: 16

```
Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Ile Pro Glu Asp Leu Ser Thr Thr Ser Gly Gly Gln Gln Ser Ser Lys
        35                  40                  45

Ser Asp Arg Val Val Gly Asp Lys Gly Leu Ser Asp Thr Pro Tyr Asp
    50                  55                  60

Ser Ser Ala Ser Tyr Glu Lys Glu Asn Glu Met Met Lys Ser His Val
65                  70                  75                  80

Met Asp Gln Ala Ile Asn Asn Ala Ile Asn Tyr Leu Gly Ala Glu Ser
                85                  90                  95

Leu Arg Pro Leu Val Gln Thr Pro Pro Gly Gly Ser Glu Val Val Pro
            100                 105                 110

Val Ile Ser Pro Met Tyr Gln Leu His Lys Pro Leu Ala Glu Gly Thr
        115                 120                 125

Pro Arg Ser Asn His Ser Ala Gln Asp Ser Ala Val Glu Asn Leu Leu
    130                 135                 140

Leu Leu Ser Lys Ala Lys Leu Val Pro Ser Glu Arg Glu Ala Ser Pro
145                 150                 155                 160

Ser Asn Ser Cys Gln Asp Ser Thr Asp Thr Glu Ser Asn Asn Glu Glu
                165                 170                 175
```

Gln Arg Ser Gly Leu Ile Tyr Leu Thr Asn His Ile Ala Pro His Ala
180 185 190

Arg Asn Gly Leu Ser Leu Lys Glu Glu His Arg Ala Tyr Asp Leu Leu
195 200 205

Arg Ala Ala Ser Glu Asn Ser Gln Asp Ala Leu Arg Val Val Ser Thr
210 215 220

Ser Gly Glu Gln Met Lys Val Tyr Lys Cys Glu His Cys Arg Val Leu
225 230 235 240

Phe Leu Asp His Val Met Tyr Thr Ile His Met Gly Cys His Gly Phe
245 250 255

Arg Asp Pro Phe Glu Cys Asn Met Cys Gly Tyr His Ser Gln Asp Arg
260 265 270

Tyr Glu Phe Ser Ser His Ile Thr Arg Gly Glu His Arg Phe His Met
275 280 285

Ser

<210> SEQ ID NO 17
<211> LENGTH: 477
<212> TYPE: PRT
<213> ORGANISM: homo sapiens

<400> SEQUENCE: 17

Met Asp Ala Asp Glu Gly Gln Asp Met Ser Gln Val Ser Gly Lys Glu
1 5 10 15

Ser Pro Pro Val Ser Asp Thr Pro Asp Glu Gly Asp Glu Pro Met Pro
20 25 30

Ile Pro Glu Asp Leu Ser Thr Thr Ser Gly Gly Gln Gln Ser Ser Lys
35 40 45

Ser Asp Arg Val Val Ala Ser Asn Val Lys Val Glu Thr Gln Ser Asp
50 55 60

Glu Glu Asn Gly Arg Ala Cys Glu Met Asn Gly Glu Glu Cys Ala Glu
65 70 75 80

Asp Leu Arg Met Leu Asp Ala Ser Gly Glu Lys Met Asn Gly Ser His
85 90 95

Arg Asp Gln Gly Ser Ser Ala Leu Ser Gly Val Gly Gly Ile Arg Leu
100 105 110

Pro Asn Gly Lys Leu Lys Cys Asp Ile Cys Gly Ile Ile Cys Ile Gly
115 120 125

Pro Asn Val Leu Met Val His Lys Arg Ser His Thr Gly Glu Arg Pro
130 135 140

Phe Gln Cys Asn Gln Cys Gly Ala Ser Phe Thr Gln Lys Gly Asn Leu
145 150 155 160

Leu Arg His Ile Lys Leu His Ser Gly Glu Lys Pro Phe Lys Cys His
165 170 175

Leu Cys Asn Tyr Ala Cys Arg Arg Arg Asp Ala Leu Thr Gly His Leu
180 185 190

Arg Thr His Ser Val Ile Lys Glu Glu Thr Asn His Ser Glu Met Ala
195 200 205

Glu Asp Leu Cys Lys Ile Gly Ser Glu Arg Ser Leu Val Leu Asp Arg
210 215 220

Leu Ala Ser Asn Val Ala Lys Arg Lys Ser Ser Met Pro Gln Lys Phe
225 230 235 240

Leu Gly Asp Lys Gly Leu Ser Asp Thr Pro Tyr Asp Ser Ser Ala Ser
245 250 255

Tyr Glu Lys Glu Asn Glu Met Met Lys Ser His Val Met Asp Gln Ala
260 265 270

Ile Asn Asn Ala Ile Asn Tyr Leu Gly Ala Glu Ser Leu Arg Pro Leu
275 280 285

Val Gln Thr Pro Pro Gly Gly Ser Glu Val Val Pro Val Ile Ser Pro
290 295 300

Met Tyr Gln Leu His Lys Pro Leu Ala Glu Gly Thr Pro Arg Ser Asn
305 310 315 320

His Ser Ala Gln Asp Ser Ala Val Glu Asn Leu Leu Leu Leu Ser Lys
325 330 335

Ala Lys Leu Val Pro Ser Glu Arg Glu Ala Ser Pro Ser Asn Ser Cys
340 345 350

Gln Asp Ser Thr Asp Thr Glu Ser Asn Asn Glu Glu Gln Arg Ser Gly
355 360 365

Leu Ile Tyr Leu Thr Asn His Ile Ala Pro His Ala Arg Asn Gly Leu
370 375 380

Ser Leu Lys Glu Glu His Arg Ala Tyr Asp Leu Leu Arg Ala Ala Ser
385 390 395 400

Glu Asn Ser Gln Asp Ala Leu Arg Val Val Ser Thr Ser Gly Glu Gln
405 410 415

Met Lys Val Tyr Lys Cys Glu His Cys Arg Val Leu Phe Leu Asp His
420 425 430

Val Met Tyr Thr Ile His Met Gly Cys His Gly Phe Arg Asp Pro Phe
435 440 445

Glu Cys Asn Met Cys Gly Tyr His Ser Gln Asp Arg Tyr Glu Phe Ser
450 455 460

Ser His Ile Thr Arg Gly Glu His Arg Phe His Met Ser
465 470 475

<210> SEQ ID NO 18
<211> LENGTH: 226
<212> TYPE: PRT
<213> ORGANISM: homo sapiens

<400> SEQUENCE: 18

Met Asp Ala Asp Glu Gly Gln Asp Met Ser Gln Val Ser Gly Lys Glu
1 5 10 15

Ser Pro Pro Val Ser Asp Thr Pro Asp Glu Gly Asp Glu Pro Met Pro
20 25 30

Ile Pro Glu Asp Leu Ser Thr Thr Ser Gly Gly Gln Gln Ser Ser Lys
35 40 45

Ser Asp Arg Val Val Ala Ser Asn Val Lys Val Glu Thr Gln Ser Asp
50 55 60

Glu Glu Asn Gly Arg Ala Cys Glu Met Asn Gly Glu Glu Cys Ala Glu
65 70 75 80

Asp Leu Arg Met Leu Asp Ala Ser Gly Glu Lys Met Asn Gly Ser His
85 90 95

Arg Asp Gln Gly Ser Ser Ala Leu Ser Gly Val Gly Gly Ile Arg Leu
100 105 110

Pro Asn Gly Lys Leu Lys Cys Asp Ile Cys Gly Ile Ile Cys Ile Gly
115 120 125

Pro Asn Val Leu Met Val His Lys Arg Ser His Thr Gly Glu Arg Pro
130 135 140

Phe Gln Cys Asn Gln Cys Gly Ala Ser Phe Thr Gln Lys Gly Asn Leu 145 150 155 160

Leu Arg His Ile Lys Leu His Ser Gly Glu Lys Pro Phe Lys Cys His
165 170 175

Leu Cys Asn Tyr Ala Cys Arg Arg Arg Asp Ala Leu Thr Gly His Leu
180 185 190

Arg Thr His Ser Val Ile Lys Glu Glu Thr Asn His Ser Glu Met Ala
195 200 205

Glu Asp Leu Cys Lys Ile Gly Ser Glu Ile Ser Arg Ala Gly Gln Thr
210 215 220

Ser Lys
225

<210> SEQ ID NO 19
<211> LENGTH: 519
<212> TYPE: PRT
<213> ORGANISM: artificial sequence
<220> FEATURE:
<223> OTHER INFORMATION: synthetic construct
<220> FEATURE:
<221> NAME/KEY: misc_feature
<222> LOCATION: (1)..(283)
<223> OTHER INFORMATION: Xaa can be any naturally occurring amino acid
<220> FEATURE:
<221> NAME/KEY: misc_feature
<222> LOCATION: (508)..(508)
<223> OTHER INFORMATION: Xaa can be any naturally occurring amino acid

<400> SEQUENCE: 19

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Xaa Xaa Xaa Xaa Xaa Xaa
65 70 75 80

Xaa Xaa Xaa Xaa Xaa Xaa Xaa Xaa Xaa Xaa Xaa Xaa Xaa Xaa Xaa Xaa
85 90 95

Xaa Xaa Xaa Xaa Xaa Xaa Xaa Xaa Xaa Xaa Xaa Xaa Xaa Xaa Xaa Xaa
100 105 110

Xaa Xaa Xaa Xaa Xaa Xaa Xaa Xaa Xaa Xaa Xaa Xaa Xaa Xaa Xaa Xaa
115 120 125

Xaa Xaa Xaa Xaa Xaa Xaa Xaa Xaa Xaa Xaa Xaa Xaa Xaa Xaa Xaa Xaa
130 135 140

Xaa Xaa Xaa Xaa Xaa Xaa Xaa Xaa Xaa Xaa Xaa Xaa Xaa Xaa Xaa Xaa
145 150 155 160

Xaa Xaa Xaa Xaa Xaa Xaa Xaa Xaa Xaa Xaa Xaa Xaa Xaa Xaa Xaa Xaa
165 170 175

Xaa Xaa Xaa Xaa Xaa Xaa Xaa Xaa Xaa Xaa Xaa Xaa Xaa Xaa Xaa Xaa
180 185 190

Xaa Xaa Xaa Xaa Xaa Xaa Xaa Xaa Xaa Xaa Xaa Xaa Xaa Xaa Xaa Xaa
195 200 205

Xaa Xaa Xaa Xaa Xaa Xaa Xaa Xaa Xaa Xaa Xaa Xaa Xaa Xaa Xaa Xaa
210 215 220

Xaa Xaa Xaa Xaa Xaa Xaa Xaa Xaa Xaa Xaa Xaa Xaa Xaa Xaa Xaa Xaa
225 230 235 240

```
Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Gly Asp Lys Gly Leu
        275                 280                 285

Ser Asp Thr Pro Tyr Asp Ser Ser Ala Ser Tyr Glu Lys Glu Asn Glu
    290                 295                 300

Met Met Lys Ser His Val Met Asp Gln Ala Ile Asn Asn Ala Ile Asn
305                 310                 315                 320

Tyr Leu Gly Ala Glu Ser Leu Arg Pro Leu Val Gln Thr Pro Pro Gly
                325                 330                 335

Gly Ser Glu Val Val Pro Val Ile Ser Pro Met Tyr Gln Leu His Lys
            340                 345                 350

Pro Leu Ala Glu Gly Thr Pro Arg Ser Asn His Ser Ala Gln Asp Ser
        355                 360                 365

Ala Val Glu Asn Leu Leu Leu Leu Ser Lys Ala Lys Leu Val Pro Ser
    370                 375                 380

Glu Arg Glu Ala Ser Pro Ser Asn Ser Cys Gln Asp Ser Thr Asp Thr
385                 390                 395                 400

Glu Ser Asn Asn Glu Glu Gln Arg Ser Gly Leu Ile Tyr Leu Thr Asn
                405                 410                 415

His Ile Ala Pro His Ala Arg Asn Gly Leu Ser Leu Lys Glu Glu His
            420                 425                 430

Arg Ala Tyr Asp Leu Leu Arg Ala Ala Ser Glu Asn Ser Gln Asp Ala
        435                 440                 445

Leu Arg Val Val Ser Thr Ser Gly Glu Gln Met Lys Val Tyr Lys Cys
    450                 455                 460

Glu His Cys Arg Val Leu Phe Leu Asp His Val Met Tyr Thr Ile His
465                 470                 475                 480

Met Gly Cys His Gly Phe Arg Asp Pro Phe Glu Cys Asn Met Cys Gly
                485                 490                 495

Tyr His Ser Gln Asp Arg Tyr Glu Phe Ser Ser Xaa Ile Thr Arg Gly
            500                 505                 510

Glu His Arg Phe His Met Ser
        515
```

<210> SEQ ID NO 20
<211> LENGTH: 519
<212> TYPE: PRT
<213> ORGANISM: artificial sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:

<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (235)..(236)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (258)..(258)
<223> OTHER INFORMATION: Xaa can be any naturally occurring amino acid
<220> FEATURE:
<221> NAME/KEY: misc_feature
<222> LOCATION: (287)..(287)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid
<220> FEATURE:
<221> NAME/KEY: misc_feature
<222> LOCATION: (296)..(298)
<223> OTHER INFORMATION: Xaa can be any naturally occurring amino acid
<220> FEATURE:
<221> NAME/KEY: misc_feature
<222> LOCATION: (301)..(303)
<223> OTHER INFORMATION: Xaa can be any naturally occurring amino acid
<220> FEATURE:
<221> NAME/KEY: misc_feature
<222> LOCATION: (306)..(306)
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (345)..(345)
<223> OTHER INFORMATION: Xaa can be any naturally occurring amino acid
<220> FEATURE:
<221> NAME/KEY: misc_feature
<222> LOCATION: (353)..(355)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (381)..(381)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (404)..(404)
<223> OTHER INFORMATION: Xaa can be any naturally occurring amino acid
<220> FEATURE:
<221> NAME/KEY: misc_feature
<222> LOCATION: (419)..(419)
<223> OTHER INFORMATION: Xaa can be any naturally occurring amino acid
<220> FEATURE:
<221> NAME/KEY: misc_feature
<222> LOCATION: (427)..(427)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (436)..(437)
<223> OTHER INFORMATION: Xaa can be any naturally occurring amino acid
<220> FEATURE:
<221> NAME/KEY: misc_feature
<222> LOCATION: (449)..(449)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (516)..(516)
<223> OTHER INFORMATION: Xaa can be any naturally occurring amino acid
<220> FEATURE:
<221> NAME/KEY: misc_feature
<222> LOCATION: (518)..(518)
<223> OTHER INFORMATION: Xaa can be any naturally occurring amino acid

<400> SEQUENCE: 20

```
Met Asp Xaa Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Xaa Pro Glu Asp Leu Ser Thr Thr Ser Gly Xaa Gln Gln Xaa Ser Lys
        35                  40                  45

Ser Asp Arg Xaa Xaa Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Xaa Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Xaa Xaa Tyr Pro Val Ile
225                 230                 235                 240

Lys Glu Glu Thr Asn His Xaa Glu Met Ala Glu Asp Leu Cys Lys Ile
                245                 250                 255
```

```
Gly Xaa Glu Arg Ser Leu Val Leu Asp Arg Leu Ala Ser Asn Val Ala
            260                 265                 270

Lys Arg Lys Ser Ser Met Pro Gln Lys Phe Leu Gly Asp Lys Xaa Leu
        275                 280                 285

Ser Asp Xaa Pro Tyr Asp Ser Xaa Xaa Xaa Tyr Glu Xaa Xaa Xaa Glu
    290                 295                 300

Met Xaa Lys Ser His Val Met Asp Gln Ala Ile Asn Asn Ala Ile Asn
305                 310                 315                 320

Tyr Leu Gly Ala Glu Ser Leu Arg Pro Leu Val Gln Thr Pro Pro Xaa
                325                 330                 335

Gly Ser Glu Val Val Pro Val Ile Xaa Pro Met Tyr Gln Leu His Lys
            340                 345                 350

Xaa Xaa Xaa Glu Xaa Thr Pro Arg Ser Asn His Ser Ala Gln Asp Xaa
        355                 360                 365

Ala Val Xaa Asn Leu Leu Leu Leu Ser Lys Ala Lys Xaa Val Xaa Ser
    370                 375                 380

Glu Arg Glu Ala Ser Pro Ser Asn Ser Cys Gln Asp Ser Thr Asp Thr
385                 390                 395                 400

Glu Ser Asn Xaa Glu Glu Gln Arg Ser Gly Leu Ile Tyr Leu Thr Asn
                405                 410                 415

His Ile Xaa Pro His Ala Arg Asn Gly Leu Xaa Leu Lys Glu Glu Xaa
            420                 425                 430

Arg Ala Tyr Xaa Xaa Leu Arg Ala Ala Ser Glu Asn Ser Gln Asp Ala
        435                 440                 445

Xaa Arg Val Val Ser Thr Ser Gly Glu Gln Xaa Lys Val Tyr Lys Cys
    450                 455                 460

Glu His Cys Arg Val Leu Phe Leu Asp His Val Met Tyr Thr Ile His
465                 470                 475                 480

Met Gly Cys His Gly Phe Arg Asp Pro Phe Glu Cys Asn Met Cys Gly
                485                 490                 495

Tyr His Ser Gln Asp Arg Tyr Glu Phe Ser Ser His Ile Thr Arg Gly
            500                 505                 510

Glu His Arg Xaa His Xaa Ser
        515
```

<210> SEQ ID NO 21
<211> LENGTH: 6255
<212> TYPE: DNA
<213> ORGANISM: homo sapiens

<400> SEQUENCE: 21

```
actctaacaa gtgactgcgc ggcccgcgcc cggggcggtg actgcggcaa gccccctggg      60

tccccgcgcg gcgcatccca gcctgggcgg gacgctcggc cgcggcgagg cgggcaagcc     120

tggcagggca gagggagccc cggctccgag gttgctcttc gcacccgagg atcagtcttg     180

gccccaaagc gcgacgcaca aatccacata acctgaggac catggatgct gatgagggtc     240

aagacatgtc ccaagtttca gggaaggaaa gcccccctgt aagcgatact ccagatgagg     300

gcgatgagcc catgccgatc cccgaggacc tctccaccac ctcgggagga cagcaaagct     360

ccaagagtga cagagtcgtg gccagtaatg ttaaagtaga gactcagagt gatgaagaga     420

atgggcgtgc ctgtgaaatg aatggggaag aatgtgcgga ggatttacga atgcttgatg     480

cctcgggaga gaaaatgaat ggctcccaca gggaccaagg cagctcggct ttgtcgggag     540

ttggaggcat tcgacttcct aacggaaaac taaagtgtga tatctgtggg atcatttgca     600
```

tcgggcccaa tgtgctcatg gttcacaaaa gaagccacac tggagaacgg cccttccagt 660
gcaatcagtg cggggcctca ttcacccaga agggcaacct gctccggcac atcaagctgc 720
attccgggga gaagcccttc aaatgccacc tctgcaacta cgcctgccgc cggagggacg 780
ccctcactgg ccacctgagg acgcactccg ttggtaaacc tcacaaatgt ggatattgtg 840
gccgaagcta taaacagcga agctctttag aggaacataa agagcgctgc cacaactact 900
tggaaagcat gggccttccg ggcacactgt acccagtcat taaagaagaa actaatcaca 960
gtgaaatggc agaagacctg tgcaagatag gatcagagag atctctcgtg ctggacagac 1020
tagcaagtaa cgtcgccaaa cgtaagagct ctatgcctca gaaatttctt ggggacaagg 1080
gcctgtccga cacgccctac gacagcagcg ccagctacga gaaggagaac gaaatgatga 1140
agtcccacgt gatggaccaa gccatcaaca acgccatcaa ctacctgggg gccgagtccc 1200
tgcgcccgct ggtgcagacg cccccgggcg gttccgaggt ggtcccggtc atcagcccga 1260
tgtaccagct gcacaagccg ctcgcggagg gcaccccgcg ctccaaccac tcggcccagg 1320
acagcgccgt ggagaacctg ctgctgctct ccaaggccaa gttggtgccc tcggagcgcg 1380
aggcgtcccc gagcaacagc tgccaagact ccacggacac cgagagcaac aacgaggagc 1440
agcgcagcgg tctcatctac ctgaccaacc acatcgcccc gcacgcgcgc aacgggctgt 1500
cgctcaagga ggagcaccgc gcctacgacc tgctgcgcgc cgcctccgag aactcgcagg 1560
acgcgctccg cgtggtcagc accagcgggg agcagatgaa ggtgtacaag tgcgaacact 1620
gccgggtgct cttcctggat cacgtcatgt acaccatcca catgggctgc cacggcttcc 1680
gtgatccttt tgagtgcaac atgtgcggct accacagcca ggaccggtac gagttctcgt 1740
cgcacataac gcgaggggag caccgcttcc acatgagcta aagccctccc gcgcccccac 1800
cccagacccc gagccacccc aggaaaagca caaggactgc cgccttctcg ctcccgccag 1860
cagcatagac tggactggac cagacaatgt tgtgtttgga tttgtaactg ttttttgttt 1920
tttgtttgag ttggttgatt ggggtttgat ttgcttttga aaagattttt atttttagag 1980
gcagggctgc attgggagca tccagaactg ctaccttcct agatgtttcc ccagaccgct 2040
ggctgagatt ccctcacctg tcgcttccta gaatcccctt ctccaaacga ttagtctaaa 2100
ttttcagaga gaaatagata aaacacgcca cagcctggga aggagcgtgc tctaccctgt 2160
gctaagcacg gggttcgcgc accaggtgtc tttttccagt ccccagaagc agagagcaca 2220
gcccctgctg tgtgggtctg caggtgagca gacaggacag gtgtgccgcc acccaagtgc 2280
caagacacag cagggccaac aacctgtgcc caggccagct tcgagctaca tgcatctagg 2340
gcggagaggc tgcacttgtg agagaaaata ctatttcaag tcatattctg cgtaggaaaa 2400
tgaattggtt ggggaaagtc gtgtctgtca gactgccctg ggtggaggga gacgccgggc 2460
tagagccttt gggatcgtcc tggattcact ggctttgcgg aggctgctca gatggcctga 2520
gcctcccgag gcttgctgcc ccgtaggagg agactgtctt cccgtgggca tatctgggga 2580
gccctgttcc ccgctttttc actcccatac ctttaatggc ccccaaaatc tgtcactaca 2640
atttaaacac cagtcccgaa atttggatct tctttctttt tgaatctctc aaacggcaac 2700
attcctcaga aaccaaagct ttatttcaaa tctcttcctt ccctggctgg ttccatctag 2760
taccagaggc ctcttttcct gaagaaatcc aatcctagcc ctcattttaa ttatgtacat 2820
ctgtttgtag ccacaagcct gaatttctca gtgttggtaa gtttctttac ctaccctcac 2880
tatatattat tctcgtttta aaacccataa aggagtgatt tagaacagtc attaattttc 2940
aactcaatga aatatgtgaa gcccagcatc tctgttgcta acacacagag ctcacctgtt 3000

```
tgaaaccaag ctttcaaaca tgttgaagct ctttactgta aaggcaagcc agcatgtgtg   3060
tccacacata cataggatgg ctggctctgc acctgtagga tattggaatg cacagggcaa   3120
ttgagggact gagccagacc ttcggagagt aatgccacca gatcccctag gaaagaggag   3180
gcaaatggca ctgcaggtga gaaccccgcc catccgtgct atgacatgga ggcactgaag   3240
cccgaggaag gtgtgtggag attctaatcc caacaagcaa gggtctcctt caagattaat   3300
gctatcaatc attaaggtca ttactctcaa ccacctaggc aatgaagaat ataccatttc   3360
aaatatttac agtacttgtc ttcaccaaca ctgtcccaag gtgaaatgaa gcaacagaga   3420
ggaaattgta cataagtacc tcagcattta atccaaacag gggttcttag tctcagcact   3480
atgacatttt gggctgacta cttatttgtt aggcgggagc tctcctgtgc attgtaggat   3540
aattagcagt atccctggtg gctacccaat agacgccagt agcaccccga attgacaacc   3600
caaactctcc agacatcacc aactgtcccc tgcgaggaga aatcactcct gggggagaac   3660
cactgaccca aatgaattct aaaccaatca aatgtctggg aagccctcca agaaaaaaaa   3720
tagaaaagca cttgaagaat attcccaata ttcccggtca gcagtatcaa ggctgacttg   3780
tgttcatgtg gagtcattat aaattctata aatcaattat tccccttcgg tcttaaaaat   3840
atatttcctc ataaacattt gagttttgtt gaaaagatgg agtttacaaa gataccattc   3900
ttgagtcatg gatttctctg ctcacagaag ggtgtggcat ttggaaacgg gaataaacaa   3960
aattgctgca ccaatgcact gagtgaagga agagagacag aggatcaagg gctttagaca   4020
gcactccttc aatatgcaat cacagagaaa gatgcgcctt atccaagtta atatctctaa   4080
ggtgagagcc ttcttagagt cagtttgttg caaatttcac ctactctgtt cttttccatc   4140
catcccccctg agtcagttgg ttgaagggag ttatttttc aagtggaatt caaacaaagc   4200
tcaaaccaga actgtaaata gtgattgcag gaattctttt ctaaactgct ttgccctttc   4260
ctctcactgc cttttatagc caatataaat gtctctttgc acaccttttg ttgtggtttt   4320
atattgtaac accattttc tttgaaacta ttgtatttaa agtaaggttt catattatgt   4380
cagcaagtaa ttaacttatg tttaaaaggt ggccatatca tgtaccaaaa gttgctgaag   4440
tttctcttct agctggtaaa gtaggagttt gcatgacttc acactttttt tgcgtagttt   4500
cttctgttgt atgatggcgt gagtgtgtgt cttgggtacc gctgtgtact actgtgtgcc   4560
tagattccat gcactctcgt tgtgtttgaa gtaaatattg gagaccggag ggtaacaggt   4620
tggcctgttg attacagcta gtaatcgctg tgtcttgttc cgccccctcc ctgacacccc   4680
agcttcccag gatgtggaaa gcctggatct cagctccttg ccccatatcc cttctgtaat   4740
ttgtacctaa agagtgtgat tatcctaatt caagagtcac taaaactcat cacattatca   4800
ttgcatatca gcaaagggta aagtcctagc accaattgct tcacatacca gcatgttcca   4860
tttccaattt agaattagcc acataataaa atcttagaat cttccttgag aaagagctgc   4920
ctgagatgta gttttgttat atggttcccc accgaccatt tttgtgcttt tttcttgttt   4980
tgttttgttt tgactgcact gtgagttttg tagtgtcctc ttcttgccaa aacaaacgcg   5040
agatgaactg gacttatgta gacaaatcgt gatgccagtg tatccttcct ttcttcagtt   5100
ccagcaataa tgaatggtca actttttaa aatctagatc tctctcattc atttcaatgt   5160
atttttactt taagatgaac caaaattatt agacttattt aagatgtaca ggcatcagaa   5220
aaaagaagca cataatgctt ttggtgcgat ggcactcact gtgaacatgt gtaaccacat   5280
attaatatgc aatattgttt ccaatacttt ctaatacagt tttttataat gttgtgtgtg   5340
```

```
gtgattgttc aggtcgaatc tgttgtatcc agtacagctt taggtcttca gctgcccttc   5400

tggcgagtac atgcacagga ttgtaaatga gaaatgcagt catatttcca gtctgcctct   5460

atgatgatgt taaattattg ctgtttagct gtgaacaagg gatgtaccac tggaggaata   5520

gagtatcctt ttgtacacat tttgaaatgc ttcttctgta gtgatagaac aaataaatgc   5580

aacgaatact ctgtctgccc tatcccgtga agtccacact ggcgtaagag aaggcccagc   5640

agagcaggaa tctgcctaga ctttctccca atgagatccc aatatgagag ggagaagaga   5700

tgggcctcag gacagctgca ataccacttg ggaacacatg tggtgtcttg atgtggccag   5760

cgcagcagtt cagcacaacg tacctcccat ctacaacagt gctggacgtg ggaattctaa   5820

gtcccagtct tgagggtggg tggagatgga gggcaacaag agatacattt ccagttctcc   5880

actgcagcat gcttcagtca ttctgtgagt ggccgggccc agggccctca caatttcact   5940

accttgtctt ttacatagtc ataagaatta tcctcaacat agccttttga cgctgtaaat   6000

cttgagtatt catttaccct tttctgatct cctggaaaca gctgcctgcc tgcattgcac   6060

ttctcttccc gaggagtggg gtaaatttaa aagtcaagtt atagtttgga tgttagtata   6120

gaattttgaa attgggaatt aaaaatcagg actggggact gggagaccaa aaatttctga   6180

tcccatttct gatggatgtg tcacaccttt tctgtcaaaa taaaatgtct tggaggttat   6240

gactccttgg tgaaa                                                    6255
```

<210> SEQ ID NO 22
<211> LENGTH: 6191
<212> TYPE: DNA
<213> ORGANISM: homo sapiens

<400> SEQUENCE: 22

```
attgtgaaag aaagctggga agagctccgc ggccaagtta gcaggacact ctaacaagtg     60

actgcgcggc ccgcgcccgg ggcggtgact gcggcaagcc ccctgggtcc ccgcgcggcg    120

catcccagcc tgggcgggac gctcggccgc ggcgaggcgg gcaagcctgg cagggcagag    180

ggagccccgg ctccgaggtt gctcttcgca cccgaggatc agtcttggcc ccaaagcgcg    240

acgcacaaat ccacataacc tgaggaccat ggatgctgat gagggtcaag acatgtccca    300

agtttcaggg aaggaaagcc cccctgtaag cgatactcca gatgagggcg atgagcccat    360

gccgatcccc gaggacctct ccaccacctc gggaggacag caaagctcca agagtgacag    420

agtcgtggcc agtaatgtta aagtagagac tcagagtgat gaagagaatg ggcgtgcctg    480

tgaaatgaat ggggaagaat gtgcggagga tttacgaatg cttgatgcct cgggagagaa    540

aatgaatggc tcccacaggg accaaggcag ctcggctttg tcgggagttg gaggcattcg    600

acttcctaac ggaaaactaa agtgtgatat ctgtgggatc atttgcatcg ggcccaatgt    660

gctcatggtt cacaaaagaa gccacactgg agaacggccc ttccagtgca atcagtgcgg    720

ggcctcattc acccagaagg gcaacctgct ccggcacatc aagctgcatt ccggggagaa    780

gcccttcaaa tgccacctct gcaactacgc ctgccgccgg agggacgccc tcactggcca    840

cctgaggacg cactccgtca ttaaagaaga aactaatcac agtgaaatgg cagaagacct    900

gtgcaagata ggatcagaga gatctctcgt gctggacaga ctagcaagta acgtcgccaa    960

acgtaagagc tctatgcctc agaaatttct tggggacaag ggcctgtccg acacgcccta   1020

cgacagcagc gccagctacg agaaggagaa cgaaatgatg aagtcccacg tgatggacca   1080

agccatcaac aacgccatca actacctggg ggccgagtcc ctgcgcccgc tggtgcagac   1140

gcccccgggc ggttccgagg tggtcccggt catcagcccg atgtaccagc tgcacaagcc   1200
```

```
gctcgcggag ggcaccccgc gctccaacca ctcggcccag gacagcgccg tggagaacct   1260
gctgctgctc tccaaggcca agttggtgcc ctcggagcgc gaggcgtccc cgagcaacag   1320
ctgccaagac tccacggaca ccgagagcaa caacgaggag cagcgcagcg gtctcatcta   1380
cctgaccaac cacatcgccc cgcacgcgcg caacgggctg tcgctcaagg aggagcaccg   1440
cgcctacgac ctgctgcgcg ccgcctccga gaactcgcag gacgcgctcc gcgtggtcag   1500
caccagcggg gagcagatga aggtgtacaa gtgcgaacac tgccgggtgc tcttcctgga   1560
tcacgtcatg tacaccatcc acatgggctg ccacggcttc cgtgatcctt ttgagtgcaa   1620
catgtgcggc taccacagcc aggaccggta cgagttctcg tcgcacataa cgcgaggggga  1680
gcaccgcttc cacatgagct aaagccctcc cgcgccccca ccccagaccc cgagccaccc   1740
caggaaaagc acaaggactg ccgccttctc gctcccgcca gcagcataga ctggactgga   1800
ccagacaatg ttgtgtttgg atttgtaact gtttttttgtt ttttgtttga gttggttgat  1860
tggggtttga tttgcttttg aaaagatttt tatttttaga ggcagggctg cattgggagc   1920
atccagaact gctaccttcc tagatgtttc cccagaccgc tggctgagat tccctcacct   1980
gtcgcttcct agaatcccct tctccaaacg attagtctaa attttcagag agaaatagat   2040
aaaacacgcc acagcctggg aaggagcgtg ctctaccctg tgctaagcac ggggttcgcg   2100
caccaggtgt ctttttccag tccccagaag cagagagcac agcccctgct gtgtgggtct   2160
gcaggtgagc agacaggaca ggtgtgccgc cacccaagtg ccaagacaca gcagggccaa   2220
caacctgtgc ccaggccagc ttcgagctac atgcatctag ggcggagagg ctgcacttgt   2280
gagagaaaat actatttcaa gtcatattct gcgtaggaaa atgaattggt tggggaaagt   2340
cgtgtctgtc agactgccct gggtggaggg agacgccggg ctagagcctt tgggatcgtc   2400
ctggattcac tggctttgcg gaggctgctc agatggcctg agcctcccga ggcttgctgc   2460
cccgtaggag gagactgtct tcccgtgggc atatctgggg agccctgttc cccgcttttt   2520
cactcccata cctttaatgg cccccaaaat ctgtcactac aatttaaaca ccagtcccga   2580
aatttggatc ttctttcttt ttgaatctct caaacggcaa cattcctcag aaaccaaagc   2640
tttatttcaa atctcttcct tccctggctg gttccatcta gtaccagagg cctcttttcc   2700
tgaagaaatc caatcctagc cctcatttta attatgtaca tctgtttgta gccacaagcc   2760
tgaatttctc agtgttggta agtttcttta cctaccctca ctatatatta ttctcgtttt   2820
aaaacccata aaggagtgat ttagaacagt cattaatttt caactcaatg aaatatgtga   2880
agcccagcat ctctgttgct aacacacaga gctcacctgt ttgaaaccaa gctttcaaac   2940
atgttgaagc tctttactgt aaaggcaagc cagcatgtgt gtccacacat acataggatg   3000
gctggctctg cacctgtagg atattggaat gcacagggca attgagggac tgagccagac   3060
cttcggagag taatgccacc agatccccta ggaaagagga ggcaaatggc actgcaggtg   3120
agaaccccgc ccatccgtgc tatgacatgg aggcactgaa gcccgaggaa ggtgtgtgga   3180
gattctaatc ccaacaagca agggtctcct tcaagattaa tgctatcaat cattaaggtc   3240
attactctca accacctagg caatgaagaa tataccattt caaatattta cagtacttgt   3300
cttcaccaac actgtcccaa ggtgaaatga agcaacagag aggaaattgt acataagtac   3360
ctcagcattt aatccaaaca ggggttctta gtctcagcac tatgacattt tgggctgact   3420
acttatttgt taggcgggag ctctcctgtg cattgtagga taattagcag tatccctggt   3480
ggctacccaa tagacgccag tagcaccccg aattgacaac ccaaactctc cagacatcac   3540
```

caactgtccc ctgcgaggag aaatcactcc tgggggagaa ccactgaccc aaatgaattc 3600
taaaccaatc aaatgtctgg gaagccctcc aagaaaaaaa atagaaaagc acttgaagaa 3660
tattcccaat attcccggtc agcagtatca aggctgactt gtgttcatgt ggagtcatta 3720
taaattctat aaatcaatta ttccccttcg gtcttaaaaa tatatttcct cataaacatt 3780
tgagttttgt tgaaaagatg gagtttacaa agataccatt cttgagtcat ggatttctct 3840
gctcacagaa gggtgtggca tttggaaacg ggaataaaca aaattgctgc accaatgcac 3900
tgagtgaagg aagagagaca gaggatcaag ggctttagac agcactcctt caatatgcaa 3960
tcacagagaa agatgcgcct tatccaagtt aatatctcta aggtgagagc cttcttagag 4020
tcagtttgtt gcaaatttca cctactctgt tcttttccat ccatccccct gagtcagttg 4080
gttgaaggga gttatttttt caagtggaat tcaaacaaag ctcaaaccag aactgtaaat 4140
agtgattgca ggaattcttt tctaaactgc tttgcccttt cctctcactg ccttttatag 4200
ccaatataaa tgtctctttg cacacctttt gttgtggttt tatattgtaa caccattttt 4260
ctttgaaact attgtattta aagtaaggtt tcatattatg tcagcaagta attaacttat 4320
gtttaaaagg tggccatatc atgtaccaaa agttgctgaa gtttctcttc tagctggtaa 4380
agtaggagtt tgcatgactt cacacttttt ttgcgtagtt tcttctgttg tatgatggcg 4440
tgagtgtgtg tcttgggtac cgctgtgtac tactgtgtgc ctagattcca tgcactctcg 4500
ttgtgtttga agtaaatatt ggagaccgga gggtaacagg ttggcctgtt gattacagct 4560
agtaatcgct gtgtcttgtt ccgccccctc cctgacaccc cagcttccca ggatgtggaa 4620
agcctggatc tcagctcctt gccccatatc ccttctgtaa tttgtaccta aagagtgtga 4680
ttatcctaat tcaagagtca ctaaaactca tcacattatc attgcatatc agcaaagggt 4740
aaagtcctag caccaattgc ttcacatacc agcatgttcc atttccaatt tagaattagc 4800
cacataataa aatcttagaa tcttccttga gaaagagctg cctgagatgt agttttgtta 4860
tatggttccc caccgaccat ttttgtgctt ttttcttgtt ttgttttgtt ttgactgcac 4920
tgtgagtttt gtagtgtcct cttcttgcca aaacaaacgc gagatgaact ggacttatgt 4980
agacaaatcg tgatgccagt gtatccttcc tttcttcagt tccagcaata atgaatggtc 5040
aacttttttta aaatctagat ctctctcatt catttcaatg tatttttact ttaagatgaa 5100
ccaaaattat tagacttatt taagatgtac aggcatcaga aaaaagaagc acataatgct 5160
tttggtgcga tggcactcac tgtgaacatg tgtaaccaca tattaatatg caatattgtt 5220
tccaatactt tctaatacag ttttttataa tgttgtgtgt ggtgattgtt caggtcgaat 5280
ctgttgtatc cagtacagct ttaggtcttc agctgccctt ctggcgagta catgcacagg 5340
attgtaaatg agaaatgcag tcatatttcc agtctgcctc tatgatgatg ttaaattatt 5400
gctgtttagc tgtgaacaag ggatgtacca ctggaggaat agagtatcct tttgtacaca 5460
ttttgaaatg cttcttctgt agtgatagaa caaataaatg caacgaatac tctgtctgcc 5520
ctatcccgtg aagtccacac tggcgtaaga gaaggcccag cagagcagga atctgcctag 5580
actttctccc aatgagatcc caatatgaga gggagaagag atgggcctca ggacagctgc 5640
aataccactt gggaacacat gtggtgtctt gatgtggcca gcgcagcagt tcagcacaac 5700
gtacctccca tctacaacag tgctggacgt gggaattcta agtcccagtc ttgagggtgg 5760
gtggagatgg agggcaacaa gagatacatt tccagttctc cactgcagca tgcttcagtc 5820
attctgtgag tggccgggcc cagggccctc acaatttcac taccttgtct tttacatagt 5880
cataagaatt atcctcaaca tagccttttg acgctgtaaa tcttgagtat tcatttaccc 5940
ttttctgatc tcctggaaac agctgcctgc ctgcattgca cttctcttcc cgaggagtgg 6000
ggtaaattta aaagtcaagt tatagtttgg atgttagtat agaattttga aattgggaat 6060
taaaaatcag gactggggac tgggagacca aaaatttctg atcccatttc tgatggatgt 6120
gtcacacctt ttctgtcaaa ataaaatgtc ttggaggtta tgactccttg gtgaaaaaaa 6180
aaaaaaaaaa a 6191

<210> SEQ ID NO 23
<211> LENGTH: 6029
<212> TYPE: DNA
<213> ORGANISM: homo sapiens

<400> SEQUENCE: 23
atatttggca agtggttcca cctttctctg caccctggtg gagtgtgaag gcagcagagg 60 aacctttttgg aggaggaaga ggacacagag gccctgtagc caggcaccaa gatccctccc 120
aggtggctgg gtctgagggg aactccgagc agccctaggt cctcaaagtc tggatttgtg 180
tggaaaaggc agctctcact tggccttggc gaggcctcgg ttggttgata acctgaggac 240
catggatgct gatgagggtc aagacatgtc ccaagtttca gggaaggaaa gcccccctgt 300
aagcgatact ccagatgagg gcgatgagcc catgccgatc cccgaggacc tctccaccac 360
ctcgggagga cagcaaagct ccaagagtga cagagtcgtg ggagaacggc ccttccagtg 420
caatcagtgc ggggcctcat tcacccagaa gggcaacctg ctccggcaca tcaagctgca 480
ttccggggag aagcccttca aatgccacct ctgcaactac gcctgccgcc ggagggacgc 540
cctcactggc cacctgagga cgcactccgt tggtaaacct cacaaatgtg gatattgtgg 600
ccgaagctat aaacagcgaa gctctttaga ggaacataaa gagcgctgcc acaactactt 660
ggaaagcatg ggccttccgg gcacactgta cccagtcatt aaagaagaaa ctaatcacag 720
tgaaatggca gaagacctgt gcaagatagg atcagagaga tctctcgtgc tggacagact 780
agcaagtaac gtcgccaaac gtaagagctc tatgcctcag aaatttcttg gggacaaggg 840
cctgtccgac acgccctacg acagcagcgc cagctacgag aaggagaacg aaatgatgaa 900
gtcccacgtg atggaccaag ccatcaacaa cgccatcaac tacctggggg ccgagtccct 960
gcgcccgctg gtgcagacgc ccccgggcgg ttccgaggtg gtcccggtca tcagcccgat 1020
gtaccagctg cacaagccgc tcgcggaggg caccccgcgc tccaaccact cggcccagga 1080
cagcgccgtg gagaacctgc tgctgctctc caaggccaag ttggtgccct cggagcgcga 1140
ggcgtccccg agcaacagct gccaagactc cacggacacc gagagcaaca acgaggagca 1200
gcgcagcggt ctcatctacc tgaccaacca catcgccccg cacgcgcgca acgggctgtc 1260
gctcaaggag gagcaccgcg cctacgacct gctgcgcgcc gcctccgaga actcgcagga 1320
cgcgctccgc gtggtcagca ccagcgggga gcagatgaag gtgtacaagt gcgaacactg 1380
ccgggtgctc ttcctggatc acgtcatgta caccatccac atgggctgcc acggcttccg 1440
tgatcctttt gagtgcaaca tgtgcggcta ccacagccag gaccggtacg agttctcgtc 1500
gcacataacg cgaggggagc accgcttcca catgagctaa agccctcccg cgcccccacc 1560
ccagaccccg agccacccca ggaaaagcac aaggactgcc gccttctcgc tcccgccagc 1620
agcatagact ggactggacc agacaatgtt gtgtttggat ttgtaactgt tttttgtttt 1680
ttgtttgagt tggttgattg gggtttgatt tgcttttgaa aagattttta tttttagagg 1740
cagggctgca ttgggagcat ccagaactgc taccttccta gatgtttccc cagaccgctg 1800

-continued

```
gctgagattc cctcacctgt cgcttcctag aatccccttc tccaaacgat tagtctaaat   1860
tttcagagag aaatagataa aacacgccac agcctgggaa ggagcgtgct ctaccctgtg   1920
ctaagcacgg ggttcgcgca ccaggtgtct ttttccagtc cccagaagca gagagcacag   1980
cccctgctgt gtgggtctgc aggtgagcag acaggacagg tgtgccgcca cccaagtgcc   2040
aagacacagc agggccaaca acctgtgccc aggccagctt cgagctacat gcatctaggg   2100
cggagaggct gcacttgtga gagaaaatac tatttcaagt catattctgc gtaggaaaat   2160
gaattggttg gggaaagtcg tgtctgtcag actgccctgg gtggagggag acgccgggct   2220
agagcctttg ggatcgtcct ggattcactg gctttgcgga ggctgctcag atggcctgag   2280
cctcccgagg cttgctgccc cgtaggagga gactgtcttc ccgtgggcat atctggggag   2340
ccctgttccc cgctttttca ctcccatacc tttaatggcc cccaaaatct gtcactacaa   2400
tttaaacacc agtcccgaaa tttggatctt ctttcttttt gaatctctca aacggcaaca   2460
ttcctcagaa accaaagctt tatttcaaat ctcttccttc cctggctggt tccatctagt   2520
accagaggcc tcttttcctg aagaaatcca atcctagccc tcattttaat tatgtacatc   2580
tgtttgtagc cacaagcctg aatttctcag tgttggtaag tttctttacc taccctcact   2640
atatattatt ctcgttttaa aacccataaa ggagtgattt agaacagtca ttaattttca   2700
actcaatgaa atatgtgaag cccagcatct ctgttgctaa cacacagagc tcacctgttt   2760
gaaaccaagc tttcaaacat gttgaagctc tttactgtaa aggcaagcca gcatgtgtgt   2820
ccacacatac ataggatggc tggctctgca cctgtaggat attggaatgc acagggcaat   2880
tgagggactg agccagacct tcggagagta atgccaccag atcccctagg aaagaggagg   2940
caaatggcac tgcaggtgag aaccccgccc atccgtgcta tgacatggag gcactgaagc   3000
ccgaggaagg tgtgtggaga ttctaatccc aacaagcaag ggtctccttc aagattaatg   3060
ctatcaatca ttaaggtcat tactctcaac cacctaggca atgaagaata taccatttca   3120
aatatttaca gtacttgtct tcaccaacac tgtcccaagg tgaaatgaag caacagagag   3180
gaaattgtac ataagtacct cagcatttaa tccaaacagg ggttcttagt ctcagcacta   3240
tgacattttg ggctgactac ttatttgtta ggcgggagct ctcctgtgca ttgtaggata   3300
attagcagta tccctggtgg ctacccaata gacgccagta gcaccccgaa ttgacaaccc   3360
aaactctcca gacatcacca actgtcccct gcgaggagaa atcactcctg gggggagaacc   3420
actgacccaa atgaattcta aaccaatcaa atgtctggga agccctccaa gaaaaaaaat   3480
agaaaagcac ttgaagaata ttcccaatat tcccggtcag cagtatcaag gctgacttgt   3540
gttcatgtgg agtcattata aattctataa atcaattatt ccccttcggt cttaaaaata   3600
tatttcctca taaacatttg agttttgttg aaaagatgga gtttacaaag ataccattct   3660
tgagtcatgg atttctctgc tcacagaagg gtgtggcatt tggaaacggg aataaacaaa   3720
attgctgcac caatgcactg agtgaaggaa gagagacaga ggatcaaggg ctttagacag   3780
cactccttca atatgcaatc acagagaaag atgcgcctta tccaagttaa tatctctaag   3840
gtgagagcct tcttagagtc agtttgttgc aaatttcacc tactctgttc ttttccatcc   3900
atccccctga gtcagttggt tgaagggagt tattttttca agtggaattc aaacaaagct   3960
caaaccagaa ctgtaaatag tgattgcagg aattcttttc taaactgctt tgccctttcc   4020
tctcactgcc ttttatagcc aatataaatg tctctttgca caccttttgt tgtggtttta   4080
tattgtaaca ccatttttct ttgaaactat tgtatttaaa gtaaggtttc atattatgtc   4140
agcaagtaat taacttatgt ttaaaaggtg gccatatcat gtaccaaaag ttgctgaagt   4200
```

ttctcttcta gctggtaaag taggagtttg catgacttca cacttttttt gcgtagtttc 4260
ttctgttgta tgatggcgtg agtgtgtgtc ttgggtaccg ctgtgtacta ctgtgtgcct 4320
agattccatg cactctcgtt gtgtttgaag taaatattgg agaccggagg gtaacaggtt 4380
ggcctgttga ttacagctag taatcgctgt gtcttgttcc gccccctccc tgacacccca 4440
gcttcccagg atgtggaaag cctggatctc agctccttgc cccatatccc ttctgtaatt 4500
tgtacctaaa gagtgtgatt atcctaattc aagagtcact aaaactcatc acattatcat 4560
tgcatatcag caaagggtaa agtcctagca ccaattgctt cacataccag catgttccat 4620
ttccaattta gaattagcca cataataaaa tcttagaatc ttccttgaga aagagctgcc 4680
tgagatgtag ttttgttata tggttcccca ccgaccattt ttgtgctttt ttcttgtttt 4740
gttttgtttt gactgcactg tgagttttgt agtgtcctct tcttgccaaa acaaacgcga 4800
gatgaactgg acttatgtag acaaatcgtg atgccagtgt atccttcctt tcttcagttc 4860
cagcaataat gaatggtcaa ctttttaaa atctagatct ctctcattca tttcaatgta 4920
tttttacttt aagatgaacc aaaattatta gacttattta agatgtacag gcatcagaaa 4980
aaagaagcac ataatgcttt tggtgcgatg gcactcactg tgaacatgtg taaccacata 5040
ttaatatgca atattgtttc caatactttc taatacagtt ttttataatg ttgtgtgtgg 5100
tgattgttca ggtcgaatct gttgtatcca gtacagcttt aggtcttcag ctgcccttct 5160
ggcgagtaca tgcacaggat tgtaaatgag aaatgcagtc atatttccag tctgcctcta 5220
tgatgatgtt aaattattgc tgtttagctg tgaacaaggg atgtaccact ggaggaatag 5280
agtatccttt tgtacacatt ttgaaatgct tcttctgtag tgatagaaca aataaatgca 5340
acgaatactc tgtctgccct atcccgtgaa gtccacactg gcgtaagaga aggcccagca 5400
gagcaggaat ctgcctagac tttctcccaa tgagatccca atatgagagg gagaagagat 5460
gggcctcagg acagctgcaa taccacttgg gaacacatgt ggtgtcttga tgtggccagc 5520
gcagcagttc agcacaacgt acctcccatc tacaacagtg ctggacgtgg gaattctaag 5580
tcccagtctt gagggtgggt ggagatggag ggcaacaaga gatacatttc cagttctcca 5640
ctgcagcatg cttcagtcat tctgtgagtg gccgggccca gggccctcac aatttcacta 5700
ccttgtcttt tacatagtca taagaattat cctcaacata gccttttgac gctgtaaatc 5760
ttgagtattc atttaccctt ttctgatctc ctggaaacag ctgcctgcct gcattgcact 5820
tctcttcccg aggagtgggg taaatttaaa agtcaagtta tagtttggat gttagtatag 5880
aattttgaaa ttgggaatta aaaatcagga ctggggactg ggagaccaaa aatttctgat 5940
cccatttctg atggatgtgt cacacctttt ctgtcaaaat aaaatgtctt ggaggttatg 6000
actccttggt gaaaaaaaaa aaaaaaaaa 6029

<210> SEQ ID NO 24
<211> LENGTH: 5772
<212> TYPE: DNA
<213> ORGANISM: homo sapiens

<400> SEQUENCE: 24
ataacctgag gaccatggat gctgatgagg gtcaagacat gtcccaagtt tcagggaagg 60
aaagcccccc tgtaagcgat actccagatg agggcgatga gcccatgccg atccccgagg 120
acctctccac cacctcggga ggacagcaaa gctccaagag tgacagagtc gtgggagaac 180
ggcccttcca gtgcaatcag tgcggggcct cattcaccca gaagggcaac ctgctccggc 240

```
acatcaagct gcattccggg gagaagccct tcaaatgcca cctctgcaac tacgcctgcc    300
gccggaggga cgccctcact ggccacctga ggacgcactc cgttggtaaa cctcacaaat    360
gtggatattg tggccgaagc tataaacagc gaagctcttt agaggaacat aaagagcgct    420
gccacaacta cttggaaagc atgggccttc cgggcacact gtacccagtc attaaagaag    480
aaactaatca cagtgaaatg gcagaagacc tgtgcaagat aggatcagag agatctctcg    540
tgctggacag actagcaagt aacgtcgcca aacgggacaa gggcctgtcc gacacgccct    600
acgacagcag cgccagctac gagaaggaga acgaaatgat gaagtcccac gtgatggacc    660
aagccatcaa caacgccatc aactacctgg gggccgagtc cctgcgcccg ctggtgcaga    720
cgcccccggg cggttccgag gtggtcccgg tcatcagccc gatgtaccag ctgcacaagc    780
cgctcgcgga gggcaccccg cgctccaacc actcggccca ggacagcgcc gtggagaacc    840
tgctgctgct ctccaaggcc aagttggtgc cctcggagcg cgaggcgtcc ccgagcaaca    900
gctgccaaga ctccacggac accgagagca acaacgagga gcagcgcagc ggtctcatct    960
acctgaccaa ccacatcgcc ccgcacgcgc gcaacgggct gtcgctcaag gaggagcacc   1020
gcgcctacga cctgctgcgc gccgcctccg agaactcgca ggacgcgctc cgcgtggtca   1080
gcaccagcgg ggagcagatg aaggtgtaca agtgcgaaca ctgccgggtg ctcttcctgg   1140
atcacgtcat gtacaccatc cacatgggct gccacggctt ccgtgatcct tttgagtgca   1200
acatgtgcgg ctaccacagc caggaccggt acgagttctc gtcgcacata acgcgagggg   1260
agcaccgctt ccacatgagc taaagccctc ccgcgccccc accccagacc ccgagccacc   1320
ccaggaaaag cacaaggact gccgccttct cgctcccgcc agcagcatag actggactgg   1380
accagacaat gttgtgtttg gatttgtaac tgttttttgt tttttgtttg agttggttga   1440
ttggggtttg atttgctttt gaaaagattt ttatttttag aggcagggct gcattgggag   1500
catccagaac tgctaccttc ctagatgttt ccccagaccg ctggctgaga ttccctcacc   1560
tgtcgcttcc tagaatcccc ttctccaaac gattagtcta aattttcaga gagaaataga   1620
taaaacacgc cacagcctgg gaaggagcgt gctctaccct gtgctaagca cggggttcgc   1680
gcaccaggtg tctttttcca gtccccagaa gcagagagca cagcccctgc tgtgtgggtc   1740
tgcaggtgag cagacaggac aggtgtgccg ccacccaagt gccaagacac agcagggcca   1800
acaacctgtg cccaggccag cttcgagcta catgcatcta gggcggagag gctgcacttg   1860
tgagagaaaa tactatttca agtcatattc tgcgtaggaa aatgaattgg ttggggaaag   1920
tcgtgtctgt cagactgccc tgggtggagg gagacgccgg gctagagcct ttgggatcgt   1980
cctggattca ctggctttgc ggaggctgct cagatggcct gagcctcccg aggcttgctg   2040
ccccgtagga ggagactgtc ttcccgtggg catatctggg gagccctgtt ccccgctttt   2100
tcactcccat acctttaatg gcccccaaaa tctgtcacta caatttaaac accagtcccg   2160
aaatttggat cttctttctt tttgaatctc tcaaacggca acattcctca gaaaccaaag   2220
ctttatttca aatctcttcc ttccctggct ggttccatct agtaccagag gcctcttttc   2280
ctgaagaaat ccaatcctag ccctcatttt aattatgtac atctgtttgt agccacaagc   2340
ctgaatttct cagtgttggt aagtttcttt acctaccctc actatatatt attctcgttt   2400
taaaacccat aaaggagtga tttagaacag tcattaattt tcaactcaat gaaatatgtg   2460
aagcccagca tctctgttgc taacacacag agctcacctg tttgaaacca agctttcaaa   2520
catgttgaag ctctttactg taaaggcaag ccagcatgtg tgtccacaca tacataggat   2580
ggctggctct gcacctgtag gatattggaa tgcacagggc aattgaggga ctgagccaga   2640
```

ccttcggaga gtaatgccac cagatcccct aggaaagagg aggcaaatgg cactgcaggt 2700
gagaaccccg cccatccgtg ctatgacatg gaggcactga agcccgagga aggtgtgtgg 2760
agattctaat cccaacaagc aagggtctcc ttcaagatta atgctatcaa tcattaaggt 2820
cattactctc aaccacctag gcaatgaaga atataccatt tcaaatattt acagtacttg 2880
tcttcaccaa cactgtccca aggtgaaatg aagcaacaga gaggaaattg tacataagta 2940
cctcagcatt taatccaaac aggggttctt agtctcagca ctatgacatt ttgggctgac 3000
tacttatttg ttaggcggga gctctcctgt gcattgtagg ataattagca gtatccctgg 3060
tggctaccca atagacgcca gtagcacccc gaattgacaa cccaaactct ccagacatca 3120
ccaactgtcc cctgcgagga gaaatcactc ctgggggaga accactgacc caaatgaatt 3180
ctaaaccaat caaatgtctg ggaagccctc caagaaaaaa aatagaaaag cacttgaaga 3240
atattcccaa tattcccggt cagcagtatc aaggctgact tgtgttcatg tggagtcatt 3300
ataaattcta taaatcaatt attccccttc ggtcttaaaa atatatttcc tcataaacat 3360
ttgagttttg ttgaaaagat ggagtttaca aagataccat tcttgagtca tggatttctc 3420
tgctcacaga agggtgtggc atttggaaac gggaataaac aaaattgctg caccaatgca 3480
ctgagtgaag gaagagagac agaggatcaa gggctttaga cagcactcct tcaatatgca 3540
atcacagaga aagatgcgcc ttatccaagt taatatctct aaggtgagag ccttcttaga 3600
gtcagtttgt tgcaaatttc acctactctg ttcttttcca tccatccccc tgagtcagtt 3660
ggttgaaggg agttattttt tcaagtggaa ttcaaacaaa gctcaaacca gaactgtaaa 3720
tagtgattgc aggaattctt ttctaaactg ctttgccctt tcctctcact gccttttata 3780
gccaatataa atgtctcttt gcacaccttt tgttgtggtt ttatattgta acaccatttt 3840
tctttgaaac tattgtattt aaagtaaggt ttcatattat gtcagcaagt aattaactta 3900
tgtttaaaag gtggccatat catgtaccaa aagttgctga agtttctctt ctagctggta 3960
aagtaggagt ttgcatgact tcacactttt tttgcgtagt ttcttctgtt gtatgatggc 4020
gtgagtgtgt gtcttgggta ccgctgtgta ctactgtgtg cctagattcc atgcactctc 4080
gttgtgtttg aagtaaatat tggagaccgg agggtaacag gttggcctgt tgattacagc 4140
tagtaatcgc tgtgtcttgt tccgccccct ccctgacacc ccagcttccc aggatgtgga 4200
aagcctggat ctcagctcct tgccccatat cccttctgta atttgtacct aaagagtgtg 4260
attatcctaa ttcaagagtc actaaaactc atcacattat cattgcatat cagcaaaggg 4320
taaagtccta gcaccaattg cttcacatac cagcatgttc catttccaat ttagaattag 4380
ccacataata aaatcttaga atcttccttg agaaagagct gcctgagatg tagttttgtt 4440
atatggttcc ccaccgacca tttttgtgct tttttcttgt tttgttttgt tttgactgca 4500
ctgtgagttt tgtagtgtcc tcttcttgcc aaaacaaacg cgagatgaac tggacttatg 4560
tagacaaatc gtgatgccag tgtatccttc ctttcttcag ttccagcaat aatgaatggt 4620
caactttttt aaaatctaga tctctctcat tcatttcaat gtatttttac tttaagatga 4680
accaaaatta ttagacttat ttaagatgta caggcatcag aaaaaagaag cacataatgc 4740
ttttggtgcg atggcactca ctgtgaacat gtgtaaccac atattaatat gcaatattgt 4800
ttccaatact ttctaataca gttttttata atgttgtgtg tggtgattgt tcaggtcgaa 4860
tctgttgtat ccagtacagc tttaggtctt cagctgccct tctggcgagt acatgcacag 4920
gattgtaaat gagaaatgca gtcatatttc cagtctgcct ctatgatgat gttaaattat 4980

-continued

```
tgctgtttag ctgtgaacaa gggatgtacc actggaggaa tagagtatcc ttttgtacac   5040

attttgaaat gcttcttctg tagtgataga acaaataaat gcaacgaata ctctgtctgc   5100

cctatcccgt gaagtccaca ctggcgtaag agaaggccca gcagagcagg aatctgccta   5160

gactttctcc caatgagatc ccaatatgag agggagaaga gatgggcctc aggacagctg   5220

caataccact tgggaacaca tgtggtgtct tgatgtggcc agcgcagcag ttcagcacaa   5280

cgtacctccc atctacaaca gtgctggacg tgggaattct aagtcccagt cttgagggtg   5340

ggtggagatg gagggcaaca agagatacat ttccagttct ccactgcagc atgcttcagt   5400

cattctgtga gtggccgggc ccagggccct cacaatttca ctaccttgtc ttttacatag   5460

tcataagaat tatcctcaac atagcctttt gacgctgtaa atcttgagta ttcatttacc   5520

cttttctgat ctcctggaaa cagctgcctg cctgcattgc acttctcttc ccgaggagtg   5580

gggtaaattt aaaagtcaag ttatagtttg gatgttagta tagaattttg aaattgggaa   5640

ttaaaaatca ggactgggga ctgggagacc aaaaatttct gatcccattt ctgatggatg   5700

tgtcacacct tttctgtcaa aataaaatgt cttggaggtt atgactcctt ggtgaaaaaa   5760

aaaaaaaaaa aa                                                       5772
```

<210> SEQ ID NO 25
<211> LENGTH: 5802
<212> TYPE: DNA
<213> ORGANISM: homo sapiens

<400> SEQUENCE: 25

```
ataacctgag gaccatggat gctgatgagg gtcaagacat gtcccaagtt tcagggaagg     60

aaagcccccc tgtaagcgat actccagatg agggcgatga gcccatgccg atccccgagg    120

acctctccac cacctcggga ggacagcaaa gctccaagag tgacagagtc gtggccagta    180

atgttaaagt agagactcag agtgatgaag agaatgggcg tgcctgtgaa atgaatgggg    240

aagaatgtgc ggaggattta cgaatgcttg atgcctcggg agagaaaatg aatggctccc    300

acagggacca aggcagctcg gctttgtcgg gagttggagg cattcgactt cctaacggaa    360

aactaaagtg tgatatctgt gggatcattt gcatcgggcc caatgtgctc atggttcaca    420

aaagaagcca cactggagaa cggcccttcc agtgcaatca gtgcggggcc tcattcaccc    480

agaagggcaa cctgctccgg cacatcaagc tgcattccgg ggagaagccc ttcaaatgcc    540

acctctgcaa ctacgcctgc cgccggaggg acgccctcac tggccacctg aggacgcact    600

ccggggacaa gggcctgtcc gacacgccct acgacagcag cgccagctac gagaaggaga    660

acgaaatgat gaagtcccac gtgatggacc aagccatcaa caacgccatc aactacctgg    720

gggccgagtc cctgcgcccg ctggtgcaga cgcccccggg cggttccgag gtggtcccgg    780

tcatcagccc gatgtaccag ctgcacaagc cgctcgcgga gggcaccccg cgctccaacc    840

actcggccca ggacagcgcc gtggagaacc tgctgctgct ctccaaggcc aagttggtgc    900

cctcggagcg cgaggcgtcc ccgagcaaca gctgccaaga ctccacggac accgagagca    960

acaacgagga gcagcgcagc ggtctcatct acctgaccaa ccacatcgcc ccgcacgcgc   1020

gcaacgggct gtcgctcaag gaggagcacc gcgcctacga cctgctgcgc gccgcctccg   1080

agaactcgca ggacgcgctc cgcgtggtca gcaccagcgg ggagcagatg aaggtgtaca   1140

agtgcgaaca ctgccgggtg ctcttcctgg atcacgtcat gtacaccatc cacatgggct   1200

gccacggctt ccgtgatcct tttgagtgca acatgtgcgg ctaccacagc caggaccggt   1260

acgagttctc gtcgcacata acgcgagggg agcaccgctt ccacatgagc taaagccctc   1320
```

ccgcgccccc accccagacc ccgagccacc ccaggaaaag cacaaggact gccgccttct 1380
cgctcccgcc agcagcatag actggactgg accagacaat gttgtgtttg gatttgtaac 1440
tgttttttgt tttttgtttg agttggttga ttggggtttg atttgctttt gaaaagattt 1500
ttatttttag aggcagggct gcattgggag catccagaac tgctaccttc ctagatgttt 1560
ccccagaccg ctggctgaga ttccctcacc tgtcgcttcc tagaatcccc ttctccaaac 1620
gattagtcta aattttcaga gagaaataga taaaacacgc cacagcctgg gaaggagcgt 1680
gctctaccct gtgctaagca cggggttcgc gcaccaggtg tctttttcca gtccccagaa 1740
gcagagagca cagcccctgc tgtgtgggtc tgcaggtgag cagacaggac aggtgtgccg 1800
ccacccaagt gccaagacac agcagggcca acaacctgtg cccaggccag cttcgagcta 1860
catgcatcta gggcggagag gctgcacttg tgagagaaaa tactatttca agtcatattc 1920
tgcgtaggaa aatgaattgg ttggggaaag tcgtgtctgt cagactgccc tgggtggagg 1980
gagacgccgg gctagagcct ttgggatcgt cctggattca ctggctttgc ggaggctgct 2040
cagatggcct gagcctcccg aggcttgctg ccccgtagga ggagactgtc ttcccgtggg 2100
catatctggg gagccctgtt ccccgctttt tcactcccat acctttaatg gcccccaaaa 2160
tctgtcacta caatttaaac accagtcccg aaatttggat cttctttctt tttgaatctc 2220
tcaaacggca acattcctca gaaaccaaag ctttatttca aatctcttcc ttccctggct 2280
ggttccatct agtaccagag gcctcttttc ctgaagaaat ccaatcctag ccctcatttt 2340
aattatgtac atctgtttgt agccacaagc ctgaatttct cagtgttggt aagtttcttt 2400
acctaccctc actatatatt attctcgttt taaaacccat aaaggagtga tttagaacag 2460
tcattaattt tcaactcaat gaaatatgtg aagcccagca tctctgttgc taacacacag 2520
agctcacctg tttgaaacca agctttcaaa catgttgaag ctctttactg taaaggcaag 2580
ccagcatgtg tgtccacaca tacataggat ggctggctct gcacctgtag gatattggaa 2640
tgcacagggc aattgaggga ctgagccaga ccttcggaga gtaatgccac cagatcccct 2700
aggaaagagg aggcaaatgg cactgcaggt gagaaccccg cccatccgtg ctatgacatg 2760
gaggcactga agcccgagga aggtgtgtgg agattctaat cccaacaagc aagggtctcc 2820
ttcaagatta atgctatcaa tcattaaggt cattactctc aaccacctag gcaatgaaga 2880
atataccatt tcaaatattt acagtacttg tcttcaccaa cactgtccca aggtgaaatg 2940
aagcaacaga gaggaaattg tacataagta cctcagcatt taatccaaac aggggttctt 3000
agtctcagca ctatgacatt ttgggctgac tacttatttg ttaggcggga gctctcctgt 3060
gcattgtagg ataattagca gtatccctgg tggctaccca atagacgcca gtagcacccc 3120
gaattgacaa cccaaactct ccagacatca ccaactgtcc cctgcgagga gaaatcactc 3180
ctgggggaga accactgacc caaatgaatt ctaaaccaat caaatgtctg ggaagccctc 3240
caagaaaaaa aatagaaaag cacttgaaga atattcccaa tattcccggt cagcagtatc 3300
aaggctgact tgtgttcatg tggagtcatt ataaattcta taaatcaatt attccccttc 3360
ggtcttaaaa atatatttcc tcataaacat ttgagttttg ttgaaaagat ggagtttaca 3420
aagataccat tcttgagtca tggatttctc tgctcacaga agggtgtggc atttggaaac 3480
gggaataaac aaaattgctg caccaatgca ctgagtgaag gaagagagac agaggatcaa 3540
gggctttaga cagcactcct tcaatatgca atcacagaga aagatgcgcc ttatccaagt 3600
taatatctct aaggtgagag ccttcttaga gtcagtttgt tgcaaatttc acctactctg 3660

-continued

```
ttcttttcca tccatccccc tgagtcagtt ggttgaaggg agttattttt tcaagtggaa   3720
ttcaaacaaa gctcaaacca gaactgtaaa tagtgattgc aggaattctt ttctaaactg   3780
ctttgccctt tcctctcact gccttttata gccaatataa atgtctcttt gcacaccttt   3840
tgttgtggtt ttatattgta acaccatttt tctttgaaac tattgtattt aaagtaaggt   3900
ttcatattat gtcagcaagt aattaactta tgtttaaaag gtggccatat catgtaccaa   3960
aagttgctga agtttctctt ctagctggta aagtaggagt ttgcatgact tcacactttt   4020
tttgcgtagt ttcttctgtt gtatgatggc gtgagtgtgt gtcttgggta ccgctgtgta   4080
ctactgtgtg cctagattcc atgcactctc gttgtgtttg aagtaaatat tggagaccgg   4140
agggtaacag gttggcctgt tgattacagc tagtaatcgc tgtgtcttgt tccgccccct   4200
ccctgacacc ccagcttccc aggatgtgga aagcctggat ctcagctcct tgccccatat   4260
cccttctgta atttgtacct aaagagtgtg attatcctaa ttcaagagtc actaaaactc   4320
atcacattat cattgcatat cagcaaaggg taaagtccta gcaccaattg cttcacatac   4380
cagcatgttc catttccaat ttagaattag ccacataata aaatcttaga atcttccttg   4440
agaaagagct gcctgagatg tagttttgtt atatggttcc ccaccgacca tttttgtgct   4500
tttttcttgt tttgttttgt tttgactgca ctgtgagttt tgtagtgtcc tcttcttgcc   4560
aaaacaaacg cgagatgaac tggacttatg tagacaaatc gtgatgccag tgtatccttc   4620
ctttcttcag ttccagcaat aatgaatggt caactttttt aaaatctaga tctctctcat   4680
tcatttcaat gtatttttac tttaagatga accaaaatta ttagacttat ttaagatgta   4740
caggcatcag aaaaaagaag cacataatgc ttttggtgcg atggcactca ctgtgaacat   4800
gtgtaaccac atattaatat gcaatattgt ttccaatact ttctaataca gtttttttata   4860
atgttgtgtg tggtgattgt tcaggtcgaa tctgttgtat ccagtacagc tttaggtctt   4920
cagctgccct tctggcgagt acatgcacag gattgtaaat gagaaatgca gtcatatttc   4980
cagtctgcct ctatgatgat gttaaattat tgctgtttag ctgtgaacaa gggatgtacc   5040
actggaggaa tagagtatcc ttttgtacac attttgaaat gcttcttctg tagtgataga   5100
acaaataaat gcaacgaata ctctgtctgc cctatcccgt gaagtccaca ctggcgtaag   5160
agaaggccca gcagagcagg aatctgccta gactttctcc caatgagatc ccaatatgag   5220
agggagaaga gatgggcctc aggacagctg caataccact tgggaacaca tgtggtgtct   5280
tgatgtggcc agcgcagcag ttcagcacaa cgtacctccc atctacaaca gtgctggacg   5340
tgggaattct aagtcccagt cttgagggtg ggtggagatg gagggcaaca agagatacat   5400
ttccagttct ccactgcagc atgcttcagt cattctgtga gtggccgggc ccagggccct   5460
cacaatttca ctaccttgtc ttttacatag tcataagaat tatcctcaac atagcctttt   5520
gacgctgtaa atcttgagta ttcatttacc cttttctgat ctcctggaaa cagctgcctg   5580
cctgcattgc acttctcttc ccgaggagtg gggtaaattt aaaagtcaag ttatagtttg   5640
gatgttagta tagaattttg aaattgggaa ttaaaaatca ggactgggga ctgggagacc   5700
aaaaatttct gatcccattt ctgatggatg tgtcacacct tttctgtcaa aataaaatgt   5760
cttggaggtt atgactcctt ggtgaaaaaa aaaaaaaaaa aa                      5802
```

<210> SEQ ID NO 26
<211> LENGTH: 5708
<212> TYPE: DNA
<213> ORGANISM: homo sapiens

<400> SEQUENCE: 26

```
gagcgggctg cagccggcgg cggcgccagc agataacctg aggaccatgg atgctgatga     60
gggtcaagac atgtcccaag tttcagggaa ggaaagcccc cctgtaagcg atactccaga    120
tgagggcgat gagcccatgc cgatccccga ggacctctcc accacctcgg gaggacagca    180
aagctccaag agtgacagag tcgtgggaga acggcccttc cagtgcaatc agtgcggggc    240
ctcattcacc cagaagggca acctgctccg gcacatcaag ctgcattccg ggagaagcc     300
cttcaaatgc cacctctgca actacgcctg ccgccggagg gacgccctca ctggccacct    360
gaggacgcac tccgtcatta aagaagaaac taatcacagt gaaatggcag aagacctgtg    420
caagatagga tcagagagat ctctcgtgct ggacagacta gcaagtaacg tcgccaaacg    480
taagagctct atgcctcaga aatttcttgg ggacaagggc ctgtccgaca cgccctacga    540
cagcagcgcc agctacgaga aggagaacga aatgatgaag tcccacgtga tggaccaagc    600
catcaacaac gccatcaact acctgggggc cgagtccctg cgcccgctgg tgcagacgcc    660
cccgggcggt tccgaggtgg tcccggtcat cagcccgatg taccagctgc acaagccgct    720
cgcggagggc accccgcgct ccaaccactc ggcccaggac agcgccgtgg agaacctgct    780
gctgctctcc aaggccaagt tggtgccctc ggagcgcgag gcgtccccga gcaacagctg    840
ccaagactcc acggacaccg agagcaacaa cgaggagcag cgcagcggtc tcatctacct    900
gaccaaccac atcgccccgc acgcgcgcaa cgggctgtcg ctcaaggagg agcaccgcgc    960
ctacgacctg ctgcgcgccg cctccgagaa ctcgcaggac gcgctccgcg tggtcagcac   1020
cagcggggag cagatgaagg tgtacaagtg cgaacactgc cgggtgctct tcctggatca   1080
cgtcatgtac accatccaca tgggctgcca cggcttccgt gatccttttg agtgcaacat   1140
gtgcggctac cacagccagg accggtacga gttctcgtcg cacataacgc gaggggagca   1200
ccgcttccac atgagctaaa gccctcccgc gcccccaccc cagaccccga gccaccccag   1260
gaaaagcaca aggactgccg ccttctcgct cccgccagca gcatagactg gactggacca   1320
gacaatgttg tgtttggatt tgtaactgtt ttttgttttt tgtttgagtt ggttgattgg   1380
ggtttgattt gcttttgaaa agatttttat ttttagaggc agggctgcat tgggagcatc   1440
cagaactgct accttcctag atgtttcccc agaccgctgg ctgagattcc ctcacctgtc   1500
gcttcctaga atccccttct ccaaacgatt agtctaaatt ttcagagaga aatagataaa   1560
acacgccaca gcctgggaag gagcgtgctc taccctgtgc taagcacggg gttcgcgcac   1620
caggtgtctt tttccagtcc ccagaagcag agagcacagc ccctgctgtg tgggtctgca   1680
ggtgagcaga caggacaggt gtgccgccac ccaagtgcca agacacagca gggccaacaa   1740
cctgtgccca ggccagcttc gagctacatg catctagggc ggagaggctg cacttgtgag   1800
agaaaatact atttcaagtc atattctgcg taggaaaatg aattggttgg ggaaagtcgt   1860
gtctgtcaga ctgccctggg tggagggaga cgccgggcta gagcctttgg gatcgtcctg   1920
gattcactgg ctttgcggag gctgctcaga tggcctgagc ctcccgaggc ttgctgcccc   1980
gtaggaggag actgtcttcc cgtgggcata tctggggagc cctgttcccc gctttttcac   2040
tcccatacct ttaatggccc ccaaaatctg tcactacaat ttaaacacca gtcccgaaat   2100
ttggatcttc tttctttttg aatctctcaa acggcaacat tcctcagaaa ccaaagcttt   2160
atttcaaatc tcttccttcc ctggctggtt ccatctagta ccagaggcct cttttcctga   2220
agaaatccaa tcctagccct cattttaatt atgtacatct gtttgtagcc acaagcctga   2280
atttctcagt gttggtaagt ttctttacct accctcacta tatattattc tcgttttaaa   2340
```

-continued

```
acccataaag gagtgattta gaacagtcat taattttcaa ctcaatgaaa tatgtgaagc   2400
ccagcatctc tgttgctaac acacagagct cacctgtttg aaaccaagct ttcaaacatg   2460
ttgaagctct ttactgtaaa ggcaagccag catgtgtgtc cacacataca taggatggct   2520
ggctctgcac ctgtaggata ttggaatgca cagggcaatt gagggactga gccagacctt   2580
cggagagtaa tgccaccaga tcccctagga aagaggaggc aaatggcact gcaggtgaga   2640
accccgccca tccgtgctat gacatggagg cactgaagcc cgaggaaggt gtgtggagat   2700
tctaatccca acaagcaagg gtctccttca agattaatgc tatcaatcat taaggtcatt   2760
actctcaacc acctaggcaa tgaagaatat accatttcaa atatttacag tacttgtctt   2820
caccaacact gtcccaaggt gaaatgaagc aacagagagg aaattgtaca taagtacctc   2880
agcatttaat ccaaacaggg gttcttagtc tcagcactat gacattttgg gctgactact   2940
tatttgttag gcgggagctc tcctgtgcat tgtaggataa ttagcagtat ccctggtggc   3000
tacccaatag acgccagtag caccccgaat tgacaaccca aactctccag acatcaccaa   3060
ctgtcccctg cgaggagaaa tcactcctgg gggagaacca ctgacccaaa tgaattctaa   3120
accaatcaaa tgtctgggaa gccctccaag aaaaaaaata gaaaagcact tgaagaatat   3180
tcccaatatt cccggtcagc agtatcaagg ctgacttgtg ttcatgtgga gtcattataa   3240
attctataaa tcaattattc cccttcggtc ttaaaaatat atttcctcat aaacatttga   3300
gttttgttga aaagatggag tttacaaaga taccattctt gagtcatgga tttctctgct   3360
cacagaaggg tgtggcattt ggaaacggga ataaacaaaa ttgctgcacc aatgcactga   3420
gtgaaggaag agagacagag gatcaagggc tttagacagc actccttcaa tatgcaatca   3480
cagagaaaga tgcgccttat ccaagttaat atctctaagg tgagagcctt cttagagtca   3540
gtttgttgca aatttcacct actctgttct tttccatcca tccccctgag tcagttggtt   3600
gaagggagtt attttttcaa gtggaattca aacaaagctc aaaccagaac tgtaaatagt   3660
gattgcagga attcttttct aaactgcttt gccctttcct ctcactgcct tttatagcca   3720
atataaatgt ctctttgcac accttttgtt gtggttttat attgtaacac catttttctt   3780
tgaaactatt gtatttaaag taaggtttca tattatgtca gcaagtaatt aacttatgtt   3840
taaaaggtgg ccatatcatg taccaaaagt tgctgaagtt tctcttctag ctggtaaagt   3900
aggagtttgc atgacttcac acttttttg cgtagtttct tctgttgtat gatggcgtga   3960
gtgtgtgtct tgggtaccgc tgtgtactac tgtgtgccta gattccatgc actctcgttg   4020
tgtttgaagt aaatattgga gaccggaggg taacaggttg gcctgttgat tacagctagt   4080
aatcgctgtg tcttgttccg ccccctccct gacaccccag cttcccagga tgtggaaagc   4140
ctggatctca gctccttgcc ccatatccct tctgtaattt gtacctaaag agtgtgatta   4200
tcctaattca agagtcacta aaactcatca cattatcatt gcatatcagc aaagggtaaa   4260
gtcctagcac caattgcttc acataccagc atgttccatt tccaatttag aattagccac   4320
ataataaaat cttagaatct tccttgagaa agagctgcct gagatgtagt tttgttatat   4380
ggttccccac cgaccatttt tgtgcttttt tcttgttttg ttttgttttg actgcactgt   4440
gagttttgta gtgtcctctt cttgccaaaa caaacgcgag atgaactgga cttatgtaga   4500
caaatcgtga tgccagtgta tccttccttt cttcagttcc agcaataatg aatggtcaac   4560
ttttttaaaa tctagatctc tctcattcat ttcaatgtat ttttacttta agatgaacca   4620
aaattattag acttatttaa gatgtacagg catcagaaaa aagaagcaca taatgctttt   4680
ggtgcgatgg cactcactgt gaacatgtgt aaccacatat taatatgcaa tattgtttcc   4740
```

```
aatactttct aatacagttt tttataatgt tgtgtgtggt gattgttcag gtcgaatctg   4800

ttgtatccag tacagcttta ggtcttcagc tgcccttctg gcgagtacat gcacaggatt   4860

gtaaatgaga aatgcagtca tatttccagt ctgcctctat gatgatgtta aattattgct   4920

gtttagctgt gaacaaggga tgtaccactg gaggaataga gtatcctttt gtacacattt   4980

tgaaatgctt cttctgtagt gatagaacaa ataaatgcaa cgaatactct gtctgcccta   5040

tcccgtgaag tccacactgg cgtaagagaa ggcccagcag agcaggaatc tgcctagact   5100

ttctcccaat gagatcccaa tatgagaggg agaagagatg ggcctcagga cagctgcaat   5160

accacttggg aacacatgtg gtgtcttgat gtggccagcg cagcagttca gcacaacgta   5220

cctcccatct acaacagtgc tggacgtggg aattctaagt cccagtcttg agggtgggtg   5280

gagatggagg gcaacaagag atacatttcc agttctccac tgcagcatgc ttcagtcatt   5340

ctgtgagtgg ccgggcccag ggccctcaca atttcactac cttgtctttt acatagtcat   5400

aagaattatc ctcaacatag ccttttgacg ctgtaaatct tgagtattca tttacccttt   5460

tctgatctcc tggaaacagc tgcctgcctg cattgcactt ctcttcccga ggagtggggt   5520

aaatttaaaa gtcaagttat agtttggatg ttagtataga attttgaaat tgggaattaa   5580

aaatcaggac tggggactgg gagaccaaaa atttctgatc ccatttctga tggatgtgtc   5640

acaccttttc tgtcaaaata aaatgtcttg gaggttatga ctccttggtg aaaaaaaaaa   5700

aaaaaaaa                                                             5708
```

<210> SEQ ID NO 27
<211> LENGTH: 5646
<212> TYPE: DNA
<213> ORGANISM: homo sapiens

<400> SEQUENCE: 27

```
ataacctgag gaccatggat gctgatgagg gtcaagacat gtcccaagtt tcagggaagg     60

aaagcccccc tgtaagcgat actccagatg agggcgatga gcccatgccg atccccgagg    120

acctctccac cacctcggga ggacagcaaa gctccaagag tgacagagtc gtgggagaac    180

ggcccttcca gtgcaatcag tgcggggcct cattcaccca gaagggcaac ctgctccggc    240

acatcaagct gcattccggg gagaagccct tcaaatgcca cctctgcaac tacgcctgcc    300

gccggaggga cgccctcact ggccacctga ggacgcactc cgtcattaaa gaagaaacta    360

atcacagtga aatggcagaa gacctgtgca agataggatc agagagatct ctcgtgctgg    420

acagactagc aagtaacgtc gccaaacggg acaagggcct gtccgacacg ccctacgaca    480

gcagcgccag ctacgagaag gagaacgaaa tgatgaagtc ccacgtgatg gaccaagcca    540

tcaacaacgc catcaactac ctgggggccg agtccctgcg cccgctggtg cagacgcccc    600

cgggcggttc cgaggtggtc ccggtcatca gcccgatgta ccagctgcac aagccgctcg    660

cggagggcac cccgcgctcc aaccactcgg cccaggacag cgccgtggag aacctgctgc    720

tgctctccaa ggccaagttg gtgccctcgg agcgcgaggc gtccccgagc aacagctgcc    780

aagactccac ggacaccgag agcaacaacg aggagcagcg cagcggtctc atctacctga    840

ccaaccacat cgccccgcac gcgcgcaacg ggctgtcgct caaggaggag caccgcgcct    900

acgacctgct gcgcgccgcc tccgagaact cgcaggacgc gctccgcgtg gtcagcacca    960

gcggggagca gatgaaggtg tacaagtgcg aacactgccg ggtgctcttc ctggatcacg   1020

tcatgtacac catccacatg ggctgccacg gcttccgtga tccttttgag tgcaacatgt   1080
```

gcggctacca cagccaggac cggtacgagt tctcgtcgca cataacgcga ggggagcacc 1140
gcttccacat gagctaaagc cctcccgcgc ccccacccca gaccccgagc caccccagga 1200
aaagcacaag gactgccgcc ttctcgctcc cgccagcagc atagactgga ctggaccaga 1260
caatgttgtg tttggatttg taactgtttt ttgtttttg tttgagttgg ttgattgggg 1320
tttgatttgc ttttgaaaag atttttattt ttagaggcag ggctgcattg ggagcatcca 1380
gaactgctac cttcctagat gtttccccag accgctggct gagattccct cacctgtcgc 1440
ttcctagaat ccccttctcc aaacgattag tctaaatttt cagagagaaa tagataaaac 1500
acgccacagc ctgggaagga gcgtgctcta ccctgtgcta agcacggggt tcgcgcacca 1560
ggtgtctttt tccagtcccc agaagcagag agcacagccc ctgctgtgtg ggtctgcagg 1620
tgagcagaca ggacaggtgt gccgccaccc aagtgccaag acacagcagg gccaacaacc 1680
tgtgcccagg ccagcttcga gctacatgca tctagggcgg agaggctgca cttgtgagag 1740
aaaatactat ttcaagtcat attctgcgta ggaaaatgaa ttggttgggg aaagtcgtgt 1800
ctgtcagact gccctgggtg gagggagacg ccgggctaga gcctttggga tcgtcctgga 1860
ttcactggct ttgcggaggc tgctcagatg gcctgagcct cccgaggctt gctgccccgt 1920
aggaggagac tgtcttcccg tgggcatatc tggggagccc tgttccccgc tttttcactc 1980
ccataccttt aatggccccc aaaatctgtc actacaattt aaacaccagt cccgaaattt 2040
ggatcttctt tctttttgaa tctctcaaac ggcaacattc ctcagaaacc aaagctttat 2100
ttcaaatctc ttccttccct ggctggttcc atctagtacc agaggcctct tttcctgaag 2160
aaatccaatc ctagccctca ttttaattat gtacatctgt ttgtagccac aagcctgaat 2220
ttctcagtgt tggtaagttt ctttacctac cctcactata tattattctc gttttaaaac 2280
ccataaagga gtgatttaga acagtcatta attttcaact caatgaaata tgtgaagccc 2340
agcatctctg ttgctaacac acagagctca cctgtttgaa accaagcttt caaacatgtt 2400
gaagctcttt actgtaaagg caagccagca tgtgtgtcca cacatacata ggatggctgg 2460
ctctgcacct gtaggatatt ggaatgcaca gggcaattga gggactgagc cagaccttcg 2520
gagagtaatg ccaccagatc ccctaggaaa gaggaggcaa atggcactgc aggtgagaac 2580
cccgcccatc cgtgctatga catggaggca ctgaagcccg aggaaggtgt gtggagattc 2640
taatcccaac aagcaagggt ctccttcaag attaatgcta tcaatcatta aggtcattac 2700
tctcaaccac ctaggcaatg aagaatatac catttcaaat atttacagta cttgtcttca 2760
ccaacactgt cccaaggtga aatgaagcaa cagagaggaa attgtacata agtacctcag 2820
catttaatcc aaacaggggt tcttagtctc agcactatga cattttgggc tgactactta 2880
tttgttaggc gggagctctc ctgtgcattg taggataatt agcagtatcc ctggtggcta 2940
cccaatagac gccagtagca ccccgaattg acaacccaaa ctctccagac atcaccaact 3000
gtcccctgcg aggagaaatc actcctgggg gagaaccact gacccaaatg aattctaaac 3060
caatcaaatg tctgggaagc cctccaagaa aaaaaataga aaagcacttg aagaatattc 3120
ccaatattcc cggtcagcag tatcaaggct gacttgtgtt catgtggagt cattataaat 3180
tctataaatc aattattccc cttcggtctt aaaaatatat ttcctcataa acatttgagt 3240
tttgttgaaa agatggagtt tacaaagata ccattcttga gtcatggatt tctctgctca 3300
cagaagggtg tggcatttgg aaacgggaat aaacaaaatt gctgcaccaa tgcactgagt 3360
gaaggaagag agacagagga tcaagggctt tagacagcac tccttcaata tgcaatcaca 3420
gagaaagatg cgccttatcc aagttaatat ctctaaggtg agagccttct tagagtcagt 3480

```
ttgttgcaaa tttcacctac tctgttcttt tccatccatc cccctgagtc agttggttga   3540
agggagttat tttttcaagt ggaattcaaa caaagctcaa accagaactg taaatagtga   3600
ttgcaggaat tcttttctaa actgctttgc cctttcctct cactgccttt tatagccaat   3660
ataaatgtct ctttgcacac cttttgttgt ggttttatat tgtaacacca tttttctttg   3720
aaactattgt atttaaagta aggtttcata ttatgtcagc aagtaattaa cttatgttta   3780
aaaggtggcc atatcatgta ccaaaagttg ctgaagtttc tcttctagct ggtaaagtag   3840
gagtttgcat gacttcacac tttttttgcg tagtttcttc tgttgtatga tggcgtgagt   3900
gtgtgtcttg ggtaccgctg tgtactactg tgtgcctaga ttccatgcac tctcgttgtg   3960
tttgaagtaa atattggaga ccggagggta acaggttggc ctgttgatta cagctagtaa   4020
tcgctgtgtc ttgttccgcc ccctccctga caccccagct tcccaggatg tggaaagcct   4080
ggatctcagc tccttgcccc atatcccttc tgtaatttgt acctaaagag tgtgattatc   4140
ctaattcaag agtcactaaa actcatcaca ttatcattgc atatcagcaa agggtaaagt   4200
cctagcacca attgcttcac ataccagcat gttccatttc caatttagaa ttagccacat   4260
aataaaatct tagaatcttc cttgagaaag agctgcctga gatgtagttt tgttatatgg   4320
ttccccaccg accatttttg tgctttttc ttgttttgtt ttgttttgac tgcactgtga   4380
gttttgtagt gtcctcttct tgccaaaaca aacgcgagat gaactggact tatgtagaca   4440
aatcgtgatg ccagtgtatc cttcctttct tcagttccag caataatgaa tggtcaactt   4500
ttttaaaatc tagatctctc tcattcattt caatgtattt ttactttaag atgaaccaaa   4560
attattagac ttatttaaga tgtacaggca tcagaaaaaa gaagcacata atgcttttgg   4620
tgcgatggca ctcactgtga acatgtgtaa ccacatatta atatgcaata ttgtttccaa   4680
tactttctaa tacagttttt tataatgttg tgtgtggtga ttgttcaggt cgaatctgtt   4740
gtatccagta cagctttagg tcttcagctg cccttctggc gagtacatgc acaggattgt   4800
aaatgagaaa tgcagtcata tttccagtct gcctctatga tgatgttaaa ttattgctgt   4860
ttagctgtga acaagggatg taccactgga ggaatagagt atccttttgt acacattttg   4920
aaatgcttct tctgtagtga tagaacaaat aaatgcaacg aatactctgt ctgccctatc   4980
ccgtgaagtc cacactggcg taagagaagg cccagcagag caggaatctg cctagacttt   5040
ctcccaatga gatcccaata tgagagggag aagagatggg cctcaggaca gctgcaatac   5100
cacttgggaa cacatgtggt gtcttgatgt ggccagcgca gcagttcagc acaacgtacc   5160
tcccatctac aacagtgctg gacgtgggaa ttctaagtcc cagtcttgag ggtgggtgga   5220
gatggagggc aacaagagat acatttccag ttctccactg cagcatgctt cagtcattct   5280
gtgagtggcc gggcccaggg ccctcacaat ttcactacct tgtcttttac atagtcataa   5340
gaattatcct caacatagcc ttttgacgct gtaaatcttg agtattcatt taccctttc   5400
tgatctcctg gaaacagctg cctgcctgca ttgcacttct cttcccgagg agtggggtaa   5460
atttaaaagt caagttatag tttggatgtt agtatagaat tttgaaattg ggaattaaaa   5520
atcaggactg gggactggga gaccaaaaat ttctgatccc atttctgatg gatgtgtcac   5580
accttttctg tcaaaataaa atgtcttgga ggttatgact ccttggtgaa aaaaaaaaaa   5640
aaaaaa                                                              5646
```

<210> SEQ ID NO 28
<211> LENGTH: 5634
<212> TYPE: DNA

<213> ORGANISM: homo sapiens

<400> SEQUENCE: 28
ataacctgag gaccatggat gctgatgagg gtcaagacat gtcccaagtt tcagggaagg 60
aaagcccccc tgtaagcgat actccagatg agggcgatga gcccatgccg atccccgagg 120
acctctccac cacctcggga ggacagcaaa gctccaagag tgacagagtc gtggccagta 180
atgttaaagt agagactcag agtgatgaag agaatgggcg tgcctgtgaa atgaatgggg 240
aagaatgtgc ggaggattta cgaatgcttg atgcctcggg agagaaaatg aatggctccc 300
acagggacca aggcagctcg gctttgtcgg gagttggagg cattcgactt cctaacggaa 360
aactaaagtg tgatatctgt gggatcattt gcatcgggcc caatgtgctc atggttcaca 420
aaagaagcca cactggggac aagggcctgt ccgacacgcc ctacgacagc agcgccagct 480
acgagaagga gaacgaaatg atgaagtccc acgtgatgga ccaagccatc aacaacgcca 540
tcaactacct gggggccgag tccctgcgcc cgctggtgca gacgcccccg ggcggttccg 600
aggtggtccc ggtcatcagc ccgatgtacc agctgcacaa gccgctcgcg gagggcaccc 660
cgcgctccaa ccactcggcc caggacagcg ccgtggagaa cctgctgctg ctctccaagg 720
ccaagttggt gccctcggag cgcgaggcgt ccccgagcaa cagctgccaa gactccacgg 780
acaccgagag caacaacgag gagcagcgca gcggtctcat ctacctgacc aaccacatcg 840
ccccgcacgc gcgcaacggg ctgtcgctca aggaggagca ccgcgcctac gacctgctgc 900
gcgccgcctc cgagaactcg caggacgcgc tccgcgtggt cagcaccagc ggggagcaga 960
tgaaggtgta caagtgcgaa cactgccggg tgctcttcct ggatcacgtc atgtacacca 1020
tccacatggg ctgccacggc ttccgtgatc cttttgagtg caacatgtgc ggctaccaca 1080
gccaggaccg gtacgagttc tcgtcgcaca taacgcgagg ggagcaccgc ttccacatga 1140
gctaaagccc tcccgcgccc ccaccccaga ccccgagcca ccccaggaaa agcacaagga 1200
ctgccgcctt ctcgctcccg ccagcagcat agactggact ggaccagaca atgttgtgtt 1260
tggatttgta actgtttttt gtttttgtt tgagttggtt gattggggtt tgatttgctt 1320
ttgaaaagat ttttattttt agaggcaggg ctgcattggg agcatccaga actgctacct 1380
tcctagatgt ttccccagac cgctggctga gattccctca cctgtcgctt cctagaatcc 1440
ccttctccaa acgattagtc taaattttca gagagaaata gataaaacac gccacagcct 1500
gggaaggagc gtgctctacc ctgtgctaag cacggggttc gcgcaccagg tgtctttttc 1560
cagtccccag aagcagagag cacagcccct gctgtgtggg tctgcaggtg agcagacagg 1620
acaggtgtgc cgccacccaa gtgccaagac acagcagggc caacaacctg tgcccaggcc 1680
agcttcgagc tacatgcatc tagggcggag aggctgcact tgtgagagaa aatactattt 1740
caagtcatat tctgcgtagg aaaatgaatt ggttggggaa agtcgtgtct gtcagactgc 1800
cctgggtgga gggagacgcc gggctagagc ctttgggatc gtcctggatt cactggcttt 1860
gcggaggctg ctcagatggc ctgagcctcc cgaggcttgc tgccccgtag gaggagactg 1920
tcttcccgtg ggcatatctg gggagccctg ttccccgctt tttcactccc ataccttttaa 1980 tggcccccaa aatctgtcac tacaatttaa acaccagtcc cgaaatttgg atcttctttc 2040
tttttgaatc tctcaaacgg caacattcct cagaaaccaa agctttattt caaatctctt 2100
ccttccctgg ctggttccat ctagtaccag aggcctcttt tcctgaagaa atccaatcct 2160
agccctcatt ttaattatgt acatctgttt gtagccacaa gcctgaattt ctcagtgttg 2220
gtaagtttct ttacctaccc tcactatata ttattctcgt tttaaaaccc ataaaggagt 2280

```
gatttagaac agtcattaat tttcaactca atgaaatatg tgaagcccag catctctgtt   2340
gctaacacac agagctcacc tgtttgaaac caagctttca aacatgttga agctctttac   2400
tgtaaaggca agccagcatg tgtgtccaca catacatagg atggctggct ctgcacctgt   2460
aggatattgg aatgcacagg gcaattgagg gactgagcca gaccttcgga gagtaatgcc   2520
accagatccc ctaggaaaga ggaggcaaat ggcactgcag gtgagaaccc cgcccatccg   2580
tgctatgaca tggaggcact gaagcccgag gaaggtgtgt ggagattcta atcccaacaa   2640
gcaagggtct ccttcaagat taatgctatc aatcattaag gtcattactc tcaaccacct   2700
aggcaatgaa gaatatacca tttcaaatat ttacagtact tgtcttcacc aacactgtcc   2760
caaggtgaaa tgaagcaaca gagaggaaat tgtacataag tacctcagca tttaatccaa   2820
acaggggttc ttagtctcag cactatgaca ttttgggctg actacttatt tgttaggcgg   2880
gagctctcct gtgcattgta ggataattag cagtatccct ggtggctacc caatagacgc   2940
cagtagcacc ccgaattgac aacccaaact ctccagacat caccaactgt cccctgcgag   3000
gagaaatcac tcctggggga gaaccactga cccaaatgaa ttctaaacca atcaaatgtc   3060
tgggaagccc tccaagaaaa aaaatagaaa agcacttgaa gaatattccc aatattcccg   3120
gtcagcagta tcaaggctga cttgtgttca tgtggagtca ttataaattc tataaatcaa   3180
ttattcccct tcggtcttaa aaatatattt cctcataaac atttgagttt tgttgaaaag   3240
atggagttta caaagatacc attcttgagt catggatttc tctgctcaca gaagggtgtg   3300
gcatttggaa acgggaataa acaaaattgc tgcaccaatg cactgagtga aggaagagag   3360
acagaggatc aagggcttta gacagcactc cttcaatatg caatcacaga gaaagatgcg   3420
ccttatccaa gttaatatct ctaaggtgag agccttctta gagtcagttt gttgcaaatt   3480
tcacctactc tgttcttttc catccatccc cctgagtcag ttggttgaag ggagttattt   3540
tttcaagtgg aattcaaaca aagctcaaac cagaactgta aatagtgatt gcaggaattc   3600
ttttctaaac tgctttgccc tttcctctca ctgcctttta tagccaatat aaatgtctct   3660
ttgcacacct tttgttgtgg ttttatattg taacaccatt tttctttgaa actattgtat   3720
ttaaagtaag gtttcatatt atgtcagcaa gtaattaact tatgtttaaa aggtggccat   3780
atcatgtacc aaaagttgct gaagtttctc ttctagctgg taaagtagga gtttgcatga   3840
cttcacactt tttttgcgta gtttcttctg ttgtatgatg gcgtgagtgt gtgtcttggg   3900
taccgctgtg tactactgtg tgcctagatt ccatgcactc tcgttgtgtt tgaagtaaat   3960
attggagacc ggagggtaac aggttggcct gttgattaca gctagtaatc gctgtgtctt   4020
gttccgcccc ctccctgaca ccccagcttc ccaggatgtg gaaagcctgg atctcagctc   4080
cttgccccat atcccttctg taatttgtac ctaaagagtg tgattatcct aattcaagag   4140
tcactaaaac tcatcacatt atcattgcat atcagcaaag ggtaaagtcc tagcaccaat   4200
tgcttcacat accagcatgt tccatttcca atttagaatt agccacataa taaaatctta   4260
gaatcttcct tgagaaagag ctgcctgaga tgtagttttg ttatatggtt ccccaccgac   4320
catttttgtg ctttttttctt gttttgtttt gttttgactg cactgtgagt tttgtagtgt   4380
cctcttcttg ccaaaacaaa cgcgagatga actggactta tgtagacaaa tcgtgatgcc   4440
agtgtatcct tcctttcttc agttccagca ataatgaatg gtcaactttt ttaaaatcta   4500
gatctctctc attcatttca atgtattttt actttaagat gaaccaaaat tattagactt   4560
atttaagatg tacaggcatc agaaaaaaga agcacataat gcttttggtg cgatggcact   4620
```

```
cactgtgaac atgtgtaacc acatattaat atgcaatatt gtttccaata ctttctaata   4680

cagtttttta taatgttgtg tgtggtgatt gttcaggtcg aatctgttgt atccagtaca   4740

gctttaggtc ttcagctgcc cttctggcga gtacatgcac aggattgtaa atgagaaatg   4800

cagtcatatt tccagtctgc ctctatgatg atgttaaatt attgctgttt agctgtgaac   4860

aagggatgta ccactggagg aatagagtat ccttttgtac acattttgaa atgcttcttc   4920

tgtagtgata gaacaaataa atgcaacgaa tactctgtct gccctatccc gtgaagtcca   4980

cactggcgta agagaaggcc cagcagagca ggaatctgcc tagactttct cccaatgaga   5040

tcccaatatg agagggagaa gagatgggcc tcaggacagc tgcaatacca cttgggaaca   5100

catgtggtgt cttgatgtgg ccagcgcagc agttcagcac aacgtacctc ccatctacaa   5160

cagtgctgga cgtgggaatt ctaagtccca gtcttgaggg tgggtggaga tggagggcaa   5220

caagagatac atttccagtt ctccactgca gcatgcttca gtcattctgt gagtggccgg   5280

gcccagggcc ctcacaattt cactaccttg tcttttacat agtcataaga attatcctca   5340

acatagcctt ttgacgctgt aaatcttgag tattcattta cccttttctg atctcctgga   5400

aacagctgcc tgcctgcatt gcacttctct tcccgaggag tggggtaaat ttaaaagtca   5460

agttatagtt tggatgttag tatagaattt tgaaattggg aattaaaaat caggactggg   5520

gactgggaga ccaaaaattt ctgatcccat ttctgatgga tgtgtcacac cttttctgtc   5580

aaaataaaat gtcttggagg ttatgactcc ttggtgaaaa aaaaaaaaaa aaaa         5634
```

```
<210> SEQ ID NO 29
<211> LENGTH: 586
<212> TYPE: PRT
<213> ORGANISM: mus musculus

<400> SEQUENCE: 29

Met His Thr Pro Pro Ala Leu Pro Arg Arg Phe Gln Gly Gly Gly Arg
1               5                   10                  15

Val Arg Thr Pro Gly Ser His Arg Gln Gly Lys Asp Asn Leu Glu Arg
            20                  25                  30

Glu Leu Ser Gly Gly Cys Ala Pro Asp Phe Leu Pro Gln Ala Gln Asp
        35                  40                  45

Ser Asn His Phe Ile Met Glu Ser Leu Phe Cys Glu Ser Ser Gly Asp
    50                  55                  60

Ser Ser Leu Glu Lys Glu Phe Leu Gly Ala Pro Val Gly Pro Ser Val
65                  70                  75                  80

Ser Thr Pro Asn Ser Gln His Ser Ser Pro Ser Arg Ser Leu Ser Ala
                85                  90                  95

Asn Ser Ile Lys Val Glu Met Tyr Ser Asp Glu Glu Ser Ser Arg Leu
            100                 105                 110

Leu Gly Pro Asp Glu Arg Leu Leu Asp Lys Asp Asp Ser Val Ile Val
        115                 120                 125

Glu Asp Ser Leu Ser Glu Pro Leu Gly Tyr Cys Asp Gly Ser Gly Pro
    130                 135                 140

Glu Pro His Ser Pro Gly Gly Ile Arg Leu Pro Asn Gly Lys Leu Lys
145                 150                 155                 160

Cys Asp Val Cys Gly Met Val Cys Ile Gly Pro Asn Val Leu Met Val
                165                 170                 175

His Lys Arg Ser His Thr Gly Glu Arg Pro Phe His Cys Asn Gln Cys
            180                 185                 190

Gly Ala Ser Phe Thr Gln Lys Gly Asn Leu Leu Arg His Ile Lys Leu
```

```
        195                 200                 205

His Ser Gly Glu Lys Pro Phe Lys Cys Pro Phe Cys Asn Tyr Ala Cys
    210                 215                 220

Arg Arg Arg Asp Ala Leu Thr Gly His Leu Arg Thr His Ser Val Ser
225                 230                 235                 240

Ser Pro Thr Val Gly Lys Pro Tyr Lys Cys Asn Tyr Cys Gly Arg Ser
                245                 250                 255

Tyr Lys Gln Gln Ser Thr Leu Glu Glu His Lys Glu Arg Cys His Asn
            260                 265                 270

Tyr Leu Gln Ser Leu Ser Thr Asp Ala Gln Ala Leu Thr Gly Gln Pro
        275                 280                 285

Gly Asp Glu Ile Arg Asp Leu Glu Met Val Pro Asp Ser Met Leu His
    290                 295                 300

Pro Ser Thr Glu Arg Pro Thr Phe Ile Asp Arg Leu Ala Asn Ser Leu
305                 310                 315                 320

Thr Lys Arg Lys Arg Ser Thr Pro Gln Lys Phe Val Gly Glu Lys Gln
                325                 330                 335

Met Arg Phe Ser Leu Ser Asp Leu Pro Tyr Asp Val Asn Ala Ser Gly
            340                 345                 350

Gly Tyr Glu Lys Asp Val Glu Leu Val Ala His His Gly Leu Glu Pro
        355                 360                 365

Gly Phe Gly Gly Ser Leu Ala Phe Val Gly Thr Glu His Leu Arg Pro
    370                 375                 380

Leu Arg Leu Pro Pro Thr Asn Cys Ile Ser Glu Leu Thr Pro Val Ile
385                 390                 395                 400

Ser Ser Val Tyr Thr Gln Met Gln Pro Ile Pro Ser Arg Leu Glu Leu
                405                 410                 415

Pro Gly Ser Arg Glu Ala Gly Glu Gly Pro Glu Asp Leu Gly Asp Gly
            420                 425                 430

Gly Pro Leu Leu Tyr Arg Ala Arg Gly Ser Leu Thr Asp Pro Gly Ala
        435                 440                 445

Ser Pro Ser Asn Gly Cys Gln Asp Ser Thr Asp Thr Glu Ser Asn His
    450                 455                 460

Glu Asp Arg Ile Gly Gly Val Val Ser Leu Pro Gln Gly Pro Pro Pro
465                 470                 475                 480

Gln Pro Pro Pro Thr Ile Val Val Gly Arg His Ser Pro Ala Tyr Ala
                485                 490                 495

Lys Glu Asp Pro Lys Pro Gln Glu Gly Leu Leu Arg Gly Thr Pro Gly
            500                 505                 510

Pro Ser Lys Glu Val Leu Arg Val Val Gly Glu Ser Gly Glu Pro Val
        515                 520                 525

Lys Ala Phe Lys Cys Glu His Cys Arg Ile Leu Phe Leu Asp His Val
    530                 535                 540

Met Phe Thr Ile His Met Gly Cys His Gly Phe Arg Asp Pro Phe Glu
545                 550                 555                 560

Cys Asn Ile Cys Gly Tyr His Ser Gln Asp Arg Tyr Glu Phe Ser Ser
                565                 570                 575

His Ile Val Arg Gly Glu His Lys Val Gly
            580                 585
```

<210> SEQ ID NO 30
<211> LENGTH: 533
<212> TYPE: PRT
<213> ORGANISM: mus musculus

<400> SEQUENCE: 30

```
Met Glu Ser Leu Phe Cys Glu Ser Ser Gly Asp Ser Ser Leu Glu Lys
1               5                   10                  15

Glu Phe Leu Gly Ala Pro Val Gly Pro Ser Val Ser Thr Pro Asn Ser
            20                  25                  30

Gln His Ser Ser Pro Ser Arg Ser Leu Ser Ala Asn Ser Ile Lys Val
        35                  40                  45

Glu Met Tyr Ser Asp Glu Glu Ser Ser Arg Leu Leu Gly Pro Asp Glu
    50                  55                  60

Arg Leu Leu Asp Lys Asp Asp Ser Val Ile Val Glu Asp Ser Leu Ser
65                  70                  75                  80

Glu Pro Leu Gly Tyr Cys Asp Gly Ser Gly Pro Glu Pro His Ser Pro
                85                  90                  95

Gly Gly Ile Arg Leu Pro Asn Gly Lys Leu Lys Cys Asp Val Cys Gly
            100                 105                 110

Met Val Cys Ile Gly Pro Asn Val Leu Met Val His Lys Arg Ser His
        115                 120                 125

Thr Gly Glu Arg Pro Phe His Cys Asn Gln Cys Gly Ala Ser Phe Thr
    130                 135                 140

Gln Lys Gly Asn Leu Leu Arg His Ile Lys Leu His Ser Gly Glu Lys
145                 150                 155                 160

Pro Phe Lys Cys Pro Phe Cys Asn Tyr Ala Cys Arg Arg Arg Asp Ala
                165                 170                 175

Leu Thr Gly His Leu Arg Thr His Ser Val Ser Ser Pro Thr Val Gly
            180                 185                 190

Lys Pro Tyr Lys Cys Asn Tyr Cys Gly Arg Ser Tyr Lys Gln Gln Ser
        195                 200                 205

Thr Leu Glu Glu His Lys Glu Arg Cys His Asn Tyr Leu Gln Ser Leu
    210                 215                 220

Ser Thr Asp Ala Gln Ala Leu Thr Gly Gln Pro Gly Asp Glu Ile Arg
225                 230                 235                 240

Asp Leu Glu Met Val Pro Asp Ser Met Leu His Pro Ser Thr Glu Arg
                245                 250                 255

Pro Thr Phe Ile Asp Arg Leu Ala Asn Ser Leu Thr Lys Arg Lys Arg
            260                 265                 270

Ser Thr Pro Gln Lys Phe Val Gly Glu Lys Gln Met Arg Phe Ser Leu
        275                 280                 285

Ser Asp Leu Pro Tyr Asp Val Asn Ala Ser Gly Gly Tyr Glu Lys Asp
    290                 295                 300

Val Glu Leu Val Ala His His Gly Leu Glu Pro Gly Phe Gly Gly Ser
305                 310                 315                 320

Leu Ala Phe Val Gly Thr Glu His Leu Arg Pro Leu Arg Leu Pro Pro
                325                 330                 335

Thr Asn Cys Ile Ser Glu Leu Thr Pro Val Ile Ser Ser Val Tyr Thr
            340                 345                 350

Gln Met Gln Pro Ile Pro Ser Arg Leu Glu Leu Pro Gly Ser Arg Glu
        355                 360                 365

Ala Gly Glu Gly Pro Glu Asp Leu Gly Asp Gly Gly Pro Leu Leu Tyr
    370                 375                 380

Arg Ala Arg Gly Ser Leu Thr Asp Pro Gly Ala Ser Pro Ser Asn Gly
385                 390                 395                 400

Cys Gln Asp Ser Thr Asp Thr Glu Ser Asn His Glu Asp Arg Ile Gly
```

```
                405                 410                 415

Gly Val Val Ser Leu Pro Gln Gly Pro Pro Pro Gln Pro Pro Pro Thr
            420                 425                 430

Ile Val Val Gly Arg His Ser Pro Ala Tyr Ala Lys Glu Asp Pro Lys
        435                 440                 445

Pro Gln Glu Gly Leu Leu Arg Gly Thr Pro Gly Pro Ser Lys Glu Val
    450                 455                 460

Leu Arg Val Val Gly Glu Ser Gly Glu Pro Val Lys Ala Phe Lys Cys
465                 470                 475                 480

Glu His Cys Arg Ile Leu Phe Leu Asp His Val Met Phe Thr Ile His
                485                 490                 495

Met Gly Cys His Gly Phe Arg Asp Pro Phe Glu Cys Asn Ile Cys Gly
            500                 505                 510

Tyr His Ser Gln Asp Arg Tyr Glu Phe Ser Ser His Ile Val Arg Gly
        515                 520                 525

Glu His Lys Val Gly
    530


<210> SEQ ID NO 31
<211> LENGTH: 531
<212> TYPE: PRT
<213> ORGANISM: mus musculus

<400> SEQUENCE: 31

Met Phe Ile Pro Val Gly Ser Gly Asp Ser Ser Leu Glu Lys Glu Phe
1               5                   10                  15

Leu Gly Ala Pro Val Gly Pro Ser Val Ser Thr Pro Asn Ser Gln His
            20                  25                  30

Ser Ser Pro Ser Arg Ser Leu Ser Ala Asn Ser Ile Lys Val Glu Met
        35                  40                  45

Tyr Ser Asp Glu Glu Ser Ser Arg Leu Leu Gly Pro Asp Glu Arg Leu
    50                  55                  60

Leu Asp Lys Asp Asp Ser Val Ile Val Glu Asp Ser Leu Ser Glu Pro
65                  70                  75                  80

Leu Gly Tyr Cys Asp Gly Ser Gly Pro Glu Pro His Ser Pro Gly Gly
                85                  90                  95

Ile Arg Leu Pro Asn Gly Lys Leu Lys Cys Asp Val Cys Gly Met Val
            100                 105                 110

Cys Ile Gly Pro Asn Val Leu Met Val His Lys Arg Ser His Thr Gly
        115                 120                 125

Glu Arg Pro Phe His Cys Asn Gln Cys Gly Ala Ser Phe Thr Gln Lys
    130                 135                 140

Gly Asn Leu Leu Arg His Ile Lys Leu His Ser Gly Glu Lys Pro Phe
145                 150                 155                 160

Lys Cys Pro Phe Cys Asn Tyr Ala Cys Arg Arg Arg Asp Ala Leu Thr
                165                 170                 175

Gly His Leu Arg Thr His Ser Val Ser Ser Pro Thr Val Gly Lys Pro
            180                 185                 190

Tyr Lys Cys Asn Tyr Cys Gly Arg Ser Tyr Lys Gln Gln Ser Thr Leu
        195                 200                 205

Glu Glu His Lys Glu Arg Cys His Asn Tyr Leu Gln Ser Leu Ser Thr
    210                 215                 220

Asp Ala Gln Ala Leu Thr Gly Gln Pro Gly Asp Glu Ile Arg Asp Leu
225                 230                 235                 240
```

Glu Met Val Pro Asp Ser Met Leu His Pro Ser Thr Glu Arg Pro Thr
245 250 255

Phe Ile Asp Arg Leu Ala Asn Ser Leu Thr Lys Arg Lys Arg Ser Thr
260 265 270

Pro Gln Lys Phe Val Gly Glu Lys Gln Met Arg Phe Ser Leu Ser Asp
275 280 285

Leu Pro Tyr Asp Val Asn Ala Ser Gly Gly Tyr Glu Lys Asp Val Glu
290 295 300

Leu Val Ala His His Gly Leu Glu Pro Gly Phe Gly Gly Ser Leu Ala
305 310 315 320

Phe Val Gly Thr Glu His Leu Arg Pro Leu Arg Leu Pro Pro Thr Asn
325 330 335

Cys Ile Ser Glu Leu Thr Pro Val Ile Ser Ser Val Tyr Thr Gln Met
340 345 350

Gln Pro Ile Pro Ser Arg Leu Glu Leu Pro Gly Ser Arg Glu Ala Gly
355 360 365

Glu Gly Pro Glu Asp Leu Gly Asp Gly Gly Pro Leu Leu Tyr Arg Ala
370 375 380

Arg Gly Ser Leu Thr Asp Pro Gly Ala Ser Pro Ser Asn Gly Cys Gln
385 390 395 400

Asp Ser Thr Asp Thr Glu Ser Asn His Glu Asp Arg Ile Gly Gly Val
405 410 415

Val Ser Leu Pro Gln Gly Pro Pro Pro Gln Pro Pro Pro Thr Ile Val
420 425 430

Val Gly Arg His Ser Pro Ala Tyr Ala Lys Glu Asp Pro Lys Pro Gln
435 440 445

Glu Gly Leu Leu Arg Gly Thr Pro Gly Pro Ser Lys Glu Val Leu Arg
450 455 460

Val Val Gly Glu Ser Gly Glu Pro Val Lys Ala Phe Lys Cys Glu His
465 470 475 480

Cys Arg Ile Leu Phe Leu Asp His Val Met Phe Thr Ile His Met Gly
485 490 495

Cys His Gly Phe Arg Asp Pro Phe Glu Cys Asn Ile Cys Gly Tyr His
500 505 510

Ser Gln Asp Arg Tyr Glu Phe Ser Ser His Ile Val Arg Gly Glu His
515 520 525

Lys Val Gly
530

<210> SEQ ID NO 32
<211> LENGTH: 686
<212> TYPE: PRT
<213> ORGANISM: mus musculus

<400> SEQUENCE: 32

Met His Thr Pro Pro Ala Leu Pro Arg Arg Phe Gln Gly Gly Gly Arg
1 5 10 15

Val Arg Thr Pro Gly Ser His Arg Gln Gly Lys Asp Asn Leu Glu Arg
20 25 30

Glu Leu Ser Gly Gly Cys Ala Pro Asp Phe Leu Pro Gln Ala Gln Asp
35 40 45

Ser Asn His Phe Ile Met Glu Ser Leu Phe Cys Glu Ser Ser Gly Asp
50 55 60

Ser Ser Leu Glu Lys Glu Phe Leu Gly Ala Pro Val Gly Pro Ser Val
65 70 75 80

-continued

```
Ser Thr Pro Asn Ser Gln His Ser Ser Pro Ser Arg Ser Leu Ser Ala
                85                  90                  95

Asn Ser Ile Lys Val Glu Met Tyr Ser Asp Glu Glu Ser Ser Arg Leu
            100                 105                 110

Leu Gly Pro Asp Glu Arg Leu Leu Asp Lys Asp Asp Ser Val Ile Val
        115                 120                 125

Glu Asp Ser Leu Ser Glu Pro Leu Gly Tyr Cys Asp Gly Ser Gly Pro
    130                 135                 140

Glu Pro His Ser Pro Gly Gly Ile Arg Leu Pro Asn Gly Lys Leu Lys
145                 150                 155                 160

Cys Asp Val Cys Gly Met Val Cys Ile Gly Pro Asn Val Leu Met Val
                165                 170                 175

His Lys Arg Ser His Thr Gly Glu Arg Pro Phe His Cys Asn Gln Cys
            180                 185                 190

Gly Ala Ser Phe Thr Gln Lys Gly Asn Leu Leu Arg His Ile Lys Leu
        195                 200                 205

His Ser Gly Glu Lys Pro Phe Lys Cys Pro Phe Cys Asn Tyr Ala Cys
    210                 215                 220

Arg Arg Arg Asp Ala Leu Thr Gly His Leu Arg Thr His Ser Val Ser
225                 230                 235                 240

Ser Pro Thr Val Gly Lys Pro Tyr Lys Cys Asn Tyr Cys Gly Arg Ser
                245                 250                 255

Tyr Lys Gln Gln Ser Thr Leu Glu Glu His Lys Glu Arg Cys His Asn
            260                 265                 270

Tyr Leu Gln Ser Leu Ser Thr Asp Ala Gln Ala Leu Thr Gly Gln Pro
        275                 280                 285

Gly Asp Glu Ile Arg Asp Leu Glu Met Val Pro Asp Ser Met Leu His
    290                 295                 300

Pro Ser Thr Glu Arg Pro Thr Phe Ile Asp Arg Leu Ala Asn Ser Leu
305                 310                 315                 320

Thr Lys Arg Lys Arg Ser Thr Pro Gln Lys Phe Val Gly Glu Lys Gln
                325                 330                 335

Met Arg Phe Ser Leu Ser Asp Leu Pro Tyr Asp Val Asn Ala Ser Gly
            340                 345                 350

Gly Tyr Glu Lys Asp Val Glu Leu Val Ala His His Gly Leu Glu Pro
        355                 360                 365

Gly Phe Gly Gly Ser Leu Ala Phe Val Gly Thr Glu His Leu Arg Pro
    370                 375                 380

Leu Arg Leu Pro Pro Thr Asn Cys Ile Ser Glu Leu Thr Pro Val Ile
385                 390                 395                 400

Ser Ser Val Tyr Thr Gln Met Gln Pro Ile Pro Ser Arg Leu Glu Leu
                405                 410                 415

Pro Gly Ser Arg Glu Ala Gly Glu Gly Pro Glu Asp Leu Gly Asp Gly
            420                 425                 430

Gly Pro Leu Leu Tyr Arg Ala Arg Gly Ser Leu Thr Asp Pro Gly Ala
        435                 440                 445

Ser Pro Ser Asn Gly Cys Gln Asp Ser Thr Asp Thr Glu Ser Asn His
    450                 455                 460

Glu Asp Arg Ile Gly Gly Val Val Ser Leu Pro Gln Gly Pro Pro Pro
465                 470                 475                 480

Gln Pro Pro Pro Thr Ile Val Val Gly Arg His Ser Pro Ala Tyr Ala
                485                 490                 495
```

Lys Glu Asp Pro Lys Pro Gln Glu Gly Leu Leu Arg Gly Thr Pro Gly
500 505 510

Pro Ser Lys Glu Val Leu Arg Val Val Gly Glu Ser Gly Glu Pro Val
515 520 525

Lys Ala Phe Lys Cys Glu His Cys Arg Ile Leu Phe Leu Asp His Val
530 535 540

Met Phe Thr Ile His Met Gly Cys His Gly Phe Arg Asp Pro Phe Glu
545 550 555 560

Cys Asn Ile Cys Gly Tyr His Ser Gln Asp Arg Thr Arg Arg Leu Val
565 570 575

Pro Arg Leu Leu Gly Pro Val Met Ile Asn Gly Arg Glu Lys Gly Asp
580 585 590

Val Ser Phe Leu Ser Ala Asn Phe Gln Tyr Asn Gln Lys Asn Cys Pro
595 600 605

Arg Met Asn Tyr Thr Tyr Val Pro Val Asn His Ser Thr Leu Val Pro
610 615 620

Ala Arg Met Gly Arg Thr Gln Leu Gly Val Thr Ser Thr Ala Leu Ser
625 630 635 640

Ile Leu Ser Ser Arg His Arg Ala Gly Glu Ala Val Phe Ser Gly Gly
645 650 655

Cys Arg His Ser Gly Tyr Ser Asp Asn Arg Gly Phe Val Arg Pro Cys
660 665 670

Arg Arg Arg His Ser Ser Ile Ala Gly Gly Ser Leu Ser Leu
675 680 685

<210> SEQ ID NO 33
<211> LENGTH: 686
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(61)
<223> OTHER INFORMATION: Xaa can be any naturally occurring amino acid
<220> FEATURE:
<221> NAME/KEY: misc_feature
<222> LOCATION: (572)..(580)
<223> OTHER INFORMATION: Xaa can be any naturally occurring amino acid
<220> FEATURE:
<221> NAME/KEY: misc_feature
<222> LOCATION: (582)..(686)
<223> OTHER INFORMATION: Xaa can be any naturally occurring amino acid

<400> SEQUENCE: 33

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Xaa Xaa Xaa Xaa Xaa Xaa Xaa Xaa Xaa Xaa Xaa Ser Gly Asp
50 55 60

Ser Ser Leu Glu Lys Glu Phe Leu Gly Ala Pro Val Gly Pro Ser Val
65 70 75 80

Ser Thr Pro Asn Ser Gln His Ser Ser Pro Ser Arg Ser Leu Ser Ala
85 90 95

Asn Ser Ile Lys Val Glu Met Tyr Ser Asp Glu Glu Ser Ser Arg Leu
100 105 110

```
Leu Gly Pro Asp Glu Arg Leu Leu Asp Lys Asp Asp Ser Val Ile Val
        115                 120                 125

Glu Asp Ser Leu Ser Glu Pro Leu Gly Tyr Cys Asp Gly Ser Gly Pro
    130                 135                 140

Glu Pro His Ser Pro Gly Gly Ile Arg Leu Pro Asn Gly Lys Leu Lys
145                 150                 155                 160

Cys Asp Val Cys Gly Met Val Cys Ile Gly Pro Asn Val Leu Met Val
                165                 170                 175

His Lys Arg Ser His Thr Gly Glu Arg Pro Phe His Cys Asn Gln Cys
            180                 185                 190

Gly Ala Ser Phe Thr Gln Lys Gly Asn Leu Leu Arg His Ile Lys Leu
        195                 200                 205

His Ser Gly Glu Lys Pro Phe Lys Cys Pro Phe Cys Asn Tyr Ala Cys
    210                 215                 220

Arg Arg Arg Asp Ala Leu Thr Gly His Leu Arg Thr His Ser Val Ser
225                 230                 235                 240

Ser Pro Thr Val Gly Lys Pro Tyr Lys Cys Asn Tyr Cys Gly Arg Ser
                245                 250                 255

Tyr Lys Gln Gln Ser Thr Leu Glu Glu His Lys Glu Arg Cys His Asn
            260                 265                 270

Tyr Leu Gln Ser Leu Ser Thr Asp Ala Gln Ala Leu Thr Gly Gln Pro
        275                 280                 285

Gly Asp Glu Ile Arg Asp Leu Glu Met Val Pro Asp Ser Met Leu His
    290                 295                 300

Pro Ser Thr Glu Arg Pro Thr Phe Ile Asp Arg Leu Ala Asn Ser Leu
305                 310                 315                 320

Thr Lys Arg Lys Arg Ser Thr Pro Gln Lys Phe Val Gly Glu Lys Gln
                325                 330                 335

Met Arg Phe Ser Leu Ser Asp Leu Pro Tyr Asp Val Asn Ala Ser Gly
            340                 345                 350

Gly Tyr Glu Lys Asp Val Glu Leu Val Ala His His Gly Leu Glu Pro
        355                 360                 365

Gly Phe Gly Gly Ser Leu Ala Phe Val Gly Thr Glu His Leu Arg Pro
    370                 375                 380

Leu Arg Leu Pro Pro Thr Asn Cys Ile Ser Glu Leu Thr Pro Val Ile
385                 390                 395                 400

Ser Ser Val Tyr Thr Gln Met Gln Pro Ile Pro Ser Arg Leu Glu Leu
                405                 410                 415

Pro Gly Ser Arg Glu Ala Gly Glu Gly Pro Glu Asp Leu Gly Asp Gly
            420                 425                 430

Gly Pro Leu Leu Tyr Arg Ala Arg Gly Ser Leu Thr Asp Pro Gly Ala
        435                 440                 445

Ser Pro Ser Asn Gly Cys Gln Asp Ser Thr Asp Thr Glu Ser Asn His
    450                 455                 460

Glu Asp Arg Ile Gly Gly Val Val Ser Leu Pro Gln Gly Pro Pro Pro
465                 470                 475                 480

Gln Pro Pro Pro Thr Ile Val Val Gly Arg His Ser Pro Ala Tyr Ala
                485                 490                 495

Lys Glu Asp Pro Lys Pro Gln Glu Gly Leu Leu Arg Gly Thr Pro Gly
            500                 505                 510

Pro Ser Lys Glu Val Leu Arg Val Val Gly Glu Ser Gly Glu Pro Val
        515                 520                 525

Lys Ala Phe Lys Cys Glu His Cys Arg Ile Leu Phe Leu Asp His Val
```

```
    530                 535                 540

Met Phe Thr Ile His Met Gly Cys His Gly Phe Arg Asp Pro Phe Glu
545                 550                 555                 560

Cys Asn Ile Cys Gly Tyr His Ser Gln Asp Arg Xaa Xaa Xaa Xaa Xaa
                565                 570                 575

Xaa Xaa Xaa Xaa Gly Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa Xaa
    610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa
        675                 680                 685


<210> SEQ ID NO 34
<211> LENGTH: 5152
<212> TYPE: DNA
<213> ORGANISM: mus musculus

<400> SEQUENCE: 34

acacacgagg ctctcagcac atacaccctg ggctgagcgg ttctgccggc tgcagccgtg      60

ggcccctgct caccgtgcgg ctgccactgc ctgcgaaatg acggcggttc ccctcacttc     120

caggaatcca cgcttcctgg aaggtgagtg gctgggctca cccctgcctg ccaccgagac     180

gcagacatgc acacaccacc cgcactccct cgccgtttcc aaggcggcgg ccgcgttcgc     240

accccagggt ctcaccggca agggaaggat aatctggaga gggagctctc aggagggtgt     300

gctccggatt tcttgcctca ggcccaggac tccaaccatt ttataatgga atctttattt     360

tgtgaaagta gcggggactc atctctggag aaggagttcc ttggggcccc agtggggccc     420

tcggtgagca ccccaaacag ccaacactct tcacccagcc gctcgctcag tgccaactcc     480

atcaaggtgg agatgtacag cgatgaggag tcgagcagac tgctggggcc ggatgaacgg     540

ctcctggata aggatgacag tgtgattgtg gaagactcat tgtcagagcc cttaggctac     600

tgcgatggaa gtgggccaga gcctcactcc cctggcggca tccggctacc caacggcaag     660

ctcaagtgcg acgtctgcgg catggtctgc attgggccca atgtgctcat ggtacacaag     720

cgcagccaca ctggggagag gcccttccac tgtaatcagt gtggtgcctc cttcacacag     780

aagggcaatc tgcttcgcca catcaagctg cactcggggg agaagccctt caagtgcccc     840

ttctgcaact atgcctgccg ccggcgtgac gcactcactg gccacctccg cacacactca     900

gtctcctccc ccaccgtggg caaaccctac aagtgcaact actgtggccg gagctacaaa     960

cagcaaagta ccctggagga gcacaaggag aggtgccaca actacctaca gagtctcagc    1020

actgatgccc aagctctgac tggccagcca ggtgatgaaa tccgtgacct ggagatggtg    1080

cctgactcaa tgctgcaccc atcgactgaa cggccaactt tcattgatcg tttggccaac    1140

agcctcacca aacgcaagcg ttccacccca cagaagtttg taggtgaaaa gcagatgcgc    1200

ttcagcctct cagaccttcc ctatgatgtg aatgccagcg gtggctatga aaaggacgta    1260
```

gagttggtgg cacaccatgg cctggagcct ggctttggag ggtctctagc ctttgtgggt 1320
acagagcatc tgcgtcccct ccgcctccca cccaccaact gcatctcaga actcacacct 1380
gtcatcagct ctgtgtacac ccaaatgcag cccatcccca gccgactgga gcttccaggg 1440
tcccgagaag caggtgaggg accggaggac ctgggagatg gaggtcccct cctttatcgg 1500
gcccgaggct ctctgactga ccctggggca tcccccagca atggctgcca ggactccaca 1560
gatacagaga gcaaccacga agaccggatt ggtggggtgg tatcccttcc tcagggtccc 1620
ccaccccaac ctcctcccac catagtggtg ggccggcaca gtcccgccta tgccaaagag 1680
gaccccaaac cacaggaggg gttactgcgg ggcaccccag gcccctccaa ggaagtgctt 1740
cgggtggtgg gtgagagtgg tgagccagtg aaggccttta agtgtgaaca ctgccgcatc 1800
ctctttctgg accacgtcat gttcaccatc cacatgggct gccacggctt cagagaccct 1860
tttgagtgta acatctgtgg ttatcacagc caggatcggt atgagttctc ttcccacatc 1920
gtccgggggg aacataaggt gggctagaga cctctttccc cacagcctgc tctcagcccg 1980
gcccccaccc tactgcccta cctacagggg tctagcccaa ttcctgttac accctaagga 2040
gttttgcgtt gtagccccac ccactggccg cctcacttca cacttgactc caaccgtctt 2100
tgcctgttcc cttctaccct gaccgatttg agcatttcga caagacaagt ctcttgctta 2160
tatttctcct tctaacctct ctccccggca catttgcttt ttaaattgac tttaacttgg 2220
ccttttctta gtttactgca atctctggcc actccttcat tcttctgccc atggctccct 2280
tctgctctaa gcctagattt ttttttattt tattattatt attattatta ttacttgtgt 2340
gtgtgtgtgg atcccacatc ctccaacagc tccaggggtt ggaagctcct ctctgtgcta 2400
agagacgttg ggcttcttgc tttaatcctc acccttattt atctgaccct tcacttttga 2460
tgctgatacc tcccaacggc cccaccttag ctctgtggca ttattatctc ctctctggga 2520
cctttcagcc cggcactcca tacctctcgt gcccactcac tttaggcagc ttgcactatt 2580
cttaaatgaa tgaagaattt cctcatttgc aggtaggagg ggctgtagaa actctcccca 2640
ggcactgtgg actgagggtc ctcttgacct cacctgggaa tccgagctcc ctaaagacta 2700
cattcaggac ctccctctag gatgtgatac cacccttccc tctccctggc tcacccctca 2760
acaccactct ggtctcaact cgccactctt gtcagttggt ggcttttctc tccttggaat 2820
gcccccattt tatattctca ggggctaagg ctagacctgc taccctttct ctgacacaca 2880
gagagagctg caggtaccta gctgagaacc agggcatggg aagggggatg ggtagaactc 2940
tctcctccac ctttcaaaca cttacactcc agtgaccttc ctaggctctc agggactcct 3000
tctgtcccca tattatgaga aaccagcggg ttgctgctcg atgaccaggg gtctctcaac 3060
cctgtcagtc acgctgcctt tttcctccct tccagcagga ctcgccgtct cgtccccagg 3120
ctcctgggcc ctgttatgat caatggcagg gagaaagggg atgtctcttt tctctctgcc 3180
aattttcagt ataaccaaaa aaactgtccc aggatgaact acacgtatgt gcccgtcaac 3240
cattccaccc ttgtcccagc aagaatggga cggacacagc tgggagtcac ctccactgcc 3300
ctttccatac ttagctccag acacagggca ggagaggcag tcttctctgg tggttgcaga 3360
cactctggct attcggataa tcgaggattc gtgagaccat gcaggaggag gcatagctcc 3420
attgcaggtg gaagtctctc tctctaaaga gttccctgcc agggccacaa ccatcccact 3480
ctctgcttct ttgagattca aaccaaagga tgtttttttct atatttaaag aaaaggaaaa 3540
aaaaagaaaa gaaaaaaaaa aaaaaccaaa cacaacacct cataagttat agtcttggtc 3600
ttcaccctcc ctttctcttc ccttccgtcc atcttccttc ccacgtgccc tttctttatc 3660
tcttctgcct ctccctactt tcctcactcc ctgttaggga cgttgagagg cacgagaaag 3720
ggtgggctag atcagatcct gggactgggg ctcttaagca ttccgaagag agtcgacttt 3780
ctcctatcgg gagaagggta gtggggtgaa aaccactctt ttctcttctt ccttcggccc 3840
tggcactgct tcccaaaagg accagattgg cagagagcag ctctgtgggg ctgttcttcc 3900
ctgacaatgt agcaataagc aggtgctgcc aaaggcaaga gaatgaggtc tgagctctga 3960
aaggagtggt cccgagacaa gggaagggtc gccacaacag agccttggca ctaattcctt 4020
cttgggctgg cacacagctg aggttactgt ctgggcttct cctcaaccat tctggttgtg 4080
agctcccatt agacccgctc ccacctcttc tgtgtctgcc ctgtattcga ggacacctca 4140
gaaggactta gtccctctga ggcgctagag ccttagagtg ccccacccct ccctttgttt 4200
agtcagtctt agcacctgtg acctcccagg aacacaaagg actatgctcc tccgaggcta 4260
tgctaacgcc catgagagca gaggtggaag ggacaagacc aggtgctagg gaggaggggg 4320
catggcgtct ctctccagcc caccactgca ctttaaccag ggtcttaggt acaaaatgct 4380
acttttcagg gccttccagc tctggaacct caaacatcct catgctctct cccagatcct 4440
tttgcataaa aaaaaacaaa acaaaaaaac caacaacaaa aaaagtaaag aaaaagaaga 4500
aaacaacaac aaaaaacaaa atgccaaaat ccacacagag aaaagaggtg ttctctctct 4560
ctcttttttt tattactctt aaaaaaacaa caccacaaaa aagtggaggg aagggagaga 4620
atttctaaat agacactttt ccagaccttt gtgtgtgtgt gtgtgtgtgt gtgtgtgtgt 4680
gtgtgtatgt gtgtgtgtgt gtgtgtgtgt gtgtgtgtgt gtgtgtgtca gtgtccaagc 4740
tgcaagtgga attttataat acttctggca gcttctttcc ttgtgtatat aatatatata 4800
tatttttaat cagaaattat gaagatcaaa aatagaataa acacagaagc aagtgcaata 4860
ccacctctcc ttctccccag agttcctctg tagcctgttc ggtgtcccct ttggcccttg 4920
acccttgacc ttgtctctct tcctctggtt cctgacctat tctccccttc cctcttttta 4980
aagagttttt ctcttttctc aaagggggtt aaaccagctt ttgagactta ctgcaaagca 5040
ttttgtatat gtaacatact gtaagtaaat atttgtgtaa tggagaaata ctactgtaag 5100
ttttgtactg tactggctga aggtctgtta taaataaaca cgagtaattt aa 5152

<210> SEQ ID NO 35
<211> LENGTH: 1761
<212> TYPE: DNA
<213> ORGANISM: mus musculus

<400> SEQUENCE: 35
atgcacacac cacccgcact ccctcgccgt ttccaaggcg gcggccgcgt tcgcacccca 60
gggtctcacc ggcaagggaa ggataatctg gagagggagc tctcaggagg gtgtgctccg 120
gatttcttgc ctcaggccca ggactccaac cattttataa tggaatcttt attttgtgaa 180
agtagcgggg actcatctct ggagaaggag ttccttgggg ccccagtggg gccctcggtg 240
agcaccccaa acagccaaca ctcttcaccc agccgctcgc tcagtgccaa ctccatcaag 300
gtggagatgt acagcgatga ggagtcgagc agactgctgg ggccggatga acggctcctg 360
gataaggatg acagtgtgat tgtggaagac tcattgtcag agcccttagg ctactgcgat 420
ggaagtgggc cagagcctca ctcccctggc ggcatccggc tacccaacgg caagctcaag 480
tgcgacgtct gcggcatggt ctgcattggg cccaatgtgc tcatggtaca caagcgcagc 540
cacactgggg agaggccctt ccactgtaat cagtgtggtg cctccttcac acagaagggc 600
aatctgcttc gccacatcaa gctgcactcg ggggagaagc ccttcaagtg ccccttctgc 660
aactatgcct gccgccggcg tgacgcactc actggccacc tccgcacaca ctcagtctcc 720
tcccccaccg tgggcaaacc ctacaagtgc aactactgtg gccggagcta caaacagcaa 780
agtaccctgg aggagcacaa ggagaggtgc cacaactacc tacagagtct cagcactgat 840
gcccaagctc tgactggcca gccaggtgat gaaatccgtg acctggagat ggtgcctgac 900
tcaatgctgc acccatcgac tgaacggcca actttcattg atcgtttggc caacagcctc 960
accaaacgca agcgttccac cccacagaag tttgtaggtg aaaagcagat gcgcttcagc 1020
ctctcagacc ttccctatga tgtgaatgcc agcggtggct atgaaaagga cgtagagttg 1080
gtggcacacc atggcctgga gcctggcttt ggagggtctc tagcctttgt gggtacagag 1140
catctgcgtc ccctccgcct cccacccacc aactgcatct cagaactcac acctgtcatc 1200
agctctgtgt acacccaaat gcagcccatc cccagccgac tggagcttcc agggtcccga 1260
gaagcaggtg agggaccgga ggacctggga gatggaggtc ccctccttta tcgggcccga 1320
ggctctctga ctgaccctgg ggcatccccc agcaatggct gccaggactc cacagataca 1380
gagagcaacc acgaagaccg gattggtggg gtggtatccc ttcctcaggg tcccccaccc 1440
caacctcctc ccaccatagt ggtgggccgg cacagtcccg cctatgccaa agaggacccc 1500
aaaccacagg aggggttact gcggggcacc ccaggcccct ccaaggaagt gcttcgggtg 1560
gtgggtgaga gtggtgagcc agtgaaggcc tttaagtgtg aacactgccg catcctcttt 1620
ctggaccacg tcatgttcac catccacatg ggctgccacg gcttcagaga ccccttttgag 1680 tgtaacatct gtggttatca cagccaggat cggtatgagt tctcttccca catcgtccgg 1740
ggggaacata aggtgggcta g 1761

<210> SEQ ID NO 36
<211> LENGTH: 5224
<212> TYPE: DNA
<213> ORGANISM: mus musculus

<400> SEQUENCE: 36
acacacgagg ctctcagcac atacaccctg ggctgagcgg ttctgccggc tgcagccgtg 60
ggcccctgct caccgtgcgg ctgccactgc ctgcgaaatg acggcggttc ccctcacttc 120
caggaatcca cgcttcctgg aaggtgagtg gctgggctca cccctgcctg ccaccgagac 180
gcagacatgc acacaccacc cgcactccct cgccgtttcc aaggcggcgg ccgcgttcgc 240
accccagggt ctcaccggca agggaaggat aatctggaga gggagctctc aggagggtgt 300
gctccggatt tcttgcctca ggcccaggac tccaaccatt ttataatgga atctttattt 360
tgtgaaagcc tttgcgcata tacccatgca tgttcatgtt agcagataat atagacggct 420
gtgatgttta tcccagtagg tagcggggac tcatctctgg agaaggagtt ccttggggcc 480
ccagtggggc cctcggtgag caccccaaac agccaacact cttcacccag ccgctcgctc 540
agtgccaact ccatcaaggt ggagatgtac agcgatgagg agtcgagcag actgctgggg 600
ccggatgaac ggctcctgga taaggatgac agtgtgattg tggaagactc attgtcagag 660
cccttaggct actgcgatgg aagtgggcca gagcctcact cccctggcgg catccggcta 720
cccaacggca agctcaagtg cgacgtctgc ggcatggtct gcattgggcc caatgtgctc 780
atggtacaca agcgcagcca cactggggag aggcccttcc actgtaatca gtgtggtgcc 840
tccttcacac agaagggcaa tctgcttcgc cacatcaagc tgcactcggg ggagaagccc 900
ttcaagtgcc ccttctgcaa ctatgcctgc cgccggcgtg acgcactcac tggccacctc 960

-continued

```
cgcacacact cagtctcctc ccccaccgtg ggcaaaccct acaagtgcaa ctactgtggc   1020
cggagctaca aacagcaaag taccctggag gagcacaagg agaggtgcca caactaccta   1080
cagagtctca gcactgatgc ccaagctctg actggccagc caggtgatga aatccgtgac   1140
ctggagatgg tgcctgactc aatgctgcac ccatcgactg aacggccaac tttcattgat   1200
cgtttggcca acagcctcac caaacgcaag cgttccaccc cacagaagtt tgtaggtgaa   1260
aagcagatgc gcttcagcct ctcagacctt ccctatgatg tgaatgccag cggtggctat   1320
gaaaaggacg tagagttggt ggcacaccat ggcctggagc ctggctttgg agggtctcta   1380
gcctttgtgg gtacagagca tctgcgtccc ctccgcctcc cacccaccaa ctgcatctca   1440
gaactcacac ctgtcatcag ctctgtgtac acccaaatgc agcccatccc cagccgactg   1500
gagcttccag ggtcccgaga agcaggtgag ggaccggagg acctgggaga tggaggtccc   1560
ctcctttatc gggcccgagg ctctctgact gaccctgggg catcccccag caatggctgc   1620
caggactcca cagatacaga gagcaaccac gaagaccgga ttggtggggt ggtatccctt   1680
cctcagggtc ccccacccca acctcctccc accatagtgg tgggccggca cagtcccgcc   1740
tatgccaaag aggaccccaa accacaggag gggttactgc ggggcacccc aggcccctcc   1800
aaggaagtgc ttcgggtggt gggtgagagt ggtgagccag tgaaggcctt taagtgtgaa   1860
cactgccgca tcctctttct ggaccacgtc atgttcacca tccacatggg ctgccacggc   1920
ttcagagacc cttttgagtg taacatctgt ggttatcaca gccaggatcg gtatgagttc   1980
tcttcccaca tcgtccgggg ggaacataag gtgggctaga gacctctttc cccacagcct   2040
gctctcagcc cggcccccac cctactgccc tacctacagg ggtctagccc aattcctgtt   2100
acaccctaag gagttttgcg ttgtagcccc acccactggc cgcctcactt cacacttgac   2160
tccaaccgtc tttgcctgtt cccttctacc ctgaccgatt tgagcatttc gacaagacaa   2220
gtctcttgct tatatttctc cttctaacct ctctccccgg cacatttgct ttttaaattg   2280
actttaactt ggccttttct tagtttactg caatctctgg ccactccttc attcttctgc   2340
ccatggctcc cttctgctct aagcctagat tttttttat tttattatta ttattattat   2400
tattacttgt gtgtgtgtgt ggatcccaca tcctccaaca gctccagggg ttggaagctc   2460
ctctctgtgc taagagacgt tgggcttctt gctttaatcc tcacccttat ttatctgacc   2520
cttcactttt gatgctgata cctcccaacg gccccacctt agctctgtgg cattattatc   2580
tcctctctgg gacctttcag cccggcactc catacctctc gtgcccactc actttaggca   2640
gcttgcacta ttcttaaatg aatgaagaat ttcctcattt gcaggtagga ggggctgtag   2700
aaactctccc caggcactgt ggactgaggg tcctcttgac ctcacctggg aatccgagct   2760
ccctaaagac tacattcagg acctccctct aggatgtgat accacccttc cctctccctg   2820
gctcacccct caacaccact ctggtctcaa ctcgccactc ttgtcagttg gtggcttttc   2880
tctccttgga atgcccccat tttatattct caggggctaa ggctagacct gctacccttt   2940
ctctgacaca cagagagagc tgcaggtacc tagctgagaa ccagggcatg ggaaggggga   3000
tgggtagaac tctctcctcc acctttcaaa cacttacact ccagtgacct tcctaggctc   3060
tcagggactc cttctgtccc catattatga gaaaccagcg ggttgctgct cgatgaccag   3120
gggtctctca accctgtcag tcacgctgcc tttttcctcc cttccagcag gactcgccgt   3180
ctcgtcccca ggctcctggg ccctgttatg atcaatggca gggagaaagg ggatgtctct   3240
tttctctctg ccaattttca gtataaccaa aaaaactgtc ccaggatgaa ctacacgtat   3300
```

```
gtgcccgtca accattccac ccttgtccca gcaagaatgg gacggacaca gctgggagtc   3360
acctccactg ccctttccat acttagctcc agacacaggg caggagaggc agtcttctct   3420
ggtggttgca gacactctgg ctattcggat aatcgaggat tcgtgagacc atgcaggagg   3480
aggcatagct ccattgcagg tggaagtctc tctctctaaa gagttccctg ccagggccac   3540
aaccatccca ctctctgctt ctttgagatt caaaccaaag gatgtttttt ctatatttaa   3600
agaaaaggaa aaaaaaagaa aagaaaaaaa aaaaaaacca aacacaacac ctcataagtt   3660
atagtcttgg tcttcaccct ccctttctct tcccttccgt ccatcttcct tcccacgtgc   3720
cctttcttta tctcttctgc ctctccctac tttcctcact ccctgttagg gacgttgaga   3780
ggcacgagaa agggtgggct agatcagatc ctgggactgg ggctcttaag cattccgaag   3840
agagtcgact ttctcctatc gggagaaggg tagtggggtg aaaaccactc ttttctcttc   3900
ttccttcggc cctggcactg cttcccaaaa ggaccagatt ggcagagagc agctctgtgg   3960
ggctgttctt ccctgacaat gtagcaataa gcaggtgctg ccaaaggcaa gagaatgagg   4020
tctgagctct gaaaggagtg gtcccgagac aagggaaggg tcgccacaac agagccttgg   4080
cactaattcc ttcttgggct ggcacacagc tgaggttact gtctgggctt ctcctcaacc   4140
attctggttg tgagctccca ttagacccgc tcccacctct tctgtgtctg ccctgtattc   4200
gaggacacct cagaaggact tagtccctct gaggcgctag agccttagag tgccccaccc   4260
ctccctttgt ttagtcagtc ttagcacctg tgacctccca ggaacacaaa ggactatgct   4320
cctccgaggc tatgctaacg cccatgagag cagaggtgga agggacaaga ccaggtgcta   4380
gggaggaggg ggcatggcgt ctctctccag cccaccactg cactttaacc agggtcttag   4440
gtacaaaatg ctacttttca gggccttcca gctctggaac ctcaaacatc ctcatgctct   4500
ctcccagatc cttttgcata aaaaaaaaca aaacaaaaaa accaacaaca aaaaaagtaa   4560
agaaaaagaa gaaaacaaca acaaaaaaca aaatgccaaa atccacacag agaaaagagg   4620
tgttctctct ctctcttttt tttattactc ttaaaaaaac aacaccacaa aaaagtggag   4680
ggaagggaga gaatttctaa atagacactt ttccagacct ttgtgtgtgt gtgtgtgtgt   4740
gtgtgtgtgt gtgtgtgtat gtgtgtgtgt gtgtgtgtgt gtgtgtgtgt gtgtgtgtgt   4800
cagtgtccaa gctgcaagtg gaattttata atacttctgg cagcttcttt ccttgtgtat   4860
ataatatata tatattttta atcagaaatt atgaagatca aaaatagaat aaacacagaa   4920
gcaagtgcaa taccacctct ccttctcccc agagttcctc tgtagcctgt tcggtgtccc   4980
ctttggccct tgacccttga ccttgtctct cttcctctgg ttcctgacct attctcccct   5040
tccctctttt taaagagttt ttctcttttc tcaaaggggg ttaaaccagc ttttgagact   5100
tactgcaaag cattttgtat atgtaacata ctgtaagtaa atatttgtgt aatggagaaa   5160
tactactgta agttttgtac tgtactggct gaaggtctgt tataaataaa cacgagtaat   5220
ttaa                                                                 5224
```

<210> SEQ ID NO 37
<211> LENGTH: 585
<212> TYPE: PRT
<213> ORGANISM: homo sapiens

<400> SEQUENCE: 37

```
Met His Thr Pro Pro Ala Leu Pro Arg Arg Phe Gln Gly Gly Gly Arg
1               5                   10                  15

Val Arg Thr Pro Gly Ser His Arg Gln Gly Lys Asp Asn Leu Glu Arg
            20                  25                  30
```

-continued

```
Asp Pro Ser Gly Gly Cys Val Pro Asp Phe Leu Pro Gln Ala Gln Asp
        35                  40                  45

Ser Asn His Phe Ile Met Glu Ser Leu Phe Cys Glu Ser Ser Gly Asp
    50                  55                  60

Ser Ser Leu Glu Lys Glu Phe Leu Gly Ala Pro Val Gly Pro Ser Val
65                  70                  75                  80

Ser Thr Pro Asn Ser Gln His Ser Ser Pro Ser Arg Ser Leu Ser Ala
                85                  90                  95

Asn Ser Ile Lys Val Glu Met Tyr Ser Asp Glu Glu Ser Ser Arg Leu
            100                 105                 110

Leu Gly Pro Asp Glu Arg Leu Leu Glu Lys Asp Asp Ser Val Ile Val
        115                 120                 125

Glu Asp Ser Leu Ser Glu Pro Leu Gly Tyr Cys Asp Gly Ser Gly Pro
    130                 135                 140

Glu Pro His Ser Pro Gly Gly Ile Arg Leu Pro Asn Gly Lys Leu Lys
145                 150                 155                 160

Cys Asp Val Cys Gly Met Val Cys Ile Gly Pro Asn Val Leu Met Val
                165                 170                 175

His Lys Arg Ser His Thr Gly Glu Arg Pro Phe His Cys Asn Gln Cys
            180                 185                 190

Gly Ala Ser Phe Thr Gln Lys Gly Asn Leu Leu Arg His Ile Lys Leu
        195                 200                 205

His Ser Gly Glu Lys Pro Phe Lys Cys Pro Phe Cys Asn Tyr Ala Cys
    210                 215                 220

Arg Arg Arg Asp Ala Leu Thr Gly His Leu Arg Thr His Ser Val Ser
225                 230                 235                 240

Ser Pro Thr Val Gly Lys Pro Tyr Lys Cys Asn Tyr Cys Gly Arg Ser
                245                 250                 255

Tyr Lys Gln Gln Ser Thr Leu Glu Glu His Lys Glu Arg Cys His Asn
            260                 265                 270

Tyr Leu Gln Ser Leu Ser Thr Glu Ala Gln Ala Leu Ala Gly Gln Pro
        275                 280                 285

Gly Asp Glu Ile Arg Asp Leu Glu Met Val Pro Asp Ser Met Leu His
    290                 295                 300

Ser Ser Ser Glu Arg Pro Thr Phe Ile Asp Arg Leu Ala Asn Ser Leu
305                 310                 315                 320

Thr Lys Arg Lys Arg Ser Thr Pro Gln Lys Phe Val Gly Glu Lys Gln
                325                 330                 335

Met Arg Phe Ser Leu Ser Asp Leu Pro Tyr Asp Val Asn Ser Gly Gly
            340                 345                 350

Tyr Glu Lys Asp Val Glu Leu Val Ala His His Ser Leu Glu Pro Gly
        355                 360                 365

Phe Gly Ser Ser Leu Ala Phe Val Gly Ala Glu His Leu Arg Pro Leu
    370                 375                 380

Arg Leu Pro Pro Thr Asn Cys Ile Ser Glu Leu Thr Pro Val Ile Ser
385                 390                 395                 400

Ser Val Tyr Thr Gln Met Gln Pro Leu Pro Gly Arg Leu Glu Leu Pro
                405                 410                 415

Gly Ser Arg Glu Ala Gly Glu Gly Pro Glu Asp Leu Ala Asp Gly Gly
            420                 425                 430

Pro Leu Leu Tyr Arg Pro Arg Gly Pro Leu Thr Asp Pro Gly Ala Ser
        435                 440                 445
```

```
Pro Ser Asn Gly Cys Gln Asp Ser Thr Asp Thr Glu Ser Asn His Glu
    450                 455                 460

Asp Arg Val Ala Gly Val Val Ser Leu Pro Gln Gly Pro Pro Pro Gln
465                 470                 475                 480

Pro Pro Pro Thr Ile Val Val Gly Arg His Ser Pro Ala Tyr Ala Lys
                485                 490                 495

Glu Asp Pro Lys Pro Gln Glu Gly Leu Leu Arg Gly Thr Pro Gly Pro
            500                 505                 510

Ser Lys Glu Val Leu Arg Val Val Gly Glu Ser Gly Glu Pro Val Lys
        515                 520                 525

Ala Phe Lys Cys Glu His Cys Arg Ile Leu Phe Leu Asp His Val Met
    530                 535                 540

Phe Thr Ile His Met Gly Cys His Gly Phe Arg Asp Pro Phe Glu Cys
545                 550                 555                 560

Asn Ile Cys Gly Tyr His Ser Gln Asp Arg Tyr Glu Phe Ser Ser His
                565                 570                 575

Ile Val Arg Gly Glu His Lys Val Gly
            580                 585


<210> SEQ ID NO 38
<211> LENGTH: 585
<212> TYPE: PRT
<213> ORGANISM: homo sapiens

<400> SEQUENCE: 38

Met His Thr Pro Pro Ala Leu Pro Arg Arg Phe Gln Gly Gly Gly Arg
1               5                   10                  15

Val Arg Thr Pro Gly Ser His Arg Gln Gly Lys Asp Asn Leu Glu Arg
            20                  25                  30

Asp Pro Ser Gly Gly Cys Val Pro Asp Phe Leu Pro Gln Ala Gln Asp
        35                  40                  45

Ser Asn His Phe Ile Met Glu Ser Leu Phe Cys Glu Ser Ser Gly Asp
    50                  55                  60

Ser Ser Leu Glu Lys Glu Phe Leu Gly Ala Pro Val Gly Pro Ser Val
65                  70                  75                  80

Ser Thr Pro Asn Ser Gln His Ser Ser Pro Ser Arg Ser Leu Ser Ala
                85                  90                  95

Asn Ser Ile Lys Val Glu Met Tyr Ser Asp Glu Glu Ser Ser Arg Leu
            100                 105                 110

Leu Gly Pro Asp Glu Arg Leu Leu Glu Lys Asp Asp Ser Val Ile Val
        115                 120                 125

Glu Asp Ser Leu Ser Glu Pro Leu Gly Tyr Cys Asp Gly Ser Gly Pro
    130                 135                 140

Glu Pro His Ser Pro Gly Gly Ile Arg Leu Pro Asn Gly Lys Leu Lys
145                 150                 155                 160

Cys Asp Val Cys Gly Met Val Cys Ile Gly Pro Asn Val Leu Met Val
                165                 170                 175

His Lys Arg Ser His Thr Gly Glu Arg Pro Phe His Cys Asn Gln Cys
            180                 185                 190

Gly Ala Ser Phe Thr Gln Lys Gly Asn Leu Leu Arg His Ile Lys Leu
        195                 200                 205

His Ser Gly Glu Lys Pro Phe Lys Cys Pro Phe Cys Asn Tyr Ala Cys
    210                 215                 220

Arg Arg Arg Asp Ala Leu Thr Gly His Leu Arg Thr His Ser Val Ser
225                 230                 235                 240
```

Ser Pro Thr Val Gly Lys Pro Tyr Lys Cys Asn Tyr Cys Gly Arg Ser
245 250 255

Tyr Lys Gln Gln Ser Thr Leu Glu Glu His Lys Glu Arg Cys His Asn
260 265 270

Tyr Leu Gln Ser Leu Ser Thr Glu Ala Gln Ala Leu Ala Gly Gln Pro
275 280 285

Gly Asp Glu Ile Arg Asp Leu Glu Met Val Pro Asp Ser Met Leu His
290 295 300

Ser Ser Ser Glu Arg Pro Thr Phe Ile Asp Arg Leu Ala Asn Ser Leu
305 310 315 320

Thr Lys Arg Lys Arg Ser Thr Pro Gln Lys Phe Val Gly Glu Lys Gln
325 330 335

Met Arg Phe Ser Leu Ser Asp Leu Pro Tyr Asp Val Asn Ser Gly Gly
340 345 350

Tyr Glu Lys Asp Val Glu Leu Val Ala His His Ser Leu Glu Pro Gly
355 360 365

Phe Gly Ser Ser Leu Ala Phe Val Gly Ala Glu His Leu Arg Pro Leu
370 375 380

Arg Leu Pro Pro Thr Asn Cys Ile Ser Glu Leu Thr Pro Val Ile Ser
385 390 395 400

Ser Val Tyr Thr Gln Met Gln Pro Leu Pro Gly Arg Leu Glu Leu Pro
405 410 415

Gly Ser Arg Glu Ala Gly Glu Gly Pro Glu Asp Leu Ala Asp Gly Gly
420 425 430

Pro Leu Leu Tyr Arg Pro Arg Gly Pro Leu Thr Asp Pro Gly Ala Ser
435 440 445

Pro Ser Asn Gly Cys Gln Asp Ser Thr Asp Thr Glu Ser Asn His Glu
450 455 460

Asp Arg Val Ala Gly Val Val Ser Leu Pro Gln Gly Pro Pro Pro Gln
465 470 475 480

Pro Pro Pro Thr Ile Val Val Gly Arg His Ser Pro Ala Tyr Ala Lys
485 490 495

Glu Asp Pro Lys Pro Gln Glu Gly Leu Leu Arg Gly Thr Pro Gly Pro
500 505 510

Ser Lys Glu Val Leu Arg Val Val Gly Glu Ser Gly Glu Pro Val Lys
515 520 525

Ala Phe Lys Cys Glu His Cys Arg Ile Leu Phe Leu Asp His Val Met
530 535 540

Phe Thr Ile His Met Gly Cys His Gly Phe Arg Asp Pro Phe Glu Cys
545 550 555 560

Asn Ile Cys Gly Tyr His Ser Gln Asp Arg Tyr Glu Phe Ser Ser His
565 570 575

Ile Val Arg Gly Glu His Lys Val Gly
580 585

<210> SEQ ID NO 39
<211> LENGTH: 540
<212> TYPE: PRT
<213> ORGANISM: homo sapiens

<400> SEQUENCE: 39

Met Thr Ala Val Pro Leu Thr Ser Arg Asn Pro Arg Phe Leu Glu Gly
1 5 10 15

Ser Gly Asp Ser Ser Leu Glu Lys Glu Phe Leu Gly Ala Pro Val Gly

```
            20                  25                  30

Pro Ser Val Ser Thr Pro Asn Ser Gln His Ser Ser Pro Ser Arg Ser
        35                  40                  45

Leu Ser Ala Asn Ser Ile Lys Val Glu Met Tyr Ser Asp Glu Glu Ser
    50                  55                  60

Ser Arg Leu Leu Gly Pro Asp Glu Arg Leu Leu Glu Lys Asp Asp Ser
65                  70                  75                  80

Val Ile Val Glu Asp Ser Leu Ser Glu Pro Leu Gly Tyr Cys Asp Gly
                85                  90                  95

Ser Gly Pro Glu Pro His Ser Pro Gly Gly Ile Arg Leu Pro Asn Gly
            100                 105                 110

Lys Leu Lys Cys Asp Val Cys Gly Met Val Cys Ile Gly Pro Asn Val
        115                 120                 125

Leu Met Val His Lys Arg Ser His Thr Gly Glu Arg Pro Phe His Cys
    130                 135                 140

Asn Gln Cys Gly Ala Ser Phe Thr Gln Lys Gly Asn Leu Leu Arg His
145                 150                 155                 160

Ile Lys Leu His Ser Gly Glu Lys Pro Phe Lys Cys Pro Phe Cys Asn
                165                 170                 175

Tyr Ala Cys Arg Arg Arg Asp Ala Leu Thr Gly His Leu Arg Thr His
            180                 185                 190

Ser Val Ser Ser Pro Thr Val Gly Lys Pro Tyr Lys Cys Asn Tyr Cys
        195                 200                 205

Gly Arg Ser Tyr Lys Gln Gln Ser Thr Leu Glu Glu His Lys Glu Arg
    210                 215                 220

Cys His Asn Tyr Leu Gln Ser Leu Ser Thr Glu Ala Gln Ala Leu Ala
225                 230                 235                 240

Gly Gln Pro Gly Asp Glu Ile Arg Asp Leu Glu Met Val Pro Asp Ser
                245                 250                 255

Met Leu His Ser Ser Ser Glu Arg Pro Thr Phe Ile Asp Arg Leu Ala
            260                 265                 270

Asn Ser Leu Thr Lys Arg Lys Arg Ser Thr Pro Gln Lys Phe Val Gly
        275                 280                 285

Glu Lys Gln Met Arg Phe Ser Leu Ser Asp Leu Pro Tyr Asp Val Asn
    290                 295                 300

Ser Gly Gly Tyr Glu Lys Asp Val Glu Leu Val Ala His His Ser Leu
305                 310                 315                 320

Glu Pro Gly Phe Gly Ser Ser Leu Ala Phe Val Gly Ala Glu His Leu
                325                 330                 335

Arg Pro Leu Arg Leu Pro Pro Thr Asn Cys Ile Ser Glu Leu Thr Pro
            340                 345                 350

Val Ile Ser Ser Val Tyr Thr Gln Met Gln Pro Leu Pro Gly Arg Leu
        355                 360                 365

Glu Leu Pro Gly Ser Arg Glu Ala Gly Glu Gly Pro Glu Asp Leu Ala
    370                 375                 380

Asp Gly Gly Pro Leu Leu Tyr Arg Pro Arg Gly Pro Leu Thr Asp Pro
385                 390                 395                 400

Gly Ala Ser Pro Ser Asn Gly Cys Gln Asp Ser Thr Asp Thr Glu Ser
                405                 410                 415

Asn His Glu Asp Arg Val Ala Gly Val Val Ser Leu Pro Gln Gly Pro
            420                 425                 430

Pro Pro Gln Pro Pro Pro Thr Ile Val Val Gly Arg His Ser Pro Ala
        435                 440                 445
```

Tyr Ala Lys Glu Asp Pro Lys Pro Gln Glu Gly Leu Leu Arg Gly Thr
450 455 460

Pro Gly Pro Ser Lys Glu Val Leu Arg Val Val Gly Glu Ser Gly Glu
465 470 475 480

Pro Val Lys Ala Phe Lys Cys Glu His Cys Arg Ile Leu Phe Leu Asp
485 490 495

His Val Met Phe Thr Ile His Met Gly Cys His Gly Phe Arg Asp Pro
500 505 510

Phe Glu Cys Asn Ile Cys Gly Tyr His Ser Gln Asp Arg Tyr Glu Phe
515 520 525

Ser Ser His Ile Val Arg Gly Glu His Lys Val Gly
530 535 540

<210> SEQ ID NO 40
<211> LENGTH: 538
<212> TYPE: PRT
<213> ORGANISM: homo sapiens

<400> SEQUENCE: 40

Met Asp Ile Glu Asp Cys Asn Gly Arg Ser Tyr Val Ser Gly Ser Gly
1 5 10 15

Asp Ser Ser Leu Glu Lys Glu Phe Leu Gly Ala Pro Val Gly Pro Ser
20 25 30

Val Ser Thr Pro Asn Ser Gln His Ser Ser Pro Ser Arg Ser Leu Ser
35 40 45

Ala Asn Ser Ile Lys Val Glu Met Tyr Ser Asp Glu Glu Ser Ser Arg
50 55 60

Leu Leu Gly Pro Asp Glu Arg Leu Leu Glu Lys Asp Asp Ser Val Ile
65 70 75 80

Val Glu Asp Ser Leu Ser Glu Pro Leu Gly Tyr Cys Asp Gly Ser Gly
85 90 95

Pro Glu Pro His Ser Pro Gly Gly Ile Arg Leu Pro Asn Gly Lys Leu
100 105 110

Lys Cys Asp Val Cys Gly Met Val Cys Ile Gly Pro Asn Val Leu Met
115 120 125

Val His Lys Arg Ser His Thr Gly Glu Arg Pro Phe His Cys Asn Gln
130 135 140

Cys Gly Ala Ser Phe Thr Gln Lys Gly Asn Leu Leu Arg His Ile Lys
145 150 155 160

Leu His Ser Gly Glu Lys Pro Phe Lys Cys Pro Phe Cys Asn Tyr Ala
165 170 175

Cys Arg Arg Arg Asp Ala Leu Thr Gly His Leu Arg Thr His Ser Val
180 185 190

Ser Ser Pro Thr Val Gly Lys Pro Tyr Lys Cys Asn Tyr Cys Gly Arg
195 200 205

Ser Tyr Lys Gln Gln Ser Thr Leu Glu Glu His Lys Glu Arg Cys His
210 215 220

Asn Tyr Leu Gln Ser Leu Ser Thr Glu Ala Gln Ala Leu Ala Gly Gln
225 230 235 240

Pro Gly Asp Glu Ile Arg Asp Leu Glu Met Val Pro Asp Ser Met Leu
245 250 255

His Ser Ser Ser Glu Arg Pro Thr Phe Ile Asp Arg Leu Ala Asn Ser
260 265 270

Leu Thr Lys Arg Lys Arg Ser Thr Pro Gln Lys Phe Val Gly Glu Lys

-continued 275 280 285

Gln Met Arg Phe Ser Leu Ser Asp Leu Pro Tyr Asp Val Asn Ser Gly
290 295 300

Gly Tyr Glu Lys Asp Val Glu Leu Val Ala His His Ser Leu Glu Pro
305 310 315 320

Gly Phe Gly Ser Ser Leu Ala Phe Val Gly Ala Glu His Leu Arg Pro
325 330 335

Leu Arg Leu Pro Pro Thr Asn Cys Ile Ser Glu Leu Thr Pro Val Ile
340 345 350

Ser Ser Val Tyr Thr Gln Met Gln Pro Leu Pro Gly Arg Leu Glu Leu
355 360 365

Pro Gly Ser Arg Glu Ala Gly Glu Gly Pro Glu Asp Leu Ala Asp Gly
370 375 380

Gly Pro Leu Leu Tyr Arg Pro Arg Gly Pro Leu Thr Asp Pro Gly Ala
385 390 395 400

Ser Pro Ser Asn Gly Cys Gln Asp Ser Thr Asp Thr Glu Ser Asn His
405 410 415

Glu Asp Arg Val Ala Gly Val Val Ser Leu Pro Gln Gly Pro Pro Pro
420 425 430

Gln Pro Pro Pro Thr Ile Val Val Gly Arg His Ser Pro Ala Tyr Ala
435 440 445

Lys Glu Asp Pro Lys Pro Gln Glu Gly Leu Leu Arg Gly Thr Pro Gly
450 455 460

Pro Ser Lys Glu Val Leu Arg Val Val Gly Glu Ser Gly Glu Pro Val
465 470 475 480

Lys Ala Phe Lys Cys Glu His Cys Arg Ile Leu Phe Leu Asp His Val
485 490 495

Met Phe Thr Ile His Met Gly Cys His Gly Phe Arg Asp Pro Phe Glu
500 505 510

Cys Asn Ile Cys Gly Tyr His Ser Gln Asp Arg Tyr Glu Phe Ser Ser
515 520 525

His Ile Val Arg Gly Glu His Lys Val Gly
530 535

<210> SEQ ID NO 41
<211> LENGTH: 483
<212> TYPE: PRT
<213> ORGANISM: homo sapiens

<400> SEQUENCE: 41

Met Tyr Ser Asp Glu Glu Ser Ser Arg Leu Leu Gly Pro Asp Glu Arg
1 5 10 15

Leu Leu Glu Lys Asp Asp Ser Val Ile Val Glu Asp Ser Leu Ser Glu
20 25 30

Pro Leu Gly Tyr Cys Asp Gly Ser Gly Pro Glu Pro His Ser Pro Gly
35 40 45

Gly Ile Arg Leu Pro Asn Gly Lys Leu Lys Cys Asp Val Cys Gly Met
50 55 60

Val Cys Ile Gly Pro Asn Val Leu Met Val His Lys Arg Ser His Thr
65 70 75 80

Gly Glu Arg Pro Phe His Cys Asn Gln Cys Gly Ala Ser Phe Thr Gln
85 90 95

Lys Gly Asn Leu Leu Arg His Ile Lys Leu His Ser Gly Glu Lys Pro
100 105 110

```
Phe Lys Cys Pro Phe Cys Asn Tyr Ala Cys Arg Arg Arg Asp Ala Leu
        115                 120                 125

Thr Gly His Leu Arg Thr His Ser Val Ser Ser Pro Thr Val Gly Lys
    130                 135                 140

Pro Tyr Lys Cys Asn Tyr Cys Gly Arg Ser Tyr Lys Gln Gln Ser Thr
145                 150                 155                 160

Leu Glu Glu His Lys Glu Arg Cys His Asn Tyr Leu Gln Ser Leu Ser
                165                 170                 175

Thr Glu Ala Gln Ala Leu Ala Gly Gln Pro Gly Asp Glu Ile Arg Asp
            180                 185                 190

Leu Glu Met Val Pro Asp Ser Met Leu His Ser Ser Ser Glu Arg Pro
        195                 200                 205

Thr Phe Ile Asp Arg Leu Ala Asn Ser Leu Thr Lys Arg Lys Arg Ser
    210                 215                 220

Thr Pro Gln Lys Phe Val Gly Glu Lys Gln Met Arg Phe Ser Leu Ser
225                 230                 235                 240

Asp Leu Pro Tyr Asp Val Asn Ser Gly Gly Tyr Glu Lys Asp Val Glu
                245                 250                 255

Leu Val Ala His His Ser Leu Glu Pro Gly Phe Gly Ser Ser Leu Ala
            260                 265                 270

Phe Val Gly Ala Glu His Leu Arg Pro Leu Arg Leu Pro Pro Thr Asn
        275                 280                 285

Cys Ile Ser Glu Leu Thr Pro Val Ile Ser Ser Val Tyr Thr Gln Met
    290                 295                 300

Gln Pro Leu Pro Gly Arg Leu Glu Leu Pro Gly Ser Arg Glu Ala Gly
305                 310                 315                 320

Glu Gly Pro Glu Asp Leu Ala Asp Gly Gly Pro Leu Leu Tyr Arg Pro
                325                 330                 335

Arg Gly Pro Leu Thr Asp Pro Gly Ala Ser Pro Ser Asn Gly Cys Gln
            340                 345                 350

Asp Ser Thr Asp Thr Glu Ser Asn His Glu Asp Arg Val Ala Gly Val
        355                 360                 365

Val Ser Leu Pro Gln Gly Pro Pro Pro Gln Pro Pro Pro Thr Ile Val
    370                 375                 380

Val Gly Arg His Ser Pro Ala Tyr Ala Lys Glu Asp Pro Lys Pro Gln
385                 390                 395                 400

Glu Gly Leu Leu Arg Gly Thr Pro Gly Pro Ser Lys Glu Val Leu Arg
                405                 410                 415

Val Val Gly Glu Ser Gly Glu Pro Val Lys Ala Phe Lys Cys Glu His
            420                 425                 430

Cys Arg Ile Leu Phe Leu Asp His Val Met Phe Thr Ile His Met Gly
        435                 440                 445

Cys His Gly Phe Arg Asp Pro Phe Glu Cys Asn Ile Cys Gly Tyr His
    450                 455                 460

Ser Gln Asp Arg Tyr Glu Phe Ser Ser His Ile Val Arg Gly Glu His
465                 470                 475                 480

Lys Val Gly
```

<210> SEQ ID NO 42
<211> LENGTH: 585
<212> TYPE: PRT
<213> ORGANISM: artificial sequence
<220> FEATURE:
<223> OTHER INFORMATION: synthetic construct
<220> FEATURE:

<221> NAME/KEY: misc_feature
<222> LOCATION: (1)..(102)
<223> OTHER INFORMATION: Xaa can be any naturally occurring amino acid

<400> SEQUENCE: 42

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Met Tyr Ser Asp Glu Glu Ser Ser Arg Leu
            100                 105                 110

Leu Gly Pro Asp Glu Arg Leu Leu Glu Lys Asp Asp Ser Val Ile Val
        115                 120                 125

Glu Asp Ser Leu Ser Glu Pro Leu Gly Tyr Cys Asp Gly Ser Gly Pro
    130                 135                 140

Glu Pro His Ser Pro Gly Gly Ile Arg Leu Pro Asn Gly Lys Leu Lys
145                 150                 155                 160

Cys Asp Val Cys Gly Met Val Cys Ile Gly Pro Asn Val Leu Met Val
                165                 170                 175

His Lys Arg Ser His Thr Gly Glu Arg Pro Phe His Cys Asn Gln Cys
            180                 185                 190

Gly Ala Ser Phe Thr Gln Lys Gly Asn Leu Leu Arg His Ile Lys Leu
        195                 200                 205

His Ser Gly Glu Lys Pro Phe Lys Cys Pro Phe Cys Asn Tyr Ala Cys
    210                 215                 220

Arg Arg Arg Asp Ala Leu Thr Gly His Leu Arg Thr His Ser Val Ser
225                 230                 235                 240

Ser Pro Thr Val Gly Lys Pro Tyr Lys Cys Asn Tyr Cys Gly Arg Ser
                245                 250                 255

Tyr Lys Gln Gln Ser Thr Leu Glu Glu His Lys Glu Arg Cys His Asn
            260                 265                 270

Tyr Leu Gln Ser Leu Ser Thr Glu Ala Gln Ala Leu Ala Gly Gln Pro
        275                 280                 285

Gly Asp Glu Ile Arg Asp Leu Glu Met Val Pro Asp Ser Met Leu His
    290                 295                 300

Ser Ser Ser Glu Arg Pro Thr Phe Ile Asp Arg Leu Ala Asn Ser Leu
305                 310                 315                 320

Thr Lys Arg Lys Arg Ser Thr Pro Gln Lys Phe Val Gly Glu Lys Gln
                325                 330                 335

Met Arg Phe Ser Leu Ser Asp Leu Pro Tyr Asp Val Asn Ser Gly Gly
            340                 345                 350

Tyr Glu Lys Asp Val Glu Leu Val Ala His His Ser Leu Glu Pro Gly
        355                 360                 365

Phe Gly Ser Ser Leu Ala Phe Val Gly Ala Glu His Leu Arg Pro Leu
    370                 375                 380

Arg Leu Pro Pro Thr Asn Cys Ile Ser Glu Leu Thr Pro Val Ile Ser
```

```
385                 390                 395                 400

Ser Val Tyr Thr Gln Met Gln Pro Leu Pro Gly Arg Leu Glu Leu Pro
            405                 410                 415

Gly Ser Arg Glu Ala Gly Glu Gly Pro Glu Asp Leu Ala Asp Gly Gly
            420                 425                 430

Pro Leu Leu Tyr Arg Pro Arg Gly Pro Leu Thr Asp Pro Gly Ala Ser
        435                 440                 445

Pro Ser Asn Gly Cys Gln Asp Ser Thr Asp Thr Glu Ser Asn His Glu
    450                 455                 460

Asp Arg Val Ala Gly Val Val Ser Leu Pro Gln Gly Pro Pro Pro Gln
465                 470                 475                 480

Pro Pro Pro Thr Ile Val Val Gly Arg His Ser Pro Ala Tyr Ala Lys
            485                 490                 495

Glu Asp Pro Lys Pro Gln Glu Gly Leu Leu Arg Gly Thr Pro Gly Pro
            500                 505                 510

Ser Lys Glu Val Leu Arg Val Val Gly Glu Ser Gly Glu Pro Val Lys
        515                 520                 525

Ala Phe Lys Cys Glu His Cys Arg Ile Leu Phe Leu Asp His Val Met
    530                 535                 540

Phe Thr Ile His Met Gly Cys His Gly Phe Arg Asp Pro Phe Glu Cys
545                 550                 555                 560

Asn Ile Cys Gly Tyr His Ser Gln Asp Arg Tyr Glu Phe Ser Ser His
            565                 570                 575

Ile Val Arg Gly Glu His Lys Val Gly
            580                 585
```

<210> SEQ ID NO 43
<211> LENGTH: 586
<212> TYPE: PRT
<213> ORGANISM: artificial sequence
<220> FEATURE:
<223> OTHER INFORMATION: synthetic construct
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (350)..(350)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid
<220> FEATURE:
<221> NAME/KEY: misc_feature
<222> LOCATION: (372)..(372)
<223> OTHER INFORMATION: Xaa can be any naturally occurring amino acid
<220> FEATURE:
<221> NAME/KEY: misc_feature
<222> LOCATION: (379)..(379)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (412)..(412)
<223> OTHER INFORMATION: Xaa can be any naturally occurring amino acid
<220> FEATURE:
<221> NAME/KEY: misc_feature
<222> LOCATION: (430)..(430)
<223> OTHER INFORMATION: Xaa can be any naturally occurring amino acid
<220> FEATURE:
<221> NAME/KEY: misc_feature
<222> LOCATION: (439)..(439)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (468)..(469)
<223> OTHER INFORMATION: Xaa can be any naturally occurring amino acid

<400> SEQUENCE: 43

```
Met His Thr Pro Pro Ala Leu Pro Arg Arg Phe Gln Gly Gly Gly Arg
1               5                   10                  15

Val Arg Thr Pro Gly Ser His Arg Gln Gly Lys Asp Asn Leu Glu Arg
            20                  25                  30

Xaa Xaa Ser Gly Gly Cys Xaa Pro Asp Phe Leu Pro Gln Ala Gln Asp
        35                  40                  45

Ser Asn His Phe Ile Met Glu Ser Leu Phe Cys Glu Ser Ser Gly Asp
    50                  55                  60

Ser Ser Leu Glu Lys Glu Phe Leu Gly Ala Pro Val Gly Pro Ser Val
65                  70                  75                  80

Ser Thr Pro Asn Ser Gln His Ser Ser Pro Ser Arg Ser Leu Ser Ala
                85                  90                  95

Asn Ser Ile Lys Val Glu Met Tyr Ser Asp Glu Glu Ser Ser Arg Leu
            100                 105                 110

Leu Gly Pro Asp Glu Arg Leu Leu Xaa Lys Asp Asp Ser Val Ile Val
        115                 120                 125

Glu Asp Ser Leu Ser Glu Pro Leu Gly Tyr Cys Asp Gly Ser Gly Pro
    130                 135                 140

Glu Pro His Ser Pro Gly Gly Ile Arg Leu Pro Asn Gly Lys Leu Lys
145                 150                 155                 160

Cys Asp Val Cys Gly Met Val Cys Ile Gly Pro Asn Val Leu Met Val
                165                 170                 175

His Lys Arg Ser His Thr Gly Glu Arg Pro Phe His Cys Asn Gln Cys
            180                 185                 190

Gly Ala Ser Phe Thr Gln Lys Gly Asn Leu Leu Arg His Ile Lys Leu
        195                 200                 205

His Ser Gly Glu Lys Pro Phe Lys Cys Pro Phe Cys Asn Tyr Ala Cys
    210                 215                 220
```

```
Arg Arg Arg Asp Ala Leu Thr Gly His Leu Arg Thr His Ser Val Ser
225                 230                 235                 240

Ser Pro Thr Val Gly Lys Pro Tyr Lys Cys Asn Tyr Cys Gly Arg Ser
                245                 250                 255

Tyr Lys Gln Gln Ser Thr Leu Glu Glu His Lys Glu Arg Cys His Asn
            260                 265                 270

Tyr Leu Gln Ser Leu Ser Thr Xaa Ala Gln Ala Leu Xaa Gly Gln Pro
        275                 280                 285

Gly Asp Glu Ile Arg Asp Leu Glu Met Val Pro Asp Ser Met Leu His
    290                 295                 300

Xaa Ser Xaa Glu Arg Pro Thr Phe Ile Asp Arg Leu Ala Asn Ser Leu
305                 310                 315                 320

Thr Lys Arg Lys Arg Ser Thr Pro Gln Lys Phe Val Gly Glu Lys Gln
                325                 330                 335

Met Arg Phe Ser Leu Ser Asp Leu Pro Tyr Asp Val Asn Xaa Ser Gly
            340                 345                 350

Gly Tyr Glu Lys Asp Val Glu Leu Val Ala His His Xaa Leu Glu Pro
        355                 360                 365

Gly Phe Gly Xaa Ser Leu Ala Phe Val Gly Xaa Glu His Leu Arg Pro
    370                 375                 380

Leu Arg Leu Pro Pro Thr Asn Cys Ile Ser Glu Leu Thr Pro Val Ile
385                 390                 395                 400

Ser Ser Val Tyr Thr Gln Met Gln Pro Xaa Pro Xaa Arg Leu Glu Leu
                405                 410                 415

Pro Gly Ser Arg Glu Ala Gly Glu Gly Pro Glu Asp Leu Xaa Asp Gly
            420                 425                 430

Gly Pro Leu Leu Tyr Arg Xaa Arg Gly Xaa Leu Thr Asp Pro Gly Ala
        435                 440                 445

Ser Pro Ser Asn Gly Cys Gln Asp Ser Thr Asp Thr Glu Ser Asn His
    450                 455                 460

Glu Asp Arg Xaa Xaa Gly Val Val Ser Leu Pro Gln Gly Pro Pro Pro
465                 470                 475                 480

Gln Pro Pro Pro Thr Ile Val Val Gly Arg His Ser Pro Ala Tyr Ala
                485                 490                 495

Lys Glu Asp Pro Lys Pro Gln Glu Gly Leu Leu Arg Gly Thr Pro Gly
            500                 505                 510

Pro Ser Lys Glu Val Leu Arg Val Val Gly Glu Ser Gly Glu Pro Val
        515                 520                 525

Lys Ala Phe Lys Cys Glu His Cys Arg Ile Leu Phe Leu Asp His Val
    530                 535                 540

Met Phe Thr Ile His Met Gly Cys His Gly Phe Arg Asp Pro Phe Glu
545                 550                 555                 560

Cys Asn Ile Cys Gly Tyr His Ser Gln Asp Arg Tyr Glu Phe Ser Ser
                565                 570                 575

His Ile Val Arg Gly Glu His Lys Val Gly
            580                 585
```

<210> SEQ ID NO 44
<211> LENGTH: 5506
<212> TYPE: DNA
<213> ORGANISM: homo sapiens

<400> SEQUENCE: 44

```
gaagctgtcc gtgtcctggg ccccatgacc tctggggcct tggcttcccc agctggcaga     60
```

```
ggattgggcc ttccctaggg cccccccttt ctccctccca cccgcaggcc catccatctc    120
tctctctctc tcttgcacac actcttgcct ctctcaggca tttgttgtgc agttcctctt    180
tgtctgctgg gcacgagggg caacagcatc tgcctttccc tccctgtgca cacacccacc    240
acccacccc ttcactgtct tggaaaaggg atgctgtagc ctagcatctc ccccactata    300
tacacatata cattctctcc agccccctcc ccaagcacat ccaagcgtgc tctcccctct    360
ccttctctcc ctctctctct ctctctctct cacacacaca cacacacaca cactcaacac    420
acatacaccc tgggctgagc tgctcttgct ggctgcagcc gtgggcctct gctcaccgtg    480
ccgctgctgc tgcctgcgaa atgacggcgg ttcccctcac ttccaggaat ccacgcttcc    540
tggaaggtga gtggctgggc tcacccctgc ctgccactga gacgcagaca tgcatacacc    600
acccgcactc cctcgccgtt tccaaggcgg cggccgcgtt cgcaccccag ggtctcaccg    660
gcaagggaag gataatctgg agagggatcc ctcaggaggg tgtgttccgg atttcttgcc    720
tcaggcccaa gactccaacc attttataat ggaatcttta ttttgtgaaa gtagcgggga    780
ctcatctctg gagaaggagt tcctcggggc cccagtgggg ccctcggtga gcacccccaa    840
cagccagcac tcttctccta gccgctcact cagtgccaac tccatcaagg tggagatgta    900
cagcgatgag gagtcaagca gactgctggg gccagatgag cggctcctgg aaaaggacga    960
cagcgtgatt gtggaagatt cattgtctga gcccctgggc tactgtgatg ggagtgggcc   1020
agagcctcac tcccctgggg gcatccggct gcccaatggc aagctcaagt gtgacgtctg   1080
cggcatggtc tgtattggac ccaacgtgct catggtgcac aagcgcagtc acactggtga   1140
aaggcccttc cattgcaacc agtgtggtgc ctccttcacc cagaagggga acctgctgcg   1200
ccacatcaag ctgcactctg ggagaagcc ctttaaatgt cccttctgca actatgcctg   1260
ccgccggcgt gatgcactca ctggtcacct ccgcacacac tcagtctcct ctcccacagt   1320
gggcaagccc tacaagtgta actactgtgg ccggagctac aaacagcaga gtaccctgga   1380
ggagcacaag gagcggtgcc ataactacct acagagtctc agcactgaag cccaagcttt   1440
ggctggccaa ccaggtgacg aaatacgtga cctggagatg gtgccagact ccatgctgca   1500
ctcatcctct gagcggccaa ctttcatcga tcgtctggcc aatagcctca ccaaacgcaa   1560
gcgttccaca ccccagaagt ttgtaggcga aaagcagatg cgcttcagcc tctcagacct   1620
cccctatgat gtgaactcgg gtggctatga aaaggatgtg gagttggtgg cacaccacag   1680
cctagagcct ggctttggaa gttccctggc ctttgtgggt gcagagcatc tgcgtcccct   1740
ccgccttcca cccaccaatt gcatctcaga actcacgcct gtcatcagct ctgtctacac   1800
ccagatgcag cccctccctg gtcgactgga gcttccagga tcccgagaag caggtgaggg   1860
acctgaggac ctggctgatg gaggtcccct cctctaccgg ccccgaggcc ccctgactga   1920
ccctggggca tcccccagca atggctgcca ggactccaca gacacagaaa gcaaccacga   1980
agatcgggtt gcgggggtgg tatccctccc tcagggtccc ccaccccagc cacctcccac   2040
cattgtggtg ggccggcaca gtcctgccta cgccaaagag gaccccaagc cacaggaggg   2100
gttattgcgg ggcaccccag gcccctccaa ggaagtgctt cgggtggtgg gcgagagtgg   2160
tgagcctgtg aaggccttca agtgtgagca ctgccgtatc ctcttcctgg accacgtcat   2220
gttcactatc cacatgggct gccatggctt cagagaccct tttgagtgca acatctgtgg   2280
ttatcacagc caggaccggt acgaattctc ttcccacatt gtccgggggg agcataaggt   2340
gggctagcaa cctctccctc tctcctcagt ccaccactcc actgccctga ctacaggcat   2400
tgatccctgt ccccaccatt tcccaaggag ttttgctttg tagccctcac tactggccac   2460
```

```
ctgacctcac acctgaccct gacccctcct cacctattct cttcctctat cctgaccgat   2520
gtaagcattg tgatgaaaca gatcttttgc ttatgttttt cctttttatc ttctctcatc   2580
ccagcatact gagttattta ttaattagtt gatttatttt tgccttttta aattttaact   2640
tatatcagtc acttgccact cccccaccct cctgtccaca actcctttcc actttaggcc   2700
aatttttctc tcttagatct tccagcagcc ccaggggtag gaagctcctc ttagtactaa   2760
gagacttcaa gcttcttgct ttaagtcctc accctttaca ttatctaatt cttcagtttt   2820
gatgctgata cctgccccccg gccctacctt agctctgtgg cattatatct cctctctggg   2880
actcttcaac ctggtactcc atacctcttg tgccctctca ctttaggcag cttgcactat   2940
tcttgaatga atgaagaatt atttcctcat ttggaagtag gagggactga agaaattctc   3000
cccaggcact gtgggactga gagtcctatt cccctagtaa taggtcatat tcccctagta   3060
atatgagttc tcaaagccta cattcaggat ctccctctag gatgtgatag atctggtccc   3120
tctccttgaa ctacccctcc acacgctcta gtcccttcaa cctaccggtc tattaagtgg   3180
tggcttttct ctccttggag tgccccaatt ttatattctc aggggccaag gctaggtctg   3240
caaccctctg tctctgacag attgggagcc acaggtgcct aattgggaac cagggcatgg   3300
gaaaggagtg ggtcaaaatt cttctctttc tcctccacct ctcaaacttc ttcactatag   3360
tgaccttcct aggctctcag ggctccttc agtccccatc ctatgagaaa ctagtgggtt   3420
gctgcctgat gacaaggggt tgtttcagcc cctcagtcat gctgccttct gctgctccct   3480
cccagcagga ttcaccctct cattcccggg ctcctgggcc ctgttcttag gatcagtggc   3540
agggagaaac gggtatctct tttctctctt ctaattttca gtataaccaa aaattatccc   3600
agcatgagca cgggcacgtg cccttcaccc cattccaccc ttgttccagc aagactggga   3660
tgggtacaac tgaactgggg tcttccttta ctaccccctt ctacactcag ctcccagaca   3720
cagggtagga ggggggactg ctggctactg cagagaccct tggctatttg agtaacctag   3780
gattagtgag aaggggcaga aggagataca actccactgc aagtggaggt ttctttctac   3840
aagagttttc tgcccaaggc cacagccatc ccactctctg cttccttgag attcaaacca   3900
aaggctgttt ttctatgttt aaagaaaaaa aaaagtaaaa accaaacaca acacctcaca   3960
agttgtaact cttggtcctt ctctctctcc ttttctcttc ccttccttcc ccttccatct   4020
ttctttccac atgtcctttc cttattggct cttttacctc ctacttttct cactccctat   4080
cagggatatt ttgggggggg atggtaaagg gtgggctaag gaacagaccc tgggattagg   4140
gccttaaggg ctctgagagg agtctacctt gccttcttat gggaagggag accctaaaaa   4200
actttctcct ctttgtcctc ctttttctcc cccactctga ggtttcccca agagaaccag   4260
attggcaggg agaagcattg tggggcaatt gttcctcctt gacaatgtag caataaatag   4320
atgctgccaa gggcagaaaa tggggaggtt agctcagagc agagtagtct ctagagaaag   4380
gaagaatcct caacggcacc ctggggtgct agctcctttt tagaatgtca gcagagctga   4440
gattaatatc tgggcttttc ctgaactatt ctggttattg agcccttcct gttagaccta   4500
ccgcctccca cctcttctgt gtctgctgtg tatttggtga cacttcataa ggactagtcc   4560
cttctggggt atcagagcct tagggtgccc ccatcccctt ccccagtcaa ctgtggcacc   4620
tgtaacctcc cggaacatga aggactatgc tctgaggcta tactctgtgc ccatgagagc   4680
agagactgga agggcaagac caggtgctaa ggaggggaga gggggcatcc tgtctctctc   4740
cagaccatca ctgcacttta accagggtct taggtacaaa atcctacttt tcagagcctt   4800
```

ccagctctgg aacctcaaac atcctcatgc tctctcccag ctccttttgc ataaaaaaaa 4860
aagtaaagaa aaagaaaaaa aaatacacac acactgaaac ccacatggag aaaagaggtg 4920
tttcctttta tattgctatt caaaatcaat accaccaaca aaatatttct aagtagacac 4980
ttttccagac ctttgttttt ttgtgtcagt gtccaagctg cagataggat tttgtaatac 5040
ttctggcagc ttctttcctt gtgtacataa tatatatata tacatatata tatatatttt 5100
taatcagaag ttatgaagaa caaaaagaaa aaataaacac agaagcaagt gcaataccac 5160
ctctcttctc cctctctcct agggtttcct ttgtagccta tgtttggtgt ctcttttgac 5220
ctttacccct tcacctcctc ctctcttctt ctgattcccc tccccccctt ttttaaagag 5280
tttttctcct ttctcaaggg gagttaaact agcttttgag acttattgca aagcattttg 5340
tatatgtaat atattgtaag taaatatttg tgtaacggag atatactact gtaagttttg 5400
tactgtactg gctgaaagtc tgttataaat aaacatgagt aatttaacac caaaaaaaaa 5460
aaaaaaaaaa aaaaaaaaaa aaaaaaaaaa aaaaaaaaaa aaaaaa 5506

<210> SEQ ID NO 45
<211> LENGTH: 5076
<212> TYPE: DNA
<213> ORGANISM: homo sapiens

<400> SEQUENCE: 45
ggaccaatga aggaattatt ggcatgcact aaaggagata gcaagatggg tcagacacac 60
atatgagagt cattggcaac acccgggtaa tgtaaggaat ccacgcttcc tggaaggtga 120
gtggctgggc tcacccctgc ctgccactga gacgcagaca tgcatacacc acccgcactc 180
cctcgccgtt tccaaggcgg cggccgcgtt cgcaccccag ggtctcaccg gcaagggaag 240
gataatctgg agagggatcc ctcaggaggg tgtgttccgg atttcttgcc tcaggcccaa 300
gactccaacc attttataat ggaatcttta ttttgtgaaa gtagcgggga ctcatctctg 360
gagaaggagt tcctcggggc cccagtgggg ccctcggtga gcacccccaa cagccagcac 420
tcttctccta gccgctcact cagtgccaac tccatcaagg tggagatgta cagcgatgag 480
gagtcaagca gactgctggg gccagatgag cggctcctgg aaaaggacga cagcgtgatt 540
gtggaagatt cattgtctga gcccctgggc tactgtgatg ggagtgggcc agagcctcac 600
tcccctgggg gcatccggct gcccaatggc aagctcaagt gtgacgtctg cggcatggtc 660
tgtattggac ccaacgtgct catggtgcac aagcgcagtc acactggtga aaggcccttc 720
cattgcaacc agtgtggtgc ctccttcacc cagaagggga acctgctgcg ccacatcaag 780
ctgcactctg gggagaagcc ctttaaatgt cccttctgca actatgcctg ccgccggcgt 840
gatgcactca ctggtcacct ccgcacacac tcagtctcct ctcccacagt gggcaagccc 900
tacaagtgta actactgtgg ccggagctac aaacagcaga gtaccctgga ggagcacaag 960
gagcggtgcc ataactacct acagagtctc agcactgaag cccaagcttt ggctggccaa 1020
ccaggtgacg aaatacgtga cctggagatg gtgccagact ccatgctgca ctcatcctct 1080
gagcggccaa ctttcatcga tcgtctggcc aatagcctca ccaaacgcaa gcgttccaca 1140
ccccagaagt ttgtaggcga aaagcagatg cgcttcagcc tctcagacct cccctatgat 1200
gtgaactcgg gtggctatga aaaggatgtg gagttggtgg cacaccacag cctagagcct 1260
ggctttggaa gttccctggc ctttgtgggt gcagagcatc tgcgtcccct ccgccttcca 1320
cccaccaatt gcatctcaga actcacgcct gtcatcagct ctgtctacac ccagatgcag 1380
cccctccctg gtcgactgga gcttccagga tcccgagaag caggtgaggg acctgaggac 1440
ctggctgatg gaggtcccct cctctaccgg ccccgaggcc ccctgactga ccctggggca 1500
tcccccagca atggctgcca ggactccaca gacacagaaa gcaaccacga agatcgggtt 1560
gcgggggtgg tatccctccc tcagggtccc ccaccccagc cacctcccac cattgtggtg 1620
ggccggcaca gtcctgccta cgccaaagag gaccccaagc cacaggaggg gttattgcgg 1680
ggcaccccag gcccctccaa ggaagtgctt cgggtggtgg gcgagagtgg tgagcctgtg 1740
aaggccttca agtgtgagca ctgccgtatc ctcttcctgg accacgtcat gttcactatc 1800
cacatgggct gccatggctt cagagaccct tttgagtgca acatctgtgg ttatcacagc 1860
caggaccggt acgaattctc ttcccacatt gtccgggggg agcataaggt gggctagcaa 1920
cctctccctc tctcctcagt ccaccactcc actgccctga ctacaggcat tgatccctgt 1980
ccccaccatt tcccaaggag ttttgctttg tagccctcac tactggccac ctgacctcac 2040
acctgaccct gacccctcct cacctattct cttcctctat cctgaccgat gtaagcattg 2100
tgatgaaaca gatcttttgc ttatgttttt cctttttatc ttctctcatc ccagcatact 2160
gagttattta ttaattagtt gatttatttt tgccttttta aattttaact tatatcagtc 2220
acttgccact cccccaccct cctgtccaca actcctttcc actttaggcc aatttttctc 2280
tcttagatct tccagcagcc ccaggggtag gaagctcctc ttagtactaa gagacttcaa 2340
gcttcttgct ttaagtcctc accctttaca ttatctaatt cttcagtttt gatgctgata 2400 cctgccccccg gccctacctt agctctgtgg cattatatct cctctctggg actcttcaac 2460
ctggtactcc atacctcttg tgccctctca ctttaggcag cttgcactat tcttgaatga 2520
atgaagaatt atttcctcat ttggaagtag gagggactga agaaattctc cccaggcact 2580
gtgggactga gagtcctatt cccctagtaa taggtcatat tcccctagta atatgagttc 2640
tcaaagccta cattcaggat ctccctctag gatgtgatag atctggtccc tctccttgaa 2700
ctacccctcc acacgctcta gtcccttcaa cctaccggtc tattaagtgg tggcttttct 2760
ctccttggag tgccccaatt ttatattctc aggggccaag gctaggtctg caaccctctg 2820
tctctgacag attgggagcc acaggtgcct aattgggaac cagggcatgg gaaaggagtg 2880
ggtcaaaatt cttctctttc tcctccacct ctcaaacttc ttcactatag tgaccttcct 2940
aggctctcag gggctccttc agtccccatc ctatgagaaa ctagtgggtt gctgcctgat 3000
gacaaggggt tgtttcagcc cctcagtcat gctgccttct gctgctccct cccagcagga 3060
ttcaccctct cattcccggg ctcctgggcc ctgttcttag gatcagtggc agggagaaac 3120
gggtatctct tttctctctt ctaattttca gtataaccaa aaattatccc agcatgagca 3180
cgggcacgtg cccttcaccc cattccaccc ttgttccagc aagactggga tgggtacaac 3240
tgaactgggg tcttccttta ctaccccctt ctacactcag ctcccagaca cagggtagga 3300 gggggactg ctggctactg cagagaccct tggctatttg agtaacctag gattagtgag 3360
aaggggcaga aggagataca actccactgc aagtggaggt ttctttctac aagagttttc 3420
tgcccaaggc cacagccatc ccactctctg cttccttgag attcaaacca aaggctgttt 3480
ttctatgttt aaagaaaaaa aaaagtaaaa accaaacaca acacctcaca agttgtaact 3540
cttggtcctt ctctctctcc ttttctcttc ccttccttcc ccttccatct ttctttccac 3600
atgtcctttc cttattggct cttttacctc ctacttttct cactccctat cagggatatt 3660
ttgggggggg atggtaaagg gtgggctaag gaacagaccc tgggattagg gccttaaggg 3720
ctctgagagg agtctacctt gccttcttat gggaagggag accctaaaaa actttctcct 3780
ctttgtcctc ctttttctcc cccactctga ggtttcccca agagaaccag attggcaggg 3840
agaagcattg tggggcaatt gttcctcctt gacaatgtag caataaatag atgctgccaa 3900
gggcagaaaa tggggaggtt agctcagagc agagtagtct ctagagaaag gaagaatcct 3960
caacggcacc ctggggtgct agctcctttt tagaatgtca gcagagctga gattaatatc 4020
tgggcttttc ctgaactatt ctggttattg agcccttcct gttagaccta ccgcctccca 4080
cctcttctgt gtctgctgtg tatttggtga cacttcataa ggactagtcc cttctggggt 4140
atcagagcct tagggtgccc ccatcccctt ccccagtcaa ctgtggcacc tgtaacctcc 4200
cggaacatga aggactatgc tctgaggcta tactctgtgc ccatgagagc agagactgga 4260
agggcaagac caggtgctaa ggaggggaga gggggcatcc tgtctctctc cagaccatca 4320
ctgcacttta accagggtct taggtacaaa atcctacttt tcagagcctt ccagctctgg 4380
aacctcaaac atcctcatgc tctctcccag ctccttttgc ataaaaaaaa aagtaaagaa 4440
aaagaaaaaa aaatacacac acactgaaac ccacatggag aaaagaggtg tttcctttta 4500
tattgctatt caaaatcaat accaccaaca aaatatttct aagtagacac ttttccagac 4560
ctttgttttt ttgtgtcagt gtccaagctg cagataggat tttgtaatac ttctggcagc 4620
ttctttcctt gtgtacataa tatatatata tacatatata tatatatttt taatcagaag 4680
ttatgaagaa caaaaagaaa aaataaacac agaagcaagt gcaataccac ctctcttctc 4740
cctctctcct agggtttcct ttgtagccta tgtttggtgt ctcttttgac ctttacccct 4800
tcacctcctc ctctcttctt ctgattcccc tccccccctt ttttaaagag tttttctcct 4860
ttctcaaggg gagttaaact agcttttgag acttattgca aagcattttg tatatgtaat 4920
atattgtaag taaatatttg tgtaacggag atatactact gtaagttttg tactgtactg 4980
gctgaaagtc tgttataaat aaacatgagt aatttaacac caaaaaaaaa aaaaaaaaaa 5040
aaaaaaaaaa aaaaaaaaaa aaaaaaaaaa aaaaaa 5076

<210> SEQ ID NO 46
<211> LENGTH: 5227
<212> TYPE: DNA
<213> ORGANISM: homo sapiens

<400> SEQUENCE: 46
gaagctgtcc gtgtcctggg ccccatgacc tctggggcct tggcttcccc agctggcaga 60
ggattgggcc ttccctaggg cccccccttt ctccctccca cccgcaggcc catccatctc 120
tctctctctc tcttgcacac actcttgcct ctctcaggca tttgttgtgc agttcctctt 180
tgtctgctgg gcacgagggg caacagcatc tgcctttccc tccctgtgca cacacccacc 240
acccaccccc ttcactgtct tggaaaaggg atgctgtagc ctagcatctc ccccactata 300
tacacatata cattctctcc agccccctcc ccaagcacat ccaagcgtgc tctcccctct 360
ccttctctcc ctctctctct ctctctctct cacacacaca cacacacaca cactcaacac 420
acatacaccc tgggctgagc tgctcttgct ggctgcagcc gtgggcctct gctcaccgtg 480
ccgctgctgc tgcctgcgaa atgacggcgg ttcccctcac ttccaggaat ccacgcttcc 540
tggaaggtag cggggactca tctctggaga aggagttcct cggggcccca gtggggccct 600
cggtgagcac ccccaacagc cagcactctt ctcctagccg ctcactcagt gccaactcca 660
tcaaggtgga gatgtacagc gatgaggagt caagcagact gctggggcca gatgagcggc 720
tcctggaaaa ggacgacagc gtgattgtgg aagattcatt gtctgagccc ctgggctact 780
gtgatgggag tgggccagag cctcactccc ctgggggcat ccggctgccc aatggcaagc 840

```
tcaagtgtga cgtctgcggc atggtctgta ttggacccaa cgtgctcatg gtgcacaagc    900
gcagtcacac tggtgaaagg cccttccatt gcaaccagtg tggtgcctcc ttcacccaga    960
aggggaacct gctgcgccac atcaagctgc actctgggga gaagcccttt aaatgtccct   1020
tctgcaacta tgcctgccgc cggcgtgatg cactcactgg tcacctccgc acacactcag   1080
tctcctctcc cacagtgggc aagccctaca agtgtaacta ctgtggccgg agctacaaac   1140
agcagagtac cctggaggag cacaaggagc ggtgccataa ctacctacag agtctcagca   1200
ctgaagccca agctttggct ggccaaccag gtgacgaaat acgtgacctg gagatggtgc   1260
cagactccat gctgcactca tcctctgagc ggccaacttt catcgatcgt ctggccaata   1320
gcctcaccaa acgcaagcgt tccacacccc agaagtttgt aggcgaaaag cagatgcgct   1380
tcagcctctc agacctcccc tatgatgtga actcgggtgg ctatgaaaag gatgtggagt   1440
tggtggcaca ccacagccta gagcctggct ttggaagttc cctggccttt gtgggtgcag   1500
agcatctgcg tcccctccgc cttccaccca ccaattgcat ctcagaactc acgcctgtca   1560
tcagctctgt ctacacccag atgcagcccc tccctggtcg actggagctt ccaggatccc   1620
gagaagcagg tgagggacct gaggacctgg ctgatggagg tcccctcctc taccggcccc   1680
gaggcccccct gactgaccct ggggcatccc ccagcaatgg ctgccaggac tccacagaca   1740
cagaaagcaa ccacgaagat cgggttgcgg gggtggtatc cctccctcag ggtcccccac   1800
cccagccacc tcccaccatt gtggtgggcc ggcacagtcc tgcctacgcc aaagaggacc   1860
ccaagccaca ggaggggtta ttgcggggca ccccaggccc ctccaaggaa gtgcttcggg   1920
tggtgggcga gagtggtgag cctgtgaagg ccttcaagtg tgagcactgc cgtatcctct   1980
tcctggacca cgtcatgttc actatccaca tgggctgcca tggcttcaga gacccttttg   2040
agtgcaacat ctgtggttat cacagccagg accggtacga attctcttcc cacattgtcc   2100
ggggggagca taaggtgggc tagcaacctc tccctctctc ctcagtccac cactccactg   2160
ccctgactac aggcattgat ccctgtcccc accatttccc aaggagtttt gctttgtagc   2220
cctcactact ggccacctga cctcacacct gaccctgacc cctcctcacc tattctcttc   2280
ctctatcctg accgatgtaa gcattgtgat gaaacagatc ttttgcttat gtttttcctt   2340
tttatcttct ctcatcccag catactgagt tatttattaa ttagttgatt tatttttgcc   2400
tttttaaatt ttaacttata tcagtcactt gccactcccc caccctcctg tccacaactc   2460
ctttccactt taggccaatt tttctctctt agatcttcca gcagccccag gggtaggaag   2520
ctcctcttag tactaagaga cttcaagctt cttgctttaa gtcctcaccc tttacattat   2580
ctaattcttc agttttgatg ctgatacctg cccccggccc taccttagct ctgtggcatt   2640
atatctcctc tctgggactc ttcaacctgg tactccatac ctcttgtgcc ctctcacttt   2700
aggcagcttg cactattctt gaatgaatga agaattattt cctcatttgg aagtaggagg   2760
gactgaagaa attctcccca ggcactgtgg gactgagagt cctattcccc tagtaatagg   2820
tcatattccc ctagtaatat gagttctcaa agcctacatt caggatctcc ctctaggatg   2880
tgatagatct ggtccctctc cttgaactac ccctccacac gctctagtcc cttcaaccta   2940
ccggtctatt aagtggtggc ttttctctcc ttggagtgcc ccaattttat attctcaggg   3000
gccaaggcta ggtctgcaac cctctgtctc tgacagattg ggagccacag gtgcctaatt   3060
gggaaccagg gcatgggaaa ggagtgggtc aaaattcttc tctttctcct ccacctctca   3120
aacttcttca ctatagtgac cttcctaggc tctcaggggc tccttcagtc cccatcctat   3180
```

```
gagaaactag tgggttgctg cctgatgaca aggggttgtt tcagcccctc agtcatgctg   3240
ccttctgctg ctccctccca gcaggattca ccctctcatt cccgggctcc tgggccctgt   3300
tcttaggatc agtggcaggg agaaacgggt atctcttttc tctcttctaa ttttcagtat   3360
aaccaaaaat tatcccagca tgagcacggg cacgtgccct tcaccccatt ccacccttgt   3420
tccagcaaga ctgggatggg tacaactgaa ctggggtctt cctttactac cccettctac   3480
actcagctcc cagacacagg gtaggagggg ggactgctgg ctactgcaga gacccttggc   3540
tatttgagta acctaggatt agtgagaagg ggcagaagga gatacaactc cactgcaagt   3600
ggaggtttct ttctacaaga gttttctgcc caaggccaca gccatcccac tctctgcttc   3660
cttgagattc aaaccaaagg ctgtttttct atgtttaaag aaaaaaaaaa gtaaaaacca   3720
aacacaacac ctcacaagtt gtaactcttg gtccttctct ctctcctttt ctcttccctt   3780
ccttcccctt ccatctttct ttccacatgt cctttcctta ttggctcttt tacctcctac   3840
ttttctcact ccctatcagg gatattttgg ggggggatgg taaagggtgg gctaaggaac   3900
agaccctggg attagggcct taagggctct gagaggagtc taccttgcct tcttatggga   3960
agggagaccc taaaaaactt tctcctcttt gtcctccttt ttctccccca ctctgaggtt   4020
tccccaagag aaccagattg gcagggagaa gcattgtggg gcaattgttc ctccttgaca   4080
atgtagcaat aaatagatgc tgccaagggc agaaaatggg gaggttagct cagagcagag   4140
tagtctctag agaaaggaag aatcctcaac ggcaccctgg ggtgctagct cctttttaga   4200
atgtcagcag agctgagatt aatatctggg cttttcctga actattctgg ttattgagcc   4260
cttcctgtta gacctaccgc ctcccacctc ttctgtgtct gctgtgtatt tggtgacact   4320
tcataaggac tagtcccttc tggggtatca gagccttagg gtgcccccat ccccttcccc   4380
agtcaactgt ggcacctgta acctcccgga acatgaagga ctatgctctg aggctatact   4440
ctgtgcccat gagagcagag actggaaggg caagaccagg tgctaaggag gggagagggg   4500
gcatcctgtc tctctccaga ccatcactgc actttaacca gggtcttagg tacaaaatcc   4560
tacttttcag agccttccag ctctggaacc tcaaacatcc tcatgctctc tcccagctcc   4620
ttttgcataa aaaaaaaagt aaagaaaaag aaaaaaaaat acacacacac tgaaacccac   4680
atggagaaaa gaggtgtttc cttttatatt gctattcaaa atcaatacca ccaacaaaat   4740
atttctaagt agacactttt ccagaccttt gttttttttgt gtcagtgtcc aagctgcaga   4800
taggattttg taatacttct ggcagcttct ttccttgtgt acataatata tatatataca   4860
tatatatata tatttttaat cagaagttat gaagaacaaa aagaaaaaat aaacacagaa   4920
gcaagtgcaa taccacctct cttctccctc tctcctaggg tttcctttgt agcctatgtt   4980
tggtgtctct tttgaccttt accccttcac ctcctcctct cttcttctga ttcccctccc   5040
cccctttttt aaagagtttt tctcctttct caaggggagt taaactagct tttgagactt   5100
attgcaaagc attttgtata tgtaatatat tgtaagtaaa tatttgtgta acggagatat   5160
actactgtaa gttttgtact gtactggctg aaagtctgtt ataaataaac atgagtaatt   5220
taacacc                                                              5227
```

<210> SEQ ID NO 47
<211> LENGTH: 4834
<212> TYPE: DNA
<213> ORGANISM: homo sapiens

<400> SEQUENCE: 47

```
gcgcgcgcgc ggagacacct cagtctacat ggggaggaca gagaagcgca aagaacaaga     60
```

```
gaaaagatgc atccatctga gatctaaaag gagacaatga gaatctcttt aaaatggaca    120
tagaagactg caatggccgc tcctatgtgt ctggtagcgg ggactcatct ctggagaagg    180
agttcctcgg ggccccagtg gggccctcgg tgagcacccc caacagccag cactcttctc    240
ctagccgctc actcagtgcc aactccatca aggtggagat gtacagcgat gaggagtcaa    300
gcagactgct ggggccagat gagcggctcc tggaaaagga cgacagcgtg attgtggaag    360
attcattgtc tgagcccctg ggctactgtg atgggagtgg gccagagcct cactcccctg    420
ggggcatccg gctgcccaat ggcaagctca agtgtgacgt ctgcggcatg gtctgtattg    480
gacccaacgt gctcatggtg cacaagcgca gtcacactgg tgaaaggccc ttccattgca    540
accagtgtgg tgcctccttc acccagaagg ggaacctgct gcgccacatc aagctgcact    600
ctggggagaa gccctttaaa tgtcccttct gcaactatgc ctgccgccgg cgtgatgcac    660
tcactggtca cctccgcaca cactcagtct cctctcccac agtgggcaag ccctacaagt    720
gtaactactg tggccggagc tacaaacagc agagtaccct ggaggagcac aaggagcggt    780
gccataacta cctacagagt ctcagcactg aagcccaagc tttggctggc caaccaggtg    840
acgaaatacg tgacctggag atggtgccag actccatgct gcactcatcc tctgagcggc    900
caactttcat cgatcgtctg gccaatagcc tcaccaaacg caagcgttcc acaccccaga    960
agtttgtagg cgaaaagcag atgcgcttca gcctctcaga cctcccctat gatgtgaact   1020
cgggtggcta tgaaaaggat gtggagttgg tggcacacca cagcctagag cctggctttg   1080
gaagttccct ggcctttgtg ggtgcagagc atctgcgtcc cctccgcctt ccacccacca   1140
attgcatctc agaactcacg cctgtcatca gctctgtcta cacccagatg cagcccctcc   1200
ctggtcgact ggagcttcca ggatcccgag aagcaggtga gggacctgag gacctggctg   1260
atggaggtcc cctcctctac cggccccgag gcccccctgac tgaccctggg gcatccccca   1320
gcaatggctg ccaggactcc acagacacag aaagcaacca cgaagatcgg gttgcggggg   1380
tggtatccct ccctcagggt cccccacccc agccacctcc caccattgtg gtgggccggc   1440
acagtcctgc ctacgccaaa gaggacccca agccacagga ggggttattg cggggcaccc   1500
caggcccctc caaggaagtg cttcgggtgg tgggcgagag tggtgagcct gtgaaggcct   1560
tcaagtgtga gcactgccgt atcctcttcc tggaccacgt catgttcact atccacatgg   1620
gctgccatgg cttcagagac ccttttgagt gcaacatctg tggttatcac agccaggacc   1680
ggtacgaatt ctcttcccac attgtccggg gggagcataa ggtgggctag caacctctcc   1740
ctctctcctc agtccaccac tccactgccc tgactacagg cattgatccc tgtccccacc   1800
atttcccaag gagttttgct ttgtagccct cactactggc cacctgacct cacacctgac   1860
cctgacccct cctcacctat tctcttcctc tatcctgacc gatgtaagca ttgtgatgaa   1920
acagatcttt tgcttatgtt tttccttttt atcttctctc atcccagcat actgagttat   1980
ttattaatta gttgatttat ttttgccttt ttaaatttta acttatatca gtcacttgcc   2040
actcccccac cctcctgtcc acaactcctt tccactttag gccaattttt ctctcttaga   2100
tcttccagca gccccagggg taggaagctc ctcttagtac taagagactt caagcttctt   2160
gctttaagtc ctcacccttt acattatcta attcttcagt tttgatgctg atacctgccc   2220
ccggccctac cttagctctg tggcattata tctcctctct gggactcttc aacctggtac   2280
tccatacctc ttgtgccctc tcactttagg cagcttgcac tattcttgaa tgaatgaaga   2340
attatttcct catttggaag taggagggac tgaagaaatt ctccccaggc actgtgggac   2400
```

```
tgagagtcct attcccctag taataggtca tattccccta gtaatatgag ttctcaaagc   2460
ctacattcag gatctccctc taggatgtga tagatctggt ccctctcctt gaactacccc   2520
tccacacgct ctagtccctt caacctaccg gtctattaag tggtggcttt tctctccttg   2580
gagtgcccca attttatatt ctcaggggcc aaggctaggt ctgcaaccct ctgtctctga   2640
cagattggga gccacaggtg cctaattggg aaccagggca tgggaaagga gtgggtcaaa   2700
attcttctct ttctcctcca cctctcaaac ttcttcacta tagtgacctt cctaggctct   2760
caggggctcc ttcagtcccc atcctatgag aaactagtgg gttgctgcct gatgacaagg   2820
ggttgtttca gcccctcagt catgctgcct tctgctgctc cctcccagca ggattcaccc   2880
tctcattccc gggctcctgg gccctgttct taggatcagt ggcagggaga aacgggtatc   2940
tcttttctct cttctaattt tcagtataac caaaaattat cccagcatga gcacgggcac   3000
gtgcccttca ccccattcca cccttgttcc agcaagactg ggatgggtac aactgaactg   3060
gggtcttcct ttactacccc cttctacact cagctcccag acacagggta ggagggggga   3120
ctgctggcta ctgcagagac ccttggctat ttgagtaacc taggattagt gagaaggggc   3180
agaaggagat acaactccac tgcaagtgga ggtttctttc tacaagagtt ttctgcccaa   3240
ggccacagcc atcccactct ctgcttcctt gagattcaaa ccaaaggctg tttttctatg   3300
tttaaagaaa aaaaaaagta aaaaccaaac acaacacctc acaagttgta actcttggtc   3360
cttctctctc tccttttctc ttcccttcct tccccttcca tctttctttc cacatgtcct   3420
ttccttattg gctcttttac ctcctacttt tctcactccc tatcagggat attttggggg   3480
gggatggtaa agggtgggct aaggaacaga ccctgggatt agggccttaa gggctctgag   3540
aggagtctac cttgccttct tatgggaagg gagaccctaa aaaactttct cctctttgtc   3600
ctccttttc tcccccactc tgaggtttcc ccaagagaac cagattggca gggagaagca   3660
ttgtggggca attgttcctc cttgacaatg tagcaataaa tagatgctgc caagggcaga   3720
aaatggggag gttagctcag agcagagtag tctctagaga aaggaagaat cctcaacggc   3780
accctggggt gctagctcct ttttagaatg tcagcagagc tgagattaat atctgggctt   3840
ttcctgaact attctggtta ttgagccctt cctgttagac ctaccgcctc ccacctcttc   3900
tgtgtctgct gtgtatttgg tgacacttca taaggactag tcccttctgg ggtatcagag   3960
ccttagggtg cccccatccc cttccccagt caactgtggc acctgtaacc tcccggaaca   4020
tgaaggacta tgctctgagg ctatactctg tgcccatgag agcagagact ggaagggcaa   4080
gaccaggtgc taaggagggg agagggggca tcctgtctct ctccagacca tcactgcact   4140
ttaaccaggg tcttaggtac aaaatcctac ttttcagagc cttccagctc tggaacctca   4200
aacatcctca tgctctctcc cagctccttt tgcataaaaa aaaaagtaaa gaaaaagaaa   4260
aaaaaataca cacacactga aacccacatg gagaaaagag gtgtttcctt ttatattgct   4320
attcaaaatc aataccacca acaaaatatt tctaagtaga cacttttcca gacctttgtt   4380
tttttgtgtc agtgtccaag ctgcagatag gattttgtaa tacttctggc agcttctttc   4440
cttgtgtaca taatatatat atatacatat atatatatat ttttaatcag aagttatgaa   4500
gaacaaaaag aaaaaataaa cacagaagca agtgcaatac cacctctctt ctccctctct   4560
cctagggttt cctttgtagc ctatgtttgg tgtctctttt gacctttacc ccttcacctc   4620
ctcctctctt cttctgattc ccctcccccc cttttttaaa gagtttttct cctttctcaa   4680
ggggagttaa actagctttt gagacttatt gcaaagcatt ttgtatatgt aatatattgt   4740
aagtaaatat ttgtgtaacg gagatatact actgtaagtt ttgtactgta ctggctgaaa   4800
```

gtctgttata aataaacatg agtaatttaa cacc 4834

<210> SEQ ID NO 48
<211> LENGTH: 5357
<212> TYPE: DNA
<213> ORGANISM: homo sapiens

<400> SEQUENCE: 48
gaagctgtcc gtgtcctggg ccccatgacc tctggggcct tggcttcccc agctggcaga 60
ggattgggcc ttccctaggg ccccccccttt ctccctccca cccgcaggcc catccatctc 120
tctctctctc tcttgcacac actcttgcct ctctcaggca tttgttgtgc agttcctctt 180
tgtctgctgg gcacgagggg caacagcatc tgcctttccc tccctgtgca cacacccacc 240
acccaccccc ttcactgtct tggaaaaggg atgctgtagc ctagcatctc ccccactata 300
tacacatata cattctctcc agccccctcc ccaagcacat ccaagcgtgc tctcccctct 360
ccttctctcc ctctctctct ctctctctct cacacacaca cacacacaca cactcaacac 420
acatacaccc tgggctgagc tgctcttgct ggctgcagcc gtgggcctct gctcaccgtg 480
ccgctgctgc tgcctgcgaa atgacggcgg ttcccctcac ttccaggaat ccacgcttcc 540
tggaaggtga gtggctgggc tcacccctgc ctgccactga gacgcagaca tgcatacacc 600
acccgcactc cctcgccgtt tccaaggcgg cggccgcgtt cgcaccccag ggtctcaccg 660
gcaagggaag gataatgtag cggggactca tctctggaga aggagttcct cggggcccca 720
gtggggccct cggtgagcac ccccaacagc cagcactctt ctcctagccg ctcactcagt 780
gccaactcca tcaaggtgga gatgtacagc gatgaggagt caagcagact gctggggcca 840
gatgagcggc tcctggaaaa ggacgacagc gtgattgtgg aagattcatt gtctgagccc 900
ctgggctact gtgatgggag tggccagagg cctcactccc ctgggggcat ccggctgccc 960
aatggcaagc tcaagtgtga cgtctgcggc atggtctgta ttggacccaa cgtgctcatg 1020
gtgcacaagc gcagtcacac tggtgaaagg ccccttccatt gcaaccagtg tggtgcctcc 1080
ttcacccaga aggggaacct gctgcgccac atcaagctgc actctgggga gaagcccttt 1140
aaatgtccct tctgcaacta tgcctgccgc cggcgtgatg cactcactgg tcacctccgc 1200
acacactcag tctcctctcc cacagtgggc aagccctaca agtgtaacta ctgtggccgg 1260
agctacaaac agcagagtac cctggaggag cacaaggagc ggtgccataa ctacctacag 1320
agtctcagca ctgaagccca agctttggct ggccaaccag gtgacgaaat acgtgacctg 1380
gagatggtgc cagactccat gctgcactca tcctctgagc ggccaacttt catcgatcgt 1440
ctggccaata gcctcaccaa acgcaagcgt tccacacccc agaagtttgt aggcgaaaag 1500
cagatgcgct tcagcctctc agacctcccc tatgatgtga actcgggtgg ctatgaaaag 1560
gatgtggagt tggtggcaca ccacagccta gagcctggct ttggaagttc cctggccttt 1620
gtgggtgcag agcatctgcg tcccctccgc cttccaccca ccaattgcat ctcagaactc 1680
acgcctgtca tcagctctgt ctacacccag atgcagcccc tccctggtcg actggagctt 1740
ccaggatccc gagaagcagg tgagggacct gaggacctgg ctgatggagg tcccctcctc 1800
taccggcccc gaggcccccct gactgaccct ggggcatccc ccagcaatgg ctgccaggac 1860
tccacagaca cagaaagcaa ccacgaagat cgggttgcgg gggtggtatc cctccctcag 1920
ggtcccccac cccagccacc tcccaccatt gtggtgggcc ggcacagtcc tgcctacgcc 1980
aaagaggacc ccaagccaca ggagggggtta ttgcggggca ccccaggccc ctccaaggaa 2040
gtgcttcggg tggtgggcga gagtggtgag cctgtgaagg ccttcaagtg tgagcactgc 2100
cgtatcctct tcctggacca cgtcatgttc actatccaca tgggctgcca tggcttcaga 2160
gacccttttg agtgcaacat ctgtggttat cacagccagg accggtacga attctcttcc 2220
cacattgtcc gggggagca taaggtgggc tagcaacctc tccctctctc ctcagtccac 2280
cactccactg ccctgactac aggcattgat ccctgtcccc accatttccc aaggagtttt 2340
gctttgtagc cctcactact ggccacctga cctcacacct gaccctgacc cctcctcacc 2400
tattctcttc ctctatcctg accgatgtaa gcattgtgat gaaacagatc ttttgcttat 2460
gtttttcctt tttatcttct ctcatcccag catactgagt tatttattaa ttagttgatt 2520
tatttttgcc tttttaaatt ttaacttata tcagtcactt gccactcccc caccctcctg 2580
tccacaactc ctttccactt taggccaatt tttctctctt agatcttcca gcagccccag 2640
gggtaggaag ctcctcttag tactaagaga cttcaagctt cttgctttaa gtcctcaccc 2700
tttacattat ctaattcttc agttttgatg ctgatacctg cccccggccc taccttagct 2760
ctgtggcatt atatctcctc tctgggactc ttcaacctgg tactccatac ctcttgtgcc 2820
ctctcacttt aggcagcttg cactattctt gaatgaatga agaattattt cctcatttgg 2880
aagtaggagg gactgaagaa attctcccca ggcactgtgg gactgagagt cctattcccc 2940
tagtaatagg tcatattccc ctagtaatat gagttctcaa agcctacatt caggatctcc 3000
ctctaggatg tgatagatct ggtccctctc cttgaactac ccctccacac gctctagtcc 3060
cttcaaccta ccggtctatt aagtggtggc ttttctctcc ttggagtgcc ccaattttat 3120
attctcaggg gccaaggcta ggtctgcaac cctctgtctc tgacagattg ggagccacag 3180
gtgcctaatt gggaaccagg gcatgggaaa ggagtgggtc aaaattcttc tctttctcct 3240
ccacctctca aacttcttca ctatagtgac cttcctaggc tctcaggggc tccttcagtc 3300
cccatcctat gagaaactag tgggttgctg cctgatgaca aggggttgtt tcagcccctc 3360
agtcatgctg ccttctgctg ctccctccca gcaggattca ccctctcatt cccgggctcc 3420
tgggccctgt tcttaggatc agtggcaggg agaaacgggt atctcttttc tctcttctaa 3480
ttttcagtat aaccaaaaat tatcccagca tgagcacggg cacgtgccct tcaccccatt 3540
ccacccttgt tccagcaaga ctgggatggg tacaactgaa ctggggtctt cctttactac 3600
ccccttctac actcagctcc cagacacagg gtaggagggg ggactgctgg ctactgcaga 3660
gacccttggc tatttgagta acctaggatt agtgagaagg ggcagaagga gatacaactc 3720
cactgcaagt ggaggtttct ttctacaaga gttttctgcc caaggccaca gccatcccac 3780
tctctgcttc cttgagattc aaaccaaagg ctgtttttct atgtttaaag aaaaaaaaaa 3840
gtaaaaacca aacacaacac ctcacaagtt gtaactcttg gtccttctct ctctcctttt 3900
ctcttccctt ccttcccctt ccatctttct ttccacatgt cctttcctta ttggctcttt 3960
tacctcctac ttttctcact ccctatcagg gatattttgg ggggggatgg taaagggtgg 4020
gctaaggaac agaccctggg attagggcct taagggctct gagaggagtc taccttgcct 4080
tcttatggga agggagaccc taaaaaactt tctcctcttt gtcctccttt ttctccccca 4140
ctctgaggtt tccccaagag aaccagattg gcagggagaa gcattgtggg gcaattgttc 4200
ctccttgaca atgtagcaat aaatagatgc tgccaagggc agaaaatggg gaggttagct 4260
cagagcagag tagtctctag agaaaggaag aatcctcaac ggcaccctgg ggtgctagct 4320
cctttttaga atgtcagcag agctgagatt aatatctggg cttttcctga actattctgg 4380
ttattgagcc cttcctgtta gacctaccgc ctcccacctc ttctgtgtct gctgtgtatt 4440
tggtgacact tcataaggac tagtcccttc tggggtatca gagccttagg gtgcccccat 4500
ccccttcccc agtcaactgt ggcacctgta acctcccgga acatgaagga ctatgctctg 4560
aggctatact ctgtgcccat gagagcagag actggaaggg caagaccagg tgctaaggag 4620
gggagagggg gcatcctgtc tctctccaga ccatcactgc actttaacca gggtcttagg 4680
tacaaaatcc tacttttcag agccttccag ctctggaacc tcaaacatcc tcatgctctc 4740
tcccagctcc ttttgcataa aaaaaaaagt aaagaaaaag aaaaaaaaat acacacacac 4800
tgaaacccac atggagaaaa gaggtgtttc cttttatatt gctattcaaa atcaatacca 4860
ccaacaaaat atttctaagt agacactttt ccagaccttt gttttttgt gtcagtgtcc 4920 aagctgcaga taggattttg taatacttct ggcagcttct ttccttgtgt acataatata 4980
tatatataca tatatatata tatttttaat cagaagttat gaagaacaaa aagaaaaaat 5040
aaacacagaa gcaagtgcaa taccacctct cttctccctc tctcctaggg tttcctttgt 5100
agcctatgtt tggtgtctct tttgaccttt accccttcac ctcctcctct cttcttctga 5160
ttcccctccc cccttttttt aaagagtttt tctcctttct caaggggagt taaactagct 5220
tttgagactt attgcaaagc attttgtata tgtaatatat tgtaagtaaa tatttgtgta 5280
acggagatat actactgtaa gttttgtact gtactggctg aaagtctgtt ataaataaac 5340
atgagtaatt taacacc 5357

<210> SEQ ID NO 49
<211> LENGTH: 1002
<212> TYPE: DNA
<213> ORGANISM: mus musculus

<400> SEQUENCE: 49
atgggcgggg agggccttcg tgcgtcgccg cgccgccgtc cccttctccc tctccagcct 60
cggggctgtc cgcgggggga cggctgcctt cgggggggac ggggcagggc ggggttcggc 120
ttctggcgtg tgaccggcgg ctctagagcc tctgctaacc atgttcatgc cttcttcttt 180
ttcctacagc tcctgggcaa cgtgctggtt attgtgctgt ctcatcattt tggcaaagaa 240
ttgctcgagc tcaagcttcg aattcgcgtc cccaactcgt tctcccccgc gacagtttgg 300
cccggcatgg agagctctgg caagatggag agtggagccg gccagcagcc gcagcccccg 360
cagcccttcc tgcctcccgc agcctgcttc tttgcgaccg cggcggcggc ggcagcggcg 420
gcggccgcgg cagctcagag cgcgcagcag caacagccgc aggcgccgcc gcagcaggcg 480
ccgcagctga gcccggtggc cgacagccag ccctcagggg gcggtcacaa gtcagcggcc 540
aagcaggtca agcgccagcg ctcgtcctct ccggaactga tgcgctgcaa acgccggctc 600
aacttcagcg gcttcggcta cagcctgcca cagcagcagc cggccgccgt ggcgcgccgc 660
aacgagcgcg agcgcaaccg ggtcaagttg gtcaacctgg gttttgccac cctccgggag 720
catgtcccca acggcgcggc caacaagaag atgagcaagg tggagacgct gcgctcggcg 780
gtcgagtaca tccgcgcgct gcagcagctg ctggacgagc acgacgcggt gagcgctgcc 840
tttcaggcgg gcgtcctgtc gcccaccatc tcccccaact actccaacga cttgaactct 900
atggcgggtt ctccggtctc gtcctactcc tccgacgagg gatcctacga ccctcttagc 960
ccagaggaac aagagctgct ggactttacc aactggttct ga 1002

<210> SEQ ID NO 50
<211> LENGTH: 678
<212> TYPE: DNA

<213> ORGANISM: mus musculus

<400> SEQUENCE: 50
atggcccaga aggaagaggc tgctgtggcc actgaggctg cctcccagaa tggggaggat 60
ctggagaacc tggacgaccc tgagaagctg aaagagctga ttgagctgcc gccctttgag 120
attgtcacag gagaacggct gcctgccaac ttctttaaat tccagttccg gaatgtggag 180
tacagttccg ggaggaacaa gaccttcctc tgctatgtgg ttgaagcaca gggcaagggg 240
ggccaagtgc aggcatctcg gggataccta gaggatgagc atgcggctgc ccatgcagag 300
gaagctttct tcaacaccat cctgccagcc ttcgacccag ccctgcggta caatgtcacc 360
tggtatgtgt cctccagccc ctgtgcagcg tgtgctgacc gcattatcaa aacccttagc 420
aagaccaaga acctgcgtct gctcattctg gtgggtcgac tcttcatgtg ggaggagccg 480
gagatccagg ctgctctgaa gaagctgaag gaggctggct gtaaactgcg catcatgaag 540
ccccaggact tcgaatatgt ctggcagaat tttgtggagc aagaagaggg tgaatccaag 600
gcctttcagc cctgggagga cattcaggag aacttcctat actacgagga gaagttggca 660
gacatcctga aggggtga 678

<210> SEQ ID NO 51
<211> LENGTH: 3564
<212> TYPE: DNA
<213> ORGANISM: mus musculus

<400> SEQUENCE: 51
atggacgtgg actctgagga gaagcgccat cgcacacggt ccaaaggggt tcgagttcct 60
gtggagccag ccatacaaga gctgttcagc tgtcccactc caggctgcga cggcagtggt 120
cacgtcagtg gcaaatatgc acgacacaga agtgtatatg gttgtccctt ggctaaaaaa 180
agaaaaacgc aagataaaca gccccaagaa cctgctccca agcgaaaacc atttgcagta 240
aaagcagata gttcctcagt agacgaatgt tatgagagtg atggtactga agacatggat 300
gataaggagg aagatgatga tgaggagttc tctgaagaca atgatgagca aggggatgat 360
gacgacgaag atgaggtgga tcgggaagac gaggaggaga tcgaggagga agatgatgaa 420
gaagatgatg atgatgaaga tggtgacgat gtagaagagg aagaagagga tgatgatgaa 480
gaggaggaag aagaggaaga ggaagaagaa aatgaagacc atcaaatgag ttgtactcga 540
ataatgcagg acacagacaa ggatgataac aacaatgatg agtatgataa ctatgatgaa 600
ctggtagcta agtcgctatt aaatcttggc aaaattgctg aggatgcagc ataccgagcc 660
aggactgaat cagagatgaa cagcaatacc tccaatagtc tggaggacga tagtgacaaa 720
aacgaaaacc tcggtcggaa aagcgaactg agtctagact tagacagtga tgttgttaga 780
gaaacagtgg actcccttaa gctgttagca caaggacatg gtgttgtgct atcagagaat 840
atcagtgaca gaagttatgc tgaggggatg tcacagcagg acagtagaaa tatgaactat 900
gtcatgctag ggaagcccat gaacaatgga ctcatggaga agatggtgga ggagagtgat 960
gaggaagtgt gtctaagtag tctagagtgc ctgaggaacc agtgctttga cctggccagg 1020
aaactcagcg agaccaaccc acaggacagg agtcagccac ccaacatgag tgtgcgccaa 1080
catgtccggc aagaggacga cttccctggg aggacgccag acaggagcta ctcggatatg 1140
atgaacctta tgcggctgga ggagcagctc agtcccaggt ctagaacgtt ctccagctgt 1200
gccaaggagg atgggtgtca tgagagggat gatgacacca cctcagtgaa ctcagacagg 1260
tctgaggaag tgtttgacat gaccaagggc aacctgactc tgctagagaa agccattgcc 1320

-continued

```
ttggagacag agagagccaa ggccatgcgg gagaagatgg ccatggatgc tgggagaagg   1380
gataacctga gatcctatga ggaccagtct ccaagacagc tggctgggga agacagaaaa   1440
tccaaatcca gtgacagcca tgtcaaaaag ccatactatg gtaaagatcc ctcaagaaca   1500
gaaaagagag agagcaagtg tccaaccccc gggtgtgatg gaaccggcca cgtaactggg   1560
ctttacccgc atcaccgcag tctgtctgga tgcccgcaca aagatagggt ccctccagaa   1620
attcttgcca tgcatgaaaa tgttctcaag tgtcccactc caggctgcac agggcgaggg   1680
catgtgaata gcaacaggaa ctcgcacaga agcctctctg gatgccccat tgctgctgca   1740
gaaaaactgg caaaggccca agagaaacac cagagctgtg atgtgtccaa atccaaccag   1800
gcctcagacc gagtcctcag gccaatgtgc tttgtcaaac agcttgagat tcctcagtat   1860
ggctacagaa acaatgttcc cacaaccaca ccacgctcca acctggccaa ggagcttgag   1920
aaatactcca agacttcgtt tgagtacaac agttacgaca accatactta tggcaaaaga   1980
gccatagctc ccaaggtgca aaccagggac atatccccca aggatatga cgatgccaag   2040
cggtactgca agaatgccag ccccagcagc agcaccacca gcagctatgc acctagcagc   2100
agcagcaacc tcagctgtgg tggtggcagc agcgccagta gcacgtgtag caagagcagc   2160
tttgactaca cacatgacat ggaggccgca cacatggcag ccacagccat tctcaacctg   2220
tccacacgtt gtcgtgaaat gccacagaac ctgtccacca agccacagga cctgtgtact   2280
gcccggaacc cagacatgga ggtggatgag aatggcaccc tggacctgag catgaacaag   2340
cagaggcctc gagacagctg ctgcccagtc ctgacacccc tggaacccat gtctccgcag   2400
cagcaggccg tgatgagcag ccgatgcttc cagctgagcg agggggattg ctgggacttg   2460
cctgtagact acaccaaaat gaagcctcgg agggtagatg aggatgagcc caaagagatt   2520
accccagaag acttggaccc attccaggag gctctggaag aaagacggta tccaggggag   2580
gtgaccatcc caagccccaa acccaagtac cctcagtgca aggaaagcaa aaaggactta   2640
ataactctgt ctggctgccc cctggcggac aaaagcattc gaagtatgct ggccaccagt   2700
tcccaagagc tcaagtgccc cacccctggc tgtgacggtt ctggacacat cactggcaat   2760
tacgcttctc atcgaagcct ttctgggtgc ccgagagcaa agaagagtgg catccggata   2820
gcacagagca aagaggacaa ggaagaccag gagccaatca ggtgtccggt acctggctgt   2880
gacggtcagg gacacatcac tgggaagtat gcatcccacc gcagcgcctc cgggtgtccc   2940
ttggcagcca agaggcagaa agatgggtac cttaatggct cccagttctc ctggaagtcg   3000
gtcaagacgg agggcatgtc ctgccctacc cccgggtgtg atgggtcagg acacgtcagt   3060
ggcagcttcc tcacacaccg cagcttgtca ggatgtccaa gagccacatc agcaatgaag   3120
aaagcaaagc tgtctggaga acagatgttg actatcaagc agcgagccag caacggtata   3180
gaaaatgatg aagaaatcaa gcagttagat gaagagatca aggagcttaa tgagtccaat   3240
tcccagatgg aggctgacat gatcaaactc agaactcaga tcaccacaat ggagagcaac   3300
ctgaagacga ttgaggagga gaacaaagtc attgaacagc agaatgagtc gctcttgcac   3360
gagttggcca acctgagcca gtccctgatc cacagcctcg ccaacatcca gctgcctcac   3420
atggatccaa tcaatgaaca aaattttgat gcttacgtga ctactttgac ggaaatgtat   3480
acaaatcaag atcgttatca gagtccagaa aataaagccc tactggaaaa tataaagcag   3540
gctgtgagag gaattcaggt ctga                                          3564
```

<210> SEQ ID NO 52

<211> LENGTH: 2349
<212> TYPE: DNA
<213> ORGANISM: mus musculus

<400> SEQUENCE: 52
atgctggact gcagtgactg tgttctagac tcaagaatga ataatccatc agaaaccaat 60
aaatcatcta tggagagtga agatgccagc acaggcacac aaaccaatgg tctggacttt 120
cagaaacagc ccgtgcccgt tggaggagcg atctccacag cccaggccca ggccttcctc 180
ggacatcttc accaggtcca gctagctggg acaagtttac aggctgctgc tcagtcttta 240
aatgtacagt ctaaatccag tgaagagtcg ggagattcgc agcagtcgag ccagccttct 300
tcccagccgc cttcagtgca gtcagccatt ccccagaccc agctaatgct ggctgggga 360 cagataactg ggctcacgtt gaccccagcc cagcaacagt tactgctaca gcaggcgcag 420
gcccaggccc agctcctggc cgctgcagtg cagcaacact ccgccagcca acagcacagt 480
gctgctgggg ccaccatctc agcctccgcc gccacaccca tgacgcagat ccccctgtct 540
cagcccatac agattgcaca ggatcttcaa caattgcaac agcttcagca gcaaaatctc 600
aacttgcaac agtttgtgtt ggtgcaccca accaccaacc tgcaaccagc acagtttatc 660
atctcacaga ccccccaggg ccagcagggt ctcctgcaag cgcaaaatct tttaacgcaa 720
ctacctcagc aaagccaagc caacctccta cagccacagc caagcatcac cctcacgtcc 780
cagcctacca ccccaactcg cacaatagca gcagcctcag ttcagacact tccacagagc 840
cagtcaacac caaagcgaat tgacactccc agcttggagg agcccagtga ccttgaggag 900
cttgagcagt ttgccaagac tttcaaacaa agacgaatca aacttggatt cactcagggt 960
gatgttgggc tcgctatggg gaaattatat ggaaatgact tcagccaaac caccatctct 1020
cgctttgaag ccttgaacct cagctttaag aacatgtgca agttaaagcc ccttttagag 1080
aagtggctaa atgatgcaga gaacctctca tctgattcta cagcatctag cccaagtgct 1140
ttgaattctc caggattggg ggctgagggc ttgaatcgta ggaggaaaaa acgcaccagc 1200
atagagacca acatccgtgt ggccttagag aagagtttca tggagaatca aaagcctacc 1260
tcggaagaca tcaccttgat tgctgaacag ctcaatatgg aaaaggaggt gattcgtgtt 1320
tggttttgta accgccgcca gaaggagaaa agaatcaacc cgcccagcag tggtgggacc 1380
agcagctcac ctatcaaagc aattttcccc agcccagcct cattggtggc aaccactcca 1440
agccttgtga caagcagtac ggcaactacc ctcacagtca accctgtcct ccctttaacc 1500
agtgctgctg tgactaatct ctctcttaca gatcaagatc ttagaagagg atgcagctgg 1560
gaagtgctta ggagtctacc agacagagtc accaccacag caggcactac agactcgacg 1620
tccaacaaca acacggccac ggtgatttcc acagcacccc ctgcttcctc agcagtcaca 1680
tccccttcct tgagtccctc tccctctgcc tcggcctcca cctcagaggc ctccagtgcc 1740
agtgagacca acacgacaca gaccacctcc acgcctcttc cctcccctct cggagccagc 1800
caggtgatgg tgaccacgcc cggcttacag acagcagccg ccgctctcca aggagcggca 1860
cagttgccag caaacgccag tcttgctgct atggctgctg ctgcgggact cagcccaggc 1920
ctcatggcac cctcacagtt tgctgctgga ggtgccttac tcagtctcag tccggggact 1980
ctgggcagtg ctctcagccc agccctaatg agcaacagta cactggcaac gattcaagct 2040
cttgcttcta gtggctctct tccaataacg tctctggatg caactgggaa cctggtattt 2100
gccaatgcag gaggagcccc gaacatcgtg actgcacctc tgttcctgaa ccctcagaac 2160
ctctctctgc tcaccagcaa cccagtaagc ttggtttctg ccgctgcagc ctccacaggg 2220
aactctgcac ctacagccag ccttcatgcc tcctccacct caactgagtc catccagagc 2280
tctctgttca cagtcgcctc tgccagtggg cctgcttcca ccaccacagc tgcctccaag 2340
gcacagtaa 2349

<210> SEQ ID NO 53
<211> LENGTH: 1392
<212> TYPE: DNA
<213> ORGANISM: mus musculus

<400> SEQUENCE: 53
atggttcatt ccagcatggg ggctccagaa ataagaatgt ctaagcccct ggaggccgag 60
aagcaaagtc tggactcccc gtcagagcac acagacaccg aaagaaatgg acccgacatt 120
aaccatcaga acccccagaa taaagcgtcc ccattctctg tgtccccaac tggccccagc 180
accaagatca aggctgaaga ccccagtggc gattcagccc cagcagcacc cccgcccccc 240
cagccggctc agcctcatct gccccaggcc caactcatgc tgacgggcag ccagctagct 300
ggggacatac agcaactcct ccagctccag cagctggtgc ttgtccccgg ccaccacctc 360
cagccacctg ctcagttcct gctgccacag gcacagcaga gtcagccagg cctgctacca 420
acgccaaatc tattccagct acctcaacaa acccagggag ctctcctgac ctcccagccc 480
cgggctgggc ttcctacaca gcccccgaaa tgcttggagc cgccctccca cccggaggag 540
cccagcgatc tggaggagct ggaacagttt gctcgcacct tcaagcaacg ccgcatcaag 600
ctgggcttca cacagggtga tgtgggcctg gccatgggca agctctatgg caacgacttc 660
agccaaacga ccatttcccg cttcgaggcc ctcaacctga gcttcaagaa catgtgtaaa 720
ctcaagcccc tcctggagaa gtggctcaac gacgcagaga ctatgtctgt ggattcaagc 780
ctacccagcc caaaccagct gagcagcccc agcctgggtt tcgacgggct gccggggcgg 840
agacgcaaga agaggaccag catcgagacg aatgtccgct tcgccttaga gaagagtttc 900
ctagcgaacc agaagcctac ctcagaggag atcctgctga tcgcagagca gctgcacatg 960
gagaaggaag tgatccgcgt ctggttctgc aaccggcgcc agaaggagaa acgcatcaac 1020
ccttgcagtg cggcccccat gctgcccagc ccgggaaagc cgaccagcta cagccctcac 1080
ctggtcacac cccaaggggg cgcagggacc ttaccattgt cccaagcttc tagcagtctg 1140
agcacaacag ttactacctt atcctcagct gtggggacgc tccatcccag ccggacagca 1200
ggagggggtg ggggtggggg cggagctgcg ccccccctca attccatccc ctctgtcact 1260
cccccacccc cggccaccac caacagcaca aacccgagcc ctcaaggcag ccactcggct 1320
attggcttgt cgggcctgaa ccccagcgcg ggccctggcc tctggtggaa ccctgcccct 1380
taccagcctt ga 1392

<210> SEQ ID NO 54
<211> LENGTH: 3501
<212> TYPE: DNA
<213> ORGANISM: mus musculus

<400> SEQUENCE: 54
atggatcttg gaacagctga aagcacccgg tgcaccgacc cacctgcagg caagcctcca 60
atggcagcca agcgcaaagg cggcctgaag ctcaacgcca tctgtgccaa gctcagccga 120
caggtggtcg tggagaaggg agcagaggcc ggctcccaag ccgaaggtag cccactacat 180
ccccgggaca aagagcgcag tggccctgag tctggggtga gccgggctcc ccgaagtgaa 240

```
gaagacaaga ggcgggcagt gatcgagaaa tgggtcaatg gagagtactg tgaggatccc    300
gcacccaccc cagtgttggg gcgtattgcc cgtgatcagg agctgccccc agagggtgtc    360
tacatggtcc agccacaggg ctgcagtgac gaagaagacc atgcagaaga gccctcaaaa    420
gataacagtg tcctggagga gaaggagtca gatggtacgg cttctaaaga tgacagcggc    480
cccagcacca ggcaggcttc aggagaaacc tcctctctga gggactacgc tgcttccacc    540
atgaccgagt tcctcggcat gtttggctac gatgaccaga acaccaggga tgagctggcc    600
aagaagatca gctttgagaa gccgcatgca ggctccaccc ccgaggtggc tgcctcttcc    660
atgttgccct cctctgagga taccctcagc aagcgggcgc gcttctccaa atacgaggaa    720
tacatccgta agctcaaggc cggcgagcaa cttccctggc cagcccacgg gagcaaagcc    780
gaggaccggg caggcaagga ggtggtgggt cccttaccca gcctacggct gcccagcaac    840
acggcccacc tggaaaccaa ggccaccatc ctgccactgc catcacacag cagtgtccag    900
atgcagaatc tggtagctcg tgcttccaag tatgacttct tcatccacaa actgaagaca    960
ggcgagaacc tgaggcccca gaatggaagc acttacaaga agccatccaa gtatgacctg   1020
gagaatgtca agtacttgca cctcttcaaa cccggggaag gcagccctga catgggcggg   1080
gccatcgcct tcaagacagg caaggtgggg cgcccctcta agtacgacgt tcggggcatc   1140
cagaagccag gccctaccaa gattccgccc gcccccagcc tggttcctac acccctcacc   1200
aatgtgccca gtgctcccag cacccccgga ccaggaccgg agccacctgc ctccttgtcc   1260
ttcaacactc ccgagtacct gaagtcaacc ttttccaaaa cagactccat caccacagga   1320
actgtctcca ctgtcaagaa cggattgccc acagataaac cagctgtcac cgaagatgta   1380
aacatttacc agaaatatat tgccaggttc tcaggaagtc agcactgcgg tcacatccac   1440
tgcgcctacc agtaccgtga gcactatcac tgcctggacc cggagtgcaa ctaccagcgg   1500
ttcacaagca agcaggatgt gatccgacat tacaacatgc acaagaagcg cgacaactcc   1560
ctgcagcacg gcttcatgcg cttcagcccg ctggacgact gcagtgtcta ctaccacggc   1620
tgccacctca atgggaagag cacccactac cactgcatgc aggtgggatg taacaaggta   1680
tacacaagta cgtcggatgt gatgactcac gagaacttcc acaagaagaa cacccagctc   1740
atcaacgatg gcttccagcg cttccgagcc acggaggact gcggcacagc tgactgtcag   1800
ttctatggac agaagaccac acacttccac tgcaggcgcc ctggctgcac attcaccttc   1860
aagaacaagt gtgacatcga gaagcacaag agctaccaca tcaaggatga tgcctacgcc   1920
aaggacggct tcaagaagtt ctacaagtac gaggagtgca aatacgaggg ctgcatgtac   1980
agcaaggcca ccaaccattt ccactgcatc cgcgccggct gcggcttcac cttcacctcc   2040
accagccaga tgacctcaca caagcgcaag cacgagcggc ggcacatccg gtcctcgggg   2100
gccctggggc tgccggcctc cctgctgggc gccaaggaca cggagcacga ggaatccagc   2160
aacgatgacc tcgtggactt ctctgccctg agcagcaaga actccagcct gagcgcctcc   2220
cccaccagcc agcaatcgtc cgcatccctg gccgctgcgg ctgccgccac cactgctgag   2280
gccatcccca gtgccaccaa gcctcccaat agcaagatgg caggcctgct gccccagggc   2340
ctgtctggtt ccatcccctt agcactggcc ctctctaact caggcctgcc caccaccaca   2400
ccctatttcc ctctgcttcc taaccgtggg agcgcctcat tgcctgtggg atctccaggg   2460
ctcctgggct ccatgtcctc tggggccaca acctcagcaa cccctgacat gccggccctg   2520
atggcttcca gagctggaga ctcggccccc acggctgcca cctctctctc ggtgccccct   2580
gcctccatca ttgagagaat ctctgcaagc aaaggcctca tctcacccat gatggctaga   2640
```

```
ctggctgcgg ccgccctcaa gccctctgcc acctttgacc caggaagtgg gcagcagccc   2700
acccccacca agttccccca ggcccaggtg aagcaggagc ctgacagtgc tggcacccca   2760
ggtccccacg aggcctccca agaccgcagt ctagacctga ccgtgaagga tcccagtaat   2820
gaatcaaatg gccacgcagt ctcggcaaat tcatctcttt tatcctcgct tatgaataag   2880
atgtctcagg gcaaccccag cctcgaaagc ttcctgagca tcaagacaga agcggagggg   2940
agccccgccg gggagccctc gcctttcttg ggcaaggccg tgaaggcact agttcaagag   3000
aagctgtcag agccttggaa ggtgtatctc cgcaggtttg gtaccaagga cttctgtgat   3060
gcccagtgtg acttcctcca caaggcgcat ttccattgtg tagtggagga gtgcggtgcg   3120
cttttcagca ccttggacgg agccatcaaa catgcaaact tccacttccg gacagaggga   3180
ggaacagcaa aaggaacccc agaggcttcc ttcccgacct ctgctgctga gaccaaacct   3240
cccttggcac cctcgtccct gccagcacct cctggcacca tggtcgctgg atcttctctg   3300
gaggggcctg ctcccagccc ggtctctgtg ccctccaccc ccaccctgct cgcctggaag   3360
cagctggctt ccaccatacc ccagatgcct cagattccct cctcagtgcc tcacctgccc   3420
acctcgcccc tggcgacgac gtctctagag agcgccaagc ctcaggtcaa acccgggttc   3480
ctccagttcc aggacaagtg a                                              3501
```

<210> SEQ ID NO 55
<211> LENGTH: 1338
<212> TYPE: DNA
<213> ORGANISM: mus musculus

<400> SEQUENCE: 55

```
atggcgaccg cagcgtctaa ccactacagc ctgctcacct ccagcgcctc catcgtacat     60
gccgagccgc ctggcggcat gcagcagggc gcagggggct accgcgaggc gcagagcctg    120
gtgcagggcg actacggcgc gctgcagagc aacgggcacc cgctcagcca cgctcaccag    180
tggatcaccg cgctgtccca cggcggcggc ggcgggggcg gcggcggcgg tggaggaggc    240
gggggaggcg gcgggggagg cggcgacggc tccccgtggt ccaccagccc cctaggccag    300
ccggacatca agccctcggt ggtggtacag cagggtggcc gaggcgacga gctgcacggg    360
ccaggagcgc tgcagcaaca gcatcaacag caacagcaac agcagcagca gcagcagcag    420
cagcagcagc agcaacagca gcagcaacaa cagcgaccgc cacatctggt gcaccacgct    480
gccaaccacc atcccgggcc cggggcatgg cggagtgcgg cggctgcagc tcacctccct    540
ccctccatgg gagcttccaa cggcggtttg ctctattcgc agccgagctt cacggtgaac    600
ggcatgctgg gcgcaggagg gcagccggct gggctgcacc accacggcct gagggacgcc    660
cacgatgagc cacaccatgc agaccaccac ccgcatccgc actctcaccc acaccagcaa    720
ccgcccccgc cacctccccc acaaggccca ccgggccacc caggcgcgca ccacgacccg    780
cactcggacg aggacacgcc gacctcagac gacctggagc agttcgccaa gcaattcaag    840
cagaggcgga tcaaactcgg atttactcaa gcagacgtgg ggctggcgct tggcaccctg    900
tacggcaacg tgttctcgca gaccaccatc tgcaggtttg aggccctgca gctgagcttc    960
aagaacatgt gcaagctgaa gcctttgttg aacaagtggt tggaagaggc agactcatcc   1020
tcgggcagcc ccaccagcat agacaagatc gcagcgcaag ggcgcaaacg gaaaaagcgg   1080
acctccatcg aggtgagcgt caagggggct ctggagagcc atttcctcaa atgccctaag   1140
ccctcggccc aggagatcac ctccctcgcg gacagcttac agctggagaa ggaggtggtg   1200
```

agagtttggt tttgtaacag gagacagaaa gagaaaagga tgacccctcc cggagggact 1260
ctgccgggcg ccgaggatgt gtatgggggt agtagggaca cgccaccaca ccacggggtg 1320
cagacgcccg tccagtga 1338

<210> SEQ ID NO 56
<211> LENGTH: 6847
<212> TYPE: DNA
<213> ORGANISM: Artificial sequence
<220> FEATURE:
<223> OTHER INFORMATION: synthetic construct

<400> SEQUENCE: 56
acgtcgacat tgattattga ctagttatta atagtaatca attacggggt cattagttca 60
tagcccatat atggagttcc gcgttacata acttacggta aatggcccgc ctggctgacc 120
gcccaacgac ccccgcccat tgacgtcaat aatgacgtat gttcccatag taacgccaat 180
agggactttc cattgacgtc aatgggtgga ctatttacgg taaactgccc acttggcagt 240
acatcaagtg tatcatatgc caagtacgcc ccctattgac gtcaatgacg gtaaatggcc 300
cgcctggcat tatgcccagt acatgacctt atgggacttt cctacttggc agtacatcta 360
cgtattagtc atcgctatta ccatgggtcg aggtgagccc cacgttctgc ttcactctcc 420
ccatctcccc cccctcccca cccccaattt tgtatttatt tattttttaa ttattttgtg 480
cagcgatggg ggcggggggg gggggggcgc gcgccaggcg gggcggggcg gggcgagggg 540
cggggcgggg cgaggcggag aggtgcggcg gcagccaatc agagcggcgc gctccgaaag 600
tttcctttta tggcgaggcg gcggcggcgg cggccctata aaaagcgaag cgcgcggcgg 660
gcgggagtcg ctgcgttgcc ttcgccccgt gccccgctcc gcgccgcctc gcgccgcccg 720
ccccggctct gactgaccgc gttactccca caggtgagcg ggcgggacgg cccttctcct 780
ccgggctgta attagcgctt ggtttaatga cggctcgttt cttttctgtg gctgcgtgaa 840
agccttaaag ggctccggga gggccctttg tgcggggggg agcggctcgg ggggtgcgtg 900
cgtgtgtgtg tgcgtgggga gcgccgcgtg cggcccgcgc tgcccggcgg ctgtgagcgc 960
tgcgggcgcg gcgcggggct ttgtgcgctc cgcgtgtgcg cgaggggagc gcggccgggg 1020
gcggtgcccc gcggtgcggg ggggctgcga ggggaacaaa ggctgcgtgc ggggtgtgtg 1080
cgtggggggg tgagcagggg gtgtgggcgc ggcggtcggg ctgtaacccc cccctgcacc 1140
cccctccccg agttgctgag cacggcccgg cttcgggtgc ggggctccgt gcggggcgtg 1200
gcgcggggct cgccgtgccg ggcggggggt ggcggcaggt gggggtgccg ggcggggcgg 1260
ggccgcctcg ggccggggag ggctcggggg aggggcgcgg cggcccccgga gcgccggcgg 1320 ctgtcgaggc gcggcgagcc gcagccattg ccttttatgg taatcgtgcg agagggcgca 1380
gggacttcct ttgtcccaaa tctggcggag ccgaaatctg ggaggcgccg ccgcaccccc 1440
tctagcgggc gcgggcgaag cggtgcggcg ccggcaggaa ggaaatgggc ggggagggcc 1500
ttcgtgcgtc gccgcgccgc cgtccccttc tccatctcca gcctcggggc tgccgcaggg 1560
ggacggctgc cttcgggggg gacggggcag ggcggggttc ggcttctggc gtgtgaccgg 1620
cggctctaga gcctctgcta accatgttca tgccttcttc tttttcctac agctcctggg 1680
caacgtgctg gttattgtgc tgtctcatca ttttggcaaa gaattcctcg atcgagggac 1740
ctaataactt cgtatagcat acattatacg aagttatatt aagggttccg caagcttcct 1800
agactagtcg acggtatcga taccatggtg agcaagggcg aggaggataa catggccatc 1860
atcaaggagt tcatgcgctt caaggtgcac atggagggct ccgtgaacgg ccacgagttc 1920
gagatcgagg gcgagggcga gggccgcccc tacgagggca cccagaccgc caagctgaag 1980
gtgaccaagg gtggcccccct gcccttcgcc tgggacatcc tgtcccctca gttcatgtac 2040
ggctccaagg cctacgtgaa gcaccccgcc gacatccccg actacttgaa gctgtccttc 2100
cccgagggct tcaagtggga gcgcgtgatg aacttcgagg acggcggcgt ggtgaccgtg 2160
acccaggact cctccctgca ggacggcgag ttcatctaca aggtgaagct gcgcggcacc 2220
aacttcccct ccgacggccc cgtaatgcag aagaagacga tgggctggga ggcctcctcc 2280
gagcggatgt accccgagga cggcgccctg aagggcgaga tcaagcagag gctgaagctg 2340
aaggacggcg gccactacga cgctgaggtc aagaccacct acaaggccaa gaagcccgtg 2400
cagctgcccg gcgcctacaa cgtcaacatc aagttggaca tcacctccca caacgaggac 2460
tacaccatcg tggaacagta cgaacgcgcc gagggccgcc actccaccgg cggcatggac 2520
gagctgtaca agtaagcatg cccgacggcg aggatctcgt cgtgacccat ggcgatgcct 2580
gcttgccgaa tatcatggtg gaaaatggcc gcttttctgg attcatcgac tgtggccggc 2640
tgggtgtggc ggaccgctat caggacatag cgttggctac ccgtgatatt gctgaagagc 2700
ttggcggcga atgggctgac cgcttcctcg tgctttacgg tatcgccgct cccgattcgc 2760
agcgcatcgc cttctatcgc cttcttgacg agttcttctg aggggatcaa ttctctaggc 2820
ttgggatctt tgtgaaggaa ccttacttct gtggtgtgac ataattggac aaactaccta 2880
cagagattta aagctctaag gtaaatataa aatttttaag tgtataatgt gttaaactac 2940
tgattctaat tgtttgtgta ttttagattc acagtcccaa ggctcatttc aggcccctca 3000
gtcctcacag tctgttcatg atcataatca gccataccac atttgtagag gttttacttg 3060
ctttaaaaaa cctcccacac ctccccctga acctgaaaca taaaatgaat gcaattgttg 3120
ttgttaactt gtttattgca gcttataatg gttacaaata aagcaatagc atcacaaatt 3180
tcacaaataa agcatttttt tcactgcatt ctagttgtgt ttgtccaaac tcatcaatgt 3240
atcttatcat gtctggatca taatcagcca taccacattt gtagaggttt tacttgcttt 3300
aaaaaacctt ccccacacct ccccctgaac tgaaacataa aatgaatgca attgttgttg 3360
ttaacttgtt tattgcagct tataatggtt acaaataaag caatagcatc acaaatttca 3420
caaataaagc attttttca ctgcattcta gttgtggttt gtccaaactc atcaatgtat 3480
cttatcatgt ctggatcata atcagccata ccacatttgt agaggtttta cttgctttaa 3540
aaaacctccc acacctcccc ctgaacctga aacataaaat gaatgcaatt gttgttgtta 3600
acttgtttat tgcagcttat aatggttaca aataaagcaa tagcatcaca aatttcacaa 3660
ataaagcatt tttttcactg cattctagtt gtggtttgtc caaactcatc aatgtatctt 3720
atcatgtctg gatccactag ttctagctag tctaggtcga tgcaggataa cttcgtatag 3780
catacattat acgaagttat agatcttggg tacccgctcg agctcaagct tcgaattctg 3840
cagtcgacgg taccgcgggc ccggccgcga tctttttccc tctgccaaaa attatgggga 3900
catcatgaag ccccttgagc atctgacttc tggctaataa aggaaattta ttttcattgc 3960
aatagtgtgt tggaattttt tgtgtctctc actcggaagg acatatggga gggcaaatca 4020
tttaaaacat cagaatgagt atttggttta gagtttggca acatatgcca tatgctggct 4080
gccatgaaca aaggtggcta taaagaggtc atcagtatat gaaacagccc cctgctgtcc 4140
attccttatt ccatagaaaa gccttgactt gaggttagat tttttttata ttttgttttg 4200
tgttattttt ttctttaaca tccctaaaat tttccttaca tgttttacta gccagatttt 4260

-continued

```
tcctcctctc ctgactactc ccagtcatag ctgtccctct tctcttatga agatccctcg   4320
acctgcagcc caagcttggc gtaatcatgg tcatagctgt ttcctgtgtg aaattgttat   4380
ccgctcacaa ttccacacaa catacgagcc ggaagcataa agtgtaaagc ctggggtgcc   4440
taatgagtga gctaactcac attaattgcg ttgcgctcac tgcccgcttt ccagtcggga   4500
aacctgtcgt gccagcggat ccgcatctca attagtcagc aaccatagtc ccgcccctaa   4560
ctccgcccat cccgccccta actccgccca gttccgccca ttctccgccc catggctgac   4620
taattttttt tatttatgca gaggccgagg ccgcctcggc ctctgagcta ttccagaagt   4680
agtgaggagg cttttttgga ggcctaggct tttgcaaaaa gctaacttgt ttattgcagc   4740
ttataatggt tacaaataaa gcaatagcat cacaaatttc acaaataaag catttttttc   4800
actgcattct agttgtggtt tgtccaaact catcaatgta tcttatcatg tctggatccg   4860
ctgcattaat gaatcggcca acgcgcgggg agaggcggtt tgcgtattgg gcgctcttcc   4920
gcttcctcgc tcactgactc gctgcgctcg gtcgttcggc tgcggcgagc ggtatcagct   4980
cactcaaagg cggtaatacg gttatccaca gaatcagggg ataacgcagg aaagaacatg   5040
tgagcaaaag gccagcaaaa ggccaggaac cgtaaaaagg ccgcgttgct ggcgtttttc   5100
cataggctcc gcccccctga cgagcatcac aaaaatcgac gctcaagtca gaggtggcga   5160
aacccgacag gactataaag ataccaggcg tttccccctg gaagctccct cgtgcgctct   5220
cctgttccga ccctgccgct taccggatac ctgtccgcct ttctcccttc gggaagcgtg   5280
gcgctttctc aatgctcacg ctgtaggtat ctcagttcgg tgtaggtcgt tcgctccaag   5340
ctgggctgtg tgcacgaacc ccccgttcag cccgaccgct gcgccttatc cggtaactat   5400
cgtcttgagt ccaacccggt aagacacgac ttatcgccac tggcagcagc cactggtaac   5460
aggattagca gagcgaggta tgtaggcggt gctacagagt tcttgaagtg gtggcctaac   5520
tacggctaca ctagaaggac agtatttggt atctgcgctc tgctgaagcc agttaccttc   5580
ggaaaaagag ttggtagctc ttgatccggc aaacaaacca ccgctggtag cggtggtttt   5640
tttgtttgca agcagcagat tacgcgcaga aaaaaaggat ctcaagaaga tcctttgatc   5700
ttttctacgg ggtctgacgc tcagtggaac gaaaactcac gttaagggat tttggtcatg   5760
agattatcaa aaaggatctt cacctagatc cttttaaatt aaaaatgaag ttttaaatca   5820
atctaaagta tatatgagta aacttggtct gacagttacc aatgcttaat cagtgaggca   5880
cctatctcag cgatctgtct atttcgttca tccatagttg cctgactccc cgtcgtgtag   5940
ataactacga tacgggaggg cttaccatct ggccccagtg ctgcaatgat accgcgagac   6000
ccacgctcac cggctccaga tttatcagca ataaaccagc cagccggaag ggccgagcgc   6060
agaagtggtc ctgcaacttt atccgcctcc atccagtcta ttaattgttg ccgggaagct   6120
agagtaagta gttcgccagt taatagtttg cgcaacgttg ttgccattgc tacaggcatc   6180
gtggtgtcac gctcgtcgtt tggtatggct tcattcagct ccggttccca acgatcaagg   6240
cgagttacat gatcccccat gttgtgcaaa aaagcggtta gctccttcgg tcctccgatc   6300
gttgtcagaa gtaagttggc cgcagtgtta tcactcatgg ttatggcagc actgcataat   6360
tctcttactg tcatgccatc cgtaagatgc ttttctgtga ctggtgagta ctcaaccaag   6420
tcattctgag aatagtgtat gcggcgaccg agttgctctt gcccggcgtc aatacgggat   6480
aataccgcgc cacatagcag aactttaaaa gtgctcatca ttggaaaacg ttcttcgggg   6540
cgaaaactct caaggatctt accgctgttg agatccagtt cgatgtaacc cactcgtgca   6600
cccaactgat cttcagcatc ttttactttc accagcgttt ctgggtgagc aaaaacagga   6660
```

aggcaaaatg ccgcaaaaaa gggaataagg gcgacacgga aatgttgaat actcatactc 6720
ttcctttttc aatattattg aagcatttat cagggttatt gtctcatgag cggatacata 6780
tttgaatgta tttagaaaaa taaacaaata ggggttccgc gcacatttcc ccgaaaagtg 6840
ccacctg 6847

<210> SEQ ID NO 57
<211> LENGTH: 8562
<212> TYPE: DNA
<213> ORGANISM: Artificial sequence
<220> FEATURE:
<223> OTHER INFORMATION: synthetic construct

<400> SEQUENCE: 57
acgtcgacat tgattattga ctagttatta atagtaatca attacggggt cattagttca 60
tagcccatat atggagttcc gcgttacata acttacggta aatggcccgc ctggctgacc 120
gcccaacgac ccccgcccat tgacgtcaat aatgacgtat gttcccatag taacgccaat 180
agggactttc cattgacgtc aatgggtgga ctatttacgg taaactgccc acttggcagt 240
acatcaagtg tatcatatgc caagtacgcc ccctattgac gtcaatgacg gtaaatggcc 300
cgcctggcat tatgcccagt acatgacctt atgggacttt cctacttggc agtacatcta 360
cgtattagtc atcgctatta ccatgggtcg aggtgagccc cacgttctgc ttcactctcc 420
ccatctcccc cccctcccca cccccaattt tgtatttatt tattttttaa ttattttgtg 480
cagcgatggg ggcggggggg gggggggcgc gcgccaggcg gggcggggcg gggcgagggg 540
cggggcgggg cgaggcggag aggtgcggcg gcagccaatc agagcggcgc gctccgaaag 600
tttcctttta tggcgaggcg gcggcggcgg cggccctata aaaagcgaag cgcgcggcgg 660
gcgggagtcg ctgcgttgcc ttcgccccgt gccccgctcc gcgccgcctc gcgccgcccg 720
ccccggctct gactgaccgc gttactccca caggtgagcg ggcgggacgg cccttctcct 780
ccgggctgta attagcgctt ggtttaatga cggctcgttt cttttctgtg gctgcgtgaa 840
agccttaaag ggctccggga gggccctttg tgcggggggg agcggctcgg ggggtgcgtg 900
cgtgtgtgtg tgcgtgggga gcgccgcgtg cggcccgcgc tgcccggcgg ctgtgagcgc 960
tgcgggcgcg gcgcggggct ttgtgcgctc cgcgtgtgcg cgaggggagc gcggccgggg 1020
gcggtgcccc gcggtgcggg ggggctgcga ggggaacaaa ggctgcgtgc ggggtgtgtg 1080
cgtggggggg tgagcagggg gtgtgggcgc ggcggtcggg ctgtaacccc cccctgcacc 1140
cccctccccg agttgctgag cacggcccgg cttcgggtgc ggggctccgt gcggggcgtg 1200
gcgcggggct cgccgtgccg ggcggggggt ggcggcaggt gggggtgccg ggcggggcgg 1260
ggccgcctcg ggccggggag ggctcggggg aggggcgcgg cggcccccgga gcgccggcgg 1320 ctgtcgaggc gcggcgagcc gcagccattg ccttttatgg taatcgtgcg agagggcgca 1380
gggacttcct ttgtcccaaa tctggcggag ccgaaatctg ggaggcgccg ccgcaccccc 1440
tctagcgggc gcgggcgaag cggtgcggcg ccggcaggaa ggaaatgggc ggggagggcc 1500
ttcgtgcgtc gccgcgccgc cgtccccttc tccatctcca gcctcggggc tgccgcaggg 1560
ggacggctgc cttcgggggg gacggggcag ggcggggttc ggcttctggc gtgtgaccgg 1620
cggctctaga gcctctgcta accatgttca tgccttcttc tttttcctac agctcctggg 1680
caacgtgctg gttattgtgc tgtctcatca ttttggcaaa gaattcctcg atcgagggac 1740
ctaataactt cgtatagcat acattatacg aagttatatt aagggttccg caagcttcct 1800
agactagtcg acggtatcga taccatggtg agcaagggcg aggaggataa catggccatc 1860
atcaaggagt tcatgcgctt caaggtgcac atggagggct ccgtgaacgg ccacgagttc 1920
gagatcgagg gcgagggcga gggccgcccc tacgagggca cccagaccgc caagctgaag 1980
gtgaccaagg gtggccccct gcccttcgcc tgggacatcc tgtcccctca gttcatgtac 2040
ggctccaagg cctacgtgaa gcaccccgcc gacatccccg actacttgaa gctgtccttc 2100
cccgagggct tcaagtggga gcgcgtgatg aacttcgagg acggcggcgt ggtgaccgtg 2160
acccaggact cctccctgca ggacggcgag ttcatctaca aggtgaagct gcgcggcacc 2220
aacttcccct ccgacggccc cgtaatgcag aagaagacga tgggctggga ggcctcctcc 2280
gagcggatgt accccgagga cggcgccctg aagggcgaga tcaagcagag gctgaagctg 2340
aaggacggcg gccactacga cgctgaggtc aagaccacct acaaggccaa gaagcccgtg 2400
cagctgcccg gcgcctacaa cgtcaacatc aagttggaca tcacctccca caacgaggac 2460
tacaccatcg tggaacagta cgaacgcgcc gagggccgcc actccaccgg cggcatggac 2520
gagctgtaca agtaagcatg cccgacggcg aggatctcgt cgtgacccat ggcgatgcct 2580
gcttgccgaa tatcatggtg gaaaatggcc gcttttctgg attcatcgac tgtggccggc 2640
tgggtgtggc ggaccgctat caggacatag cgttggctac ccgtgatatt gctgaagagc 2700
ttggcggcga atgggctgac cgcttcctcg tgctttacgg tatcgccgct cccgattcgc 2760
agcgcatcgc cttctatcgc cttcttgacg agttcttctg aggggatcaa ttctctaggc 2820
ttgggatctt tgtgaaggaa ccttacttct gtggtgtgac ataattggac aaactaccta 2880
cagagattta aagctctaag gtaaatataa aatttttaag tgtataatgt gttaaactac 2940
tgattctaat tgtttgtgta ttttagattc acagtcccaa ggctcatttc aggcccctca 3000
gtcctcacag tctgttcatg atcataatca gccataccac atttgtagag gttttacttg 3060
ctttaaaaaa cctcccacac ctccccctga acctgaaaca taaaatgaat gcaattgttg 3120
ttgttaactt gtttattgca gcttataatg gttacaaata aagcaatagc atcacaaatt 3180
tcacaaataa agcatttttt tcactgcatt ctagttgtgt ttgtccaaac tcatcaatgt 3240
atcttatcat gtctggatca taatcagcca taccacattt gtagaggttt tacttgcttt 3300
aaaaaacctt ccccacacct ccccctgaac tgaaacataa aatgaatgca attgttgttg 3360
ttaacttgtt tattgcagct tataatggtt acaaataaag caatagcatc acaaatttca 3420
caaataaagc atttttttca ctgcattcta gttgtggttt gtccaaactc atcaatgtat 3480
cttatcatgt ctggatcata atcagccata ccacatttgt agaggtttta cttgctttaa 3540
aaaacctccc acacctcccc ctgaacctga aacataaaat gaatgcaatt gttgttgtta 3600
acttgtttat tgcagcttat aatggttaca aataaagcaa tagcatcaca aatttcacaa 3660
ataaagcatt tttttcactg cattctagtt gtggtttgtc caaactcatc aatgtatctt 3720
atcatgtctg gatccactag ttctagctag tctaggtcga tgcaggataa cttcgtatag 3780
catacattat acgaagttat agatcttggg tacccgctcg aatcacaagt ttgtacaaaa 3840
aagctgaacg agaaacgtaa aatgatataa atatcaatat attaaattag attttgcata 3900
aaaaacagac tacataatac tgtaaaacac aacatatcca gtcactatgg cggccgcatt 3960
aggcacccca ggctttacac tttatgcttc cggctcgtat aatgtgtgga ttttgagtta 4020
ggatccgtcg agattttcag gagctaagga agctaaaatg gagaaaaaaa tcactggata 4080
taccaccgtt gatatatccc aatggcatcg taaagaacat tttgaggcat ttcagtcagt 4140
tgctcaatgt acctataacc agaccgttca gctggatatt acggcctttt taaagaccgt 4200
aaagaaaaat aagcacaagt tttatccggc ctttattcac attcttgccc gcctgatgaa 4260
tgctcatccg gaattccgta tggcaatgaa agacggtgag ctggtgatat gggatagtgt 4320
tcacccttgt tacaccgttt tccatgagca aactgaaacg ttttcatcgc tctggagtga 4380
ataccacgac gatttccggc agtttctaca catatattcg caagatgtgg cgtgttacgg 4440
tgaaaacctg gcctatttcc ctaaagggtt tattgagaat atgtttttcg tctcagccaa 4500
tccctgggtg agtttcacca gttttgattt aaacgtggcc aatatggaca acttcttcgc 4560
ccccgttttc accatgggca aatattatac gcaaggcgac aaggtgctga tgccgctggc 4620
gattcaggtt catcatgccg tttgtgatgg cttccatgtc ggcagaatgc ttaatgaatt 4680
acaacagtac tgcgatgagt ggcagggcgg ggcgtaaacg cgtggatccg gcttactaaa 4740
agccagataa cagtatgcgt atttgcgcgc tgatttttgc ggtataagaa tatatactga 4800
tatgtatacc cgaagtatgt caaaaagagg tatgctatga agcagcgtat tacagtgaca 4860
gttgacagcg acagctatca gttgctcaag gcatatatga tgtcaatatc tccggtctgg 4920
taagcacaac catgcagaat gaagcccgtc gtctgcgtgc cgaacgctgg aaagcggaaa 4980
atcaggaagg gatggctgag gtcgcccggt ttattgaaat gaacggctct tttgctgacg 5040
agaacagggg ctggtgaaat gcagtttaag gtttacacct ataaaagaga gagccgttat 5100
cgtctgtttg tggatgtaca gagtgatatt attgacacgc ccgggcgacg gatggtgatc 5160
cccctggcca gtgcacgtct gctgtcagat aaagtctccc gtgaacttta cccggtggtg 5220
catatcgggg atgaaagctg gcgcatgatg accaccgata tggccagtgt gccggtctcc 5280
gttatcgggg aagaagtggc tgatctcagc caccgcgaaa atgacatcaa aaacgccatt 5340
aacctgatgt tctggggaat ataaatgtca ggctccctta tacacagcca gtctgcaggt 5400
cgaccatagt gactggatat gttgtgtttt acagtattat gtagtctgtt ttttatgcaa 5460
aatctaattt aatatattga tatttatatc attttacgtt tctcgttcag ctttcttgta 5520
caaagtggtg attcgagctc aagcttcgaa ttctgcagtc gacggtaccg cgggcccggc 5580
cgcgatcttt ttccctctgc caaaaattat ggggacatca tgaagcccct tgagcatctg 5640
acttctggct aataaaggaa atttattttc attgcaatag tgtgttggaa ttttttgtgt 5700
ctctcactcg gaaggacata tgggagggca aatcatttaa aacatcagaa tgagtatttg 5760
gtttagagtt tggcaacata tgccatatgc tggctgccat gaacaaaggt ggctataaag 5820
aggtcatcag tatatgaaac agccccctgc tgtccattcc ttattccata gaaaagcctt 5880
gacttgaggt tagatttttt ttatattttg ttttgtgtta tttttttctt taacatccct 5940
aaaattttcc ttacatgttt tactagccag atttttcctc ctctcctgac tactcccagt 6000
catagctgtc cctcttctct tatgaagatc cctcgacctg cagcccaagc ttggcgtaat 6060
catggtcata gctgtttcct gtgtgaaatt gttatccgct cacaattcca cacaacatac 6120
gagccggaag cataaagtgt aaagcctggg gtgcctaatg agtgagctaa ctcacattaa 6180
ttgcgttgcg ctcactgccc gctttccagt cgggaaacct gtcgtgccag cggatccgca 6240
tctcaattag tcagcaacca tagtcccgcc cctaactccg cccatcccgc ccctaactcc 6300
gcccagttcc gcccattctc cgccccatgg ctgactaatt ttttttattt atgcagaggc 6360
cgaggccgcc tcggcctctg agctattcca gaagtagtga ggaggctttt ttggaggcct 6420
aggcttttgc aaaaagctaa cttgtttatt gcagcttata atggttacaa ataaagcaat 6480
agcatcacaa atttcacaaa taaagcattt ttttcactgc attctagttg tggtttgtcc 6540
aaactcatca atgtatctta tcatgtctgg atccgctgca ttaatgaatc ggccaacgcg 6600
cggggagagg cggtttgcgt attgggcgct cttccgcttc ctcgctcact gactcgctgc 6660
gctcggtcgt tcggctgcgg cgagcggtat cagctcactc aaaggcggta atacggttat 6720
ccacagaatc aggggataac gcaggaaaga acatgtgagc aaaaggccag caaaaggcca 6780
ggaaccgtaa aaaggccgcg ttgctggcgt ttttccatag gctccgcccc cctgacgagc 6840
atcacaaaaa tcgacgctca agtcagaggt ggcgaaaccc gacaggacta taaagatacc 6900
aggcgtttcc ccctggaagc tccctcgtgc gctctcctgt tccgaccctg ccgcttaccg 6960
gatacctgtc cgcctttctc ccttcgggaa gcgtggcgct ttctcaatgc tcacgctgta 7020
ggtatctcag ttcggtgtag gtcgttcgct ccaagctggg ctgtgtgcac gaaccccccg 7080
ttcagcccga ccgctgcgcc ttatccggta actatcgtct tgagtccaac ccggtaagac 7140
acgacttatc gccactggca gcagccactg gtaacaggat tagcagagcg aggtatgtag 7200
gcggtgctac agagttcttg aagtggtggc ctaactacgg ctacactaga aggacagtat 7260
ttggtatctg cgctctgctg aagccagtta ccttcggaaa aagagttggt agctcttgat 7320
ccggcaaaca aaccaccgct ggtagcggtg gtttttttgt ttgcaagcag cagattacgc 7380
gcagaaaaaa aggatctcaa gaagatcctt tgatcttttc tacggggtct gacgctcagt 7440
ggaacgaaaa ctcacgttaa gggattttgg tcatgagatt atcaaaaagg atcttcacct 7500
agatcctttt aaattaaaaa tgaagtttta aatcaatcta aagtatatat gagtaaactt 7560
ggtctgacag ttaccaatgc ttaatcagtg aggcacctat ctcagcgatc tgtctatttc 7620
gttcatccat agttgcctga ctccccgtcg tgtagataac tacgatacgg gagggcttac 7680
catctggccc cagtgctgca atgataccgc gagacccacg ctcaccggct ccagatttat 7740
cagcaataaa ccagccagcc ggaagggccg agcgcagaag tggtcctgca actttatccg 7800
cctccatcca gtctattaat tgttgccggg aagctagagt aagtagttcg ccagttaata 7860
gtttgcgcaa cgttgttgcc attgctacag gcatcgtggt gtcacgctcg tcgtttggta 7920
tggcttcatt cagctccggt tcccaacgat caaggcgagt tacatgatcc cccatgttgt 7980
gcaaaaaagc ggttagctcc ttcggtcctc cgatcgttgt cagaagtaag ttggccgcag 8040
tgttatcact catggttatg gcagcactgc ataattctct tactgtcatg ccatccgtaa 8100
gatgcttttc tgtgactggt gagtactcaa ccaagtcatt ctgagaatag tgtatgcggc 8160
gaccgagttg ctcttgcccg gcgtcaatac gggataatac cgcgccacat agcagaactt 8220
taaaagtgct catcattgga aaacgttctt cggggcgaaa actctcaagg atcttaccgc 8280
tgttgagatc cagttcgatg taacccactc gtgcacccaa ctgatcttca gcatctttta 8340
ctttcaccag cgtttctggg tgagcaaaaa caggaaggca aaatgccgca aaaaagggaa 8400
taagggcgac acggaaatgt tgaatactca tactcttcct ttttcaatat tattgaagca 8460
tttatcaggg ttattgtctc atgagcggat acatatttga atgtatttag aaaaataaac 8520
aaataggggt tccgcgcaca tttccccgaa aagtgccacc tg 8562

<210> SEQ ID NO 58
<211> LENGTH: 8568
<212> TYPE: DNA
<213> ORGANISM: Artificial sequence
<220> FEATURE:
<223> OTHER INFORMATION: synthetic construct

<400> SEQUENCE: 58
acgtcgacat tgattattga ctagttatta atagtaatca attacggggt cattagttca 60
tagcccatat atggagttcc gcgttacata acttacggta aatggcccgc ctggctgacc 120
gcccaacgac ccccgcccat tgacgtcaat aatgacgtat gttcccatag taacgccaat 180
agggactttc cattgacgtc aatgggtgga ctatttacgg taaactgccc acttggcagt 240
acatcaagtg tatcatatgc caagtacgcc ccctattgac gtcaatgacg gtaaatggcc 300
cgcctggcat tatgcccagt acatgacctt atgggacttt cctacttggc agtacatcta 360
cgtattagtc atcgctatta ccatgggtcg aggtgagccc cacgttctgc ttcactctcc 420
ccatctcccc cccctcccca cccccaattt tgtatttatt tattttttaa ttattttgtg 480
cagcgatggg ggcggggggg gggggggcgc gcgccaggcg gggcggggcg gggcgagggg 540
cggggcgggg cgaggcggag aggtgcggcg gcagccaatc agagcggcgc gctccgaaag 600
tttcctttta tggcgaggcg gcggcggcgg cggccctata aaaagcgaag cgcgcggcgg 660
gcgggagtcg ctgcgttgcc ttcgccccgt gccccgctcc gcgccgcctc gcgccgcccg 720
ccccggctct gactgaccgc gttactccca caggtgagcg ggcgggacgg cccttctcct 780
ccgggctgta attagcgctt ggtttaatga cggctcgttt cttttctgtg gctgcgtgaa 840
agccttaaag ggctccggga gggccctttg tgcggggggg agcggctcgg ggggtgcgtg 900
cgtgtgtgtg tgcgtgggga gcgccgcgtg cggcccgcgc tgcccggcgg ctgtgagcgc 960
tgcgggcgcg gcgcggggct ttgtgcgctc cgcgtgtgcg cgaggggagc gcggccgggg 1020
gcggtgcccc gcggtgcggg ggggctgcga ggggaacaaa ggctgcgtgc ggggtgtgtg 1080
cgtggggggg tgagcagggg gtgtgggcgc ggcggtcggg ctgtaacccc cccctgcacc 1140
cccctccccg agttgctgag cacggcccgg cttcgggtgc ggggctccgt gcggggcgtg 1200
gcgcggggct cgccgtgccg ggcggggggt ggcggcaggt gggggtgccg ggcggggcgg 1260
ggccgcctcg ggccggggag ggctcggggg aggggcgcgg cggcccccgga gcgccggcgg 1320 ctgtcgaggc gcggcgagcc gcagccattg ccttttatgg taatcgtgcg agagggcgca 1380
gggacttcct ttgtcccaaa tctggcggag ccgaaatctg ggaggcgccg ccgcaccccc 1440
tctagcgggc gcgggcgaag cggtgcggcg ccggcaggaa ggaaatgggc ggggagggcc 1500
ttcgtgcgtc gccgcgccgc cgtccccttc tccatctcca gcctcggggc tgccgcaggg 1560
ggacggctgc cttcgggggg gacggggcag ggcggggttc ggcttctggc gtgtgaccgg 1620
cggctctaga gcctctgcta accatgttca tgccttcttc tttttcctac agctcctggg 1680
caacgtgctg gttattgtgc tgtctcatca ttttggcaaa gaattcctcg atcgagggac 1740
ctaataactt cgtatagcat acattatacg aagttatatt aagggttccg caagcttcct 1800
agactagtcg acggtatcga taccatggtg agcaagggcg aggaggataa catggccatc 1860
atcaaggagt tcatgcgctt caaggtgcac atggagggct ccgtgaacgg ccacgagttc 1920
gagatcgagg gcgagggcga gggccgcccc tacgagggca cccagaccgc caagctgaag 1980
gtgaccaagg gtggccccct gcccttcgcc tgggacatcc tgtcccctca gttcatgtac 2040
ggctccaagg cctacgtgaa gcaccccgcc gacatccccg actacttgaa gctgtccttc 2100
cccgagggct tcaagtggga gcgcgtgatg aacttcgagg acggcggcgt ggtgaccgtg 2160
acccaggact cctccctgca ggacggcgag ttcatctaca aggtgaagct gcgcggcacc 2220
aacttcccct ccgacggccc cgtaatgcag aagaagacga tgggctggga ggcctcctcc 2280
gagcggatgt accccgagga cggcgccctg aagggcgaga tcaagcagag gctgaagctg 2340
aaggacggcg gccactacga cgctgaggtc aagaccacct acaaggccaa gaagcccgtg 2400
cagctgcccg gcgcctacaa cgtcaacatc aagttggaca tcacctccca caacgaggac 2460
tacaccatcg tggaacagta cgaacgcgcc gagggccgcc actccaccgg cggcatggac 2520
gagctgtaca agtaagcatg cccgacggcg aggatctcgt cgtgacccat ggcgatgcct 2580
gcttgccgaa tatcatggtg gaaaatggcc gcttttctgg attcatcgac tgtggccggc 2640
tgggtgtggc ggaccgctat caggacatag cgttggctac ccgtgatatt gctgaagagc 2700
ttggcggcga atgggctgac cgcttcctcg tgctttacgg tatcgccgct cccgattcgc 2760
agcgcatcgc cttctatcgc cttcttgacg agttcttctg aggggatcaa ttctctaggc 2820
ttgggatctt tgtgaaggaa ccttacttct gtggtgtgac ataattggac aaactaccta 2880
cagagattta aagctctaag gtaaatataa aatttttaag tgtataatgt gttaaactac 2940
tgattctaat tgtttgtgta ttttagattc acagtcccaa ggctcatttc aggcccctca 3000
gtcctcacag tctgttcatg atcataatca gccataccac atttgtagag gttttacttg 3060
ctttaaaaaa cctcccacac ctccccctga acctgaaaca taaaatgaat gcaattgttg 3120
ttgttaactt gtttattgca gcttataatg gttacaaata aagcaatagc atcacaaatt 3180
tcacaaataa agcatttttt tcactgcatt ctagttgtgt ttgtccaaac tcatcaatgt 3240
atcttatcat gtctggatca taatcagcca taccacattt gtagaggttt tacttgcttt 3300
aaaaaacctt ccccacacct ccccctgaac tgaaacataa aatgaatgca attgttgttg 3360
ttaacttgtt tattgcagct tataatggtt acaaataaag caatagcatc acaaatttca 3420
caaataaagc atttttttca ctgcattcta gttgtggttt gtccaaactc atcaatgtat 3480
cttatcatgt ctggatcata atcagccata ccacatttgt agaggtttta cttgctttaa 3540
aaaacctccc acacctcccc ctgaacctga aacataaaat gaatgcaatt gttgttgtta 3600
acttgtttat tgcagcttat aatggttaca aataaagcaa tagcatcaca aatttcacaa 3660
ataaagcatt tttttcactg cattctagtt gtggtttgtc caaactcatc aatgtatctt 3720
atcatgtctg gatccactag ttctagctag tctaggtcga tgcaggataa cttcgtatag 3780
catacattat acgaagttat agatcttggg tacccgctcg agctcaagct tcgaattctg 3840
cagtcgacgg taccgcgggc cccaaataat gattttattt tgactgatag tgacctgttc 3900
gttgcaacaa attgataagc aatgcttttt tataatgcca actttgtaca aaaaagcagg 3960
ctttaaagga accaattcag tcgactggat ccggtaccga attccagcag gagataacct 4020
gaagacaatg gatgtcgatg agggtcaaga catgtcccaa gtttcaggaa aggagagccc 4080
cccagtcagt gacactccag atgaagggga tgagcccatg cctgtccctg aggacctgtc 4140
cactacctct ggagcacagc agaactccaa gagtgatcga ggcatggcca gtaatgttaa 4200
agtagagact cagagtgatg aagagaatgg gcgtgcctgt gaaatgaatg gggaagaatg 4260
tgcagaggat ttacgaatgc ttgatgcctc gggagagaaa atgaatggct cccacaggga 4320
ccaaggcagc tcggctttgt caggagttgg aggcattcga cttcctaacg gaaaactaaa 4380
gtgtgatatc tgtgggatcg tttgcatcgg gcccaatgtg ctcatggttc acaaaagaag 4440
tcatactggt gaacggcctt tccagtgcaa ccagtgtggg gcctccttta cccagaaagg 4500
caacctcctg cggcacatca agctgcactc gggtgagaag cccttcaaat gccatctttg 4560
caactatgcc tgccgccgga gggacgccct caccggccac ctgaggacgc actccgttgg 4620
taagcctcac aaatgtggat attgtggccg gagctataaa cagcgaagct ctttagagga 4680
gcataaagag cgatgccaca actacttgga aagcatgggc cttccgggca tgtacccagt 4740
cattaaggaa gaaactaacc acaacgagat ggcagaagac ctgtgcaaga taggagcaga 4800
gaggtccctt gtcctggaca ggctggcaag caatgtcgcc aaacgtaaga gctctatgcc 4860
tcagaaattt cttggagaca agtgcctgtc agacatgccc tatgacagtg ccaactatga 4920
gaaggaggat atgatgacat cccacgtgat ggaccaggcc atcaacaatg ccatcaacta 4980
cctgggggct gagtccctgc gcccattggt gcagacaccc cccggtagct ccgaggtggt 5040
gccagtcatc agctccatgt accagctgca caagcccccc tcagatggcc ccccacggtc 5100
caaccattca gcacaggacg ccgtggataa cttgctgctg ctgtccaagg ccaagtctgt 5160
gtcatcggag cgagaggcct ccccgagcaa cagctgccaa gactccacag atacagagag 5220
caacgcggag gaacagcgca gcggccttat ctacctaacc aaccacatca acccgcatgc 5280
acgcaatggg ctggctctca aggaggagca gcgcgcctac gaggtgctga gggcggcctc 5340
agagaactcg caggatgcct tccgtgtggt cagcacgagt ggcgagcagc tgaaggtgta 5400
caagtgcgaa cactgccgcg tgctcttcct ggatcacgtc atgtatacca ttcacatggg 5460
ctgccatggc tttcgggatc cctttgagtg taacatgtgt ggttatcaca gccaggacag 5520
gtacgagttc tcatcccata tcacgcgggg ggagcatcgt taccacctga gctaagaatt 5580
cgcggccgcg atctttttcc ctctgccaaa aattatgggg acatcatgaa gccccttgag 5640
catctgactt ctggctaata aaggaaattt attttcattg caatagtgtg ttggaatttt 5700
ttgtgtctct cactcggaag gacatatggg agggcaaatc atttaaaaca tcagaatgag 5760
tatttggttt agagtttggc aacatatgcc atatgctggc tgccatgaac aaaggtggct 5820
ataaagaggt catcagtata tgaaacagcc ccctgctgtc cattccttat tccatagaaa 5880
agccttgact tgaggttaga ttttttttat attttgtttt gtgttatttt tttctttaac 5940
atccctaaaa ttttccttac atgttttact agccagattt ttcctcctct cctgactact 6000
cccagtcata gctgtccctc ttctcttatg aagatccctc gacctgcagc ccaagcttgg 6060
cgtaatcatg gtcatagctg tttcctgtgt gaaattgtta tccgctcaca attccacaca 6120
acatacgagc cggaagcata aagtgtaaag cctggggtgc ctaatgagtg agctaactca 6180
cattaattgc gttgcgctca ctgcccgctt tccagtcggg aaacctgtcg tgccagcgga 6240
tccgcatctc aattagtcag caaccatagt cccgccccta actccgccca tcccgcccct 6300
aactccgccc agttccgccc attctccgcc ccatggctga ctaatttttt ttatttatgc 6360
agaggccgag gccgcctcgg cctctgagct attccagaag tagtgaggag gcttttttgg 6420
aggcctaggc ttttgcaaaa agctaacttg tttattgcag cttataatgg ttacaaataa 6480
agcaatagca tcacaaattt cacaaataaa gcattttttt cactgcattc tagttgtggt 6540
ttgtccaaac tcatcaatgt atcttatcat gtctggatcc gctgcattaa tgaatcggcc 6600
aacgcgcggg gagaggcggt ttgcgtattg ggcgctcttc cgcttcctcg ctcactgact 6660
cgctgcgctc ggtcgttcgg ctgcggcgag cggtatcagc tcactcaaag gcggtaatac 6720
ggttatccac agaatcaggg gataacgcag gaaagaacat gtgagcaaaa ggccagcaaa 6780
aggccaggaa ccgtaaaaag gccgcgttgc tggcgttttt ccataggctc cgcccccctg 6840
acgagcatca caaaaatcga cgctcaagtc agaggtggcg aaacccgaca ggactataaa 6900
gataccaggc gtttccccct ggaagctccc tcgtgcgctc tcctgttccg accctgccgc 6960
ttaccggata cctgtccgcc tttctccctt cgggaagcgt ggcgctttct caatgctcac 7020
gctgtaggta tctcagttcg gtgtaggtcg ttcgctccaa gctgggctgt gtgcacgaac 7080
cccccgttca gcccgaccgc tgcgccttat ccggtaacta tcgtcttgag tccaacccgg 7140
taagacacga cttatcgcca ctggcagcag ccactggtaa caggattagc agagcgaggt 7200
atgtaggcgg tgctacagag ttcttgaagt ggtggcctaa ctacggctac actagaagga 7260
cagtatttgg tatctgcgct ctgctgaagc cagttacctt cggaaaaaga gttggtagct 7320
cttgatccgg caaacaaacc accgctggta gcggtggttt ttttgtttgc aagcagcaga 7380
ttacgcgcag aaaaaaagga tctcaagaag atcctttgat cttttctacg gggtctgacg 7440
ctcagtggaa cgaaaactca cgttaaggga ttttggtcat gagattatca aaaaggatct 7500
tcacctagat ccttttaaat taaaaatgaa gttttaaatc aatctaaagt atatatgagt 7560
aaacttggtc tgacagttac caatgcttaa tcagtgaggc acctatctca gcgatctgtc 7620
tatttcgttc atccatagtt gcctgactcc ccgtcgtgta gataactacg atacgggagg 7680
gcttaccatc tggccccagt gctgcaatga taccgcgaga cccacgctca ccggctccag 7740
atttatcagc aataaaccag ccagccggaa gggccgagcg cagaagtggt cctgcaactt 7800
tatccgcctc catccagtct attaattgtt gccgggaagc tagagtaagt agttcgccag 7860
ttaatagttt gcgcaacgtt gttgccattg ctacaggcat cgtggtgtca cgctcgtcgt 7920
ttggtatggc ttcattcagc tccggttccc aacgatcaag gcgagttaca tgatccccca 7980
tgttgtgcaa aaaagcggtt agctccttcg gtcctccgat cgttgtcaga agtaagttgg 8040
ccgcagtgtt atcactcatg gttatggcag cactgcataa ttctcttact gtcatgccat 8100
ccgtaagatg cttttctgtg actggtgagt actcaaccaa gtcattctga gaatagtgta 8160
tgcggcgacc gagttgctct tgcccggcgt caatacggga taataccgcg ccacatagca 8220
gaactttaaa agtgctcatc attggaaaac gttcttcggg gcgaaaactc tcaaggatct 8280
taccgctgtt gagatccagt tcgatgtaac ccactcgtgc acccaactga tcttcagcat 8340
cttttacttt caccagcgtt tctgggtgag caaaaacagg aaggcaaaat gccgcaaaaa 8400
agggaataag ggcgacacgg aaatgttgaa tactcatact cttccttttt caatattatt 8460
gaagcattta tcagggttat tgtctcatga gcggatacat atttgaatgt atttagaaaa 8520
ataaacaaat aggggttccg cgcacatttc cccgaaaagt gccacctg 8568

<210> SEQ ID NO 59
<211> LENGTH: 8664
<212> TYPE: DNA
<213> ORGANISM: Artificial sequence
<220> FEATURE:
<223> OTHER INFORMATION: synthetic construct

<400> SEQUENCE: 59
acgtcgacat tgattattga ctagttatta atagtaatca attacggggt cattagttca 60
tagcccatat atggagttcc gcgttacata acttacggta aatggcccgc ctggctgacc 120
gcccaacgac ccccgcccat tgacgtcaat aatgacgtat gttcccatag taacgccaat 180
agggactttc cattgacgtc aatgggtgga ctatttacgg taaactgccc acttggcagt 240
acatcaagtg tatcatatgc caagtacgcc ccctattgac gtcaatgacg gtaaatggcc 300
cgcctggcat tatgcccagt acatgacctt atgggacttt cctacttggc agtacatcta 360
cgtattagtc atcgctatta ccatgggtcg aggtgagccc cacgttctgc ttcactctcc 420
ccatctcccc cccctcccca cccccaattt tgtatttatt tattttttaa ttattttgtg 480
cagcgatggg ggcggggggg gggggggcgc gcgccaggcg gggcggggcg gggcgagggg 540
cggggcgggg cgaggcggag aggtgcggcg gcagccaatc agagcggcgc gctccgaaag 600
tttcctttta tggcgaggcg gcggcggcgg cggccctata aaaagcgaag cgcgcggcgg 660

```
gcgggagtcg ctgcgttgcc ttcgccccgt gccccgctcc gcgccgcctc gcgccgcccg    720
ccccggctct gactgaccgc gttactccca caggtgagcg ggcgggacgg cccttctcct    780
ccgggctgta attagcgctt ggtttaatga cggctcgttt cttttctgtg gctgcgtgaa    840
agccttaaag ggctccggga gggccctttg tgcggggggg agcggctcgg ggggtgcgtg    900
cgtgtgtgtg tgcgtgggga gcgccgcgtg cggcccgcgc tgcccggcgg ctgtgagcgc    960
tgcgggcgcg gcgcggggct ttgtgcgctc cgcgtgtgcg cgaggggagc gcggccgggg   1020
gcggtgcccc gcggtgcggg ggggctgcga ggggaacaaa ggctgcgtgc ggggtgtgtg   1080
cgtggggggg tgagcagggg gtgtgggcgc ggcggtcggg ctgtaacccc cccctgcacc   1140
cccctccccg agttgctgag cacggcccgg cttcgggtgc ggggctccgt gcggggcgtg   1200
gcgcggggct cgccgtgccg ggcggggggt ggcggcaggt gggggtgccg ggcggggcgg   1260
ggccgcctcg ggccggggag ggctcggggg aggggcgcgg cggcccccgga gcgccggcgg   1320
ctgtcgaggc gcggcgagcc gcagccattg ccttttatgg taatcgtgcg agagggcgca   1380
gggacttcct ttgtcccaaa tctggcggag ccgaaatctg ggaggcgccg ccgcaccccc   1440
tctagcgggc gcgggcgaag cggtgcggcg ccggcaggaa ggaaatgggc ggggagggcc   1500
ttcgtgcgtc gccgcgccgc cgtccccttc tccatctcca gcctcggggc tgccgcaggg   1560
ggacggctgc cttcgggggg gacggggcag ggcggggttc ggcttctggc gtgtgaccgg   1620
cggctctaga gcctctgcta accatgttca tgccttcttc tttttcctac agctcctggg   1680
caacgtgctg gttattgtgc tgtctcatca ttttggcaaa gaattcctcg atcgagggac   1740
ctaataactt cgtatagcat acattatacg aagttatatt aagggttccg caagcttcct   1800
agactagtcg acggtatcga taccatggtg agcaagggcg aggaggataa catggccatc   1860
atcaaggagt tcatgcgctt caaggtgcac atggagggct ccgtgaacgg ccacgagttc   1920
gagatcgagg gcgagggcga gggccgcccc tacgagggca cccagaccgc caagctgaag   1980
gtgaccaagg gtggccccct gcccttcgcc tgggacatcc tgtcccctca gttcatgtac   2040
ggctccaagg cctacgtgaa gcaccccgcc gacatccccg actacttgaa gctgtccttc   2100
cccgagggct tcaagtggga gcgcgtgatg aacttcgagg acggcggcgt ggtgaccgtg   2160
acccaggact cctccctgca ggacggcgag ttcatctaca aggtgaagct gcgcggcacc   2220
aacttcccct ccgacggccc cgtaatgcag aagaagacga tgggctggga ggcctcctcc   2280
gagcggatgt accccgagga cggcgccctg aagggcgaga tcaagcagag gctgaagctg   2340
aaggacggcg gccactacga cgctgaggtc aagaccacct acaaggccaa gaagcccgtg   2400
cagctgcccg gcgcctacaa cgtcaacatc aagttggaca tcacctccca caacgaggac   2460
tacaccatcg tggaacagta cgaacgcgcc gagggccgcc actccaccgg cggcatggac   2520
gagctgtaca agtaagcatg cccgacggcg aggatctcgt cgtgacccat ggcgatgcct   2580
gcttgccgaa tatcatggtg gaaaatggcc gcttttctgg attcatcgac tgtggccggc   2640
tgggtgtggc ggaccgctat caggacatag cgttggctac ccgtgatatt gctgaagagc   2700
ttggcggcga atgggctgac cgcttcctcg tgctttacgg tatcgccgct cccgattcgc   2760
agcgcatcgc cttctatcgc cttcttgacg agttcttctg aggggatcaa ttctctaggc   2820
ttgggatctt tgtgaaggaa ccttacttct gtggtgtgac ataattggac aaactaccta   2880
cagagattta aagctctaag gtaaatataa aatttttaag tgtataatgt gttaaactac   2940
tgattctaat tgtttgtgta ttttagattc acagtcccaa ggctcatttc aggcccctca   3000
```

gtcctcacag tctgttcatg atcataatca gccataccac atttgtagag gttttacttg 3060
ctttaaaaaa cctcccacac ctccccctga acctgaaaca taaaatgaat gcaattgttg 3120
ttgttaactt gtttattgca gcttataatg gttacaaata aagcaatagc atcacaaatt 3180
tcacaaataa agcatttttt tcactgcatt ctagttgtgt ttgtccaaac tcatcaatgt 3240
atcttatcat gtctggatca taatcagcca taccacattt gtagaggttt tacttgcttt 3300
aaaaaacctt ccccacacct ccccctgaac tgaaacataa aatgaatgca attgttgttg 3360
ttaacttgtt tattgcagct tataatggtt acaaataaag caatagcatc acaaatttca 3420
caaataaagc atttttttca ctgcattcta gttgtggttt gtccaaactc atcaatgtat 3480
cttatcatgt ctggatcata atcagccata ccacatttgt agaggtttta cttgctttaa 3540
aaaacctccc acacctcccc ctgaacctga aacataaaat gaatgcaatt gttgttgtta 3600
acttgtttat tgcagcttat aatggttaca aataaagcaa tagcatcaca aatttcacaa 3660
ataaagcatt tttttcactg cattctagtt gtggtttgtc caaactcatc aatgtatctt 3720
atcatgtctg gatccactag ttctagctag tctaggtcga tgcaggataa cttcgtatag 3780
catacattat acgaagttat agatcttggg tacccgctcg agctcaagct tcgaattctg 3840
cagtcgacgg taccgcgggc ccatcacaag tttgtacaaa aaagcaggct ttaaaggaac 3900
caattcagtc gactggatcc acaartaacg gccgccagtg tgctggaatt cgcccttcca 3960
agtccctgag tggttgtttt cttcccactg accaaatctg gagagggagc tctcaggagg 4020
gtgtgctccg gatttcttgc ctcaggccca ggactccaac cattttataa tggaatcttt 4080
atttgtgaa agtagcgggg actcatctct ggagaaggag ttccttgggg ccccagtggg 4140
gccctcggtg agcaccccaa acagccaaca ctcttcaccc agccgctcgc tcagtgccaa 4200
ctccatcaag gtggagatgt acagcgatga ggagtcgagc agactgctgg ggccggatga 4260
acggctcctg gataaggatg acagtgtgat tgtggaagac tcattgtcag agcccttagg 4320
ctactgcgat ggaagtgggc cagagcctca ctcccctggc ggcatccggc tacccaacgg 4380
caagctcaag tgcgacgtct gcggcatggt ctgcattggg cccaatgtgc tcatggtaca 4440
caagcgcagc cacactgggg agaggccctt ccactgtaat cagtgtggtg cctccttcac 4500
acagaagggc aatctgcttc gccacatcaa gctgcactcg ggggagaagc ccttcaagtg 4560
ccccttctgc aactatgcct gccgccggcg tgacgcactc actggccacc tccgcacaca 4620
ctcagtctcc tcccccaccg tgggcaaacc ctacaagtgc aactactgtg gccggagcta 4680
caaacagcaa agtaccctgg aggagcacaa ggagaggtgc cacaactacc tacagagtct 4740
cagcactgat gcccaagctc tgactggcca gccaggtgat gaaatccgtg acctggagat 4800
ggtgcctgac tcaatgctgc acccatcgac tgaacggcca actttcattg atcgtttggc 4860
caacagcctc accaaacgca agcgttccac cccacagaag tttgtaggtg aaaagcagat 4920
gcgcttcagc ctctcagacc ttccctatga tgtgaatgcc agcggtggct atgaaaagga 4980
cgtagagttg gtggcacacc atggcctgga gcctggcttt ggagggtctc tagcctttgt 5040
gggtacagag catctgcgtc ccctccgcct cccacccacc aactgcatct cagaactcac 5100
acctgtcatc agctctgtgt acacccaaat gcagcccatc cccagccgac tggagcttcc 5160
agggtcccga gaagcaggtg agggaccgga ggacctggga gatggaggtc cctcctttta 5220
tcgggcccga ggctctctga ctgaccctgg ggcatccccc agcaatggct gccaggactc 5280
cacagataca gagagcaacc acgaagaccg gattggtggg gtggtatccc ttcctcaggg 5340
tcccccaccc caacctcctc ccaccatagt ggtgggccgg cacagtcccg cctatgccaa 5400

```
agaggacccc aaaccacagg aggggttact gcggggcacc ccaggcccct ccaaggaagt   5460
gcttcgggtg gtgggtgaga gtggtgagcc agtgaaggcc tttaagtgtg aacactgccg   5520
catcctcttt ctggaccacg tcatgttcac catccacatg ggctgccacg gcttcagaga   5580
ccctttgag tgtaacatct gtggttatca cagccaggat cggtatgagt tctcttccca   5640
catcgtccgg ggggaacata aggtgggcta ggaattcgcg gccgcgatct tttccctct    5700
gccaaaaatt atggggacat catgaagccc cttgagcatc tgacttctgg ctaataaagg   5760
aaatttattt tcattgcaat agtgtgttgg aatttttgt gtctctcact cggaaggaca    5820
tatgggaggg caaatcattt aaaacatcag aatgagtatt tggtttagag tttggcaaca   5880
tatgccatat gctggctgcc atgaacaaag gtggctataa agaggtcatc agtatatgaa   5940
acagccccct gctgtccatt ccttattcca tagaaaagcc ttgacttgag gttagatttt   6000
ttttatattt tgttttgtgt tattttttc tttaacatcc ctaaaatttt ccttacatgt    6060
tttactagcc agatttttcc tcctctcctg actactccca gtcatagctg tccctcttct   6120
cttatgaaga tccctcgacc tgcagcccaa gcttggcgta atcatggtca tagctgtttc   6180
ctgtgtgaaa ttgttatccg ctcacaattc cacacaacat acgagccgga agcataaagt   6240
gtaaagcctg gggtgcctaa tgagtgagct aactcacatt aattgcgttg cgctcactgc   6300
ccgctttcca gtcgggaaac ctgtcgtgcc agcggatccg catctcaatt agtcagcaac   6360
catagtcccg cccctaactc cgcccatccc gcccctaact ccgcccagtt ccgcccattc   6420
tccgccccat ggctgactaa ttttttttat ttatgcagag gccgaggccg cctcggcctc   6480
tgagctattc cagaagtagt gaggaggctt ttttggaggc ctaggctttt gcaaaaagct   6540
aacttgttta ttgcagctta taatggttac aaataaagca atagcatcac aaatttcaca   6600
aataaagcat ttttttcact gcattctagt tgtggtttgt ccaaactcat caatgtatct   6660
tatcatgtct ggatccgctg cattaatgaa tcggccaacg cgcggggaga ggcggtttgc   6720
gtattgggcg ctcttccgct tcctcgctca ctgactcgct gcgctcggtc gttcggctgc   6780
ggcgagcggt atcagctcac tcaaaggcgg taatacggtt atccacagaa tcaggggata   6840
acgcaggaaa gaacatgtga gcaaaaggcc agcaaaaggc caggaaccgt aaaaaggccg   6900
cgttgctggc gtttttccat aggctccgcc cccctgacga gcatcacaaa aatcgacgct   6960
caagtcagag gtggcgaaac ccgacaggac tataaagata ccaggcgttt ccccctggaa   7020
gctccctcgt gcgctctcct gttccgaccc tgccgcttac cggatacctg tccgcctttc   7080
tcccttcggg aagcgtggcg ctttctcaat gctcacgctg taggtatctc agttcggtgt   7140
aggtcgttcg ctccaagctg ggctgtgtgc acgaaccccc cgttcagccc gaccgctgcg   7200
ccttatccgg taactatcgt cttgagtcca acccggtaag acacgactta tcgccactgg   7260
cagcagccac tggtaacagg attagcagag cgaggtatgt aggcggtgct acagagttct   7320
tgaagtggtg gcctaactac ggctacacta gaaggacagt atttggtatc tgcgctctgc   7380
tgaagccagt taccttcgga aaaagagttg gtagctcttg atccggcaaa caaaccaccg   7440
ctggtagcgg tggttttttt gtttgcaagc agcagattac gcgcagaaaa aaaggatctc   7500
aagaagatcc tttgatcttt tctacggggt ctgacgctca gtggaacgaa aactcacgtt   7560
aagggatttt ggtcatgaga ttatcaaaaa ggatcttcac ctagatcctt ttaaattaaa   7620
aatgaagttt taaatcaatc taaagtatat atgagtaaac ttggtctgac agttaccaat   7680
gcttaatcag tgaggcacct atctcagcga tctgtctatt tcgttcatcc atagttgcct   7740
```

gactccccgt cgtgtagata actacgatac gggagggctt accatctggc cccagtgctg 7800
caatgatacc gcgagaccca cgctcaccgg ctccagattt atcagcaata aaccagccag 7860
ccggaagggc cgagcgcaga agtggtcctg caactttatc cgcctccatc cagtctatta 7920
attgttgccg ggaagctaga gtaagtagtt cgccagttaa tagtttgcgc aacgttgttg 7980
ccattgctac aggcatcgtg gtgtcacgct cgtcgtttgg tatggcttca ttcagctccg 8040
gttcccaacg atcaaggcga gttacatgat cccccatgtt gtgcaaaaaa gcggttagct 8100
ccttcggtcc tccgatcgtt gtcagaagta agttggccgc agtgttatca ctcatggtta 8160
tggcagcact gcataattct cttactgtca tgccatccgt aagatgcttt tctgtgactg 8220
gtgagtactc aaccaagtca ttctgagaat agtgtatgcg gcgaccgagt tgctcttgcc 8280
cggcgtcaat acgggataat accgcgccac atagcagaac tttaaaagtg ctcatcattg 8340
gaaaacgttc ttcggggcga aaactctcaa ggatcttacc gctgttgaga tccagttcga 8400
tgtaacccac tcgtgcaccc aactgatctt cagcatcttt tactttcacc agcgtttctg 8460
ggtgagcaaa aacaggaagg caaaatgccg caaaaaaggg aataagggcg acacggaaat 8520
gttgaatact catactcttc ctttttcaat attattgaag catttatcag ggttattgtc 8580
tcatgagcgg atacatattt gaatgtattt agaaaaataa acaaataggg gttccgcgca 8640
catttccccg aaaagtgcca cctg 8664

<210> SEQ ID NO 60
<211> LENGTH: 4975
<212> TYPE: DNA
<213> ORGANISM: Artificial sequence
<220> FEATURE:
<223> OTHER INFORMATION: synthetic construct

<400> SEQUENCE: 60
gtcctgcagg cagctgcgcg ctcgctcgct cactgaggcc gcccgggcaa agcccgggcg 60
tcgggcgacc tttggtcgcc cggcctcagt gagcgagcga gcgcgcagag agggagtggc 120
caactccatc actaggggtt cctgcggccg cacgcgtcgt ggtacctctg gtcgttacat 180
aacttacggt aaatggcccg cctggctgac cgcccaacga cccccgccca ttgacgtcaa 240
taatgacgta tgttcccata gtaacgccaa tagggacttt ccattgacgt caatgggtgg 300
agtatttacg gtaaactgcc cacttggcag tacatcaagt gtatcatatg ccaagtacgc 360
cccctattga cgtcaatgac ggtaaatggc ccgcctggca ttatgcccag tacatgacct 420
tatgggactt tcctacttgg cagtacatta ctcgaggcca cgttctgctt cactctcccc 480 atctccccccc ccctccccac ccccaatttt gtatttattt atttttaat tattttgtgc 540 agcgatgggg gcgggggggg gggggggcg cgcgccaggc ggggcggggc ggggcgaggg 600
gcggggcggg gcgaggcgga gaggtgcggc ggcagccaat cagagcggcg cgctccgaaa 660
gtttcctttt atggcgaggc ggcggcggcg gcggccctat aaaaagcgaa gcgcgcggcg 720
ggcgggagcg ggatcagcca ccgcggtggc ggcctagagt cgacgaggaa ctgaaaaacc 780
agaaagttaa ctggtaagtt tagtcttttt gtcttttatt tcaggtcccg gatccggtgg 840
tggtgcaaat caaagaactg ctcctcagtg gatgttgcct ttacttctag gcctgtacgg 900
aagtgttact tctgctctaa aagctgcgga attgtacccg cggccgatcc accggtcgcc 960
accatggtga gcaagggcga ggagctgttc accggggtgg tgcccatcct ggtcgagctg 1020
gacggcgacg taaacggcca caagttcagc gtgtccggcg agggcgaggg cgatgccacc 1080
tacggcaagc tgaccctgaa gttcatctgc accaccggca agctgcccgt gccctggccc 1140 acccctcgtga ccaccctgac ctacggcgtg cagtgcttca gccgctaccc cgaccacatg 1200
aagcagcacg acttcttcaa gtccgccatg cccgaaggct acgtccagga gcgcaccatc 1260
ttcttcaagg acgacggcaa ctacaagacc cgcgccgagg tgaagttcga gggcgacacc 1320
ctggtgaacc gcatcgagct gaagggcatc gacttcaagg aggacggcaa catcctgggg 1380
cacaagctgg agtacaacta caacagccac aacgtctata tcatggccga caagcagaag 1440
aacggcatca aggtgaactt caagatccgc cacaacatcg aggacggcag cgtgcagctc 1500
gccgaccact accagcagaa cacccccatc ggcgacggcc ccgtgctgct gcccgacaac 1560
cactacctga gcacccagtc cgccctgagc aaagacccca acgagaagcg cgatcacatg 1620
gtcctgctgg agttcgtgac cgccgccggg atcactctcg gcatggacga gctgtacaag 1680
taaagcgaag cttgcctcga gcagcgctgc tcgagagatc tacgggtggc atccctgtga 1740
cccctcccca gtgcctctcc tggccctgga agttgccact ccagtgccca ccagccttgt 1800
cctaataaaa ttaagttgca tcattttgtc tgactaggtg tccttctata atattatggg 1860
gtggaggggg gtggtatgga gcaaggggca agttgggaag acaacctgta gggcctgcgg 1920
ggtctattgg gaaccaagct ggagtgcagt ggcacaatct tggctcactg caatctccgc 1980
ctcctgggtt caagcgattc tcctgcctca gcctcccgag ttgttgggat tccaggcatg 2040
catgaccagg ctcagctaat tttgtttttt ttggtagaga cggggtttca ccatattggc 2100
caggctggtc tccaactcct aatctcaggt gatctaccca ccttggcctc ccaaattgct 2160
gggattacag gcgtgaacca ctgctccctt ccctgtcctt ctgattttgt aggtaaccac 2220
gtgcggaccg agcggccgca ggaaccccta gtgatggagt tggccactcc ctctctgcgc 2280
gctcgctcgc tcactgaggc cgggcgacca aaggtcgccc gacgcccggg ctttgcccgg 2340
gcggcctcag tgagcgagcg agcgcgcagc tgcctgcagg ggcgcctgat gcggtatttt 2400
ctccttacgc atctgtgcgg tatttcacac cgcatacgtc aaagcaacca tagtacgcgc 2460
cctgtagcgg cgcattaagc gcggcgggtg tggtggttac gcgcagcgtg accgctacac 2520
ttgccagcgc cctagcgccc gctcctttcg ctttcttccc ttcctttctc gccacgttcg 2580
ccggctttcc ccgtcaagct ctaaatcggg ggctcccttt agggttccga tttagtgctt 2640
tacggcacct cgaccccaaa aaacttgatt tgggtgatgg ttcacgtagt gggccatcgc 2700
cctgatagac ggtttttcgc cctttgacgt tggagtccac gttctttaat agtggactct 2760
tgttccaaac tggaacaaca ctcaacccta tctcgggcta ttcttttgat ttataaggga 2820
ttttgccgat ttcggcctat tggttaaaaa atgagctgat ttaacaaaaa tttaacgcga 2880
attttaacaa aatattaacg tttacaattt tatggtgcac tctcagtaca atctgctctg 2940
atgccgcata gttaagccag ccccgacacc cgccaacacc cgctgacgcg ccctgacggg 3000
cttgtctgct cccggcatcc gcttacagac aagctgtgac cgtctccggg agctgcatgt 3060
gtcagaggtt ttcaccgtca tcaccgaaac gcgcgagacg aaagggcctc gtgatacgcc 3120
tatttttata ggttaatgtc atgataataa tggtttctta gacgtcaggt ggcacttttc 3180
ggggaaatgt gcgcggaacc cctatttgtt tatttttcta aatacattca aatatgtatc 3240
cgctcatgag acaataaccc tgataaatgc ttcaataata ttgaaaaagg aagagtatga 3300
gtattcaaca tttccgtgtc gcccttattc ccttttttgc ggcattttgc cttcctgttt 3360
ttgctcaccc agaaacgctg gtgaaagtaa aagatgctga agatcagttg ggtgcacgag 3420
tgggttacat cgaactggat ctcaacagcg gtaagatcct tgagagtttt cgccccgaag 3480
aacgttttcc aatgatgagc acttttaaag ttctgctatg tggcgcggta ttatcccgta 3540
ttgacgccgg gcaagagcaa ctcggtcgcc gcatacacta ttctcagaat gacttggttg 3600
agtactcacc agtcacagaa aagcatctta cggatggcat gacagtaaga gaattatgca 3660
gtgctgccat aaccatgagt gataacactg cggccaactt acttctgaca acgatcggag 3720
gaccgaagga gctaaccgct tttttgcaca acatggggga tcatgtaact cgccttgatc 3780
gttgggaacc ggagctgaat gaagccatac caaacgacga gcgtgacacc acgatgcctg 3840
tagcaatggc aacaacgttg cgcaaactat taactggcga actacttact ctagcttccc 3900
ggcaacaatt aatagactgg atggaggcgg ataaagttgc aggaccactt ctgcgctcgg 3960
cccttccggc tggctggttt attgctgata aatctggagc cggtgagcgt gggtctcgcg 4020
gtatcattgc agcactgggg ccagatggta agccctcccg tatcgtagtt atctacacga 4080
cggggagtca ggcaactatg gatgaacgaa atagacagat cgctgagata ggtgcctcac 4140
tgattaagca ttggtaactg tcagaccaag tttactcata tatactttag attgatttaa 4200
aacttcattt ttaatttaaa aggatctagg tgaagatcct ttttgataat ctcatgacca 4260
aaatccctta acgtgagttt tcgttccact gagcgtcaga ccccgtagaa aagatcaaag 4320
gatcttcttg agatcctttt tttctgcgcg taatctgctg cttgcaaaca aaaaaaccac 4380
cgctaccagc ggtggtttgt ttgccggatc aagagctacc aactcttttt ccgaaggtaa 4440
ctggcttcag cagagcgcag ataccaaata ctgtccttct agtgtagccg tagttaggcc 4500
accacttcaa gaactctgta gcaccgccta catacctcgc tctgctaatc ctgttaccag 4560
tggctgctgc cagtggcgat aagtcgtgtc ttaccgggtt ggactcaaga cgatagttac 4620
cggataaggc gcagcggtcg ggctgaacgg ggggttcgtg cacacagccc agcttggagc 4680
gaacgaccta caccgaactg agatacctac agcgtgagct atgagaaagc gccacgcttc 4740
ccgaagggag aaaggcggac aggtatccgg taagcggcag ggtcggaaca ggagagcgca 4800
cgagggagct tccaggggga aacgcctggt atctttatag tcctgtcggg tttcgccacc 4860
tctgacttga gcgtcgattt ttgtgatgct cgtcaggggg gcggagccta tggaaaaacg 4920
ccagcaacgc ggccttttta cggttcctgg ccttttgctg gccttttgct cacat 4975

<210> SEQ ID NO 61
<211> LENGTH: 5824
<212> TYPE: DNA
<213> ORGANISM: Artificial sequence
<220> FEATURE:
<223> OTHER INFORMATION: synthetic construct

<400> SEQUENCE: 61
gtcctgcagg cagctgcgcg ctcgctcgct cactgaggcc gcccgggcaa agcccgggcg 60
tcgggcgacc tttggtcgcc cggcctcagt gagcgagcga gcgcgcagag agggagtggc 120
caactccatc actaggggtt cctgcggccg cacgcgtcgt ggtacctctg gtcgttacat 180
aacttacggt aaatggcccg cctggctgac cgcccaacga cccccgccca ttgacgtcaa 240
taatgacgta tgttcccata gtaacgccaa tagggacttt ccattgacgt caatgggtgg 300
agtatttacg gtaaactgcc cacttggcag tacatcaagt gtatcatatg ccaagtacgc 360
cccctattga cgtcaatgac ggtaaatggc ccgcctggca ttatgcccag tacatgacct 420
tatgggactt tcctacttgg cagtacatta ctcgaggcca cgttctgctt cactctcccc 480
atctcccccc ccctccccac ccccaatttt gtatttattt atttttaat tattttgtgc 540 agcgatgggg gcgggggggg gggggggcg cgcgccaggc ggggcggggc ggggcgaggg 600

```
gcggggcggg gcgaggcgga gaggtgcggc ggcagccaat cagagcggcg cgctccgaaa    660
gtttcctttt atggcgaggc ggcggcggcg gcggccctat aaaaagcgaa gcgcgcggcg    720
ggcgggagcg ggatcagcca ccgcggtggc ggcctagagt cgacgaggaa ctgaaaaacc    780
agaaagttaa ctggtaagtt tagtcttttt gtcttttatt tcaggtcccg gatccggtgg    840
tggtgcaaat caaagaactg ctcctcagtg gatgttgcct ttacttctag gcctgtacgg    900
aagtgttact tctgctctaa aagctgcgga attgtacccg cggccgatcc accggtaccg    960
aattccagca ggagataacc tgaagacaat ggatgtcgat gagggtcaag acatgtccca   1020
agtttcagga aaggagagcc ccccagtcag tgacactcca gatgaagggg atgagcccat   1080
gcctgtccct gaggacctgt ccactacctc tggagcacag cagaactcca agagtgatcg   1140
aggcatggcc agtaatgtta aagtagagac tcagagtgat gaagagaatg ggcgtgcctg   1200
tgaaatgaat ggggaagaat gtgcagagga tttacgaatg cttgatgcct cgggagagaa   1260
aatgaatggc tcccacaggg accaaggcag ctcggctttg tcaggagttg gaggcattcg   1320
acttcctaac ggaaaactaa agtgtgatat ctgtgggatc gtttgcatcg ggcccaatgt   1380
gctcatggtt cacaaaagaa gtcatactgg tgaacggcct ttccagtgca accagtgtgg   1440
ggcctccttt acccagaaag gcaacctcct gcggcacatc aagctgcact cgggtgagaa   1500
gcccttcaaa tgccatcttt gcaactatgc ctgccgccgg agggacgccc tcaccggcca   1560
cctgaggacg cactccgttg gtaagcctca caaatgtgga tattgtggcc ggagctataa   1620
acagcgaagc tctttagagg agcataaaga gcgatgccac aactacttgg aaagcatggg   1680
ccttccgggc atgtacccag tcattaagga agaaactaac cacaacgaga tggcagaaga   1740
cctgtgcaag ataggagcag agaggtccct tgtcctggac aggctggcaa gcaatgtcgc   1800
caaacgtaag agctctatgc ctcagaaatt tcttggagac aagtgcctgt cagacatgcc   1860
ctatgacagt gccaactatg agaaggagga tatgatgaca tcccacgtga tggaccaggc   1920
catcaacaat gccatcaact acctgggggc tgagtccctg cgcccattgg tgcagacacc   1980
ccccggtagc tccgaggtgg tgccagtcat cagctccatg taccagctgc acaagccccc   2040
ctcagatggc ccccccacggt ccaaccattc agcacaggac gccgtggata acttgctgct   2100
gctgtccaag gccaagtctg tgtcatcgga gcgagaggcc tccccgagca acagctgcca   2160
agactccaca gatacagaga gcaacgcgga ggaacagcgc agcggcctta tctacctaac   2220
caaccacatc aacccgcatg cacgcaatgg gctggctctc aaggaggagc agcgcgccta   2280
cgaggtgctg agggcggcct cagagaactc gcaggatgcc ttccgtgtgg tcagcacgag   2340
tggcgagcag ctgaaggtgt acaagtgcga acactgccgc gtgctcttcc tggatcacgt   2400
catgtatacc attcacatgg gctgccatgg ctttcgggat ccctttgagt gtaacatgtg   2460
tggttatcac agccaggaca ggtacgagtt ctcatcccat atcacgcggg gggagcatcg   2520
ttaccacctg agctaaaagc ttgcctcgag cagcgctgct cgagagatct acgggtggca   2580
tccctgtgac ccctccccag tgcctctcct ggccctggaa gttgccactc cagtgcccac   2640
cagccttgtc ctaataaaat taagttgcat cattttgtct gactaggtgt ccttctataa   2700
tattatgggg tggagggggg tggtatggag caaggggcaa gttgggaaga caacctgtag   2760
ggcctgcggg gtctattggg aaccaagctg gagtgcagtg gcacaatctt ggctcactgc   2820
aatctccgcc tcctgggttc aagcgattct cctgcctcag cctcccgagt tgttgggatt   2880
ccaggcatgc atgaccaggc tcagctaatt tttgtttttt tggtagagac ggggtttcac   2940
```

-continued catattggcc aggctggtct ccaactccta atctcaggtg atctacccac cttggcctcc 3000
caaattgctg ggattacagg cgtgaaccac tgctcccttc cctgtccttc tgattttgta 3060
ggtaaccacg tgcggaccga gcggccgcag gaacccctag tgatggagtt ggccactccc 3120
tctctgcgcg ctcgctcgct cactgaggcc gggcgaccaa aggtcgcccg acgcccgggc 3180
tttgcccggg cggcctcagt gagcgagcga gcgcgcagct gcctgcaggg gcgcctgatg 3240
cggtattttc tccttacgca tctgtgcggt atttcacacc gcatacgtca aagcaaccat 3300
agtacgcgcc ctgtagcggc gcattaagcg cggcgggtgt ggtggttacg cgcagcgtga 3360
ccgctacact tgccagcgcc ctagcgcccg ctcctttcgc tttcttccct tcctttctcg 3420
ccacgttcgc cggctttccc cgtcaagctc taaatcgggg gctcccttta gggttccgat 3480
ttagtgcttt acggcacctc gaccccaaaa aacttgattt gggtgatggt tcacgtagtg 3540
ggccatcgcc ctgatagacg gtttttcgcc ctttgacgtt ggagtccacg ttctttaata 3600
gtggactctt gttccaaact ggaacaacac tcaaccctat ctcgggctat tcttttgatt 3660
tataagggat tttgccgatt tcggcctatt ggttaaaaaa tgagctgatt taacaaaaat 3720
ttaacgcgaa ttttaacaaa atattaacgt ttacaatttt atggtgcact ctcagtacaa 3780
tctgctctga tgccgcatag ttaagccagc cccgacaccc gccaacaccc gctgacgcgc 3840
cctgacgggc ttgtctgctc ccggcatccg cttacagaca agctgtgacc gtctccggga 3900
gctgcatgtg tcagaggttt tcaccgtcat caccgaaacg cgcgagacga aagggcctcg 3960
tgatacgcct atttttatag gttaatgtca tgataataat ggtttcttag acgtcaggtg 4020
gcacttttcg gggaaatgtg cgcggaaccc ctatttgttt atttttctaa atacattcaa 4080
atatgtatcc gctcatgaga caataaccct gataaatgct tcaataatat tgaaaaagga 4140
agagtatgag tattcaacat ttccgtgtcg cccttattcc cttttttgcg gcattttgcc 4200
ttcctgtttt tgctcaccca gaaacgctgg tgaaagtaaa agatgctgaa gatcagttgg 4260
gtgcacgagt gggttacatc gaactggatc tcaacagcgg taagatcctt gagagttttc 4320
gccccgaaga acgttttcca atgatgagca cttttaaagt tctgctatgt ggcgcggtat 4380
tatcccgtat tgacgccggg caagagcaac tcggtcgccg catacactat tctcagaatg 4440
acttggttga gtactcacca gtcacagaaa agcatcttac ggatggcatg acagtaagag 4500
aattatgcag tgctgccata accatgagtg ataacactgc ggccaactta cttctgacaa 4560
cgatcggagg accgaaggag ctaaccgctt ttttgcacaa catgggggat catgtaactc 4620
gccttgatcg ttgggaaccg gagctgaatg aagccatacc aaacgacgag cgtgacacca 4680
cgatgcctgt agcaatggca acaacgttgc gcaaactatt aactggcgaa ctacttactc 4740
tagcttcccg gcaacaatta atagactgga tggaggcgga taaagttgca ggaccacttc 4800
tgcgctcggc ccttccggct ggctggttta ttgctgataa atctggagcc ggtgagcgtg 4860
ggtctcgcgg tatcattgca gcactggggc cagatggtaa gccctcccgt atcgtagtta 4920
tctacacgac ggggagtcag gcaactatgg atgaacgaaa tagacagatc gctgagatag 4980
gtgcctcact gattaagcat tggtaactgt cagaccaagt ttactcatat atactttaga 5040
ttgatttaaa acttcatttt taatttaaaa ggatctaggt gaagatcctt tttgataatc 5100
tcatgaccaa aatcccttaa cgtgagtttt cgttccactg agcgtcagac cccgtagaaa 5160
agatcaaagg atcttcttga gatccttttt ttctgcgcgt aatctgctgc ttgcaaacaa 5220
aaaaaccacc gctaccagcg gtggtttgtt tgccggatca agagctacca actctttttc 5280
cgaaggtaac tggcttcagc agagcgcaga taccaaatac tgtccttcta gtgtagccgt 5340
agttaggcca ccacttcaag aactctgtag caccgcctac atacctcgct ctgctaatcc 5400
tgttaccagt ggctgctgcc agtggcgata agtcgtgtct taccgggttg gactcaagac 5460
gatagttacc ggataaggcg cagcggtcgg gctgaacggg gggttcgtgc acacagccca 5520
gcttggagcg aacgacctac accgaactga gatacctaca gcgtgagcta tgagaaagcg 5580
ccacgcttcc cgaagggaga aaggcggaca ggtatccggt aagcggcagg gtcggaacag 5640
gagagcgcac gagggagctt ccagggggaa acgcctggta tctttatagt cctgtcgggt 5700
ttcgccacct ctgacttgag cgtcgatttt tgtgatgctc gtcagggggg cggagcctat 5760
ggaaaaacgc cagcaacgcg gcctttttac ggttcctggc cttttgctgg ccttttgctc 5820
acat 5824

<210> SEQ ID NO 62
<211> LENGTH: 5921
<212> TYPE: DNA
<213> ORGANISM: Artificial sequence
<220> FEATURE:
<223> OTHER INFORMATION: synthetic construct

<400> SEQUENCE: 62
gtcctgcagg cagctgcgcg ctcgctcgct cactgaggcc gcccgggcaa agcccgggcg 60
tcgggcgacc tttggtcgcc cggcctcagt gagcgagcga gcgcgcagag agggagtggc 120
caactccatc actaggggtt cctgcggccg cacgcgtcgt ggtacctctg gtcgttacat 180
aacttacggt aaatggcccg cctggctgac cgcccaacga cccccgccca ttgacgtcaa 240
taatgacgta tgttcccata gtaacgccaa tagggacttt ccattgacgt caatgggtgg 300
agtatttacg gtaaactgcc cacttggcag tacatcaagt gtatcatatg ccaagtacgc 360
cccctattga cgtcaatgac ggtaaatggc ccgcctggca ttatgcccag tacatgacct 420
tatgggactt tcctacttgg cagtacatta ctcgaggcca cgttctgctt cactctcccc 480
atctcccccc ccctccccac ccccaatttt gtatttattt atttttaat tattttgtgc 540 agcgatgggg gcgggggggg gggggggcg cgcgccaggc ggggcggggc ggggcgaggg 600
gcggggcggg gcgaggcgga gaggtgcggc ggcagccaat cagagcggcg cgctccgaaa 660
gtttcctttt atggcgaggc ggcggcggcg gcggccctat aaaaagcgaa gcgcgcggcg 720
ggcgggagcg ggatcagcca ccgcggtggc ggcctagagt cgacgaggaa ctgaaaaacc 780
agaaagttaa ctggtaagtt tagtcttttt gtcttttatt tcaggtcccg gatccggtgg 840
tggtgcaaat caaagaactg ctcctcagtg gatgttgcct ttacttctag gcctgtacgg 900
aagtgttact tctgctctaa aagctgcgga attgtacccg cggccgatcc accggtaatc 960
tggagaggga gctctcagga gggtgtgctc cggatttctt gcctcaggcc caggactcca 1020
accattttat aatggaatct ttattttgtg aaagtagcgg ggactcatct ctggagaagg 1080
agttccttgg ggccccagtg ggccctcgg tgagcacccc aaacagccaa cactcttcac 1140
ccagccgctc gctcagtgcc aactccatca aggtggagat gtacagcgat gaggagtcga 1200
gcagactgct ggggccggat gaacggctcc tggataagga tgacagtgtg attgtggaag 1260
actcattgtc agagccctta ggctactgcg atggaagtgg gccagagcct cactcccctg 1320
gcggcatccg gctacccaac ggcaagctca agtgcgacgt ctgcggcatg gtctgcattg 1380
ggcccaatgt gctcatggta cacaagcgca gccacactgg ggagaggccc ttccactgta 1440
atcagtgtgg tgcctccttc acacagaagg gcaatctgct tcgccacatc aagctgcact 1500

-continued

```
cgggggagaa gcccttcaag tgccccttct gcaactatgc ctgccgccgg cgtgacgcac   1560
tcactggcca cctccgcaca cactcagtct cctcccccac cgtgggcaaa ccctacaagt   1620
gcaactactg tggccggagc tacaaacagc aaagtaccct ggaggagcac aaggagaggt   1680
gccacaacta cctacagagt ctcagcactg atgcccaagc tctgactggc cagccaggtg   1740
atgaaatccg tgacctggag atggtgcctg actcaatgct gcacccatcg actgaacggc   1800
caactttcat tgatcgtttg gccaacagcc tcaccaaacg caagcgttcc accccacaga   1860
agtttgtagg tgaaaagcag atgcgcttca gcctctcaga ccttccctat gatgtgaatg   1920
ccagcggtgg ctatgaaaag gacgtagagt tggtggcaca ccatggcctg gagcctggct   1980
ttggagggtc tctagccttt gtgggtacag agcatctgcg tcccctccgc ctcccaccca   2040
ccaactgcat ctcagaactc acacctgtca tcagctctgt gtacacccaa atgcagccca   2100
tccccagccg actggagctt ccagggtccc gagaagcagg tgagggaccg gaggacctgg   2160
gagatggagg tcccctcctt tatcgggccc gaggctctct gactgaccct ggggcatccc   2220
ccagcaatgg ctgccaggac tccacagata cagagagcaa ccacgaagac cggattggtg   2280
gggtggtatc ccttcctcag ggtcccccac cccaacctcc tcccaccata gtggtgggcc   2340
ggcacagtcc cgcctatgcc aaagaggacc ccaaaccaca ggaggggtta ctgcggggca   2400
ccccaggccc ctccaaggaa gtgcttcggg tggtgggtga gagtggtgag ccagtgaagg   2460
cctttaagtg tgaacactgc cgcatcctct ttctggacca cgtcatgttc accatccaca   2520
tgggctgcca cggcttcaga gaccctttttg agtgtaacat ctgtggttat cacagccagg   2580
atcggtatga gttctcttcc cacatcgtcc ggggggaaca taaggtgggc tagaagcttg   2640
cctcgagcag cgctgctcga gagatctacg ggtggcatcc ctgtgacccc tccccagtgc   2700
ctctcctggc cctggaagtt gccactccag tgcccaccag ccttgtccta ataaaattaa   2760
gttgcatcat tttgtctgac taggtgtcct tctataatat tatggggtgg aggggggtgg   2820
tatggagcaa ggggcaagtt gggaagacaa cctgtagggc ctgcggggtc tattgggaac   2880
caagctggag tgcagtggca caatcttggc tcactgcaat ctccgcctcc tgggttcaag   2940
cgattctcct gcctcagcct cccgagttgt tgggattcca ggcatgcatg accaggctca   3000
gctaattttt gtttttttgg tagagacggg gtttcaccat attggccagg ctggtctcca   3060
actcctaatc tcaggtgatc tacccacctt ggcctcccaa attgctggga ttacaggcgt   3120
gaaccactgc tcccttccct gtccttctga ttttgtaggt aaccacgtgc ggaccgagcg   3180
gccgcaggaa cccctagtga tggagttggc cactccctct ctgcgcgctc gctcgctcac   3240
tgaggccggg cgaccaaagg tcgcccgacg cccgggcttt gcccgggcgg cctcagtgag   3300
cgagcgagcg cgcagctgcc tgcaggggcg cctgatgcgg tattttctcc ttacgcatct   3360
gtgcggtatt tcacaccgca tacgtcaaag caaccatagt acgcgccctg tagcggcgca   3420
ttaagcgcgg cgggtgtggt ggttacgcgc agcgtgaccg ctacacttgc cagcgcccta   3480
gcgcccgctc ctttcgcttt cttcccttcc tttctcgcca cgttcgccgg ctttccccgt   3540
caagctctaa atcgggggct ccctttaggg ttccgattta gtgctttacg gcacctcgac   3600
cccaaaaaac ttgatttggg tgatggttca cgtagtgggc catcgccctg atagacggtt   3660
tttcgccctt tgacgttgga gtccacgttc tttaatagtg gactcttgtt ccaaactgga   3720
acaacactca accctatctc gggctattct tttgatttat aagggatttt gccgatttcg   3780
gcctattggt taaaaaatga gctgatttaa caaaaattta acgcgaattt taacaaaata   3840
ttaacgttta caattttatg gtgcactctc agtacaatct gctctgatgc cgcatagtta   3900
```

agccagcccc gacacccgcc aacacccgct gacgcgccct gacgggcttg tctgctcccg 3960
gcatccgctt acagacaagc tgtgaccgtc tccgggagct gcatgtgtca gaggttttca 4020
ccgtcatcac cgaaacgcgc gagacgaaag ggcctcgtga tacgcctatt tttataggtt 4080
aatgtcatga taataatggt ttcttagacg tcaggtggca cttttcgggg aaatgtgcgc 4140
ggaaccccta tttgtttatt tttctaaata cattcaaata tgtatccgct catgagacaa 4200
taaccctgat aaatgcttca ataatattga aaaaggaaga gtatgagtat tcaacatttc 4260
cgtgtcgccc ttattccctt ttttgcggca ttttgccttc ctgtttttgc tcacccagaa 4320
acgctggtga aagtaaaaga tgctgaagat cagttgggtg cacgagtggg ttacatcgaa 4380
ctggatctca acagcggtaa gatccttgag agttttcgcc ccgaagaacg ttttccaatg 4440
atgagcactt ttaaagttct gctatgtggc gcggtattat cccgtattga cgccgggcaa 4500
gagcaactcg gtcgccgcat acactattct cagaatgact tggttgagta ctcaccagtc 4560
acagaaaagc atcttacgga tggcatgaca gtaagagaat tatgcagtgc tgccataacc 4620
atgagtgata acactgcggc caacttactt ctgacaacga tcggaggacc gaaggagcta 4680
accgcttttt tgcacaacat gggggatcat gtaactcgcc ttgatcgttg ggaaccggag 4740
ctgaatgaag ccataccaaa cgacgagcgt gacaccacga tgcctgtagc aatggcaaca 4800
acgttgcgca aactattaac tggcgaacta cttactctag cttcccggca acaattaata 4860
gactggatgg aggcggataa agttgcagga ccacttctgc gctcggccct tccggctggc 4920
tggtttattg ctgataaatc tggagccggt gagcgtgggt ctcgcggtat cattgcagca 4980
ctggggccag atggtaagcc ctcccgtatc gtagttatct acacgacggg gagtcaggca 5040
actatggatg aacgaaatag acagatcgct gagataggtg cctcactgat taagcattgg 5100
taactgtcag accaagttta ctcatatata ctttagattg atttaaaact tcatttttaa 5160
tttaaaagga tctaggtgaa gatccttttt gataatctca tgaccaaaat cccttaacgt 5220
gagttttcgt tccactgagc gtcagacccc gtagaaaaga tcaaaggatc ttcttgagat 5280
cctttttttc tgcgcgtaat ctgctgcttg caaacaaaaa aaccaccgct accagcggtg 5340
gtttgtttgc cggatcaaga gctaccaact ctttttccga aggtaactgg cttcagcaga 5400
gcgcagatac caaatactgt ccttctagtg tagccgtagt taggccacca cttcaagaac 5460
tctgtagcac cgcctacata cctcgctctg ctaatcctgt taccagtggc tgctgccagt 5520
ggcgataagt cgtgtcttac cgggttggac tcaagacgat agttaccgga taaggcgcag 5580
cggtcgggct gaacgggggg ttcgtgcaca cagcccagct tggagcgaac gacctacacc 5640
gaactgagat acctacagcg tgagctatga gaaagcgcca cgcttcccga agggagaaag 5700
gcggacaggt atccggtaag cggcagggtc ggaacaggag agcgcacgag ggagcttcca 5760
gggggaaacg cctggtatct ttatagtcct gtcgggtttc gccacctctg acttgagcgt 5820
cgatttttgt gatgctcgtc aggggggcgg agcctatgga aaaacgccag caacgcggcc 5880
tttttacggt tcctggcctt ttgctggcct tttgctcaca t 5921

<210> SEQ ID NO 63
<211> LENGTH: 7979
<212> TYPE: DNA
<213> ORGANISM: Artificial sequence
<220> FEATURE:
<223> OTHER INFORMATION: synthetic construct

<400> SEQUENCE: 63

```
tcgacggatc gggagatctc ccgatcccct atggtgcact ctcagtacaa tctgctctga     60
tgccgcatag ttaagccagt atctgctccc tgcttgtgtg ttggaggtcg ctgagtagtg    120
cgcgagcaaa atttaagcta caacaaggca aggcttgacc gacaattgca tgaagaatct    180
gcttagggtt aggcgttttg cgctgcttcg cgatgtacgg gccagatata cgcgttgaca    240
ttgattattg actagttatt aatagtaatc aattacgggg tcattagttc atagcccata    300
tatggagttc cgcgttacat aacttacggt aaatggcccg cctggctgac cgcccaacga    360
cccccgccca ttgacgtcaa taatgacgta tgttcccata gtaacgccaa tagggacttt    420
ccattgacgt caatgggtgg agtatttacg gtaaactgcc cacttggcag tacatcaagt    480
gtatcatatg ccaagtacgc cccctattga cgtcaatgac ggtaaatggc ccgcctggca    540
ttatgcccag tacatgacct tatgggactt tcctacttgg cagtacatct acgtattagt    600
catcgctatt accatggtga tgcggttttg gcagtacatc aatgggcgtg gatagcggtt    660
tgactcacgg ggatttccaa gtctccaccc cattgacgtc aatgggagtt tgttttggca    720
ccaaaatcaa cgggactttc caaaatgtcg taacaactcc gccccattga cgcaaatggg    780
cggtaggcgt gtacggtggg aggtctatat aagcagcgcg ttttgcctgt actgggtctc    840
tctggttaga ccagatctga gcctgggagc tctctggcta actagggaac ccactgctta    900
agcctcaata aagcttgcct tgagtgcttc aagtagtgtg tgcccgtctg ttgtgtgact    960
ctggtaacta gagatccctc agaccctttt agtcagtgtg gaaaatctct agcagtggcg   1020
cccgaacagg gacttgaaag cgaaagggaa accagaggag ctctctcgac gcaggactcg   1080
gcttgctgaa gcgcgcacgg caagaggcga ggggcggcga ctggtgagta cgccaaaaat   1140
tttgactagc ggaggctaga aggagagaga tgggtgcgag agcgtcagta ttaagcgggg   1200
gagaattaga tcgcgatggg aaaaaattcg gttaaggcca gggggaaaga aaaaatataa   1260
attaaaacat atagtatggg caagcaggga gctagaacga ttcgcagtta atcctggcct   1320
gttagaaaca tcagaaggct gtagacaaat actgggacag ctacaaccat cccttcagac   1380
aggatcagaa gaacttagat cattatataa tacagtagca accctctatt gtgtgcatca   1440
aaggatagag ataaaagaca ccaaggaagc tttagacaag atagaggaag agcaaaacaa   1500
aagtaagacc accgcacagc aagcggccgc tgatcttcag acctggagga ggagatatga   1560
gggacaattg gagaagtgaa ttatataaat ataaagtagt aaaaattgaa ccattaggag   1620
tagcacccac caaggcaaag agaagagtgg tgcagagaga aaaaagagca gtgggaatag   1680
gagctttgtt ccttgggttc ttgggagcag caggaagcac tatgggcgca gcgtcaatga   1740
cgctgacggt acaggccaga caattattgt ctggtatagt gcagcagcag aacaatttgc   1800
tgagggctat tgaggcgcaa cagcatctgt tgcaactcac agtctggggc atcaagcagc   1860
tccaggcaag aatcctggct gtggaaagat acctaaagga tcaacagctc ctggggattt   1920
ggggttgctc tggaaaactc atttgcacca ctgctgtgcc ttggaatgct agttggagta   1980
ataaatctct ggaacagatt tggaatcaca cgacctggat ggagtgggac agagaaatta   2040
acaattacac aagcttaata cactccttaa ttgaagaatc gcaaaaccag caagaaaaga   2100
atgaacaaga attattggaa ttagataaat gggcaagttt gtggaattgg tttaacataa   2160
caaattggct gtggtatata aaattattca taatgatagt aggaggcttg gtaggtttaa   2220
gaatagtttt tgctgtactt tctatagtga atagagttag gcagggatat tcaccattat   2280
cgtttcagac ccacctccca accccgaggg gacccgacag gcccgaagga atagaagaag   2340
aaggtggaga gagagacaga gacagatcca ttcgattagt gaacggatcg gcactgcgtg   2400
```

```
cgccaattct gcagacaaat ggcagtattc atccacaatt ttaaaagaaa aggggggatt   2460
ggggggtaca gtgcagggga aagaatagta gacataatag caacagacat acaaactaaa   2520
gaattacaaa aacaaattac aaaaattcaa aattttcggg tttattacag ggacagcaga   2580
gatccagttt ggttaattaa cccgtgtcgg ctccagatct ggcctccgcg ccgggttttg   2640
gcgcctcccg cgggcgcccc cctcctcacg gcgagcgctg ccacgtcaga cgaagggcgc   2700
agcgagcgtc ctgatccttc cgcccggacg ctcaggacag cggcccgctg ctcataagac   2760
tcggccttag aaccccagta tcagcagaag gacattttag gacgggactt gggtgactct   2820
agggcactgg ttttctttcc agagagcgga acaggcgagg aaaagtagtc ccttctcggc   2880
gattctgcgg agggatctcc gtggggcggt gaacgccgat gattatataa ggacgcgccg   2940
ggtgtggcac agctagttcc gtcgcagccg ggatttgggt cgcggttctt gtttgtggat   3000
cgctgtgatc gtcacttggt gagtagcggg ctgctgggct ggccggggct ttcgtggccg   3060
ccgggccgct cggtgggacg gaagcgtgtg gagagaccgc caagggctgt agtctgggtc   3120
cgcgagcaag gttgccctga actgggggtt ggggggagcg cagcaaaatg gcggctgttc   3180
ccgagtcttg aatggaagac gcttgtgagg cgggctgtga ggtcgttgaa acaaggtggg   3240
gggcatggtg ggcggcaaga acccaaggtc ttgaggcctt cgctaatgcg ggaaagctct   3300
tattcgggtg agatgggctg gggcaccatc tggggaccct gacgtgaagt ttgtcactga   3360
ctggagaact cggtttgtcg tctgttgcgg gggcggcagt tatggcggtg ccgttgggca   3420
gtgcacccgt acctttggga gcgcgcgccc tcgtcgtgtc gtgacgtcac ccgttctgtt   3480
ggcttataat gcagggtggg gccacctgcc ggtaggtgtg cggtaggctt ttctccgtcg   3540
caggacgcag ggttcgggcc tagggtaggc tctcctgaat cgacaggcgc cggacctctg   3600
gtgaggggag ggataagtga ggcgtcagtt tctttggtcg gttttatgta cctatcttct   3660
taagtagctg aagctccggt tttgaactat gcgctcgggg ttggcgagtg tgttttgtga   3720
agttttttag gcaccttttg aaatgtaatc atttgggtca atatgtaatt ttcagtgtta   3780
gactagtaaa ttgtccgcta aattctggcc gtttttggct tttttgttag acgaagcttg   3840
ggcccgggaa ttaattcacc atgtctagac tggacaagag caaagtcata aacggcgctc   3900
tggaattact caatggagtc ggtatcgaag gcctgacgac aaggaaactc gctcaaaagc   3960
tgggagttga gcagcctacc ctgtactggc acgtgaagaa caagcgggcc ctgctcgatg   4020
ccctgccaat cgagatgctg gacaggcatc atacccactt ctgccccctg gaaggcgagt   4080
catggcaaga ctttctgcgg aacaacgcca agtcattccg ctgtgctctc ctctcacatc   4140
gcgacggggc taaagtgcat ctcggcaccc gcccaacaga gaaacagtac gaaaccctgg   4200
aaaatcagct cgcgttcctg tgtcagcaag gcttctccct ggagaacgca ctgtacgctc   4260
tgtccgccgt gggccacttt acactgggct gcgtattgga ggaacaggag catcaagtag   4320
caaaagagga aagagagaca cctaccaccg attctatgcc cccacttctg agacaagcaa   4380
ttgagctgtt cgaccggcag ggagccgaac ctgccttcct tttcggcctg gaactaatca   4440
tatgtggcct ggagaaacag ctaaagtgcg aaagcggcgg gccggccgac gcccttgacg   4500
attttgactt agacatgctc ccagccgatg cccttgacga ctttgacctt gatatgctgc   4560
ctgctgacgc tcttgacgat tttgaccttg acatgctccc cgggtaacta agtaaggatc   4620
aattcgatat caagcttatc gataatcaac ctctggatta caaaatttgt gaaagattga   4680
ctggtattct taactatgtt gctcctttta cgctatgtgg atacgctgct ttaatgcctt   4740
```

tgtatcatgc tattgcttcc cgtatggctt tcattttctc ctccttgtat aaatcctggt 4800
tgctgtctct ttatgaggag ttgtggcccg ttgtcaggca acgtggcgtg gtgtgcactg 4860
tgtttgctga cgcaaccccc actggttggg gcattgccac cacctgtcag ctcctttccg 4920
ggactttcgc tttccccctc cctattgcca cggcggaact catcgccgcc tgccttgccc 4980
gctgctggac aggggctcgg ctgttgggca ctgacaattc cgtggtgttg tcggggaaat 5040
catcgtcctt tccttggctg ctcgcctgtg ttgccacctg gattctgcgc gggacgtcct 5100
tctgctacgt cccttcggcc ctcaatccag cggaccttcc ttcccgcggc ctgctgccgg 5160
ctctgcggcc tcttccgcgt cttcgccttc gccctcagac gagtcggatc tccctttggg 5220
ccgcctcccc gcatcgatac cgtcgacctc gagacctaga aaaacatgga gcaatcacaa 5280
gtagcaatac agcagctacc aatgctgatt gtgcctggct agaagcacaa gaggaggagg 5340
aggtgggttt tccagtcaca cctcaggtac ctttaagacc aatgacttac aaggcagctg 5400
tagatcttag ccacttttta aaagaaaagg ggggactgga agggctaatt cactcccaac 5460
gaagacaaga tatccttgat ctgtggatct accacacaca aggctacttc cctgattggc 5520
agaactacac accagggcca gggatcagat atccactgac ctttggatgg tgctacaagc 5580
tagtaccagt tgagcaagag aaggtagaag aagccaatga aggagagaac acccgcttgt 5640
tacaccctgt gagcctgcat gggatggatg acccggagag agaagtatta gagtggaggt 5700
ttgacagccg cctagcattt catcacatgg cccgagagct gcatccggac tgtactgggt 5760
ctctctggtt agaccagatc tgagcctggg agctctctgg ctaactaggg aacccactgc 5820
ttaagcctca ataaagcttg ccttgagtgc ttcaagtagt gtgtgcccgt ctgttgtgtg 5880
actctggtaa ctagagatcc ctcagaccct tttagtcagt gtggaaaatc tctagcaggg 5940
cccgtttaaa cccgctgatc agcctcgact gtgccttcta gttgccagcc atctgttgtt 6000
tgcccctccc ccgtgccttc cttgaccctg gaaggtgcca ctcccactgt cctttcctaa 6060
taaaatgagg aaattgcatc gcattgtctg agtaggtgtc attctattct ggggggtggg 6120
gtggggcagg acagcaaggg ggaggattgg gaagacaata gcaggcatgt gagcaaaagg 6180
ccagcaaaag gccaggaacc gtaaaaaggc cgcgttgctg gcgtttttcc ataggctccg 6240
ccccctgac gagcatcaca aaaatcgacg ctcaagtcag aggtggcgaa acccgacagg 6300
actataaaga taccaggcgt ttccccctgg aagctccctc gtgcgctctc ctgttccgac 6360
cctgccgctt accggatacc tgtccgcctt tctcccttcg ggaagcgtgg cgctttctca 6420
tagctcacgc tgtaggtatc tcagttcggt gtaggtcgtt cgctccaagc tgggctgtgt 6480
gcacgaaccc cccgttcagc ccgaccgctg cgccttatcc ggtaactatc gtcttgagtc 6540
caacccggta agacacgact tatcgccact ggcagcagcc actggtaaca ggattagcag 6600
agcgaggtat gtaggcggtg ctacagagtt cttgaagtgg tggcctaact acggctacac 6660
tagaagaaca gtatttggta tctgcgctct gctgaagcca gttaccttcg gaaaaagagt 6720
tggtagctct tgatccggca aacaaaccac cgctggtagc ggtggttttt ttgtttgcaa 6780
gcagcagatt acgcgcagaa aaaaaggatc tcaagaagat cctttgatct tttctacggg 6840
gtctgacgct cagtggaacg aaaactcacg ttaagggatt ttggtcatga gattatcaaa 6900
aaggatcttc acctagatcc ttttaaatta aaaatgaagt tttaaatcaa tctaaagtat 6960
atatgagtaa acttggtctg acagttacca atgcttaatc agtgaggcac ctatctcagc 7020
gatctgtcta tttcgttcat ccatagttgc ctgactcccc gtcgtgtaga taactacgat 7080
acgggagggc ttaccatctg gccccagtgc tgcaatgata ccgcgagacc cacgctcacc 7140
ggctccagat ttatcagcaa taaaccagcc agccggaagg gccgagcgca gaagtggtcc 7200
tgcaacttta tccgcctcca tccagtctat taattgttgc cgggaagcta gagtaagtag 7260
ttcgccagtt aatagtttgc gcaacgttgt tgccattgct acaggcatcg tggtgtcacg 7320
ctcgtcgttt ggtatggctt cattcagctc cggttcccaa cgatcaaggc gagttacatg 7380
atcccccatg ttgtgcaaaa aagcggttag ctccttcggt cctccgatcg ttgtcagaag 7440
taagttggcc gcagtgttat cactcatggt tatggcagca ctgcataatt ctcttactgt 7500
catgccatcc gtaagatgct tttctgtgac tggtgagtac tcaaccaagt cattctgaga 7560
atagtgtatg cggcgaccga gttgctcttg cccggcgtca atacgggata ataccgcgcc 7620
acatagcaga actttaaaag tgctcatcat tggaaaacgt tcttcggggc gaaaactctc 7680
aaggatctta ccgctgttga gatccagttc gatgtaaccc actcgtgcac ccaactgatc 7740
ttcagcatct tttactttca ccagcgtttc tgggtgagca aaaacaggaa ggcaaaatgc 7800
cgcaaaaaag ggaataaggg cgacacggaa atgttgaata ctcatactct tcctttttca 7860
atattattga agcatttatc agggttattg tctcatgagc ggatacatat ttgaatgtat 7920
ttagaaaaat aaacaaatag gggttccgcg cacatttccc cgaaaagtgc cacctgacg 7979

<210> SEQ ID NO 64
<211> LENGTH: 9714
<212> TYPE: DNA
<213> ORGANISM: Artificial sequence
<220> FEATURE:
<223> OTHER INFORMATION: synthetic construct

<400> SEQUENCE: 64
cgcgtatgca tctcgagggc ccggtacctt taagaccaat gacttacaag gcagctgtag 60
atcttagcca ctttttaaaa gaaaaggggg gactggaagg gctagctcac tcccaacgaa 120
gacaagatct gctttttgct tgtactgggt ctctctggtt agaccagatc tgagcctggg 180
agctctctgg ctaactaggg aacccactgc ttaagcctca ataaagcttg ccttgagtgc 240
ttcaagtagt gtgtgcccgt ctgttgtgtg actctggtaa ctagagatcc ctcagaccct 300
tttagtcagt gtggaaaatc tctagcagta gtagttcatg tcatcttatt attcagtatt 360
tataacttgc aaagaaatga atatcagaga gtgagaggaa cttgtttatt gcagcttata 420
atggttacaa ataaagcaat agcatcacaa atttcacaaa taaagcattt ttttcactgc 480
attctagttg tggtttgtcc aaactcatca atgtatctta tcatgtctgg ctctagctat 540
cccgccccta actccgccca gttccgccca ttctccgccc catggctgac taattttttt 600
tatttatgca gaggccgagg ccgcctcggc ctctgagcta ttccagaagt agtgaggagg 660 ctttttgga ggcctaggct tttgcgtcga gacgtaccca attcgcccta tagtgagtcg 720
tattacgcgc gctcactggc cgtcgtttta caacgtcgtg actgggaaaa ccctggcgtt 780
acccaactta atcgccttgc agcacatccc cctttcgcca gctggcgtaa tagcgaagag 840
gcccgcaccg atcgcccttc ccaacagttg cgcagcctga atggcgaatg gcgcgacgcg 900
ccctgtagcg gcgcattaag cgcggcgggt gtggtggtta cgcgcagcgt gaccgctaca 960
cttgccagcg ccctagcgcc cgctcctttc gctttcttcc cttcctttct cgccacgttc 1020
gccggctttc cccgtcaagc tctaaatcgg gggctccctt tagggttccg atttagtgct 1080
ttacggcacc tcgaccccaa aaaacttgat tagggtgatg gttcacgtag tgggccatcg 1140
ccctgataga cggtttttcg ccctttgacg ttggagtcca cgttctttaa tagtggactc 1200

```
ttgttccaaa ctggaacaac actcaaccct atctcggtct attcttttga tttataaggg   1260
attttgccga tttcggccta ttggttaaaa aatgagctga tttaacaaaa atttaacgcg   1320
aattttaaca aaatattaac gtttacaatt tcccaggtgg cacttttcgg ggaaatgtgc   1380
gcggaacccc tatttgttta tttttctaaa tacattcaaa tatgtatccg ctcatgagac   1440
aataaccctg ataaatgctt caataatatt gaaaaaggaa gagtatgagt attcaacatt   1500
tccgtgtcgc ccttattccc ttttttgcgg cattttgcct tcctgttttt gctcacccag   1560
aaacgctggt gaaagtaaaa gatgctgaag atcagttggg tgcacgagtg ggttacatcg   1620
aactggatct caacagcggt aagatccttg agagttttcg ccccgaagaa cgttttccaa   1680
tgatgagcac ttttaaagtt ctgctatgtg gcgcggtatt atcccgtatt gacgccgggc   1740
aagagcaact cggtcgccgc atacactatt ctcagaatga cttggttgag tactcaccag   1800
tcacagaaaa gcatcttacg gatggcatga cagtaagaga attatgcagt gctgccataa   1860
ccatgagtga taacactgcg gccaacttac ttctgacaac gatcggagga ccgaaggagc   1920
taaccgcttt tttgcacaac atgggggatc atgtaactcg ccttgatcgt tgggaaccgg   1980
agctgaatga agccatacca aacgacgagc gtgacaccac gatgcctgta gcaatggcaa   2040
caacgttgcg caaactatta actggcgaac tacttactct agcttcccgg caacaattaa   2100
tagactggat ggaggcggat aaagttgcag gaccacttct gcgctcggcc cttccggctg   2160
gctggtttat tgctgataaa tctggagccg gtgagcgtgg gtctcgcggt atcattgcag   2220
cactggggcc agatggtaag ccctcccgta tcgtagttat ctacacgacg gggagtcagg   2280
caactatgga tgaacgaaat agacagatcg ctgagatagg tgcctcactg attaagcatt   2340
ggtaactgtc agaccaagtt tactcatata tactttagat tgatttaaaa cttcattttt   2400
aatttaaaag gatctaggtg aagatccttt ttgataatct catgaccaaa atcccttaac   2460
gtgagttttc gttccactga gcgtcagacc ccgtagaaaa gatcaaagga tcttcttgag   2520
atcctttttt tctgcgcgta atctgctgct tgcaaacaaa aaaaccaccg ctaccagcgg   2580
tggtttgttt gccggatcaa gagctaccaa ctctttttcc gaaggtaact ggcttcagca   2640
gagcgcagat accaaatact gtccttctag tgtagccgta gttaggccac cacttcaaga   2700
actctgtagc accgcctaca tacctcgctc tgctaatcct gttaccagtg gctgctgcca   2760
gtggcgataa gtcgtgtctt accgggttgg actcaagacg atagttaccg gataaggcgc   2820
agcggtcggg ctgaacgggg ggttcgtgca cacagcccag cttggagcga acgacctaca   2880
ccgaactgag atacctacag cgtgagctat gagaaagcgc cacgcttccc gaagggagaa   2940
aggcggacag gtatccggta agcggcaggg tcggaacagg agagcgcacg agggagcttc   3000
caggggggaaa cgcctggtat ctttatagtc ctgtcgggtt tcgccacctc tgacttgagc   3060
gtcgattttt gtgatgctcg tcaggggggc ggagcctatg gaaaaacgcc agcaacgcgg   3120
cctttttacg gttcctggcc ttttgctggc cttttgctca catgttcttt cctgcgttat   3180
cccctgattc tgtggataac cgtattaccg cctttgagtg agctgatacc gctcgccgca   3240
gccgaacgac cgagcgcagc gagtcagtga gcgaggaagc ggaagagcgc ccaatacgca   3300
aaccgcctct ccccgcgcgt tggccgattc attaatgcag ctggcacgac aggtttcccg   3360
actggaaagc gggcagtgag cgcaacgcaa ttaatgtgag ttagctcact cattaggcac   3420
cccaggcttt acactttatg cttccggctc gtatgttgtg tggaattgtg agcggataac   3480
aatttcacac aggaaacagc tatgaccatg attacgccaa gcgcgcaatt aaccctcact   3540
aaagggaaca aaagctggag ctgcaagctt aatgtagtct tatgcaatac tcttgtagtc   3600
```

```
ttgcaacatg gtaacgatga gttagcaaca tgccttacaa ggagagaaaa agcaccgtgc   3660
atgccgattg gtggaagtaa ggtggtacga tcgtgcctta ttaggaaggc aacagacggg   3720
tctgacatgg attggacgaa ccactgaatt gccgcattgc agagatattg tatttaagtg   3780
cctagctcga tacaataaac gggtctctct ggttagacca gatctgagcc tgggagctct   3840
ctggctaact agggaaccca ctgcttaagc ctcaataaag cttgccttga gtgcttcaag   3900
tagtgtgtgc ccgtctgttg tgtgactctg gtaactagag atccctcaga cccttttagt   3960
cagtgtggaa aatctctagc agtggcgccc gaacagggac ctgaaagcga aagggaaacc   4020
agagctctct cgacgcagga ctcggcttgc tgaagcgcgc acggcaagag gcgaggggcg   4080
gcgactggtg agtacgccaa aaattttgac tagcggaggc tagaaggaga gagatgggtg   4140
cgagagcgtc agtattaagc gggggagaat tagatcgcga tgggaaaaaa ttcggttaag   4200
gccaggggga aagaaaaaat ataaattaaa acatatagta tgggcaagca gggagctaga   4260
acgattcgca gttaatcctg gcctgttaga aacatcagaa ggctgtagac aaatactggg   4320
acagctacaa ccatcccttc agacaggatc agaagaactt agatcattat ataatacagt   4380
agcaaccctc tattgtgtgc atcaaaggat agagataaaa gacaccaagg aagctttaga   4440
caagatagag gaagagcaaa acaaaagtaa gaccaccgca cagcaagcgg ccgctgatct   4500
tcagacctgg aggaggagat atgagggaca attggagaag tgaattatat aaatataaag   4560
tagtaaaaat tgaaccatta ggagtagcac ccaccaaggc aaagagaaga gtggtgcaga   4620
gagaaaaaag agcagtggga ataggagctt tgttccttgg gttcttggga gcagcaggaa   4680
gcactatggg cgcagcctca atgacgctga cggtacaggc cagacaatta ttgtctggta   4740
tagtgcagca gcagaacaat ttgctgaggg ctattgaggc gcaacagcat ctgttgcaac   4800
tcacagtctg gggcatcaag cagctccagg caagaatcct ggctgtggaa agatacctaa   4860
aggatcaaca gctcctgggg atttggggtt gctctggaaa actcatttgc accactgctg   4920
tgccttggaa tgctagttgg agtaataaat ctctggaaca gattggaatc acacgacctg   4980
gatggagtgg gacagagaaa ttaacaatta cacaagctta atacactcct taattgaaga   5040
atcgcaaaac cagcaagaaa agaatgaaca agaattattg gaattagata aatgggcaag   5100
tttgtggaat tggtttaaca taacaaattg gctgtggtat ataaaattat tcataatgat   5160
agtaggaggc ttggtaggtt taagaatagt ttttgctgta ctttctatag tgaatagagt   5220
taggcaggga tattcaccat tatcgtttca gacccacctc ccaaccccga ggggacccga   5280
caggcccgaa ggaatagaag aagaaggtgg agagagagac agagacagat ccattcgatt   5340
agtgaacgga tctcgacggt taacttttaa aagaaaaggg gggattgggg ggtacagtgc   5400
aggggaaaga atagtagaca taatagcaac agacatacaa actaaagaat tacaaaaaca   5460
aattacaaaa attcaaaatt ttattccagt gtggtggaat tgagtattcc agtgtggtgg   5520
aattctgcag atatcaacaa gtttgtacaa aaaagcaggc ttatccctat cagtgataga   5580
gaaaagtgaa agtcgagttt accactccct atcagtgata gagaaaagtg aaagtcgagt   5640
ttaccactcc ctatcagtga tagagaaaag tgaaagtcga gtttaccact ccctatcagt   5700
gatagagaaa agtgaaagtc gagtttacca ctccctatca gtgatagaga aaagtgaaag   5760
tcgagtttac cactccctat cagtgataga gaaaagtgaa agtcgagttt accactccct   5820
atcagtgata gagaaaagtg aaagtcgagc tcggtacccg ggtcgaggta ggcgtgtacg   5880
gtgggaggcc tatataagca gagctcgttt agtgaaccgt cagatcgcct ggagacgcca   5940
```

tccacgctgt tttgacctcc atagaagaca ccgggaccga tccagcctcc gcggccccga 6000
attcatggat gtcgatgagg gtcaagacat gtcccaagtt tcaggaaagg agagcccccc 6060
agtcagtgac actccagatg aaggggatga gcccatgcct gtccctgagg acctgtccac 6120
tacctctgga gcacagcaga actccaagag tgatcgaggc atggccagta atgttaaagt 6180
agagactcag agtgatgaag agaatgggcg tgcctgtgaa atgaatgggg aagaatgtgc 6240
agaggattta cgaatgcttg atgcctcggg agagaaaatg aatggctccc acagggacca 6300
aggcagctcg gctttgtcag gagttggagg cattcgactt cctaacggaa aactaaagtg 6360
tgatatctgt gggatcgttt gcatcgggcc caatgtgctc atggttcaca aaagaagtca 6420
tactggtgaa cggcctttcc agtgcaacca gtgtggggcc tcctttaccc agaaaggcaa 6480
cctcctgcgg cacatcaagc tgcactcggg tgagaagccc ttcaaatgcc atctttgcaa 6540
ctatgcctgc cgccggaggg acgccctcac cggccacctg aggacgcact ccgttggtaa 6600
gcctcacaaa tgtggatatt gtggccggag ctataaacag cgaagctctt tagaggagca 6660
taaagagcga tgccacaact acttggaaag catgggcctt ccgggcatgt acccagtcat 6720
taaggaagaa actaaccaca acgagatggc agaagacctg tgcaagatag gagcagagag 6780
gtcccttgtc ctggacaggc tggcaagcaa tgtcgccaaa cgtaagagct ctatgcctca 6840
gaaatttctt ggagacaagt gcctgtcaga catgccctat gacagtgcca actatgagaa 6900
ggaggatatg atgacatccc acgtgatgga ccaggccatc aacaatgcca tcaactacct 6960
gggggctgag tccctgcgcc cattggtgca gacacccccc ggtagctccg aggtggtgcc 7020
agtcatcagc tccatgtacc agctgcacaa gcccccctca gatggccccc cacggtccaa 7080
ccattcagca caggacgccg tggataactt gctgctgctg tccaaggcca agtctgtgtc 7140
atcggagcga gaggcctccc cgagcaacag ctgccaagac tccacagata cagagagcaa 7200
cgcggaggaa cagcgcagcg gccttatcta cctaaccaac cacatcaacc cgcatgcacg 7260
caatgggctg gctctcaagg aggagcagcg cgcctacgag gtgctgaggg cggcctcaga 7320
gaactcgcag gatgccttcc gtgtggtcag cacgagtggc gagcagctga aggtgtacaa 7380
gtgcgaacac tgccgcgtgc tcttcctgga tcacgtcatg tataccattc acatgggctg 7440
ccatggcttt cgggatccct ttgagtgtaa catgtgtggt tatcacagcc aggacaggta 7500
cgagttctca tcccatatca cgcgggggga gcatcgttac cacctgagct aaaacccagc 7560
tttcttgtac aaagtggttg atatccagca cagtggcggc cgctcgacaa tcaacctctg 7620
gattacaaaa tttgtgaaag attgactggt attcttaact atgttgctcc ttttacgcta 7680
tgtggatacg ctgctttaat gcctttgtat catgctattg cttcccgtat ggctttcatt 7740
ttctcctcct tgtataaatc ctggttgctg tctctttatg aggagttgtg gcccgttgtc 7800
aggcaacgtg gcgtggtgtg cactgtgttt gctgacgcaa cccccactgg ttggggcatt 7860
gccaccacct gtcagctcct ttccgggact ttcgctttcc ccctccctat tgccacggcg 7920
gaactcatcg ccgcctgcct tgcccgctgc tggacagggg ctcggctgtt gggcactgac 7980
aattccgtgg tgttgtcggg gaagctgacg tcctttccat ggctgctcgc ctgtgttgcc 8040
acctggattc tgcgcgggac gtccttctgc tacgtccctt cggccctcaa tccagcggac 8100
cttccttccc gcggcctgct gccggctctg cggcctcttc cgcgtcttcg ccttcgccct 8160
cagacgagtc ggatctccct ttgggccgcc tccccgcctg gaattctacc gggtagggga 8220
ggcgcttttc ccaaggcagt ctggagcatg cgctttagca gccccgctgg gcacttggcg 8280
ctacacaagt ggcctctggc ctcgcacaca ttccacatcc accggtaggc gccaaccggc 8340
tccgttcttt ggtggcccct tcgcgccacc ttctactcct cccctagtca ggaagttccc 8400
ccccgccccg cagctcgcgt cgtgcaggac gtgacaaatg gaagtagcac gtctcactag 8460
tctcgtgcag atggacagca ccgctgagca atggaagcgg gtaggccttt ggggcagcgg 8520
ccaatagcag ctttgctcct tcgctttctg ggctcagagg ctgggaaggg gtgggtccgg 8580
gggcgggctc aggggcgggc tcaggggcgg ggcgggcgcc cgaaggtcct ccggaggccc 8640
ggcattctgc acgcttcaaa agcgcacgtc tgccgcgctg ttctcctctt cctcatctcc 8700
gggcctttcg acctgcagcc caagcttacc acactcctgc atctgccgcc accatggcgg 8760
aaggatccgt cgccaggcag cctgacctct tgacctgcga cgatgagccg atccatatcc 8820
ccggtgccat ccaaccgcat ggactgctgc tcgccctcgc cgccgacatg acgatcgttg 8880
ccggcagcga caaccttccc gaactcaccg gactggcgat cggcgccctg atcggccgct 8940
ctgcggccga tgtcttcgac tcggagacgc acaaccgtct gacgatcgcc ttggccgagc 9000
ccggggcggc cgtcggagca ccgatcactg tcggcttcac gatgcgaaag gacgcaggct 9060
tcatcggctc ctggcatcgc catgatcagc tcatcttcct cgagctcgag cctccccagc 9120
gggacgtcgc cgagccgcag gcgttcttcc gccgcaccaa cagcgccatc cgccgcctgc 9180
aggccgccga aaccttggaa agcgcctgcg ccgccgcggc gcaagaggtg cggaagatta 9240
ccggcttcga tcgggtgatg atctatcgct tcgcctccga cttcagcggc gaagtgatcg 9300
cagaggatcg gtgcgccgag gtcgagtcaa aactaggcct gcactatcct gcctcaaccg 9360
tgccggcgca ggcccgtcgg ctctatacca tcaacccggt acggatcatt cccgatatca 9420
attatcggcc ggtgccggtc accccagacc tcaatccggt caccgggcgg ccgattgatc 9480
ttagcttcgc catcctgcgc agcgtctcgc ccgtccatct ggaattcatg cgcaacatag 9540
gcatgcacgg cacgatgtcg atctcgattt tgcgcggcga gcgactgtgg ggattgatcg 9600
tttgccatca ccgaacgccg tactacgtcg atctcgatgg ccgccaagcc tgcgagctag 9660
tcgcccaggt tctggcctgg cagatcggcg tgatggaaga gtgagtcgac gcga 9714

<210> SEQ ID NO 65
<211> LENGTH: 9120
<212> TYPE: DNA
<213> ORGANISM: Artificial sequence
<220> FEATURE:
<223> OTHER INFORMATION: synthetic construct

<400> SEQUENCE: 65
cgcgttgaca ttgattattg actagttatt aatagtaatc aattacgggg tcattagttc 60
atagcccata tatggagttc cgcgttacat aacttacggt aaatggcccg cctggctgac 120
cgcccaacga cccccgccca ttgacgtcaa taatgacgta tgttcccata gtaacgccaa 180
tagggacttt ccattgacgt caatgggtgg agtatttacg gtaaactgcc cacttggcag 240
tacatcaagt gtatcatatg ccaagtacgc cccctattga cgtcaatgac ggtaaatggc 300
ccgcctggca ttatgcccag tacatgacct tatgggactt tcctacttgg cagtacatct 360
acgtattagt catcgctatt accatggtga tgcggttttg gcagtacatc aatgggcgtg 420
gatagcggtt tgactcacgg ggatttccaa gtctccaccc cattgacgtc aatgggagtt 480
tgttttggca ccaaaatcaa cgggactttc caaaatgtcg taacaactcc gccccattga 540
cgcaaatggg cggtaggcgt gtacggtggg aggtctatat aagcagcgcg ttttgcctgt 600
actgggtctc tctggttaga ccagatctga gcctgggagc tctctggcta actagggaac 660

```
ccactgctta agcctcaata aagcttgcct tgagtgcttc aagtagtgtg tgcccgtctg    720
ttgtgtgact ctggtaacta gagatccctc agaccctttt agtcagtgtg gaaaatctct    780
agcagtggcg cccgaacagg gacttgaaag cgaaagggaa accagaggag ctctctcgac    840
gcaggactcg gcttgctgaa gcgcgcacgg caagaggcga ggggcggcga ctggtgagta    900
cgccaaaaat tttgactagc ggaggctaga aggagagaga tgggtgcgag agcgtcagta    960
ttaagcgggg gagaattaga tcgcgatggg aaaaaattcg gttaaggcca gggggaaaga   1020
aaaaatataa attaaaacat atagtatggg caagcaggga gctagaacga ttcgcagtta   1080
atcctggcct gttagaaaca tcagaaggct gtagacaaat actgggacag ctacaaccat   1140
cccttcagac aggatcagaa gaacttagat cattatataa tacagtagca accctctatt   1200
gtgtgcatca aaggatagag ataaaagaca ccaaggaagc tttagacaag atagaggaag   1260
agcaaaacaa aagtaagacc accgcacagc aagcggccgc tgatcttcag acctggagga   1320
ggagatatga gggacaattg gagaagtgaa ttatataaat ataaagtagt aaaaattgaa   1380
ccattaggag tagcacccac caaggcaaag agaagagtgg tgcagagaga aaaaagagca   1440
gtgggaatag gagctttgtt ccttgggttc ttgggagcag caggaagcac tatgggcgca   1500
gcgtcaatga cgctgacggt acaggccaga caattattgt ctggtatagt gcagcagcag   1560
aacaatttgc tgagggctat tgaggcgcaa cagcatctgt tgcaactcac agtctggggc   1620
atcaagcagc tccaggcaag aatcctggct gtggaaagat acctaaagga tcaacagctc   1680
ctggggattt ggggttgctc tggaaaactc atttgcacca ctgctgtgcc ttggaatgct   1740
agttggagta ataaatctct ggaacagatt tggaatcaca cgacctggat ggagtgggac   1800
agagaaatta acaattacac aagcttaata cactccttaa ttgaagaatc gcaaaaccag   1860
caagaaaaga atgaacaaga attattggaa ttagataaat gggcaagttt gtggaattgg   1920
tttaacataa caaattggct gtggtatata aaattattca taatgatagt aggaggcttg   1980
gtaggtttaa gaatagtttt tgctgtactt tctatagtga atagagttag gcagggatat   2040
tcaccattat cgtttcagac ccacctccca accccgaggg gacccgacag gcccgaagga   2100
atagaagaag aaggtggaga gagagacaga gacagatcca ttcgattagt gaacggatcg   2160
gcactgcgtg cgccaattct gcagacaaat ggcagtattc atccacaatt ttaaaagaaa   2220
aggggggatt ggggggtaca gtgcagggga aagaatagta gacataatag caacagacat   2280
acaaactaaa gaattacaaa aacaaattac aaaaattcaa aattttcggg tttattacag   2340
ggacagcaga gatccagttt ggttagatct cgagtttacc actccctatc agtgatagag   2400
aaaagtgaaa gtcgagttta ccactcccta tcagtgatag agaaaagtga aagtcgagtt   2460
taccactccc tatcagtgat agagaaaagt gaaagtcgag tttaccactc cctatcagtg   2520
atagagaaaa gtgaaagtcg agtttaccac tccctatcag tgatagagaa aagtgaaagt   2580
cgagtttacc actccctatc agtgatagag aaaagtgaaa gtcgagttta ccactcccta   2640
tcagtgatag agaaaagtga aagtcgagct cggtacccgg gtcgaggtag gcgtgtacgg   2700
tgggaggcct atataagcag agctcgttta gtgaaccgtc agatcgcctg gagacgccat   2760
ccacgctgtt ttgacctcca tagaagacac cgggaccgat ccagcctccg cggccccgaa   2820
ttccgccacc atggtgagca agggcgagga gctgttcacc ggggtggtgc ccatcctggt   2880
cgagctggac ggcgacgtaa acggccacaa gttcagcgtg tccggcgagg gcgagggcga   2940
tgccacctac ggcaagctga ccctgaagtt catctgcacc accggcaagc tgcccgtgcc   3000
ctggcccacc ctcgtgacca ccctgaccta cggcgtgcag tgcttcagcc gctaccccga   3060
```

ccacatgaag cagcacgact tcttcaagtc cgccatgccc gaaggctacg tccaggagcg 3120
caccatcttc ttcaaggacg acggcaacta caagacccgc gccgaggtga agttcgaggg 3180
cgacaccctg gtgaaccgca tcgagctgaa gggcatcgac ttcaaggagg acggcaacat 3240
cctggggcac aagctggagt acaactacaa cagccacaac gtctatatca tggccgacaa 3300
gcagaagaac ggcatcaagg tgaacttcaa gatccgccac aacatcgagg acggcagcgt 3360
gcagctcgcc gaccactacc agcagaacac ccccatcggc gacggccccg tgctgctgcc 3420
cgacaaccac tacctgagca cccagtccgc cctgagcaaa gaccccaacg agaagcgcga 3480
tcacatggtc ctgctggagt tcgtgaccgc cgccgggatc actctcggca tggacgagct 3540
gtacaagtaa acgcgtgaat tcgatatcaa gcttatcgat aatcaacctc tggattacaa 3600
aatttgtgaa agattgactg gtattcttaa ctatgttgct ccttttacgc tatgtggata 3660
cgctgcttta atgcctttgt atcatgctat tgcttcccgt atggctttca ttttctcctc 3720
cttgtataaa tcctggttgc tgtctcttta tgaggagttg tggcccgttg tcaggcaacg 3780
tggcgtggtg tgcactgtgt ttgctgacgc aacccccact ggttggggca ttgccaccac 3840
ctgtcagctc ctttccggga ctttcgcttt ccccctccct attgccacgg cggaactcat 3900
cgccgcctgc cttgcccgct gctggacagg ggctcggctg ttgggcactg acaattccgt 3960
ggtgttgtcg gggaaatcat cgtcctttcc ttggctgctc gcctgtgttg ccacctggat 4020
tctgcgcggg acgtccttct gctacgtccc ttcggccctc aatccagcgg accttccttc 4080
ccgcggcctg ctgccggctc tgcggcctct tccgcgtctt cgccttcgcc ctcagacgag 4140
tcggatctcc ctttgggccg cctccccgca tcgataccgt cgacctcgag acctagaaaa 4200
acatggagca atcacaagta gcaatacagc agctaccaat gctgattgtg cctggctaga 4260
agcacaagag gaggaggagg tgggttttcc agtcacacct caggtacctt taagaccaat 4320
gacttacaag gcagctgtag atcttagcca ctttttaaaa gaaaaggggg gactggaagg 4380
gctaattcac tcccaacgaa gacaagatat ccttgatctg tggatctacc acacacaagg 4440
ctacttccct gattggcaga actacacacc agggccaggg atcagatatc cactgacctt 4500
tggatggtgc tacaagctag taccagttga gcaagagaag gtagaagaag ccaatgaagg 4560
agagaacacc cgcttgttac accctgtgag cctgcatggg atggatgacc cggagagaga 4620
agtattagag tggaggtttg acagccgcct agcatttcat cacatggccc gagagctgca 4680
tccggactgt actgggtctc tctggttaga ccagatctga gcctgggagc tctctggcta 4740
actagggaac ccactgctta agcctcaata aagcttgcct tgagtgcttc aagtagtgtg 4800
tgcccgtctg ttgtgtgact ctggtaacta gagatccctc agaccctttt agtcagtgtg 4860
gaaaatctct agcagggccc gtttaaaccc gctgatcagc ctcgactgtg ccttctagtt 4920
gccagccatc tgttgtttgc ccctcccccg tgccttcctt gaccctggaa ggtgccactc 4980
ccactgtcct ttcctaataa aatgaggaaa ttgcatcgca ttgtctgagt aggtgtcatt 5040
ctattctggg gggtggggtg gggcaggaca gcaaggggga ggattgggaa gacaatagca 5100
ggcatgctgg ggatgcggtg ggctctatgg cttctgaggc ggaaagaacc agctggggct 5160
ctagggggta tccccacgcg ccctgtagcg gcgcattaag cgcggcgggt gtggtggtta 5220
cgcgcagcgt gaccgctaca cttgccagcg ccctagcgcc cgctcctttc gctttcttcc 5280
cttcctttct cgccacgttc gccggctttc cccgtcaagc tctaaatcgg gggctccctt 5340
tagggttccg atttagtgct ttacggcacc tcgaccccaa aaaacttgat tagggtgatg 5400

```
gttcacgtag tgggccatcg ccctgataga cggtttttcg ccctttgacg ttggagtcca   5460
cgttctttaa tagtggactc ttgttccaaa ctggaacaac actcaaccct atctcggtct   5520
attcttttga tttataaggg attttgccga tttcggccta ttggttaaaa aatgagctga   5580
tttaacaaaa atttaacgcg aattaattct gtggaatgtg tgtcagttag ggtgtggaaa   5640
gtccccaggc tccccagcag gcagaagtat gcaaagcatg catctcaatt agtcagcaac   5700
caggtgtgga aagtccccag gctccccagc aggcagaagt atgcaaagca tgcatctcaa   5760
ttagtcagca accatagtcc cgcccctaac tccgcccatc ccgcccctaa ctccgcccag   5820
ttccgcccat tctccgcccc atggctgact aatttttttt atttatgcag aggccgaggc   5880
cgcctctgcc tctgagctat tccagaagta gtgaggaggc ttttttggag gcctaggctt   5940
ttgcaaaaag ctcccgggag cttgtatatc cattttcgga tctgatcagc acgtgttgac   6000
aattaatcat cggcatagta tatcggcata gtataatacg acaaggtgag gaactaaacc   6060
atggccaagt tgaccagtgc cgttccggtg ctcaccgcgc gcgacgtcgc cggagcggtc   6120
gagttctgga ccgaccggct cgggttctcc cgggacttcg tggaggacga cttcgccggt   6180
gtggtccggg acgacgtgac cctgttcatc agcgcggtcc aggaccaggt ggtgccggac   6240
aacaccctgg cctgggtgtg ggtgcgcggc ctggacgagc tgtacgccga gtggtcggag   6300
gtcgtgtcca cgaacttccg ggacgcctcc gggccggcca tgaccgagat cggcgagcag   6360
ccgtgggggc gggagttcgc cctgcgcgac ccggccggca actgcgtgca cttcgtggcc   6420
gaggagcagg actgacacgt gctacgagat ttcgattcca ccgccgcctt ctatgaaagg   6480
ttgggcttcg gaatcgtttt ccgggacgcc ggctggatga tcctccagcg cggggatctc   6540
atgctggagt tcttcgccca ccccaacttg tttattgcag cttataatgg ttacaaataa   6600
agcaatagca tcacaaattt cacaaataaa gcattttttt cactgcattc tagttgtggt   6660
ttgtccaaac tcatcaatgt atcttatcat gtctgtatac cgtcgacctc tagctagagc   6720
ttggcgtaat catggtcata gctgtttcct gtgtgaaatt gttatccgct cacaattcca   6780
cacaacatac gagccggaag cataaagtgt aaagcctggg gtgcctaatg agtgagctaa   6840
ctcacattaa ttgcgttgcg ctcactgccc gctttccagt cgggaaacct gtcgtgccag   6900
ctgcattaat gaatcggcca acgcgcgggg agaggcggtt tgcgtattgg gcgctcttcc   6960
gcttcctcgc tcactgactc gctgcgctcg gtcgttcggc tgcggcgagc ggtatcagct   7020
cactcaaagg cggtaatacg gttatccaca gaatcagggg ataacgcagg aaagaacatg   7080
tgagcaaaag gccagcaaaa ggccaggaac cgtaaaaagg ccgcgttgct ggcgtttttc   7140
cataggctcc gcccccctga cgagcatcac aaaaatcgac gctcaagtca gaggtggcga   7200
aacccgacag gactataaag ataccaggcg tttccccctg gaagctccct cgtgcgctct   7260
cctgttccga ccctgccgct taccggatac ctgtccgcct ttctcccttc gggaagcgtg   7320
gcgctttctc atagctcacg ctgtaggtat ctcagttcgg tgtaggtcgt tcgctccaag   7380
ctgggctgtg tgcacgaacc ccccgttcag cccgaccgct gcgccttatc cggtaactat   7440
cgtcttgagt ccaacccggt aagacacgac ttatcgccac tggcagcagc cactggtaac   7500
aggattagca gagcgaggta tgtaggcggt gctacagagt tcttgaagtg gtggcctaac   7560
tacggctaca ctagaagaac agtatttggt atctgcgctc tgctgaagcc agttaccttc   7620
ggaaaaagag ttggtagctc ttgatccggc aaacaaacca ccgctggtag cggtggtttt   7680
tttgtttgca agcagcagat tacgcgcaga aaaaaaggat ctcaagaaga tcctttgatc   7740
ttttctacgg ggtctgacgc tcagtggaac gaaaactcac gttaagggat tttggtcatg   7800
```

agattatcaa aaaggatctt cacctagatc cttttaaatt aaaaatgaag ttttaaatca 7860
atctaaagta tatatgagta aacttggtct gacagttacc aatgcttaat cagtgaggca 7920
cctatctcag cgatctgtct atttcgttca tccatagttg cctgactccc cgtcgtgtag 7980
ataactacga tacgggaggg cttaccatct ggccccagtg ctgcaatgat accgcgagac 8040
ccacgctcac cggctccaga tttatcagca ataaaccagc cagccggaag ggccgagcgc 8100
agaagtggtc ctgcaacttt atccgcctcc atccagtcta ttaattgttg ccgggaagct 8160
agagtaagta gttcgccagt taatagtttg cgcaacgttg ttgccattgc tacaggcatc 8220
gtggtgtcac gctcgtcgtt tggtatggct tcattcagct ccggttccca acgatcaagg 8280
cgagttacat gatcccccat gttgtgcaaa aaagcggtta gctccttcgg tcctccgatc 8340
gttgtcagaa gtaagttggc cgcagtgtta tcactcatgg ttatggcagc actgcataat 8400
tctcttactg tcatgccatc cgtaagatgc ttttctgtga ctggtgagta ctcaaccaag 8460
tcattctgag aatagtgtat gcggcgaccg agttgctctt gcccggcgtc aatacgggat 8520
aataccgcgc cacatagcag aactttaaaa gtgctcatca ttggaaaacg ttcttcgggg 8580
cgaaaactct caaggatctt accgctgttg agatccagtt cgatgtaacc cactcgtgca 8640
cccaactgat cttcagcatc ttttactttc accagcgttt ctgggtgagc aaaaacagga 8700
aggcaaaatg ccgcaaaaaa gggaataagg gcgacacgga aatgttgaat actcatactc 8760
ttcctttttc aatattattg aagcatttat cagggttatt gtctcatgag cggatacata 8820
tttgaatgta tttagaaaaa taaacaaata ggggttccgc gcacatttcc ccgaaaagtg 8880
ccacctgacg tcgacggatc gggagatctc ccgatcccct atggtgcact ctcagtacaa 8940
tctgctctga tgccgcatag ttaagccagt atctgctccc tgcttgtgtg ttggaggtcg 9000
ctgagtagtg cgcgagcaaa atttaagcta caacaaggca aggcttgacc gacaattgca 9060
tgaagaatct gcttagggtt aggcgttttg cgctgcttcg cgatgtacgg gccagatata 9120

<210> SEQ ID NO 66
<211> LENGTH: 10111
<212> TYPE: DNA
<213> ORGANISM: Artificial sequence
<220> FEATURE:
<223> OTHER INFORMATION: synthetic construct

<400> SEQUENCE: 66
cgcgttgaca ttgattattg actagttatt aatagtaatc aattacgggg tcattagttc 60
atagcccata tatggagttc cgcgttacat aacttacggt aaatggcccg cctggctgac 120
cgcccaacga cccccgccca ttgacgtcaa taatgacgta tgttcccata gtaacgccaa 180
tagggacttt ccattgacgt caatgggtgg agtatttacg gtaaactgcc cacttggcag 240
tacatcaagt gtatcatatg ccaagtacgc cccctattga cgtcaatgac ggtaaatggc 300
ccgcctggca ttatgcccag tacatgacct tatgggactt tcctacttgg cagtacatct 360
acgtattagt catcgctatt accatggtga tgcggttttg gcagtacatc aatgggcgtg 420
gatagcggtt tgactcacgg ggatttccaa gtctccaccc cattgacgtc aatgggagtt 480
tgttttggca ccaaaatcaa cgggactttc caaaatgtcg taacaactcc gccccattga 540
cgcaaatggg cggtaggcgt gtacggtggg aggtctatat aagcagcgcg ttttgcctgt 600
actgggtctc tctggttaga ccagatctga gcctgggagc tctctggcta actagggaac 660
ccactgctta agcctcaata aagcttgcct tgagtgcttc aagtagtgtg tgcccgtctg 720

-continued ttgtgtgact ctggtaacta gagatccctc agaccctttt agtcagtgtg gaaaatctct 780
agcagtggcg cccgaacagg gacttgaaag cgaaagggaa accagaggag ctctctcgac 840
gcaggactcg gcttgctgaa gcgcgcacgg caagaggcga ggggcggcga ctggtgagta 900
cgccaaaaat tttgactagc ggaggctaga aggagagaga tgggtgcgag agcgtcagta 960
ttaagcgggg gagaattaga tcgcgatggg aaaaaattcg gttaaggcca gggggaaaga 1020
aaaaatataa attaaaacat atagtatggg caagcaggga gctagaacga ttcgcagtta 1080
atcctggcct gttagaaaca tcagaaggct gtagacaaat actgggacag ctacaaccat 1140
cccttcagac aggatcagaa gaacttagat cattatataa tacagtagca accctctatt 1200
gtgtgcatca aaggatagag ataaaagaca ccaaggaagc tttagacaag atagaggaag 1260
agcaaaacaa aagtaagacc accgcacagc aagcggccgc tgatcttcag acctggagga 1320
ggagatatga gggacaattg gagaagtgaa ttatataaat ataaagtagt aaaaattgaa 1380
ccattaggag tagcacccac caaggcaaag agaagagtgg tgcagagaga aaaaagagca 1440
gtgggaatag gagctttgtt ccttgggttc ttgggagcag caggaagcac tatgggcgca 1500
gcgtcaatga cgctgacggt acaggccaga caattattgt ctggtatagt gcagcagcag 1560
aacaatttgc tgagggctat tgaggcgcaa cagcatctgt tgcaactcac agtctggggc 1620
atcaagcagc tccaggcaag aatcctggct gtggaaagat acctaaagga tcaacagctc 1680
ctggggattt ggggttgctc tggaaaactc atttgcacca ctgctgtgcc ttggaatgct 1740
agttggagta ataaatctct ggaacagatt tggaatcaca cgacctggat ggagtgggac 1800
agagaaatta acaattacac aagcttaata cactccttaa ttgaagaatc gcaaaaccag 1860
caagaaaaga atgaacaaga attattggaa ttagataaat gggcaagttt gtggaattgg 1920
tttaacataa caaattggct gtggtatata aaattattca taatgatagt aggaggcttg 1980
gtaggtttaa gaatagtttt tgctgtactt tctatagtga atagagttag gcagggatat 2040
tcaccattat cgtttcagac ccacctccca accccgaggg gacccgacag gcccgaagga 2100
atagaagaag aaggtggaga gagagacaga gacagatcca ttcgattagt gaacggatcg 2160
gcactgcgtg cgccaattct gcagacaaat ggcagtattc atccacaatt ttaaaagaaa 2220
aggggggatt ggggggtaca gtgcagggga aagaatagta gacataatag caacagacat 2280
acaaactaaa gaattacaaa aacaaattac aaaaattcaa aattttcggg tttattacag 2340
ggacagcaga gatccagttt ggttagatct cgagtttacc actccctatc agtgatagag 2400
aaaagtgaaa gtcgagttta ccactcccta tcagtgatag agaaaagtga aagtcgagtt 2460
taccactccc tatcagtgat agagaaaagt gaaagtcgag tttaccactc cctatcagtg 2520
atagagaaaa gtgaaagtcg agtttaccac tccctatcag tgatagagaa aagtgaaagt 2580
cgagtttacc actccctatc agtgatagag aaaagtgaaa gtcgagttta ccactcccta 2640
tcagtgatag agaaaagtga aagtcgagct cggtacccgg gtcgaggtag gcgtgtacgg 2700
tgggaggcct atataagcag agctcgttta gtgaaccgtc agatcgcctg gagacgccat 2760
ccacgctgtt ttgacctcca tagaagacac cgggaccgat ccagcctccg cggccccgaa 2820
ttaattcgcc cttccaagtc cctgagtggt tgttttcttc ccactgacca aagctggaga 2880
gggagctctc aggagggtgt gctccggatt tcttgcctca ggcccaggac tccaaccatt 2940
ttataatgga atctttattt tgtgaaagta gcggggactc atctctggag aaggagttcc 3000
ttggggcccc agtggggccc tcggtgagca ccccaaacag ccaacactct tcacccagcc 3060
gctcgctcag tgccaactcc atcaaggtgg agatgtacag cgatgaggag tcgagcagac 3120
tgctggggcc ggatgaacgg ctcctggata aggatgacag tgtgattgtg gaagactcat 3180
tgtcagagcc cttaggctac tgcgatggaa gtgggccaga gcctcactcc cctggcggca 3240
tccggctacc caacggcaag ctcaagtgcg acgtctgcgg catggtctgc attgggccca 3300
atgtgctcat ggtacacaag cgcagccaca ctggggagag gcccttccac tgtaatcagt 3360
gtggtgcctc cttcacacag aagggcaatc tgcttcgcca catcaagctg cactcggggg 3420
agaagccctt caagtgcccc ttctgcaact atgcctgccg ccggcgtgac gcactcactg 3480
gccacctccg cacacactca gtctcctccc ccaccgtggg caaaccctac aagtgcaact 3540
actgtggccg gagctacaaa cagcaaagta ccctggagga gcacaaggag aggtgccaca 3600
actacctaca gagtctcagc actgatgccc aagctctgac tggccagcca ggtgatgaaa 3660
tccgtgacct ggagatggtg cctgactcaa tgctgcaccc atcgactgaa cggccaactt 3720
tcattgatcg tttggccaac agcctcacca aacgcaagcg ttccacccca cagaagtttg 3780
taggtgaaaa gcagatgcgc ttcagcctct cagaccttcc ctatgatgtg aatgccagcg 3840
gtggctatga aaaggacgta gagttggtgg cacaccatgg cctggagcct ggctttggag 3900
ggtctctagc ctttgtgggt acagagcatc tgcgtcccct ccgcctccca cccaccaact 3960
gcatctcaga actcacacct gtcatcagct ctgtgtacac ccaaatgcag cccatcccca 4020
gccgactgga gcttccaggg tcccgagaag caggtgaggg accggaggac ctgggagatg 4080
gaggtcccct cctttatcgg gcccgaggct ctctgactga ccctggggca tcccccagca 4140
atggctgcca ggactccaca gatacagaga gcaaccacga agaccggatt ggtggggtgg 4200
tatcccttcc tcagggtccc ccaccccaac ctcctcccac catagtggtg ggccggcaca 4260
gtcccgccta tgccaaagag gaccccaaac cacaggaggg gttactgcgg ggcaccccag 4320
gcccctccaa ggaagtgctt cgggtggtgg gtgagagtgg tgagccagtg aaggccttta 4380
agtgtgaaca ctgccgcatc ctctttctgg accacgtcat gttcaccatc cacatgggct 4440
gccacggctt cagagaccct tttgagtgta acatctgtgg ttatcacagc caggatcggt 4500
atgagttctc ttcccacatc gtccgggggg aacataaggt gggctaggaa ttcgatatca 4560
agcttatcga taatcaacct ctggattaca aaatttgtga aagattgact ggtattctta 4620
actatgttgc tccttttacg ctatgtggat acgctgcttt aatgcctttg tatcatgcta 4680
ttgcttcccg tatggctttc attttctcct ccttgtataa atcctggttg ctgtctcttt 4740
atgaggagtt gtggcccgtt gtcaggcaac gtggcgtggt gtgcactgtg tttgctgacg 4800
caacccccac tggttggggc attgccacca cctgtcagct cctttccggg actttcgctt 4860
tccccctccc tattgccacg gcggaactca tcgccgcctg ccttgcccgc tgctggacag 4920
gggctcggct gttgggcact gacaattccg tggtgttgtc ggggaaatca tcgtcctttc 4980
cttggctgct cgcctgtgtt gccacctgga ttctgcgcgg gacgtccttc tgctacgtcc 5040
cttcggccct caatccagcg gaccttcctt cccgcggcct gctgccggct ctgcggcctc 5100
ttccgcgtct tcgccttcgc cctcagacga gtcggatctc cctttgggcc gcctccccgc 5160
atcgataccg tcgacctcga gacctagaaa aacatggagc aatcacaagt agcaatacag 5220
cagctaccaa tgctgattgt gcctggctag aagcacaaga ggaggaggag gtgggttttc 5280
cagtcacacc tcaggtacct ttaagaccaa tgacttacaa ggcagctgta gatcttagcc 5340
actttttaaa agaaaagggg ggactggaag ggctaattca ctcccaacga agacaagata 5400
tccttgatct gtggatctac cacacacaag gctacttccc tgattggcag aactacacac 5460
cagggccagg gatcagatat ccactgacct ttggatggtg ctacaagcta gtaccagttg 5520
agcaagagaa ggtagaagaa gccaatgaag gagagaacac ccgcttgtta caccctgtga 5580
gcctgcatgg gatggatgac ccggagagag aagtattaga gtggaggttt gacagccgcc 5640
tagcatttca tcacatggcc cgagagctgc atccggactg tactgggtct ctctggttag 5700
accagatctg agcctgggag ctctctggct aactagggaa cccactgctt aagcctcaat 5760
aaagcttgcc ttgagtgctt caagtagtgt gtgcccgtct gttgtgtgac tctggtaact 5820
agagatccct cagacccttt tagtcagtgt ggaaaatctc tagcagggcc cgtttaaacc 5880
cgctgatcag cctcgactgt gccttctagt tgccagccat ctgttgtttg cccctccccc 5940
gtgccttcct tgaccctgga aggtgccact cccactgtcc tttcctaata aaatgaggaa 6000
attgcatcgc attgtctgag taggtgtcat tctattctgg ggggtggggt ggggcaggac 6060
agcaaggggg aggattggga agacaatagc aggcatgctg gggatgcggt gggctctatg 6120
gcttctgagg cggaaagaac cagctggggc tctagggggt atccccacgc gccctgtagc 6180
ggcgcattaa gcgcggcggg tgtggtggtt acgcgcagcg tgaccgctac acttgccagc 6240
gccctagcgc ccgctccttt cgctttcttc ccttcctttc tcgccacgtt cgccggcttt 6300
ccccgtcaag ctctaaatcg ggggctccct ttagggttcc gatttagtgc tttacggcac 6360
ctcgacccca aaaaacttga ttagggtgat ggttcacgta gtgggccatc gccctgatag 6420
acggtttttc gccctttgac gttggagtcc acgttcttta atagtggact cttgttccaa 6480
actggaacaa cactcaaccc tatctcggtc tattcttttg atttataagg gattttgccg 6540
atttcggcct attggttaaa aaatgagctg atttaacaaa aatttaacgc gaattaattc 6600
tgtggaatgt gtgtcagtta gggtgtggaa agtccccagg ctccccagca ggcagaagta 6660
tgcaaagcat gcatctcaat tagtcagcaa ccaggtgtgg aaagtcccca ggctccccag 6720
caggcagaag tatgcaaagc atgcatctca attagtcagc aaccatagtc ccgcccctaa 6780
ctccgcccat cccgccccta actccgccca gttccgccca ttctccgccc catggctgac 6840
taattttttt tatttatgca gaggccgagg ccgcctctgc ctctgagcta ttccagaagt 6900
agtgaggagg cttttttgga ggcctaggct tttgcaaaaa gctcccggga gcttgtatat 6960
ccattttcgg atctgatcag cacgtgttga caattaatca tcggcatagt atatcggcat 7020
agtataatac gacaaggtga ggaactaaac catggccaag ttgaccagtg ccgttccggt 7080
gctcaccgcg cgcgacgtcg ccggagcggt cgagttctgg accgaccggc tcgggttctc 7140
ccgggacttc gtggaggacg acttcgccgg tgtggtccgg gacgacgtga ccctgttcat 7200
cagcgcggtc caggaccagg tggtgccgga caacaccctg gcctgggtgt gggtgcgcgg 7260
cctggacgag ctgtacgccg agtggtcgga ggtcgtgtcc acgaacttcc gggacgcctc 7320
cgggccggcc atgaccgaga tcggcgagca gccgtggggg cgggagttcg ccctgcgcga 7380
cccggccggc aactgcgtgc acttcgtggc cgaggagcag gactgacacg tgctacgaga 7440
tttcgattcc accgccgcct tctatgaaag gttgggcttc ggaatcgttt tccgggacgc 7500
cggctggatg atcctccagc gcggggatct catgctggag ttcttcgccc accccaactt 7560
gtttattgca gcttataatg gttacaaata aagcaatagc atcacaaatt tcacaaataa 7620
agcatttttt tcactgcatt ctagttgtgg tttgtccaaa ctcatcaatg tatcttatca 7680
tgtctgtata ccgtcgacct ctagctagag cttggcgtaa tcatggtcat agctgtttcc 7740
tgtgtgaaat tgttatccgc tcacaattcc acacaacata cgagccggaa gcataaagtg 7800
taaagcctgg ggtgcctaat gagtgagcta actcacatta attgcgttgc gctcactgcc 7860

```
cgctttccag tcgggaaacc tgtcgtgcca gctgcattaa tgaatcggcc aacgcgcggg   7920
gagaggcggt ttgcgtattg ggcgctcttc cgcttcctcg ctcactgact cgctgcgctc   7980
ggtcgttcgg ctgcggcgag cggtatcagc tcactcaaag gcggtaatac ggttatccac   8040
agaatcaggg gataacgcag gaaagaacat gtgagcaaaa ggccagcaaa aggccaggaa   8100
ccgtaaaaag gccgcgttgc tggcgttttt ccataggctc cgcccccctg acgagcatca   8160
caaaaatcga cgctcaagtc agaggtggcg aaacccgaca ggactataaa gataccaggc   8220
gtttccccct ggaagctccc tcgtgcgctc tcctgttccg accctgccgc ttaccggata   8280
cctgtccgcc tttctccctt cgggaagcgt ggcgctttct catagctcac gctgtaggta   8340
tctcagttcg gtgtaggtcg ttcgctccaa gctgggctgt gtgcacgaac cccccgttca   8400
gcccgaccgc tgcgccttat ccggtaacta tcgtcttgag tccaacccgg taagacacga   8460
cttatcgcca ctggcagcag ccactggtaa caggattagc agagcgaggt atgtaggcgg   8520
tgctacagag ttcttgaagt ggtggcctaa ctacggctac actagaagaa cagtatttgg   8580
tatctgcgct ctgctgaagc cagttacctt cggaaaaaga gttggtagct cttgatccgg   8640
caaacaaacc accgctggta gcggtggttt ttttgtttgc aagcagcaga ttacgcgcag   8700
aaaaaaagga tctcaagaag atcctttgat cttttctacg gggtctgacg ctcagtggaa   8760
cgaaaactca cgttaaggga ttttggtcat gagattatca aaaaggatct tcacctagat   8820
ccttttaaat taaaaatgaa gttttaaatc aatctaaagt atatatgagt aaacttggtc   8880
tgacagttac caatgcttaa tcagtgaggc acctatctca gcgatctgtc tatttcgttc   8940
atccatagtt gcctgactcc ccgtcgtgta gataactacg atacgggagg gcttaccatc   9000
tggccccagt gctgcaatga taccgcgaga cccacgctca ccggctccag atttatcagc   9060
aataaaccag ccagccggaa gggccgagcg cagaagtggt cctgcaactt tatccgcctc   9120
catccagtct attaattgtt gccgggaagc tagagtaagt agttcgccag ttaatagttt   9180
gcgcaacgtt gttgccattg ctacaggcat cgtggtgtca cgctcgtcgt ttggtatggc   9240
ttcattcagc tccggttccc aacgatcaag gcgagttaca tgatccccca tgttgtgcaa   9300
aaaagcggtt agctccttcg gtcctccgat cgttgtcaga agtaagttgg ccgcagtgtt   9360
atcactcatg gttatggcag cactgcataa ttctcttact gtcatgccat ccgtaagatg   9420
cttttctgtg actggtgagt actcaaccaa gtcattctga gaatagtgta tgcggcgacc   9480
gagttgctct tgcccggcgt caatacggga taataccgcg ccacatagca gaactttaaa   9540
agtgctcatc attggaaaac gttcttcggg gcgaaaactc tcaaggatct taccgctgtt   9600
gagatccagt tcgatgtaac ccactcgtgc acccaactga tcttcagcat cttttacttt   9660
caccagcgtt tctgggtgag caaaaacagg aaggcaaaat gccgcaaaaa agggaataag   9720
ggcgacacgg aaatgttgaa tactcatact cttccttttt caatattatt gaagcattta   9780
tcagggttat tgtctcatga gcggatacat atttgaatgt atttagaaaa ataaacaaat   9840
aggggttccg cgcacatttc cccgaaaagt gccacctgac gtcgacggat cgggagatct   9900
cccgatcccc tatggtgcac tctcagtaca atctgctctg atgccgcata gttaagccag   9960
tatctgctcc ctgcttgtgt gttggaggtc gctgagtagt gcgcgagcaa aatttaagct  10020
acaacaaggc aaggcttgac cgacaattgc atgaagaatc tgcttagggt taggcgtttt  10080
gcgctgcttc gcgatgtacg ggccagatat a                                 10111
```

<210> SEQ ID NO 67

<211> LENGTH: 6190
<212> TYPE: DNA
<213> ORGANISM: Artificial sequence
<220> FEATURE:
<223> OTHER INFORMATION: synthetic construct

<400> SEQUENCE: 67
caaaaggcca ggaaccgtaa aaaggccgcg ttgctggcgt ttttccatag gctccgcccc 60
cctgacgagc atcacaaaaa tcgacgctca agtcagaggt ggcgaaaccc gacaggacta 120
taaagatacc aggcgtttcc ccctggaagc tccctcgtgc gctctcctgt tccgaccctg 180
ccgcttaccg gatacctgtc cgcctttctc ccttcgggaa gcgtggcgct ttctcatagc 240
tcacgctgta ggtatctcag ttcggtgtag gtcgttcgct ccaagctggg ctgtgtgcac 300
gaaccccccg ttcagcccga ccgctgcgcc ttatccggta actatcgtct tgagtccaac 360
ccggtaagac acgacttatc gccactggca gcagccactg gtaacaggat tagcagagcg 420
aggtatgtag gcggtgctac agagttcttg aagtggtggc ctaactacgg ctacactaga 480
agacagtatt tggtatctgc gctctgctga agccagttac cttcggaaaa agagttggta 540
gctcttgatc cggcaaacaa accaccgctg gtagcggtgg tttttttgtt tgcaagcagc 600
agattacgcg cagaaaaaaa ggatctcaag aagatccttt gatcttttct acggggtctg 660
acgctcagtg gaacgaaaac tcacgttaag ggattttggt catgagatta tcaaaaagga 720
tcttcaccta gatcctttta aattaaaaat gaagttttaa atcaatctaa agtatatatg 780
agtaaacttg gtctgacagt taccaatgct taatcagtga ggcacctatc tcagcgatct 840
gtctatttcg ttcatccata gttgcctgac tccccgtcgt gtagataact acgatacggg 900
agggcttacc atctggcccc agtgctgcaa tgataccgcg agacccacgc tcaccggctc 960
cagatttatc agcaataaac cagccagccg gaagggccga gcgcagaagt ggtcctgcaa 1020
ctttatccgc ctccatccag tctattaatt gttgccggga agctagagta agtagttcgc 1080
cagttaatag tttgcgcaac gttgttgcca ttgctacagg catcgtggtg tcacgctcgt 1140
cgtttggtat ggcttcattc agctccggtt cccaacgatc aaggcgagtt acatgatccc 1200
ccatgttgtg caaaaaagcg gttagctcct tcggtcctcc gatcgttgtc agaagtaagt 1260
tggccgcagt gttatcactc atggttatgg cagcactgca taattctctt actgtcatgc 1320
catccgtaag atgcttttct gtgactggtg agtactcaac caagtcattc tgagaatagt 1380
gtatgcggcg accgagttgc tcttgcccgg cgtcaatacg ggataatacc gcgccacata 1440
gcagaacttt aaaagtgctc atcattggaa aacgttcttc ggggcgaaaa ctctcaagga 1500
tcttaccgct gttgagatcc agttcgatgt aacccactcg tgcacccaac tgatcttcag 1560
catcttttac tttcaccagc gtttctgggt gagcaaaaac aggaaggcaa aatgccgcaa 1620
aaaagggaat aagggcgaca cggaaatgtt gaatactcat actcttcctt tttcaatatt 1680
attgaagcat ttatcagggt tattgtctca tgagcggata catatttgaa tgtatttaga 1740
aaaataaaca aataggggtt ccgcgcacat ttccccgaaa agtgccacct gggtcgacat 1800
tgattattga ctagttatta atagtaatca attacggggt cattagttca tagcccatat 1860
atggagttcc gcgttacata acttacggta aatggcccgc ctggctgacc gcccaacgac 1920
ccccgcccat tgacgtcaat aatgacgtat gttcccatag taacgccaat agggactttc 1980
cattgacgtc aatgggtgga gtatttacgg taaactgccc acttggcagt acatcaagtg 2040
tatcatatgc caagtacgcc ccctattgac gtcaatgacg gtaaatggcc cgcctggcat 2100
tatgcccagt acatgacctt atgggacttt cctacttggc agtacatcta cgtattagtc 2160

```
atcgctatta ccatggtcga ggtgagcccc acgttctgct tcactctccc catctccccc   2220
ccctccccac ccccaatttt gtatttattt atttttaat tattttgtgc agcgatgggg   2280
gcgggggggg gggggggcg cgcgccaggc ggggcggggc ggggcgaggg gcggggcggg   2340
gcgaggcgga gaggtgcggc ggcagccaat cagagcggcg cgctccgaaa gtttcctttt   2400
atggcgaggc ggcggcggcg gcggccctat aaaaagcgaa gcgcgcggcg ggcgggagtc   2460
gctgcgttgc cttcgccccg tgccccgctc cgcgccgcct cgcgccgccc gccccggctc   2520
tgactgaccg cgttactccc acaggtgagc gggcgggacg gcccttctcc tccgggctgt   2580
aattagcgct tggtttaatg acggctcgtt tcttttctgt ggctgcgtga aagccttaaa   2640
gggctccggg agggcccttt gtgcgggggg gagcggctcg gggggtgcgt gcgtgtgtgt   2700
gtgcgtgggg agcgccgcgt gcggcccgcg ctgcccggcg gctgtgagcg ctgcgggcgc   2760
ggcgcggggc tttgtgcgct ccgcgtgtgc gcgaggggag cgcggccggg ggcggtgccc   2820
cgcggtgcgg gggggctgcg aggggaacaa aggctgcgtg cggggtgtgt gcgtgggggg   2880
gtgagcaggg ggtgtgggcg cggcggtcgg gctgtaaccc ccccctgcac ccccctcccc   2940
gagttgctga gcacggcccg gcttcgggtg cggggctccg tacggggcgt ggcgcggggc   3000
tcgccgtgcc gggcgggggg tggcggcagg tgggggtgcc gggcggggcg gggccgcctc   3060
gggccgggga gggctcgggg gaggggcgcg gcggcccccg gagcgccggc ggctgtcgag   3120
gcgcggcgag ccgcagccat tgccttttat ggtaatcgtg cgagagggcg cagggacttc   3180
ctttgtccca aatctgtgcg gagccgaaat ctgggaggcg ccgccgcacc ccctctagcg   3240
ggcgcggggc gaagcggtgc ggcgccggca ggaaggaaat gggcggggag ggccttcgtg   3300
cgtcgccgcg ccgccgtccc cttctccctc tccagcctcg gggctgtccg cggggggacg   3360
gctgccttcg ggggggacgg ggcagggcgg ggttcggctt ctggcgtgtg accggcggct   3420
ctagagcctc tgctaaccat gttcatgcct tcttcttttt cctacagctc ctgggcaacg   3480
tgctggttat tgtgctgtct catcattttg gcaaagaatt gctcgagctc aagcttcgaa   3540
ttctgcagtc gacggtaccg cgggcccggg atccgcccct ctccctcccc ccccccctaac   3600
gttactggcc gaagccgctt ggaataaggc cggtgtgcgt ttgtctatat gttattttcc   3660
accatattgc cgtcttttgg caatgtgagg gcccggaaac ctggccctgt cttcttgacg   3720
agcattccta ggggtctttc ccctctcgcc aaaggaatgc aaggtctgtt gaatgtcgtg   3780
aaggaagcag ttcctctgga agcttcttga agacaaacaa cgtctgtagc gaccctttgc   3840
aggcagcgga accccccacc tggcgacagg tgcctctgcg gccaaaagcc acgtgtataa   3900
gatacacctg caaaggcggc acaaccccag tgccacgttg tgagttggat agttgtggaa   3960
agagtcaaat ggctctcctc aagcgtattc aacaaggggc tgaaggatgc ccagaaggta   4020
ccccattgta tgggatctga tctggggcct cggtacacat gctttacatg tgtttagtcg   4080
aggttaaaaa aacgtctagg ccccccgaac cacggggacg tggttttcct ttgaaaaaca   4140
cgatgataat atggccacaa ccatggtgag caagggcgag gagctgttca ccggggtggt   4200
gcccatcctg gtcgagctgg acggcgacgt aaacggccac aagttcagcg tgtccggcga   4260
gggcgagggc gatgccacct acggcaagct gaccctgaag ttcatctgca ccaccggcaa   4320
gctgcccgtg ccctggccca ccctcgtgac caccctgacc tacggcgtgc agtgcttcag   4380
ccgctacccc gaccacatga agcagcacga cttcttcaag tccgccatgc ccgaaggcta   4440
cgtccaggag cgcaccatct tcttcaagga cgacggcaac tacaagaccc gcgccgaggt   4500
```

gaagttcgag ggcgacaccc tggtgaaccg catcgagctg aagggcatcg acttcaagga 4560
ggacggcaac atcctggggc acaagctgga gtacaactac aacagccaca acgtctatat 4620
catggccgac aagcagaaga acggcatcaa ggtgaacttc aagatccgcc acaacatcga 4680
ggacggcagc gtgcagctcg ccgaccacta ccagcagaac acccccatcg gcgacggccc 4740
cgtgctgctg cccgacaacc actacctgag cacccagtcc gccctgagca aagaccccaa 4800
cgagaagcgc gatcacatgg tcctgctgga gttcgtgacc gccgccggga tcactctcgg 4860
catggacgag ctgtacaagt aaagcggccg caattcactc ctcaggtgca ggctgcctat 4920
cagaaggtgg tggctggtgt ggccaatgcc ctggctcaca aataccactg agatcttttt 4980
ccctctgcca aaaattatgg ggacatcatg aagccccttg agcatctgac ttctggctaa 5040
taaaggaaat ttattttcat tgcaatagtg tgttggaatt ttttgtgtct atcactcgga 5100
aggacatatg ggagggcaaa tcatttaaaa catcagaatg agtatttggt ttagagtttg 5160
gcaacatatg cccatatgct ggctgccatg aacaaaggtt ggctataaag aggtcatcag 5220
tatatgaaac agccccctgc tgtccattcc ttattccata gaaaagcctt gacttgaggt 5280
tagatttttt ttatattttg ttttgtgtta ttttttttctt taacatccct aaaattttcc 5340
ttacatgttt tactagccag atttttcctc ctctcctgac tactcccagt catagctgtc 5400
cctcttctct tatggagatc cctcgacctg caccgtcgac cagctggtcg acggtgcacc 5460
gtcgaccagc ttggcgtaat catggtcata gctgtttcct gtgtgaaatt gttatccgct 5520
cacaattcca cacaacatac gagccggaag cataaagtgt aaagcctggg gtgcctaatg 5580
agtgagctaa ctcacattaa ttgcgttgcg ctcactgccc gctttccagt cgggaaacct 5640
gtcgtgccag cggatccgca tctcaattag tcagcaacca tagtcccgcc cctaactccg 5700
cccatcccgc ccctaactcc gcccagttcc gcccattctc cgccccatgg ctgactaatt 5760
ttttttattt atgcagaggc cgaggccgcc tcggcctctg agctattcca gaagtagtga 5820
ggaggctttt ttggaggcct aggcttttgc aaaaagctaa cttgtttatt gcagcttata 5880
atggttacaa ataaagcaat agcatcacaa atttcacaaa taaagcattt ttttcactgc 5940
attctagttg tggtttgtcc aaactcatca atgtatctta tcatgtctgg atccgctgca 6000
ttaatgaatc ggccaacgcg cggggagagg cggtttgcgt attgggcgct cttccgcttc 6060
ctcgctcact gactcgctgc gctcggtcgt tcggctgcgg cgagcggtat cagctcactc 6120
aaaggcggta atacggttat ccacagaatc aggggataac gcaggaaaga acatgtgagc 6180
aaaaggccag 6190

<210> SEQ ID NO 68
<211> LENGTH: 8084
<212> TYPE: DNA
<213> ORGANISM: Artificial sequence
<220> FEATURE:
<223> OTHER INFORMATION: synthetic construct

<400> SEQUENCE: 68
caaaaggcca ggaaccgtaa aaaggccgcg ttgctggcgt ttttccatag gctccgcccc 60
cctgacgagc atcacaaaaa tcgacgctca agtcagaggt ggcgaaaccc gacaggacta 120
taaagatacc aggcgtttcc ccctggaagc tccctcgtgc gctctcctgt tccgaccctg 180
ccgcttaccg gatacctgtc cgcctttctc ccttcgggaa gcgtggcgct ttctcatagc 240
tcacgctgta ggtatctcag ttcggtgtag gtcgttcgct ccaagctggg ctgtgtgcac 300
gaaccccccg ttcagcccga ccgctgcgcc ttatccggta actatcgtct tgagtccaac 360

```
ccggtaagac acgacttatc gccactggca gcagccactg gtaacaggat tagcagagcg    420
aggtatgtag gcggtgctac agagttcttg aagtggtggc ctaactacgg ctacactaga    480
agacagtatt tggtatctgc gctctgctga agccagttac cttcggaaaa agagttggta    540
gctcttgatc cggcaaacaa accaccgctg gtagcggtgg tttttttgtt tgcaagcagc    600
agattacgcg cagaaaaaaa ggatctcaag aagatccttt gatcttttct acggggtctg    660
acgctcagtg gaacgaaaac tcacgttaag ggattttggt catgagatta tcaaaaagga    720
tcttcaccta gatcctttta aattaaaaat gaagttttaa atcaatctaa agtatatatg    780
agtaaacttg gtctgacagt taccaatgct taatcagtga ggcacctatc tcagcgatct    840
gtctatttcg ttcatccata gttgcctgac tccccgtcgt gtagataact acgatacggg    900
agggcttacc atctggcccc agtgctgcaa tgataccgcg agacccacgc tcaccggctc    960
cagatttatc agcaataaac cagccagccg gaagggccga gcgcagaagt ggtcctgcaa   1020
ctttatccgc ctccatccag tctattaatt gttgccggga agctagagta agtagttcgc   1080
cagttaatag tttgcgcaac gttgttgcca ttgctacagg catcgtggtg tcacgctcgt   1140
cgtttggtat ggcttcattc agctccggtt cccaacgatc aaggcgagtt acatgatccc   1200
ccatgttgtg caaaaaagcg gttagctcct tcggtcctcc gatcgttgtc agaagtaagt   1260
tggccgcagt gttatcactc atggttatgg cagcactgca taattctctt actgtcatgc   1320
catccgtaag atgcttttct gtgactggtg agtactcaac caagtcattc tgagaatagt   1380
gtatgcggcg accgagttgc tcttgcccgg cgtcaatacg ggataatacc gcgccacata   1440
gcagaacttt aaaagtgctc atcattggaa aacgttcttc ggggcgaaaa ctctcaagga   1500
tcttaccgct gttgagatcc agttcgatgt aacccactcg tgcacccaac tgatcttcag   1560
catcttttac tttcaccagc gtttctgggt gagcaaaaac aggaaggcaa aatgccgcaa   1620
aaaagggaat aagggcgaca cggaaatgtt gaatactcat actcttcctt tttcaatatt   1680
attgaagcat ttatcagggt tattgtctca tgagcggata catatttgaa tgtatttaga   1740
aaaataaaca aataggggtt ccgcgcacat ttccccgaaa agtgccacct gggtcgacat   1800
tgattattga ctagttatta atagtaatca attacggggt cattagttca tagcccatat   1860
atggagttcc gcgttacata acttacggta aatggcccgc ctggctgacc gcccaacgac   1920
ccccgcccat tgacgtcaat aatgacgtat gttcccatag taacgccaat agggactttc   1980
cattgacgtc aatgggtgga gtatttacgg taaactgccc acttggcagt acatcaagtg   2040
tatcatatgc caagtacgcc ccctattgac gtcaatgacg gtaaatggcc cgcctggcat   2100
tatgcccagt acatgacctt atgggacttt cctacttggc agtacatcta cgtattagtc   2160
atcgctatta ccatggtcga ggtgagcccc acgttctgct tcactctccc catctccccc   2220
ccctccccac ccccaatttt gtatttattt atttttaat tattttgtgc agcgatgggg   2280
gcgggggggg gggggggcg cgcgccaggc ggggcggggc ggggcgaggg gcggggcggg   2340
gcgaggcgga gaggtgcggc ggcagccaat cagagcggcg cgctccgaaa gtttcctttt   2400
atggcgaggc ggcggcggcg gcggccctat aaaaagcgaa gcgcgcggcg ggcgggagtc   2460
gctgcgttgc cttcgccccg tgccccgctc cgcgccgcct cgcgccgccc gccccggctc   2520
tgactgaccg cgttactccc acaggtgagc gggcgggacg gcccttctcc tccgggctgt   2580
aattagcgct tggtttaatg acggctcgtt tcttttctgt ggctgcgtga aagccttaaa   2640
gggctccggg agggcccttt gtgcgggggg gagcggctcg gggggtgcgt gcgtgtgtgt   2700
```

-continued

```
gtgcgtgggg agcgccgcgt gcggcccgcg ctgcccggcg gctgtgagcg ctgcgggcgc   2760
ggcgcggggc tttgtgcgct ccgcgtgtgc gcgaggggag cgcggccggg ggcggtgccc   2820
cgcggtgcgg gggggctgcg aggggaacaa aggctgcgtg cggggtgtgt gcgtgggggg   2880
gtgagcaggg ggtgtgggcg cggcggtcgg gctgtaaccc ccccctgcac ccccctcccc   2940
gagttgctga gcacggcccg gcttcgggtg cggggctccg tacggggcgt ggcgcggggc   3000
tcgccgtgcc gggcgggggg tggcggcagg tgggggtgcc gggcggggcg gggccgcctc   3060
gggccgggga gggctcgggg gaggggcgcg gcggcccccg gagcgccggc ggctgtcgag   3120
gcgcggcgag ccgcagccat tgccttttat ggtaatcgtg cgagagggcg cagggacttc   3180
ctttgtccca aatctgtgcg gagccgaaat ctgggaggcg ccgccgcacc ccctctagcg   3240
ggcgcggggc gaagcggtgc ggcgccggca ggaaggaaat gggcggggag ggccttcgtg   3300
cgtcgccgcg ccgccgtccc cttctccctc tccagcctcg gggctgtccg cggggggacg   3360
gctgccttcg ggggggacgg ggcagggcgg ggttcggctt ctggcgtgtg accggcggct   3420
ctagagcctc tgctaaccat gttcatgcct tcttcttttt cctacagctc ctgggcaacg   3480
tgctggttat tgtgctgtct catcattttg gcaaagaatt gctcgagctc aagcttcgaa   3540
ttatcaacaa gtttgtacaa aaaagcaggc tttaaaggaa ccaattcagt cgactggatc   3600
cggtaccgaa ttcatgcaca caccacccgc actccctcgc cgtttccaag gcggcggccg   3660
cgttcgcacc ccagggtctc accggcaagg gaaggataat ctggagaggg agctctcagg   3720
agggtgtgct ccggatttct tgcctcaggc ccaggactcc aaccatttta taatggaatc   3780
tttattttgt gaaagtagcg gggactcatc tctggagaag gagttccttg gggccccagt   3840
ggggccctcg gtgagcaccc caaacagcca acactcttca cccagccgct cgctcagtgc   3900
caactccatc aaggtggaga tgtacagcga tgaggagtcg agcagactgc tggggccgga   3960
tgaacggctc ctggataagg atgacagtgt gattgtggaa gactcattgt cagagccctt   4020
aggctactgc gatggaagtg ggccagagcc tcactcccct ggcggcatcc ggctacccaa   4080
cggcaagctc aagtgcgacg tctgcggcat ggtctgcatt gggcccaatg tgctcatggt   4140
acacaagcgc agccacactg gggagaggcc cttccactgt aatcagtgtg gtgcctcctt   4200
cacacagaag ggcaatctgc ttcgccacat caagctgcac tcgggggaga agcccttcaa   4260
gtgccccttc tgcaactatg cctgccgccg gcgtgacgca ctcactggcc acctccgcac   4320
acactcagtc tcctccccca ccgtgggcaa accctacaag tgcaactact gtggccggag   4380
ctacaaacag caaagtaccc tggaggagca caaggagagg tgccacaact acctacagag   4440
tctcagcact gatgcccaag ctctgactgg ccagccaggt gatgaaatcc gtgacctgga   4500
gatggtgcct gactcaatgc tgcacccatc gactgaacgg ccaactttca ttgatcgttt   4560
ggccaacagc ctcaccaaac gcaagcgttc caccccacag aagtttgtag gtgaaaagca   4620
gatgcgcttc agcctctcag accttcccta tgatgtgaat gccagcggtg gctatgaaaa   4680
ggacgtagag ttggtggcac accatggcct ggagcctggc tttggagggt ctctagcctt   4740
tgtgggtaca gagcatctgc gtcccctccg cctcccaccc accaactgca tctcagaact   4800
cacacctgtc atcagctctg tgtacaccca aatgcagccc atccccagcc gactggagct   4860
tccagggtcc cgagaagcag gtgagggacc ggaggacctg ggagatggag gtcccctcct   4920
ttatcgggcc cgaggctctc tgactgaccc tggggcatcc cccagcaatg gctgccagga   4980
ctccacagat acagagagca accacgaaga ccggattggt ggggtggtat cccttcctca   5040
gggtccccca ccccaacctc ctcccaccat agtggtgggc cggcacagtc ccgcctatgc   5100
```

caaagaggac cccaaaccac aggaggggtt actgcggggc accccaggcc cctccaagga 5160
agtgcttcgg gtggtgggtg agagtggtga gccagtgaag gcctttaagt gtgaacactg 5220
ccgcatcctc tttctggacc acgtcatgtt caccatccac atgggctgcc acggcttcag 5280
agaccctttt gagtgtaaca tctgtggtta tcacagccag gatcggtatg agttctcttc 5340
ccacatcgtc cggggggaac ataaggtggg ctaggaattc gcggccgcac tcgagatatc 5400
tagacccagc tttcttgtac aaagtggttg ataattctgc agtcgacggt accgcgggcc 5460
cgggatccgc ccctctccct cccccccccc taacgttact ggccgaagcc gcttggaata 5520
aggccggtgt gcgtttgtct atatgttatt ttccaccata ttgccgtctt ttggcaatgt 5580
gagggcccgg aaacctggcc ctgtcttctt gacgagcatt cctaggggtc tttcccctct 5640
cgccaaagga atgcaaggtc tgttgaatgt cgtgaaggaa gcagttcctc tggaagcttc 5700
ttgaagacaa acaacgtctg tagcgaccct ttgcaggcag cggaaccccc cacctggcga 5760
caggtgcctc tgcggccaaa agccacgtgt ataagataca cctgcaaagg cggcacaacc 5820
ccagtgccac gttgtgagtt ggatagttgt ggaaagagtc aaatggctct cctcaagcgt 5880
attcaacaag gggctgaagg atgcccagaa ggtaccccat tgtatgggat ctgatctggg 5940
gcctcggtac acatgcttta catgtgttta gtcgaggtta aaaaaacgtc taggcccccc 6000
gaaccacggg gacgtggttt tcctttgaaa aacacgatga taatatggcc acaaccatgg 6060
tgagcaaggg cgaggagctg ttcaccgggg tggtgcccat cctggtcgag ctggacggcg 6120
acgtaaacgg ccacaagttc agcgtgtccg gcgagggcga gggcgatgcc acctacggca 6180
agctgaccct gaagttcatc tgcaccaccg gcaagctgcc cgtgccctgg cccaccctcg 6240
tgaccaccct gacctacggc gtgcagtgct tcagccgcta ccccgaccac atgaagcagc 6300
acgacttctt caagtccgcc atgcccgaag gctacgtcca ggagcgcacc atcttcttca 6360
aggacgacgg caactacaag acccgcgccg aggtgaagtt cgagggcgac accctggtga 6420
accgcatcga gctgaagggc atcgacttca aggaggacgg caacatcctg gggcacaagc 6480
tggagtacaa ctacaacagc cacaacgtct atatcatggc cgacaagcag aagaacggca 6540
tcaaggtgaa cttcaagatc cgccacaaca tcgaggacgg cagcgtgcag ctcgccgacc 6600
actaccagca gaacaccccc atcggcgacg gccccgtgct gctgcccgac aaccactacc 6660
tgagcaccca gtccgccctg agcaaagacc ccaacgagaa gcgcgatcac atggtcctgc 6720
tggagttcgt gaccgccgcc gggatcactc tcggcatgga cgagctgtac aagtaaagcg 6780
gccgcaattc actcctcagg tgcaggctgc ctatcagaag gtggtggctg gtgtggccaa 6840
tgccctggct cacaaatacc actgagatct tttccctct gccaaaaatt atggggacat 6900
catgaagccc cttgagcatc tgacttctgg ctaataaagg aaatttattt tcattgcaat 6960
agtgtgttgg aattttttgt gtctatcact cggaaggaca tatgggaggg caaatcattt 7020
aaaacatcag aatgagtatt tggtttagag tttggcaaca tatgcccata tgctggctgc 7080
catgaacaaa ggttggctat aaagaggtca tcagtatatg aaacagcccc ctgctgtcca 7140
ttccttattc catagaaaag ccttgacttg aggttagatt ttttttatat tttgttttgt 7200
gttatttttt tctttaacat ccctaaaatt ttccttacat gttttactag ccagattttt 7260
cctcctctcc tgactactcc cagtcatagc tgtccctctt ctcttatgga gatccctcga 7320
cctgcaccgt cgaccagctg gtcgacggtg caccgtcgac cagcttggcg taatcatggt 7380
catagctgtt tcctgtgtga aattgttatc cgctcacaat tccacacaac atacgagccg 7440
gaagcataaa gtgtaaagcc tggggtgcct aatgagtgag ctaactcaca ttaattgcgt 7500
tgcgctcact gcccgctttc cagtcgggaa acctgtcgtg ccagcggatc cgcatctcaa 7560
ttagtcagca accatagtcc cgcccctaac tccgcccatc ccgcccctaa ctccgcccag 7620
ttccgcccat tctccgcccc atggctgact aattttttt atttatgcag aggccgaggc 7680
cgcctcggcc tctgagctat tccagaagta gtgaggaggc ttttttggag gcctaggctt 7740
ttgcaaaaag ctaacttgtt tattgcagct tataatggtt acaaataaag caatagcatc 7800
acaaatttca caaataaagc atttttttca ctgcattcta gttgtggttt gtccaaactc 7860
atcaatgtat cttatcatgt ctggatccgc tgcattaatg aatcggccaa cgcgcgggga 7920
gaggcggttt gcgtattggg cgctcttccg cttcctcgct cactgactcg ctgcgctcgg 7980
tcgttcggct gcggcgagcg gtatcagctc actcaaaggc ggtaatacgg ttatccacag 8040
aatcagggga taacgcagga aagaacatgt gagcaaaagg ccag 8084

<210> SEQ ID NO 69
<211> LENGTH: 22
<212> TYPE: DNA
<213> ORGANISM: Artificial sequence
<220> FEATURE:
<223> OTHER INFORMATION: synthetic construct

<400> SEQUENCE: 69
cgagcagtgc acatctcagt tc 22

<210> SEQ ID NO 70
<211> LENGTH: 20
<212> TYPE: DNA
<213> ORGANISM: Artificial sequence
<220> FEATURE:
<223> OTHER INFORMATION: synthetic construct

<400> SEQUENCE: 70
aactggaggg ctgggttacc 20

<210> SEQ ID NO 71
<211> LENGTH: 23
<212> TYPE: DNA
<213> ORGANISM: Artificial sequence
<220> FEATURE:
<223> OTHER INFORMATION: synthetic construct

<400> SEQUENCE: 71
aagctcctgt gtgacatgtt caa 23

<210> SEQ ID NO 72
<211> LENGTH: 23
<212> TYPE: DNA
<213> ORGANISM: Artificial sequence
<220> FEATURE:
<223> OTHER INFORMATION: synthetic construct

<400> SEQUENCE: 72
aagctcctgt gtgacatgtt caa 23

RECOMBINANT NERVOUS SYSTEM CELLS AND METHODS TO GENERATE THEM

CROSS REFERENCE TO RELATED APPLICATIONS

This application is a National Entry Application of PCT application Serial No CA2019/051568 filed on Nov. 5, 2019 and published in English under PCT Article 21(2), which itself claims benefit of U.S. provisional application Ser. No. 62/755,657, filed on Nov. 5, 2018. All documents above are incorporated herein in their entirety by reference.

STATEMENT REGARDING FEDERALLY SPONSORED RESEARCH OR DEVELOPMENT

N.A.

FIELD OF THE DISCLOSURE

The present disclosure relates to recombinant nervous system cells and methods to generate them. More specifically, the present disclosure is concerned with recombinant nervous system cells (e.g., cone photoreceptors) and methods to generate them from neuroepithelial cells and adult glial cells.

REFERENCE TO SEQUENCE LISTING

Pursuant to 37 C.F.R. 1.821(c), a sequence listing is submitted herewith as an ASCII compliant text file named 2489-USPTO-SEQUENCE LISTING-12810-724_ST25, that was created on March Apr. 15, 2021 and having a size of 408 kilobytes. The content of the aforementioned file named 2489-USPTO-SEQUENCE LISTING-12810-724_ST25 is hereby incorporated by reference in its entirety.

BACKGROUND OF THE DISCLOSURE

Millions of North Americans suffer from irreversible vision loss due to retinal degenerative diseases such as retinitis pigmentosa, age-related macular degeneration, cone-rod dystrophies, Leber congenital amaurosis, Stargardt disease, and Usher syndrome. The common cause of sight impairments in these diseases is the progressive death of the light-sensing cells of the retina; the rod and cone photoreceptors. While rod photoreceptor degeneration leads to night blindness and reduced peripheral vision, it is the loss of cones that is the most devastating to patients as these cells provide the most-important daylight and high acuity macular vision in humans. Notably, even in diseases that affect rods due to mutations in rod genes (e.g., retinitis pigmentosa), the degeneration of rods eventually leads to the loss of cones at late stages of the disease. Considering the importance of cone photoreceptors for daylight vision, this secondary loss of cones is a major clinical problem. Although there are currently some treatments available to slow disease progression and cone loss in certain conditions (e.g., anti-VEGF therapy for wet macular degeneration), there are no cures available to restore normal vision for any retinal degenerative diseases. Since the incidence of age-related retinal degeneration is expected to increase drastically in coming years due to the aging population, new therapies are urgently needed.

One possibility to restore vision would be to replenish the lost photoreceptor cells. The preferred approach to achieve this has been with photoreceptor transplantation, for which considerable advances have been made in the last 10 to 15 years (reviewed by Santos-Ferreira et al., 2017). However, there has been a recent set back in the field with the important finding that the vast majority of what was originally thought to be "integrated" photoreceptors were actually host cells that had taken up the fluorescent reporter from the transplanted cells (Ortin-Martinez et al., 2016; Pearson et al., 2016; Santos-Ferreira et al., 2016; Singh et al., 2016). These studies revealed that the integration efficiency of transplanted cells was much lower than previously interpreted, raising concerns on whether transplantation approaches are even possible in the retina. New avenues of research are consequently required to bypass this integration limitation for photoreceptor regeneration.

The present description refers to a number of documents, the content of which is herein incorporated by reference in their entirety.

SUMMARY OF THE DISCLOSURE

The present disclosure exploits an endogenous source of cells to regenerate photoreceptors for use within the retina. The present disclosure reports the generation (production) of neurons (e.g., cone photoreceptors-like cells) ex vivo by modifying mammalian neuroepithelial cells so that they recombinantly express IKAROS Family Zinc Finger 4 (Ikzf4). It also reports the generation (production) of neurons (e.g., cone photoreceptors-like cells) in vitro, ex vivo, and in vivo by modifying mammalian glial cells (e.g., Müller glia cells) so that they recombinantly co-express IKAROS Family Zinc Finger 1 (Ikzf1) and IKAROS Family Zinc Finger 4 (Ikzf4).

More specifically, in accordance with the present disclosure, there are provided the following items:

- Item 1. A recombinant nervous system cell comprising nucleic acid encoding IKAROS Family Zinc Finger 4 (Ikzf4) and/or IKAROS Family Zinc Finger 1 (Ikzf1).
- Item 2. The recombinant cell of item 1, which is a retinal cell.
- Item 3. The recombinant cell of item 2, comprising nucleic acid encoding Ikzf4.
- Item 4. The recombinant cell of any one of items 1-3, which is a neuroepithelial cell.
- Item 5. The recombinant cell of any one of items 1-3, which is a glial cell.
- Item 6. The recombinant cell of item 5, which is a Müller cell.
- Item 7. The recombinant cell of any one of items 1-3, which is a neuron.
- Item 8. The recombinant cell of any one of items 1-7, which expresses Ikzf4 and Ikzf1.
- Item 9. The recombinant cell of item 8, which is a cone photoreceptor.
- Item 10. The recombinant cell of any one of items 1-9, wherein the nucleic acid is operably linked to a glial specific promoter.
- Item 11. The recombinant cell of any one of items 1-10, wherein the nucleic acid is comprised in an adeno-associated vector (AAV).
- Item 12. The recombinant cell of item 11, wherein the AAV is of the Shh10 serotype.
- Item 13. The recombinant cell of any one of items 1-10, wherein the nucleic acid is comprised in a lentiviral vector.
- Item 14. A cell population comprising the cell defined in any one of items 1-13.

Item 15. A vector comprising a glial specific promoter operably-linked to a nucleic acid molecule encoding IKAROS Family Zinc Finger 1 (Ikzf1) and/or a nucleic acid molecule encoding IKAROS Family Zinc Finger 4 (Ikzf4).

Item 16. The vector of item 15, comprising Ikzf1.

Item 17. The vector of item 15 or 16, comprising Ikzf4.

Item 18. The vector of any one of items 15-17, which is an adeno-associated viral vector (AAV).

Item 19. The vector of item 18, which is of the Shh10 serotype.

Item 20. The vector of any one of items 15-17, which is a lentiviral vector.

Item 21. A pharmaceutical composition comprising (a)(i) a nucleic acid encoding IKAROS Family Zinc Finger 1 (Ikzf1); and/or a nucleic acid encoding IKAROS Family Zinc Finger 4 (Ikzf4); or (ii) the vector defined in any one of items 14-19; and (b) a pharmaceutically acceptable carrier.

Item 22. A transgenic non-human animal comprising the recombinant nervous system cell defined in any one of items 1-13; or the vector defined in any one of items 15-20.

Item 23. A method of producing a recombinant cone photoreceptor, comprising:

(a) introducing a nucleic acid molecule encoding IKAROS Family Zinc Finger 1 (Ikzf1) in a Müller glia cell; and introducing a nucleic acid molecule encoding IKAROS Family Zinc Finger 4 (Ikzf4) in the Müller glia cell; or introducing a nucleic acid molecule encoding Ikzf4 in a retinal neuroepithelial cell;

whereby the retinal neuroepithelial cell or the Müller glia is reprogrammed into a recombinant cone photoreceptor.

Item 24. The method of item 23, wherein the introducing of (a) and (b) or (B) is ex vivo.

Item 25. The method of item 23, wherein the introducing of (a) and (b) or (B) is in vivo in a mammalian subject in need thereof.

Item 26. The method of any one of items 23-25, wherein the introducing of (a) and (b) or (B) is intraocular.

Item 27. The method of any one of items 23-26, wherein each of the nucleic acid molecules of (a) and (b) is in a vector.

Item 28. The method of any one of items 23-27, wherein the introducing of (a) and (b) is performed by electroporation.

Item 29. The method of any one of items 23-27, wherein the introducing of (a) and (b) is performed by viral-based gene delivery.

Item 30. The method of item 29, wherein the viral-based gene delivery is an adeno-associated virus (AAV) gene delivery.

Item 31. The method of item 30, wherein the AAV is of the ShH10 serotype.

In other embodiments, there is provided a use of (a) a nucleic acid molecule encoding IKAROS Family Zinc Finger 1 (Ikzf1) for introduction in a Müller glia cell; and of a nucleic acid molecule encoding IKAROS Family Zinc Finger 4 (Ikzf4) for introduction in the Müller glia cell; or (b) a nucleic acid molecule encoding Ikzf4 for introduction in a retinal neuroepithelial cell, whereby the retinal neuroepithelial cell or the Müller glia is reprogrammed into a recombinant cone photoreceptor.

In other embodiments, there is provided (a) a nucleic acid molecule encoding IKAROS Family Zinc Finger 1 (Ikzf1) and of a nucleic acid molecule encoding IKAROS Family Zinc Finger 4 (Ikzf4) for their use in reprogramming a Müller glia cell into a recombinant cone photoreceptor; or (b) a nucleic acid molecule encoding Ikzf4 for its use in reprogramming a retinal neuroepithelial cell into a recombinant cone photoreceptor.

In other embodiments, there is provided a use (a) of a nucleic acid molecule encoding IKAROS Family Zinc Finger 1 (Ikzf1) and of a nucleic acid molecule encoding IKAROS Family Zinc Finger 4 (Ikzf4) for their use in reprogramming a Müller glia cell into a recombinant cone photoreceptor; or (b) of a nucleic acid molecule encoding Ikzf4 for its use in reprogramming a retinal neuroepithelial cell into a recombinant cone photoreceptor.

Other objects, advantages and features of the present disclosure will become more apparent upon reading of the following non-restrictive description of specific embodiments thereof, given by way of example only with reference to the accompanying drawings.

In the appended drawings:

FIGS. 1A-H. Ikzf4 is expressed in the developing retina and sufficient to promote cone production. (FIGS. 1A-A" and FIG. B-B") Immunostaining of Ikzf4 (left panel, dark grey) with Otx2, a marker for photoreceptors (rods and cones (middle panel, pale grey) showed merged (right panel) in E15 mouse retinas. (FIG. 1B-B") Zoomed-in images of (FIG. 1A-A"): arrows show co-expression of Ikzf4 (dark grey) and Otx2 (pale grey) in some cells. (FIGS. 1C-C" and FIGS. 1D-D") Examples of P0 retinal explants electroporated cultured for 14 days, sectioned and immunostained for $RxR_\gamma$ (marker for cone photoreceptors, designated Rxrg in the FIGs). Arrows show co-localization of GFP and Rxrγ. (FIG. 1E) Quantification of GFP+ cells in the Outer Nuclear Layer (ONL) expressing $RxR_\gamma$. (FIG. 1F) RT-qPCR analysis of Ikzf4 overexpression at P0+6 DIV (eyes removed on day of birth+6 Days in-vitro) using primers specific to NrI and Nr2e3, two critical rod differentiation genes. (FIGS. 1G-G'" and FIG. 1H-H'") Examples of control GFP (FIG. 1G) or Ikzf4 with GFP (FIG. 1H) overexpression in P0+14 DIV stained with Nr2e3 and Otx2. Arrow indicate GFP-positive, Nr2e3-negative cells expressing Otx2. ONL: Outer nuclear layer. P: Post-natal day. INL: Inner nuclear layer. RPL: Retinal progenitor layer. DIV: Days in vitro. p<0.01, *p<0.001, ****p<0.0001.

Figure 2A:
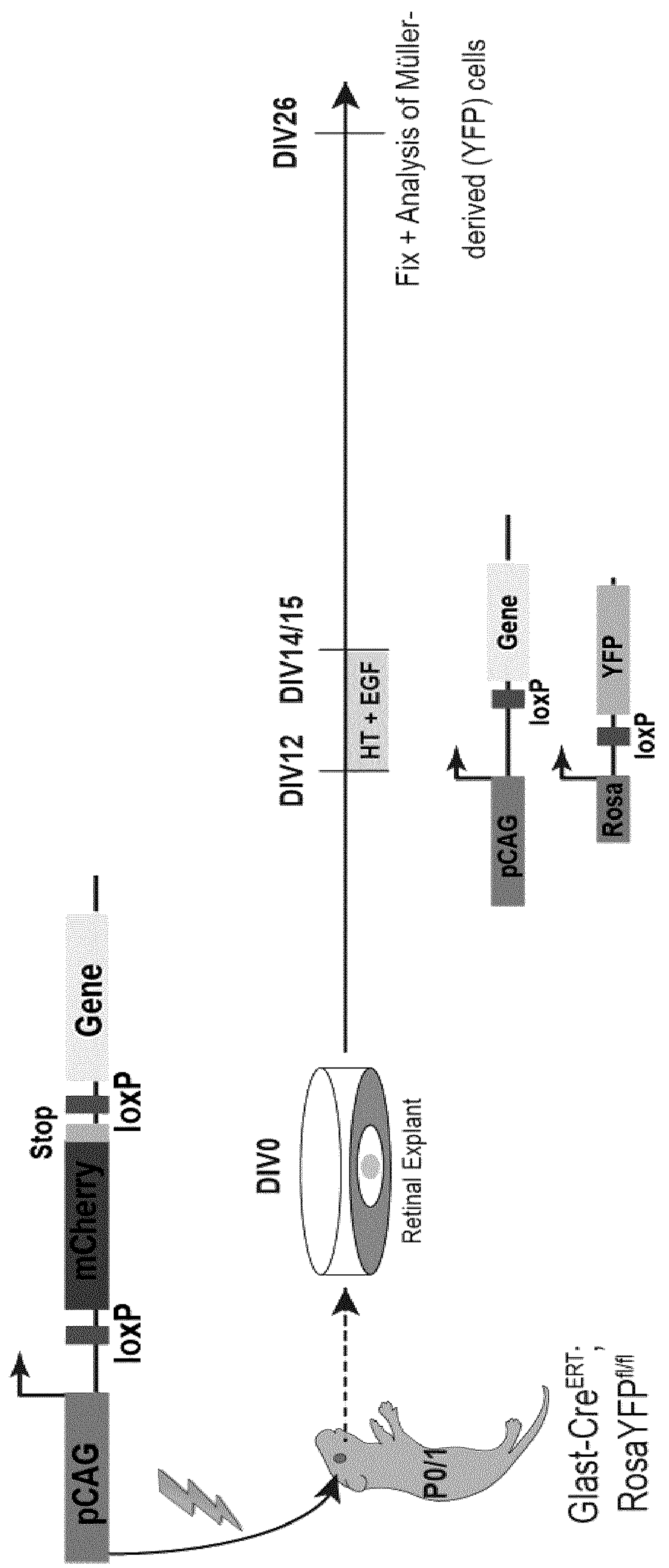

FIGS. 2A-B: Screen for Müller glia reprogramming into photoreceptors. (FIG. 2A) Screen protocol for conditional modification of gene expression in Müller glia. A conditional overexpression construct was electroporated in the retina of $GlastCre^{ERT}$;$RosaYFP^{fl/fl}$ mice and retinas were explanted. HT and EGF were added to the media at DIV12 (activating the expression of the gene of interest and permanent YFP labelling of Müller glia and derived cells) and explants fixed at DIV26. (FIG. 2B) List of conditions tested with the approach in (FIG. 2A). Combinations were obtained by co-electroporations. HT: Hydroxytamoxifen. YFP: Yellow Fluorescent Protein. DIV: Days in vitro. P: Post-natal day.

Figure 3A:
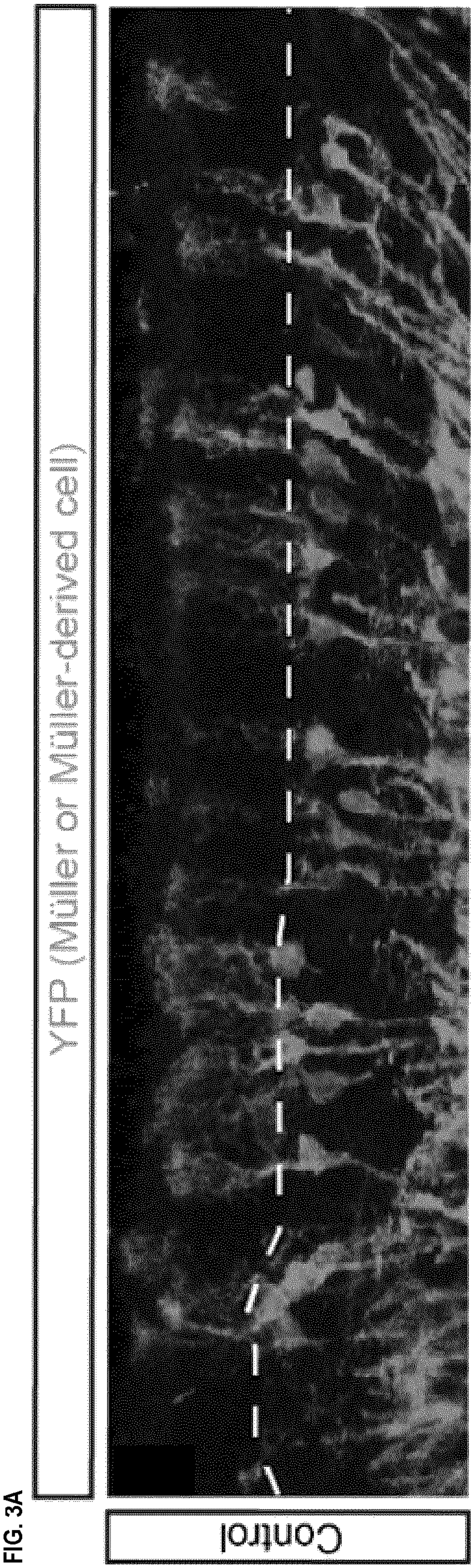
Figure 3B:
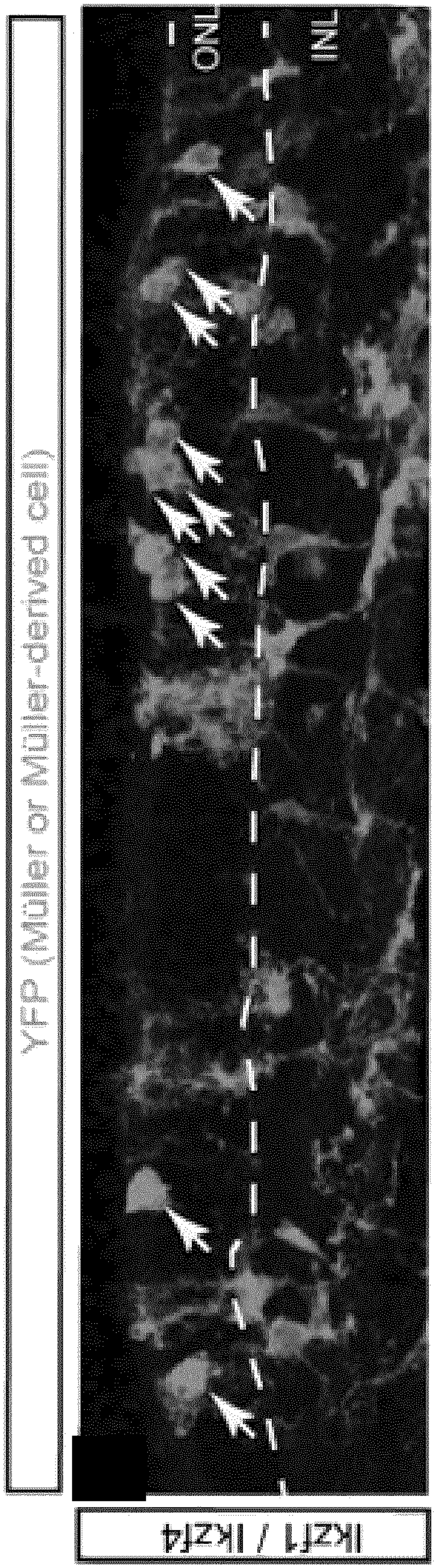
Figure 3F:
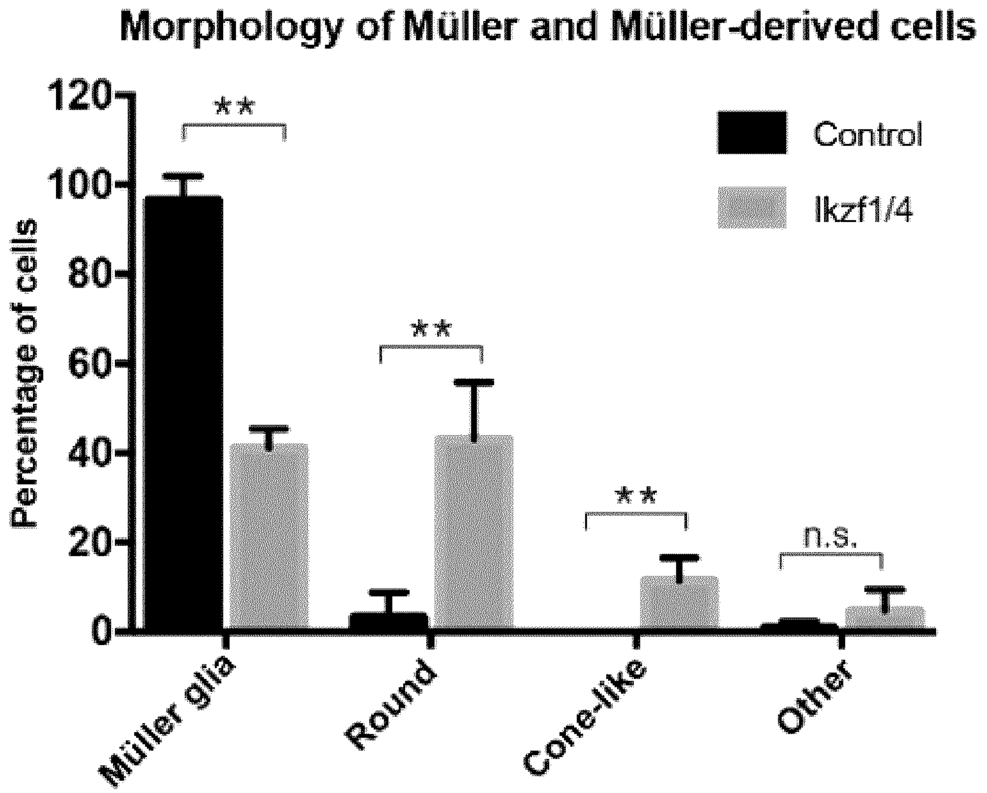

FIGS. 3A-H: Ikzf1/4 induces changes of morphology and localization of Müller-derived cells. (FIGS. 3A-B) Overview of YFP cells in control and Ikzf1/4 conditions. (FIG. 3A) YFP cells in electroporated regions have normal Müller glia morphology and have their cell bodies located within the inner nuclear layer (INL). (FIG. 3B) A subset of YFP cells (arrows) in Ikzf1/4 electroporated regions change morphology and localize to the apical side of the ONL. (FIGS. 3C-C", D-D" and E-E") Example of morphology of YFP reprogrammed cells in Ikzf1/4 condition: (FIGS. 3C-C") round cells, (FIGS. 3D-D") cone-like cells, (FIGS. 3E-E")

other unrecognizable morphology. Dotted line indicates apical side of ONL. (FIG. 3F) Quantification of the morphology of YFP mCherry cells in control and Ikzf1/4 conditions. Mann-Whitney tests with Bonferroni correction for multiple comparisons. (n=6) (FIG. 3G) Quantification of the localization of YFP mCherry cells in control and Ikzf1/4 conditions. Mann-Whitney tests with Bonferroni correction for multiple comparisons. (n=6) (FIG. 3H) Correlation between morphology and localization of YFP mCherry cells in Ikzf1/4 condition. 2-way ANOVA with Dunnett's post hoc test for comparisons of the localization of round, cone-like, and other with Müller glia (n=6). INL: Inner nuclear layer. ONL: Outer nuclear layer. p<0.01, **p<0.0001.

Figure 4D:
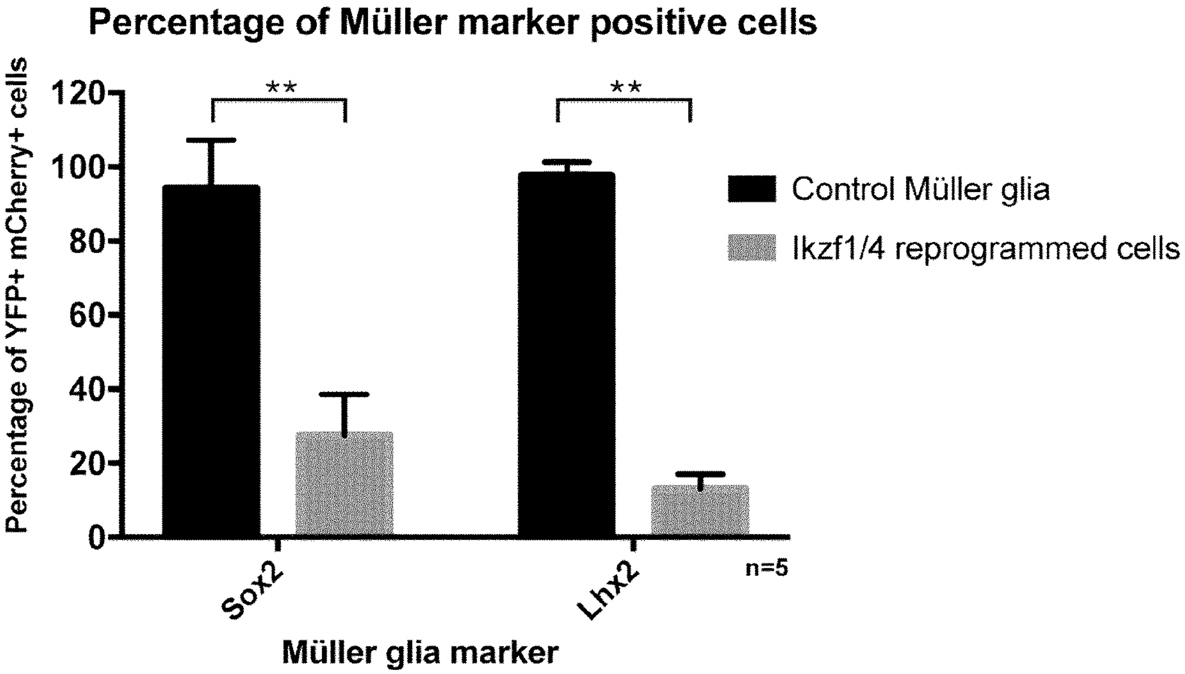
Figure 4E:
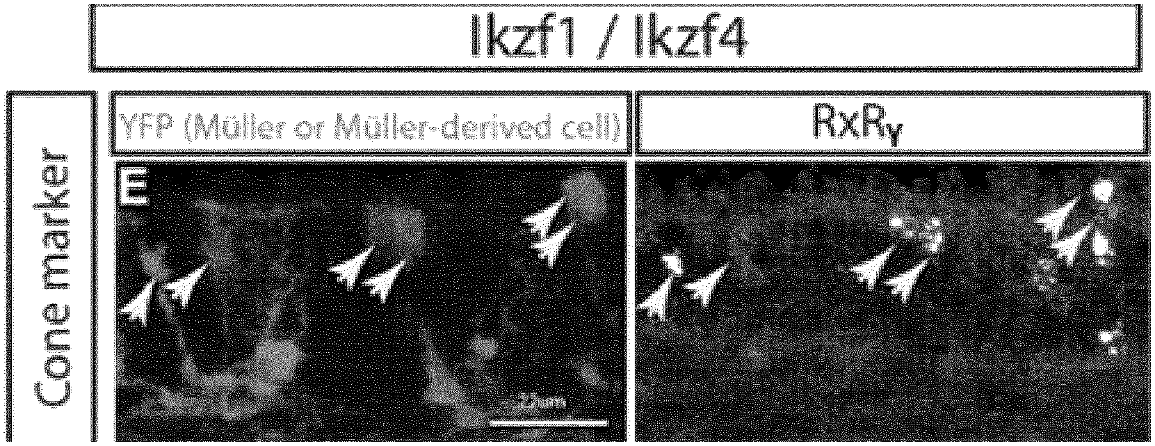
Figure 4F:
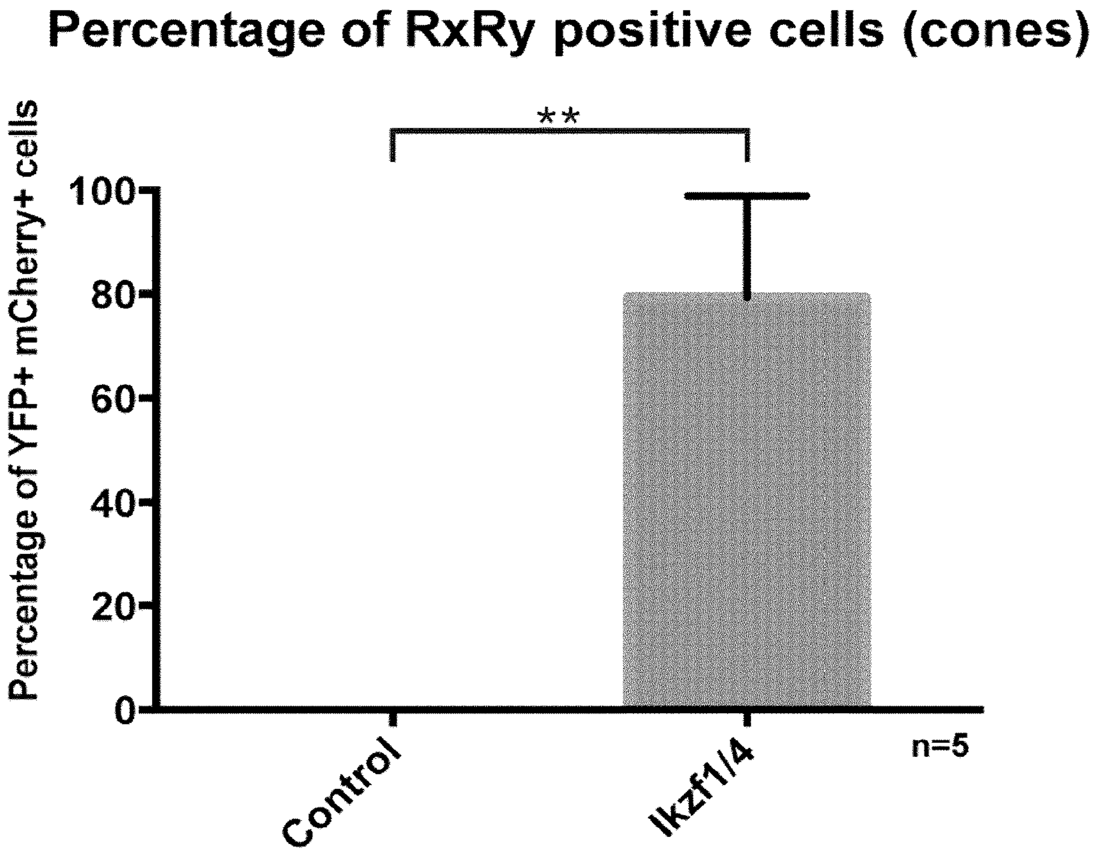

FIGS. 4A-F: Ikzf1/4 reprogrammed cells lack Müller markers and express the early cone marker RxR$_\gamma$. (FIGS. 4A-C) YFP reprogrammed cells (arrows) do not express the Müller glia markers Sox2 (FIG. 4A) or Lhx2 (FIGS. 4B-C). (FIG. 4D) Quantification of Müller glia marker expression of control Müller glia and Ikzf1/4 reprogrammed cells. Mann-Whitney tests of Ikzf1/4 vs control (n=5). (FIG. 4E) YFP reprogrammed cells (arrows) express the early cone marker RxR$_\gamma$ (white). (FIG. 4F) Quantification of RxR$_\gamma$ in control Müller glia and Ikzf1/4 reprogrammed cells. Mann-Whitney test (n=5). **p<0.01.

FIGS. 5A-D. Ikzf4 expression in Müller glia ex vivo induces RxR$_\gamma$ expression but keeps Müller morphology and marker expression. (FIGS. 5A-B) Arrows point to Ikzf4 electroporated Müller glia (YFP) which co-label with RxRγ. These cells have normal Müller glia morphology. (FIGS. 5C-D) Ikzf4 electroporated Müller glia (YFP) expression of the Müller marker Lhx2. (FIG. 5C) Ikzf4 electroporated cell (arrow) co-labels with Lhx2 as generally observed in this condition. (FIG. 5D) Rare Ikzf4 electroporated cell (arrow) that does not co-label with Lhx2, but still has Müller glia-like morphology. YFP: Yellow fluorescent protein.

Figure 6A:
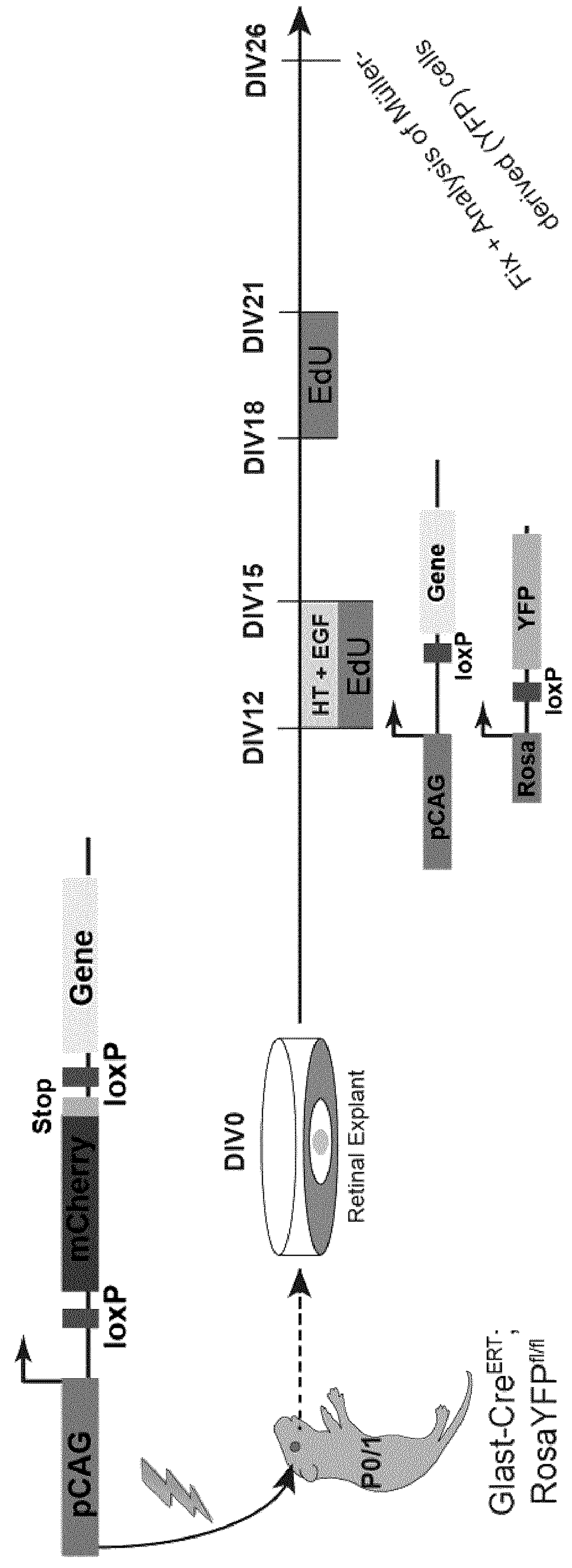
Figure 6B:
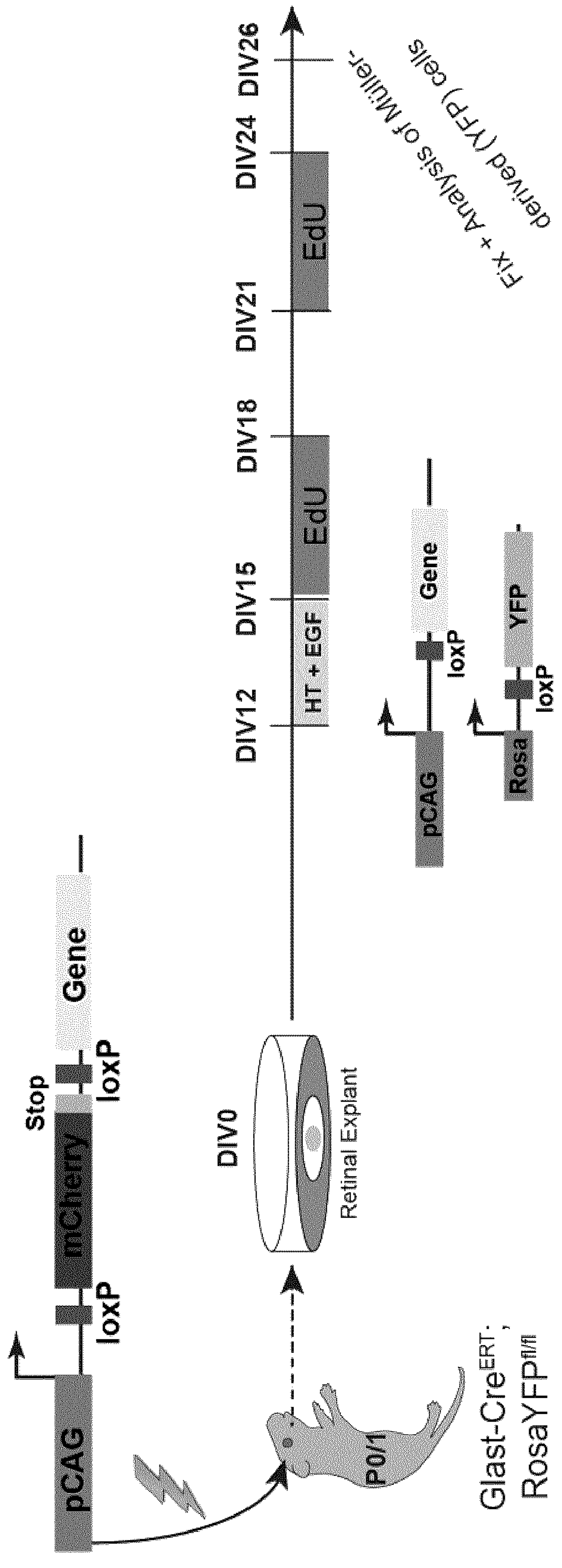
Figure 6C:
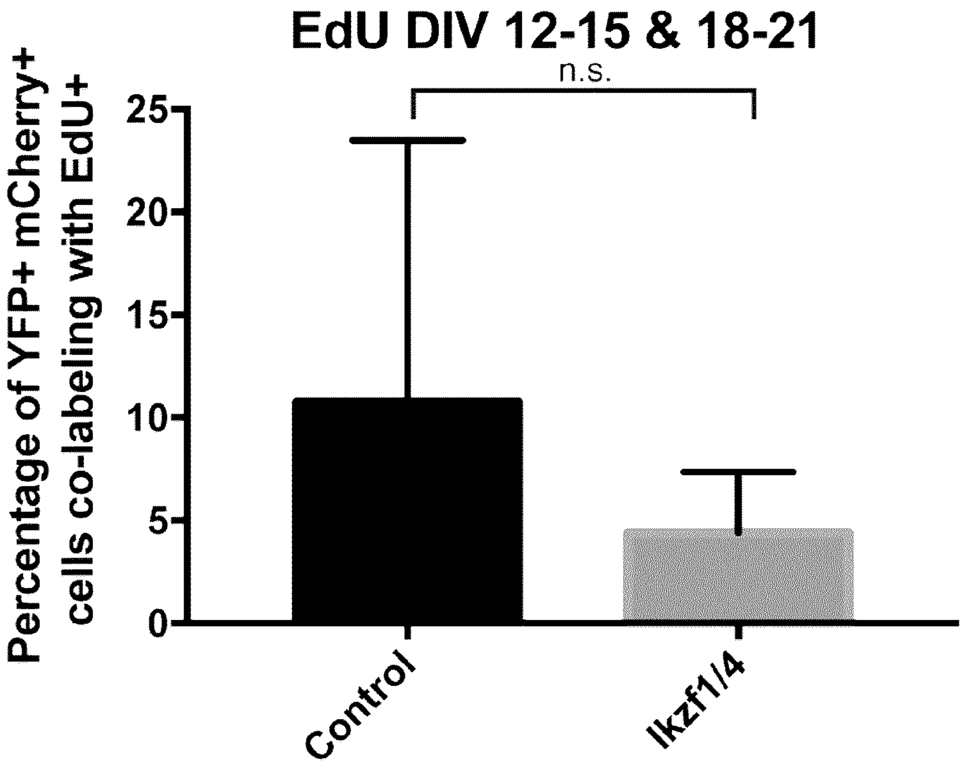
Figure 6D:
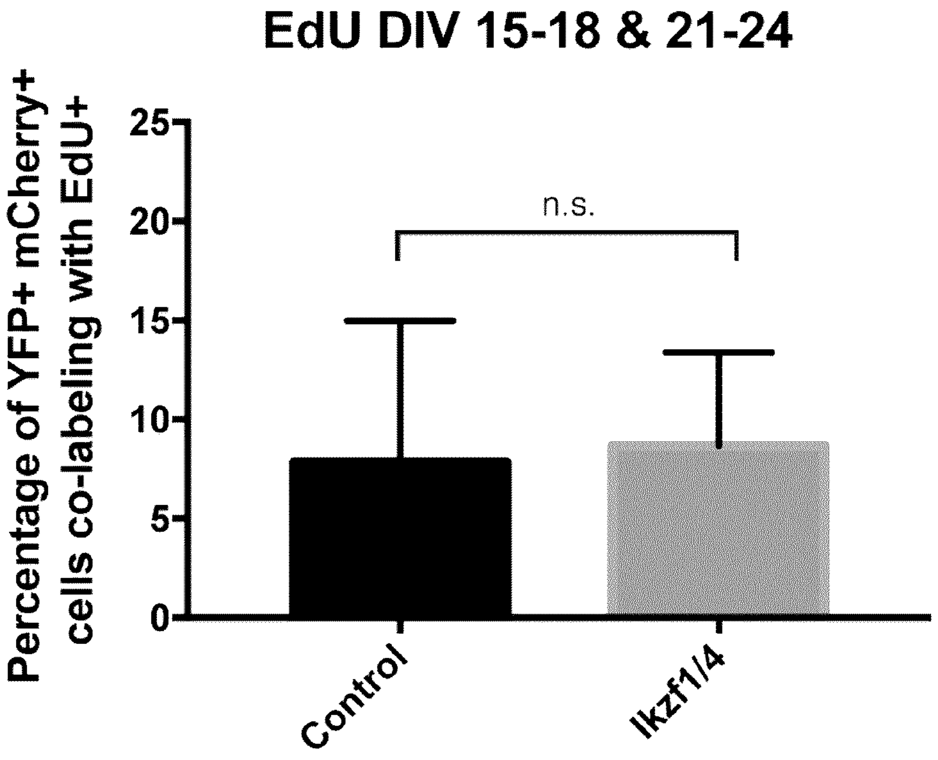

FIGS. 6A-D: Ikzf1/4 does not promote proliferation. (FIGS. 6A-B) Ex vivo EdU experimental protocols. Following protocol from FIG. 2, with EdU added to the media from DIV12-15 and 18-21 (FIG. 6A) or from DIV15-18 and 21-24 (FIG. 6B). (FIG. 6C) Quantifications of EdU incorporation in YFP+ mCherry+ cells in control vs Ikzf1/4 when EdU is added from DIV12-15 and 18-21. T-test comparison of control vs Ikzf1/4 (Control n=4; Ikzf1/4 n=5). (FIG. 6D) Quantifications of EdU incorporation in YFP+ mCherry+ cells in control vs Ikzf1/4 when EdU is added from DIV15-18 and 21-24. T-test comparison of control vs Ikzf1/4 (Control n=4; Ikzf1/4 n=5). YFP: Yellow fluorescent protein. HT: Hydroxytamoxifen. P: Post-natal day. DIV: Days in vitro. Ns: non-significant.

Figure 7C:
Figure 8A:
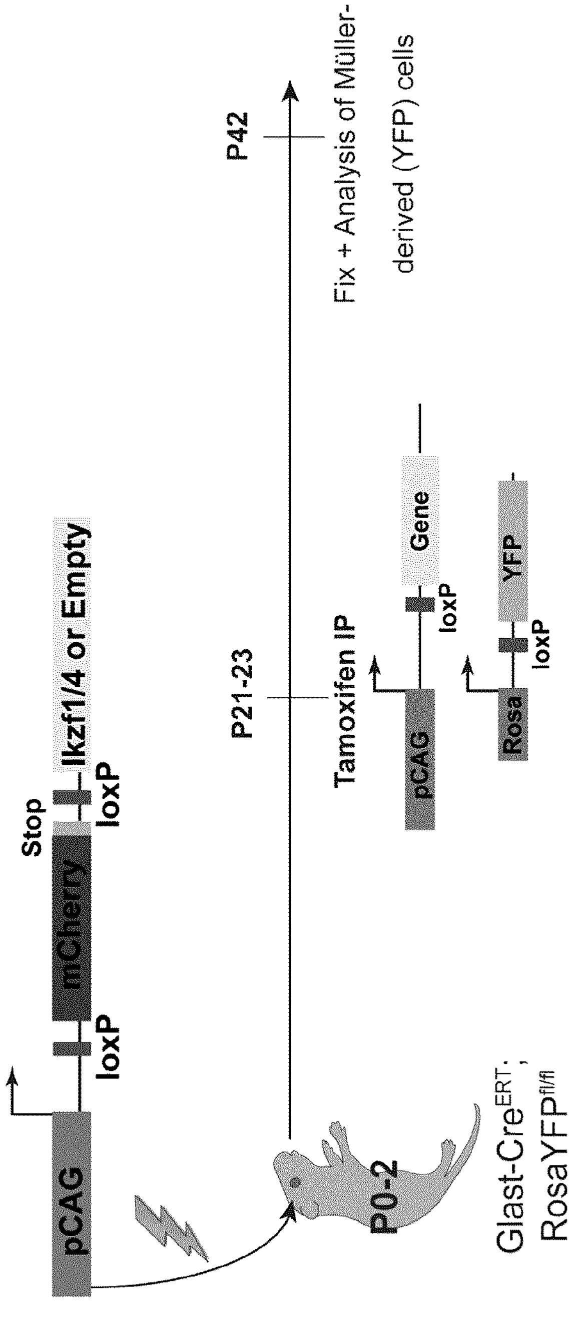
Figure 8B:
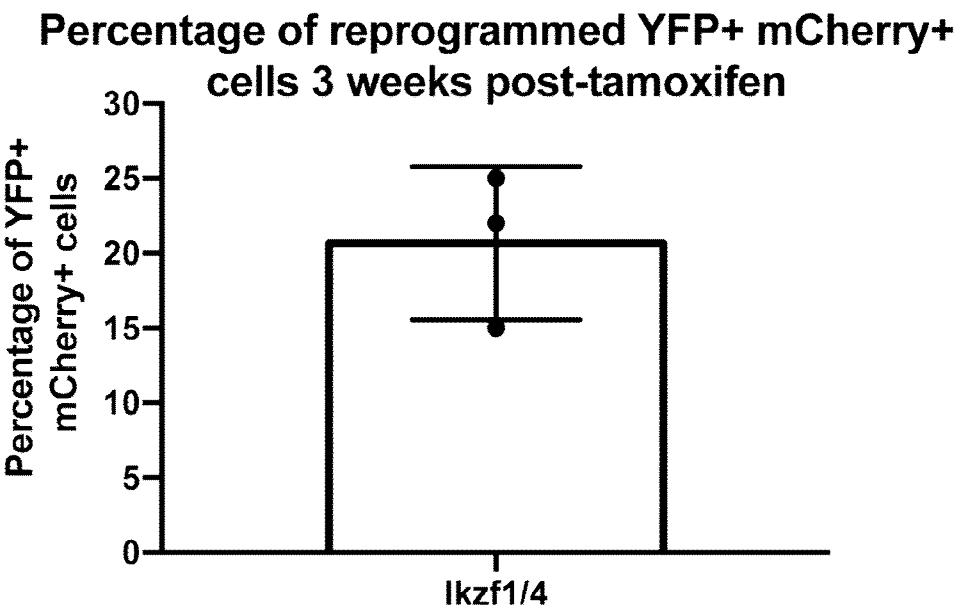
Figure 8C:
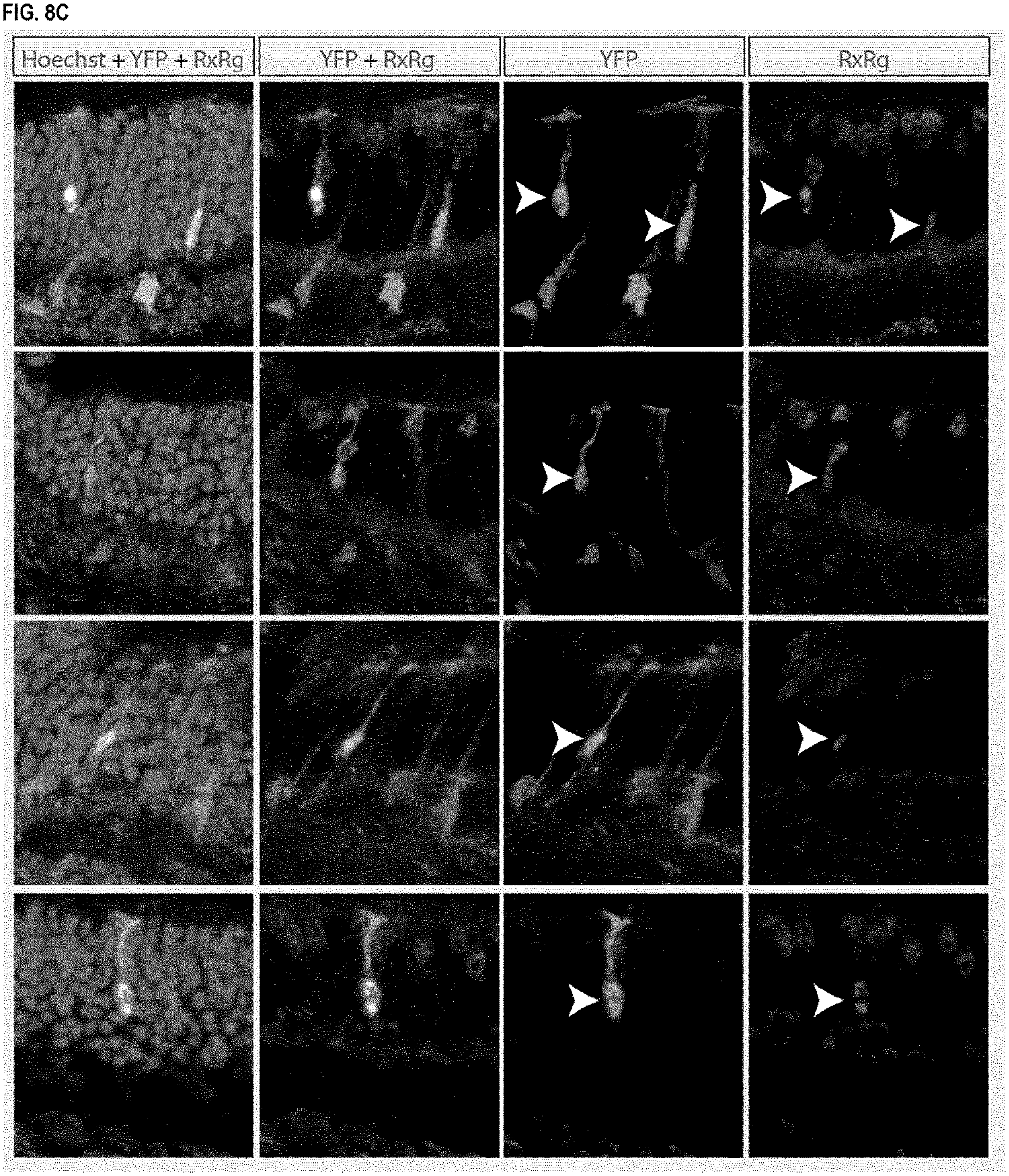
Figure 8D:
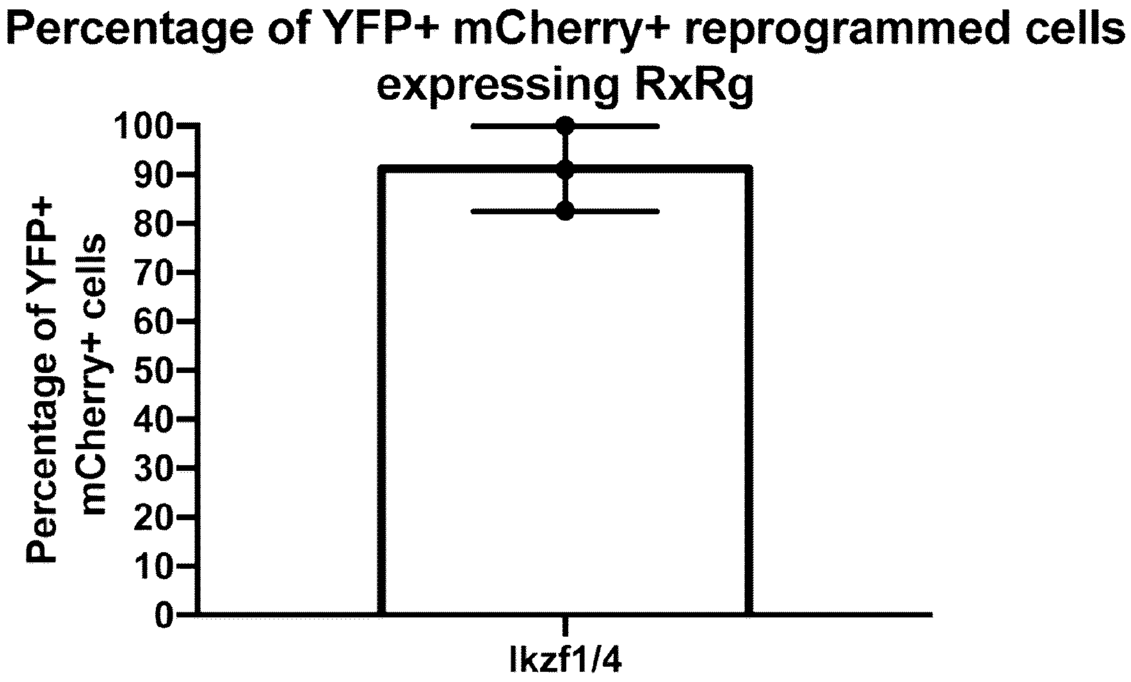
Figure 8E:
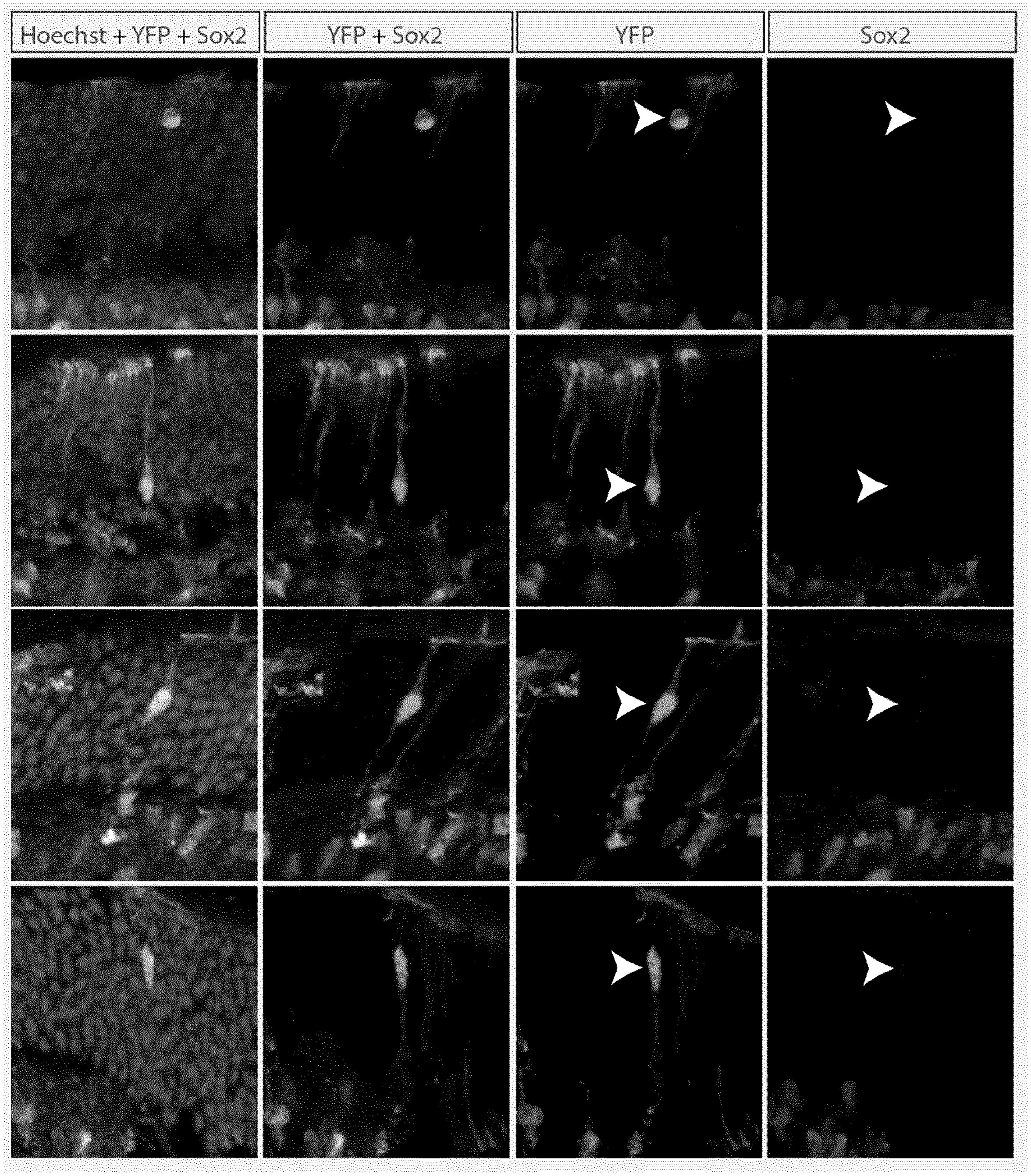
Figure 8F:
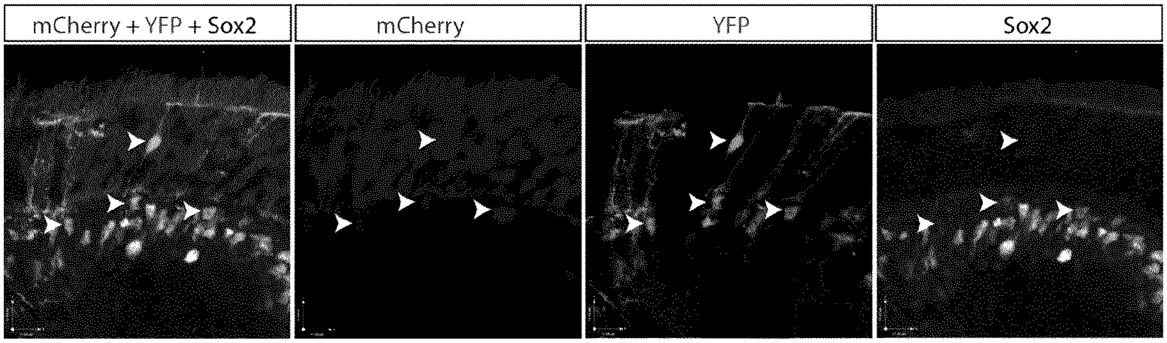
Figure 8G:
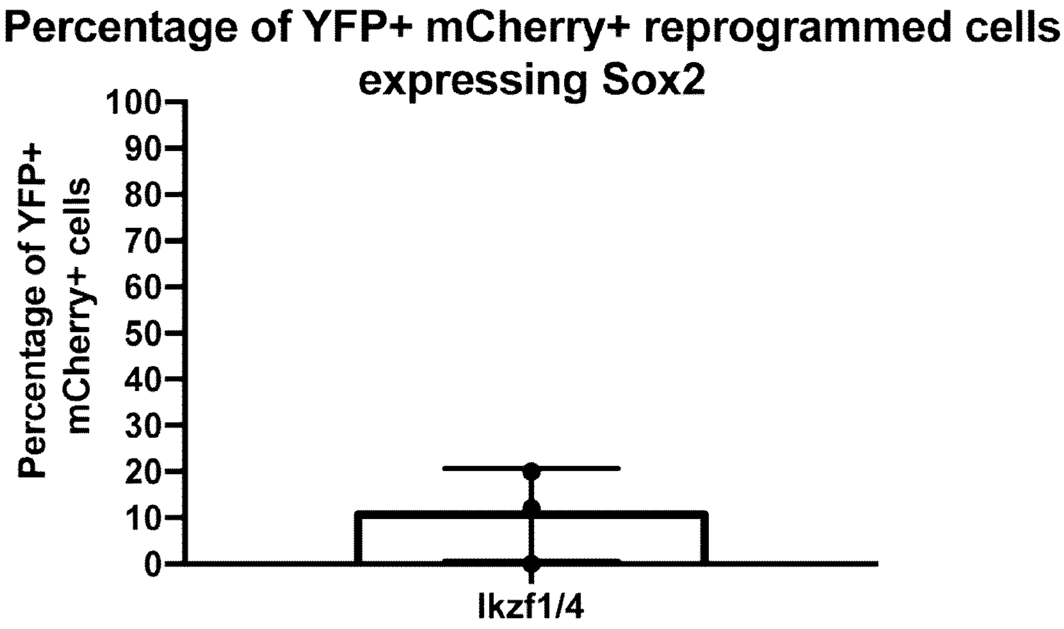

FIGS. 7A-C. Ikzf1/4 expression in Müller glia culture promotes expression of cone markers RxR$_\gamma$ and s-opsin. (FIG. 7A) Control Müller glia culture infected with a GFP-lentiviral vector do not express RxR$_\gamma$ or s-opsin. (FIGS. 7B-B') Some cells (arrows) start expressing s-opsin and RxR$_\gamma$ when infected with Ikzf1- and Ikzf4-lentiviral vectors. (FIG. 7C) Fold change, compared to control, in mRNA levels for photoreceptor genes by RT-qPCR. Both RxR$_\gamma$ and s-opsin are upregulated.

FIGS. 8A-G: 3 weeks of In vivo expression of Ikzf1/4 in Müller glia of the adult mouse retina leads to their reprogramming to cone-like cells. (FIG. 8A) Protocol for in vivo Ikzf1/4 expression. Retinal electroporation of GlastCre$^{ERT}$; RosaYFP$^{fl/fl}$ P0-2 (post-natal days 0-2) animals with conditional expression construct. Tamoxifen IP injections from P21-23 and euthanasia at P42. (FIG. 8B) Quantification of reprogrammed cells in Ikzf1/4 condition 3 weeks post-tamoxifen (n=3). (FIGS. 8C-D) The reprogrammed YFP cells (arrows) locate to the ONL, change morphology, and express the early cone marker RxR$_\gamma$ (quantified in FIG. 8D; n=3) (RxR$_\gamma$ designated Rxrg in FIGS. 8C-D). (FIG. 8E-G) (FIG. 8E) The reprogrammed YFP cells (arrows) do not express the Müller marker Sox2 (quantified in FIG. 8G; n=3). (FIG. 8F) A gradient of Sox2 expression can be observed in YFP+ mCherry+ cells (arrows), with some cells expressing low levels of Sox2, whereas others do not express any detectable Sox2. P: Post-natal day. IP: Intraperitoneal injection. YFP: Yellow fluorescent protein. ONL: Outer nuclear layer.

Figure 9A:
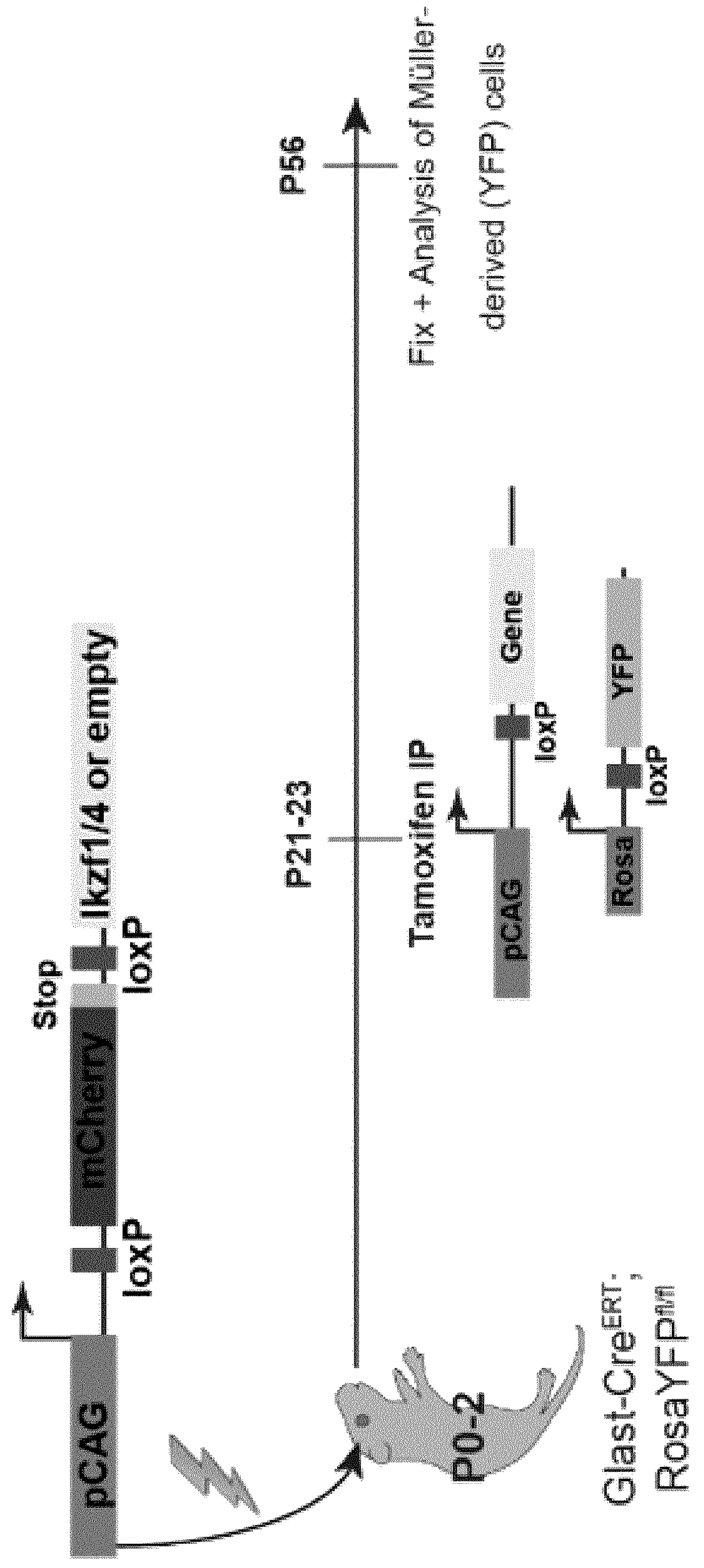
Figure 9B:
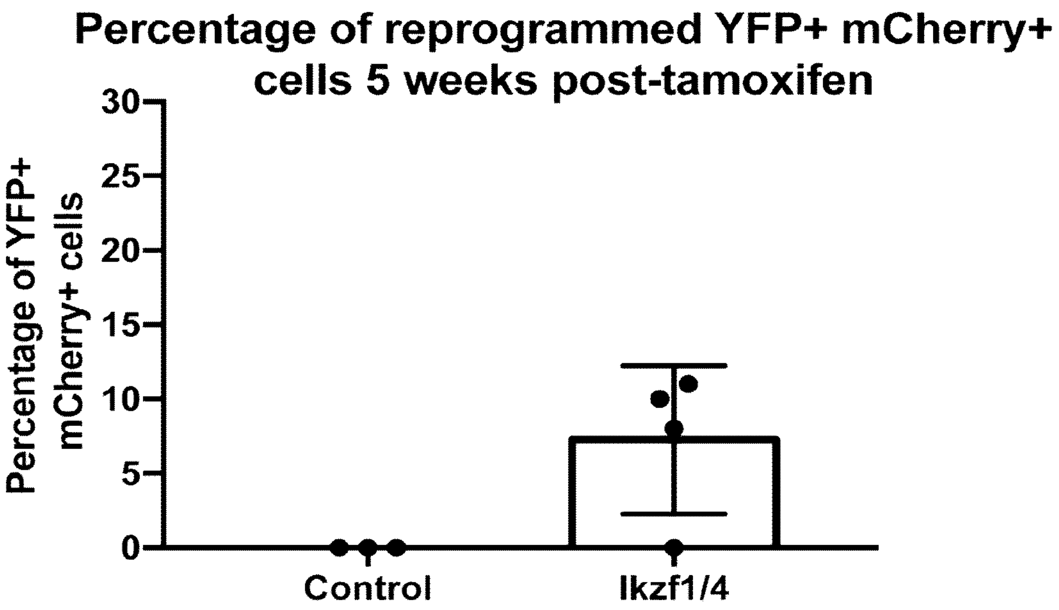

FIGS. 9A-B: Some reprogrammed cone-like cells are still present 5 weeks post-tamoxifen. (FIG. 9A) Protocol for in vivo Ikzf1/4 expression in Müller glia. Same as FIG. 8A, but animals euthanized at P56. (FIG. 9B) Quantification of reprogrammed cells after 5 weeks of Ikzf1/4 expression (control n=3; Ikzf1/4 n=4). P: Post-natal day.

Figure 10A:
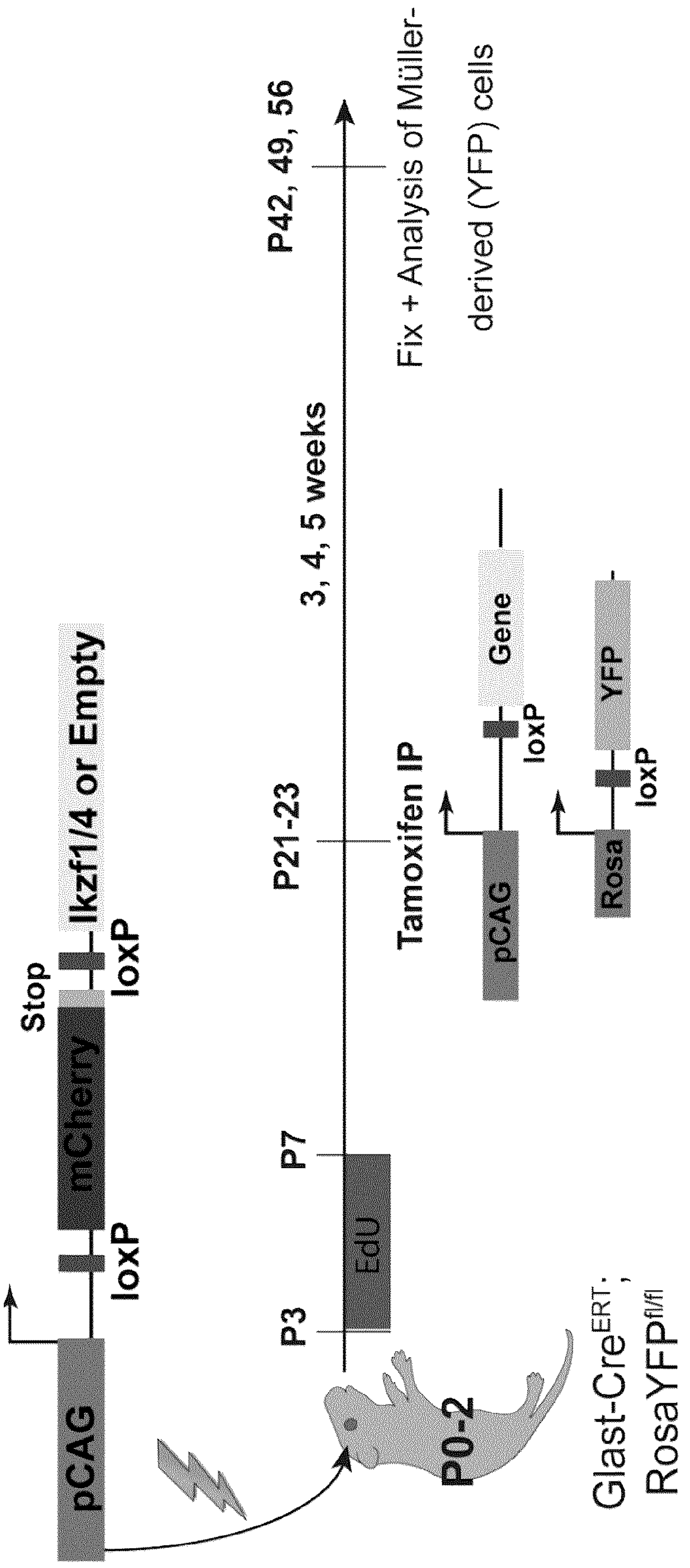
Figure 10B:
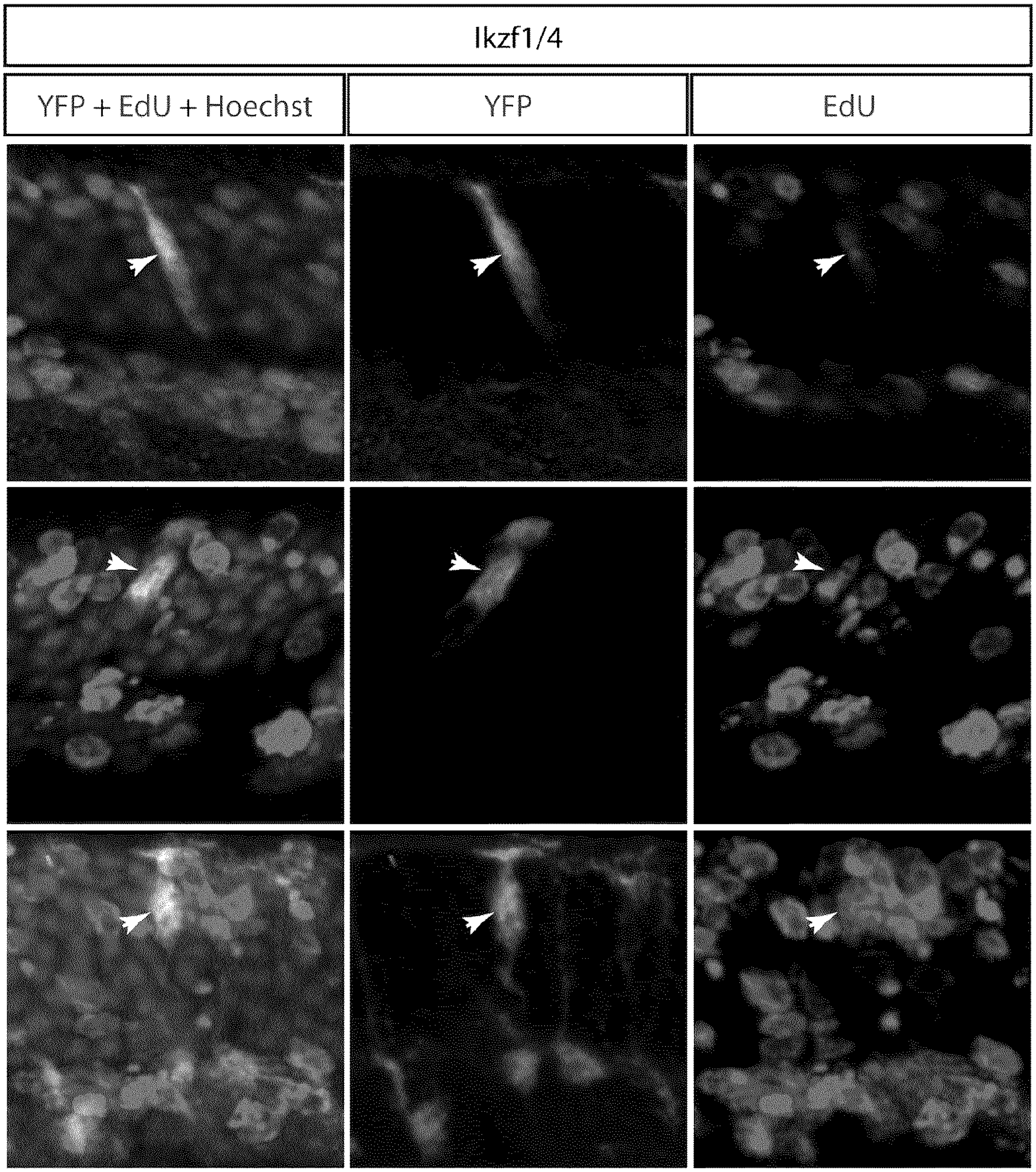

FIGS. 10A-B: 2'-Deoxy-5-ethynyluridine (EdU) tracing of YFP+ mCherry+ cone-like cells. (FIG. 10A) In vivo experimental protocol: Similar to FIG. 8A, with EdU IP injections from P3-P7, which labels late-born cells including Müller glia but not the early born cones. (FIG. 10B) Some reprogrammed YFP+ cells (arrows) are EdU+, indicating that they were generated after EdU administration. P: Post-natal day.

Figure 11A:
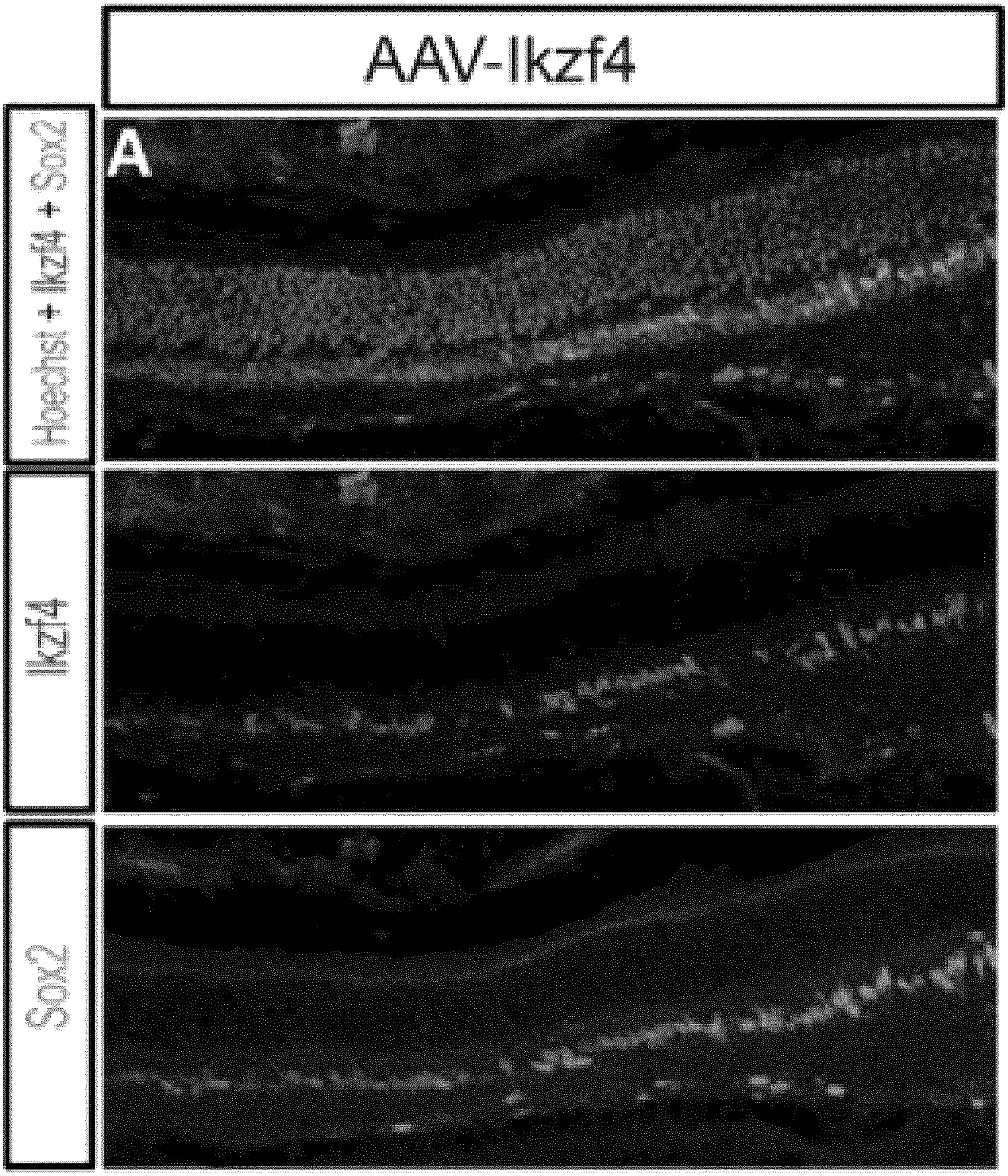
Figure 11D:
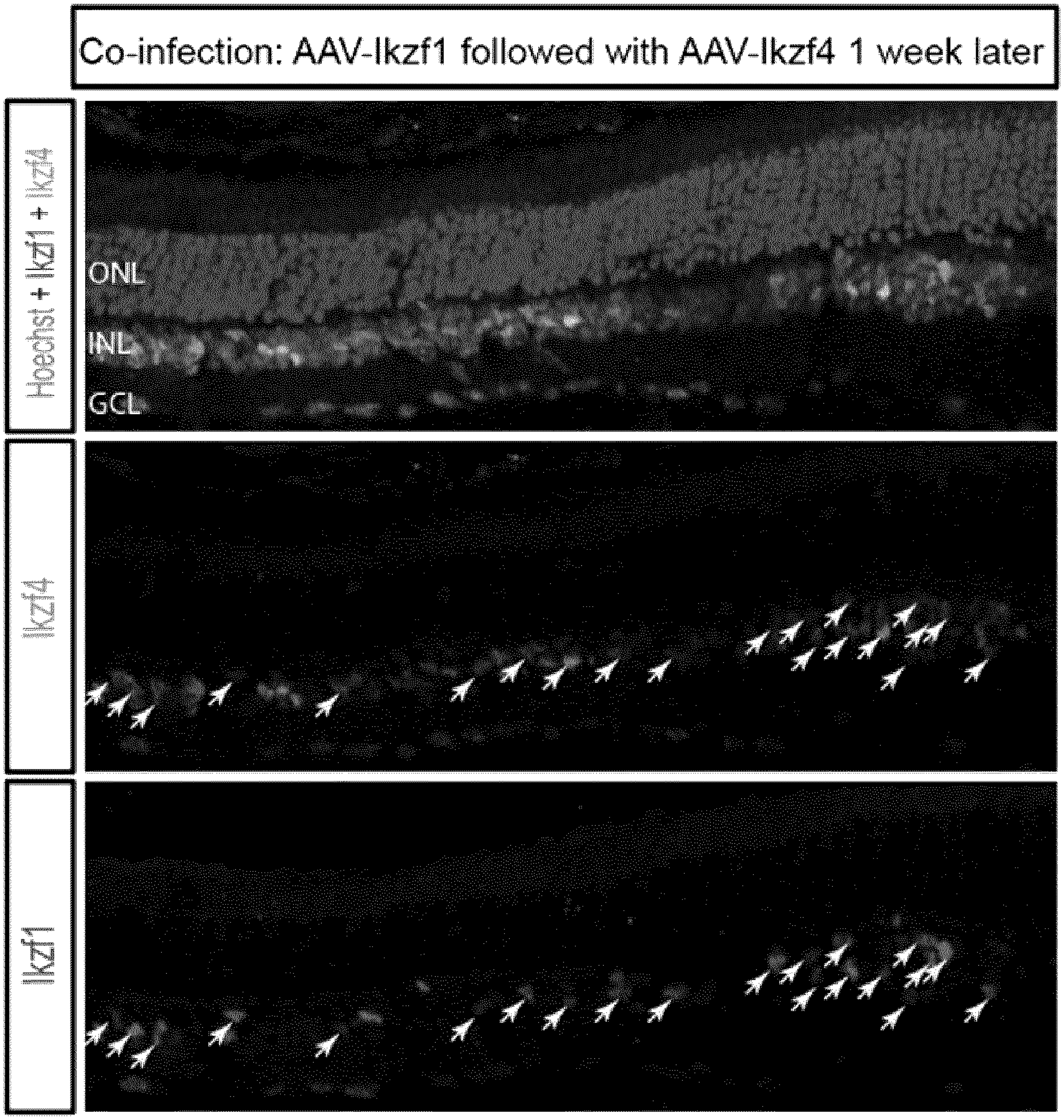

FIGS. 11A-D: Shh10 AAV-Ikzf4 infects Müller glia in vivo and promotes expression of RxR$_\gamma$. (FIG. 11A) Retina 4 weeks post-AAV-Ikzf4 infection. Ikzf4 staining co-labels with Müller glia marker Sox2 in vivo. (FIGS. 11B-C) Ikzf4 co-labels with RxR$_\gamma$ in the INL (FIG. 11B) which is absent in control conditions (FIG. 11C). (FIGS. 11B'-B''') Zoomed view of boxed area in FIG. 11B. Arrows point to Ikzf4 RxR$_\gamma$ cells in the INL. (ONL RxR$_\gamma$ labels endogenous cone photoreceptors.) (FIG. 11D) Co-infection of Ikzf1 and Ikzf4 with 1-week delay. Arrows point to Ikzf1+Ikzf4+ cells in the INL. Some cells also label in the GCL layer. GCL: ganglion cell layer. INL: Inner nuclear layer. ONL: Outer nuclear layer.

FIGS. 12A-H: FIG. 12A: amino acid sequences of mouse Ikzf1 isoforms and consensus thereof (SEQ ID NOs: 1 to 5); FIG. 12B: alignment of the mouse Ikzf1 isoforms and consensus thereof (SEQ ID NOs: 1 to 5); and FIGS. 12C-12H: nucleic acid sequences of mouse Ikzf1 isoforms (SEQ ID NOs: 6 to 10).

FIGS. 13A-F: FIGS. 13A-B: amino acid sequences of human Ikzf1 isoforms and consensus thereof (SEQ ID NOs: 11 to 19); FIGS. 13C-D: alignment of the human Ikzf1 isoforms and consensus thereof (SEQ ID NOs: 11 to 19); and FIGS. 13E-F: alignment of the human Ikzf1 isoform 1 and mouse Ikzf1 isoform a and consensus thereof (SEQ ID NOs: 1, 11 and 20).

FIGS. 14A-L: nucleic acid sequences of human Ikzf1 isoforms (SEQ ID NOs: 21 to 28).

FIGS. 15A-C: FIG. 15A: amino acid sequences of mouse Ikzf4 isoforms and consensus thereof (SEQ ID NOs: 29 to 33); and FIGS. 15B-C: alignment of mouse Ikzf4 isoforms and consensus thereof (SEQ ID NOs:29 to 33).

FIGS. 16A-E: nucleic acid sequences of mouse Ikzf4 isoforms (SEQ ID NOs: 34 to 36).

FIGS. 17A-D: FIG. 17A: amino acid sequences of human Ikzf4 isoforms and consensus thereof (SEQ ID NOs: 37 to 42); FIGS. 17B-C: alignment of human Ikzf4 isoforms and consensus thereof (SEQ ID NOs: 37 to 42); and FIG. 17D: alignment of the human Ikzf4 isoform a and mouse Ikzf4 isoform 1 and consensus thereof (SEQ ID NOs: 37, 29 and to 43).

FIGS. 18A-G: nucleic acid sequences of human Ikzf4 isoforms (SEQ ID NOs: 44 to 48).

FIGS. 19A-D: nucleic acid sequences of mouse Ascl1, Apobec2, Myt11, Pouf2f1, Pouf2f2, Caszlv2 and Brn2 (SEQ ID NOs: 49 to 55).

FIGS. 20A-M: Nucleic acid sequences of vectors pCALL2-loxp-mCherry-stop-loxp-multiple cloning sites (FIGS. 20A-B); pCALL2-loxp-mCherry-stop-loxp-Gateway cassette (FIGS. 20C-E); pCALL2-loxp-mCherry-stop-loxp-Ikzf1 (FIGS. 20E-G); pCALL2-loxp-mCherry-stop-loxp-Ikzf4 (FIGS. 20G-J); pssAAV-CAG-GFP (FIGS. 20J-K); pssAAV-CAG-Ikzf1 (FIGS. 20K-L); pssAAV-CAG-Ikzf4 (FIGS. 20L-M) (SEQ ID NOs: 56 to 62).

FIGS. 21A-N: Nucleic acid sequences of lentiviral vectors FUW-M2rtTA (Addgene, Inc., Plasmid #20342) (lentiviral vector) (FIGS. 21A-C); pMule-Lenti-Dest-Ikzf1-iRFP (lentiviral vector) (FIGS. 21D-F); TET-o-FUW-EGFP (lentiviral vector) (FIGS. 21G-J); and TET-O-FUS-Ikzf4 (lentiviral vector) (FIGS. 21K-N) (SEQ ID NOs: 63 to 66).

FIGS. 22A-E: Nucleic acid sequences of lentiviral vectors pCIG-GFP (control for FIG. 1; FIGS. 22A-B); and pCIG-Ikzf4-GFP (used in FIG. 1; FIGS. 22C-E) (SEQ ID NOs: 67 to 68).

DESCRIPTION OF ILLUSTRATIVE EMBODIMENTS

Definitions

The use of the terms "a" and "an" and "the" and similar referents in the context of describing the technology (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the disclosure and does not pose a limitation on the scope of the disclosure unless otherwise claimed.

No language in the specification should be construed as indicating any non-claimed element as essential to the practice of the disclosure.

Herein, the term "about" has its ordinary meaning. In embodiments, it may mean plus or minus 10% of the numerical value qualified.

Unless otherwise defined, all technical and scientific terms used herein have the same meaning as commonly understood by one of ordinary skill in the art to which this disclosure belongs.

Cells

In a one aspect, the present disclosure relates to a recombinant nervous system cell (e.g., mammalian such as human) expressing Ikzf1 and/or Ikzf4. As used herein the terms "nervous system cell" refers to neuroepithelial cells, glial cells and neurons. In accordance with the present disclosure, recombinant nervous system cells (e.g., neuroepithelial cells, glial cells) that are manipulated (e.g., cells transformed or transfected) to express Ikzf1 and/or Ikzf4 will become (i.e., be reprogrammed as) neurons, as a result of this expression. For example, and without being so limited, recombinant neuroepithelial cells that are manipulated (e.g., cells transformed or transfected) to express Ikzf4 cells will become cone photoreceptor (see e.g., Examples 2-3) and Müller glia cells that are manipulated (e.g., cells transformed or transfected) to express Ikzf1 and Ikzf4 will become cone photoreceptor cells (see e.g., Examples 4-10).

In an embodiment, nervous system cells targeted by methods described herein are endogenous retinal nervous system cells of a subject in need for cone photoreceptors. In this embodiment, vectors of the present disclosure are introduced in the eye(s) of the subject in need thereof and the targeted cells are reprogrammed in vivo. Alternatively, in other embodiments, recombinant cells are reprogrammed ex vivo or in vitro. For such embodiments of the methods described herein, sources of nervous system cells can be embryonic nervous system cells (e.g., embryonic neuroepithelial cells), adult nervous system cells (e.g., adult Müller glia cells can be isolated from postmortem human tissue), embryonic stem cells transformed into nervous system cells such as neuroepithelial cells by the Zhong et al. 2014 method, or induced pluripotent stem cells (IPSCs) transformed into nervous system cells such as neuroepithelial cells by the Nakano et al. 2012 method.

In a specific embodiment, the recombinant nervous system cell is a retinal nervous system cell. As used herein the term "retinal nervous system cell" refers to retinal neuroepithelial cells, retinal glial cells and retinal neurons. In specific embodiments, such cells can be adult cells.

In another specific embodiment, the recombinant nervous system cell is a glial cell (e.g., Müller glia cell).

In another specific embodiment, the recombinant nervous system cell is a neuron (e.g., cone photoreceptor). In another specific embodiment, the recombinant nervous system cell is a cone photoreceptor. In another embodiment it is a cell having cone morphologies and expresses at least one of (at least two of, or at least three of, or all four of) cone arrestin, $RxR_{\gamma}$, S-opsin and PNA.

The term "recombinant" in the expression "recombinant retinal neuron cell" refers to a cell that has been genetically modified (e.g., transformed or transfected) to express Ikzf1 and Ikzf4.

IKAROS Family Zinc Finger 1 (Ikzf1) and IKAROS Family Zinc Finger 4 (Ikzf4) are transcriptions factors that belong to the family of zinc-finger DNA-binding proteins associated with chromatin remodeling. Ikzf1 is known to open chromatin (Bottardi S, Mavoungou L, Pak H, et al. The IKAROS interaction with a complex including chromatin remodeling and transcription elongation activities is required for hematopoiesis. PLoS Genet. 2014; 10 (12): e1004827. Published 2014 Dec. 4. doi:10.1371/journal.pgen.1004827). As shown herein Ikzf4 is able to induce cone production.

As used herein, the term "Ikzf1" refers to a biologically active Ikzf1 and unless the context suggests otherwise, encompasses any functional isoform of the Ikzf1 including, without being so limited in e.g., those depicted in human Uniprot Q13422-1, Q13422-2, Q13422-3, Q13422-4, Q13422-5, Q13422-6, Q13422-7 and Q13422-8 or any orthologue thereof e.g., mouse) (see also e.g., FIGS. 12-14).

In specific embodiments, it refers to any one of the mouse Ikzf1 isoform a (NP_001020768), human Ikzf1 isoform 1 (Q13422) or any consensus derived therefrom (see e.g., FIGS. 13E-F).

As used herein, the term "Ikzf4" refers to a biologically active Ikzf4 and unless the context suggests otherwise, encompasses any functional isoform of the Ikzf4 including, without being so limited in e.g., those depicted in human Uniprot Q9H2S9-1 and Q9H2S9-2 or any orthologue thereof (e.g., mouse) (see e.g., FIGS. 15-18). In specific embodiments, it refers to any one of the mouse Ikzf4 isoform 1 (Q8C208), human Ikzf1 isoform a (NP_071910.3) or any consensus derived therefrom (see e.g., FIGS. 17B-D).

The instant disclosure encompasses the use of Ikzf1 and Ikzf4 that can differ from the native proteins (e.g., human and other mammalian orthologues). For instance, proteins can be used that satisfy the consensus sequences derived from the alignments in FIGS. 12-18. In specific embodiment of these consensuses, each variable position in the consensus sequences is defined as being any amino acid, or absent when this position is absent in one or more of the orthologues presented in the alignment. In specific embodiment of these consensuses, each X in the consensus sequences is defined as being any amino acid that constitutes a conserved or semi-conserved substitution of any of the amino acid in the corresponding position in the orthologues presented in the alignment, or absent when this position is absent in one or more of the orthologues presented in the alignment. In FIGS. 12-18, conservative substitutions are denoted by the symbol ":" and semi-conservative substitutions are denoted by the symbol ".". In another embodiment, each X refers to any amino acid belonging to the same class as any of the amino acid residues in the corresponding position in the orthologues presented in the alignment, or absent when this position is absent in one or more of the orthologues presented in the alignment. In another embodiment, each X refers to any amino acid in the corresponding position of the orthologues presented in the alignment, or absent when this position is absent in one or more of the orthologues presented in the alignment. The Table below indicates which amino acid belongs to each amino acid class.

| Class | Name of the amino acids |
|---|---|
| Aliphatic | Glycine, Alanine, Valine, Leucine, Isoleucine |
| Hydroxyl or Sulfur/ Selenium-containing | Serine, Cysteine, Selenocysteine, Threonine, Methionine |
| Cyclic | Proline |
| Aromatic | Phenylalanine, Tyrosine, Tryptophan |
| Basic | Histidine, Lysine, Arginine |
| Acidic and their Amide | Aspartate, Glutamate, Asparagine, Glutamine |

Other functional Ikzf1 and Ikzf4 variants may also be obtained by deletion of 1, 2, 3, 4, 5, 10, 15 or 10 and up to 30, 40, 50 or 60 amino acids of the native or sequences satisfying the consensus Ikzf1 and Ikzf4 sequences e.g., at the N-terminal end and/or the C-terminal end of these protein, preferably the N-terminal end. Similarly, protein construct comprising Ikzf1 and Ikzf4 may also encompass additional amino acids (1, 2, 3, 4, 5, 10, 15 or 10 and up to 30, 40, 50 or 60 amino acids) at the N- and/or C-terminal of the native or sequences satisfying the consensus Ikzf1 and Ikzf4 sequences. Such additional amino acids may be the result of cloning or could be added to increase the stability or targeting of the proteins.

Nucleic Acids, Vectors, Cells

The present disclosure also relates to nucleic acids comprising nucleotide sequences encoding the above-mentioned Ikzf1 and/or Ikzf4. The nucleic acid can be a DNA or an RNA. The nucleic acid sequence can be deduced by the skilled artisan on the basis of the disclosed amino acid sequences. In a specific embodiment, the nucleic acid is any one of the nucleic acid sequences depicted in FIGS. 12C-H, 14A-L, 16A-E, 18A-G or encodes any one of the amino acid sequences (mouse, humans or consensus derived from alignments of these sequences) as depicted in any one of FIGS. 12A-B, 13A-F, 15A-C, 17A-D and consensuses derived thereof.

The Ikzf1 and/or Ikzf4 could also be modified for better expression/stability/yield in the cell; codon optimization for expression in the heterologous nervous system cell such as glial cells (e.g., Müller glia cell); use of different combinations of promoter/terminators for optimal co-expression of multiple nucleic acids.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutations may include addition, deletion, or substitution of an amino acid; a conservative amino acid substitution is defined herein as the substitution of an amino acid residue for another amino acid residue with similar chemical properties (e.g., size, charge, or polarity).

In a non-limiting example, a conservative mutation may be an amino acid substitution. Such a conservative amino acid substitution may be a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (He or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2, BLAST-P, BLAST-N, COBALT or FASTA-N, or any other appropriate software/tool that is known in the art (Johnson, et al. 2008).

The substantially identical sequences of the present disclosure may be at least 75% identical; in another example, the substantially identical sequences may be at least 80, 85, 90, 95, 96, 97, 98 or 99% identical at the amino acid level to sequences described herein.

In another aspect, the present disclosure relates to a vector comprising a promotor operably-linked to a nucleic acid molecule encoding Ikzf1 and/or a nucleic acid molecule encoding Ikzf4.

The vectors can be of any type suitable, e.g., for expression of said polypeptides or propagation of genes encoding said polypeptides in a particular organism. The organism may be of eukaryotic origin (e.g., human). The specific choice of vector depends on the host organism and is known to a person skilled in the art. In an embodiment, the vector comprises transcriptional regulatory sequences or a promoter operably-linked to a nucleic acid comprising a sequence encoding an Ikzf1 and/or Ikzf4 of the disclosure. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequence.

Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous. "Transcriptional regulatory sequences" or "transcriptional regulatory elements" are generic terms that refer to DNA sequences, such as initiation and termination signals (terminators), enhancers, and promoters, splicing signals, polyadenylation signals, etc., which induce or control transcription of protein coding sequences with which they are operably-linked.

Without being so limited, vectors useful to express the Ikzf1 and Ikzf4 of the present disclosure include any vector containing a glial (e.g., Müller cell)-specific promoter to drive expression of Ikzf1 and/or Ikzf4 or nonspecific promoters to drive expression of Ikzf1 and/or Ikzf4 in neuroepithelial cells; or, when certain viral vector serotypes are used, can target specifically Müller glia through the viral capsid. Many useful (human) cell expression vectors, are commercially available, e.g., from Addgene, Inc., Invitrogen™ the American Type Culture Collection or the Euroscarf collection.

Promoters useful to express the Ikzf1 and/or Ikzf4 of the present disclosure include glial-specific promoters Slc1a3 (solute carrier family 1 (glial high-affinity glutamate transporter, member 3), also called Glutamate Aspartate Transporter (GLAST)) promoter, Lhx2 promoter, and Sox9 promoter. Promoters useful to express the Ikzf1 and/or Ikzf4 of the present disclosure in cells such as neuroepithelial cells include nonspecific promoters such as CAG and CMV.

Without being so limited, in certain embodiments, it may be useful to include in the constructs disclosed herein means to reduce or stop expression of Ikzf1 and/or Ikzf4 include Tet-On (expression only in the presence of tetracyclin/doxycyxlin whereas Tet-off is always expressed except when tetracyclin/doxycyxlin is present).

The term "heterologous coding sequence" refers herein to a nucleic acid molecule that is not normally produced by the host cell in nature.

A recombinant expression vector (plasmid, viral vector) comprising a nucleic acid molecule(s) of the present disclosure may be introduced into a cell, e.g., a Müller cell or a neuroepithelial cell, capable of expressing the protein coding region from the defined recombinant expression vector. Accordingly, the present disclosure also relates to cells (host cells) comprising the nucleic acid and/or vector as described above. The terms "host cell" and "recombinant cell" are used interchangeably herein. Such terms refer not only to the particular subject cell, but also to the progeny or potential progeny of such a cell. Because certain modifications may occur in succeeding generations due to either mutation or environmental influences, such progeny(ies) may not, in fact, be identical to the parent cell, but are still included within the scope of the term as used herein. Vectors can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), Sambrook and Russell (supra) and other laboratory manuals. Methods for introducing nucleic acids into mammalian cells in vivo are also known and may be used to deliver the vector DNA of the disclosure to a subject for gene therapy.

In specific embodiments, as indicated above, the cells expressing Ikzf1 and/or Ikzf4 are mammalian nervous system cells such as neuroepithelial cells, glial cells (e.g., retinal glial cells) or neurons.

In another aspect, the present disclosure relates to a method of producing a recombinant cone photoreceptor, comprising: (a) introducing a nucleic acid molecule encoding IKAROS Family Zinc Finger 1 (Ikzf1) in a Müller glia cell; and (b) introducing a nucleic acid molecule encoding IKAROS Family Zinc Finger 4 (Ikzf4) in the Müller glia cell, whereby the Müller glia is transformed into a recombinant cone photoreceptor. In specific embodiments, (a) and (b) can be in vitro, ex vivo or in vivo. The introduction/administration of (a) and (b) can be simultaneous or sequential in any order (i.e. (a) before (b) or (b) before (a). When administration is simultaneous, a single nucleic acid (vector) can be used to encode both Ikzf1 and Ikzf4. When the introducing (a) and (b) is in vivo, the subject may be a subject in need thereof.

As used herein the terms "sequential" in the context of introducing or administering (a) and (b) sequentially refers to successive introduction or administration of (a) and (b). In specific embodiments, the two introductions or administration may be separated by about 1 week.

In another aspect, there is provided a method of preventing or treating a disease or condition associated with a cone photoreceptor degeneration or a symptom thereof, comprising: (a) administering a nucleic acid molecule encoding IKAROS Family Zinc Finger 1 (Ikzf1) in a Müller glia cell; and (b) administering a nucleic acid molecule encoding IKAROS Family Zinc Finger 4 (Ikzf4) in the Müller glia cell, to a subject in need thereof. The nucleic acids are advantageously administered in a therapeutically effective amount.

As used herein the term "disease or condition associated with cone photoreceptor degeneration" refers to retinal degenerative diseases such as retinitis pigmentosa, age-related macular degeneration, cone-rod dystrophies, Leber congenital amaurosis, Stargardt disease, and Usher syndrome. As used herein the term "or a symptom thereof" refers as least to the degeneration of cone photoreceptor including a reduction in cone photoreceptor number and/or activity or a reduction in vision.

The introduction or administering of (a) and/or (b) (route of administration) can be intraocular such as but not limited to intravitreal or sub-retinal.

As used herein the term "subject" is meant to refer to any mammal including human, mice, rat, dog, cat, pig, cow, monkey, horse, etc. In a particular embodiment, it refers to a human.

As used herein, the term "subject in need thereof" in the above-disclosed methods is meant to refer to a subject that would benefit from receiving a nucleic acid molecule encoding Ikzf1 and a nucleic acid molecule encoding Ikzf4 in a Müller glia cell in accordance with the present disclosure (e.g., for introduction into Müller glia cell by e.g., intravitreal or sub-retinal administration). In specific embodiments, it refers to a subject that already has a disease or condition associated with a cone photoreceptor degeneration or a symptom thereof. In another embodiment it further refers to a subject that has as retinitis pigmentosa, age-related macular degeneration, cone-rod dystrophies, Leber congenital amaurosis, Stargardt disease, and Usher syndrome.

As used herein, the term "prevent/preventing/prevention" or "treat/treating/treatment", refers to eliciting the desired biological response, i.e., a prophylactic and therapeutic effect, respectively in a subject. In accordance with the present disclosure, the therapeutic effect comprises one or more of a decrease/reduction in the severity, intensity and/or duration of the disease or condition associated with a cone photoreceptor degeneration or a symptom thereof (referred to hereinafter in the present paragraph as "disease, condition or any symptom thereof") following administration of the nucleic acids, vectors (e.g., AAV), cells or pharmaceutical composition ("agent") of the present disclosure when compared to its severity, intensity and/or duration in the subject prior to treatment or as compared to that/those in a non-treated control subject having the disease, condition or any symptom thereof. In accordance with the disclosure, a prophylactic effect may comprise a delay in the onset of the disease, condition or any symptom thereof in an asymptomatic subject at risk of experiencing the disease, condition or any symptom thereof at a future time; or a decrease/reduction in the severity, intensity and/or duration of disease, condition or any symptom thereof occurring following administration of the agent of the present disclosure, when compared to the timing of their onset or their severity, intensity and/or duration in a non-treated control subject (i.e. asymptomatic subject at risk of experiencing the disease, condition or any symptom thereof); and/or a decrease/reduction in the progression of any pre-existing disease, condition or any symptom thereof in a subject following administration of the agent of the present disclosure when compared to the progression of the disease, condition or any symptom thereof in a non-treated control subject having such pre-existing disease, condition or any symptom thereof. As used herein, in a therapeutic treatment, the agent of the present disclosure is administered after the onset of the disease, condition or any symptom thereof. As used herein, in a prophylactic treatment, the agent of the present disclosure is administered before the onset of the disease, condition or any symptom thereof or after the onset thereof but before the progression thereof.

Combination

In addition to nucleotide sequences encoding the above-mentioned Ikzf1 and/or Ikzf4, other factors can be used in accordance with the methods disclosed herein could enhance differentiation of the reprogrammed cells into mature cone photoreceptors, including, without being so limited, factors involved in cone differentiation, survival, chromatin remodelling, and proliferation, either in the form of co-administered or sequentially administered nucleic acids encoding such factors or as co-administered or sequentially administered small molecules, proteins, etc. In specific embodiments, the recombinant cell disclosed herein comprise heterologous nucleic acid encoding Ikzf1 and/or Ikzf4, and one more heterologous nucleic acid encoding one of the above factors, or 2 or less of these factors, 3 or less, 4 or less, 5 or less, 6 or less, 7 or less, 8 or less, 9 or less, or 10 or less additional heterologous nucleic acid heterologous nucleic acid encoding one of the above factors. As used herein, the term "heterologous" refers to nucleic acid that was voluntarily introduced in the host cell (endogenously or exogenously) as disclosed herein.

Dosage

Any amount of the nucleic acids, vectors, cells or pharmaceutical compositions disclosed herein ("agent") can be administered to a subject. The dosages will depend on many factors including the mode of administration and the age of the subject. Typically, the amount of agent of the disclosure contained within a single dose will be an amount that effectively prevent, or treat a disease or condition associated with a cone photoreceptor degeneration or a symptom thereof without inducing significant toxicity. As used herein the term "therapeutically effective amount" is meant to refer to an amount effective to achieve the desired therapeutic effect while avoiding adverse side effects. The dose varies with the type of administration, Typically, the agent in accordance with the present disclosure can be administered to subjects in doses ranging from 0.001 to 500 mg (of nucleic acid, viral particle or composition comprising either with a pharmaceutically acceptable carrier)/per eye and, in a more specific embodiment, about 0.1 to about 100 mg/per eye, and, in a more specific embodiment, about 0.2 to about 20 mg/per eye, and in a more specific embodiment, about 0.2 to about 10 mg/per eye.

In mice for example, when electroporation was used, 1 μl of DNA solution was administered at 3 μg/μl/eye (i.e. 3 μg (0.003 mg) of DNA/eye). When viral-gene therapy was used (i.e. AAV), 2 μl/eye of ShH10-Ikzf1 at a titer of 6.96E+12 vg/ml and 2 μl/eye of ShH10 Ikzf4 at a titer of 5.87E+13 vg/ml. The allometric scaling method of Mahmood et al. (Mahmood et al. 2003) can be used to extrapolate the dose from mice to human. The dosage will be adapted by the clinician in accordance with conventional factors such as the extent of the disease and different parameters from the patient.

The therapeutically effective amount of the agent of the instant disclosure may also be measured directly. Typically, a pharmaceutical composition of the disclosure can be administered in an amount from about 0.001 mg up to about 500 mg per eye as a single dose (e.g., 0.05, 0.01, 0.1, 0.2, 0.3, 0.5, 0.7, 0.8, 1 mg, 2 mg, 3 mg, 4 mg, 5 mg, 10 mg, 15 mg, 20 mg, 30 mg, 50 mg, 100 mg, or 250 mg). In specific embodiment, the action of the dose is applied for about one month.

These are simply guidelines since the actual dose must be carefully selected and titrated by the attending physician based upon clinical factors unique to each patient or by a nutritionist. The optimal daily dose will be determined by methods known in the art and will be influenced by factors such as the age of the patient as indicated above and other clinically relevant factors. In addition, patients may be taking medications for other diseases or conditions. The other medications may be continued during the time that an agent in accordance with the instant disclosure is given to the patient, but it is particularly advisable in such cases to begin with low doses to determine if adverse side effects are experienced.

Carriers/Vehicles

As used herein "pharmaceutically acceptable carrier" or "excipient" includes any and all solvents, dispersion media, coatings, antibacterial and antifungal agents, physiological media, and the like that are physiologically compatible. In embodiments, the carrier is suitable for ocular administration. Pharmaceutically acceptable carriers for ocular administration include sterile aqueous solutions (e.g., saline) or dispersions and sterile powders for the extemporaneous preparation of sterile injectable solutions or dispersion. The use of such media and agents, such as for ocular application, is well known in the art. Except insofar as any conventional media or agent is incompatible with the compounds of the disclosure, use thereof in the compositions of the disclosure is contemplated. Supplementary active compounds can also be incorporated into the compositions.

Administration and Introduction

The above-mentioned nucleic acids or vectors may be delivered to cells in vivo (to induce the expression of the Ikzf1 and Ikzf4 in accordance with the present disclosure) using methods well known in the art such as direct injection of DNA, receptor-mediated DNA uptake, viral-mediated transfection or non-viral transfection and lipid-based transfection, all of which may involve the use of gene therapy vectors. Direct injection has been used to introduce naked DNA into cells in vivo. A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor. Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes. In specific embodiment, the vector(s) comprise a system to turn off Ikzf1 and/or Ikzf4 after a specific time period after administration (e.g., tetracycline-inducible promoters, which are turned off once tetracycline is removed).

As used herein, the term "decrease" or "reduction" (e.g., of a disease or condition associated with a cone photoreceptor degeneration or of a symptom thereof) refers to a reduction of at least 10% as compared to a control subject (a subject not treated with an agent of the present disclosure), in an embodiment of at least 20% lower, in a further embodiment of at least 30% lower, in a further embodiment of at least 40% lower, in a further embodiment of at least 50% lower, in a further embodiment of at least 60% lower, in a further embodiment of at least 70% lower, in a further embodiment of at least 80% lower, in a further embodiment of at least 90% lower, in a further embodiment of 100% (complete inhibition).

Similarly, as used herein, the term "increase" or "increasing" (e.g., of an Ikzf1 and/or Ikzf4 biological activity in a method of the present disclosure of at least 10% as compared to a control, in an embodiment of at least 20% higher, in a further embodiment of at least 30% higher, in a further embodiment of at least 40% higher, in a further embodiment of at least 50% higher, in a further embodiment of at least 60% higher, in a further embodiment of at least 70% higher, in a further embodiment of at least 80% higher, in a further embodiment of at least 90% higher, in a further embodiment of 100% higher, in a further embodiment of 200% higher, etc. The "control" for use as reference in the method disclosed herein of preventing or treating a disease or condition associated with a cone photoreceptor degeneration or of a symptom thereof may be e.g., a control subject that has a disease or condition associated with a cone photoreceptor degeneration or of a symptom thereof, and that is not treated with an agent present disclosure.

The nucleic acids disclosed herein could be advantageously delivered through gene therapy.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts and may be used for gene therapy as well as for simple protein expression. "Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral; particle that comprises a polynucleotide to be delivered into a host cell, either in vivo, ex vivo or in vitro. Examples of viral vectors include retroviral vectors, adeno-associated virus vectors (see e.g., Example 10 and FIGS. 20J-M), adenovirus vectors such as those described in Petit et al., 2016 for gene therapy in the eye, Pellissier et al., 2014 for injection intravitreally in the retina and Yao et al. 2018 for injection in the retina; alphavirus vectors such as Semliki Forest virus-based vectors and Sindbis virus-based vectors; lentivirus-based viral vectors and the like (see Example 8 and FIGS. 21A-N).

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. AAVs include more than 10 serotypes. In a specific embodiment, the AAV serotype Shh10 which harbors a Müller-cell specific capsid is used (see e.g., FIG. 11). In other embodiments, AAV serotypes specific for neuroepithelial cells are used. See, e.g., International PCT Application No. WO 95/27071. Ads are easy to grow and do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Vectors that contain both a promoter and a cloning site into which a polynucleotide can be operatively linked are well known in the art. Such vectors are capable of transcribing RNA and are commercially available from sources such as Stratagene (La Jolla, CA) and Promega Biotech (Madison, WI). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation.

Recombinant cone photoreceptors as disclosed herein could be used in therapy for transplantation in the eyes of subjects in need thereof or be used as a research tool for drugs and other treatments and transfection conditions.

The present disclosure is illustrated in further details by the following non-limiting examples.

Example 1: Material and Methods

Animals. Animal work was performed in accordance with the Canadian Council on animal care and IRCM guidelines. GlastCre$^{ERT}$ mice (stock 012586) and the RosaYFP$^{fl/fl}$ reporter mice (stock 006148) were obtained from The Jackson Laboratory. GlastCre$^{ERT}$ mice is a BAC transgenic line expressing CreERT under the control of the Slc1a3 (solute carrier family 1 (glial high-affinity glutamate transporter, member 3), also called Glutamate Aspartate Transporter (GLAST)) promoter. When crossed with a strain containing a loxP site flanked sequence, the offspring are useful for generating tamoxifen-induced, Cre-mediated recombination of DNA regions specifically in glial cells in the adult or progenitor cells in the embryo. The RosaYFP$^{fl/fl}$ mutant mice have a loxP-flanked STOP sequence followed by the Yellow Fluorescent Protein gene (YFP) inserted into the Gt(ROSA) 26S or locus. When bred to mice expressing Cre recombinase, the STOP sequence is deleted and EYFP expression is observed in the cre-expressing tissue(s) of the double mutant offspring. These mutant mice may be useful in monitoring the activity of Cre in living tissues and tracing the lineage of cells that have expressed Cre in embryos, young, and adult mice at desired time points.

DNA constructs. PCALL2, a conditional targeting vector, was obtained from Pierre Mattar (and originally from Dr. Corrine Lobe) and digested with ClaI and SphI to insert mCherry, a fluorophore, (amplified from MSCV-mCherry) in the Loxp cassette. IRES-EGFP was removed with SmaI and NotI digestions. A Gateway™ cassette DNA sequence was added within the multiple cloning site (MCS) for some gene sequence insertions with the Gateway™ Cloning System (Thermo Fisher Scientific Inc.), while others were inserted directly in the MCS by restriction digestions or with In-Fusion™ cloning technology (Clontech™). Ikzf1 was obtained from Dr. Georgopoulos. Caz1v2 and Pou2f1 sequences were generated by Dr. Mattar and Ikzf4 by Christine Jolicoeur. Pou2f2 was obtained from IMAGE™ (40046279). Brn2, Ascl1, and Myt1l sequences were amplified from plasmids obtained from Addgene, Inc. (#27151, 27150, and 27152 respectively). Apobec2b was provided by Dr. Di Noia.

Ex vivo work. Eyes from post-natal days 0-1 (P0-1). GlastCre$^{ERT}$;RosaYFP$^{fl/fl}$ mice were collected in PBS under sterile conditions. Vectors (3 ug/ul) described above were injected sub-retinally and a current (50 millisec duration, 950 millisec interval, 40-50 volts, unipolar electrodes; BTX ECM 830) was applied over the eye with the positive electrode facing the cornea. Retinas were then dissected out in PBS and placed on a culture insert (Millicell™) in a 6-well plate (Flacon) containing 1.3 ml of equilibrated media (DMEM with 10% FBS and 1×pen/strep; Gibco). Explants were left in 5% $CO_2$ incubator with 90% humidity for the duration of the culture, with media-change 3 times per week. At DIV12 (Days in vitro 12), hydroxytamoxifen (Cayman Chemical Co., cat #13258-1) was added to culture media at a final concentration of 5 uM and EGF (PreproTech™) at a concentration of 100 ng/mL and were kept in media until DIV14/15. When indicated, 2'-Deoxy-5-ethynyluridine (EdU) (Abcam™), a DNA synthesis monitoring probe, was added to the media at a concentration of 10 ug/ml at DIV12, 15, 18, and/or 21 and left for 3 days. At DIV26, media was removed from the well and replaced with 1 ml of 4% Paraformaldehyde (PFA; Electron microscopy sciences) for 5 minutes at room temperature. 1 ml 4% PFA was then added over the culture insert and left for another 5-minute incubation at room temperature. Explants were quickly washed with PBS and left in 20% sucrose in PBS at 4° C. for 2-5 hours before being removed from the culture insert with curved forceps and frozen in a 20% sucrose:OCT (Sakura Finetek USA, Inc.) solution for cryosectionning.

In vivo work. Wild-type or GlastCre$^{ERT}$;RosaYFP$^{fl/fl}$ P0-2 mice were anesthetized on ice, injected sub-retinally with 1 ul of DNA vectors (3 ug/ul) in 1 eye and subjected to an electrical current (50 millisec duration, 950 millisec interval, 80 volts, unipolar electrodes) over the eyes with the positive electrode over the injected eye. When indicated, some animals were injected intraperitoneally with EdU (Abcam™) from P3-7 to label cells that have undergone S-phase during this period. From P21-23 inclusively, the animals were injected intraperitoneally daily with 90 ug of tamoxifen (Toronto Research Chemicals and Cedarlane Labs) per gram of body weight. Animals were euthanized by $CO_2$ between P37-P56. Eyes were collected, fixed for 5 min in 4% PFA at room temperature, washed with PBS, and left in 20% sucrose for 4-6 hours at 4° C. before being frozen in 20% sucrose:OCT for cryosectionning.

Immunohistochemistry. Blocks were cryostat (Leica)-sectioned at 25 μm. Slides were incubated in PBS for 2 minutes to remove OCT and left in blocking solution (PBS, 3% bovine serum albumin (BSA) (Sigma-Aldrich™), and 0.3% non-ionic surfactant Triton™-100× (Sigma-Aldrich™)) for 1 hour at room temperature. They were then incubated in primary antibody solution (in blocking) overnight at room temperature (see Table.1 below for antibody list).

TABLE 1

| Primary antibodies | | | |
|---|---|---|---|
| Antigen | Species | Company (cat. #) | Concentration used |
| Ikzf1 (M-20) | Goat | Santa Cruz Biotechnology (SC-9859) | 1/100 |

TABLE 1-continued

| Primary antibodies | | | |
|---|---|---|---|
| Antigen | Species | Company (cat. #) | Concentration used |
| Ikzf4 | Mouse | Sigma-Aldrich ™ (SAB1407877) | 1/100 |
| Ikzf4 | Rabbit | Millipore Sigma ™ | 1/200 |
| Chx10 | Sheep | Exalpha Biologicals (X1180P) | 1/200 |
| Brn3b | Goat | Santa Cruz Biotechnology (SC-6026) | 1/200 |
| Cleaved caspase 3 | Rabbit | New England Biolabs (cat# 9661) | 1/100 |
| Lhx2 | Mouse | CDI Labs (15-389) | 1/100 |
| Sox2 | Rabbit | Abcam Biochemicals (AB97959) | 1/100 |
| Rxrγ | Rabbit | Abcam Biochemicals (AB15518) | 1/100 |
| GFP | Chicken | Abcam Biochemicals (AB13970) | 1/1000 |
| GFP | Rabbit | Invitrogen ™ (A11122) | 1/400 |
| Cone arrestin | Rabbit | Millipore-Sigma ™ (AB15282) | 1/1000 |
| S-opsin | Goat | Santa Cruz Biotechnology (SC-14363 P) | 1/1000 |
| Lectin PNA conjugates-647 | — | Molecular probes (L-32460) | 1/500 |
| Nr2E3 | Rabbit | Chemicon (discontinued) | 1/200 |

This was followed with 3 washes in PBS and secondary antibody incubation in PBS for 1 hour at room temperature. The slides were washed again with PBS and incubated with Hoechst (1/10,000 in PBS; Molecular probes) for 5 minutes at room temperature. The slides were then washed and mounted with Mowiol or underwent EdU click-T™ (Abcam™) reaction following the company's protocol (modified to use ½ of recommended B-component in order to reduce potential bleed-through of AlexaFluor-647).

Lentivirus production To produce lentivirus, 293FT cells (Thermo Fishes Scientific) were plated onto 10 cm dishes (Corning). When plates were 70% confluent, transfection media was produced. Transfection media consisted of 1 ml of DMEM (Gibco) with 5 ug of psPAX2 (Addgene, Inc., Cat.Nr. 12260), 10 ug of pMD.2G (Addgene, Inc., Cat.Nr. 12259), 10 ug of plasmid of interest and 45 ul of PEI (Polyethylenimine, Polysciences). After adding PEI, the transfection media was left to incubate for 15 minutes at room temperature and then was added dropwise to the cell dish. 6 hours after adding transfection media, cell media was replaced with fresh DMEM supplied with 5% BSA (Sigma-Aldrich™). Lentiviral collection and spindown was performed at 24 h and 48 h after initial media change by using Lenti-X™-concentrator (Clontech™) with the according protocol (Clontech™, PT4421-2). Lentiviral titer was determined by using the Lenti-X™ qRT-PCR Titration Kit (Clontech™).

Müller glia culture. Müller glia were cultured from P8-10 CD1 wild-type mice following a previously published protocol (Liu et al., 2017) and were passaged 3 times before being seeded in 24-well plates containing coverslips coated with 0.1% bovine gelatin (Sigma-Aldrich™). 24 h after seeding, media was replaced with 500 ul per well of lentiviral media (containing LV-M2-rtTA; LV-tet-Ikzf1; LV-tet-Eos at each MOI 10) supplied with 8 μg/ml of hexadimethrine bromide Polybrene™ (Sigma-Aldrich™) and spinfected for 1 h at 2000 rpm. 1-day post-infection (dpi), lentiviral media was exchanged with full DMEM supplemented with 2 ug/ml of doxycycline (dox, Sigma-Aldrich™). Half of the media was exchanged with new dox-supplemented full DMEM every 2-3 days. At 9 dpi, until 21 dpi, half of the media was switched every 2-3 days with retinal maturation medium (Gonzalez-Cordero et al., 2017) supplemented with 2 ug/ml dox. At 21 dpi, cells were fixed in 4% PFA (Electron Microscopy Sciences) for 15 min at room temperature or lysed in the lysis buffer Qiagen™ buffer RLT for RNA isolation and qPCR.

RNA isolation and Quantitative PCR. Retinal explants were dissociated with 100 units of papain (Worthington, LS003124). GFP+ cells were FAC-sorted from the dissociated retinal explants 6 days after electroporation. Collected cells were sorted directly into Qiagen™ Buffer RLT plus and RNeasy™ microkit (Qiagen N.V., 74004) was used to isolate RNA from the cells as instructed by the manufacturers protocol. Isolated RNA was reverse transcribed using Superscript™ VILO Master Mix (Thermofisher Scientific, 11755050). cDNA was amplified by quantitative PCR using SYBR™ Green Master mix (Thermofisher Scientific, A25742). Primers used were NrI pF: CGAGCAGTGCA-CATCTCAGTTC (SEQ ID NO: 69), pR: AACTG-GAGGGCTGGGTTACC (SEQ ID NO: 70), Nr2e3 pF: AAGCTCCTGTGTGACATGTTCAA (SEQ ID NO: 71), pR: AAGCTCCTGTGTGACATGTTCAA (SEQ ID NO: 72).

Adeno associated viruses. Viral vectors (see FIG. 20J-M) were packaged by Dr. Dalkara. Animals were anesthetized by isoflurane and injected intravitreally with 2 ul of AVV per eye (delay of 1 week between infections). Animals were euthanized by $CO_2$ and eyes fixed for 5 minutes as described above or 1 hour for retinal whole mount (in which case, the retinas were then dissected out and cut in 4 petals).

Microscopy and cell counts. All images were obtained by SP8 confocal microscopy (Leica™), analyzed on Volocity™ software (Perkin Elmer), and processed on Fiji™ (ImageJ), and Adobe™ Illustrator (Adobe Inc). For explant cell count, YFP+ mCherry+ cells were analyzed unless specified that only Ikzf1/4 morphologically reprogrammed cells were analyzed, which corresponds to YFP+ mCherry+ cells with round or cone-like morphologies.

Statistics. Statistical analyses were performed with Prism™ software (GraphPad Software, LLC.).

Example 2: Ikzf4 is Expressed in the Developing Retina During the Window of Cone Genesis and Sufficient to Promote Cone Production The expression of Ikzf4 was studied in the mouse retina during the temporal window of cone genesis. As the antibody specific to Ikzf4 was raised in the same species as the early cone marker antibody, the inventors could not investigate whether Ikzf4 co-localizes with Rxrγ, a marker for cone photoreceptors. To overcome this issue, Otx2, a marker for photoreceptor precursors at E15, was used. Since cone photoreceptors are born during the embryonic stages of mouse retinogenesis (Rapaport et al., 2004; Young, 1985a, b), the majority of the Otx2+ cells at this age are cone photoreceptor precursors. Expression of Ikzf4 was detected in the retinal progenitor layer, and in some Otx2+ cells (FIGS. 1 A-B), suggesting that it is expressed in both proliferating retinal stem/progenitors and cone photoreceptor precursors during retinal development.

Example 3: Ikzf4 is Sufficient to Promote Cone Photoreceptors when Expressed Ex Vivo in Retinal Stem/Progenitor Cells (Neuroepithelial Cells)

The functional role of Ikzf4 in the developing retina was next investigated. It was tested whether Ikzf4 was sufficient to induce cone production in late-stage retinas, a stage at which no cones are normally generated. P0 retinal explants (i.e. neuroepithelial cells, namely multipotent cells) were electroporated with vectors expressing either only GFP (see FIGS. 22A-B (pCIG-GFP)) or Ikzf4-IRES-GFP (see FIGS. 22C-E; (pCIG-Ikzf4-GFP)) and the explants cultured for an additional 14 days. Remarkably, in the Ikzf4 condition, almost all the GFP+ cells located in the photoreceptor layer expressed $RxR_{\gamma}$ (designated Rxrg on FIGS. 1C-D) (FIGS. 1 C-D), a marker for cone photoreceptors, whereas only a few were observed in the control GFP condition (FIG. 1E).

Figure 1F:
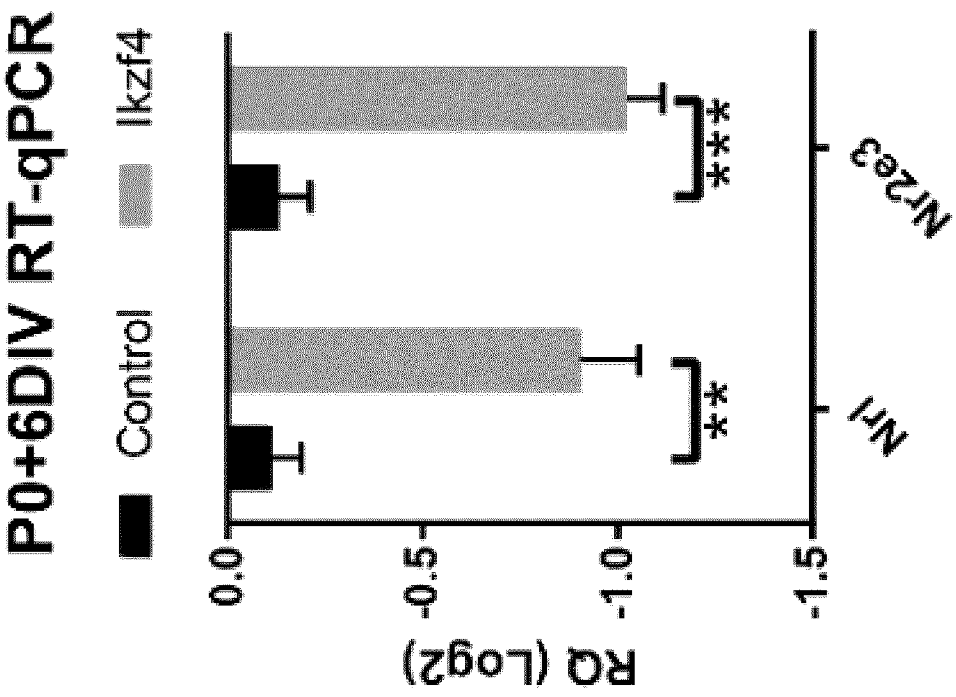

Next was assessed whether Ikzf4 overexpression leads to a reduction of mRNA levels of NrI and Nr2e3, two critical rod differentiation genes, the repression of which is known to lead to the generation of a retina composed of cone-like cells only (Mears et al, 2001). To test this, P0 retinas were electroporated with control GFP or Ikzf4-IRES-GFP and the GFP+ population were sorted after 6 days, mRNA isolated and RT-qPCR performed using primers specific to NrI and Nr2e3. A significant reduction of mRNA expression of both NrI and Nr2e3 was detected (FIG. 1F). To validate these findings, the protein expression of Nr2e3 (rod photoreceptor marker) was investigated, along with that of Otx2, a protein which labels rod and cone photoreceptors and bipolar cells at this stage. Corroborating the RT-qPCR results, a lack of expression of the rod-specific marker Nr2e3 was detected in Ikzf4-IRES-GFP-expressing cells, whereas these cells still expressed the pan-photoreceptor marker Otx2 (FIGS. 1 G-H).

Taken together, these results suggest that Ikzf4 is sufficient to induce a repression of rod genes (i.e., NrI and Nr2e3) and induce cone production in late stage retinas.

Example 4: Co-Expression of Ikzf1 and Ikzf4 can Reprogram Müller Glia into Immature Cone-Like Cells Ex Vivo in Retinal Explants in Terms of Shape The Müller-specific Cre mouse line Glast-$Cre^{ERT}$, which also carried the $RosaYFP^{fl/fl}$ reporter ($GlastCre^{ERT}$;$RosaYFP^{fl/fl}$), was used, allowing to lineage-trace all Müller-derived cells by imaging the YFP fluorescence. Retinas were electroporated at postnatal day 0-1 (P0/1) with Cre-dependent expression constructs containing mCherry, a fluorophore, ((pCAG-loxP-mCherry-stop-loxP-gene (FIGS. 20A-J)) and were explanted for ex vivo culture (FIG. 2A). At day in vitro 12 (DIV12), the expression of the genes of interest (see FIG. 2B) was activated and Müller glia and their progeny were permanently labelled with YFP by adding hydroxytamoxifen (activating $Cre^{ERT}$) to the culture medium along with EGF to stimulate proliferation. The explants were then fixed at DIV26 and the YFP+ cells within electroporated regions were analyzed (mCherry-labelled) for photoreceptor-like morphologies and their expression of Müller glia and photoreceptor markers.

It was noticed that mCherry continued to be expressed within Müller glia that had activated Cre, allowing to focus the analysis on electroporated Müller cells (YFP co-labelling with mCherry). The genes screened were Ikzf1 (FIG. 12A-NP_001020768.1) (Elliott et al., 2008), Casz1v2 (Mattar et al., 2015), Ascl1, Brn2, Myt1l (Vierbuchen et al., 2010), and Apobec2b (Powell et al., 2012), Pou2f1, Pou2f2 (Javed et al., manuscript in preparation), and the newly identified cone factor Ikzf4 (FIG. 15A—Q8C208-1; FIG. 1).

Out of 23 gene expression combinations screened (see FIG. 2B for list), one of them, the co-expression of Ikzf1 and of the novel cone factor Ikzf4 induced clear morphological changes of the YFP+ cells (FIGS. 3 A-F). Under normal conditions, Müller glia have large cell bodies located in the inner nuclear layer (INL) of the retina and complex processes that extend both to the apical side of the outer nuclear layer (ONL), where photoreceptors are located, as well as towards the ganglion cell layer. In control conditions, as expected, 96.3% of YFP+ mCherry+(electroporated) cells showed this normal Müller glia morphology, whereas in the Ikzf1/4 condition, only 41.1% of YFP+ mCherry+ cells had Müller glia morphology. The other Ikzf1/4 cells were round (43.0%), cone-like (11.4%), or did not have a recognizable morphology (4.6%) (FIG. 3F).

Figure 3G:
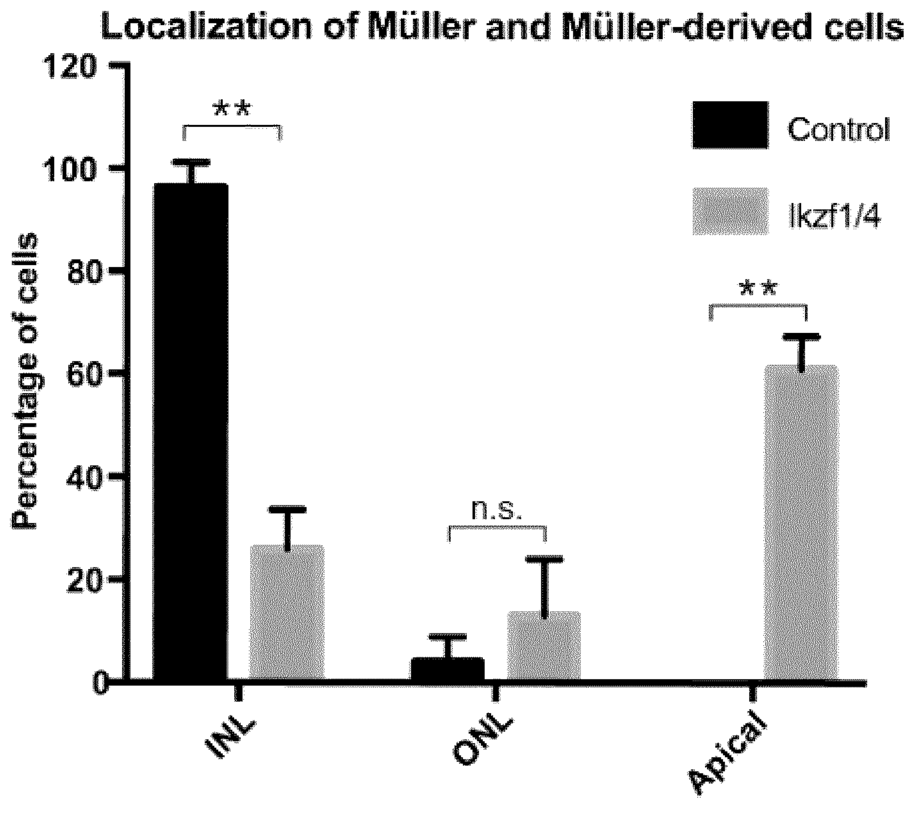

Example 5: Co-Expression of Ikzf1 and Ikzf4 can Reprogram Müller Glia into Immature Cone-Like Cells Ex Vivo in Retinal Explants in Terms of Localization In addition to morphology changes, the majority (61.1%) of YFP+ mCherry+ cells in the Ikzf1/4 condition moved to the apical side of the retina (in the ONL), where cone photoreceptors are usually located (FIG. 3G). Another 13.0% were localized within the rest of the ONL and 25.9%, mostly Müller-like cells, stayed within the INL. This is in contrast to control cells that were mostly (96.1%) localized in the INL.

Figure 3H:
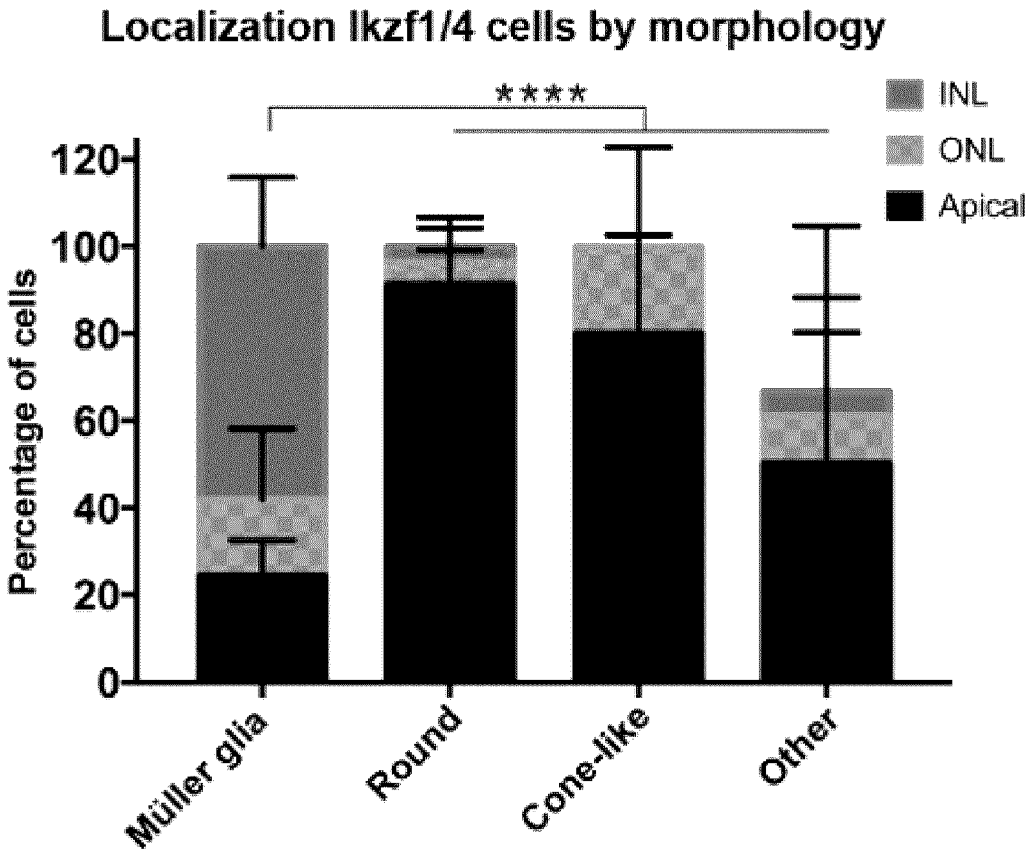

Furthermore, within the Ikzf1/4 expressing population, the observed change in morphology was associated with a re-localization to the apical side of the ONL: whereas only 3% of Müller-like cells located to the apical side of the ONL, 91.3% of round cells, and 79.9% of cone-like cells were found there (FIG. 3H). Hence, the morphology change of YFP+ cells in the Ikzf1/Ikzf4 condition seems to be associated with their re-localization from the INL to the ONL where photoreceptor cells reside.

Example 6: Co-Expression of Ikzf1 and Ikzf4 can Reprogram Müller Glia into Immature Cone-Like Cells Ex Vivo in Retinal Explants in Terms of Markers To analyze whether these morphologically reprogrammed cells (cone-like and round population) kept their Müller identity, immunofluorescence were performed for the Müller glia markers Lhx2, and Sox2 (FIGS. 4A-D). It was found that only 10% of these cells expressed Lhx2 compared to 98% for control Müller glia and 26% expressed Sox2 compared to 94% for control Müller glia, indicating that the morphologically reprogrammed cells downregulate their Müller glia gene expression.

It was next assessed whether the reprogrammed cells expressed photoreceptor markers by immunofluorescence (FIGS. 4 E-F). Interestingly, 78.3% of reprogrammed cells expressed $RxR_{\gamma}$, an early cone photoreceptor marker, compared to 0% of control Müller glia. However, only rare cells expressing the more mature cone-marker s-opsin were found and none expressing other mature cone markers, suggesting that Müller glia are capable of producing immature cone-like cells after expression of Ikzf1/4. It was also validated that these cells did not express markers for other cell types. Reprogrammed cells were Brn3b-negative (ganglion cell marker) and Chx10-negative (bipolar marker) (Data not shown). Additionally, they were negative for the apoptosis marker cleaved-caspase 3 (Data not shown).

It is important to note that single overexpression of either Ikzf1 or Ikzf4 did not induce this reprogramming. Indeed, Ikzf1 did not produce changes in Müller glia (Data not shown), at least to the extent analyzed, while Ikzf4 induced RxRγ expression, but did not change their morphology and very rarely induced downregulation of Müller glia markers (FIGS. 5 A-D showing representative photographs).

Example 7: Co-Expression of Ikzf1 and Ikzf4 in Müller Glia do not Promote their Proliferation (Ex Vivo)

To determine whether Ikzf1/4-expressing Müller glia proliferate before reprogramming to cone-like cells ex vivo, EdU time course experiments (EdU being the proliferation marker) were performed spanning DIV12-24, which corresponds to the time point at which is added hydroxytamoxifen, all the way to 2 days before fixation.

One set of experiments spanned DIV12-15 and DIV15-18 (FIG. 6A) and the other DIV15-18 and DIV 21-24 (FIG. 6B). No difference was found between the control YFP+ mCherry+ and Ikzf1/4 YFP+ mCherry+ cells in both sets of experiments (FIG. 6 C-D). In these experiments, Ikzf1/4 expression in Müller glia did not promote proliferation.

Example 8: Co-Expression of Ikzf1 and Ikzf4 Produces RxRγ+s-Opsin+ Cells in Müller Glia Culture (In Vitro)

It was next tested whether Ikzf1 and Ikzf4 expression would be sufficient to reprogram Müller glia in culture assays. Müller cell cultures were prepared following a published protocol (Liu et al., 2017) and infected with Ikzf1- and Ikzf4-expressing lentiviral vectors. The cells were cultured in a medium supplemented with taurine and retinoic acid, which were previously reported to promote photoreceptor maturation (Altshuler et al., 1993; Kelley et al., 1994).

Four weeks later, some RxRγ+s-opsin+ cells were observed by immunofluorescence and gene induction was detected by RT-qPCR (FIGS. 7A-B showing representative photographs of the same experiment). These cells were never observed in control experiments infected with a GFP lentiviral vector (see control in FIG. 7A). This experiment suggests that Ikzf1/Ikzf4 can reprogram Müller glia into cones expressing mature markers like s-opsin when cultured under conditions that promote cone maturation (taurine+ retinoic acid). Other cone markers such GNAT1, ThrB et RORb were not detected in this experiment (FIG. 7C).

Example 9: Co-Expression of Ikzf1 and Ikzf4 Reprogram Müller glia to Cone-Like Cells In Vivo In order to test whether Ikzf1/4 expression could also reprogram Müller glia in vivo, the Cre-dependent Ikzf1/4 (pCAG-loxP-mCherry-Stop-loxP-Ikzf1/4; Pcall, same vectors as used in ex vivo experiments above; See FIGS. 20F-J) or empty constructs (pCAG-loxP-mCherry-Stop-loxP-empty; Pcall, same vectors as used in ex vivo experiments above; See FIGS. 20A-E) (FIG. 8A) were co-electroporated in vivo in GlastCre$^{ERT}$;RosaYFP$^{fl/fl}$ animals.

Cre$^{ERT}$ was activated with 3 consecutive tamoxifen injections from P21-P23, permanently labelling Müller glia and any derived progeny with YFP and initiating the expression of Ikzf1/4 in these cells (FIG. 8 A). At 3 weeks post tamoxifen, 20% of YFP+ mCherry+ cells in the Ikzf1/4 condition were reprogrammed to cone-like cells (FIG. 8B). 91% of these reprogrammed cells were RxRγ-positive (FIGS. 8 C-D) and only 10% expressed the Müller glia marker Sox2 (FIGS. 8 E, G), similar to what was observed ex vivo. Interestingly, a gradient of Sox2 expression was observed in some YFP+ mCherry+ cells (FIG. 8 F) with some Müller glia expressing normal levels of Sox2, others light levels, and others none. This suggests that some cells might not be fully reprogrammed yet at this stage and still express low levels of Sox2.

To investigate whether the reprogrammed cells could survive in the retina, the above in vivo experiment was repeated and animals were sacrificed 5 weeks post-tamoxifen (FIG. 9B). Seven % of YFP+ mCherry+ cells were reprogrammed to cone-like cells at this stage (FIG. 9B) indicating that some cells may be lost over time.

As an additional lineage tracing method and to exclude the possibility of YFP transfer, the previous in vivo protocol was repeated with intraperitoneal injections of EdU from P3-P7 (FIG. 10A). EdU thus would incorporate in the nuclei of late-born cells, including Müller glia, whereas the early-born cones would not be labelled. Some reprogrammed cone-like cells were EdU+(FIG. 10B) indicating that these cells were not endogenous cones labelled with YFP from material transfer, but were instead generated de novo from postnatal Müller cells.

Example 10: Reprogramming with Adeno-Associated Viral Vectors (AAV)

AAVs have been previously used safely in humans and even in the eye for gene therapy (Petit et al., 2016). The Shh10 AAV serotype is mostly specific to Müller glia when injected intravitreally in the retina (Pellissier et al., 2014), although infection of RGCs and sometimes photoreceptors depending on injection site was also observed.

The use of AAV for Müller glia reprogramming in vivo was tested (i.e. AAV-Ikzf1 (FIGS. 20K-L); and AAV-Ikzf4 (FIGS. 20L-M)). PssAAV-CAG-GFP (obtained from Dr. Dalkara) were cut with AgEI+HindIII to remove GFP. Ikzf1 and Ikzf4 sequences were PCR-amplified from pCALL2 vectors described above and inserted in the pssAAV-CAG by In Fusion cloning to produce pssAAV-CAG-Ikzf1 and pssAAV-CAG-Ikzf4.

It was first found that infecting adult retinas in vivo with AAV-Ikzf4 induced expression of Ikzf4 in a large proportion of Müller glia (FIG. 11 A). Additionally, Ikzf4 induced expression of RxRγ in these cells (FIGS. 11 B-C), similar to what was observed in explants. It was found that co-infection of both Ikzf1 and Ikzf4 leads to the expression of Ikzf4 only. Delayed infections were therefore tested, and it was determined that 1-week delay between infections (Ikzf1 first, followed by Ikzf4 one week later), leads to co-expression of these genes within Müller glia (FIG. 11 D).

Müller glia reprogramming with these infections are currently tested for the production of cone-like cells. Glast-CreERT;RosaYFP mice, previously injected with tamoxifen to active permanent YFP expression in Müller cells, are intravitreally injected with AAV-Ikzf1 and AAV-Ikzf4 1 week later or AAV-Tomato as control. They are then sacrificed 5-7 weeks later and analyzed for YFP+(Müller-derived) cones by immunofluorescence.

Example 11: Testing Functionality

To test the function of the reprogrammed cones, membrane potential is recorded in response to light and the reactivity of the cone is compared to that of endogenous cones. Alpha ganglion cells within the electroporated regions are also analyzed to determine whether de novo cones connect with synaptic partners and integrate retinal circuitry. Müller glia are also reprogrammed in 2 mouse models of retinitis pigmentosa to test whether Müller-derived cones restore vision. Experiments described in Example 9 are repeated in GlastCreERT;RosaYFP; Pde6bRD1 mice. These mice were obtained from Jackson Laboratory (strain 000659) and have the RD1 mutation in Pde6b gene, which leads to rod photoreceptor cell death and blindness by P21. Cone photoreceptors also degenerate with barely any present by P100.

Another retinal degeneration model used is the intraperitoneal injection of the drug N-methyl-N-nitrosourea (MNU), which kills photoreceptors by 7 days after injection (Tao et al., 2015) Experiments described in Example 9 are repeated with an intraperitoneal injection of MNU 1 week before tamoxifen administration to effectively kill photoreceptor cells before reprogramming Müller glia in cones. Vision can then be tested with behavioral tests (e.g., visual water tests, optomotor reflex) and by electroretinogram recordings.

Example 12: Mechanism of Reprogramming

To obtain insights into the underlying mechanism of reprogramming, RNA and ATAC-sequencing of Ikzf1/4-expressing Müller cultures at different time points are performed, allowing to identify both the transcriptomic changes and chromatin remodelling (respectively) occurring during reprogramming. Of particular interest is whether Müller glia go through an intermediate progenitor state or directly transdifferentiate into cones. scRNA-sequencing of in vivo Ikzf1/4 reprogrammed cells is also underway to better characterise the Müller-derived cells. These experiments will also identify targets to enhance reprogramming efficiency, as well as survival, and maturation of the cone-like cells.

Enhancing Maturation of Cone-Like Cells

Transitory transfection methods are additionally tested to limit potential toxicity from continuous Ikzf1/4 overexpression to determine whether this will improve cell survival. These methods include the doxycycline-inducible Tet-On system, which drives expression of Ikzf1 and Ikzf4 only in the presence of doxycycline, allowing to turn on and off their expression, as well as Ikzf1 and Ikzf4 protein transfections which are degraded by the cells and thus transiently present.

The scope of the claims should not be limited by the embodiments set forth in the examples but should be given the broadest interpretation consistent with the description as a whole.

REFERENCES

Altshuler, D., Lo Turco, J. J., Rush, J., and Cepko, C. (1993). Taurine promotes the differentiation of a vertebrate retinal cell type in vitro. Development, 1317-1328.

Bernardos, R. L., Barthel, L. K., Meyers, J. R., and Raymond, P. A. (2007). Late-stage neuronal progenitors in the retina are radial Muller glia that function as retinal stem cells. The Journal of neuroscience: the official journal of the Society for Neuroscience 27, 7028-7040.

Blackshaw, S., Harpavat, S., Trimarchi, J., Cai, L., Huang, H., Kuo, W. P., Weber, G., Lee, K., Fraioli, R. E., Cho, S. H., et al. (2004). Genomic analysis of mouse retinal development. PLoS biology 2, E247.

Elliott, J., Jolicoeur, C., Ramamurthy, V., and Cayouette, M. (2008). Ikaros confers early temporal competence to mouse retinal progenitor cells. Neuron 60, 26-39.

Fausett, B. V., and Goldman, D. (2006). A role for alpha1 tubulin-expressing Muller glia in regeneration of the injured zebrafish retina. The Journal of neuroscience: the official journal of the Society for Neuroscience 26, 6303-6313.

Fimbel, S. M., Montgomery, J. E., Burket, C. T., and Hyde, D. R. (2007). Regeneration of inner retinal neurons after intravitreal injection of ouabain in zebrafish. The Journal of neuroscience: the official journal of the Society for Neuroscience 27, 1712-1724.

Gonzalez-Cordero, A., Kruczek, K., Naeem, A., Fernando, M., Kloc, M., Ribeiro, J., Goh, D., Duran, Y., Blackford, S. J. I., Abelleira-Hervas, L., et al. (2017). Recapitulation of Human Retinal Development from Human Pluripotent Stem Cells Generates Transplantable Populations of Cone Photoreceptors. Stem cell reports 9, 820-837.

Hamon, A., Roger, J. E., Yang, X.-J., and Perron, M. (2016). Müller Glial Cell-Dependent Regeneration of the Neural Retina—An Overview Across Vertebrate Model Systems. Developmental dynamics reviews.

Jadhav, A. P., Roesch, K., and Cepko, C. L. (2009). Development and neurogenic potential of Muller glial cells in the vertebrate retina. Progress in retinal and eye research 28, 249-262.

Johnson M, et al. (2008) *Nucleic Acids Res.* 36:W5-W9; Papadopoulos J S and Agarwala R (2007) *Bioinformatics* 23:1073-79

Jorstad, N. L., Wilken, M. S., Grimes, W. N., Wohl, S. G., VandenBosch, L. S., Yoshimatsu, T., Wong, R. O., Rieke, F., and Reh, T. A. (2017). Stimulation of functional neuronal regeneration from Muller glia in adult mice. Nature 548, 103-107.

Kassen, S. C., Ramanan, V., Montgomery, J. E., C, T. B., Liu, C. G., Vihtelic, T. S., and Hyde, D. R. (2007). Time course analysis of gene expression during light-induced photoreceptor cell death and regeneration in albino zebrafish. Developmental neurobiology 67, 1009-1031.

Kelley, M. W., Turner, J. K., and Reh, T. A. (1994). Retinoic acid promotes differentiation of photoreceptors in vitro. Development, 2091-2102.

Liu, X., Tang, L., and Liu, Y. (2017). Mouse Müller Cell Isolation and Culture Bio-protocol 7.

Mattar, P., Ericson, J., Blackshaw, S., and Cayouette, M. (2015). A conserved regulatory logic controls temporal identity in mouse neural progenitors. Neuron 85, 497-504.

Mears A J, Kondo M, Swain P K, Takada Y, Bush R A, Saunders T L, Sieving P A, Swaroop A. (2001). Nrl is required for rod photoreceptor development. Nat Genet 29(4):447-52.

Nakano, T., Ando S., Takata N., Kawada M., Muguruma K., Sekiguchi K., Saito K., Yonemura S., Eiraku M., Sasai Y., (2012) Self-Formation of Optic Cups and Storable Stratified Neural Retina from Human ESCs *Cell Stem Cell* 10, 771-785.

Ortin-Martinez, A., Tsai, E. L., Nickerson, P. E., Bergeret, M., Lu, Y., Smiley, S., Comanita, L., and Wallace, V. A. (2016). A Reinterpretation of Cell Transplantation: GFP Transfer from Donor to Host Photoreceptors. Stem cells 35, 932-939.

Pearson, R. A., Gonzalez-Cordero, A., West, E. L., Ribeiro, J. R., Aghaizu, N., Goh, D., Sampson, R. D., Georgiadis, A., Waldron, P. V., Duran, Y., et al. (2016). Donor and host photoreceptors engage in material transfer following transplantation of post-mitotic photoreceptor precursors. Nature communications 7, 13029.
Pellissier, L. P., Hoek, R. M., Vos, R. M., Aartsen, W. M., Klimczak, R. R., Hoyng, S. A., Flannery, J. G., and Wijnholds, J. (2014). Specific tools for targeting and expression in Muller glial cells. Molecular therapy Methods & clinical development 1, 14009.
Petit, L., Khanna, H., and Punzo, C. (2016). Advances in Gene Therapy for Diseases of the Eye. Hum Gene Ther 27, 563-579.
Powell, C., Elsaeidi, F., and Goldman, D. (2012). Injury-dependent Muller glia and ganglion cell reprogramming during tissue regeneration requires Apobec2a and Apobec2b. The Journal of neuroscience: the official journal of the Society for Neuroscience 32, 1096-1109.
Rapaport, D. H., Wong, L. L., Wood, E. D., Yasumura, D., and LaVail, M. M. (2004). Timing and topography of cell genesis in the rat retina. J Comp Neurol 474, 304-324.
Roesch, K., Jadhav, A. P., Trimarchi, J. M., Stadler, M. B., Roska, B., Sun, B. B., and Cepko, C. L. (2008). The transcriptome of retinal Müller glial cells. The Journal of comparative neurology 509, 225-238.
Santos-Ferreira, T., Llonch, S., Borsch, O., Postel, K., Haas, J., and Ader, M. (2016). Retinal transplantation of photoreceptors results in donor-host cytoplasmic exchange. Nature communications 7, 13028.
Santos-Ferreira, T. F., Borsch, O., and Ader, M. (2017). Rebuilding the Missing Part-A Review on Photoreceptor Transplantation. Front Syst Neurosci 10, 1-14.
Senut, M. C., Gulati-Leekha, A., and Goldman, D. (2004). An element in the alpha1-tubulin promoter is necessary for retinal expression during optic nerve regeneration but not after eye injury in the adult zebrafish. The Journal of neuroscience: the official journal of the Society for Neuroscience 24, 7663-7673.
Singh, M. S., Balmer, J., Barnard, A. R., Aslam, S. A., Moralli, D., Green, C. M., Barnea-Cramer, A., Duncan, I., and MacLaren, R. E. (2016). Transplanted photoreceptor precursors transfer proteins to host photoreceptors by a mechanism of cytoplasmic fusion. Nature communications 7, 13537.
Tao Y., Chen T., Fang W., Peng G., Wang L., Qin L., Liu B., Huang Y. F. The temporal topography of the N-Methyl-N-nitrosourea induced photoreceptor degeneration in mouse retina (2015) *Scientific Reports* volume 5, Article number: 18612.
Ueki, Y., Wilken, M. S., Cox, K. E., Chipman, L., Jorstad, N., Sternhagen, K., Simic, M., Ullom, K., Nakafuku, M., and Reh, T. A. (2015). Transgenic expression of the proneural transcription factor Ascl1 in Muller glia stimulates retinal regeneration in young mice. Proceedings of the National Academy of Sciences of the United States of America 112, 13717-13722.
Vierbuchen, T., Ostermeier, A., Pang, Z. P., Kokubu, Y., Sudhof, T. C., and Wernig, M. (2010). Direct conversion of fibroblasts to functional neurons by defined factors. Nature 463, 1035-1041.
Yao, K., Qiu, S., Wang, Y. V., Park, S. J. H., Mohns, E. J., Mehta, B., Liu, X., Chang, B., Zenisek, D., Crair, M. C., et al. (2018). Restoration of vision after de novo genesis of rod photoreceptors in mammalian retinas. Nature 560, 484-488.
Young, R. W. (1985a). Cell differentiation in the retina of the mouse. Anat Rec 212, 199-205.
Young, R. W. (1985b). Cell proliferation during postnatal development of the retina in the mouse. Brain Res 353, 229-239.
Zhong X., Gutierrez C., Xue T., Hampton C., Vergara M. N., Cao L., Peters A., Soon Park T., Zambidis E. T., Meyer J. S., Gamm D. M., Yau K.-W., Canto-Soler M. V., Generation of three-dimensional retinal tissue with functional photoreceptors from human iPSCs, (2014) Nature Communications 5:4047. DOI: 10.1038.

The invention claimed is:

1. An isolated recombinant mammal adult Müller cell comprising nucleic acid encoding IKAROS Family Zinc Finger 4 (Ikzf4) set forth in any one of SEQ ID NOs: 29 to 32, and 37 to 41, and nucleic acid encoding IKAROS Family Zinc Finger 1 (Ikzf1) set forth in any one of SEQ ID NOs: 1 to 4, and 11 to 18, or an isolated cell population comprising the cell, wherein the nucleic acids are comprised in an adeno-associated virus (AAV) vector or a lentiviral vector.

2. The isolated recombinant mammalian cell or isolated cell population of claim 1, wherein the nucleic acids are operably linked to a glial specific promoter.

3. The isolated recombinant mammalian cell or isolated cell population of claim 1, wherein the nucleic acids are comprised in an AAV vector.

4. The isolated recombinant mammalian cell or isolated cell population of claim 1, wherein the nucleic acids are comprised in a lentiviral vector.

5. A vector comprising a glial specific promoter operably linked to a nucleic acid molecule encoding IKAROS Family Zinc Finger 1 (Ikzf1) set forth in any one of SEQ ID NOs: 1 to 4, and 11 to 18 and to a nucleic acid molecule encoding IKAROS Family Zinc Finger 4 (Ikzf4) set forth in any one of SEQ ID NOs: 29 to 32, and 37 to 41.

6. The vector of claim 5, which is an adeno-associated virus (AAV) vector.

7. The vector of claim 5, which is a lentiviral vector.

8. A pharmaceutical composition comprising (a)(i) a nucleic acid encoding IKAROS Family Zinc Finger 1 (Ikzf1) set forth in any one of SEQ ID NOs: 1 to 4, and 11 to 18; and a nucleic acid encoding IKAROS Family Zinc Finger 4 (Ikzf4) set forth in any one of SEQ ID NOs: 29 to 32, and 37 to 41, wherein the nucleic acids encoding Ikzf4 and Ikzf1 are comprised in an adeno-associated virus (AAV) vector or a lentiviral vector; (ii) the isolated recombinant mammalian adult cell or isolated cell population defined in claim 1; or (iii) the vector defined in claim 4; and (b) a pharmaceutically acceptable carrier.

9. A method of producing a recombinant cone photoreceptor, comprising:

(A) (a) introducing a nucleic acid molecule encoding IKAROS Family Zinc Finger 1 (Ikzf1) set forth in any one of SEQ ID NOs: 1 to 4, and 11 to 18, in a mammalian Müller glia cell; and (b) introducing a nucleic acid molecule encoding IKAROS Family Zinc Finger 4 (Ikzf4) set forth in any one of SEQ ID NOs: 29 to 32, and 37 to 41 in the mammalian Müller glia cell;

whereby the mammalian Müller glia cell is reprogrammed into a recombinant cone photoreceptor.

10. The method of claim 9, wherein the introducing of (a) and (b) is ex vivo.

11. The method of claim 9, wherein the introducing of (a) and (b) is intraocular.

12. The method of claim 9, wherein each of the nucleic acid molecules of (a) and (b) is in a vector.

13. The method of claim 9, wherein the introducing of (a) and (b) is performed by electroporation.

14. The method of claim 9, wherein the introducing of (a) and (b) is performed by viral-based gene delivery.

15. The method of claim 14, wherein the viral-based gene delivery is an adeno-associated virus (AAV) gene delivery.

16. The isolated recombinant cell or isolated cell population of claim 3, wherein the AAV is of the ShH10 serotype.

17. The vector of claim 6, wherein the AAV is of the ShH10 serotype.

18. The method of claim 15, wherein the AAV is of the ShH10 serotype.

19. A transgenic non-human mammal comprising an isolated recombinant adult Müller cell comprising a nucleic acid encoding IKAROS Family Zinc Finger 1 (Ikzf1) set forth in any one of SEQ ID NOs: 1 to 4, and 11 to 18; and a nucleic acid encoding IKAROS Family Zinc Finger 4 (Ikzf4) set forth in any one of SEQ ID NOs: 29 to 32, and 37 to 41.

* * * * *